US008263378B2

(12) United States Patent
Elliott et al.

(10) Patent No.: US 8,263,378 B2

(45) Date of Patent: Sep. 11, 2012

(54) HUMAN β-ADRENERGIC RECEPTOR KINASE POLYPEPTIDE AND METHODS

(75) Inventors: Vicki S. Elliott, San Jose, CA (US); Reena Khare, Saratoga, CA (US); Thomas W. Richardson, Belmont, CA (US); Joseph P. Marquis, San Jose, CA (US); Anita Swarnakar, San Francisco, CA (US); April J. A. Hafalia, Daly City, CA (US); Shanya D. Becha, San Francisco, CA (US); Narinder K. Chawla-Walia, Union City, CA (US); Mariah R. Baughn, Los Angeles, CA (US); Soo Yeun Lee, Daly, CA (US); Uyen K. Tran, San Jose, CA (US); Henry Yue, Sunnyvale, CA (US); Danniel B. Nguyen, San Jose, CA (US); Michael B. Thornton, Oakland, CA (US); Rajagopal Gururajan, San Jose, CA (US); Ameena R. Gandhi, San Francisco, CA (US); Yan Lu, Mountain View, CA (US); Monique G. Yao, Mountain View, CA (US); Joana X. Li, Millbrae, CA (US); Wen Luo, San Diego, CA (US); Ernestine A. Lee, Kensington, CA (US); Ian J. Forsythe, Edmonton (CA); Craig H. Ison, San Jose, CA (US); Amy D. Wilson, Encino, CA (US); Pei Jin, Palo Alto, CA (US)

(73) Assignee: Incyte Corporation, Wilmington, DE (US)

( * ) Notice: Subject to any disclaimer, the term of this patent is extended or adjusted under 35 U.S.C. 154(b) by 12 days.

(21) Appl. No.: 12/923,407

(22) Filed: Sep. 20, 2010
(Under 37 CFR 1.47)

(65) Prior Publication Data

US 2012/0014937 A1 Jan. 19, 2012

Related U.S. Application Data

(62) Division of application No. 10/554,917, filed as application No. PCT/US2004/009215 on Mar. 24, 2004, now Pat. No. 7,829,682.

(60) Provisional application No. 60/528,750, filed on Dec. 10, 2003, provisional application No. 60/524,415, filed on Nov. 20, 2003, provisional application No. 60/494,656, filed on Aug. 12, 2003, provisional application No. 60/476,408, filed on Jun. 5, 2003, provisional application No. 60/469,441, filed on May 9, 2003, provisional application No. 60/467,491, filed on Apr. 30, 2003.

(51) Int. Cl.
*C12N 9/12* (2006.01)

(52) U.S. Cl. ........................................................ 435/194

(58) Field of Classification Search ........................ None
See application file for complete search history.

(56) References Cited

U.S. PATENT DOCUMENTS

| | | | |
|---|---|---|---|
| 5,175,383 | A | 12/1992 | Leder et al. |
| 5,474,796 | A | 12/1995 | Brennan |
| 5,605,662 | A | 2/1997 | Heller et al. |
| 5,686,242 | A | 11/1997 | Bruice et al. |
| 5,707,618 | A | 1/1998 | Armentano et al. |
| 5,767,337 | A | 6/1998 | Roses et al. |
| 5,804,413 | A | 9/1998 | DeLuca |
| 5,807,522 | A | 9/1998 | Brown et al. |
| 5,837,458 | A | 11/1998 | Minshull et al. |
| 5,840,484 | A | 11/1998 | Seilhamer et al. |
| 5,869,275 | A | 2/1999 | Huang |
| 5,910,434 | A | 6/1999 | Rigg et al. |
| 5,914,236 | A | 6/1999 | Monsma, Jr. et al. |
| 5,932,435 | A | 8/1999 | Atkins et al. |
| 5,997,848 | A | 12/1999 | Patton et al. |
| 6,022,691 | A | 2/2000 | Bruice et al. |
| 6,057,101 | A | 5/2000 | Nandabalan et al. |
| 6,372,724 | B1 | 4/2002 | Pelleg et al. |

FOREIGN PATENT DOCUMENTS

| | | |
|---|---|---|
| WO | WO 84/03564 | 9/1984 |
| WO | WO 95/25116 | 9/1995 |
| WO | WO 95/35505 | 12/1995 |
| WO | WO02073469 | * 12/2000 |
| WO | WO 01-53312 | 7/2001 |

OTHER PUBLICATIONS

Galye et al, Identification of regions in interleukin-1 alpha important for activity. J Biol Chem. Oct. 15, 1993;268(29):22105-11.*
Whisstock et al, Prediction of protein function from protein sequence and structure. Q Rev Biophys. Aug. 2003;36(3):307-40. Review.*
GenEmbl database Acc No. AX056357 from Plowman et al, WO200073469 Dec. 7, 2000. Alignment with SEQ ID No. 13.*
Hanks SK, Quinn AM., Protein kinase catalytic domain sequence database: identification of conserved features of primary structure and classification of family members. Methods Enzymol. 1991;200:38-62.*
Iaccarino et al, Myocardial overexpression of GRK3 in transgenic mice: evidence for in vivo selectivity of GRKs. Am J Physiol. Oct. 1998;275(4 Pt 2):H1298-306.*
Peppel et al, G protein-coupled receptor kinase 3 (GRK3) gene disruption leads to loss of odorant receptor desensitization. J Biol Chem. Oct. 10, 1997;272(41):25425-8.*
U.S. Appl. No. 60/467,491, filed Apr. 30, 2003, Elliott et al.
U.S. Appl. No. 60/469,441, filed May 9, 2003, Becha et al.

(Continued)

*Primary Examiner* — Sheridan Swope
(74) *Attorney, Agent, or Firm* — Foley & Lardner LLP

(57) ABSTRACT

Various embodiments of the invention provide human kinases and phosphatases (KPP) polypeptides and polynucleotides which identify and encode KPP. Embodiments of the invention also provide expression vectors, host cells, antibodies, agonists, and antagonists. Other embodiments provide methods for diagnosing, treating, or preventing disorders associated with aberrant expression of KPP.

8 Claims, No Drawings

OTHER PUBLICATIONS

U.S. Appl. No. 60/476,408, filed Jun. 5, 2003, Yue et al.
U.S. Appl. No. 60/494,656, filed Aug. 12, 2003, Wilson et al.
U.S. Appl. No. 60/524,415, filed Nov. 20, 2003, Forsythe et al.
U.S. Appl. No. 60/528,750, filed Dec. 10, 2003, Chawla et al.
Adam, et al., "Identification of a Signal in a Murine Retrovirus That Is Sufficient for Packaging of Nonretroviral RNA into Virions," (1988) J. Viral. 62(10):3802-3806.
Altschul, S. F. et al. "Basic Local Alignment Search Tool," (1990) J. Mol. Biol. 215:403-410).
Anderson, N. L. and J. Seilhamer "A comparison of selected mRNA and protein abundances in human liver," (1997) Electrophoresis 18:533-537.
Antinozzi, P. A. et al. "Metrobolic Engineering With Recombinant Adenoviruses," (1999); Annu. Rev. Nutr. 19:511-544.
Armentano, D. et al. "Notes—Effect of Internal Viral Sequences on the Utility of Retroviral Vectors," (1987) J. Viral. 61(5):1647-1650.
Arndt, G. M. et al. "A rapid genetic screening system for identifying gene-specific suppression constructs for use in human cells," (2000) Nucleic Acids Res. 28(6):E15) or a human cell line such as HeLa cell, pp. i-viii.
Ashkenazi, A. and V. M. Divit "Apoptosis control by death and decoy receptors," (1999) Curr. Opin. Cell Biol. 11:255-260.
Bitter, G. A. et al. "[33] Expression and Secretion Vectors for Yeast," (1987) Methods Enzymol. 153:516-544.
Meyers, R. A. "Molecular Biology and Biotechnology—A Comprehensive Desk Reference," (1995) *Molecular Biology and Biotechnology*, Wiley V C H, New York N.Y., pp. 856-853.
Baltimore, D. "Gene Therapy—Intracellular immunization," (1988) Nature 335:395-396.
Bauer et al., "Inhibition of Human Immunodeficiency Virus-1 (HIV-1) Replication After Transduction of Granulocyte Colony-Stimulating Factor—Mobilized CD34+ Cells from HIV-1—Infected Donors Using Retroviral Vectors Containing Anti-HIV-1 Genes," *Blood*, (1997) vol. 89, No. 7, pp. 2259-2267.
Bender, M. A. et al. "Evidence that the Packaging Signal of Moloney Murine Leukemia Virus Extends into the *gag* Region," J. Virol. (1987) 61:1639-1646.
Blaese, R. M. et al. T Lymphocyte-Directed Gene Therapy for ADA-SCID: Initial Trial Results After 4 Years, Science (1995) 270:475-480.
Blind et al., "Cytoplasmic RNA Modulators of an Inside-out Signal-Transduction Cascade," *Proc. Natl. Acad. Sci.*, (1999) vol. 96, pp. 3606-3610.
Boado, R. J. et al. "Drug Delivery of Antisense Molecules to the Brain for Treatment of Alzheimer's Disease and Cerebral AIDS," J. Pharm. Sci. (1998) 87:1308-1315.
Bolton, A. E. and Hunter, W. M. "The Labelling of Proteins to High Specific Radioactivities by Conjugation to a $^{125}$I-Containing Acylating Agent," Biochem. J. (1973) 133:529-539.
Bonyhadi, M. L. "RevM10-Expressing T Cells Derived In Vivo from Transduced Human Hematopoietic Stem-Progenitor Cells Inhibit Human Immunodeficiency Virus Replication," J. Viral. (1997) 71(6):4707-4716.
Bordignon, C. et al. "Gene Therapy in Peripheral Blood Lymphocytes and Bone Marrow for ADA—Immunodeficient Patients," Science (1995) 270:470-475.
Boulay, J.-L. and Rezipon H. "Expression vectors and delivery systems Web alert," Curr. Opin. Biotechnol. (1998) 9:445-450.
Brody, E. N. and Gold L. "Review Article—Aptamers as therapeutic and diagnostic agents," J. Biotechnol. (2000) 74:5-13.
Brummelkamp, T. R. et al. "A System for Stable Expression of Short Interfering RNAs in Mammalian Cells," Science (2002) 296:550-553.
Buller, R. M. et al. "Decreased virulence of recombinant vaccinia virus expression vectors is associated with a thymidine kinase-negative phenotype," Nature (1985) 317:813-815.
Burge, C. and Karlin S. "Predication of Complete Gene Structures in Human Genomic DNA," J. Mol. Biol. (1997) 268:78-94.
Burge, C. and Karlin S. "Finding the genes in genomic DNA," Curr. Opin. Struct. Biol. (1998) 8:346-354.
Capecchi, M. R. "Altering the Genome by Homologous Recombination," Science (1989) 244:1288-1292.
Cavazzana-Calvo, M. et al. "Gene Therapy of Human Severe Combined Immunodeficiency (SCID)-X1 Disease," Science (2000) 288:669-672.
Chang, C.-C. et al. "Evolution of a cytokine using DNA family shuffling," Nat. Biotechnol. (1999) 17:793-797.
Charbonneau, H. and Tonics N. K. "1002 Protein Phosphatases?" Annu. Rev. Cell Biol. (1992) 8:463-493.
Chen, L. et al. "Overexpression of matrix Gla protein mRNA in malignant human breast cells: isolation by differential cDNA hybridization," Oncogene (1990) 5:1391-1395.
Christians, F. C. et al. "Directed evolution of thymidine kinase for AZT phosphorylation using DNA family shuffling," Nat. Biotechnol. (1999) 17:259-264.
Clarke, M. L. et al. "Comparative Analysis of Artificial Antisense RNA Regulation in Fission Yeast and Human Cells," Biochem. Biophys. Res. Commun. (2000) 268:8-13.
Colbere-Garapin, F. et al. "A New Dominant Hybrid Selective Marker for Higher Eukaryotic Cells," J. Mol. Biol. (1981) 150:1-14.
Crystal, R. G. "Transfer of Genes to Humans: Early Lessons and Obstacles to Success," Science (1995) 270:404-410.
Crystal, R. G. et al. "Clinical Protocol—A Phase 1 Study, in Cystic Fibrosis Patients, of the Safety Toxicity, and Biological Efficacy of a Single Administration of a Replication Deficient, Recombinant Adenovirus Carrying the cDNA of the Normal Cystic Fibrosis Transmembrane Conductance Regulator Gene in the Lung," Hum. Gene Therapy (1995) 6:643-666.
Crystal, R. G. et al. "Clinical Protocol—Evaluation of Repeat Administration of a Replication Deficient, Recombinant Adenovirus Containing the Normal Cystic Fibrosis Transmembrane Conductance Regulator cDNA to the Airways of Individuals with Cystic Fibrosis," Hum. Gene Therapy (1995) 6:667-703.
Csete, M. E. et al. "Efficient Gene Transfer to Pancreatic Islets Mediated by Adenoviral Vectors[1,2]," Transplantation (1995) 59(2):263-268.
Cunningham, B. C. And Wells J. A. "Rational design of receptor-specific variants of human growth hormone," Proc. Natl. Acad. Sci. USA (1991) 88:3407-3411.
Diamond, R. H. et al. "PRL-1, a Unique Nuclear Protein Tyrosine Phosphatase, Affects Cell Growth," Mol. Cell. Biol. (1994) 14(6):3752-62.
Dryga et al., "Identification of Mutations in a Sindbis Virus Variant Able to Establish Persistent Infection in BHK Cells: The Importance of a Mutation in the nsP2 Gene," *Virology*, (1997) vol. 228, pp. 74-83.
Dull et al., "A Third-Generation Lentivirus Vector with a Conditional Packaging System," *Journ. of Virology*, (1998) vol. 72, No. 11, pp. 8463-8471.
Eddy, S. R. "Hidden Markov models," Curr. Opin. Struct. Biol. (1996) 6:361-365.
Elbasbir, S. M. et al. "Duplexes of 21-nucleotide RNAs mediate RNA interference in cultured mammalian cells," Nature (2001) 411:494-498.
Huse, W. D. et al. "Generation of a Large Combinatorial Library of the Immunoglobulin Repertoire in Phage Lambda," Science (1989) 246:1275-1281.
Manda et al. "Identification of Genes (SPON2 and C20orf2) Differentially Expressed between Cancerous and Noncancerous Lung Cells by mRNA Differential Display," Genomics (1999) 51:5-14.
Mantovani, A. et al. "Decoy receptors: a strategy to regulate inflammatory cytokines and chemokines," Trends Immunol. (2001) 22(6):328-336.
Marshall, A. and Hodgson J. "DNA chips" An array of possibilities, Nat. Biotechnol. (1998) 16:27-31.
Marth, J. D. "Perspectives Series: Molecular Medicine in Genetically Engineered Animals—Recent Advances in Gene Mutagenesis by Site-directed Recombination," Clin. Invest. (1996) 97(9):1999-2002.
Matthews, D. J. and Wells J. A. "Engineering an interfacial zinc site to increase hormone-receptor affinity," Chem. Biol. (1994) 1:25-30.
McGregor, D. P. et al. "Spontaneous Assembly of Bivalent Single Chain Antibody Fragments in *Escherichia Coli*," Mol. Immunol. (1994) 31(3):219-226.
Miller, A. D. "Review Article—Progress Toward Human Gene Therapy," Blood (1990) 76(2):271-278.

Morgan, R. A. and Anderson W. F. "Human Gene Therapy[1]," Annu. Rev. Biochem. (1993) 62:191-217.
Morris, M. C. et al. "A new peptide vector for efficient delivery of oligonucleotides into mammalian cells," Nucleic Acids Res. (1997) 25(14):2730-2736.
Muyldermans, S. "Single domain camel antibodies: current status," J. Biotechnol. (2001) 74:277-302.
Neumann, E. et al. "Gene transfer into mouse lyoma cells by electroporation in high electric fields," EMBO J. (1982) 1:841-845.
Nowotny, P. et al. "SNP analysis to dissert human traits," Curr. Opin. Neurobiol. (2001) 11:637-641.
Nuwaysir, E. F. et al. "Microarrays and Toxicology: The Advent of Toxicogenomics," Mol. Carcinog. (1999) 24:153-159.
Orlandi, R. et al. "Cloning immunoglobulin variable domains for expression by the polymerase chain reaction,"Proc. Natl. Acad. Sci. USA (1989) 86:3833-3837.
Ormerod, M. G. "Flow Cytometry—A Practical Approach—Second Edition," Flow Cytometry Oxford, New York N.Y. (1994).
Paddison, P. J. et al. "Short hairpin RNAs (shRNAs) induce sequence-specific silencing in mammalian cells," Genes Dev. (2002) 16:948-958.
Parker, J. D. et al. "Targeted gene walking polymerase chain reaction," Nucleic Acids Res. (1991) 19(11 ):3055-3060.
Petersen et al. "Gene Expression Profiling of Advanced Lung Cancer," Int J. Cancer (2000) 86:512-517.
Poeschla, E. et al. "Development of HIV vectors for anti-HIV gene threapy," Proc. Natl. Acad. Sci. USA (1996) 93:11395-11399.
Pound, J. D. "Immunochemical Protocols—Second Edition," Immunochemical Protocols, Humana Press, Totowa N.J. (1998).
Price, C. M. "Fluorescence In Situ Hybridization," Blood Rev. (1993) 7:127-134.
Ranga, U. et al. "Cell and Viral Regulatory Elements Enhance the Expression and Function of a Human Immunodeficiency Virus Inhibitory Gene," J. Virol. (1997) 71:7020-7029.
Ranga, U. et al. "Enhanced T cell engraftment after retroviral delivery of an antiviral gene in HIV-infected individuals," Proc. Natl. Acad. Sci. USA (1998) 95:1201-1206.
Rao, V. B. "Review—Direct Sequencing of Polymerase Chain Reaction-Amplified DNA," Anal. Biochem. (1994) 216:1-14.
Riviere, I. et al. "Effects of retroviral vector design on expression of human adenosine deaminase in murine bone marrow transplant recipients engrafted with genetically modified cells," Proc. Natl. Acad. Sci. USA (1995) 92:6733-6737.
Rossi, F. M. V. and Blau H. M. "Recent advances in inducible gene expression systems," Curr. Opin. Biotechnol. (1998) 9:451-456.
Rossi, J. J. "Therapeutic antisense and ribozymes," Br. Med. Bull. (1995) 51(1):217-225.
Sambrook, J. And Russell D. W. "Molecular Cloning—A Laboratory Manual—Hybridization to Nitrocellulose Filters Containing Replicas of Bacterial Colonies," Molecular Cloning: A Laboratory Manual (2001) 3rd ed., vol. 1-3, Cold Spring Harbor Press, Cold Spring Harbor N.Y., ch. 9, pp. 1-66.
Sandig, V. et al. "Gene Transfer into Hepatocytes and Human Liver Tissue by Baculovirus Vectors," Hum. Gene Ther. (1996) 7:1937-1945.
Scanlon, K. J. et al. "Oligonucleotide-mediated modulation of mammalian gene expression[1],"FASEB J. (1995) 9:1288-1296.
Schena, M. et al. "Quantitative Monitoring of Gene Expression Patterns with a Complementary DNA Microarray," Science (1995) 270:467-470.
Schwarze, S. R. et al. "In Vivo Protein Transduction: Delivery of a Biologically Active Protein into the Mouse," Science (1999) 285:1569-1572.
Scorer, C. A. et al. "Rapid Selection Using G418 of High Copy Number Transformants of *Pichia pastoris* for High-level Foreign Gene Expression," Bio/Technology (1994) 12:181-184.
Shalon, D. et al. "A DNA Microarray System for Analyzing Complex DNA Samples Using Two-color Fluorescent Probe Hybridization," Genome Res. (1996) 6:639-645.
Su, L. "Hematopoietic Stem Cell-Based Gene Therapy for Acquired Immunodeficiency Syndrome: Efficient Transduction and Expression of RevM10 in Myeloid Cells In Vivo and In Vitro," Blood (1997) 89:2283-2290.
Takamatsu, N. "Expression of bacterial chloramphenicol acetyltransferase gene in tobacco plants mediated by TMV-RNA," EMBO J. (1987) 6:307-311.
Thomson, J. A. et al. "Embryonic Stem Cell Lines Derived from Human Blastocysts," Science (1998) 282:1145-1147.
Ulrix, W. et al. "The differentiation-related gene 1, *Drg1*, is markedly upregulated by androgens in LNCaP prostatic adenocarcinoma cells," FEBS Lett (1999) 455:23-26.
Verma, I. M. and Somia N. "Gene therapy—promises, problems and prospects," Nature (1997) 389:239-242.
Wagner, K. U. et al. "Cre-mediated gene deletion in the mammary gland," Nucleic Acids Res. (1997) 25:4323-4330.
Wahl, G. M. and Berger S. L. "[43] Molecular Hybridization of Immobilized Nucleic Acids: Theoretical Concepts and Practical Considerations," Methods Enzymol. (1987) 152:399-407.
Wang et al. "Identification of genes differentially over-expressed in lung squamous cell carcinoma using combination of cDNA subtraction and microarray analysis," Oncogene (2000) 19:1519-1528.
Way et al. "Comprehensive Messenger Ribonucleic Acid Profiling Reveals That Peroxisome Proliferator-Activated Receptor γ Activation Has Coordinate Effects on Gene Expression in Multiple Insulin-Sensitive Tissues," Endocrinology (2001) 142(3):1269-1277.
Weiss, G. A. and Lowman H. B. "Anticalins versus Antibodies: made-to-order binding proteins for small molecules," Chem. Biol. (2000) 7:R177-R184.
Wigler, M. et al. "Transfer of Purified Herpes Virus Thymidine Kinase Gene to Cultured Mouse Cells," Cell (1977) 11:223-232.
Winter, G. et al. "Review Article—Man-made antibodies," Nature (1991) 349:293-299.
Winter, J. et al. "6 The Expression of Heat Shock Protein and Cognate Genes During Plant Development," Results Probl. Cell Differ. (1991) 17:85-105.
Wistuba, I. I. et al. "Advances in Brief—Comparison of Features of Human Breast Cancer Cell Lines and Their Corresponding Tumors[1]," Clin. Cancer Res. (1998) 4:2931-2938.
Xu, H. et al. "Viral Transduction of *trkA* into Cultured Nodose and Spinal Motor Neurons Conveys NGF Responsiveness," Dev. Biol. (1994) 163:152-161.
Yu, M. et al. "A hairpin ribozyme inhibits expression of diverse strains of human immunodeficiency virus type 1," Proc. Natl. Acad. Sci. USA (1993) 90:6340-6344.
Zabner, J. et al. "Adenovirus-Mediated Gene Transfer Transiently Corrects the Chloride Transport Defect in Nasal Epithelia of Patients with Cystic Fibrosis," Cell (1993) 75:207-216.
Zufferey, R. et al. "Self-Inactivating Lentivirus Vector for Safe and Efficient In Vivo Gene Delivery," J. Virol. (1998) 72(12):9873-9880.
GenEmbl database Accession No. E03080 Shimotoono et al., Sep. 29, 1997 from JP 1991201994. Alignment SEQ ID No. 1.
Sigma, Inc., Biochemicals and Reagents for Life Science Research. Catalogue, 1997, p. 1159.
Christie et al., "The adaptation of BHK cells to a non-ammoniagenic glutamate-based culture medium," Biotechnol Bioeng, 1999, pp. 298-309, vol. 64, No. 3.
Galye et al., Identification of regions in interleukin-1 alpha important for activity, J Biol Chem., 1993, pp. 22105-22111, vol. 268, No. 29.
Whisstock et al., "Prediction of protein function from protein sequence and structure," Q Rev Biophys, 2003, pp. 307-340, vol. 36, No. 3. [Review].
Tang et al., "N_Geneseq_200812 database AC AAI558393 from WO 2001-53312," 2001, Alignment with SEQ ID No. 56.
Tang et al., "N_Geneseq_200812 database AC AAI558393 from WO 2001-53312," 2001, Alignment with SEQ ID No. 13.
Hanks, et al., "Protein kinase catalytic domain sequence database: identification of conserved features of primary structure and classification of family members," Methods Enzymol, 1991, pp. 38-62, vol. 200.
Iaccarino et al., "Myocardial overexpression of GRK3 in transgenic mice: evidence for in vivo selectivity of GRKs," Am J Physiol., 1998, pp. H1298-H1306, vol. 275 (4 Pt 2).
Peppel et al., "G protein-coupled receptor kinase 3 (GRK3) gene disruption leads to loss of odorant receptor desensitization," J Biol Chem., 1997, pp. 25425-25428, vol. 272, No. 41.

Baltimore, D., "Intracellular Immunization," (1988) *Nature* 335:395-396.

Broglie, R. et al., "Light-Regulated Expression of a Pea Ribulose-1,5-Bisphosphate Carboxylase Small Subunit Gene in Transformed Plant Cells," (1984) *Science*224:838-843.

Burton, D.R., "A large array of human monoclonal antibodies to type 1 human immunodeficiency virus from combinatorial libraries of asymptomatic seropositive individuals," (1991) *Proc. Natl. Acad. Sci. USA* 88:10134-10137.

Caruthers, M.H. et al., "New chemical methods for synthesizing polynucleotides," (1980) *Nucleic Acids Symp. Ser*. 7:215-223.

Chicz, R.M. and F.Z. Regnier, "High-Performance Liquid Chromatography: Effective Protein Purification by Various Chromatographic Modes," *Methods Enzymol*. 182:392-421.

Cole, S.P. et al., "Human monoclonal antibodies," (1984) *Mol. Cell Biol*. 62:109-120.

Coruzzi, G. et al., "Tissue-Specific and Light-Regulated Expression of a Pea Nuclear Gene Encoding the Small Subunit of rebulose-I,5-Bisphosphate Carboxylase," (1984) *EMBO J*. 3:1671-1680.

Cote, R.J. et al., "Generation of human monoclonal antibodies reactive with cellular antig," (1983) *Proc. Natl. Acad. Sci. USA* 80:2026-2030.

Creighton, T. (1984) *Proteins, Structures and Molecular Properties*, WH Freeman, New York N.Y., pp. 28-60.

Di Nicola et al., "Gene transfer into human dendritic antigen-presenting cells by vaccinia virus and adenovirus vectors," *Cancer Gene Therapy*, vol. 5, No. 6, pp. 350-356 (1998).

Duplaa, C. et al., "Quantitative analysis of polymerase chain reaction products using biotinylated dUTP incorporation," (1993) *Anal. Biochem*. 212:229-236.

Engelhard, E.K. et al., "The insect tracheal system: a conduit for the systemic spread of *Autographa californica* M nuclear polyhedrosis virus," (1994) *Proc. Natl. Acad. Sci. USA* 91:3224-3227.

Fields, S. and O. Song, "A Novel Genetic System to Detect Protein-Protein Interactions," (1989) *Nature* 340:245-246.

Heinz-Ulrich, et al., Fluorescent in situ hybridization (FISH) may be correlated with other physical and genetic map data (1995) in Meyers, *supra*, pp. 965-968.

Gatti, R.A. et al., "Localization of an Ataxia-Telangiectasia Gene to Chromosome," (1988) *Nature* 336:577-580.

Gee et al., "Potential Therapeutic Usefulness of Intermolecular Triplex DNA," *Mol. & Immuno. Approaches*, pp. 163-177 (1994).

Goins, W.F. et al., "Herpes Simplex Virus Type 1 Vector-Mediated Expression of Nerve Growth Factor Protects Dorsal Root Ganglion Neurons from Peroxide Toxicity," (1999). *J. Virol*. 73:519-532.

Goldman, C.K. et al., "In Vitro and In Vivo Gene Delivery Mediated by a Synthetic Polycationic Amino Polymer," (1997) *Nat. Biotechnol*. 15:462-466.

Gossen, M. and H. Bujard, "Tight control of gene expression in mammalian cells by tetracycline-responsive promoters," (1992) *Proc. Natl. Acad. Sci. USA* 89:5547-5551.

Gossen, M. et al., "Transcriptional Activation by Tetracyclines in Mammalian Cells," (1995) *Science* 268:1766-1769.

Graham, F.L. and A.J. Eb, "A New Technique for the Assay of Infectivity of Human Adenovirus 5 DNA," (1973) *Virology* 52:456-467.

Harrington, J.J. et al., "Formation of *De Novo* Centromere and Construction of First-Generation Human Artificial Microchromosomes," (1997) *Nat. Genet*. 15:345-355.

Harrington, M. G., "Elution of Protein from Gels," Methods Enzymol. 182:488-495 (1990).

Hartman, S.C. and R.C. Mulligan, "Two dominant-acting selectable markers for gene transfer studies in mammalian cells," (1988) *Proc. Natl. Acad. Sci. USA* 85:8047-8051.

Heller, R.A. et al., "Discovery and analysis of inflammatory disease-related genes using cDNA microarrays," (1997) *Proc. Natl. Acad. Sci. USA* 94:2150-2155.

Horn, T. et al., "Synthesis of oligonucleotides on cellulose. Part II: design and synthetic strategy to the synthesis of 22 oligodeoxynucleotides coding for Gastric Inhibitory Polypeptide (GIP)," (1980) *Nucleic Acids Symp. Ser*. 7:225-232.

Ivics, Z., "Molecular Reconstruction of *Sleeping Beauty*, a *Tc1*-like Transposon from Fish, and Its Transposition in Human Cells," (1997) *Cell* 91:501-510.

Janne, J. et al., "Transgenic bioreactors," (1998) Biotechnol. Annu. Rev. 4:55-74.

Kimmel, A.R., "Identification and Characterization of Specific Clones: Strategy for Confirming the Validity of Presumptive Clones," (1987) *Methods Enzymol*. 152:507-511.

Kohler, G. et al., "Continuous Cultures of Fused Cells Secreting Antibody of Predefined Specificity," (1975) *Nature* 256:495-497.

Kozbor, D. et al., "Specific Immunoglobulin Production and Enhanced Tumorigenicity Following Ascites Growth of Human Hybridomas," *J. Immunol. Methods* 81:31-42 (1985).

Lagerstrom, M. et al., "Capture PCR: efficient amplification of DNA fragments adjacent to a known sequence in human and YAC DNA," (1991) *PCR Methods Applic*. 1:111-119.

Lander, E.S. and D. Botstein, "Strategies for studying heterogeneous genetic traits in humans by using a linkage map of restriction fragment length polymorphisms," (1986) *Proc. Natl. Acad. Sci. USA* 83:7353-7357.

Liu, X. et al., Herpes Simplex Virus Mediated Gene Transfer to Primate Ocular Tissues, (1999) *Exp. Eye Res*. 169:385-395.

Logan, J. and T. Shenk, "Adenovirus tripartite leader sequence enhances translation of mRNAs late after infection," (1984) *Proc. Natl. Acad. Sci. USA* 81:3655-3659.

Lowy, I. et al., "Isolation of Tranforming DNA: Cloning the Hamster aprt Gene," (1980) *Cell* 22:817-823.

Melby, P.C. et al., "Quantitative Measurement of Human Cytokine Gene Expression by Polymerase Chain Reaction," (1993) *J. Immunol. Methods* 159:235-244.

Mendoza, L.G. et al., "High-throughput microarray-based enzyme-linked immunosorbent assay (ELISA)," (1999) *Biotechniques* 27:778-788.

Morrison, S.L. et al., "Chimeric human antibody molecules: mouse antigen-binding domains with human constant region domains," (1984) *Proc. Natl. Acad. Sci. USA* 81:6851-6855.

Neumann, E. et al., "Gene Transfer Into Mouse Lyoma Cells by Electroporation in High Electric Fields," (1982) *EMBO J*. 1:841-845.

Neuberger et al., "Recombinant antibodies possessing novel effector functions," *Nature*, vol. 312, pp. 604-608 (1984).

Rhodes, C.A., "Transformation of Maize by electroporation of Embryos," (1995) *Methods Mol. Biol*. 55:121-131.

Roberge, J.Y. et al., "A Strategy for a Convergent Synthesis of N-Linked Glycopeptides on a Solid Support ," (1995) *Science* 269:202-204.

Sarkar, G., "Restriction-Site PCR: A Direct Method of Unkown Sequence Retrieval Adjacent to a Known Locus by Using Universal Primers," *PCR Methods Applic* 2:318-322.

Scharf, D. et al., "Heat Stress Promoters and Transcription Factors," (1994) *Results Probl. Cell Differ*. 20:125-162.

Schena, M. et al., Parallel human genome analysis: Microarray-based expression monitoring of 1000 genes, *Proc. Natl. Acad. Sci. USA* 93:10614-10619 (1996).

Su, L., "Hematopoietic Stem Cell-Based Gene Therapy for Acquired Immunodeficiency Syndrome: Efficient Transduction and Expression of RevM10 in Myeloid Cells In Vivo and In Vitro," (1997) *Blood* 89:2283-2290.

Takeda, S. et al., "Construction of Chimaeric Processed Immunoglobulin Genes Containing Mouse Variable and Human Constant Region Sequences," (1985) *Nature* 314:452-454.

Hobbs, *The McGraw Hill Yearbook of Science and Technology* (1992) McGraw Hill, New York N.Y., pp. 191-196.

Trask, B.J., "Fluorescence in situ Hybridization," (1991) *Trends Genet*. 7:149-154.

Triglia, T. et al., "A procedure for in vitro amplification of DNA segments that lie outside the boundaries of known sequences," (1988) *Nucleic Acids Res*. 16:8186.

Van Heeke, G. and S.M. Schuster, "Expression of Human Synthetase in *Escherichia coli*," (1989) *J. Biol. Chem*. 264:5503-5509.

Adams, M. et al., "Activators of peroxisome proliferator-activated receptor gamma have depot-specific effects on human preadipocyte differentiation," (1997) *J. Clin. Invest*. 100:3149-3153.

Auwerx, J., "PPARγ, The Ultimate Thrifty Gene," (1999) *Diabetologia* 42:1033-1049.
Ausubel, F.M., et al. Short Protocols in Molecular Biology, $4^{th}$ Ed., pp. 6.3.1-7.3.6 and 2.10.3 (1999).
Barroso, I. et al., "Dominant negative mutations in human PPAR$^{\gamma}$ associated with severe insulin resistance, diabetes mellitus and hypertension," (1999) *Nature* 402:880-883.
Broglie, R. et al., "Light-Regulated Expression of a Pea Ribulose-1,5-Bisphosphate Carboxylase Small Subunit Gene in Transformed Plant Cells," (1984) *Science* 224:838-843.
Crameri, A. et al., "Improved Green Fluorescent Protein by Molecular Evoluation Using DNA Shuffling," (1996) *Nat. Biotechnol.* 14:315-319.
Fire, A. et al., "Potent and specific genetic interference by double-stranded RNA in *Caenorhabditis elegans*," (1998) *Nature* 391:806-811.
Garoff, H. and K.-J. Li, "Recent advances in gene expression using aiphavirus vectors," (1998) *Curr. Opin. Biotechnol.* 9:464-469.
Gregoire, F.M. et al., "Understanding Adipocyte Differentiation," (1998) *Physiol. Reviews* 78:783-809.
Gura, T., "A silence that speaks volumes," (2000) *Nature* 404:804-808.
Haft, D.H. et al., "TIGRFAMs: a protein family resource for the functional identification of proteins," (2001) *Nucleic Acids Res.* 29:41-43.
Howard, A.D. et al., "Orphan G-Protein-Coupled Receptors and Natural Ligand Discovery," (2001) *Trends Pharmacol. Sci.* 22:132-140.
Khazaie, K. et al., "EGF Receptor in Neoplasia and Metastasis," (1993) *Cancer and Metastasis Rev.* 12:255-274.
Kwok, P.-Y. and Z. Gu, "Single Nucleotide Polymorphism Libraries: Why and How Are We Building Them?" (1999) *Mol. Med. Today* 5:538-543.
Lee, S.W. et al. (1992), "Down-regulation of a member of the S100 gene family in mammary carcinoma cells and reexpression by azadeoxycytidine treatment," *Proc. Natl. Acad. Sci. USA* 89:2504-2508.
Letunic, I. et al., "Recent improvements to the SMART domain-based sequence annotation resource," (2002) *Nucleic Acids Res.* 30:242-244.
Lois, C. et al., "Germline Transmission and Tissue-Specific Expression of Transgenes Delivered by Lentiviral Vectors," (2002) *Science* 295:868-872.
Lowman, H.B. et al., "Mutational Analysis and Protein Engineering of Receptor-Binding Determinants in Human Placental Lactogen," (1991) *J. Biol. Chem.* 266:10982-10988.
Lueking, A. et al., "Protein Microarrays for Gene Expression and Antibody Screening," (1999) *Anal. Biochem.* 270:103-111.
Perou, C.M. et al., "Molecular portraits of human breast tumours," (2000) *Nature* 406:747-752.
Sager, R. et al., "Maspin: A Tumor Suppressing Serpin," (1996) *Curr. Top. Microbiol. Immunol.* 213:51-64
Schultz, J. et al., "SMART, a simple modular architecture research tool: Identification of signaling domains," (1998) *Proc. Natl. Acad. Sci. USA* 95:5857-5864.
Skerra, A., "'Anticalins': A New Class of Engineered Ligand-Binding Proteins With Antibody-Like Properties," (2001) *J. Biotechnol.* 74:257-275.
Slater, J.E. et al., "Environmental and Occupational Disorders," (1998) *J. Allergy Clin. Immunol.* 102:469-475.
Steiner, S. and N.L. Anderson, "Expression Profiling in Toxicology—Potentials and Limitations," (2000) *Toxicol. Lett.* 112-113:467-471.
Suzuki, A. et al., "Alteration in Expression Profiles of a Series of Diabetes-Related Genes in *db/db* Mice Following Treatment With Thiazolidinediones," (2000) *Jpn. J. Pharmacol.* 84:113-123.
Taylor, J.G. et al., "Deconstructing Type 2 Diabetes," (2001) *Trends Mol. Med.* 7:507-512.
Taylor, P.C. et al., "Immunotherapy for Rheumatoid Arthritis," (2001) *Curr. Opin. Immunol.* 13:611-616.
Taylor, S.I., "Using Genetic Variation to Study Human Disease," (1999) *Cell* 97:9-12.
Uckert, W. and W. Walther, "Retrovirus-Mediated Gene Transfer in Cancer Therapy," (1994) *Pharmacol. Ther.* 63:323-347.
Wigler, M. et al., "Transformation of mammalian cells with an amplifiable dominant-acting gene," (1980) *Proc. Natl. Acad. Sci. USA* 77:3567-3570
Wise, A. et al., "Target Validation of G-Protein Coupled Receptors," (2002) *Drub Discovery Today* 7:235-246.
Zhou, Z. et al., "Up-Regulation of Human Secreted Frizzled Homolog in Apoptosis and its Down-Regulation in Breat Tumors," (1998) *Int. J. Cancer* 78:95-99.

* cited by examiner

HUMAN β-ADRENERGIC RECEPTOR KINASE POLYPEPTIDE AND METHODS

CROSS-REFERENCE TO RELATED APPLICATIONS

This application is a divisional of U.S. patent application Ser. No. 10/554,917, filed Apr. 27, 2007, now U.S. Pat. No. 7,829,682, which is the National Phase of PCT/US2004/09215, filed Mar. 24, 2004, and published as WO 2004/098539, which claims priority under 35 U.S.C. §119(e) from U.S. Provisional Patent Application Nos. 60/528,750, filed Dec. 10, 2003, 60/524,415, filed Nov. 20, 2003, 60/494,656, filed Aug. 12, 2003, 60/476,408, filed Jun. 5, 2003, 60/469,441, filed May 9, 2003, 60/467,491, filed Apr. 30, 2003. The contents of these applications are incorporated herein by reference in their entirety.

TECHNICAL FIELD

The invention relates to novel nucleic acids, kinases and phosphatases encoded by these nucleic acids, and to the use of these nucleic acids and proteins in the diagnosis, treatment, and prevention of cardiovascular diseases, immune system disorders, neurological disorders, disorders affecting growth and development, lipid disorders, cell proliferative disorders, and cancers. The invention also relates to the assessment of the effects of exogenous compounds on the expression of nucleic acids and kinases and phosphatases.

BACKGROUND OF THE INVENTION

Reversible protein phosphorylation is the ubiquitous strategy used to control many of the intracellular events in eukaryotic cells. It is estimated that more than ten percent of proteins active in a typical mammalian cell are phosphorylated. Kinases catalyze the transfer of high-energy phosphate groups from adenosine triphosphate (ATP) to target proteins on the hydroxyamino acid residues serine, threonine, or tyrosine. Phosphatases, in contrast, remove these phosphate groups. Extracellular signals including hormones; neurotransmitters, and growth and differentiation factors can activate kinases, which can occur as cell surface receptors or as the activator of the final effector protein, as well as other locations along the signal transduction pathway. Cascades of kinases occur, as well as kinases sensitive to second messenger molecules. This system allows for the amplification of weak signals (low abundance growth factor molecules, for example), as well as the synthesis of many weak signals into an all-or-nothing response. Phosphatases, then, are essential in determining the extent of phosphorylation in the cell and, together with kinases, regulate key cellular processes such as metabolic enzyme activity, proliferation, cell growth and differentiation, cell adhesion, and cell cycle progression.

Kinases

Kinases comprise the largest known enzyme superfamily and vary widely in their target molecules. Kinases catalyze the transfer of high energy phosphate groups from a phosphate donor to a phosphate acceptor. Nucleotides usually serve as the phosphate donor in these reactions, with most kinases utilizing adenosine triphosphate (ATP). The phosphate acceptor can be any of a variety of molecules, including nucleosides, nucleotides, lipids, carbohydrates, and proteins. Proteins are phosphorylated on hydroxyamino acids. Addition of a phosphate group alters the local charge on the acceptor molecule, causing internal conformational changes and potentially influencing intermolecular contacts. Reversible protein phosphorylation is the primary method for regulating protein activity in eukaryotic cells. In general, proteins are activated by phosphorylation in response to extracellular signals such as hormones, neurotransmitters, and growth and differentiation factors. The activated proteins initiate the cell's intracellular response by way of intracellular signaling pathways and second messenger molecules such as cyclic nucleotides, calcium-calmodulin, inositol, and various mitogens, that regulate protein phosphorylation.

Kinases are involved in all aspects of a cell's function, from basic metabolic processes, such as glycolysis, to cell-cycle regulation, differentiation, and communication with the extracellular environment through signal transduction cascades. Inappropriate phosphorylation of proteins in cells has been linked to changes in cell cycle progression and cell differentiation. Changes in the cell cycle have been linked to induction of apoptosis or cancer. Changes in cell differentiation have been linked to diseases and disorders of the reproductive system, immune system, and skeletal muscle.

There are two classes of protein kinases. One class, protein tyrosine kinases (PTKs), phosphorylates tyrosine residues, and the other class, protein serine/threonine kinases (STKs), phosphorylates serine and threonine residues. Some PTKs and STKs possess structural characteristics of both families and have dual specificity for both tyrosine and serine/threonine residues. Almost all kinases contain a conserved 250-300 amino acid catalytic domain containing specific residues and sequence motifs characteristic of the kinase family. The protein kinase catalytic domain can be further divided into 11 subdomains. N-terminal subdomains I-IV fold into a two-lobed structure which binds and orients the ATP donor molecule, and subdomain V spans the two lobes. C-terminal subdomains VI-XI bind the protein substrate and transfer the gamma phosphate from ATP to the hydroxyl group of a tyrosine, serine, or threonine residue. Each of the 11 subdomains contains specific catalytic residues or amino acid motifs characteristic of that subdomain. For example, subdomain I contains an 8-amino acid glycine-rich ATP binding consensus motif, subdomain II contains a critical lysine residue required for maximal catalytic activity, and subdomains VI through IX comprise the highly conserved catalytic core. PTKs and STKs also contain distinct sequence motifs in subdomains VI and VIII which may confer hydroxyamino acid specificity.

In addition, kinases may also be classified by additional amino acid sequences, generally between 5 and 100 residues, which either flank or occur within the kinase domain. These additional amino acid sequences regulate kinase activity and determine substrate specificity. (Reviewed in Hardie, G. and S. Hanks (1995) *The Protein Kinase Facts Book*, Vol I, pp. 17-20 Academic Press, San Diego Calif.). In particular, two protein kinase signature sequences have been identified in the kinase domain, the first containing an active site lysine residue involved in ATP binding, and the second containing an aspartate residue important for catalytic activity. If a protein analyzed includes the two protein kinase signatures, the probability of that protein being a protein kinase is close to 100% (PROSITE: PDOC0100, November 1995).

Protein Tyrosine Kinases

Protein tyrosine kinases (PTKs) may be classified as either transmembrane, receptor PTKs or nontransmembrane, non-receptor PTK proteins. Transmembrane tyrosine kinases function as receptors for most growth factors. Growth factors bind to the receptor tyrosine kinase (RTK), which causes the receptor to phosphorylate itself (autophosphorylation) and specific intracellular second messenger proteins. Growth factors (GF) that associate with receptor PTKs include epidermal GF, platelet-derived GF, fibroblast GF, hepatocyte GF, insulin and insulin-like GFs, nerve GF, vascular endothelial GF, and macrophage colony stimulating factor.

Nontransmembrane, nonreceptor PTKs lack transmembrane regions and, instead, form signaling complexes with the cytosolic domains of plasma membrane receptors. Receptors that function through non-receptor PTKs include those for cytokines and hormones (growth hormone and prolactin), and antigen-specific receptors on T and B lymphocytes.

Many PTKs were first identified as oncogene products in cancer cells in which PTK activation was no longer subject to normal cellular controls. In fact, about one third of the known oncogenes encode PTKs. Furthermore, cellular transformation (oncogenesis) is often accompanied by increased tyrosine phosphorylation activity (Charbonneau, H. and N. K. Tonics (1992) Annu. Rev. Cell Biol. 8:463-493). Regulation of PTK activity may therefore be an important strategy in controlling some types of cancer.

Protein Serine/Threonine Kinases

Protein serine/threonine kinases (STKs) are nontransmembrane proteins. A subclass of STKs are known as ERKs (extracellular signal regulated kinases) or MAPs (mitogen-activated protein kinases) and are activated after cell stimulation by a variety of hormones and growth factors. Cell stimulation induces a signaling cascade leading to phosphorylation of MEK (MAP/ERK kinase) which, in turn, activates ERK via serine and threonine phosphorylation. A varied number of proteins represent the downstream effectors for the active ERK and implicate it in the control of cell proliferation and differentiation, as well as regulation of the cytoskeleton. Activation of ERK is normally transient, and cells possess dual specificity phosphatases that are responsible for its downregulation. Also, numerous studies have shown that elevated ERK activity is associated with some cancers. Other STKs include the second messenger dependent protein kinases such as the cyclic-AMP dependent protein kinases (PKA), calcium-calmodulin (CaM) dependent protein kinases, and the mitogen-activated protein kinases (MAP); the cyclin-dependent protein kinases; checkpoint and cell cycle kinases; Numb-associated kinase (Nak); human Fused (hFu); proliferation-related kinases; 5'-AMP-activated protein kinases; and kinases involved in apoptosis.

One member of the ERK family of MAP kinases, ERK 7, is a novel 61-kDa protein that has motif similarities to ERK1 and ERK2, but is not activated by extracellular stimuli as are ERK1 and ERK2 nor by the common activators, c-Jun N-terminal kinase (JNK) and p38 kinase. ERK7 regulates its nuclear localization and inhibition of growth through its C-terminal tail, not through the kinase domain as is typical with other MAP kinases (Abe, M. K. (1999) Mol. Cell. Biol. 19:1301-1312).

The second messenger dependent protein kinases primarily mediate the effects of second messengers such as cyclic AMP (cAMP), cyclic GMP, inositol triphosphate, phosphatidylinositol, 3,4,5-triphosphate, cyclic ADP ribose, arachidonic acid, diacylglycerol and calcium-calmodulin. The PKAs are involved in mediating hormone-induced cellular responses and are activated by cAMP produced within the cell in response to hormone stimulation. cAMP is an intracellular mediator of hormone action in all animal cells that have been studied. Hormone-induced cellular responses include thyroid hormone secretion, cortisol secretion, progesterone secretion, glycogen breakdown, bone resorption, and regulation of heart rate and force of heart muscle contraction. PKA is found in all animal cells and is thought to account for the effects of cAMP in most of these cells. Altered PKA expression is implicated in a variety of disorders and diseases including cancer, thyroid disorders, diabetes, atherosclerosis, and cardiovascular disease (Isselbacher, K. J. et al. (1994) *Harrison's Principles of Internal Medicine*, McGraw-Hill, New York N.Y., pp. 416-431, 1887).

The casein kinase I (CKI) gene family is another subfamily of serine/threonine protein kinases. This continuously expanding group of kinases have been implicated in the regulation of numerous cytoplasmic and nuclear processes, including cell metabolism and DNA replication and repair. CKI enzymes are present in the membranes, nucleus, cytoplasm and cytoskeleton of eukaryotic cells, and on the mitotic spindles of mammalian cells (Fish, K. J. et al. (1995) J. Biol. Chem. 270:14875-14883).

The CKI family members all have a short amino-terminal domain of 9-76 amino acids, a highly conserved kinase domain of 284 amino acids, and a variable carboxyl-terminal domain that ranges from 24 to over 200 amino acids in length (Cegielska, A. et al. (1998) J. Biol. Chem. 273:1357-1364). The CKI family is comprised of highly related proteins, as seen by the identification of isoforms of casein kinase I from a variety of sources. There are at least five mammalian isoforms, $\alpha$, $\beta$, $\gamma$, $\delta$, and $\epsilon$. Fish et al. identified CKI-epsilon from a human placenta cDNA library. It is a basic protein of 416 amino acids and is closest to CKI-delta. Through recombinant expression, it was determined to phosphorylate known CKI substrates and was inhibited by the CKI-specific inhibitor CKI-7. The human gene for CKI-epsilon was able to rescue yeast with a slow-growth phenotype caused by deletion of the yeast CKI locus, HRR250 (Fish et al., supra).

The mammalian circadian mutation tau was found to be a semidominant autosomal allele of CKI-epsilon that markedly shortens period length of circadian rhythms in Syrian hamsters. The tau locus is encoded by casein kinase I-epsilon, which is also a homolog of the *Drosophila* circadian gene double-time. Studies of both the wildtype and tau mutant CKI-epsilon enzyme indicated that the mutant enzyme has a noticeable reduction in the maximum velocity and autophosphorylation state. Further, in vitro, CKI-epsilon is able to interact with mammalian PERIOD proteins, while the mutant enzyme is deficient in its ability to phosphorylate PERIOD. Lowrey et al. have proposed that CKI-epsilon plays a major role in delaying the negative feedback signal within the transcription-translation-based autoregulatory loop that composes the core of the circadian mechanism. Therefore the CKI-epsilon enzyme is an ideal target for pharmaceutical compounds influencing circadian rhythms, jet-lag and sleep, in addition to other physiologic and metabolic processes under circadian regulation (Lowrey, P. L. et al. (2000) Science 288:483-491).

Homeodomain-interacting protein kinases (HIPKs) are serine/threonine kinases and novel members of the DYRK kinase subfamily (Hofmann, T. G. et al. (2000) Biochimie 82:1123-1127). HIPKs contain a conserved protein kinase domain separated from a domain that interacts with homeoproteins. HIPKs are nuclear kinases, and HIPK2 is highly expressed in neuronal tissue (Kim, Y. H. et al. (1998) J. Biol. Chem. 273:25875-25879; Wang, Y. et al. (2001) Biochim. Biophys. Acta 1518:168-172). HIPKs act as corepressors for homeodomian transcription factors. This corepressor activity is seen in posttranslational modifications such as ubiquitination and phosphorylation, each of which are important in the regulation of cellular protein function (Kim, Y. H. et al. (1999) Proc. Natl. Acad. Sci. USA 96:12350-12355).

The human h-warts protein, a homolog of *Drosophila* warts tumor suppressor gene, maps to chromosome 6q24-25.1. It has a serine/threonine kinase domain and is localized to centrosomes in interphase cells. It is involved in mitosis and functions as a component of the mitotic apparatus (Nishiyama, Y. et al. (1999) FEBS Lett. 459:159-165).

Calcium-Calmodulin Dependent Protein Kinases

Calcium-calmodulin dependent (CaM) kinases are involved in regulation of smooth muscle contraction, glycogen breakdown (phosphorylase kinase), and neurotransmission (CaM kinase I and CaM kinase II). CaM dependent protein kinases are activated by calmodulin, an intracellular calcium receptor, in response to the concentration of free calcium in the cell. Many CaM kinases are also activated by phosphorylation. Some CaM kinases are also activated by autophosphorylation or by other regulatory kinases. CaM kinase I phosphorylates a variety of substrates including the neurotransmitter-related proteins synapsin I and II, the gene transcription regulator, CREB, and the cystic fibrosis conductance regulator protein, CFTR (Haribabu, B. et al. (1995) EMBO J. 14:3679-3686). CaM kinase II also phosphorylates synapsin at different sites and controls the synthesis of catecholamines in the brain through phosphorylation and activation of tyrosine hydroxylase. CaM kinase II controls the synthesis of catecholamines and seratonin, through phosphorylation/activation of tyrosine hydroxylase and tryptophan hydroxylase, respectively (Fujisawa, H. (1990) BioEssays 12:27-29). The mRNA encoding a calmodulin-binding protein kinase-like protein was found to be enriched in mammalian forebrain. This protein is associated with vesicles in both axons and dendrites and accumulates largely postnatally. The amino acid sequence of this protein is similar to CaM-dependent STKs, and the protein binds calmodulin in the presence of calcium (Godbout, M. et al. (1994) J. Neurosci. 14:1-13).

Mitogen-Activated Protein Kinases

The mitogen-activated protein kinases (MAP), which mediate signal transduction from the cell surface to the nucleus via phosphorylation cascades, are another STK family that regulates intracellular signaling pathways. Several subgroups have been identified, and each manifests different substrate specificities and responds to distinct extracellular stimuli (Egan, S. E. and R. A. Weinberg (1993) Nature 365:781-783). There are three kinase modules comprising the MAP kinase cascade: MAPK (MAP), MAPK kinase (MAP2K, MAPKK, or MKK), and MKK kinase (MAP3K, MAPKKK, OR MEKK) (Wang, X. S. et al (1998) Biochem. Biophys. Res. Commun. 253:33-37). The extracellular-regulated kinase (ERK) pathway is activated by growth factors and mitogens, for example, epidermal growth factor (EGF), ultraviolet light, hyperosmolar medium, heat shock, or endotoxic lipopolysaccharide (LPS). The closely related though distinct parallel pathways, the c-Jun N-terminal kinase (JNK), or stress-activated kinase (SAPK) pathway, and the p38 kinase pathway are activated by stress stimuli and proinflammatory cytokines such as tumor necrosis factor (TNF) and interleukin-1 (IL-1). Altered MAP kinase expression is implicated in a variety of disease conditions including cancer, inflammation, immune disorders, and disorders affecting growth and development. MAP kinase signaling pathways are present in mammalian cells as well as in yeast.

Cyclin-Dependent Protein Kinases

The cyclin-dependent protein kinases (CDKs) are STKs that control the progression of cells through the cell cycle. The entry and exit of a cell from mitosis are regulated by the synthesis and destruction of a family of activating proteins called cyclins. Cyclins are small regulatory proteins that bind to and activate CDKs, which then phosphorylate and activate selected proteins involved in the mitotic process. CDKs are unique in that they require multiple inputs to become activated. In addition to cyclin binding, CDK activation requires the phosphorylation of a specific threonine residue and the dephosphorylation of a specific tyrosine residue on the CDK.

Another family of STKs associated with the cell cycle are the NIMA (never in mitosis)-related kinases (Neks). Both CDKs and Neks are involved in duplication, maturation, and separation of the microtubule organizing center, the centrosome, in animal cells (Fry, A. M. et al. (1998) EMBO J. 17:470-481).

Checkpoint and Cell Cycle Kinases

In the process of cell division, the order and timing of cell cycle transitions are under control of cell cycle checkpoints, which ensure that critical events such as DNA replication and chromosome segregation are carried out with precision. If DNA is damaged, e.g. by radiation, a checkpoint pathway is activated that arrests the cell cycle to provide time for repair. If the damage is extensive, apoptosis is induced. In the absence of such checkpoints, the damaged DNA is inherited by aberrant cells which may cause proliferative disorders such as cancer. Protein kinases play an important role in this process. For example, a specific kinase, checkpoint kinase 1 (Chk1), has been identified in yeast and mammals, and is activated by DNA damage in yeast. Activation of Chk1 leads to the arrest of the cell at the G2/M transition (Sanchez, Y. et al. (1997) Science 277:1497-1501). Specifically, Chk1 phosphorylates the cell division cycle phosphatase CDC25, inhibiting its normal function which is to dephosphorylate and activate the cyclin-dependent kinase Cdc2. Cdc2 activation controls the entry of cells into mitosis (Peng, C.-Y. et al. (1997) Science 277:1501-1505). Thus, activation of Chk1 prevents the damaged cell from entering mitosis. A deficiency in a checkpoint kinase, such as Chk1, may also contribute to cancer by failure to arrest cells with damaged DNA at other checkpoints such as G2/M.

Proliferation-Related Kinases

Proliferation-related kinase is a serum/cytokine inducible STK that is involved in regulation of the cell cycle and cell proliferation in human megakarocytic cells (Li, B. et al. (1996) J. Biol. Chem. 271:19402-19408). Proliferation-related kinase is related to the polo (derived from *Drosophila* polo gene) family of STKs implicated in cell division. Proliferation-related kinase is downregulated in lung tumor tissue and may be a proto-oncogene whose deregulated expression in normal tissue leads to oncogenic transformation.

5'-AMP-Activated Protein Kinase

A ligand-activated STK protein kinase is 5'-AMP-activated protein kinase (AMPK) (Gao, G. et al. (1996) J. Biol. Chem. 271:8675-8681). Mammalian AMPK is a regulator of fatty acid and sterol synthesis through phosphorylation of the enzymes acetyl-CoA carboxylase and hydroxymethylglutaryl-CoA reductase and mediates responses of these pathways to cellular stresses such as heat shock and depletion of glucose and ATP. AMPK is a heterotrimeric complex comprised of a catalytic alpha subunit and two non-catalytic beta and gamma subunits that are believed to regulate the activity of the alpha subunit. Subunits of AMPK have a much wider distribution in non-lipogenic tissues such as brain, heart, spleen, and lung than expected. This distribution suggests that its role may extend beyond regulation of lipid metabolism alone.

Kinases in Apoptosis

Apoptosis is a highly regulated signaling pathway leading to cell death that plays a crucial role in tissue development and homeostasis. Deregulation of this process is associated with the pathogenesis of a number of diseases including autoimmune diseases, neurodegenerative disorders, and cancer. Various STKs play key roles in this process. ZIP kinase is an STK containing a C-terminal leucine zipper domain in addition to its N-terminal protein kinase domain. This C-terminal domain appears to mediate homodimerization and activation of the kinase as well as interactions with transcription factors such as activating transcription factor, ATF4, a member of the cyclic-AMP responsive element binding protein (ATF/CREB) family of transcriptional factors (Sanjo, H. et al. (1998) J. Biol. Chem. 273:29066-29071). DRAK1 and DRAK2 are STKs that share homology with the death-associated protein kinases (DAP kinases), known to function in interferon-.gamma. induced apoptosis (Sanjo et al., supra). Like ZIP kinase, DAP kinases contain a C-terminal protein-protein interaction domain, in the form of ankyrin repeats, in addition to the N-terminal kinase domain. ZIP, DAP, and DRAK kinases induce morphological changes associated with apoptosis when transfected into NIH3T3 cells (Sanjo et al., supra). However, deletion of either the N-terminal kinase catalytic domain or the C-terminal domain of these proteins abolishes apoptosis activity, indicating that in addition to the kinase activity, activity in the C-terminal domain is also necessary for apoptosis, possibly as an interacting domain with a regulator or a specific substrate.

RICK is another STK recently identified as mediating a specific apoptotic pathway involving the death receptor, CD95 (Inohara, N. et al. (1998) J. Biol. Chem. 273:12296-12300). CD95 is a member of the tumor necrosis factor receptor superfamily and plays a critical role in the regulation and homeostasis of the immune system (Nagata, S. (1997) Cell 88:355-365). The CD95 receptor signaling pathway involves recruitment of various intracellular molecules to a receptor complex following ligand binding. This process includes recruitment of the cysteine protease caspase-8 which, in turn, activates a caspase cascade leading to cell death. RICK is composed of an N-terminal kinase catalytic domain and a C-terminal "caspase-recruitment" domain that interacts with caspase-like domains, indicating that RICK plays a role in the recruitment of caspase-8. This interpretation is supported by the fact that the expression of RICK in human 293T cells promotes activation of caspase-8 and potentiates the induction of apoptosis by various proteins involved in the CD95 apoptosis pathway (Inohara et al., supra).

Mitochondrial Protein Kinases

A novel class of eukaryotic kinases, related by sequence to prokaryotic histidine protein kinases, are the mitochondrial protein kinases (MPKs) which seem to have no sequence similarity with other eukaryotic protein kinases. These protein kinases are located exclusively in the mitochondrial matrix space and may have evolved from genes originally present in respiration-dependent bacteria which were endocytosed by primitive eukaryotic cells. MPKs are responsible for phosphorylation and inactivation of the branched-chain alpha-ketoacid dehydrogenase and pyruvate dehydrogenase complexes (Harris, R. A. et al. (1995) Adv. Enzyme Regul. 34:147-162). Five MPKs have been identified. Four members correspond to pyruvate dehydrogenase kinase isozymes, regulating the activity of the pyruvate dehydrogenase complex, which is an important regulatory enzyme at the interface between glycolysis and the citric acid cycle. The fifth member corresponds to a branched-chain alpha-ketoacid dehydrogenase kinase, important in the regulation of the pathway for the disposal of branched-chain amino acids. (Harris, R. A. et al. (1997) Adv. Enzyme Regul. 37:271-293). Both starvation and the diabetic state are known to result in a great increase in the activity of the pyruvate dehydrogenase kinase in the liver, heart and muscle of the rat. This increase contributes in both disease states to the phosphorylation and inactivation of the pyruvate dehydrogenase complex and conservation of pyruvate and lactate for gluconeogenesis (Harris (1995) supra).

Kinases with Non-Protein Substrates

Lipid and Inositol Kinases

Lipid kinases phosphorylate hydroxyl residues on lipid head groups. A family of kinases involved in phosphorylation of phosphatidylinositol (PI) has been described, each member phosphorylating a specific carbon on the inositol ring (Leevers, S. J. et al. (1999) Curr. Opin. Cell. Biol. 11:219-225). The phosphorylation of phosphatidylinositol is involved in activation of the protein kinase C signaling pathway. The inositol phospholipids (phosphoinositides) intracellular signaling pathway begins with binding of a signaling molecule to a G-protein linked receptor in the plasma membrane. This leads to the phosphorylation of phosphatidylinositol (PI) residues on the inner side of the plasma membrane by inositol kinases, thus converting PI residues to the biphosphate state ($PIP_2$). $PIP_2$ is then cleaved into inositol triphosphate ($IP_3$) and diacylglycerol. These two products act as mediators for separate signaling pathways. Cellular responses that are mediated by these pathways are glycogen breakdown in the liver in response to vasopressin, smooth muscle contraction in response to acetylcholine, and thrombin-induced platelet aggregation.

PI 3-kinase (PI3K), which phosphorylates the D3 position of PI and its derivatives, has a central role in growth factor signal cascades involved in cell growth, differentiation, and metabolism. PI3K is a heterodimer consisting of an adapter subunit and a catalytic subunit. The adapter subunit acts as a scaffolding protein, interacting with specific tyrosine-phosphorylated proteins, lipid moieties, and other cytosolic factors. When the adapter subunit binds tyrosine phosphorylated targets, such as the insulin responsive substrate (IRS)-1, the catalytic subunit is activated and converts PI (4,5) bisphosphate ($PIP_2$) to PI (3,4,5) $P_3$ ($PIP_3$). $PIP_3$ then activates a number of other proteins, including PKA, protein kinase B (PKB), protein kinase C (PKC), glycogen synthase kinase (GSK)-3, and p70 ribosomal s6 kinase. PI3K also interacts directly with the cytoskeletal organizing proteins, Rac, rho, and cdc42 (Shepherd, P. R. et al (1998) Biochem. J. 333:471-490) Animal models for diabetes, such as obese and fat mice, have altered PI3K adapter subunit levels. Specific mutations in the adapter subunit have also been found in an insulin-resistant Danish population, suggesting a role for PI3K in type-2 diabetes (Shepard, supra).

An example of lipid kinase phosphorylation activity is the phosphorylation of D-erythro-sphingosine to the sphingolipid metabolite, sphingosine-1-phosphate (SPP). SPP has emerged as a novel lipid second-messenger with both extracellular and intracellular actions (Kohama, T. et al. (1998) J. Biol. Chem. 273:23722-23728). Extracellularly, SPP is a ligand for the G-protein coupled receptor EDG-1 (endothelial-derived, G-protein coupled receptor). Intracellularly, SPP regulates cell growth, survival, motility, and cytoskeletal changes. SPP levels are regulated by sphingosine kinases that specifically phosphorylate D-erythro-sphingosine to SPP. The importance of sphingosine kinase in cell signaling is indicated by the fact that various stimuli, including platelet-derived growth factor (PDGF), nerve growth factor, and activation of protein kinase C, increase cellular levels of SPP by activation of sphingosine kinase, and the fact that competitive inhibitors of the enzyme selectively inhibit cell proliferation induced by PDGF (Kohama et al., supra).

Purine Nucleotide Kinases

The purine nucleotide kinases, adenylate kinase (ATP: AMP phosphotransferase, or AdK) and guanylate kinase (ATP:GMP phosphotransferase, or GuK) play a key role in nucleotide metabolism and are crucial to the synthesis and regulation of cellular levels of ATP and GTP, respectively. These two molecules are precursors in DNA and RNA synthesis in growing cells and provide the primary source of biochemical energy in cells (ATP), and signal transduction pathways (GTP). Inhibition of various steps in the synthesis of these two molecules has been the basis of many antiproliferative drugs for cancer and antiviral therapy (Pillwein, K. et al. (1990) Cancer Res. 50:1576-1579).

AdK is found in almost all cell types and is especially abundant in cells having high rates of ATP synthesis and utilization such as skeletal muscle. In these cells AdK is physically associated with mitochondria and myofibrils, the subcellular structures that are involved in energy production and utilization, respectively. Recent studies have demonstrated a major function for AdK in transferring high energy phosphoryls from metabolic processes generating ATP to cellular components consuming ATP (Zeleznikar, R. J. et al. (1995) J. Biol. Chem. 270:7311-7319). Thus AdK may have a pivotal role in maintaining energy production in cells, particularly those having a high rate of growth or metabolism such as cancer cells, and may provide a target for suppression of its activity in order to treat certain cancers. Alternatively, reduced AdK activity may be a source of various metabolic, muscle-energy disorders that can result in cardiac or respiratory failure and may be treatable by increasing AdK activity.

GuK, in addition to providing a key step in the synthesis of GTP for RNA and DNA synthesis, also fulfills an essential function in signal transduction pathways of cells through the regulation of GDP and GTP. Specifically, GTP binding to membrane associated G proteins mediates the activation of cell receptors, subsequent intracellular activation of adenyl cyclase, and production of the second messenger, cyclic AMP. GDP binding to G proteins inhibits these processes. GDP and GTP levels also control the activity of certain oncogenic proteins such as $p21^{ras}$ known to be involved in control of cell proliferation and oncogenesis (Bos, J. L. (1989) Cancer Res. 49:4682-4689). High ratios of GTP:GDP caused by suppression of GuK cause activation of p21' and promote oncogenesis. Increasing GuK activity to increase levels of GDP and reduce the GTP:GDP ratio may provide a therapeutic strategy to reverse oncogenesis.

GuK is an important enzyme in the phosphorylation and activation of certain antiviral drugs useful in the treatment of herpes virus infections. These drugs include the guanine homologs acyclovir and buciclovir (Miller, W. H. and R. L. Miller (1980) J. Biol. Chem. 255:7204-7207; Stenberg, K. et al. (1986) J. Biol. Chem. 261:2134-2139). Increasing GuK activity in infected cells may provide a therapeutic strategy for augmenting the effectiveness of these drugs and possibly for reducing the necessary dosages of the drugs.

Pyrimidine Kinases

The pyrimidine kinases are deoxycytidine kinase and thymidine kinase 1 and 2. Deoxycytidine kinase is located in the nucleus, and thymidine kinase 1 and 2 are found in the cytosol (Johansson, M. et al. (1997) Proc. Natl. Acad. Sci. USA 94:11941-11945). Phosphorylation of deoxyribonucleosides by pyrimidine kinases provides an alternative pathway for de novo synthesis of DNA precursors. The role of pyrimidine kinases, like purine kinases, in phosphorylation is critical to the activation of several chemotherapeutically important nucleoside analogues (Amer E. S, and S. Eriksson (1995) Pharmacol. Ther. 67:155-186).

phosphatases

Protein phosphatases are generally characterized as either serine/threonine- or tyrosine-specific based on their preferred phospho-amino acid substrate. However, some phosphatases (DSPs, for dual specificity phosphatases) can act on phosphorylated tyrosine, serine, or threonine residues. The protein serine/threonine phosphatases (PSPs) are important regulators of many cAMP-mediated hormone responses in cells. Protein tyrosine phosphatases (PTPs) play a significant role in cell cycle and cell signaling processes. Another family of phosphatases is the acid phosphatase or histidine acid phosphatase (HAP) family whose members hydrolyze phosphate esters at acidic pH conditions.

PSPs are found in the cytosol, nucleus, and mitochondria and in association with cytoskeletal and membranous structures in most tissues, especially the brain. Some PSPs require divalent cations, such as $Ca^{2+}$ or $Mn^{2+}$, for activity. PSPs play important roles in glycogen metabolism, muscle contraction, protein synthesis, T cell function, neuronal activity, oocyte maturation, and hepatic metabolism (reviewed in Cohen, P. (1989) Annu. Rev. Biochem. 58:453-508). PSPs can be separated into two classes. The PPP class includes PP1, PP2A, PP2B/calcineurin, PP4, PP5, PP6, and PP7. Members of this class are composed of a homologous catalytic subunit bearing a very highly conserved signature sequence, coupled with one or more regulatory subunits (PROSITE PDOC00115). Further interactions with scaffold and anchoring molecules determine the intracellular localization of PSPs and substrate specificity. The PPM class consists of several closely related isoforms of PP2C and is evolutionarily unrelated to the PPP class.

PP1 dephosphorylates many of the proteins phosphorylated by cyclic AMP-dependent protein kinase (PKA) and is an important regulator of many cAMP-mediated hormone responses in cells. A number of isoforms have been identified, with the alpha and beta forms being produced by alternative splicing of the same gene. Both ubiquitous and tissue-specific targeting proteins for PP1 have been identified. In the brain, inhibition of PP1 activity by the dopamine and adenosine 3',5'-monophosphate-regulated phosphoprotein of 32 kDa (DAKPP-32) is necessary for normal dopamine response in neostriatal neurons (reviewed in Price, N. E. and M. C. Mumby (1999) Curr. Opin. Neurobiol. 9:336-342). PP1, along with PP2A, has been shown to limit motility in microvascular endothelial cells, suggesting a role for PSPs in the inhibition of angiogenesis (Gabel, S. et al. (1999) Otolaryngol. Head Neck Surg. 121:463-468).

PP2A is the main serine/threonine phosphatase. The core PP2A enzyme consists of a single 36 kDa catalytic subunit (C) associated with a 65 kDa scaffold subunit (A), whose role is to recruit additional regulatory subunits (B). Three gene families encoding B subunits are known (PR55, PR61, and PR72), each of which contain multiple isoforms, and additional families may exist (Millward, T. A et al. (1999) Trends Biosci. 24:186-191). These "B-type" subunits are cell type- and tissue-specific and determine the substrate specificity, enzymatic activity, and subcellular localization of the holoenzyme. The PR55 family is highly conserved and bears a conserved motif (PROSITE PDOC00785). PR55 increases PP2A activity toward mitogen-activated protein kinase (MAPK) and MAPK kinase (MEK). PP2A dephosphorylates the MAPK active site, inhibiting the cell's entry into mitosis. Several proteins can compete with PR55 for PP2A core enzyme binding, including the CKII kinase catalytic subunit, polyomavirus middle and small T antigens, and SV40 small t antigen. Viruses may use this mechanism to commandeer PP2A and stimulate progression of the cell through the cell cycle (Pallas, D. C. et al. (1992) J. Virol. 66:886-893). Altered MAP kinase expression is also implicated in a variety of disease conditions including cancer, inflammation, immune disorders, and disorders affecting growth and development. PP2A, in fact, can dephosphorylate and modulate the activities of more than 30 protein kinases in vitro, and other evidence suggests that the same is true in vivo for such kinases as PKB, PKC, the calmodulin-dependent kinases, ERK family MAP kinases, cyclin-dependent kinases, and the I.kappa.B kinases (reviewed in Millward et al., supra). PP2A is itself a substrate for CKI and CKII kinases, and can be stimulated by polycationic macromolecules. A PP2A-like phosphatase is necessary to maintain the G1 phase destruction of mammalian cyclins A and B (Bastians, H. et al. (1999) Mol. Biol. Cell 10:3927-3941). PP2A is a major activity in the brain and is implicated in regulating neurofilament stability and normal neural function, particularly the phosphorylation of the microtubule-associated protein tau. Hyperphosphorylation of tau has been proposed to lead to the neuronal degeneration seen in Alzheimer's disease (reviewed in Price and Mumby, supra).

PP2B, or calcineurin, is a $Ca^{2+}$-activated dimeric phosphatase and is particularly abundant in the brain. It consists of catalytic and regulatory subunits, and is activated by the binding of the calcium/calmodulin complex. Calcineurin is the target of the immunosuppressant drugs cyclosporine and FK506. Along with other cellular factors, these drugs interact with calcineurin and inhibit phosphatase activity. In T cells, this blocks the calcium dependent activation of the NF-AT family of transcription factors, leading to immunosuppression. This family is widely distributed, and it is likely that calcineurin regulates gene expression in other tissues as well. In neurons, calcineurin modulates functions which range from the inhibition of neurotransmitter release to desensitization of postsynaptic NMDA-receptor coupled calcium channels to long term memory (reviewed in Price and Mumby, supra).

Other members of the PPP class have recently been identified (Cohen, P. T. (1997) Trends Biochem. Sci. 22:245-251). One of them, PP5, contains regulatory domains with tetratricopeptide repeats. It can be activated by polyunsaturated fatty acids and anionic phospholipids in vitro and appears to be involved in a number of signaling pathways, including those controlled by atrial natriuretic peptide or steroid hormones (reviewed in Andreeva, A. V. and M. A. Kutuzov (1999) Cell Signal. 11:555-562).

PP2C is a ~42 kDa monomer with broad substrate specificity and is dependent on divalent cations (mainly $Mn^{2+}$ or $Mg^{2+}$) for its activity. PP2C proteins share a conserved N-terminal region with an invariant DGH motif, which contains an aspartate residue involved in cation binding (PROSITE PDOC00792). Targeting proteins and mechanisms regulating PP2C activity have not been identified. PP2C has been shown to inhibit the stress-responsive p38 and Jun kinase (JNK) pathways (Takekawa, M. et al. (1998) EMBO J. 17:4744-4752).

In contrast to PSPs, tyrosine-specific phosphatases (PTPs) are generally monomeric proteins of very diverse size (from 20 kDa to greater than 100 kDa) and structure that function primarily in the transduction of signals across the plasma membrane. PTPs are categorized as either soluble phosphatases or transmembrane receptor proteins that contain a phosphatase domain. All PTPs share a conserved catalytic domain of about 300 amino acids which contains the active site. The active site consensus sequence includes a cysteine residue which executes a nucleophilic attack on the phosphate moiety during catalysis (Neel, B. G. and N. K. Tonics (1997) Curr. Opin. Cell Biol. 9:193-204). Receptor PTPs are made up of an N-terminal extracellular domain of variable length, a transmembrane region, and a cytoplasmic region that generally contains two copies of the catalytic domain. Although only the first copy seems to have enzymatic activity, the second copy apparently affects the substrate specificity of the first. The extracellular domains of some receptor PTPs contain fibronectin-like repeats, immunoglobulin-like domains, MAM domains (an extracellular motif likely to have an adhesive function), or carbonic anhydrase-like domains (PROSITE PDOC 00323). This wide variety of structural motifs accounts for the diversity in size and specificity of PTPs.

PTPs play important roles in biological processes such as cell adhesion, lymphocyte activation, and cell proliferation. PTPs μ and κ are involved in cell-cell contacts, perhaps regulating cadherin/catenin function. A number of PTPs affect cell spreading, focal adhesions, and cell motility, most of them via the integrin/tyrosine kinase signaling pathway (reviewed in Neel and Tonics, supra). CD45 phosphatases regulate signal transduction and lymphocyte activation (Ledbetter, J. A. et al. (1988) Proc. Natl. Acad. Sci. USA 85:8628-8632). Soluble PTPs containing Src-homology-2 domains have been identified (SHPs), suggesting that these molecules might interact with receptor tyrosine kinases. SHP-1 regulates cytokine receptor signaling by controlling the Janus family PTKs in hematopoietic cells, as well as signaling by the T-cell receptor and c-Kit (reviewed in Neel and Tonics, supra). M-phase inducer phosphatase plays a key role in the induction of mitosis by dephosphorylating and activating the PTK CDC2, leading to cell division (Sadhu, K. et al. (1990) Proc. Natl. Acad. Sci. USA 87:5139-5143). In addition, the genes encoding at least eight PTPs have been mapped to chromosomal regions that are translocated or rearranged in various neoplastic conditions, including lymphoma, small cell lung carcinoma, leukemia, adenocarcinoma, and neuroblastoma (reviewed in Charbonneau, H. and N. K. Tonks (1992) Annu. Rev. Cell Biol. 8:463-493). The PTP enzyme active site comprises the consensus sequence of the MTM1 gene family. The MTM1 gene is responsible for X-linked recessive myotubular myopathy, a congenital muscle disorder that has been linked to Xq28 (Kioschis, P. et al., (1998) Genomics 54:256-266). Many PTKs are encoded by oncogenes, and it is well known that oncogenesis is often accompanied by increased tyrosine phosphorylation activity. It is therefore possible that PTPs may serve to prevent or reverse cell transformation and the growth of various cancers by controlling the levels of tyrosine phosphorylation in cells. This is supported by studies showing that overexpression of PTP can suppress transformation in cells and that specific inhibition of PTP can enhance cell transformation (Charbonneau and Tonics, supra).

Apyrases are enzymes that efficiently hydrolyze ATP and ADP and may function either intra- or extracellularly. One type of apyrase, ATP-diphosphohydrolase, catalyzes the hydrolysis of phosphoanhydride bonds of nucleoside tri- and di-phosphates in the presence of divalent cations (Nourizad, N. et al., (2003) Protein Purif. 27:229-237).

Dual specificity phosphatases (DSPs) are structurally more similar to the PTPs than the PSPs. DSPs bear an extended PTP active site motif with an additional 7 amino acid residues. DSPs are primarily associated with cell proliferation and include the cell cycle regulators cdc25A, B, and C. The phosphatases DUSP1 and DUSP2 inactivate the MAPK family members ERK (extracellular signal-regulated kinase), JNK (c-Jun N-terminal kinase), and p38 on both tyrosine and threonine residues (PROSITE PDOC 00323, supra). In the activated state, these kinases have been implicated in neuronal differentiation, proliferation, oncogenic transformation, platelet aggregation, and apoptosis. Thus, DSPs are necessary for proper regulation of these processes (Muda, M. et al. (1996) J. Biol. Chem. 271:27205-27208). The tumor suppressor PTEN is a DSP that also shows lipid phosphatase activity. It seems to negatively regulate interactions with the extracellular matrix and maintains sensitivity to apoptosis. PTEN has been implicated in the prevention of angiogenesis (Giri, D. and M. Ittmann (1999) Hum. Pathol. 30:419-424) and abnormalities in its expression are associated with numerous cancers (reviewed in Tamura, M. et al. (1999) J. Natl. Cancer Inst. 91:1820-1828).

Histidine acid phosphatase (HAP; EXPASY EC 3.1.3.2), also known as acid phosphatase, hydrolyzes a wide spectrum of substrates including alkyl, aryl, and acyl orthophosphate monoesters and phosphorylated proteins at low pH. HAPs share two regions of conserved sequences, each centered around a histidine residue which is involved in catalytic activity. Members of the HAP family include lysosomal acid phosphatase (LAP) and prostatic acid phosphatase (PAP), both sensitive to inhibition by L-tartrate (PROSITE PDOC00538).

Synaptojanin, a polyphosphoinositide phosphatase, dephosphorylates phosphoinositides at positions 3, 4 and 5 of the inositol ring. Synaptojanin is a major presynaptic protein found at clathrin-coated endocytic intermediates in nerve terminals, and binds the clathrin coat-associated protein, EPS15. This binding is mediated by the C-terminal region of synaptojanin-170, which has 3 Asp-Pro-Phe amino acid repeats. Further, this 3 residue repeat had been found to be the binding site for the EH domains of EPS15 (Haffner, C. et al. (1997) FEBS Lett. 419:175-180). Additionally, synaptojanin may potentially regulate interactions of endocytic proteins with the plasma membrane, and be involved in synaptic vesicle recycling (Brodin, L. et al. (2000) Curr. Opin. Neurobiol. 10:312-320). Studies in mice with a targeted disruption in the synaptojanin 1 gene (Synj1) were shown to support coat formation of endocytic vesicles more effectively than was seen in wild-type mice, suggesting that Synj1 can act as a negative regulator of membrane-coat protein interactions. These findings provide genetic evidence for a crucial role of phosphoinositide metabolism in synaptic vesicle recycling (Cremona, O. et al. (1999) Cell 99:179-188).

Expression Profiling

Microarrays are analytical tools used in bioanalysis. A microarray has a plurality of molecules spatially distributed over, and stably associated with, the surface of a solid support. Microarrays of polypeptides, polynucleotides, and/or antibodies have been developed and find use in a variety of applications, such as gene sequencing, monitoring gene expression, gene mapping, bacterial identification, drug discovery, and combinatorial chemistry.

One area in particular in which microarrays find use is in gene expression analysis. Array technology can provide a simple way to explore the expression of a single polymorphic gene or the expression profile of a large number of related or unrelated genes. When the expression of a single gene is examined, arrays are employed to detect the expression of a specific gene or its variants. When an expression profile is examined, arrays provide a platform for identifying genes that are tissue specific, are affected by a substance being tested in a toxicology assay, are part of a signaling cascade, carry out housekeeping functions, or are specifically related to a particular genetic predisposition, condition, disease, or disorder.

Neurological Disorders

Characterization of region-specific gene expression in the human brain provides a context and background for molecular neurobiology on a variety of neurological disorders.

Alzheimer's disease (AD) is a progressive, neurodestructive process of the human neocortex, characterized by the deterioration of memory and higher cognitive function. A progressive and irreversible brain disorder, AD is characterized by three major pathogenic episodes involving (a) an aberrant processing and deposition of beta-amyloid precursor protein (betaAPP) to form neurotoxic beta-amyloid (betaA) peptides and an aggregated insoluble polymer of betaA that forms the senile plaque, (b) the establishment of intraneuronal neuritic tau pathology yielding widespread deposits of agyrophilic neurofibrillary tangles (NFT) and (c) the initiation and proliferation of a brain-specific inflammatory response. These three seemingly disperse attributes of AD etiopathogenesis are linked by the fact that proinflammatory microglia, reactive astrocytes and their associated cytokines and chemokines are associated with the biology of the microtubule associated protein tau, betaA speciation and aggregation. Missense mutations in the presenilin genes PS1 and PS2, implicated in early onset familial AD, cause abnormal betaAPP processing with resultant overproduction of betaA42 and related neurotoxic peptides. Specific betaA fragments such as betaA42 can further potentiate proinflammatory mechanisms. Expression of the inducible oxidoreductase cyclooxygenase-2 and cytosolic phospholipase A2 (cPLA2) is strongly activated during cerebral ischemia and trauma, epilepsy and AD, indicating the induction of proinflammatory gene pathways as a response to brain injury. Neurotoxic metals such as aluminum and zinc, both implicated in AD etiopathogenesis, and arachidonic acid, a major metabolite of brain cPLA2 activity, each polymerize hyperphosphorylated tau to form NFT-like bundles. Studies have identified a reduced risk for AD in patients aged over 70 years who were previously treated with non-steroidal anti-inflammatory drugs for non-CNS afflictions that include arthritis. (For a review of the interrelationships between the mechanisms of PS1, PS2 and betaAPP gene expression, tau and betaA deposition and the induction, regulation and proliferation in AD of the neuroinflammatory response, see Lukiw, W. J, and Bazan, N. G. (2000) Neurochem. Res. 2000 25:1173-1184).

Breast Cancer

More than 180,000 new cases of breast cancer are diagnosed each year, and the mortality rate for breast cancer approaches 10% of all deaths in females between the ages of 45-54 (Gish, K. (1999) AWIS Magazine 28:7-10). However, the survival rate based on early diagnosis of localized breast cancer is extremely high (97%), compared with the advanced stage of the disease in which the tumor has spread beyond the breast (22%). Current procedures for clinical breast examination are lacking in sensitivity and specificity, and efforts are underway to develop comprehensive gene expression profiles for breast cancer that may be used in conjunction with conventional screening methods to improve diagnosis and prognosis of this disease (Perou, C. M. et al. (2000) Nature 406:747-752).

Mutations in two genes, BRCA1 and BRCA2, are known to greatly predispose a woman to breast cancer and may be passed on from parents to children (Gish, supra). However, this type of hereditary breast cancer accounts for only about 5% to 9% of breast cancers, while the vast majority of breast cancer is due to non-inherited mutations that occur in breast epithelial cells.

The relationship between expression of epidermal growth factor (EGF) and its receptor, EGFR, to human mammary carcinoma has been particularly well studied. (See Khazaie, K. et al. (1993) Cancer and Metastasis Rev. 12:255-274, and references cited therein for a review of this area.) Overexpression of EGFR, particularly, coupled with down-regulation of the estrogen receptor, is a marker of poor prognosis in breast cancer patients. In addition, EGFR expression in breast tumor metastases is frequently elevated relative to the primary tumor, suggesting that EGFR is involved in tumor progression and metastasis. This is supported by accumulating evidence that EGF has effects on cell functions related to metastatic potential, such as cell motility, chemotaxis, secretion and differentiation. Changes in expression of other members of the erbB receptor family, of which EGFR is one, have also been implicated in breast cancer. The abundance of erbB receptors, such as HER-2/neu, HER-3, and HER-4, and their ligands in breast cancer points to their functional importance in the pathogenesis of the disease, and may therefore provide targets for therapy of the disease (Bacus, S. S. et al. (1994) Am. J. Clin. Pathol. 102:S13-S24). Other known markers of breast cancer include a human secreted frizzled protein mRNA that is downregulated in breast tumors; the matrix Gla protein which is overexpressed in human breast carcinoma cells; Drg1 or RTP, a gene whose expression is diminished in colon, breast, and prostate tumors; maspin, a tumor suppressor gene downregulated in invasive breast carcinomas; and CaN19, a member of the S100 protein family, all of which are down-regulated in mammary carcinoma cells relative to normal mammary epithelial cells (Zhou, Z. et al. (1998) Int. J. Cancer 78:95-99; Chen, L. et al. (1990) Oncogene 5:1391-1395; Ulrix, W. et al (1999) FEBS Lett 455:23-26; Sager, R. et al. (1996) Curr. Top. Microbiol. Immunol. 213:51-64; and Lee, S. W. et al. (1992) Proc. Natl. Acad. Sci. USA 89:2504-2508).

Cell lines derived from human mammary epithelial cells at various stages of breast cancer provide a useful model to study the process of malignant transformation and tumor progression as it has been shown that these cell lines retain many of the properties of their parental tumors for lengthy culture periods (Wistuba, I. I. et al. (1998) Clin. Cancer Res. 4:2931-2938). Such a model is particularly useful for comparing phenotypic and molecular characteristics of human mammary epithelial cells at various stages of malignant transformation.

Colon Cancer

While soft tissue sarcomas are relatively rare, more than 50% of new patients diagnosed with the disease will die from it. The molecular pathways leading to the development of sarcomas are relatively unknown, due to the rarity of the disease and variation in pathology. Colon cancer evolves through a multi-step process whereby pre-malignant colonocytes undergo a relatively defined sequence of events leading to tumor formation. Several factors participate in the process of tumor progression and malignant transformation including genetic factors, mutations, and selection.

To understand the nature of gene alterations in colorectal cancer, a number of studies have focused on the inherited syndromes. Familial adenomatous polyposis (FAP), is caused by mutations in the adenomatous polyposis coli gene (APC), resulting in truncated or inactive forms of the protein. This tumor suppressor gene has been mapped to chromosome 5q. Hereditary nonpolyposis colorectal cancer (HNPCC) is caused by mutations in mis-match repair genes. Although hereditary colon cancer syndromes occur in a small percentage of the population and most colorectal cancers are considered sporadic, knowledge from studies of the hereditary syndromes can be generally applied. For instance, somatic mutations in APC occur in at least 80% of sporadic colon tumors. APC mutations are thought to be the initiating event in the disease. Other mutations occur subsequently. Approximately 50% of colorectal cancers contain activating mutations in ras, while 85% contain inactivating mutations in p53. Changes in all of these genes lead to gene expression changes in colon cancer.

Lung Cancer

The potential application of gene expression profiling is particularly relevant to improving diagnosis, prognosis, and treatment of cancer, such as lung cancer. Lung cancer is the leading cause of cancer death in the United States, affecting more than 100,000 men and 50,000 women each year. Nearly 90% of the patients diagnosed with lung cancer are cigarette smokers. Tobacco smoke contains thousands of noxious substances that induce carcinogen metabolizing enzymes and covalent DNA adduct formation in the exposed bronchial epithelium. In nearly 80% of patients diagnosed with lung cancer, metastasis has already occurred. Most commonly lung cancers metastasize to pleura, brain, bone, pericardium, and liver. The decision to treat with surgery, radiation therapy, or chemotherapy is made on the basis of tumor histology, response to growth factors or hormones, and sensitivity to inhibitors or drugs. With current treatments, most patients die within one year of diagnosis. Earlier diagnosis and a systematic approach to identification, staging, and treatment of lung cancer could positively affect patient outcome.

Lung cancers progress through a series of morphologically distinct stages from hyperplasia to invasive carcinoma. Malignant lung cancers are divided into two groups comprising four histopathological classes. The Non Small Cell Lung Carcinoma (NSCLC) group includes squamous cell carcinomas, adenocarcinomas, and large cell carcinomas and accounts for about 70% of all lung cancer cases. Adenocarcinomas typically arise in the peripheral airways and often form mucin secreting glands. Squamous cell carcinomas typically arise in proximal airways. The histogenesis of squamous cell carcinomas may be related to chronic inflammation and injury to the bronchial epithelium, leading to squamous metaplasia. The Small Cell Lung Carcinoma (SCLC) group accounts for about 20% of lung cancer cases. SCLCs typically arise in proximal airways and exhibit a number of paraneoplastic syndromes including inappropriate production of adrenocorticotropin and anti-diuretic hormone.

Lung cancer cells accumulate numerous genetic lesions, many of which are associated with cytologically visible chromosomal aberrations. The high frequency of chromosomal deletions associated with lung cancer may reflect the role of multiple tumor suppressor loci in the etiology of this disease. Deletion of the short arm of chromosome 3 is found in over 90% of cases and represents one of the earliest genetic lesions leading to lung cancer. Deletions at chromosome arms 9p and 17p are also common. Other frequently observed genetic lesions include overexpression of telomerase, activation of oncogenes such as K-ras and c-myc, and inactivation of tumor suppressor genes such as RB, p53 and CDKN2.

Genes differentially regulated in lung cancer have been identified by a variety of methods. Using mRNA differential display technology, Manda et al. (1999; Genomics 51:5-14) identified five genes differentially expressed in lung cancer cell lines compared to normal bronchial epithelial cells. Among the known genes, pulmonary surfactant apoprotein A and alpha 2 macroglobulin were down regulated whereas nm23H1 was upregulated. Petersen et al. (2000; Int J. Cancer, 86:512-517) used suppression subtractive hybridization to identify 552 clones differentially expressed in lung tumor derived cell lines, 205 of which represented known genes. Among the known genes, thrombospondin-1, fibronectin, intercellular adhesion molecule 1, and cytokeratins 6 and 18 were previously observed to be differentially expressed in lung cancers. Wang et al. (2000; Oncogene 19:1519-1528)

used a combination of microarray analysis and subtractive hybridization to identify 17 genes differentially overexpressed in squamous cell carcinoma compared with normal lung epithelium. Among the known genes they identified were keratin isoform 6, KOC, SPRC, IGFb2, connexin 26, plakofillin 1 and cytokeratin 13.

Ovarian Cancer

Ovarian cancer is the leading cause of death from a gynecologic cancer. The majority of ovarian cancers are derived from epithelial cells, and 70% of patients with epithelial ovarian cancers present with late-stage disease. As a result, the long-term survival rate for this disease is very low. Identification of early-stage markers for ovarian cancer would significantly increase the survival rate. Genetic variations involved in ovarian cancer development include mutation of p53 and microsatellite instability. Gene expression patterns likely vary when normal ovary is compared to ovarian tumors.

Prostate Cancer

As with most tumors, prostate cancer develops through a multistage progression ultimately resulting in an aggressive tumor phenotype. The initial step in tumor progression involves the hyperproliferation of normal luminal and/or basal epithelial cells. Androgen responsive cells become hyperplastic and evolve into early-stage tumors. Although early-stage tumors are often androgen sensitive and respond to androgen ablation, a population of androgen independent cells evolve from the hyperplastic population. These cells represent a more advanced form of prostate tumor that may become invasive and potentially become metastatic to the bone, brain, or lung. A variety of genes may be differentially expressed during tumor progression. For example, loss of heterozygosity (LOH) is frequently observed on chromosome 8p in prostate cancer. Fluorescence in situ hybridization (FISH) revealed a deletion for at least 1 locus on 8p in 29 (69%) tumors, with a significantly higher frequency of the deletion on 8p21.2-p21.1 in advanced prostate cancer than in localized prostate cancer, implying that deletions on 8p22-p21.3 play an important role in tumor differentiation, while 8p21.2-p21.1 deletion plays a role in progression of prostate cancer (Oba, K. et al. (2001) Cancer Genet. Cytogenet. 124: 20-26).

PZ-HPV-7 was derived from epithelial cells cultured from normal tissue from the peripheral zone of the prostate. The cells were transformed by transfection with HPV 18. Immunocytochemical analysis showed expression of keratins 5 and 8 and also the early region 6 (E6) oncoprotein of HPV. The cells are negative for prostate specific antigen (PSA).

Interleukin 6 (IL-6) is a multifunctional protein that plays important roles in host defense, acute phase reactions, immune responses, and hematopoiesis. According to the type of biological responses being studied, IL-6 was previously named interferon-b2, 26-kDa protein, B cell stimulatory factor-2 (BSF-2), hybridoma/plasmacytoma growth factor, hepatocyte stimulating factor, cytotoxic T cell differentiation factor, and macrophage-granulocyte inducing factor 2A (MGI-2A). The IL-6 designation was adopted after these variously named proteins were found to be identical on the basis of their amino acid and/or nucleotide sequences. IL-6 is expressed by a variety of normal and transformed cells including T cells, B cells, monocytes/macrophages, fibroblasts, hepatocytes, keratinocytes, astrocytes, vascular endothelial cells, and various tumor cells. The production of IL-6 is upregulated by numerous signals including mitogenic or antigenic stimulation, LPS, calcium ionophore, IL-1, IL-2, IFN, TNF, PDGF, and viruses. IL-4 and IL-13 inhibit IL-6 expression in monocytes.

Obesity

The most important function of adipose tissue is its ability to store and release fat during periods of feeding and fasting. White adipose tissue is the major energy reserve in periods of excess energy use. Its primary purpose is mobilization during energy deprivation. Understanding how various molecules regulate adiposity and energy balance in physiological and pathophysiological situations may lead to the development of novel therapeutics for human obesity. Adipose tissue is also one of the important target tissues for insulin. Adipogenesis and insulin resistance in type II diabetes are linked and present intriguing relations. Most patients with type II diabetes are obese and obesity in turn causes insulin resistance.

The majority of research in adipocyte biology to date has been done using transformed mouse preadipocyte cell lines. The culture condition which stimulates mouse preadipocyte differentiation is different from that for inducing human primary preadipocyte differentiation. In addition, primary cells are diploid and may therefore reflect the in vivo context better than aneuploid cell lines. Understanding the gene expression profile during adipogenesis in humans will lead to an understanding of the fundamental mechanism of adiposity regulation. Furthermore, through comparing the gene expression profiles of adipogenesis between donors with normal weight and donors with obesity, identification of crucial genes, potential drug targets for obesity and type II diabetes, will be possible.

Thiazolidinediones (TZDs) act as agonists for the peroxisome-proliferator-activated receptor gamma (PPARγ), a member of the nuclear hormone receptor superfamily. TZDs reduce hyperglycemia, hyperinsulinemia, and hypertension, in part by promoting glucose metabolism and inhibiting gluconeogenesis. Roles for PPARγ and its agonists have been demonstrated in a wide range of pathological conditions including diabetes, obesity, hypertension, atherosclerosis, polycystic ovarian syndrome, and cancers such as breast, prostate, liposarcoma, and colon cancer.

The mechanism by which TZDs and other PPARγ agonists enhance insulin sensitivity is not fully understood, but may involve the ability of PPARγ to promote adipogenesis. When ectopically expressed in cultured preadipocytes, PPARγ is a potent inducer of adipocyte differentiation. TZDs, in combination with insulin and other factors, can also enhance differentiation of human preadipocytes in culture (Adams et al. (1997) J. Clin. Invest. 100:3149-3153). The relative potency of different TZDs in promoting adipogenesis in vitro is proportional to both their insulin sensitizing effects in vivo, and their ability to bind and activate PPARγ in vitro. Interestingly, adipocytes derived from omental adipose depots are refractory to the effects of TZDs. It has therefore been suggested that the insulin sensitizing effects of TZDs may result from their ability to promote adipogenesis in subcutaneous adipose depots (Adams et al., supra). Further, dominant negative mutations in the PPARγ gene have been identified in two non-obese subjects with severe insulin resistance, hypertension, and overt non-insulin dependent diabetes mellitus (NIDDM) (Barroso et al. (1998) Nature 402:880-883).

NIDDM is the most common form of diabetes mellitus, a chronic metabolic disease that affects 143 million people worldwide. NIDDM is characterized by abnormal glucose and lipid metabolism that results from a combination of peripheral insulin resistance and defective insulin secretion. NIDDM has a complex, progressive etiology and a high degree of heritability. Numerous complications of diabetes including heart disease, stroke, renal failure, retinopathy, and peripheral neuropathy contribute to the high rate of morbidity and mortality.

At the molecular level, PPARγ functions as a ligand activated transcription factor. In the presence of ligand, PPARγ forms a heterodimer with the retinoid X receptor (RXR) which then activates transcription of target genes containing one or more copies of a PPARγ response element (PPRE). Many genes important in lipid storage and metabolism contain PPREs and have been identified as PPARγ targets, including PEPCK, aP2, LPL, ACS, and FAT-P (Auwerx, J. (1999) Diabetologia 42:1033-1049). Multiple ligands for PPARγ have been identified. These include a variety of fatty acid metabolites; synthetic drugs belonging to the TZD class, such as Pioglitazone and Rosiglitazone (BRL49653); and certain non-glitazone tyrosine analogs such as GI262570 and GW1929. The prostaglandin derivative 15-dPGJ2 is a potent endogenous ligand for PPARγ.

Expression of PPARγ is very high in adipose but barely detectable in skeletal muscle, the primary site for insulin stimulated glucose disposal in the body. PPARγ is also moderately expressed in large intestine, kidney, liver, vascular smooth muscle, hematopoietic cells, and macrophages. The high expression of PPARγ in adipose tissue suggests that the insulin sensitizing effects of TZDs may result from alterations in the expression of one or more PPARγ regulated genes in adipose tissue. Identification of PPARγ target genes will contribute to better drug design and the development of novel therapeutic strategies for diabetes, obesity, and other conditions.

Systematic attempts to identify PPARγ target genes have been made in several rodent models of obesity and diabetes (Suzuki et al. (2000) Jpn. J. Pharmacol. 84:113-123; Way et al. (2001) Endocrinology 142:1269-1277). However, a serious drawback of the rodent gene expression studies is that significant differences exist between human and rodent models of adipogenesis, diabetes, and obesity (Taylor (1999) Cell 97:9-12; Gregoire et al. (1998) Physiol. Reviews 78:783-809). Therefore, an unbiased approach to identifying TZD regulated genes in primary cultures of human tissues is necessary to fully elucidate the molecular basis for diseases associated with PPARγ activity.

There is a need in the art for new compositions, including nucleic acids and proteins, for the diagnosis, prevention, and treatment of cardiovascular diseases, immune system disorders, neurological disorders, disorders affecting growth and development, lipid disorders, cell proliferative disorders, and cancers.

SUMMARY OF THE INVENTION

Various embodiments of the invention provide purified polypeptides, kinases and phosphatases, referred to collectively as 'KPP' and individually as 'KPP-1,' 'KPP-2,' 'KPP-3,' 'KPP-4,' 'KPP-5,' 'KPP-6,' 'KPP-8,' 'KPP-9,' 'KPP-10,' 'KPP-11,' 'KPP-12,' 'KPP-13,' 'KPP-14,' 'KPP-15,' 'KPP-16,' 'KPP-17,' 'KPP-18,' 'KPP-19,' 'KPP-20,' 'KPP-21,' 'KPP-22,' 'KPP-23', 'KPP-24,' 'KPP-25,' 'KPP-26,' 'KPP-27,' 'KPP-28,' 'KPP-29,' 'KPP-30,' 'KPP-31,' 'KPP-32,' 'KPP-33,' 'KPP-34,' 'KPP-35,' 'KPP-36,' 'KPP-37,' 'KPP-38,' 'KPP-39,' 'KPP-40,' 'KPP-41,' 'KPP-42,' and 'KPP-43' and methods for using these proteins and their encoding polynucleotides for the detection, diagnosis, and treatment of diseases and medical conditions Embodiments also provide methods for utilizing the purified kinases and phosphatases and/or their encoding polynucleotides for facilitating the drug discovery process, including determination of efficacy, dosage, toxicity, and pharmacology. Related embodiments provide methods for utilizing the purified kinases and phosphatases and/or their encoding polynucleotides for investigating the pathogenesis of diseases and medical conditions.

An embodiment provides an isolated polypeptide selected from the group consisting of a) a polypeptide comprising an amino acid sequence selected from the group consisting of SEQ ID NO:1-43, b) a polypeptide comprising a naturally occurring amino acid sequence at least 90% identical or at least about 90% identical to an amino acid sequence selected from the group consisting of SEQ ID NO:1-43, c) a biologically active fragment of a polypeptide having an amino acid sequence selected from the group consisting of SEQ ID NO:1-43, and d) an immunogenic fragment of a polypeptide having an amino acid sequence selected from the group consisting of SEQ ID NO:1-43. Another embodiment provides an isolated polypeptide comprising an amino acid sequence of SEQ ID NO:1-43.

Still another embodiment provides an isolated polynucleotide encoding a polypeptide selected from the group consisting of a) a polypeptide comprising an amino acid sequence selected from the group consisting of SEQ ID NO:1-43, b) a polypeptide comprising a naturally occurring amino acid sequence at least 90% identical or at least about 90% identical to an amino acid sequence selected from the group consisting of SEQ ID NO:1-43, c) a biologically active fragment of a polypeptide having an amino acid sequence selected from the group consisting of SEQ ID NO:1-43, and d) an immunogenic fragment of a polypeptide having an amino acid sequence selected from the group consisting of SEQ ID NO:1-43. In another embodiment, the polynucleotide encodes a polypeptide selected from the group consisting of SEQ ID NO:1-43. In an alternative embodiment, the polynucleotide is selected from the group consisting of SEQ ID NO:44-86.

Still another embodiment provides a recombinant polynucleotide comprising a promoter sequence operably linked to a polynucleotide encoding a polypeptide selected from the group consisting of a) a polypeptide comprising an amino acid sequence selected from the group consisting of SEQ ID NO:1-43, b) a polypeptide comprising a naturally occurring amino acid sequence at least 90% identical or at least about 90% identical to an amino acid sequence selected from the group consisting of SEQ ID NO:1-43, c) a biologically active fragment of a polypeptide having an amino acid sequence selected from the group consisting of SEQ ID NO:1-43, and d) an immunogenic fragment of a polypeptide having an amino acid sequence selected from the group consisting of SEQ ID NO:1-43. Another embodiment provides a cell transformed with the recombinant polynucleotide. Yet another embodiment provides a transgenic organism comprising the recombinant polynucleotide.

Another embodiment provides a method for producing a polypeptide selected from the group consisting of a) a polypeptide comprising an amino acid sequence selected from the group consisting of SEQ ID NO:1-43, b) a polypeptide comprising a naturally occurring amino acid sequence at least 90% identical or at least about 90% identical to an amino acid sequence selected from the group consisting of SEQ ID NO:1-43, c) a biologically active fragment of a polypeptide having an amino acid sequence selected from the group consisting of SEQ ID NO:1-43, and d) an immunogenic fragment of a polypeptide having an amino acid sequence selected from the group consisting of SEQ ID NO:1-43. The method comprises a) culturing a cell under conditions suitable for expression of the polypeptide, wherein said cell is transformed with a recombinant polynucleotide comprising a promoter sequence operably linked to a polynucleotide encoding the polypeptide, and b) recovering the polypeptide so expressed.

Yet another embodiment provides an isolated antibody which specifically binds to a polypeptide selected from the group consisting of a) a polypeptide comprising an amino acid sequence selected from the group consisting of SEQ ID NO:1-43, b) a polypeptide comprising a naturally occurring amino acid sequence at least 90% identical or at least about 90% identical to an amino acid sequence selected from the group consisting of SEQ ID NO:1-43, c) a biologically active fragment of a polypeptide having an amino acid sequence selected from the group consisting of SEQ ID NO:1-43, and d) an immunogenic fragment of a polypeptide having an amino acid sequence selected from the group consisting of SEQ ID NO:1-43.

Still yet another embodiment provides an isolated polynucleotide selected from the group consisting of a) a polynucleotide comprising a polynucleotide sequence selected from the group consisting of SEQ ID NO:44-86, b) a polynucleotide comprising a naturally occurring polynucleotide sequence at least 90% identical or at least about 90% identical to a polynucleotide sequence selected from the group consisting of SEQ ID NO:44-86, c) a polynucleotide complementary to the polynucleotide of a), d) a polynucleotide complementary to the polynucleotide of b), and e) an RNA equivalent of a)-d). In other embodiments, the polynucleotide can comprise at least about 20, 30, 40, 60, 80, or 100 contiguous nucleotides.

Yet another embodiment provides a method for detecting a target polynucleotide in a sample, said target polynucleotide being selected from the group consisting of a) a polynucleotide comprising a polynucleotide sequence selected from the group consisting of SEQ ID NO:44-86, b) a polynucleotide comprising a naturally occurring polynucleotide sequence at least 90% identical or at least about 90% identical to a polynucleotide sequence selected from the group consisting of SEQ ID NO:44-86, c) a polynucleotide complementary to the polynucleotide of a), d) a polynucleotide complementary to the polynucleotide of b), and e) an RNA equivalent of a)-d). The method comprises a) hybridizing the sample with a probe comprising at least 20 contiguous nucleotides comprising a sequence complementary to said target polynucleotide in the sample, and which probe specifically hybridizes to said target polynucleotide, under conditions whereby a hybridization complex is formed between said probe and said target polynucleotide or fragments thereof, and b) detecting the presence or absence of said hybridization complex. In a related embodiment, the method can include detecting the amount of the hybridization complex. In still other embodiments, the probe can comprise at least about 20, 30, 40, 60, 80, or 100 contiguous nucleotides.

Still yet another embodiment provides a method for detecting a target polynucleotide in a sample, said target polynucleotide being selected from the group consisting of a) a polynucleotide comprising a polynucleotide sequence selected from the group consisting of SEQ ID NO:44-86, b) a polynucleotide comprising a naturally occurring polynucleotide sequence at least 90% identical or at least about 90% identical to a polynucleotide sequence selected from the group consisting of SEQ ID NO:44-86, c) a polynucleotide complementary to the polynucleotide of a), d) a polynucleotide complementary to the polynucleotide of b), and e) an RNA equivalent of a)-d). The method comprises a) amplifying said target polynucleotide or fragment thereof using polymerase chain reaction amplification, and b) detecting the presence or absence of said amplified target polynucleotide or fragment thereof. In a related embodiment, the method can include detecting the amount of the amplified target polynucleotide or fragment thereof.

Another embodiment provides a composition comprising an effective amount of a polypeptide selected from the group consisting of a) a polypeptide comprising an amino acid sequence selected from the group consisting of SEQ ID NO:1-43, b) a polypeptide comprising a naturally occurring amino acid sequence at least 90% identical or at least about 90% identical to an amino acid sequence selected from the group consisting of SEQ ID NO:1-43, c) a biologically active fragment of a polypeptide having an amino acid sequence selected from the group consisting of SEQ ID NO:1-43, and d) an immunogenic fragment of a polypeptide having an amino acid sequence selected from the group consisting of SEQ ID NO:1-43, and a pharmaceutically acceptable excipient in one embodiment, the composition can comprise an amino acid sequence selected from the group consisting of SEQ ID NO:1-43. Other embodiments provide a method of treating a disease or condition associated with decreased or abnormal expression of functional KPP, comprising administering to a patient in need of such treatment the composition.

Yet another embodiment provides a method for screening a compound for effectiveness as an agonist of a polypeptide selected from the group consisting of a) a polypeptide comprising an amino acid sequence selected from the group consisting of SEQ ID NO:1-43, b) a polypeptide comprising a naturally occurring amino acid sequence at least 90% identical or at least about 90% identical to an amino acid sequence selected from the group consisting of SEQ ID NO:1-43, c) a biologically active fragment of a polypeptide having an amino acid sequence selected from the group consisting of SEQ ID NO:1-43, and d) an immunogenic fragment of a polypeptide having an amino acid sequence selected from the group consisting of SEQ ID NO:1-43. The method comprises a) contacting a sample comprising the polypeptide with a compound, and b) detecting agonist activity in the sample. Another embodiment provides a composition comprising an agonist compound identified by the method and a pharmaceutically acceptable excipient. Yet another embodiment provides a method of treating a disease or condition associated with decreased expression of functional KPP, comprising administering to a patient in need of such treatment the composition.

Still yet another embodiment provides a method for screening a compound for effectiveness as an antagonist of a polypeptide selected from the group consisting of a) a polypeptide comprising an amino acid sequence selected from the group consisting of SEQ ID NO:1-43, b) a polypeptide comprising a naturally occurring amino acid sequence at least 90% identical or at least about 90% identical to an amino acid sequence selected from the group consisting of SEQ ID NO:1-43, c) a biologically active fragment of a polypeptide having an amino acid sequence selected from the group consisting of SEQ ID NO:1-43, and d) an immunogenic fragment of a polypeptide having an amino acid sequence selected from the group consisting of SEQ ID NO:1-43. The method comprises a) contacting a sample comprising the polypeptide with a compound, and b) detecting antagonist activity in the sample. Another embodiment provides a composition comprising an antagonist compound identified by the method and a pharmaceutically acceptable excipient. Yet another embodiment provides a method of treating a disease or condition associated with overexpression of functional KPP, comprising administering to a patient in need of such treatment the composition.

Another embodiment provides a method of screening for a compound that specifically binds to a polypeptide selected from the group consisting of a) a polypeptide comprising an amino acid sequence selected from the group consisting of SEQ ID NO:1-43, b) a polypeptide comprising a naturally occurring amino acid sequence at least 90% identical or at least about 90% identical to an amino acid sequence selected from the group consisting of SEQ ID NO:1-43, c) a biologically active fragment of a polypeptide having an amino acid sequence selected from the group consisting of SEQ ID NO:1-43, and d) an immunogenic fragment of a polypeptide having an amino acid sequence selected from the group consisting of SEQ ID NO:1-43. The method comprises a) combining the polypeptide with at least one test compound under suitable conditions, and b) detecting binding of the polypeptide to the test compound, thereby identifying a compound that specifically binds to the polypeptide.

Yet another embodiment provides a method of screening for a compound that modulates the activity of a polypeptide selected from the group consisting of a) a polypeptide comprising an amino acid sequence selected from the group consisting of SEQ ID NO:1-43, b) a polypeptide comprising a naturally occurring amino acid sequence at least 90% identical or at least about 90% identical to an amino acid sequence selected from the group consisting of SEQ ID NO:1-43, c) a biologically active fragment of a polypeptide having an amino acid sequence selected from the group consisting of SEQ ID NO:1-43, and d) an immunogenic fragment of a polypeptide having an amino acid sequence selected from the group consisting of SEQ ID NO:1-43. The method comprises a) combining the polypeptide with at least one test compound under conditions permissive for the activity of the polypeptide, b) assessing the activity of the polypeptide in the presence of the test compound; and c) comparing the activity of the polypeptide in the presence of the test compound with the activity of the polypeptide in the absence of the test compound, wherein a change in the activity of the polypeptide in the presence of the test compound is indicative of a compound that modulates the activity of the polypeptide.

Still yet another embodiment provides a method for screening a compound for effectiveness in altering expression of a target polynucleotide, wherein said target polynucleotide comprises a polynucleotide sequence selected from the group consisting of SEQ ID NO:44-86, the method comprising a) contacting a sample comprising the target polynucleotide with a compound, b) detecting altered expression of the target polynucleotide, and c) comparing the expression of the target polynucleotide in the presence of varying amounts of the compound and in the absence of the compound.

Another embodiment provides a method for assessing toxicity of a test compound, said method comprising a) treating a biological sample containing nucleic acids with the test compound; b) hybridizing the nucleic acids of the treated biological sample with a probe comprising at least 20 contiguous nucleotides of a polynucleotide selected from the group consisting of i) a polynucleotide comprising a polynucleotide sequence selected from the group consisting of SEQ ID NO:44-86, ii) a polynucleotide comprising a naturally occurring polynucleotide sequence at least 90% identical or at least about 90% identical to a polynucleotide sequence selected from the group consisting of SEQ ID NO:44-86, iii) a polynucleotide having a sequence complementary to i), iv) a polynucleotide complementary to the polynucleotide of ii), and v) an RNA equivalent of i)-iv). Hybridization occurs under conditions whereby a specific hybridization complex is formed between said probe and a target polynucleotide in the biological sample, said target polynucleotide selected from the group consisting of i) a polynucleotide comprising a polynucleotide sequence selected from the group consisting of SEQ ID NO:44-86, ii) a polynucleotide comprising a naturally occurring polynucleotide sequence at least 90% identical or at least about 90% identical to a polynucleotide sequence selected from the group consisting of SEQ ID NO:44-86, iii) a polynucleotide complementary to the polynucleotide of i), iv) a polynucleotide complementary to the polynucleotide of and v) an RNA equivalent of i)-iv). Alternatively, the target polynucleotide can comprise a fragment of a polynucleotide selected from the group consisting of i)-v) above; c) quantifying the amount of hybridization complex; and d) comparing the amount of hybridization complex in the treated biological sample with the amount of hybridization complex in an untreated biological sample, wherein a difference in the amount of hybridization complex in the treated biological sample is indicative of toxicity of the test compound.

BRIEF DESCRIPTION OF THE TABLES

Table 1 summarizes the nomenclature for full length polynucleotide and polypeptide embodiments of the invention.

Table 2 shows the GenBank identification number and annotation of the nearest GenBank homolog, and the PROTEOME database identification numbers and annotations of PROTEOME database homologs, for polypeptide embodiments of the invention. The probability scores for the matches between each polypeptide and its homologs) are also shown.

Table 3 shows structural features of polypeptide embodiments, including predicted motifs and domains, along with the methods, algorithms, and searchable databases used for analysis of the polypeptides.

Table 4 lists the cDNA and/or genomic DNA fragments which were used to assemble polynucleotide embodiments, along with selected fragments of the polynucleotides.

Table 5 shows representative cDNA libraries for polynucleotide embodiments.

Table 6 provides an appendix which describes the tissues and vectors used for construction of the cDNA libraries shown in Table 5.

Table 7 shows the tools, programs, and algorithms used to analyze polynucleotides and polypeptides, along with applicable descriptions, references, and threshold parameters.

Table 8 shows single nucleotide polymorphisms found in polynucleotide sequences of the invention, along with allele frequencies in different human populations.

DESCRIPTION OF THE INVENTION

Before the present proteins, nucleic acids, and methods are described, it is understood that embodiments of the invention are not limited to the particular machines, instruments, materials, and methods described, as these may vary. It is also to be understood that the terminology used herein is for the purpose of describing particular embodiments only, and is not intended to limit the scope of the invention.

As used herein and in the appended claims, the singular forms "a," "an," and "the" include plural reference unless the context clearly dictates otherwise. Thus, for example, a reference to "a host cell" includes a plurality of such host cells, and a reference to "an antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any machines, materials, and methods similar or equivalent to those described herein can be used to practice or test the present invention, the preferred machines, materials and methods are now described. All publications mentioned herein are cited for the purpose of describing and disclosing the cell lines, protocols, reagents and vectors which are reported in the publications and which might be used in connection with various embodiments of the invention. Nothing herein is to be construed as an admission that the invention is not entitled to antedate such disclosure by virtue of prior invention:

DEFINITIONS

"KPP" refers to the amino acid sequences of substantially purified KPP obtained from any species, particularly a mammalian species, including bovine, ovine, porcine, murine, equine, and human, and from any source, whether natural, synthetic, semi-synthetic, or recombinant.

The term "agonist" refers to a molecule which intensifies or mimics the biological activity of KPP. Agonists may include proteins, nucleic acids, carbohydrates, small molecules, or any other compound or composition which modulates the activity of KPP either by directly interacting with KPP or by acting on components of the biological pathway in which KPP participates.

An "allelic variant" is an alternative form of the gene encoding KPP. Allelic variants may result from at least one mutation in the nucleic acid sequence and may result in altered mRNAs or in polypeptides whose structure or function may or may not be altered. A gene may have none, one, or many allelic variants of its naturally occurring form. Common mutational changes which give rise to allelic variants are generally ascribed to natural deletions, additions, or substitutions of nucleotides. Each of these types of changes may occur alone, or in combination with the others, one or more times in a given sequence.

"Altered" nucleic acid sequences encoding KPP include those sequences with deletions, insertions, or substitutions of different nucleotides, resulting in a polypeptide the same as KPP or a polypeptide with at least one functional characteristic of KPP. Included within this definition are polymorphisms which may or may not be readily detectable using a particular oligonucleotide probe of the polynucleotide encoding KPP, and improper or unexpected hybridization to allelic variants, with a locus other than the normal chromosomal locus for the polynucleotide encoding KPP. The encoded protein may also be "altered," and may contain deletions, insertions, or substitutions of amino acid residues which produce a silent change and result in a functionally equivalent KPP. Deliberate amino acid substitutions may be made on the basis of one or more similarities in polarity, charge, solubility, hydrophobicity, hydrophilicity, and/or the amphipathic nature of the residues, as long as the biological or immunological activity of KPP is retained. For example, negatively charged amino acids may include aspartic acid and glutamic acid, and positively charged amino acids may include lysine and arginine. Amino acids with uncharged polar side chains having similar hydrophilicity values may include: asparagine and glutamine; and serine and threonine. Amino acids with uncharged side chains having similar hydrophilicity values may include: leucine, isoleucine, and valine; glycine and alanine; and phenylalanine and tyrosine.

The terms "amino acid" and "amino acid sequence" can refer to an oligopeptide, a peptide, a polypeptide, or a protein sequence, or a fragment of any of these, and to naturally occurring or synthetic molecules. Where "amino acid sequence" is recited to refer to a sequence of a naturally occurring protein molecule, "amino acid sequence" and like terms are not meant to limit the amino acid sequence to the complete native amino acid sequence associated with the recited protein molecule.

"Amplification" relates to the production of additional copies of a nucleic acid. Amplification may be carried out using polymerase chain reaction (PCR) technologies or other nucleic acid amplification technologies well known in the art.

The term "antagonist" refers to a molecule which inhibits or attenuates the biological activity of KPP. Antagonists may include proteins such as antibodies, anticalins, nucleic acids, carbohydrates, small molecules, or any other compound or composition which modulates the activity of KPP either by directly interacting with KPP or by acting on components of the biological pathway in which KPP participates.

The term "antibody" refers to intact immunoglobulin molecules as well as to fragments thereof, such as Fab, $F(ab')_2$, and Fv fragments, which are capable of binding an epitopic determinant. Antibodies that bind KPP polypeptides can be prepared using intact polypeptides or using fragments containing small peptides of interest as the immunizing antigen. The polypeptide or oligopeptide used to immunize an animal (e.g., a mouse, a rat, or a rabbit) can be derived from the translation of RNA, or synthesized chemically, and can be conjugated to a carrier protein if desired. Commonly used carriers that are chemically coupled to peptides include bovine serum albumin, thyroglobulin, and keyhole limpet hemocyanin (KLH). The coupled peptide is then used to immunize the animal.

The term "antigenic determinant" refers to that region of a molecule (i.e., an epitope) that makes contact with a particular antibody. When a protein or a fragment of a protein is used to immunize a host animal, numerous regions of the protein may induce the production of antibodies which bind specifically to antigenic determinants (particular regions or three-dimensional structures on the protein). An antigenic determinant may compete with the intact antigen (i.e., the immunogen used to elicit the immune-response) for binding to an antibody.

The term "aptamer" refers to a nucleic acid or oligonucleotide molecule that binds to a specific molecular target. Aptamers are derived from an in vitro evolutionary process (e.g., SELEX (Systematic Evolution of Ligands by EXponential Enrichment), described in U.S. Pat. No. 5,270,163), which selects for target-specific aptamer sequences from large combinatorial libraries. Aptamer compositions may be double-stranded or single-stranded, and may include deoxyribonucleotides, ribonucleotides, nucleotide derivatives, or other nucleotide-like molecules. The nucleotide components of an aptamer may have modified sugar groups (e.g., the 2'-OH group of a ribonucleotide may be replaced by 2'-F or $2'\text{-}NH_2$), which may improve a desired property, e.g., resistance to nucleases or longer lifetime in blood. Aptamars may be conjugated to other molecules, e.g., a high molecular weight carrier to slow clearance of the aptamer from the circulatory system. Aptamers may be specifically cross-linked to their cognate ligands, e.g., by photo-activation of a cross-linker (Brody, E. N. and L. Gold (2000) J. Biotechnol. 74:5-13).

The term "intramer" refers to an aptamer which is expressed in vivo. For example, a vaccinia virus-based RNA expression system has been used to express specific RNA aptamers at high levels in the cytoplasm of leukocytes (Blind, M. et al. (1999) Proc. Natl. Acad. Sci. USA 96:3606-3610).

The term "spiegelmer" refers to an aptamer which includes L-DNA, L-RNA, or other left-handed nucleotide derivatives or nucleotide-like molecules. Aptamers containing left-handed nucleotides are resistant to degradation by naturally occurring enzymes, which normally act on substrates containing right-handed nucleotides.

The term "antisense" refers to any composition capable of base-pairing with the "sense" (coding) strand of a polynucleotide having a specific nucleic acid sequence. Antisense compositions may include DNA; RNA; peptide nucleic acid (PNA); oligonucleotides having modified backbone linkages such as phosphorothioates, methylphosphonates, or benzylphosphonates; oligonucleotides having modified sugar groups such as 2'-methoxyethyl sugars or 2'-methoxyethoxy sugars; or oligonucleotides having modified bases such as 5-methyl cytosine, 2'-deoxyuracil, or 7-deaza-2'-deoxyguanosine. Antisense molecules may be produced by any method including chemical synthesis or transcription. Once introduced into a cell, the complementary antisense molecule base pairs with a naturally occurring nucleic acid sequence produced by the cell to form duplexes which block either transcription or translation. The designation "negative" or "minus" can refer to the antisense strand, and the designation "positive" or "plus" can refer to the sense strand of a reference DNA molecule.

The term "biologically active" refers to a protein having structural, regulatory, or biochemical functions of a naturally occurring molecule. Likewise, "immunologically active" or "immunogenic" refers to the capability of the natural, recombinant, or synthetic KPP, or of any oligopeptide thereof, to induce a specific immune response in appropriate animals or cells and to bind with specific antibodies.

"Complementary" describes the relationship between two single-stranded nucleic acid sequences that anneal by base-pairing. For example, 5'-AGT-3' pairs with its complement, 3'-TCA-5'.

A "composition comprising a given polynucleotide" and a "composition comprising a given polypeptide" can refer to any composition containing the given polynucleotide or polypeptide. The composition may comprise a dry formulation or an aqueous solution. Compositions comprising polynucleotides encoding KPP or fragments of KPP may be employed as hybridization probes. The probes may be stored in freeze-dried form and may be associated with a stabilizing agent such as a carbohydrate. In hybridizations, the probe may be deployed in an aqueous solution containing salts (e.g., NaCl), detergents (e.g., sodium dodecyl sulfate; SDS), and other components (e.g., Denhardt's solution, dry milk, salmon sperm DNA, etc.).

"Consensus sequence" refers to a nucleic acid sequence which has been subjected to repeated DNA sequence analysis to resolve uncalled bases, extended using the XL-PCR kit (Applied Biosystems, Foster City Calif.) in the 5' and/or the 3' direction, and resequenced, or which has been assembled from one or more overlapping cDNA, EST, or genomic DNA fragments using a computer program for fragment assembly, such as the GELVIEW fragment assembly system (Accelrys, Burlington Mass.) or Phrap (University of Washington, Seattle Wash.). Some sequences have been both extended and assembled to produce the consensus sequence.

"Conservative amino acid substitutions" are those substitutions that are predicted to least interfere with the properties of the original protein, i.e., the structure and especially the function of the protein is conserved and not significantly changed by such substitutions. The table below shows amino acids which may be substituted for an original amino acid in a protein and which are regarded as conservative amino acid substitutions.

| Original Residue | Conservative Substitution |
|---|---|
| Ala | Gly, Ser |
| Arg | His, Lys |
| Asn | Asp, Gln, His |
| Asp | Asn, Glu |
| Cys | Ala, Ser |
| Gln | Asn, Glu, His |
| Glu | Asp, Gln, His |
| Gly | Ala |
| His | Asn, Arg, Gln, Glu |
| Ile | Leu, Val |
| Leu | Ile, Val |
| Lys | Arg, Gln, Glu |
| Met | Leu, Ile |
| Phe | His, Met, Leu, Trp, Tyr |
| Ser | Cys, Thr |
| Thr | Ser, Val |
| Trp | Phe, Tyr |
| Tyr | His, Phe, Trp |
| Val | Ile, Leu, Thr |

Conservative amino acid substitutions generally maintain (a) the structure of the polypeptide backbone in the area of the substitution, for example, as a beta sheet or alpha helical conformation, (b) the charge or hydrophobicity of the molecule at the site of the substitution, and/or (c) the bulk of the side chain.

A "deletion" refers to a change in the amino acid or nucleotide sequence that results in the absence of one or more amino acid residues or nucleotides.

The term "derivative" refers to a chemically modified polynucleotide or polypeptide. Chemical modifications of a polynucleotide can include, for example, replacement of hydrogen by an alkyl, acyl, hydroxyl, or amino group. A derivative polynucleotide encodes a polypeptide which retains at least one biological or immunological function of the natural molecule. A derivative polypeptide is one modified by glycosylation, pegylation, or any similar process that retains at least one biological or immunological function of the polypeptide from which it was derived.

A "detectable label" refers to a reporter molecule or enzyme that is capable of generating a measurable signal and is covalently or noncovalently joined to a polynucleotide or polypeptide.

"Differential expression" refers to increased or upregulated; or decreased, downregulated, or absent gene or protein expression, determined by comparing at least two different samples. Such comparisons may be carried out between, for example, a treated and an untreated sample, or a diseased and a normal sample.

"Exon shuffling" refers to the recombination of different coding regions (exons). Since an exon may represent a structural or functional domain of the encoded protein, new proteins may be assembled through the novel reassortment of stable substructures, thus allowing acceleration of the evolution of new protein functions.

A "fragment" is a unique portion of KPP or a polynucleotide encoding KPP which can be identical in sequence to, but shorter in length than, the parent sequence. A fragment may comprise up to the entire length of the defined sequence, minus one nucleotide/amino acid residue. For example, a fragment may comprise from about 5 to about 1000 contiguous nucleotides or amino acid residues. A fragment used as a probe, primer, antigen, therapeutic molecule, or for other purposes, may be at least 5, 10, 15, 16, 20, 25, 30, 40, 50, 60, 75, 100, 150, 250 or at least 500 contiguous nucleotides or amino acid residues in length. Fragments may be preferentially selected from certain regions of a molecule. For example, a polypeptide fragment may comprise a certain length of contiguous amino acids selected from the first 250 or 500 amino acids (or first 25% or 50%) of a polypeptide as shown in a certain defined sequence. Clearly these lengths are exemplary, and any length that is supported by the specification, including the Sequence Listing, tables, and figures, may be encompassed by the present embodiments.

A fragment of SEQ ID NO:44-86 can comprise a region of unique polynucleotide sequence that specifically identifies SEQ ID NO:44-86, for example, as distinct from any other sequence in the genome from which the fragment was obtained. A fragment of SEQ ID NO:44-86 can be employed in one or more embodiments of methods of the invention, for example, in hybridization and amplification technologies and in analogous methods that distinguish SEQ ID NO:44-86 from related polynucleotides. The precise length of a fragment of SEQ ID NO:44-86 and the region of SEQ ID NO:44-86 to which the fragment corresponds are routinely determinable by one of ordinary skill in the art based on the intended purpose for the fragment.

A fragment of SEQ ID NO:1-43 is encoded by a fragment of SEQ ID NO:44-86. A fragment of SEQ ID NO:1-43 can comprise a region of unique amino acid sequence that specifically identifies SEQ ID NO:1-43. For example, a fragment of SEQ ID NO:1-43 can be used as an immunogenic peptide for the development of antibodies that specifically recognize SEQ ID NO:1-43. The precise length of a fragment of SEQ ID NO:1-43 and the region of SEQ ID NO:1-43 to which the fragment corresponds can be determined based on the intended purpose for the fragment using one or more analytical methods described herein or otherwise known in the art.

A "full length" polynucleotide is one containing at least a translation initiation codon (e.g., methionine) followed by an open reading frame and a translation termination codon. A "full length" polynucleotide sequence encodes a "full length" polypeptide sequence.

"Homology" refers to sequence similarity or, alternatively, sequence identity, between two or more polynucleotide sequences or two or more polypeptide sequences.

The terms "percent identity" and "% identity," as applied to polynucleotide sequences, refer to the percentage of identical nucleotide matches between at least two polynucleotide sequences aligned using a standardized algorithm. Such an algorithm may insert, in a standardized and reproducible way, gaps in the sequences being compared in order to optimize alignment between two sequences, and therefore achieve a more meaningful comparison of the two sequences.

Percent identity between polynucleotide sequences may be determined using one or more computer algorithms or programs known in the art or described herein. For example, percent identity can be determined using the default parameters of the CLUSTAL V algorithm as incorporated into the MEGALIGN version 3.12e sequence alignment program. This program is part of the LASERGENE software package, a suite of molecular biological analysis programs (DNASTAR, Madison Wis.). CLUSTAL V is described in Higgins, D. G. and P. M. Sharp (1989; CABIOS 5:151-153) and in Higgins, D. G. et al. (1992; CABIOS 8:189-191). For pairwise alignments of polynucleotide sequences, the default parameters are set as follows: Ktuple=2, gap penalty=5, window=4, and "diagonals saved"=4. The "weighted" residue weight table is selected as the default.

Alternatively, a suite of commonly used and freely available sequence comparison algorithms which can be used is provided by the National Center for Biotechnology Information (NCBI) Basic Local Alignment Search Tool (BLAST) (Altschul, S. F. et al. (1990) J. Mol. Biol. 215:403-410), which is available from several sources, including the NCBI, Bethesda, Md., and on the Internet at ncbi.nlm.nih.gov/BLAST/. The BLAST software suite includes various sequence analysis programs including "blastn," that is used to align a known polynucleotide sequence with other polynucleotide sequences from a variety of databases. Also available is a tool called "BLAST 2 Sequences" that is used for direct pairwise comparison of two nucleotide sequences. "BLAST 2 Sequences" can be accessed and used interactively at ncbi.nlm.nih.gov/gorf/b12.html. The "BLAST 2 Sequences" tool can be used for both blastn and blastp (discussed below). BLAST programs are commonly used with gap and other parameters set to default settings. For example, to compare two nucleotide sequences, one may use blastn with the "BLAST 2 Sequences" tool Version 2.0.12 (Apr. 21, 2000) set at default parameters. Such default parameters may be, for example:

Matrix: BLOSUM62
Reward for match: 1
Penalty for mismatch: −2
Open Gap: 5 and Extension Gap: 2 penalties
Gap.times.drop-off: 50
Expect: 10
Word Size: 11
Filter: on Percent identity may be measured over the length of an entire defined sequence, for example, as defined by a particular SEQ ID number, or may be measured over a shorter length, for example, over the length of a fragment taken from a larger, defined sequence, for instance, a fragment of at least 20, at least 30, at least 40, at least 50, at least 70, at least 100, or at least 200 contiguous nucleotides. Such lengths are exemplary only, and it is understood that any fragment length supported by the sequences shown herein, in the tables, figures, or Sequence Listing, may be used to describe a length over which percentage identity may be measured.

Nucleic acid sequences that do not show a high degree of identity may nevertheless encode similar amino acid sequences due to the degeneracy of the genetic code. It is understood that changes in a nucleic acid sequence can be made using this degeneracy to produce multiple nucleic acid sequences that all encode substantially the same protein.

The phrases "percent identity" and "% identity," as applied to polypeptide sequences, refer to the percentage of identical residue matches between at least two polypeptide sequences aligned using a standardized algorithm. Methods of polypeptide sequence alignment are well-known. Some alignment methods take into account conservative amino acid substitutions. Such conservative substitutions, explained in more detail above, generally preserve the charge and hydrophobicity at the site of substitution, thus preserving the structure (and therefore function) of the polypeptide. The phrases "percent similarity" and "% similarity," as applied to polypeptide sequences, refer to the percentage of residue matches, including identical residue matches and conservative substitutions, between at least two polypeptide sequences aligned using a standardized algorithm. In contrast, conservative substitutions are not included in the calculation of percent identity between polypeptide sequences.

Percent identity between polypeptide sequences may be determined using the default parameters of the CLUSTAL V algorithm as incorporated into the MEGALIGN version 3.12e sequence alignment program (described and referenced above). For pairwise alignments of polypeptide sequences using CLUSTAL V, the default parameters are set as follows:

Ktuple=1, gap penalty=3, window=5, and "diagonals saved"=5. The PAM250 matrix is selected as the default residue weight table.

Alternatively the NCBI BLAST software suite may be used. For example, for a pairwise comparison of two polypeptide sequences, one may use the "BLAST 2 Sequences" tool Version 2.0.12 (Apr. 21, 2000) with blastp set at default parameters. Such default parameters may be, for example:

Matrix: BLOSUM62

Open Gap: 11 and Extension Gap: 1 penalties

Gap.times.drop-off: 50

Expect: 10

Word Size: 3

Filter: on

Percent identity may be measured over the length of an entire defined polypeptide sequence, for example, as defined by a particular SEQ ID number, or may be measured over a shorter length, for example, over the length of a fragment taken from a larger, defined polypeptide sequence, for instance, a fragment of at least 15, at least 20, at least 30, at least 40, at least 50, at least 70 or at least 150 contiguous residues. Such lengths are exemplary only, and it is understood that any fragment length supported by the sequences shown herein, in the tables, figures or Sequence Listing, may be used to describe a length over which percentage identity may be measured.

"Human artificial chromosomes" (HACs) are linear microchromosomes which may contain DNA sequences of about 6 kb to 10 Mb in size and which contain all of the elements required for chromosome replication, segregation and maintenance.

The term "humanized antibody" refers to an antibody molecule in which the amino acid sequence in the non-antigen binding regions has been altered so that the antibody more closely resembles a human antibody, and still retains its original binding ability.

"Hybridization" refers to the process by which a polynucleotide strand anneals with a complementary strand through base pairing under defined hybridization conditions. Specific hybridization is an indication that two nucleic acid sequences share a high degree of complementarity. Specific hybridization complexes form under permissive annealing conditions and remain hybridized after the "washing" step(s). The washing step(s) is particularly important in determining the stringency of the hybridization process, with more stringent conditions allowing less non-specific binding, i.e., binding between pairs of nucleic acid strands that are not perfectly matched. Permissive conditions for annealing of nucleic acid sequences are routinely determinable by one of ordinary skill in the art and may be consistent among hybridization experiments, whereas wash conditions may be varied among experiments to achieve the desired stringency, and therefore hybridization specificity. Permissive annealing conditions occur, for example, at 68.degree. C. in the presence of about 6.times.SSC, about 1% (w/v) SDS, and about 100 .mu.g/ml sheared, denatured salmon sperm DNA.

Generally, stringency of hybridization is expressed, in part, with reference to the temperature under which the wash step is carried out. Such wash temperatures are typically selected to be about 5° C. to 20° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. An equation for calculating $T_m$ and conditions for nucleic acid hybridization are well known and can be found in Sambrook, J. and D. W. Russell (2001; *Molecular Cloning: A Laboratory Manual,* 3rd ed., vol. 1-3, Cold Spring Harbor Press, Cold Spring Harbor N.Y., ch. 9).

High stringency conditions for hybridization between polynucleotides of the present invention include wash conditions of 68° C. in the presence of about 0.2×SSC and about 0.1% SDS, for 1 hour. Alternatively, temperatures of about 65° C., 60° C., 55° C., or 42° C. may be used. SSC concentration may be varied from about 0.1 to 2×SSC, with SDS being present at about 0.1%. Typically, blocking reagents are used to block non-specific hybridization. Such blocking reagents include, for instance, sheared and denatured salmon sperm DNA at about 100-200 μg/ml. Organic solvent, such as formamide at a concentration of about 35-50% v/v, may also be used under particular circumstances, such as for RNA:DNA hybridizations. Useful variations on these wash conditions will be readily apparent to those of ordinary skill in the art. Hybridization, particularly under high stringency conditions, may be suggestive of evolutionary similarity between the nucleotides. Such similarity is strongly indicative of a similar role for the nucleotides and their encoded polypeptides.

The term "hybridization complex" refers to a complex formed between two nucleic acids by virtue of the formation of hydrogen bonds between complementary bases. A hybridization complex may be formed in solution (e.g., $C_0t$ or $R_0t$ analysis) or formed between one nucleic acid present in solution and another nucleic acid immobilized on a solid support (e.g., paper, membranes, filters, chips, pins or glass slides, or any other appropriate substrate to which cells or their nucleic acids have been fixed).

The words "insertion" and "addition" refer to changes in an amino acid or polynucleotide sequence resulting in the addition of one or more amino acid residues or nucleotides, respectively.

"Immune response" can refer to conditions associated with inflammation, trauma, immune disorders, or infectious or genetic disease, etc. These conditions can be characterized by expression of various factors, e.g., cytokines, chemokines, and other signaling molecules, which may affect cellular and systemic defense systems.

An "immunogenic fragment" is a polypeptide or oligopeptide fragment of KPP which is capable of eliciting an immune response when introduced into a living organism, for example, a mammal. The term "immunogenic fragment" also includes any polypeptide or oligopeptide fragment of KPP which is useful in any of the antibody production methods disclosed herein or known in the art.

The term "microarray" refers to an arrangement of a plurality of polynucleotides, polypeptides, antibodies, or other chemical compounds on a substrate.

The terms "element" and "array element" refer to a polynucleotide, polypeptide, antibody, or other chemical compound having a unique and defined position on a microarray.

The term "modulate" refers to a change in the activity of KPP. For example, modulation may cause an increase or a decrease in protein activity, binding characteristics, or any other biological, functional, or immunological properties of KPP.

The phrases "nucleic acid" and "nucleic acid sequence" refer to a nucleotide, oligonucleotide, polynucleotide, or any fragment thereof. These phrases also refer to DNA or RNA of genomic or synthetic origin which may be single-stranded or double-stranded and may represent the sense or the antisense strand, to peptide nucleic acid (PNA), or to any DNA-like or RNA-like material.

"Operably linked" refers to the situation in which a first nucleic acid sequence is placed in a functional relationship with a second nucleic acid sequence. For instance, a promoter is operably linked to a coding sequence if the promoter affects the transcription or expression of the coding sequence. Operably linked DNA sequences may be in close proximity or contiguous and, where necessary to join two protein coding regions, in the same reading frame.

"Peptide nucleic acid" (PNA) refers to an antisense molecule or anti-gene agent which comprises an oligonucleotide of at least about 5 nucleotides in length linked to a peptide backbone of amino acid residues ending in lysine. The terminal lysine confers solubility to the composition. PNAs preferentially bind complementary single stranded DNA or RNA and stop transcript elongation, and may be pegylated to extend their lifespan in the cell.

"Post-translational modification" of an KPP may involve lipidation, glycosylation, phosphorylation, acetylation, racemization, proteolytic cleavage, and other modifications known in the art. These processes may occur synthetically or biochemically. Biochemical modifications will vary by cell type depending on the enzymatic milieu of KPP.

"Probe" refers to nucleic acids encoding KPP, their complements, or fragments thereof, which are used to detect identical, allelic or related nucleic acids. Probes are isolated oligonucleotides or polynucleotides attached to a detectable label or reporter molecule. Typical labels include radioactive isotopes, ligands, chemiluminescent agents, and enzymes. "Primers" are short nucleic acids, usually DNA oligonucleotides, which may be annealed to a target polynucleotide by complementary base-pairing. The primer may then be extended along the target DNA strand by a DNA polymerase enzyme. Primer pairs can be used for amplification (and identification) of a nucleic acid, e.g., by the polymerase chain reaction (PCR).

Probes and primers as used in the present invention typically comprise at least 15 contiguous nucleotides of a known sequence. In order to enhance specificity, longer probes and primers may also be employed, such as probes and primers that comprise at least 20, 25, 30, 40, 50, 60, 70, 80, 90, 100, or at least 150 consecutive nucleotides of the disclosed nucleic acid sequences. Probes and primers may be considerably longer than these examples, and it is understood that any length supported by the specification, including the tables, figures, and Sequence Listing, may be used.

Methods for preparing and using probes and primers are described in, for example, Sambrook, J. and D. W. Russell (2001; *Molecular Cloning: A Laboratory Manual,* 3rd ed., vol. 1-3, Cold Spring Harbor Press, Cold Spring Harbor N.Y.), Ausubel, F. M. et al. (1999*; Short Protocols in Molecular Biology,* 4$^{th}$ ed., John Wiley & Sons, New York N.Y.), and Innis, M. et al. (1990*; PCR Protocols, A Guide to Methods and Applications*, Academic Press, San Diego Calif.). PCR primer pairs can be derived from a known sequence, for example, by using computer programs intended for that purpose such as Primer (Version 0.5, 1991, Whitehead Institute for Biomedical Research, Cambridge Mass.).

Oligonucleotides for use as primers are selected using software known in the art for such purpose. For example, OLIGO 4.06 software is useful for the selection of PCR primer pairs of up to 100 nucleotides each, and for the analysis of oligonucleotides and larger polynucleotides of up to 5,000 nucleotides from an input polynucleotide sequence of up to 32 kilobases. Similar primer selection programs have incorporated additional features for expanded capabilities. For example, the PrimOU primer selection program (available to the public from the Genome Center at University of Texas South West Medical Center, Dallas Tex.) is capable of choosing specific primers from megabase sequences and is thus useful for designing primers on a genome-wide scope. The Primer3 primer selection program (available to the public from the Whitehead Institute/MIT Center for Genome Research, Cambridge Mass.) allows the user to input a "mispriming library," in which sequences to avoid as primer binding sites are user-specified. Primer3 is useful, in particular, for the selection of oligonucleotides for microarrays. (The source code for the latter two primer selection programs may also be obtained from their respective sources and modified to meet the user's specific needs.) The PrimeGen program (available to the public from the UK Human Genome Mapping Project Resource Centre, Cambridge UK) designs primers based on multiple sequence alignments, thereby allowing selection of primers that hybridize to either the most conserved or least conserved regions of aligned nucleic acid sequences. Hence, this program is useful for identification of both unique and conserved oligonucleotides and polynucleotide fragments. The oligonucleotides and polynucleotide fragments identified by any of the above selection methods are useful in hybridization technologies, for example, as PCR or sequencing primers, microarray elements, or specific probes to identify fully or partially complementary polynucleotides in a sample of nucleic acids. Methods of oligonucleotide selection are not limited to those described above.

A "recombinant nucleic acid" is a nucleic acid that is not naturally occurring or has a sequence that is made by an artificial combination of two or more otherwise separated segments of sequence. This artificial combination is often accomplished by chemical synthesis or, more commonly, by the artificial manipulation of isolated segments of nucleic acids, e.g., by genetic engineering techniques such as those described in Sambrook and Russell (supra). The term recombinant includes nucleic acids that have been altered solely by addition, substitution, or deletion of a portion of the nucleic acid. Frequently, a recombinant nucleic acid may include a nucleic acid sequence operably linked to a promoter sequence. Such a recombinant nucleic acid may be part of a vector that is used, for example, to transform a cell.

Alternatively, such recombinant nucleic acids may be part of a viral vector, e.g., based on a vaccinia virus, that could be use to vaccinate a mammal wherein the recombinant nucleic acid is expressed, inducing a protective immunological response in the mammal.

A "regulatory element" refers to a nucleic acid sequence usually derived from untranslated regions of a gene and includes enhancers, promoters, introns, and 5' and 3' untranslated regions (UTRs). Regulatory elements interact with host or viral proteins which control transcription, translation, or RNA stability.

"Reporter molecules" are chemical or biochemical moieties used for labeling a nucleic acid, amino acid, or antibody. Reporter molecules include radionuclides; enzymes; fluorescent, chemiluminescent, or chromogenic agents; substrates; cofactors; inhibitors; magnetic particles; and other moieties known in the art.

An "RNA equivalent," in reference to a DNA molecule, is composed of the same linear sequence of nucleotides as the reference DNA molecule with the exception that all occurrences of the nitrogenous base thymine are replaced with uracil, and the sugar backbone is composed of ribose instead of deoxyribose.

The term "sample" is used in its broadest sense. A sample suspected of containing KPP, nucleic acids encoding KPP, or fragments thereof may comprise a bodily fluid; an extract from a cell, chromosome, organelle; or membrane isolated from a cell; a cell; genomic DNA, RNA, or cDNA, in solution or bound to a substrate; a tissue; a tissue print; etc.

The terms "specific binding" and "specifically binding" refer to that interaction between a protein or peptide and an agonist, an antibody, an antagonist, a small molecule, or any natural or synthetic binding composition. The interaction is dependent upon the presence of a particular structure of the protein, e.g., the antigenic determinant or epitope, recognized by the binding molecule. For example, if an antibody is specific for epitope "A," the presence of a polypeptide comprising the epitope A, or the presence of free unlabeled A, in a reaction containing free labeled A and the antibody will reduce the amount of labeled A that binds to the antibody.

The term "substantially purified" refers to nucleic acid or amino acid sequences that are removed from their natural environment and are isolated or separated, and are at least about 60% free, preferably at least about 75% free, and most preferably at least about 90% free from other components with which they are naturally associated.

A "substitution" refers to the replacement of one or more amino acid residues or nucleotides by different amino acid residues or nucleotides, respectively.

"Substrate" refers to any suitable rigid or semi-rigid support including membranes, filters, chips, slides, wafers, fibers, magnetic or nonmagnetic beads, gels, tubing, plates, polymers, microparticles and capillaries. The substrate can have a variety of surface forms, such as wells, trenches, pins, channels and pores, to which polynucleotides or polypeptides are bound.

A "transcript image" or "expression profile" refers to the collective pattern of gene expression by a particular cell type or tissue under given conditions at a given time.

"Transformation" describes a process by which exogenous DNA is introduced into a recipient cell. Transformation may occur under natural or artificial conditions according to various methods well known in the art, and may rely on any known method for the insertion of foreign nucleic acid sequences into a prokaryotic or eukaryotic host cell. The method for transformation is selected based on the type of host cell being transformed and may include, but is not limited to, bacteriophage or viral infection, electroporation, heat shock, lipofection, and particle bombardment. The term "transformed cells" includes stably transformed cells in which the inserted DNA is capable of replication either as an autonomously replicating plasmid or as part of the host chromosome, as well as transiently transformed cells which express the inserted DNA or RNA for limited periods of time.

A "transgenic organism," as used herein, is any organism, including but not limited to animals and plants, in which one or more of the cells of the organism contains heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. In another embodiment, the nucleic acid can be introduced by infection with a recombinant viral vector, such as a lentiviral vector (Lois, C. et al. (2002) Science 295:868-872). The term genetic manipulation does not include classical cross-breeding, or in vitro fertilization, but rather is directed to the introduction of a recombinant DNA molecule. The transgenic organisms contemplated in accordance with the present invention include bacteria, cyanobacteria, fungi, plants and animals. The isolated DNA of the present invention can be introduced into the host by methods known in the art, for example infection, transfection, transformation or transconjugation. Techniques for transferring the DNA of the present invention into such organisms are widely known and provided in references such as Sambrook and Russell (supra).

A "variant" of a particular nucleic acid sequence is defined as a nucleic acid sequence having at least 40% sequence identity to the particular nucleic acid sequence over a certain length of one of the nucleic acid sequences using blastn with the "BLAST 2 Sequences" tool Version 2.0.9 (May 7, 1999) set at default parameters. Such a pair of nucleic acids may show, for example, at least 50%, at least 60%, at least 70%, at least 80%, at least 85%, at least 90%, at least 91%, at least 92%, at least 93%, at least 94%, at least 95%, at least 96%, at least 97%, at least 98%, or at least 99% or greater sequence identity over a certain defined length. A variant may be described as, for example, an "allelic" (as defined above), "splice," "species," or "polymorphic" variant. A splice variant may have significant identity to a reference molecule, but will generally have a greater or lesser number of polynucleotides due to alternate splicing during mRNA processing. The corresponding polypeptide may possess additional functional domains or lack domains that are present in the reference molecule. Species variants are polynucleotides that vary from one species to another. The resulting polypeptides will generally have significant amino acid identity relative to each other. A polymorphic variant is a variation in the polynucleotide sequence of a particular gene between individuals of a given species. Polymorphic variants also may encompass "single nucleotide polymorphisms" (SNPs) in which the polynucleotide sequence varies by one nucleotide base. The presence of SNPs may be indicative of, for example, a certain population, a disease state, or a propensity for a disease state.

A "variant" of a particular polypeptide sequence is defined as a polypeptide sequence having at least 40% sequence identity or sequence similarity to the particular polypeptide sequence over a certain length of one of the polypeptide sequences using blastp with the "BLAST 2 Sequences" tool Version 2.0.9 (May 7, 1999) set at default parameters. Such a pair of polypeptides may show, for example, at least 50%, at least 60%, at least 70%, at least 80%, at least 85%, at least 90%, at least 91%, at least 92%, at least 93%, at least 94%, at least 95%, at least 96%, at least 97%, at least 98%, or at least 99% or greater sequence identity or sequence similarity over a certain defined length of one of the polypeptides.

THE INVENTION

Various embodiments of the invention include new human kinases and phosphatases (KPP), the polynucleotides encoding KPP, and the use of these compositions for the diagnosis, treatment, or prevention of cardiovascular diseases, immune system disorders, neurological disorders, disorders affecting growth and development, lipid disorders, cell proliferative disorders, and cancers.

Table 1 summarizes the nomenclature for the full length polynucleotide and polypeptide embodiments of the invention. Each polynucleotide and its corresponding polypeptide are correlated to a single Incyte project identification number (Incyte Project ID). Each polypeptide sequence is denoted by both a polypeptide sequence identification number (Polypeptide SEQ ID NO:) and an Incyte polypeptide sequence number (Incyte Polypeptide ID) as shown. Each polynucleotide sequence is denoted by both a polynucleotide sequence identification number (Polynucleotide SEQ ID NO:) and an Incyte polynucleotide consensus sequence number (Incyte Polynucleotide ID) as shown. Column 6 shows the Incyte ID numbers of physical, full length clones corresponding to the polypeptide and polynucleotide sequences of the invention.

The full length clones encode polypeptides which have at least 95% sequence identity to the polypeptide sequences shown in column 3.

Table 2 shows sequences with homology to polypeptide embodiments of the invention as identified by BLAST analysis against the GenBank protein (genpept) database and the PROTEOME database. Columns 1 and 2 show the polypeptide sequence identification number (Polypeptide SEQ ID NO:) and the corresponding Incyte polypeptide sequence number (Incyte Polypeptide ID) for polypeptides of the invention. Column 3 shows the GenBank identification number (GenBank ID NO:) of the nearest GenBank homolog and the PROTEOME database identification numbers (PROTEOME ID NO:) of the nearest PROTEOME database homologs. Column 4 shows the probability scores for the matches between each polypeptide and its homolog(s). Column 5 shows the annotation of the GenBank and PROTEOME database homolog(s) along with relevant citations where applicable, all of which are expressly incorporated by reference herein.

Table 3 shows various structural features of the polypeptides of the invention. Columns 1 and 2 show the polypeptide sequence identification number (SEQ ID NO:) and the corresponding Incyte polypeptide sequence number (Incyte Polypeptide ID) for each polypeptide of the invention. Column 3 shows the number of amino acid residues in each polypeptide. Column 4 shows amino acid residues comprising signature sequences, domains, motifs, potential phosphorylation sites, and potential glycosylation sites. Column 5 shows analytical methods for protein structure/function analysis and in some cases, searchable databases to which the analytical methods were applied.

Together, Tables 2 and 3 summarize the properties of polypeptides of the invention, and these properties establish that the claimed polypeptides are kinases and phosphatases. For example, SEQ ID NO:11 is 78% identical, from residue M1 to residue W1219, to mouse NIK (GenBank ID g1872546) as determined by the Basic Local Alignment Search Tool (BLAST). (See Table 2.) The BLAST probability score is 0.0, which indicates the probability of obtaining the observed polypeptide sequence alignment by chance. SEQ ID NO:11 also has homology to proteins that activate the c-Jun N-terminal kinase (Mapk8) signaling pathway, and are mitogen-activated protein kinase kinase kinase kinases (MAP4K), as determined by BLAST analysis using the PROTEOME database. SEQ ID NO:11 also contains a CNH domain, a protein kinase domain, a domain found in NIK1-like kinases, and a serine/threonine kinase catalytic domain, as determined by searching for statistically significant matches in the hidden Markov model (HMM)-based PFAM and SMART databases of conserved protein families/domains. (See Table 3.) Data from BLIMPS, MOTIFS, and PROFILESCAN analyses, and BLAST analyses against the PRODOM and DOMO databases, provide further corroborative evidence that SEQ ID NO:11 is a protein kinase.

As another example, SEQ ID NO:15 is 99% identical, from residue E124 to residue I750, to human lymphoid phosphatase LyP1 (GenBank ID g4100632) as determined by the Basic Local Alignment Search Tool (BLAST). (See Table 2.) The BLAST probability score is 0.0, which indicates the probability of obtaining the observed polypeptide sequence alignment by chance. SEQ ID NO:15 also has homology to proteins that may be involved in T-cell development and are required for B-cell antigen receptor-mediated growth arrest and apoptosis and are protein tyrosine phosphatase non-receptors, as determined by BLAST analysis using the PROTEOME database. SEQ ID NO:15 also contains a protein-tyrosine phosphatase domain, a protein-tyrosine phosphatase catalytic domain, and a protein-tyrosine phosphatase catalytic motif domain as determined by searching for statistically significant matches in the hidden Markov model (HMM)-based SMART and PFAM databases of conserved protein families/domains. (See Table 3.) Data from BLIMPS, MOTIFS, and PROFILESCAN analyses, and BLAST analyses against the PRODOM and DOMO databases, provide further corroborative evidence that SEQ ID NO:15 is a protein-tyrosine phosphatase.

As another example, SEQ ID NO:24 is 99% identical, from residue M1 to residue K487, to human apyrase (GenBank ID g4583675) as determined by the Basic Local Alignment Search Tool (BLAST). (See Table 2.) The BLAST probability score is 3.7e-264, which indicates the probability of obtaining the observed polypeptide sequence alignment by chance. SEQ ID NO:24 also has homology to proteins that are localized to the lysosomal/autophagic vacuoles and are apyrase proteins, as determined by BLAST analysis using the PROTEOME database. SEQ ID NO:24 also contains a GDA1/CD39 (nucleoside phosphatase family) domain as determined by searching for statistically significant matches hi the hidden Markov model (HMM)-based PFAM database of conserved protein families/domains. (See Table 3.) Data from BLIMPS and BLAST analyses against the PRODOM and DOMO databases, provide further corroborative evidence that SEQ ID NO:24 is a nucleoside phosphatase.

As another example, SEQ ID NO:27 is 97% identical, from residue M1 to residue G76, to human SKRP1 (GenBank ID g18148911) as determined by the Basic Local Alignment Search Tool (BLAST). (See Table 2.) The BLAST probability score is 5.7e-35, which indicates the probability of obtaining the observed polypeptide sequence alignment by chance. SEQ ID NO:27 also has homology to proteins that dephosphorylate phosphotyrosine and phosphoserine, inactivate MAPK, and are proteins containing two dual specificity phosphatase catalytic domains, as determined by BLAST analysis using the PROTEOME database. Data from BLIMPS analyses provide further corroborative evidence that SEQ ID NO:27 is a dual specificity phosphatase.

As another example, SEQ ID NO:28 is 98% identical, from residue M1 to residue S449, to human protein phosphatase 4 regulatory subunit 2 (GenBank ID g8250239) as determined by the Basic Local Alignment Search Tool (BLAST). (See Table 2.) The BLAST probability score is 1.4E-241, which indicates the probability of obtaining the observed polypeptide sequence alignment by chance. SEQ ID NO:28 also has homology to human protein phosphatase 4 regulatory subunit 2, as determined by BLAST analysis using the PROTEOME database. The foregoing provide evidence that SEQ ID NO:28 is a protein phosphatase regulatory subunit.

As another example, SEQ ID NO:34 is 93% identical, from residue E39 to residue 1490, to human multifunctional calcium/calmodulin-dependent protein kinase II delta2 isoform (GenBank ID g4426595) as determined by the Basic Local Alignment Search Tool (BLAST). (See Table 2.) The BLAST probability score is 9.0e-255, which indicates the probability of obtaining the observed polypeptide sequence alignment by chance. SEQ ID NO:34 also has homology to calcium-calmodulin dependent protein kinase II delta, a member of the multifunctional CAMKII family involved in Ca2+ regulated processes, of which the alternative form delta 3 is specifically upregulated in the myocardium of patients with heart failure, as determined by BLAST analysis using the PROTEOME database. SEQ ID NO:34 also contains a protein kinase domain and a serine/threonine protein kinase catalytic domain as determined by searching for statistically significant matches in the hidden Markov model (HMM)-based PFAM and SMART databases of conserved protein families/domains. (See Table 3.) Data from BLIMPS, MOTIFS, and PROFILESCAN analyses, and BLAST analyses against the PRODOM and DOMO databases, provide further corroborative evidence that SEQ ID NO:34 is a calcium-calmodulin dependent protein kinase. The foregoing provides evidence that SEQ ID NO:34 is a calcium-calmodulin dependent protein kinase.

SEQ ID NO:1-10, SEQ ID NO:12-14, SEQ ID NO:16-23, SEQ ID NO:25-26, SEQ ID NO:29-33, and SEQ ID NO:35-43 were analyzed and annotated in a similar manner. The algorithms and parameters for the analysis of SEQ ID NO:1-43 are described in Table 7.

As shown in Table 4, the full length polynucleotide embodiments were assembled using cDNA sequences or coding (exon) sequences derived from genomic DNA, or any combination of these two types of sequences. Column 1 lists the polynucleotide sequence identification number (Polynucleotide SEQ ID NO:), the corresponding Incyte polynucleotide consensus sequence number (Incyte ID) for each polynucleotide of the invention, and the length of each polynucleotide sequence in basepairs. Column 2 shows the nucleotide start (5') and stop (3') positions of the cDNA and/or genomic sequences used to assemble the full length polynucleotide embodiments, and of fragments of the polynucleotides which are useful, for example, in hybridization or amplification technologies that identify SEQ ID NO:44-86 or that distinguish between SEQ ID NO:44-86 and related polynucleotides.

The polynucleotide fragments described in Column 2 of Table 4 may refer specifically, for example, to Incyte cDNAs derived from tissue-specific cDNA libraries or from pooled cDNA libraries. Alternatively, the polynucleotide fragments described in column 2 may refer to GenBank cDNAs or ESTs which contributed to the assembly of the full length polynucleotides. In addition, the polynucleotide fragments described in column 2 may identify sequences derived from the ENSEMBL (The Sanger Centre, Cambridge, UK) database (i.e., those sequences including the designation "ENST"). Alternatively, the polynucleotide fragments described in column 2 may be derived from the NCBI RefSeq Nucleotide Sequence Records Database (i.e., those sequences including the designation "NM" or "NT") or the NCBI RefSeq Protein Sequence Records (i.e., those sequences including the designation "NP"). Alternatively, the polynucleotide fragments described in column 2 may refer to assemblages of both cDNA and Genscan-predicted exons brought together by an "exon stitching" algorithm. For example, a polynucleotide sequence identified as FL_XXXXXX_$N_1$_$N_2$_YYYYY_$N_3$_$N_4$ represents a "stitched" sequence in which XXXXXX (is the identification number of the cluster of sequences to which the algorithm was applied, and YYYYY is the number of the prediction generated by the algorithm, and $N_{1,2,3 \ldots}$, if present, represent specific exons that may have been manually edited during analysis (See Example V). Alternatively, the polynucleotide fragments in column 2 may refer to assemblages of exons brought together by an "exon-stretching" algorithm. For example, a polynucleotide sequence identified as FLXXXXXX_gAAAAA_gBBBBB_1_N is a "stretched" sequence, with XXXXXX being the Incyte project identification number, gAAAAA being the GenBank identification number of the human genomic sequence to which the "exon-stretching" algorithm was applied, gBBBBB being the GenBank identification number or NCBI RefSeq identification number of the nearest GenBank protein homolog, and N referring to specific exons (See Example V). In instances where a RefSeq sequence was used as a protein homolog for the "exon-stretching" algorithm, a RefSeq identifier (denoted by "NM," "NP," or "NT") may be used in place of the GenBank identifier (i.e., gBBBBB).

Alternatively, a prefix identifies component sequences that were hand-edited, predicted from genomic DNA sequences, or derived from a combination of sequence analysis methods. The following Table lists examples of component sequence prefixes and corresponding sequence analysis methods associated with the prefixes (see Example IV and Example V).

| Prefix | Type of analysis and/or examples of programs |
|---|---|
| GNN, GFG, ENST | Exon prediction from genomic sequences using, for example, GENSCAN (Stanford University, CA, USA) or FGENES (Computer Genomics Group, The Sanger Centre, Cambridge, UK). |
| GBI | Hand-edited analysis of genomic sequences. |
| FL | Stitched or stretched genomic sequences (see Example V). |
| INCY | Full length transcript and exon prediction from mapping of EST sequences to the genome. Genomic location and EST composition data are combined to predict the exons and resulting transcript. |

In some cases, Incyte cDNA coverage redundant with the sequence coverage shown in Table 4 was obtained to confirm the final consensus polynucleotide sequence, but the relevant Incyte cDNA identification numbers are not shown.

Table 5 shows the representative cDNA libraries for those full length polynucleotides which were assembled using Incyte cDNA sequences. The representative cDNA library is the Incyte cDNA library which is most frequently represented by the Incyte cDNA sequences which were used to assemble and confirm the above polynucleotides. The tissues and vectors which were used to construct the cDNA libraries shown in Table 5 are described in Table 6.

Table 8 shows single nucleotide polymorphisms (SNPs) found in polynucleotide sequences of the invention, along with allele frequencies in different human populations. Columns 1 and 2 show the polynucleotide sequence identification number (SEQ ID NO:) and the corresponding Incyte project identification number (ND) for polynucleotides of the invention. Column 3 shows the Incyte identification number for the EST in which the SNP was detected (EST ID), and column 4 shows the identification number for the SNP (SNP ID). Column 5 shows the position within the EST sequence at which the SNP is located (EST SNP), and column 6 shows the position of the SNP within the full-length polynucleotide sequence (CB 1 SNP). Column 7 shows the allele found in the EST sequence. Columns 8 and 9 show the two alleles found at the SNP site. Column 10 shows the amino acid encoded by the codon including the SNP site, based upon the allele found in the EST. Columns 11-14 show the frequency of allele 1 in four different human populations. An entry of n/d (not detected) indicates that the frequency of allele 1 in the population was too low to be detected, while n/a (not available) indicates that the allele frequency was not determined for the population.

The invention also encompasses KPP variants. Various embodiments of KPP variants can have at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% amino acid sequence identity to the KPP amino acid sequence, and can contain at least one functional or structural characteristic of KPP.

Various embodiments also encompass polynucleotides which encode KPP. In a particular embodiment, the invention encompasses a polynucleotide sequence comprising a sequence selected from the group consisting of SEQ ID NO:44-86, which encodes KPP. The polynucleotide sequences of SEQ ID NO:44-86, as presented in the Sequence Listing, embrace the equivalent RNA sequences, wherein occurrences of the nitrogenous base thymine are replaced with uracil, and the sugar backbone is composed of ribose instead of deoxyribose.

The invention also encompasses variants of a polynucleotide encoding KPP. In particular, such a variant polynucleotide will have at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% polynucleotide sequence identity to a polynucleotide encoding KPP. A particular aspect of the invention encompasses a variant of a polynucleotide comprising a sequence selected from the group consisting of SEQ ID NO:44-86 which has at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% polynucleotide sequence identity to a nucleic acid sequence selected from the group consisting of SEQ ID NO:44-86. Any one of the polynucleotide variants described above can encode a polypeptide which contains at least one functional or structural characteristic of KPP.

In addition, or in the alternative, a polynucleotide variant of the invention is a splice variant of a polynucleotide encoding KPP. A splice variant may have portions which have significant sequence identity to a polynucleotide encoding KPP, but will generally have a greater or lesser number of nucleotides due to additions or deletions of blocks of sequence arising from alternate splicing during mRNA processing. A splice variant may have less than about 70%, or alternatively less than about 60%, or alternatively less than about 50% polynucleotide sequence identity to a polynucleotide encoding KPP over its entire length; however, portions of the splice variant will have at least about 70%, or alternatively at least about 85%, or alternatively at least about 95%, or alternatively 100% polynucleotide sequence identity to portions of the polynucleotide encoding KPP. For example, a polynucleotide comprising a sequence of SEQ ID NO:48, a polynucleotide comprising a sequence of SEQ ID NO:49 and a polynucleotide comprising a sequence of SEQ ID NO:50 are splice variants of each other; a polynucleotide comprising a sequence of SEQ ID NO:75 and a polynucleotide comprising a sequence of SEQ ID NO:76 are splice variants of each other; a polynucleotide comprising a sequence of SEQ ID NO:77 and a polynucleotide comprising a sequence of SEQ ID NO:78 are splice variants of each other; a polynucleotide comprising a sequence of SEQ ID NO:79 and a polynucleotide comprising a sequence of SEQ ID NO:80 are splice variants of each other; a polynucleotide comprising a sequence of SEQ ID NO:57 and a polynucleotide comprising a sequence of SEQ ID NO:62 are splice variants of each other, and a polynucleotide comprising a sequence of SEQ ID NO:68 and a polynucleotide comprising a sequence of SEQ ID NO:69 are splice variants of each other. Any one of the splice variants described above can encode a polypeptide which contains at least one functional or structural characteristic of KPP.

It will be appreciated by those skilled in the art that as a result of the degeneracy of the genetic code, a multitude of polynucleotide sequences encoding KPP, some bearing minimal similarity to the polynucleotide sequences of any known and naturally occurring gene, may be produced. Thus, the invention contemplates each and every possible variation of polynucleotide sequence that could be made by selecting combinations based on possible codon choices. These combinations are made in accordance with the standard triplet genetic code as applied to the polynucleotide sequence of naturally occurring KPP, and all such variations are to be considered as being specifically disclosed.

Although polynucleotides which encode KPP and its variants are generally capable of hybridizing to polynucleotides encoding naturally occurring KPP under appropriately selected conditions of stringency, it may be advantageous to produce polynucleotides encoding KPP or its derivatives possessing a substantially different codon usage, e.g., inclusion of non-naturally occurring codons. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding KPP and its derivatives without altering the encoded amino acid sequences include the production of RNA transcripts having more desirable properties, such as a greater half-life, than transcripts produced from the naturally occurring sequence.

The invention also encompasses production of polynucleotides which encode KPP and KPP derivatives, or fragments thereof, entirely by synthetic chemistry. After production, the synthetic polynucleotide may be inserted into any of the many available expression vectors and cell systems using reagents well known in the art. Moreover, synthetic chemistry may be used to introduce mutations into a polynucleotide encoding KPP or any fragment thereof.

Embodiments of the invention can also include polynucleotides that are capable of hybridizing to the claimed polynucleotides, and, in particular, to those having the sequences shown in SEQ ID NO:44-86 and fragments thereof, under various conditions of stringency (Wahl, G. M. and S. L. Berger (1987) Methods Enzymol. 152:399-407; Kimmel, A. R. (1987) Methods Enzymol. 152:507-511). Hybridization conditions, including annealing and wash conditions, are described in "Definitions."

Methods for DNA sequencing are well known in the art and may be used to practice any of the embodiments of the invention. The methods may employ such enzymes as the Klenow fragment of DNA polymerase I, SEQUENASE (US Biochemical, Cleveland Ohio), Taq polymerase (Applied Biosystems), thermostable T7 polymerase (Amersham Biosciences, Piscataway N.J.), or combinations of polymerases and proofreading exonucleases such as those found in the ELONGASE amplification system (Invitrogen, Carlsbad Calif.). Preferably, sequence preparation is automated with machines such as the MICROLAB 2200 liquid transfer system (Hamilton, Reno Nev.), PTC200 thermal cycler (MJ Research, Watertown Mass.) and ABI CATALYST 800 thermal cycler (Applied Biosystems). Sequencing is then carried out using either the ABI 373 or 377 DNA sequencing system (Applied Biosystems), the MEGABACE 1000 DNA sequencing system (Amersham Biosciences), or other systems known in the art. The resulting sequences are analyzed using a variety of algorithms which are well known in the art (Ausubel et al., supra, ch. 7; Meyers, R. A. (1995) *Molecular Biology and Biotechnology*, Wiley V C H, New York N.Y., pp. 856-853).

The nucleic acids encoding KPP may be extended utilizing a partial nucleotide sequence and employing various PCR-based methods known in the art to detect upstream sequences, such as promoters and regulatory elements. For example, one method which may be employed, restriction-site PCR, uses universal and nested primers to amplify unknown sequence from genomic DNA within a cloning vector (Sarkar, G. (1993) PCR Methods Applic. 2:318-322). Another method, inverse PCR, uses primers that extend in divergent directions to amplify unknown sequence from a circularized template. The template is derived from restriction fragments comprising a known genomic locus and surrounding sequences (Triglia, T. et al. (1988) Nucleic Acids Res. 16:8186). A third method, capture PCR, involves PCR amplification of DNA fragments adjacent to known sequences in human and yeast artificial chromosome DNA (Lagerstrom, M. et al. (1991) PCR Methods Applic. 1:111-119). In this method, multiple restriction enzyme digestions and ligations may be used to insert an engineered double-stranded sequence into a region of unknown sequence before performing PCR. Other methods which may be used to retrieve unknown sequences are known in the art (Parker, J. D. et al. (1991) Nucleic Acids Res. 19:3055-3060). Additionally, one may use PCR, nested primers, and PROMOTERFINDER libraries (BD Clontech, Palo Alto Calif.) to walk genomic DNA. This procedure avoids the need to screen libraries and is useful in finding intron/exon junctions. For all PCR-based methods, primers may be designed using commercially available software, such as OLIGO 4.06 primer analysis software (National Biosciences, Plymouth Minn.) or another appropriate program, to be about 22 to 30 nucleotides in length, to have a GC content of about 50% or more, and to anneal to the template at temperatures of about 68° C. to 72° C.

When screening for full length cDNAs, it is preferable to use libraries that have been size-selected to include larger cDNAs. In addition, random-primed libraries, which often include sequences containing the 5' regions of genes, are preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different nucleotide-specific, laser-stimulated fluorescent dyes, and a charge coupled device camera for detection of the emitted wavelengths. Output/light intensity may be converted to electrical signal using appropriate software (e.g., GENOTYPER and SEQUENCE NAVIGATOR, Applied Biosystems), and the entire process from loading of samples to computer analysis and electronic data display may be computer controlled. Capillary electrophoresis is especially preferable for sequencing small DNA fragments which may be present in limited amounts in a particular sample.

In another embodiment of the invention, polynucleotides or fragments thereof which encode KPP may be cloned in recombinant DNA molecules that direct expression of KPP, or fragments or functional equivalents thereof, in appropriate host cells. Due to the inherent degeneracy of the genetic code, other polynucleotides which encode substantially the same or a functionally equivalent polypeptides may be produced and used to express KPP.

The polynucleotides of the invention can be engineered, using methods generally known in the art in order to alter KPP-encoding sequences for a variety of purposes including, but not limited to, modification of the cloning, processing, and/or expression of the gene product. DNA shuffling by random fragmentation and PCR reassembly of gene fragments and synthetic oligonucleotides may be used to engineer the nucleotide sequences. For example, oligonucleotide-mediated site-directed mutagenesis may be used to introduce mutations that create new restriction sites, alter glycosylation patterns, change codon preference, produce splice variants, and so forth.

The nucleotides of the present invention may be subjected to DNA shuffling techniques such as MOLECULAR BREEDING (Maxygen Inc., Santa Clara Calif.; described in U.S. Pat. No. 5,837,458; Chang, C.-C. et al. (1999) Nat. Biotechnol. 17:793-797; Christians, F. C. et al. (1999) Nat. Biotechnol. 17:259-264; and Crameri, A. et al. (1996) Nat. Biotechnol. 14:315-319) to alter or improve the biological properties of KPP, such as its biological or enzymatic activity or its ability to bind to other molecules or compounds. DNA shuffling is a process by which a library of gene variants is produced using PCR-mediated recombination of gene fragments. The library is then subjected to selection or screening procedures that identify those gene variants with the desired properties. These preferred variants may then be pooled and further subjected to recursive rounds of DNA shuffling and selection/screening. Thus, genetic diversity is created through "artificial" breeding and rapid molecular evolution. For example, fragments of a single gene containing random point mutations may be recombined, screened, and then reshuffled until the desired properties are optimized. Alternatively, fragments of a given gene may be recombined with fragments of homologous genes in the same gene family, either from the same or different species, thereby maximizing the genetic diversity of multiple naturally occurring genes in a directed and controllable manner.

In another embodiment, polynucleotides encoding KPP may be synthesized, in whole or in part, using one or more chemical methods well known in the art (Caruthers, M. H. et al. (1980) Nucleic Acids Symp. Ser. 7:215-223; Horn, T. et al. (1980) Nucleic Acids Symp. Ser. 7:225-232). Alternatively, KPP itself or a fragment thereof may be synthesized using chemical methods known in the art. For example, peptide synthesis can be performed using various solution-phase or solid-phase techniques (Creighton, T. (1984) *Proteins, Structures and Molecular Properties*, WH Freeman, New York N.Y., pp. 55-60; Roberge, J. Y. et al. (1995) Science 269:202-204). Automated synthesis may be achieved using the ABI 431A peptide synthesizer (Applied Biosystems). Additionally, the amino acid sequence of KPP, or any part thereof, may be altered during direct synthesis and/or combined with sequences from other proteins, or any part thereof, to produce a variant polypeptide or a polypeptide having a sequence of a naturally occurring polypeptide.

The peptide may be substantially purified by preparative high performance liquid chromatography (Chiez, R. M. and F. Z. Regnier (1990) Methods Enzymol. 182:392-421). The composition of the synthetic peptides may be confirmed by amino acid analysis or by sequencing (Creighton, supra, pp. 28-53).

In order to express a biologically active KPP, the polynucleotides encoding KPP or derivatives thereof may be inserted into an appropriate expression vector, i.e., a vector which contains the necessary elements for transcriptional and translational control of the inserted coding sequence in a suitable host. These elements include regulatory sequences, such as enhancers, constitutive and inducible promoters, and 5' and 3' untranslated regions in the vector and in polynucleotides encoding KPP. Such elements may vary in their strength and specificity. Specific initiation signals may also be used to achieve more efficient translation of polynucleotides encoding KPP. Such signals include the ATG initiation codon and adjacent sequences, e.g. the Kozak sequence. In cases where a polynucleotide sequence encoding KPP and its initiation codon and upstream regulatory sequences are inserted into the appropriate expression vector, no additional transcriptional or translational control signals may be needed. However, in cases where only coding sequence, or a fragment thereof, is inserted, exogenous translational control signals including an in-frame ATG initiation codon should be provided by the vector. Exogenous translational elements and initiation codons may be of various origins, both natural and synthetic. The efficiency of expression may be enhanced by the inclusion of enhancers appropriate for the particular host cell system used (Scharf, D. et al. (1994) Results Probl. Cell Differ. 20:125-162).

Methods which are well known to those skilled in the art may be used to construct expression vectors containing polynucleotides encoding KPP and appropriate transcriptional and translational control elements. These methods include in vitro recombinant DNA techniques, synthetic techniques, and in vivo genetic recombination (Sambrook and Russell, supra, ch. 1-4, and 8; Ausubel et al., supra, ch. 1, 3, and 15).

A variety of expression vector/host systems may be utilized to contain and express polynucleotides encoding KPP. These include, but are not limited to, microorganisms such as bacteria transformed with recombinant bacteriophage, plasmid, or cosmid DNA expression vectors; yeast transformed with yeast expression vectors; insect cell systems infected with viral expression vectors (e.g., baculovirus); plant cell systems transformed with viral expression vectors (e.g., cauliflower mosaic virus, CaMV, or tobacco mosaic virus, TMV) or with bacterial expression vectors (e.g., Ti or pBR322 plasmids); or animal cell systems (Sambrook and Russell, supra; Ausubel et al., supra; Van Heeke, G. and S. M. Schuster (1989) J. Biol. Chem. 264:5503-5509; Engelhard, E. K. et al. (1994) Proc. Natl. Acad. Sci. USA 91:3224-3227; Sandig, V. et al. (1996) Hum. Gene Ther. 7:1937-1945; Takamatsu, N. EMBO J. 6:307-311; *The McGraw Hill Yearbook of Science and Technology* (1992) McGraw Hill, New York N.Y., pp. 191-196; Logan, J. and T. Shenk (1984) Proc. Natl. Acad. Sci. USA 81:3655-3659; Harrington, J. J. et al. (1997) Nat. Genet. 15:345-355). Expression vectors derived from retroviruses, adenoviruses, or herpes or vaccinia viruses, or from various bacterial plasmids, may be used for delivery of polynucleotides to the targeted organ, tissue, or cell population (Di Nicola, M. et al. (1998) Cancer Gen. Ther. 5:350-356; Yu, M. et al. (1993) Proc. Natl. Acad. Sci. USA 90:6340-6344; Buller, R. M. et al. (1985) Nature 317:813-815; McGregor, D. P. et al. (1994) Mol. Immunol. 31:219-226; Verma, I. M. and N. Sonia (1997) Nature 389:239-242). The invention is not limited by the host cell employed.

In bacterial systems, a number of cloning and expression vectors may be selected depending upon the use intended for polynucleotides encoding KPP. For example, routine cloning, subcloning, and propagation of polynucleotides encoding KPP can be achieved using a multifunctional *E. coli* vector such as PBLUESCRIPT (Stratagene, La Jolla Calif.) or PSPORT1 plasmid (Invitrogen). Ligation of polynucleotides encoding KPP into the vector's multiple cloning site disrupts the lacZ gene, allowing a colorimetric screening procedure for identification of transformed bacteria containing recombinant molecules. In addition, these vectors may be useful for in vitro transcription, dideoxy sequencing, single strand rescue with helper phage, and creation of nested deletions in the cloned sequence (Van Heeke, G. and S. M. Schuster (1989) J. Biol. Chem. 264:5503-5509). When large quantities of KPP are needed, e.g. for the production of antibodies, vectors which direct high level expression of KPP may be used. For example, vectors containing the strong, inducible SP6 or T7 bacteriophage promoter may be used.

Yeast expression systems may be used for production of KPP. A number of vectors containing constitutive or inducible promoters, such as alpha factor, alcohol oxidase, and PGH promoters, may be used in the yeast *Saccharomyces cerevisiae* or *Pichia pastoris*. In addition, such vectors direct either the secretion or intracellular retention of expressed proteins and enable integration of foreign polynucleotide sequences into the host genome for stable propagation (Ausubel et al, supra; Bitter, G. A. et al. (1987) Methods Enzymol. 153:516-544; Scorer, C. A. et al. (1994) Bio/Technology 12:181-184).

Plant systems may also be used for expression of KPP. Transcription of polynucleotides encoding KPP may be driven by viral promoters, e.g., the 35S and 19S promoters of CaMV used alone or in combination with the omega leader sequence from TMV (Takamatsu, N. (1987) EMBO J. 6:307-311). Alternatively, plant promoters such as the small subunit of RUBISCO or heat shock promoters may be used (Coruzzi, G. et al. (1984) EMBO J. 3:1671-1680; Broglie, R. et al. (1984) Science 224:838-843; Winter, J. et al. (1991) Results Probl. Cell Differ. 17:85-105). These constructs can be introduced into plant cells by direct DNA transformation or pathogen-mediated transfection (*The McGraw Hill Yearbook of Science and Technology* (1992) McGraw Hill, New York N.Y., pp. 191-196).

In mammalian cells, a number of viral-based expression systems may be utilized. In cases where an adenovirus is used as an expression vector, polynucleotides encoding KPP may be ligated into an adenovirus transcription/translation complex consisting of the late promoter and tripartite leader sequence. Insertion in a non-essential E1 or E3 region of the viral genome may be used to obtain infective virus which expresses KPP in host cells (Logan, J. and T. Shenk (1984) Proc. Natl. Acad. Sci. USA 81:3655-3659). In addition, transcription enhancers, such as the Rous sarcoma virus (RSV) enhancer, may be used to increase expression in mammalian host cells. SV40 or EBV-based vectors may also be used for high-level protein expression.

Human artificial chromosomes (HACs) may also be employed to deliver larger fragments of DNA than can be contained in and expressed from a plasmid. HACs of about 6 kb to 10 Mb are constructed and delivered via conventional delivery methods (liposomes, polycationic amino polymers, or vesicles) for therapeutic purposes (Harrington, J. J. et al. (1997) Nat. Genet. 15:345-355).

For long term production of recombinant proteins in mammalian systems, stable expression of KPP in cell lines is preferred. For example, polynucleotides encoding KPP can be transformed into cell lines using expression vectors which may contain viral origins of replication and/or endogenous expression elements and a selectable marker gene on the same or on a separate vector. Following the introduction of the vector, cells may be allowed to grow for about 1 to 2 days in enriched media before being switched to selective media. The purpose of the selectable marker is to confer resistance to a selective agent, and its presence allows growth and recovery of cells which successfully express the introduced sequences. Resistant clones of stably transformed cells may be propagated using tissue culture techniques appropriate to the cell type.

Any number of selection systems may be used to recover transformed cell lines. These include, but are not limited to, the herpes simplex virus thymidine kinase and adenine phosphoribosyltransferase genes, for use in tk' and apr' cells, respectively (Wigler, M. et al. (1977) Cell 11:223-232; Lowy, I. et al. (1980) Cell 22:817-823). Also, antimetabolite, antibiotic, or herbicide resistance can be used as the basis for selection. For example, dhfr confers resistance to methotrexate; neo confers resistance to the aminoglycosides neomycin and G-418; and als and pat confer resistance to chlorsulfuron and phosphinotricin acetyltransferase, respectively (Wigler, M. et al. (1980) Proc. Natl. Acad. Sci. USA 77:3567-3570; Colbere-Garapin, F. et al. (1981) J. Mol. Biol. 150:1-14). Additional selectable genes have been described, e.g., tipB and hisD, which alter cellular requirements for metabolites (Hartman, S. C. and R. C. Mulligan (1988) Proc. Natl. Acad. Sci. USA 85:8047-8051). Visible markers, e.g., anthocyanins, green fluorescent proteins (GFP; BD Clontech), β-glucuronidase and its substrate β-glucuronide, or luciferase and its substrate luciferin may be used. These markers can be used not only to identify transformants, but also to quantify the amount of transient or stable protein expression attributable to a specific vector system (Rhodes, C. A. (1995) Methods Mol. Biol. 55:121-131).

Although the presence/absence of marker gene expression suggests that the gene of interest is also present, the presence and expression of the gene may need to be confirmed. For example, if the sequence encoding KPP is inserted within a marker gene sequence, transformed cells containing polynucleotides encoding KPP can be identified by the absence of marker gene function. Alternatively, a marker gene can be placed in tandem with a sequence encoding KPP under the control of a single promoter. Expression of the marker gene in response to induction or selection usually indicates expression of the tandem gene as well.

In general, host cells that contain the polynucleotide encoding KPP and that express KPP may be identified by a variety of procedures known to those of skill in the art. These procedures include, but are not limited to, DNA-DNA or DNA-RNA hybridizations, PCR amplification, and protein bioassay or immunoassay techniques which include membrane, solution, or chip based technologies for the detection and/or quantification of nucleic acid or protein sequences.

Immunological methods for detecting and measuring the expression of KPP using either specific polyclonal or monoclonal antibodies are known in the art. Examples of such techniques include enzyme-linked immunosorbent assays (ELISAs), radioimmunoassays (RIM), and fluorescence activated cell sorting (FACS). A two-site, monoclonal-based immunoassay utilizing monoclonal antibodies reactive to two non-interfering epitopes on KPP is preferred, but a competitive binding assay may be employed. These and other assays are well known in the art (Hampton, R. et al. (1990) *Serological Methods, a Laboratory Manual*, APS Press, St. Paul Minn., Sect. IV; Coligan, J. E. et al. (1997) *Current Protocols in Immunology*, Greene Pub. Associates and Wiley-Interscience, New York N.Y.; Pound, J. D. (1998) *Immunochemical Protocols*, Humana Press, Totowa N.J.).

A wide variety of labels and conjugation techniques are known by those skilled in the art and may be used in various nucleic acid and amino acid assays. Means for producing labeled hybridization or PCR probes for detecting sequences related to polynucleotides encoding KPP include oligolabeling, nick translation, end-labeling, or PCR amplification using a labeled nucleotide. Alternatively, polynucleotides encoding KPP, or any fragments thereof, may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits, such as those provided by Amersham Biosciences, Promega (Madison Wis.), and US Biochemical. Suitable reporter molecules or labels which may be used for ease of detection include radionuclides, enzymes, fluorescent, chemiluminescent, or chromogenic agents, as well as substrates, cofactors, inhibitors, magnetic particles, and the like.

Host cells transformed with polynucleotides encoding KPP may be cultured under conditions suitable for the expression and recovery of the protein from cell culture. The protein produced by a transformed cell may be secreted or retained intracellularly depending on the sequence and/or the vector used. As will be understood by those of skill in the art, expression vectors containing polynucleotides which encode KPP may be designed to contain signal sequences which direct secretion of KPP through a prokaryotic or eukaryotic cell membrane.

In addition, a host cell strain may be chosen for its ability to modulate expression of the inserted polynucleotides or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" or "pro" form of the protein may also be used to specify protein targeting, folding, and/or activity. Different host cells which have specific cellular machinery and characteristic mechanisms for post-translational activities (e.g., CHO, HeLa, MDCK, HEK293, and W138) are available from the American Type Culture Collection (ATCC, Manassas Va.) and may be chosen to ensure the correct modification and processing of the foreign protein.

In another embodiment of the invention, natural, modified, or recombinant polynucleotides encoding KPP may be ligated to a heterologous sequence resulting in translation of a fusion protein in any of the aforementioned host systems. For example, a chimeric KPP protein containing a heterologous moiety that can be recognized by a commercially available antibody may facilitate the screening of peptide libraries for inhibitors of KPP activity. Heterologous protein and peptide moieties may also facilitate purification of fusion proteins using commercially available affinity matrices. Such moieties include, but are not limited to, glutathione S-transferase (GST), maltose binding protein (MBP), thioredoxin (Trx), calmodulin binding peptide (CBP), 6-His (SEQ ID NO: 87), FLAG, c-myc, and hemagglutinin (HA). GST, MBP, Trx, CBP, and 6-His (SEQ ID NO: 87) enable purification of their cognate fusion proteins on immobilized glutathione, maltose, phenylarsine oxide, calmodulin, and metal-chelate resins, respectively. FLAG, c-myc, and hemagglutinin (HA) enable immunoaffinity purification of fusion proteins using commercially available monoclonal and polyclonal antibodies that specifically recognize these epitope tags. A fusion protein may also be engineered to contain a proteolytic cleavage site located between the KPP encoding sequence and the heterologous protein sequence, so that KPP may be cleaved away from the heterologous moiety following purification. Methods for fusion protein expression and purification are discussed in Ausubel et al. (supra, ch. 10 and 16). A variety of commercially available kits may also be used to facilitate expression and purification of fusion proteins.

In another embodiment, synthesis of radiolabeled KPP may be achieved in vitro using the TNT rabbit reticulocyte lysate or wheat germ extract system (Promega). These systems couple transcription and translation of protein-coding sequences operably associated with the T7, T3, or SP6 promoters. Translation takes place in the presence of a radiolabeled amino acid precursor, for example, $^{35}$S-methionine.

KPP, fragments of KPP, or variants of KPP may be used to screen for compounds that specifically bind to KPP. One or more test compounds may be screened for specific binding to KPP. In various embodiments, 1, 2, 3, 4, 5, 10, 20, 50, 100, or 200 test compounds can be screened for specific binding to KPP. Examples of test compounds can include antibodies, anticalins, oligonucleotides, proteins (e.g., ligands or receptors), or small molecules.

In related embodiments, variants of KPP can be used to screen for binding of test compounds, such as antibodies, to KPP, a variant of KPP, or a combination of KPP and/or one or more variants KPP. In an embodiment, a variant of KPP can be used to screen for compounds that bind to a variant of KPP, but not to KPP having the exact sequence of a sequence of SEQ ID NO:1-43. KPP variants used to perform such screening can have a range of about 50% to about 99% sequence identity to KPP, with various embodiments having 60%, 70%, 75%, 80%, 85%, 90%, and 95% sequence identity.

In an embodiment, a compound identified in a screen for specific binding to KPP can be closely related to the natural ligand of KPP, e.g., a ligand or fragment thereof, a natural substrate, a structural or functional mimetic, or a natural binding partner (Coligan, J. E. et al. (1991) *Current Protocols in Immunology* 1(2): Chapter 5). In another embodiment, the compound thus identified can be a natural ligand of a receptor KPP (Howard, A. D. et al. (2001) Trends Pharmacol. Sci. 22:132-140; Wise, A. et al. (2002) Drug Discovery Today 7:235-246).

In other embodiments, a compound identified in a screen for specific binding to KPP can be closely related to the natural receptor to which KPP binds, at least a fragment of the receptor, or a fragment of the receptor including all or a portion of the ligand binding site or binding pocket. For example, the compound may be a receptor for KPP which is capable of propagating a signal, or a decoy receptor for KPP which is not capable of propagating a signal (Ashkenazi, A. and V. M. Divit (1999) Curr. Opin. Cell Biol. 11:255-260; Mantovani, A. et al. (2001) Trends Immunol. 22:328-336). The compound can be rationally designed using known techniques. Examples of such techniques include those used to construct the compound etanercept (ENBREL; Amgen Inc., Thousand Oaks Calif.), which is efficacious for treating rheumatoid arthritis in humans. Etanercept is an engineered p75 tumor necrosis factor (TNF) receptor dimer linked to the Fc portion of human $IgG_1$ (Taylor, P. C. et al. (2001) Curr. Opin. Immunol 13:611-616).

In one embodiment, two or more antibodies having similar or, alternatively, different specificities can be screened for specific binding to KPP, fragments of KPP, or variants of KPP. The binding specificity of the antibodies thus screened can thereby be selected to identify particular fragments or variants of KPP. In one embodiment, an antibody can be selected such that its binding specificity allows for preferential identification of specific fragments or variants of KPP. In another embodiment, an antibody can be selected such that its binding specificity allows for preferential diagnosis of a specific disease or condition having increased, decreased, or otherwise abnormal production of KPP.

In an embodiment, anticalins can be screened for specific binding, to KPP, fragments of KPP, or variants of KPP. Anticalins are ligand-binding proteins that have been constructed based on a lipocalin scaffold (Weiss, G. A. and H. B. Lowman (2000) Chem. Biol. 7:R177-R184; Skerra, A. (2001) J. Biotechnol. 74:257-275). The protein architecture of lipocalins can include a beta-barrel having eight antiparallel beta-strands, which supports four loops at its open end. These loops form the natural ligand-binding site of the lipocalins, a site which can be re-engineered in vitro by amino acid substitutions to impart novel binding specificities. The amino acid substitutions can be made using methods known in the art or described herein, and can include conservative substitutions (e.g., substitutions that do not alter binding specificity) or substitutions that modestly, moderately, or significantly alter binding specificity.

In one embodiment, screening for compounds which specifically bind to, stimulate, or inhibit KPP involves producing appropriate cells which express KPP, either as a secreted protein or on the cell membrane. Preferred cells can include cells from mammals, yeast, *Drosophila*, or *E. coli*. Cells expressing KPP or cell membrane fractions which contain KPP are then contacted with a test compound and binding, stimulation, or inhibition of activity of either KPP or the compound is analyzed.

An assay may simply test binding of a test compound to the polypeptide, wherein binding is detected by a fluorophore, radioisotope, enzyme conjugate, or other detectable label. For example, the assay may comprise the steps of combining at least one test compound with KPP, either in solution or affixed to a solid support, and detecting the binding of KPP to the compound. Alternatively, the assay may detect or measure binding of a test compound in the presence of a labeled competitor. Additionally, the assay may be carried out using cell-free preparations, chemical libraries, or natural product mixtures, and the test compound(s) may be free in solution or affixed to a solid support.

An assay can be used to assess the ability of a compound to bind to its natural ligand and/or to inhibit the binding of its natural ligand to its natural receptors. Examples of such assays include radio-labeling assays such as those described in U.S. Pat. No. 5,914,236 and U.S. Pat. No. 6,372,724. In a related embodiment, one or more amino acid substitutions can be introduced into a polypeptide compound (such as a receptor) to improve or alter its ability to bind to its natural ligands (Matthews, D. J. and J. A. Wells. (1994) Chem. Biol. 1:25-30). In another related embodiment, one or more amino acid substitutions can be introduced into a polypeptide compound (such as a ligand) to improve or alter its ability to bind to its natural receptors (Cunningham, B. C. and J. A. Wells (1991) Proc. Natl. Acad. Sci. USA 88:3407-3411; Lowman, H. B. et al. (1991) J. Biol. Chem. 266:10982-10988).

KPP, fragments of KPP, or variants of KPP may be used to screen for compounds that modulate the activity of KPP. Such compounds may include agonists, antagonists, or partial or inverse agonists. In one embodiment, an assay is performed under conditions permissive for KPP activity, wherein KPP is combined with at least one test compound, and the activity of KPP in the presence of a test compound is compared with the activity of KPP in the absence of the test compound. A change in the activity of KPP in the presence of the test compound is indicative of a compound that modulates the activity of KPP. Alternatively, a test compound is combined with an in vitro or cell-free system comprising KPP under conditions suitable for KPP activity, and the assay is performed. In either of these assays, a test compound which modulates the activity of KPP may do so indirectly and need not come in direct contact with the test compound. At least one and up to a plurality of test compounds may be screened.

In another embodiment, polynucleotides encoding KPP or their mammalian homologs may be "knocked out" in an animal model system using homologous recombination in embryonic stem (ES) cells. Such techniques are well known in the art and are useful for the generation of animal models of human disease (see, e.g., U.S. Pat. No. 5,175,383 and U.S. Pat. No. 5,767,337). For example, mouse ES cells, such as the mouse 129/SvJ cell line, are derived from the early mouse embryo and grown in culture. The ES cells are transformed with a vector containing the gene of interest disrupted by a marker gene, e.g., the neomycin phosphotransferase gene (neo; Capecchi, M. R. (1989) Science 244:1288-1292). The vector integrates into the corresponding region of the host genome by homologous recombination. Alternatively, homologous recombination takes place using the Cre-loxP system to knockout a gene of interest in a tissue- or developmental stage-specific manner (Marth, J. D. (1996) Clin. Invest. 97:1999-2002; Wagner, K. U. et al. (1997) Nucleic Acids Res. 25:4323-4330). Transformed ES cells are identified and microinjected into mouse cell blastocysts such as those from the C57BL/6 mouse strain. The blastocysts are surgically transferred to pseudopregnant dams, and the resulting chimeric progeny are genotyped and bred to produce heterozygous or homozygous strains. Transgenic animals thus generated may be tested with potential therapeutic or toxic agents.

Polynucleotides encoding KPP may also be manipulated in vitro in ES cells derived from human blastocysts. Human ES cells have the potential to differentiate into at least eight separate cell lineages including endoderm, mesoderm, and ectodermal cell types. These cell lineages differentiate into, for example, neural cells, hematopoietic lineages, and cardiomyocytes (Thomson, J. A. et al. (1998) Science 282:1145-1147).

Polynucleotides encoding KPP can also be used to create "knockin" humanized animals (pigs) or transgenic animals (mice or rats) to model human disease. With knockin technology, a region of a polynucleotide encoding KPP is injected into animal ES cells, and the injected sequence integrates into the animal cell genome. Transformed cells are injected into blastulae, and the blastulae are implanted as described above. Transgenic progeny or inbred lines are studied and treated with potential pharmaceutical agents to obtain information on treatment of a human disease. Alternatively, a mammal inbred to overexpress KPP, e.g., by secreting KPP in its milk, may also serve as a convenient source of that protein (Janne, J. et al. (1998) Biotechnol. Annu. Rev. 4:55-74).

Therapeutics

Chemical and structural similarity, e.g., in the context of sequences and motifs, exists between regions of KPP and kinases and phosphatases. In addition, examples of tissues expressing KPP can be found in Table 6 and can also be found in Example XI. Therefore, KPP appears to play a role in cardiovascular diseases, immune system disorders, neurological disorders, disorders affecting growth and development, lipid disorders, cell proliferative disorders, and cancers. In the treatment of disorders associated with increased KPP expression or activity, it is desirable to decrease the expression or activity of KPP. In the treatment of disorders associated with decreased KPP expression or activity, it is desirable to increase the expression or activity of KPP.

Therefore, in one embodiment, KPP or a fragment or derivative thereof may be administered to a subject to treat or prevent a disorder associated with decreased expression or activity of KPP.

Examples of such disorders include, but are not limited to, a cardiovascular disease such as arteriovenous fistula, atherosclerosis, hypertension, vasculitis, Raynaud's disease, aneurysms, arterial dissections, varicose veins, thrombophlebitis and phlebothrombosis, vascular tumors, and complications of thrombolysis, balloon angioplasty, vascular replacement, and coronary artery bypass graft surgery, congestive heart failure, ischemic heart disease, angina pectoris, myocardial infarction, hypertensive heart disease, degenerative valvular heart disease, calcific aortic valve stenosis, congenitally bicuspid aortic valve, mitral annular calcification, mitral valve prolapse, rheumatic fever and rheumatic heart disease, infective endocarditis, nonbacterial thrombotic endocarditis, endocarditis of systemic lupus erythematosus, carcinoid heart disease, cardiomyopathy, myocarditis, pericarditis, neoplastic heart disease, congenital heart disease, and complications of cardiac transplantation, congenital lung anomalies, atelectasis, pulmonary congestion and edema, pulmonary embolism, pulmonary hemorrhage, pulmonary infarction, pulmonary hypertension, vascular sclerosis, obstructive pulmonary disease, restrictive pulmonary disease, chronic obstructive pulmonary disease, emphysema, chronic bronchitis, bronchial asthma, bronchiectasis, bacterial pneumonia, viral and mycoplasmal pneumonia, lung abscess, pulmonary tuberculosis, diffuse interstitial diseases, pneumoconioses, sarcoidosis, idiopathic pulmonary fibrosis, desquamative interstitial pneumonitis, hypersensitivity pneumonitis, pulmonary eosinophilia bronchiolitis obliterans-organizing pneumonia, diffuse pulmonary hemorrhage syndromes, Goodpasture's syndromes, idiopathic pulmonary hemosiderosis, pulmonary involvement in collagen-vascular disorders, pulmonary alveolar proteinosis, lung tumors, inflammatory and noninflammatory pleural effusions, pneumothorax, pleural tumors, drug-induced lung disease, radiation-induced lung disease, and complications of lung transplantation; an immune system disorder such as acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, autoimmune polyendocrinopathy-candidiasis-ectodermal dystrophy (APECED), bronchitis, cholecystitis, contact dermatitis, Crohn's disease, atopic dermatitis, dermatomyositis, diabetes mellitus, emphysema, episodic lymphopenia with lymphocytotoxins, erythroblastosis fetalis, erythema nodosum, atrophic gastritis, glomerulonephritis, Goodpasture's syndrome, gout, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polymyositis, psoriasis, Reiter's syndrome, rheumatoid arthritis, scleroderma, Sjögren's syndrome, systemic anaphylaxis, systemic lupus erythematosus, systemic sclerosis, thrombocytopenic purpura, ulcerative colitis, uveitis, Werner syndrome, complications of cancer, hemodialysis, and extracorporeal circulation, viral, bacterial, fungal, parasitic, protozoal, and helminthic infections, and trauma; a neurological disorder such as epilepsy, ischemic cerebrovascular disease, stroke, cerebral neoplasms, Alzheimer's disease, Pick's disease, Huntington's disease, dementia, Parkinson's disease and other extrapyramidal disorders, amyotrophic lateral sclerosis and other motor neuron disorders, progressive neural muscular atrophy, retinitis pigmentosa, hereditary ataxias, multiple sclerosis and other demyelinating diseases, bacterial and viral meningitis, brain abscess, subdural empyema, epidural abscess, suppurative intracranial thrombophlebitis, myelitis and radiculitis, viral central nervous system disease, prion diseases including kuru, Creutzfeldt-Jakob disease, and Gerstmann-Straussler-Scheinker syndrome, fatal familial insomnia, nutritional and metabolic diseases of the nervous system, neurofibromatosis, tuberous sclerosis, cerebelloretinal hemangioblastomatosis, encephalotrigeminal syndrome, mental retardation and other developmental disorders of the central nervous system including Down syndrome, cerebral palsy, neuroskeletal disorders, autonomic nervous system disorders, cranial nerve disorders, spinal cord diseases, muscular dystrophy and other neuromuscular disorders, peripheral nervous system disorders, dermatomyositis and polymyositis, inherited, metabolic, endocrine, and toxic myopathies, myasthenia gravis, periodic paralysis, mental disorders including mood, anxiety, and schizophrenic disorders, seasonal affective disorder (SAD), akathesia, amnesia, catatonia, diabetic neuropathy, tardive dyskinesia, dystonias, paranoid psychoses, postherpetic neuralgia, Tourette's disorder, progressive supranuclear palsy, corticobasal degeneration, and familial frontotemporal dementia; a disorder affecting growth and development such as actinic keratosis, arteriosclerosis, atherosclerosis, bursitis, cirrhosis, hepatitis, mixed connective tissue disease (MCTD), myelofibrosis, paroxysmal nocturnal hemoglobinuria, polycythemia vera, psoriasis, primary thrombocythemia, renal tubular acidosis, anemia, Cushing's syndrome, achondroplastic dwarfism, Duchenne and Becker muscular dystrophy, epilepsy, gonadal dysgenesis, WAGR syndrome (Wilms' tumor, aniridia, genitourinary abnormalities, and mental retardation), Smith-Magenis syndrome, myelodysplastic syndrome, hereditary mucoepithelial dysplasia, hereditary keratodermas, hereditary neuropathies such as Charcot-Marie-Tooth disease and neurofibromatosis, hypothyroidism, hydrocephalus, seizure disorders such as Syndenhards chorea and cerebral palsy, spina bifida, anencephaly, craniorachischisis, congenital glaucoma, cataract, and sensorineural hearing loss; a lipid disorder such as fatty liver, cholestasis, primary biliary cirrhosis, carnitine deficiency, carnitine palmitoyltransferase deficiency, myoadenylate deaminase deficiency, hypertriglyceridemia, lipid storage disorders such Fabry's disease, Gaucher's disease, Niemann-Pick's disease, metachromatic leukodystrophy, adrenoleukodystrophy, GM.sub.2 gangliosidosis, and ceroid lipofuscinosis, abetalipoproteinemia, Tangier disease, hyperlipoproteinemia, diabetes mellitus, lipodystrophy, lipomatoses, acute panniculitis, disseminated fat necrosis, adiposis dolorosa, lipoid adrenal hyperplasia, minimal change disease, lipomas, atherosclerosis, hypercholesterolemia, hypercholesterolemia with hypertriglyceridemia, primary hypoalphalipoproteinemia, hypothyroidism, renal disease, liver disease, lecithin:cholesterol acyltransferase deficiency, cerebrotendinous xanthomatosis, sitosterolemia, hypocholesterolemia, Tay-Sachs disease, Sandhoffs disease, hyperlipidemia, hyperlipenia, lipid myopathies, and obesity; and a cell proliferative disorder such as actinic keratosis, arteriosclerosis, atherosclerosis, bursitis, cirrhosis, hepatitis, mixed connective tissue disease (MCTD), myelofibrosis, paroxysmal nocturnal hemoglobinuria, polycythemia vera, psoriasis, primary thrombocythemia, and cancers including adenocarcinoma, leukemia, lymphoma, melanoma, myeloma, sarcoma, teratocarcinoma, and, in particular, cancers of the adrenal gland, bladder, bone, bone marrow, brain, breast, cervix, colon, gall bladder, ganglia, gastrointestinal tract, heart, kidney, liver, lung, muscle, ovary, pancreas, parathyroid, penis, prostate, salivary glands, skin, spleen, testis, thymus, thyroid, uterus, leukemias such as multiple myeloma, and lymphomas such as Hodgkin's disease.

In another embodiment, a vector capable of expressing KPP or a fragment or derivative thereof may be administered to a subject to treat or prevent a disorder associated with decreased expression or activity of KPP including, but not limited to, those described above.

In a further embodiment, a composition comprising a substantially purified KPP in conjunction with a suitable pharmaceutical carrier may be administered to a subject to treat or prevent a disorder associated with decreased expression or activity of KPP including, but not limited to, those provided above.

In still another embodiment, an agonist which modulates the activity of KPP may be administered to a subject to treat or prevent a disorder associated with decreased expression or activity of KPP including, but not limited to, those listed above.

In a further embodiment, an antagonist of KPP may be administered to a subject to treat or prevent a disorder associated with increased expression or activity of KPP. Examples of such disorders include, but are not limited to, those cardiovascular diseases, immune system disorders, neurological disorders, disorders affecting growth and development, lipid disorders, cell proliferative disorders, and cancers described above. In one aspect, an antibody which specifically binds KPP may be used directly as an antagonist or indirectly as a targeting or delivery mechanism for bringing a pharmaceutical agent to cells or tissues which express KPP.

In an additional embodiment, a vector expressing the complement of the polynucleotide encoding KPP may be administered to a subject to treat or prevent a disorder associated with increased expression or activity of KPP including, but not limited to, those described above.

In other embodiments, any protein, agonist, antagonist, antibody, complementary sequence, or vector embodiments may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of KPP may be produced using methods which are generally known in the art. In particular, purified KPP may be used to produce antibodies or to screen libraries of pharmaceutical agents to identify those which specifically bind KPP. Antibodies to KPP may also be generated using methods that are well known in the art. Such antibodies may include, but are not limited to, polyclonal, monoclonal, chimeric, and single chain antibodies, Fab fragments, and fragments produced by a Fab expression library. In an embodiment, neutralizing antibodies (i.e., those which inhibit dimer formation) can be used therapeutically. Single chain antibodies (e.g., from camels or llamas) may be potent enzyme inhibitors and may have application in the design of peptide mimetics, and in the development of immuno-adsorbents and biosensors (Muyldermans, S. (2001) J. Biotechnol. 74:277-302).

For the production of antibodies, various hosts including goats, rabbits, rats, mice, camels, dromedaries, llamas, humans, and others may be immunized by injection with KPP or with any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, KLH, and dinitrophenol. Among adjuvants used in humans, BCG (bacilli Calmette-Gurin) and *Corynebacterium parvum* are especially preferable.

It is preferred that the oligopeptides, peptides, or fragments used to induce antibodies to KPP have an amino acid sequence consisting of at least about 5 amino acids, and generally will consist of at least about 10 amino acids. It is also preferable that these oligopeptides, peptides, or fragments are substantially identical to a portion of the amino acid sequence of the natural protein, Short stretches of KPP amino acids may be fused with those of another protein, such as KLH, and antibodies to the chimeric molecule may be produced.

Monoclonal antibodies to KPP may be prepared using any technique which provides for the production of antibody molecules by continuous cell lines in culture. These include, but are not limited to the hybridoma technique, the human B-cell hybridoma technique, and the EBV-hybridoma technique (Kohler, G. et al. (1975) Nature 256:495-497; Kozbor, D. et al. (1985) J. Immunol. Methods 81:31-42; Cote, R. J. et al. (1983) Proc. Natl. Acad. Sci. USA 80:2026-2030; Cole, S. P. et al. (1984) Mol. Cell. Biol. 62:109-120).

In addition, techniques developed for the production of "chimeric antibodies," such as the splicing of mouse antibody genes to human antibody genes to obtain a molecule with appropriate antigen specificity and biological activity, can be used (Morrison, S. L. et al. (1984) Proc. Natl. Acad. Sci. USA 81:6851-6855; Neuberger, M. S. et al. (1984) Nature 312: 604-608; Takeda, S. et al. (1985) Nature 314:452-454). Alternatively, techniques described for the production of single chain antibodies may be adapted, using methods known in the art, to produce KPP-specific single chain antibodies. Antibodies with related specificity, but of distinct idiotypic composition, may be generated by chain shuffling from random combinatorial immunoglobulin libraries (Burton, D. R. (1991) Proc. Natl. Acad. Sci. USA 88:10134-10137).

Antibodies may also be produced by inducing in vivo production in the lymphocyte population or by screening immunoglobulin libraries or panels of highly specific binding reagents as disclosed in the literature (Orlandi, R. et al. (1989) Proc. Natl. Acad. Sci. USA 86:3833-3837; Winter, G. et al. (1991) Nature 349:293-299).

Antibody fragments which contain specific binding sites for KPP may also be generated. For example, such fragments include, but are not limited to, $F(ab')_2$ fragments produced by pepsin digestion of the antibody molecule and Fab fragments generated by reducing the disulfide bridges of the $F(ab)_2$ fragments. Alternatively, Fab expression libraries may be constructed to allow rapid and easy identification of monoclonal Fab fragments with the desired specificity (Huse, W. D. et al. (1989) Science 246:1275-1281).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between KPP and its specific antibody. A two-site, monoclonal-based immunoassay utilizing monoclonal antibodies reactive to two non-interfering KPP epitopes is generally used, but a competitive binding assay may also be employed (Pound, supra).

Various methods such as Scatchard analysis in conjunction with radioimmunoassay techniques may be used to assess the affinity of antibodies for KPP. Affinity is expressed as an association constant, $K_a$, which is defined as the molar concentration of KPP-antibody complex divided by the molar concentrations of free antigen and free antibody under equilibrium conditions. The $K_a$ determined for a preparation of polyclonal antibodies, which are heterogeneous in their affinities for multiple KPP epitopes, represents the average affinity, or avidity, of the antibodies for KPP. The $K_a$ determined for a preparation of monoclonal antibodies, which are monospecific for a particular KPP epitope, represents a true measure of affinity. High-affinity antibody preparations with $K_a$ ranging from about $10^9$ to $10^{12}$ L/mole are preferred for use in immunoassays in which the KPP-antibody complex must withstand rigorous manipulations. Low-affinity antibody preparations with $K_a$ ranging from about $10^6$ to $10^7$ L/mole are preferred for use in immunopurification and similar procedures which ultimately require dissociation of KPP, preferably in active form, from the antibody (Catty, D. (1988) *Antibodies, Volume I: A Practical Approach*, IRL Press, Washington D.C.; Liddell, J. E. and A. Cryer (1991) *A Practical Guide to Monoclonal Antibodies*, John Wiley & Sons, New York N.Y.).

The titer and avidity of polyclonal antibody preparations may be further evaluated to determine the quality and suitability of such preparations for certain downstream applications. For example, a polyclonal antibody preparation containing at least 1-2 mg specific antibody/ml, preferably 5-10 mg specific antibody/ml, is generally employed in procedures requiring precipitation of KPP-antibody complexes. Procedures for evaluating antibody specificity, titer, and avidity, and guidelines for antibody quality and usage in various applications, are generally available (Catty, supra; Coligan et al., supra).

In another embodiment of the invention, polynucleotides encoding KPP, or any fragment or complement thereof, may be used for therapeutic purposes. In one aspect, modifications of gene expression can be achieved by designing complementary sequences or antisense molecules (DNA, RNA, PNA, or modified oligonucleotides) to the coding or regulatory regions of the gene encoding KPP. Such technology is well known in the art, and antisense oligonucleotides or larger fragments can be designed from various locations along the coding or control regions of sequences encoding KPP (Agrawal, S., ed. (1996) *Antisense Therapeutics*, Humana Press, Totawa N.J.).

In therapeutic use, any gene delivery system suitable for introduction of the antisense sequences into appropriate target cells can be used. Antisense sequences can be delivered intracellularly in the form of an expression plasmid which, upon transcription, produces a sequence complementary to at least a portion of the cellular sequence encoding the target protein (Slater, J. E. et al. (1998) J. Allergy Clin. Immunol 102:469-475; Scanlon, K. J. et al. (1995) FASEB J. 9:1288-1296). Antisense sequences can also be introduced intracellularly through the use of viral vectors, such as retrovirus and adeno-associated virus vectors (Miller, A. D. (1990) Blood 76:271-278; Ausubel et al., supra; Uckert, W. and W. Walther (1994) Pharmacol. Ther. 63:323-347). Other gene delivery mechanisms include liposome-derived systems, artificial viral envelopes, and other systems known in the art (Rossi, J. J. (1995) Br. Med. Bull. 51:217-225; Boado, R. J. et al. (1998) J. Pharm. Sci. 87:1308-1315; Morris, M. C. et al. (1997) Nucleic Acids Res. 25:2730-2736).

In another embodiment of the invention, polynucleotides encoding KPP may be used for somatic or germline gene therapy. Gene therapy may be performed to (i) correct a genetic deficiency (e.g., in the cases of severe combined immunodeficiency (SCID)-X1 disease characterized by X-linked inheritance (Cavazzana-Calvo, M. et al. (2000) Science 288:669-672), severe combined immunodeficiency syndrome associated with an inherited adenosine deaminase (ADA) deficiency (Blaese, R. M. et al. (1995) Science 270: 475-480; Bordignon, C. et al. (1995) Science 270:470-475), cystic fibrosis (Zabner, J. et al. (1993) Cell 75:207-216; Crystal, R. G. et al. (1995) Hum. Gene Therapy 6:643-666; Crystal, R. G. et al. (1995) Hum. Gene Therapy 6:667-703), thalassamias, familial hypercholesterolemia, and hemophilia resulting from Factor VIII or Factor IX deficiencies (Crystal, R. G. (1995) Science 270:404-410; Verma, I. M. and N. Somia (1997) Nature 389:239-242)), (ii) express a conditionally lethal gene product (e.g., in the case of cancers which result from unregulated cell proliferation), or (iii) express a protein which affords protection against intracellular parasites (e.g., against human retroviruses, such as human immunodeficiency virus (HIV) (Baltimore, D. (1988) Nature 335: 395-396; Poeschla, E. et al. (1996) Proc. Natl. Acad. Sci. USA 93:11395-11399), hepatitis B or C virus (HBV, HCV); fungal parasites, such as *Candida albicans* and *Paracoccidioides brasiliensis*; and protozoan parasites such as *Plasmodium falciparum* and *Trypanosoma cruzi*). In the case where a genetic deficiency in KPP expression or regulation causes disease, the expression of KPP from an appropriate population of transduced cells may alleviate the clinical manifestations caused by the genetic deficiency.

In a further embodiment of the invention, diseases or disorders caused by deficiencies in KPP are treated by constructing mammalian expression vectors encoding KPP and introducing these vectors by mechanical means into KPP-deficient cells. Mechanical transfer technologies for use with cells in vivo or ex vitro include (i) direct DNA microinjection into individual cells, (ii) ballistic gold particle delivery, (iii) liposome-mediated transfection, (iv) receptor-mediated gene transfer, and (v) the use of DNA transposons (Morgan, R. A. and W. F. Anderson (1993) Annu. Rev. Biochem. 62:191-217; Ivies, Z. (1997) Cell 91:501-510; Boulay, J.-L. and H. Rezipon (1998) Curr. Opin. Biotechnol. 9:445-450).

Expression vectors that may be effective for the expression of KPP include, but are not limited to, the PcDNA 3.1, EPITAG, PRCCMV2, PREP, PVAX, PCR2-TOPOTA vectors (Invitrogen, Carlsbad Calif.), PCMV-SCRIPT, PCMV-TAG, PEGSH/PERV (Stratagene, La Jolla Calif.), and PTET-OFF, PTET-ON, PTRE2, PTRE2-LUC, PTK-HYG (BD Clontech, Palo Alto Calif.). KPP may be expressed using (i) a constitutively active promoter, (e.g., from cytomegalovirus (CMV), Rous sarcoma virus (RSV), SV40 virus, thymidine kinase (TK), or β-actin genes), (ii) an inducible promoter (e.g., the tetracycline-regulated promoter (Gossen, M. and H. Bujard (1992) Proc. Natl. Acad. Sci. USA 89:5547-5551; Gossen, M. et al. (1995) Science 268:1766-1769; Rossi, F. M. V. and H. M. Blau (1998) Curr. Opin. Biotechnol. 9:451-456), commercially available in the T-REX plasmid (Invitrogen)); the ecdysone-inducible promoter (available in the plasmids PVGRXR and PIND; Invitrogen); the FK506/rapamycin inducible promoter; or the RU486/mifepristone inducible promoter (Rossi, F. M. V. and H. M. Blau, supra)), or (iii) a tissue-specific promoter or the native promoter of the endogenous gene encoding KPP from a normal individual.

Commercially available liposome transformation kits (e.g., the PERFECT LIPID TRANSFECTION KIT, available from Invitrogen) allow one with ordinary skill in the art to deliver polynucleotides to target cells in culture and require minimal effort to optimize experimental parameters. In the alternative, transformation is performed using the calcium phosphate method (Graham, F. L. and A. J. Eb (1973) Virology 52:456-467), or by electroporation (Neumann, E. et al. (1982) EMBO J. 1:841-845). The introduction of DNA to primary cells requires modification of these standardized mammalian transfection protocols.

In another embodiment of the invention, diseases or disorders caused by genetic defects with respect to KPP expression are treated by constructing a retrovirus vector consisting of (i) the polynucleotide encoding KPP under the control of an independent promoter or the retrovirus long terminal repeat (LTR) promoter, (ii) appropriate RNA packaging signals, and (iii) a Rev-responsive element (RRE) along with additional retrovirus cis-acting RNA sequences and coding sequences required for efficient vector propagation. Retrovirus vectors (e.g., PFB and PFBNEO) are commercially available (Stratagene) and are based on published data (Riviere, I. et al. (1995) Proc. Natl. Acad. Sci. USA 92:6733-6737), incorporated by reference herein. The vector is propagated in an appropriate vector producing cell line (VPCL) that expresses an envelope gene with a tropism for receptors on the target cells or a promiscuous envelope protein such as VSVg (Armentano, D. et al. (1987) J. Viral. 61:1647-1650; Bender, M. A. et al. (1987) J. Virol. 61:1639-1646; Adam, M. A. and A. D. Miller (1988) J. Viral. 62:3802-3806; Dull, T. et al. (1998) J. Virol. 72:8463-8471; Zufferey, R. et al. (1998) J. Virol. 72:9873-9880). U.S. Pat. No. 5,910,434 to Rigg ("Method for obtaining retrovirus packaging cell lines producing high transducing efficiency retroviral supernatant") discloses a method for obtaining retrovirus packaging cell lines and is hereby incorporated by reference. Propagation of retrovirus vectors, transduction of a population of cells (e.g., $CD4^+$ T-cells), and the return of transduced cells to a patient are procedures well known to persons skilled in the art of gene therapy and have been well documented (Ranga, U. et al. (1997) J. Virol. 71:7020-7029; Bauer, G. et al. (1997) Blood 89:2259-2267; Bonyhadi, M. L. (1997) J. Viral. 71:4707-4716; Ranga, U. et al. (1998) Proc. Natl. Acad. Sci. USA 95:1201-1206; Su, L. (1997) Blood 89:2283-2290).

In an embodiment, an adenovirus-based gene therapy delivery system is used to deliver polynucleotides encoding KPP to cells which have one or more genetic abnormalities with respect to the expression of KPP. The construction and packaging of adenovirus-based vectors are well known to those with ordinary skill in the art. Replication defective adenovirus vectors have proven to be versatile for importing genes encoding immunoregulatory proteins into intact islets in the pancreas (Csete, M. E. et al. (1995) Transplantation 27:263-268). Potentially useful adenoviral vectors are described in U.S. Pat. No. 5,707,618 to Armentano ("Adenovirus vectors for gene therapy"), hereby incorporated by reference. For adenoviral vectors, see also Antinozzi, P. A. et al. (1999; Annu. Rev. Nutr. 19:511-544) and Verma, I. M. and N. Somia (1997; Nature 18:389:239-242).

In another embodiment, a herpes-based, gene therapy delivery system is used to deliver polynucleotides encoding KPP to target cells which have one or more genetic abnormalities with respect to the expression of KPP. The use of herpes simplex virus (HSV)-based vectors may be especially valuable for introducing KPP to cells of the central nervous system, for which RSV has a tropism. The construction and packaging of herpes based vectors are well known to those with ordinary skill in the art. A replication-competent herpes simplex virus (HSV) type 1-based vector has been used to deliver a reporter gene to the eyes of primates (Liu, X. et al. (1999) Exp. Eye Res. 169:385-395). The construction of a HSV-1 virus vector has also been disclosed in detail in U.S. Pat. No. 5,804,413 to DeLuca ("Herpes simplex virus strains for gene transfer"), which is hereby incorporated by reference. U.S. Pat. No. 5,804,413 teaches the use of recombinant HSV d92 which consists of a genome containing at least one exogenous gene to be transferred to a cell under the control of the appropriate promoter for purposes including human gene therapy. Also taught by this patent are the construction and use of recombinant HSV strains deleted for ICP4, ICP27 and ICP22. For HSV vectors, see also Goins, W. F. et al. (1999; J. Virol. 73:519-532) and Xu, H. et al. (1994; Dev. Biol. 163:

152-161). The manipulation of cloned herpesvirus sequences, the generation of recombinant virus following the transfection of multiple plasmids containing different segments of the large herpesvirus genomes, the growth and propagation of herpesvirus, and the infection of cells with herpesvirus are techniques well known to those of ordinary skill in the art.

In another embodiment, an alphavirus (positive, single-stranded RNA virus) vector is used to deliver polynucleotides encoding KPP to target cells. The biology of the prototypic alphavirus, Semliki Forest Virus (SFV), has been studied extensively and gene transfer vectors have been based on the SFV genome (Garoff, H. and K.-J. Li (1998) Curr. Opin. Biotechnol. 9:464-469). During alphavirus RNA replication, a subgenomic RNA is generated that normally encodes the viral capsid proteins. This subgenomic RNA replicates to higher levels than the full length genomic RNA, resulting in the overproduction of capsid proteins relative to the viral proteins with enzymatic activity (e.g., protease and polymerase). Similarly, inserting the coding sequence for KPP into the alphavirus genome in place of the capsid-coding region results in the production of a large number of KPP-coding RNAs and the synthesis of high levels of KPP in vector transduced cells. While alphavirus infection is typically associated with cell lysis within a few days, the ability to establish a persistent infection in hamster normal kidney cells (BHK-21) with a variant of Sindbis virus (SIN) indicates that the lytic replication of alphaviruses can be altered to suit the needs of the gene therapy application (Dryga, S. A. et al. (1997) Virology 228:74-83). The wide host range of alphaviruses will allow the introduction of KPP into a variety of cell types. The specific transduction of a subset of cells in a population may require the sorting of cells prior to transduction. The methods of manipulating infectious cDNA clones of alphaviruses, performing alphavirus cDNA and RNA transfections, and performing alphavirus infections, are well known to those with ordinary skill in the art.

Oligonucleotides derived from the transcription initiation site, e.g., between about positions −10 and +10 from the start site, may also be employed to inhibit gene expression. Similarly, inhibition can be achieved using triple helix base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al. (1994) in Huber, B. E. and B. I. Carr, *Molecular and Immunologic Approaches*, Futura Publishing, Mt. Kisco N.Y., pp. 163-177). A complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. For example, engineered hammerhead motif ribozyme molecules may specifically and efficiently catalyze endonucleolytic cleavage of RNA molecules encoding KPP.

Specific ribozyme cleavage sites within any potential RNA target are initially identified by scanning the target molecule for ribozyme cleavage sites, including the following sequences: GUA, GUU, and GUC. Once identified, short RNA sequences of between 15 and 20 ribonucleotides, corresponding to the region of the target gene containing the cleavage site, may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA molecules encoding KPP. Such DNA sequences may be incorporated into a wide variety of vectors with suitable RNA polymerase promoters such as T7 or SP6. Alternatively, these cDNA constructs that synthesize complementary RNA, constitutively or inducibly, can be introduced into cell lines, cells, or tissues.

RNA molecules may be modified to increase intracellular stability and half-life. Possible modifications include, but are not limited to, the addition of flanking sequences at the 5' and/or 3' ends of the molecule, or the use of phosphorothioate or 2'O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytosine, guanine, thymine, and uracil which are not as easily recognized by endogenous endonucleases.

In other embodiments of the invention, the expression of one or more selected polynucleotides of the present invention can be altered, inhibited, decreased, or silenced using RNA interference (RNAi) or post-transcriptional gene silencing (PTGS) methods known in the art. RNAi is a post-transcriptional mode of gene silencing in which double-stranded RNA (dsRNA) introduced into a targeted cell specifically suppresses the expression of the homologous gene (i.e., the gene bearing the sequence complementary to the dsRNA). This effectively knocks out or substantially reduces the expression of the targeted gene. PTGS can also be accomplished by use of DNA or DNA fragments as well. RNAi methods are described by Fire, A. et al. (1998; Nature 391:806-811) and Gura, T. (2000; Nature 404:804-808). PTGS can also be initiated by introduction of a complementary segment of DNA into the selected tissue using gene delivery and/or viral vector delivery methods described herein or known in the art.

RNAi can be induced in mammalian cells by the use of small interfering RNA also known as siRNA. siRNA are shorter segments of dsRNA (typically about 21 to 23 nucleotides in length) that result in vivo from cleavage of introduced dsRNA by the action of an endogenous ribonuclease siRNA appear to be the mediators of the RNAi effect in mammals. The most effective siRNAs appear to be 21 nucleotide dsRNAs with 2 nucleotide 3' overhangs. The use of siRNA for inducing RNAi in mammalian cells is described by Elbasbir, S. M. et al. (2001; Nature 411:494-498).

siRNA can be generated indirectly by introduction of dsRNA into the targeted cell. Alternatively, siRNA can be synthesized directly and introduced into a cell by transfection methods and agents described herein or known in the art (such as liposome-mediated transfection, viral vector methods, or other polynucleotide delivery/introductory methods). Suitable siRNAs can be selected by examining a transcript of the target polynucleotide (e.g., mRNA) for nucleotide sequences downstream from the AUG start codon and recording the occurrence of each nucleotide and the 3' adjacent 19 to 23 nucleotides as potential siRNA target sites, with sequences having a 21 nucleotide length being preferred. Regions to be avoided for target siRNA sites include the 5' and 3' untranslated regions (UTRs) and regions near the start codon (within 75 bases), as these may be richer in regulatory protein binding sites. UTR-binding proteins and/or translation initiation complexes may interfere with binding of the siRNP endonuclease complex. The selected target sites for siRNA can then be compared to the appropriate genome database (e.g., human, etc.) using BLAST or other sequence comparison algorithms known in the art. Target sequences with significant homology to other coding sequences can be eliminated from consideration. The selected siRNAs can be produced by chemical synthesis methods known in the art or by in vitro transcription using commercially available methods and kits such as the SILENCER siRNA construction kit (Ambion, Austin Tex.).

In alternative embodiments, long-term gene silencing and/or RNAi effects can be induced in selected tissue using expression vectors that continuously express siRNA. This can be accomplished using expression vectors that are engineered to express hairpin RNAs (shRNAs) using methods known in the art (see, e.g., Brummelkamp, T. R. et al. (2002) Science 296:550-553; and Paddison, P. J. et al. (2002) Genes Dev. 16:948-958). In these and related embodiments, shRNAs can be delivered to target cells using expression vectors known in the art. An example of a suitable expression vector for delivery of siRNA is the PSILENCER 1.0-U6 (circular) plasmid (Ambion). Once delivered to the target tissue, shRNAs are processed in vivo into siRNA-like molecules capable of carrying out gene-specific silencing.

In various embodiments, the expression levels of genes targeted by RNAi or PTGS methods can be determined by assays for mRNA and/or protein analysis. Expression levels of the mRNA of a targeted gene can be determined, for example, by northern analysis methods using the NORTHERNMAX-GLY kit (Ambion); by microarray methods; by PCR methods; by real time PCR methods; and by other RNA/polynucleotide assays known in the art or described herein. Expression levels of the protein encoded by the targeted gene can be determined, for example, by microarray methods; by polyacrylamide gel electrophoresis; and by Western analysis using standard techniques known in the art.

An additional embodiment of the invention encompasses a method for screening for a compound which is effective in altering expression of a polynucleotide encoding KPP. Compounds which may be effective in altering expression of a specific polynucleotide may include, but are not limited to, oligonucleotides, antisense oligonucleotides, triple helix-forming oligonucleotides, transcription factors and other polypeptide transcriptional regulators, and non-macromolecular chemical entities which are capable of interacting with specific polynucleotide sequences. Effective compounds may alter polynucleotide expression by acting as either inhibitors or promoters of polynucleotide expression. Thus, in the treatment of disorders associated with increased KPP expression or activity, a compound which specifically inhibits expression of the polynucleotide encoding KPP may be therapeutically useful, and in the treatment of disorders associated with decreased KPP expression or activity, a compound which specifically promotes expression of the polynucleotide encoding KPP may be therapeutically useful.

In various embodiments, one or more test compounds may be screened for effectiveness in altering expression of a specific polynucleotide. A test compound may be obtained by any method commonly known in the art, including chemical modification of a compound known to be effective in altering polynucleotide expression; selection from an existing, commercially-available or proprietary library of naturally-occurring or non-natural chemical compounds; rational design of a compound based on chemical and/or structural properties of the target polynucleotide; and selection from a library of chemical compounds created combinatorially or randomly. A sample comprising a polynucleotide encoding KPP is exposed to at least one test compound thus obtained. The sample may comprise, for example, an intact or permeabilized cell, or an in vitro cell-free or reconstituted biochemical system. Alterations in the expression of a polynucleotide encoding KPP are assayed by any method commonly known in the art. Typically, the expression of a specific nucleotide is detected by hybridization with a probe having a nucleotide sequence complementary to the sequence of the polynucleotide encoding KPP. The amount of hybridization may be quantified, thus forming the basis for a comparison of the expression of the polynucleotide both with and without exposure to one or more test compounds. Detection of a change in the expression of a polynucleotide exposed to a test compound indicates that the test compound is effective in altering the expression of the polynucleotide. A screen for a compound effective in altering expression of a specific polynucleotide can be carried out, for example, using a *Schizosaccharomyces pombe* gene expression system (Atkins, D. et al. (1999) U.S. Pat. No. 5,932,435; Arndt, G. M. et al. (2000) Nucleic Acids Res. 28:E15) or a human cell line such as HeLa cell (Clarke, M. L. et al. (2000) Biochem. Biophys. Res. Commun. 268:8-13). A particular embodiment of the present invention involves screening a combinatorial library of oligonucleotides (such as deoxyribonucleotides, ribonucleotides, peptide nucleic acids, and modified oligonucleotides) for antisense activity against a specific polynucleotide sequence (Bruice, T. W. et al. (1997) U.S. Pat. No. 5,686,242; Bruice, T. W. et al. (2000) U.S. Pat. No. 6,022,691).

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections, or by polycationic amino polymers may be achieved using methods which are well known in the art (Goldman, C. K. et al. (1997) Nat. Biotechnol. 15:462-466).

Any of the therapeutic methods described above may be applied to any subject in need of such therapy, including, for example, mammals such as humans, dogs, cats, cows, horses, rabbits, and monkeys.

An additional embodiment of the invention relates to the administration of a composition which generally comprises an active ingredient formulated with a pharmaceutically acceptable excipient. Excipients may include, for example, sugars, starches, celluloses, gums, and proteins. Various formulations are commonly known and are thoroughly discussed in the latest edition of *Remington's Pharmaceutical Sciences* (Maack Publishing, Easton Pa.). Such compositions may consist of KPP, antibodies to KPP, and mimetics, agonists, antagonists, or inhibitors of KPP.

In various embodiments, the compositions described herein, such as pharmaceutical compositions, may be administered by any number of routes including, but not limited to, oral, intravenous, intramuscular, intra-arterial, intramedullary, intrathecal, intraventricular, pulmonary, transdermal, subcutaneous, intraperitoneal, intranasal, enteral, topical, sublingual, or rectal means.

Compositions for pulmonary administration may be prepared in liquid or dry powder form. These compositions are generally aerosolized immediately prior to inhalation by the patient. In the case of small molecules (e.g. traditional low molecular weight organic drugs), aerosol delivery of fast-acting formulations is well-known in the art. In the case of macromolecules (e.g. larger peptides and proteins), recent developments in the field of pulmonary delivery via the alveolar region of the lung have enabled the practical delivery of drugs such as insulin to blood circulation (see, e.g., Patton, J. S. et al., U.S. Pat. No. 5,997,848). Pulmonary delivery allows administration without needle injection, and obviates the need for potentially toxic penetration enhancers.

Compositions suitable for use in the invention include compositions wherein the active ingredients are contained in an effective amount to achieve the intended purpose. The determination of an effective dose is well within the capability of those skilled in the art.

Specialized forms of compositions may be prepared for direct intracellular delivery of macromolecules comprising KPP or fragments thereof. For example, liposome preparations containing a cell-impermeable macromolecule may promote cell fusion and intracellular delivery of the macromolecule. Alternatively, KPP or a fragment thereof may be joined to a short cationic N-terminal portion from the HIV Tat-1 protein. Fusion proteins thus generated have been found to transduce into the cells of all tissues, including the brain, in a mouse model system (Schwarze, S. R. et al. (1999) Science 285:1569-1572).

For any compound, the therapeutically effective dose can be estimated initially either in cell culture assays, e.g., of neoplastic cells, or in animal models such as mice, rats, rabbits, dogs, monkeys, or pigs. An animal model may also be used to determine the appropriate concentration range and route of administration. Such information can then be used to determine useful doses and routes for administration in humans.

A therapeutically effective dose refers to that amount of active ingredient, for example KPP or fragments thereof, antibodies of KPP, and agonists, antagonists or inhibitors of KPP, which ameliorates the symptoms or condition. Therapeutic efficacy and toxicity may be determined by standard pharmaceutical procedures in cell cultures or with experimental animals, such as by calculating the $ED_{50}$ (the dose therapeutically effective in 50% of the population) or $LD_{50}$ (the dose lethal to 50% of the population) statistics. The dose ratio of toxic to therapeutic effects is the therapeutic index, which can be expressed as the $LD_{50}/ED_{50}$ ratio. Compositions which exhibit large therapeutic indices are preferred. The data obtained from cell culture assays and animal studies are used to formulate a range of dosage for human use. The dosage contained in such compositions is preferably within a range of circulating concentrations that includes the $ED_{50}$ with little or no toxicity. The dosage varies within this range depending upon the dosage form employed, the sensitivity of the patient, and the route of administration.

The exact dosage will be determined by the practitioner, in light of factors related to the subject requiring treatment. Dosage and administration are adjusted to provide sufficient levels of the active moiety or to maintain the desired effect. Factors which may be taken into account include the severity of the disease state, the general health of the subject, the age, weight, and gender of the subject, time and frequency of administration, drug combination(s), reaction sensitivities, and response to therapy. Long-acting compositions may be administered every 3 to 4 days, every week, or biweekly depending on the half-life and clearance rate of the particular formulation.

Normal dosage amounts may vary from about 0.1 μg to 100,000 μg, up to a total dose of about 1 gram, depending upon the route of administration. Guidance as to particular dosages and methods of delivery is provided in the literature and generally available to practitioners in the art.

Those skilled in the art will employ different formulations for nucleotides than for proteins or their inhibitors. Similarly, delivery of polynucleotides or polypeptides will be specific to particular cells, conditions, locations, etc.

Diagnostic

In another embodiment, antibodies which specifically bind KPP may be used for the diagnosis of disorders characterized by expression of KPP, or in assays to monitor patients being treated with KPP or agonists, antagonists, or inhibitors of KPP. Antibodies useful for diagnostic purposes may be prepared in the same manner as described above for therapeutics. Diagnostic assays for KPP include methods which utilize the antibody and a label to detect KPP in human body fluids or in extracts of cells or tissues. The antibodies may be used with or without modification, and may be labeled by covalent or non-covalent attachment of a reporter molecule. A wide variety of reporter molecules, several of which are described above, are known in the art and may be used.

A variety of protocols for measuring KPP, including ELISAs, RIAs, and FACS, are known in the art and provide a basis for diagnosing altered or abnormal levels of KPP expression. Normal or standard values for KPP expression are established by combining body fluids or cell extracts taken from normal mammalian subjects, for example, human subjects, with antibodies to KPP under conditions suitable for complex formation. The amount of standard complex formation may be quantitated by various methods, such as photometric means. Quantities of KPP expressed in subject, control, and disease samples from biopsied tissues are compared with the standard values. Deviation between standard and subject values establishes the parameters for diagnosing disease.

In another embodiment of the invention, polynucleotides encoding KPP may be used for diagnostic purposes. The polynucleotides which may be used include oligonucleotides, complementary RNA and DNA molecules, and PNAs. The polynucleotides may be used to detect and quantify gene expression in biopsied tissues in which expression of KPP may be correlated with disease. The diagnostic assay may be used to determine absence, presence, and excess expression of KPP, and to monitor regulation of KPP levels during therapeutic intervention.

In one aspect, hybridization with PCR probes which are capable of detecting polynucleotides, including genomic sequences, encoding KPP or closely related molecules may be used to identify nucleic acid sequences which encode KPP. The specificity of the probe, whether it is made from a highly specific region, e.g., the 5' regulatory region, or from a less specific region, e.g., a conserved motif, and the stringency of the hybridization or amplification will determine whether the probe identifies only naturally occurring sequences encoding KPP, allelic variants, or related sequences.

Probes may also be used for the detection of related sequences, and may have at least 50% sequence identity to any of the KPP encoding sequences. The hybridization probes of the subject invention may be DNA or RNA and may be derived from the sequence of SEQ ID NO:44-86 or from genomic sequences including promoters, enhancers, and introns of the KPP gene.

Means for producing specific hybridization probes for polynucleotides encoding KPP include the cloning of polynucleotides encoding KPP or KPP derivatives into vectors for the production of mRNA probes. Such vectors are known in the art, are commercially available, and may be used to synthesize RNA probes in vitro by means of the addition of the appropriate RNA polymerases and the appropriate labeled nucleotides. Hybridization probes may be labeled by a variety of reporter groups, for example, by radionuclides such as $^{32}P$ or $^{35}S$, or by enzymatic labels, such as alkaline phosphatase coupled to the probe via avidin/biotin coupling systems, and the like.

Polynucleotides encoding KPP may be used for the diagnosis of disorders associated with expression of KPP. Examples of such disorders include, but are not limited to, a cardiovascular disease such as arteriovenous fistula, atherosclerosis, hypertension, vasculitis, Raynaud's disease, aneurysms, arterial dissections, varicose veins, thrombophlebitis and phlebothrombosis, vascular tumors, and complications of thrombolysis, balloon angioplasty, vascular replacement, and coronary artery bypass graft surgery, congestive heart failure, ischemic heart disease, angina pectoris, myocardial infarction, hypertensive heart disease, degenerative valvular heart disease, calcific aortic valve stenosis, congenitally bicuspid aortic valve, mitral annular calcification, mitral valve prolapse, rheumatic fever and rheumatic heart disease, infective endocarditis, nonbacterial thrombotic endocarditis, endocarditis of systemic lupus erythematosus, carcinoid heart disease, cardiomyopathy, myocarditis, pericarditis, neoplastic heart disease, congenital heart disease, and complications of cardiac transplantation, congenital lung anomalies, atelectasis, pulmonary congestion and edema, pulmonary embolism, pulmonary hemorrhage, pulmonary infarction, pulmonary hypertension, vascular sclerosis, obstructive pulmonary disease, restrictive pulmonary disease, chronic obstructive pulmonary disease, emphysema, chronic bronchitis, bronchial asthma, bronchiectasis, bacterial pneumonia, viral and mycoplasmal pneumonia, lung abscess, pulmonary tuberculosis, diffuse interstitial diseases, pneumoconioses, sarcoidosis, idiopathic pulmonary fibrosis, desquamative interstitial pneumonitis, hypersensitivity pneumonitis, pulmonary eosinophilia bronchiolitis obliterans-organizing pneumonia, diffuse pulmonary hemorrhage syndromes, Goodpasture's syndromes, idiopathic pulmonary hemosiderosis, pulmonary involvement in collagen-vascular disorders, pulmonary alveolar proteinosis, lung tumors, inflammatory and noninflammatory pleural effusions; pneumothorax, pleural tumors, drug-induced lung disease, radiation-induced lung disease, and complications of lung transplantation; an immune system disorder such as acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, autoimmune polyendocrinopathy-candidiasis-ectodermal dystrophy (APECED), bronchitis, cholecystitis, contact dermatitis, Crohn's disease, atopic dermatitis, dermatomyositis, diabetes mellitus, emphysema, episodic lymphopenia with lymphocytotoxins, erythroblastosis fetalis, erythema nodosum, atrophic gastritis, glomerulonephritis, Goodpasture's syndrome, gout, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polymyositis, psoriasis, Reiter's syndrome, rheumatoid arthritis, scleroderma, Sjögren's syndrome, systemic anaphylaxis, systemic lupus erythematosus, systemic sclerosis, thrombocytopenic purpura, ulcerative colitis, uveitis, Werner syndrome, complications of cancer, hemodialysis, and extracorporeal circulation, viral, bacterial, fungal, parasitic, protozoal, and helminthic infections, and trauma; a neurological disorder such as epilepsy, ischemic cerebrovascular disease, stroke, cerebral neoplasms, Alzheimer's disease, Pick's disease, Huntington's disease, dementia, Parkinson's disease and other extrapyramidal disorders, amyotrophic lateral sclerosis and other motor neuron disorders, progressive neural muscular atrophy, retinitis pigmentosa, hereditary ataxias, multiple sclerosis and other demyelinating diseases, bacterial and viral meningitis, brain abscess, subdural empyema, epidural abscess, suppurative intracranial thrombophlebitis, myelitis and radiculitis, viral central nervous system disease, prion diseases including kuru, Creutzfeldt-Jakob disease, and Gerstmann-Straussler-Scheinker syndrome, fatal familial insomnia, nutritional and metabolic diseases of the nervous system, neurofibromatosis, tuberous sclerosis, cerebelloretinal hemangioblastomatosis, encephalotrigeminal syndrome, mental retardation and other developmental disorders of the central nervous system including Down syndrome, cerebral palsy, neuroskeletal disorders, autonomic nervous system disorders, cranial nerve disorders, spinal cord diseases, muscular dystrophy and other neuromuscular disorders, peripheral nervous system disorders, dermatomyositis and polymyositis, inherited, metabolic, endocrine, and toxic myopathies, myasthenia gravis, periodic paralysis, mental disorders including mood, anxiety, and schizophrenic disorders, seasonal affective disorder (SAD), akathesia, amnesia, catatonia, diabetic neuropathy, tardive dyskinesia, dystonias, paranoid psychoses, postherpetic neuralgia, Tourette's disorder, progressive supranuclear palsy, corticobasal degeneration, and familial frontotemporal dementia; a disorder affecting growth and development such as actinic keratosis, arteriosclerosis, atherosclerosis, bursitis, cirrhosis, hepatitis, mixed connective tissue disease (MCTD), myelofibrosis, paroxysmal nocturnal hemoglobinuria, polycythemia vera, psoriasis, primary thrombocythemia, renal tubular acidosis, anemia, Cushing's syndrome, achondroplastic dwarfism, Duchenne and Becker muscular dystrophy, epilepsy, gonadal dysgenesis, WAGR syndrome (Wilms' tumor, aniridia, genitourinary abnormalities, and mental retardation), Smith-Magenis syndrome, myelodysplastic syndrome, hereditary mucoepithelial dysplasia, hereditary keratodermas, hereditary neuropathies such as Charcot-Marie-Tooth disease and neurofibromatosis, hypothyroidism, hydrocephalus, seizure disorders such as Syndenham's chorea and cerebral palsy, spina bifida, anencephaly, craniorachischisis, congenital glaucoma, cataract, and sensorineural hearing loss; a lipid disorder such as fatty liver, cholestasis, primary biliary cirrhosis, carnitine deficiency, carnitine palmitoyltransferase deficiency, myoadenylate deaminase deficiency, hypertriglyceridemia, lipid storage disorders such Fabry's disease, Gaucher's disease, Niemann-Pick's disease, metachromatic leukodystrophy, adrenoleukodystrophy, $GM_2$ gangliosidosis, and ceroid lipofuscinosis, abetalipoproteinemia, Tangier disease, hyperlipoproteinemia, diabetes mellitus, lipodystrophy, lipomatoses, acute panniculitis, disseminated fat necrosis, adiposis dolorosa, lipoid adrenal hyperplasia, minimal change disease, lipomas, atherosclerosis, hypercholesterolemia, hypercholesterolemia with hypertriglyceridemia, primary hypoalphalipoproteinemia, hypothyroidism, renal disease, liver disease, lecithin:cholesterol acyltransferase deficiency, cerebrotendinous xanthomatosis, sitosterolemia, hypocholesterolemia, Tay-Sachs disease, Sandhoffs disease, hyperlipidemia, hyperlipemia, lipid myopathies, and obesity; and a cell proliferative disorder such as actinic keratosis, arteriosclerosis, atherosclerosis, bursitis, cirrhosis, hepatitis, mixed connective tissue disease (MCTD), myelofibrosis, paroxysmal nocturnal hemoglobinuria, polycythemia vera, psoriasis, primary thrombocythemia, and cancers including adenocarcinoma, leukemia, lymphoma, melanoma, myeloma, sarcoma, teratocarcinoma, and, in particular, cancers of the adrenal gland, bladder, bone, bone marrow, brain, breast, cervix, colon, gall bladder, ganglia, gastrointestinal tract, heart, kidney, liver, lung, muscle, ovary, pancreas, parathyroid, penis, prostate, salivary glands, skin, spleen, testis, thymus, thyroid, uterus, leukemias such as multiple myeloma, and lymphomas such as Hodgkin's disease. Polynucleotides encoding KPP may be used in Southern or northern analysis, dot blot, or other membrane-based technologies; in PCR technologies; in dipstick, pin, and multiformat ELISA-like assays; and in microarrays utilizing fluids or tissues from patients to detect altered KPP expression. Such qualitative or quantitative methods are well known in the art.

In a particular embodiment, polynucleotides encoding KPP may be used in assays that detect the presence of associated disorders, particularly those mentioned above. Polynucleotides complementary to sequences encoding KPP may be labeled by standard methods and added to a fluid or tissue sample from a patient under conditions suitable for the formation of hybridization complexes. After a suitable incubation period, the sample is washed and the signal is quantified and compared with a standard value. If the amount of signal in the patient sample is significantly altered in comparison to a control sample then the presence of altered levels of polynucleotides encoding KPP in the sample indicates the presence of the associated disorder. Such assays may also be used to evaluate the efficacy of a particular therapeutic treatment regimen in animal studies, in clinical trials, or to monitor the treatment of an individual patient.

In order to provide a basis for the diagnosis of a disorder associated with expression of KPP, a normal or standard profile for expression is established. This may be accomplished by combining body fluids or cell extracts taken from normal subjects, either animal or human, with a sequence, or a fragment thereof, encoding KPP, under conditions suitable for hybridization or amplification. Standard hybridization may be quantified by comparing the values obtained from normal subjects with values from an experiment in which a known amount of a substantially purified polynucleotide is used. Standard values obtained in this manner may be compared with values obtained from samples from patients who are symptomatic for a disorder. Deviation from standard values is used to establish the presence of a disorder.

Once the presence of a disorder is established and a treatment protocol is initiated, hybridization assays may be repeated on a regular basis to determine if the level of expression in the patient begins to approximate that which is observed in the normal subject. The results obtained from successive assays may be used to show the efficacy of treatment over a period ranging from several days to months.

With respect to cancer, the presence of an abnormal amount of transcript (either under- or overexpressed) in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier, thereby preventing the development or further progression of the cancer.

Additional diagnostic uses for oligonucleotides designed from the sequences encoding KPP may involve the use of PCR. These oligomers may be chemically synthesized, generated enzymatically, or produced in vitro. Oligomers will preferably contain a fragment of a polynucleotide encoding KPP, or a fragment of a polynucleotide complementary to the polynucleotide encoding KPP, and will be employed under optimized conditions for identification of a specific gene or condition. Oligomers may also be employed under less stringent conditions for detection or quantification of closely related DNA or RNA sequences.

In a particular aspect, oligonucleotide primers derived from polynucleotides encoding KPP may be used to detect single nucleotide polymorphisms (SNPs). SNPs are substitutions, insertions and deletions that are a frequent cause of inherited or acquired genetic disease in humans. Methods of SNP detection include, but are not limited to, single-stranded conformation polymorphism (SSCP) and fluorescent SSCP (fSSCP) methods. In SSCP, oligonucleotide primers derived from polynucleotides encoding KPP are used to amplify DNA using the polymerase chain reaction (PCR). The DNA may be derived, for example, from diseased or normal tissue, biopsy samples, bodily fluids, and the like. SNPs in the DNA cause differences in the secondary and tertiary structures of PCR products in single-stranded form, and these differences are detectable using gel electrophoresis in non-denaturing gels. In MCP, the oligonucleotide primers are fluorescently labeled, which allows detection of the amplimers in high-throughput equipment such as DNA sequencing machines. Additionally, sequence database analysis methods, termed in silico SNP (is SNP), are capable of identifying polymorphisms by comparing the sequence of individual overlapping DNA fragments which assemble into a common consensus sequence. These computer-based methods filter out sequence variations due to laboratory preparation of DNA and sequencing errors using statistical models and automated analyses of DNA sequence chromatograms. In the alternative, SNPs may be detected and characterized by mass spectrometry using, for example, the high throughput MASSARRAY system (Sequenom, Inc., San Diego Calif.).

SNPs may be used to study the genetic basis of human disease. For example, at least 16 common SNPs have been associated with non-insulin-dependent diabetes mellitus. SNPs are also useful for examining differences in disease outcomes in monogenic disorders, such as cystic fibrosis, sickle cell anemia, or chronic granulomatous disease. For example, variants in the mannose-binding lectin, MBL2, have been shown to be correlated with deleterious pulmonary outcomes in cystic fibrosis. SNPs also have utility in pharmacogenomics, the identification of genetic variants that influence a patient's response to a drug, such as life-threatening toxicity. For example, a variation in N-acetyl transferase is associated with a high incidence of peripheral neuropathy in response to the anti-tuberculosis drug isoniazid, while a variation in the core promoter of the ALOX5 gene results in diminished clinical response to treatment with an anti-asthma drug that targets the 5-lipoxygenase pathway. Analysis of the distribution of SNPs in different populations is useful for investigating genetic drift, mutation, recombination, and selection, as well as for tracing the origins of populations and their migrations (Taylor, J. G. et al. (2001) Trends Mol. Med. 7:507-512; Kwok, P.-Y. and Z. Gu (1999) Mol. Med. Today 5:538-543; Nowotny, P. et al. (2001) Curr. Opin. Neurobiol. 11:637-641).

Methods which may also be used to quantify the expression of KPP include radiolabeling or biotinylating nucleotides, coamplification of a control nucleic acid, and interpolating results from standard curves (Melby, P. C. et al. (1993) J. Immunol. Methods 159:235-244; Duplaa, C. et al. (1993) Anal. Biochem. 212:229-236). The speed of quantitation of multiple samples may be accelerated by running the assay in a high-throughput format where the oligomer or polynucleotide of interest is presented in various dilutions and a spectrophotometric or colorimetric response gives rapid quantitation.

In further embodiments, oligonucleotides or longer fragments derived from any of the polynucleotides described herein may be used as elements on a microarray. The microarray can be used in transcript imaging techniques which monitor the relative expression levels of large numbers of genes simultaneously as described below. The microarray may also be used to identify genetic variants, mutations, and polymorphisms. This information may be used to determine gene function, to understand the genetic basis of a disorder, to diagnose a disorder, to monitor progression/regression of disease as a function of gene expression, and to develop and monitor the activities of therapeutic agents in the treatment of disease. In particular, this information may be used to develop a pharmacogenomic profile of a patient in order to select the most appropriate and effective treatment regimen for that patient. For example, therapeutic agents which are highly effective and display the fewest side effects may be selected for a patient based on his/her pharmacogenomic profile.

In another embodiment, KPP, fragments of KPP, or antibodies specific for KPP may be used as elements on a microarray. The microarray may be used to monitor or measure protein-protein interactions, drug-target interactions, and gene expression profiles, as described above.

A particular embodiment relates to the use of the polynucleotides of the present invention to generate a transcript image of a tissue or cell type. A transcript image represents the global pattern of gene expression by a particular tissue or cell type. Global gene expression patterns are analyzed by quantifying the number of expressed genes and their relative abundance under given conditions and at a given time (Seilhamer et al., "Comparative Gene Transcript Analysis," U.S. Pat. No. 5,840,484; hereby expressly incorporated by reference herein). Thus a transcript image may be generated by hybridizing the polynucleotides of the present invention or their complements to the totality of transcripts or reverse transcripts of a particular tissue or cell type. In one embodiment, the hybridization takes place in high-throughput format, wherein the polynucleotides of the present invention or their complements comprise a subset of a plurality of elements on a microarray. The resultant transcript image would provide a profile of gene activity.

Transcript images may be generated using transcripts isolated from tissues, cell lines, biopsies, or other biological samples. The transcript image may thus reflect gene expression in vivo, as in the case of a tissue or biopsy sample, or in vitro, as in the case of a cell line.

Transcript images which profile the expression of the polynucleotides of the present invention may also be used in conjunction with in vitro model systems and preclinical evaluation of pharmaceuticals, as well as toxicological testing of industrial and naturally-occurring environmental compounds. All compounds induce characteristic gene expression patterns, frequently termed molecular fingerprints or toxicant signatures, which are indicative of mechanisms of action and toxicity (Nuwaysir, E. F. et al. (1999) Mol. Carcinog. 24:153-159; Steiner, S, and N. L. Anderson (2000) Toxicol. Lett. 112-113:467-471). If a test compound has a signature similar to that of a compound with known toxicity, it is likely to share those toxic properties. These fingerprints or signatures are most useful and refined when they contain expression information from a large number of genes and gene families. Ideally, a genome-wide measurement of expression provides the highest quality signature. Even genes whose expression is not altered by any tested compounds are important as well, as the levels of expression of these genes are used to normalize the rest of the expression data. The normalization procedure is useful for comparison of expression data after treatment with different compounds. While the assignment of gene function to elements of a toxicant signature aids in interpretation of toxicity mechanisms, knowledge of gene function is not necessary for the statistical matching of signatures which leads to prediction of toxicity (see, for example, Press Release 00-02 from the National Institute of Environmental Health Sciences, released Feb. 29, 2000, available at niehs.nih.gov/oc/news/toxchip.htm). Therefore, it is important and desirable in toxicological screening using toxicant signatures to include all expressed gene sequences.

In an embodiment, the toxicity of a test compound can be assessed by treating a biological sample containing nucleic acids with the test compound. Nucleic acids that are expressed in the treated biological sample are hybridized with one or more probes specific to the polynucleotides of the present invention, so that transcript levels corresponding to the polynucleotides of the present invention may be quantified. The transcript levels in the treated biological sample are compared with levels in an untreated biological sample. Differences in the transcript levels between the two samples are indicative of a toxic response caused by the test compound in the treated sample.

Another embodiment relates to the use of the polypeptides disclosed herein to analyze the proteome of a tissue or cell type. The term proteome refers to the global pattern of protein expression in a particular tissue or cell type. Each protein component of a proteome can be subjected individually to further analysis. Proteome expression patterns, or profiles, are analyzed by quantifying the number of expressed proteins and their relative abundance under given conditions and at a given time. A profile of a cell's proteome may thus be generated by separating and analyzing the polypeptides of a particular tissue or cell type. In one embodiment, the separation is achieved using two-dimensional gel electrophoresis, in which proteins from a sample are separated by isoelectric focusing in the first dimension, and then according to molecular weight by sodium dodecyl sulfate slab gel electrophoresis in the second dimension (Steiner and Anderson, supra). The proteins are visualized in the gel as discrete and uniquely positioned spots, typically by staining the gel with an agent such as Coomassie Blue or silver or fluorescent stains. The optical density of each protein spot is generally proportional to the level of the protein in the sample. The optical densities of equivalently positioned protein spots from different samples, for example, from biological samples either treated or untreated with a test compound or therapeutic agent, are compared to identify any changes in protein spot density related to the treatment. The proteins in the spots are partially sequenced using, for example, standard methods employing chemical or enzymatic cleavage followed by mass spectrometry. The identity of the protein in a spot may be determined by comparing its partial sequence, preferably of at least 5 contiguous amino acid residues, to the polypeptide sequences of interest. In some cases, further sequence data may be obtained for definitive protein identification.

A proteomic profile may also be generated using antibodies specific for KPP to quantify the levels of KPP expression. In one embodiment, the antibodies are used as elements on a microarray, and protein expression levels are quantified by contacting the microarray with the sample and detecting the levels of protein bound to each array element (Lueking, A. et al. (1999) Anal. Biochem. 270:103-111; Mendoze, L. G. et al. (1999) Biotechniques 27:778-788). Detection may be performed by a variety of methods known in the art, for example, by reacting the proteins in the sample with a thiol- or amino-reactive fluorescent compound and detecting the amount of fluorescence bound at each array element.

Toxicant signatures at the proteome level are also useful for toxicological screening, and should be analyzed in parallel with toxicant signatures at the transcript level. There is a poor correlation between transcript and protein abundances for some proteins in some tissues (Anderson, N. L. and J. Seilhamer (1997) Electrophoresis 18:533-537), so proteome toxicant signatures may be useful in the analysis of compounds which do not significantly affect the transcript image, but which alter the proteomic profile. In addition, the analysis of transcripts in body fluids is difficult, due to rapid degradation of mRNA, so proteomic profiling may be more reliable and informative in such cases.

In another embodiment, the toxicity of a test compound is assessed by treating a biological sample containing proteins with the test compound. Proteins that are expressed in the treated biological sample are separated so that the amount of each protein can be quantified. The amount of each protein is compared to the amount of the corresponding protein in an untreated biological sample. A difference in the amount of protein between the two samples is indicative of a toxic response to the test compound in the treated sample. Individual proteins are identified by sequencing the amino acid residues of the individual proteins and comparing these partial sequences to the polypeptides of the present invention.

In another embodiment, the toxicity of a test compound is assessed by treating a biological sample containing proteins with the test compound. Proteins from the biological sample are incubated with antibodies specific to the polypeptides of the present invention. The amount of protein recognized by the antibodies is quantified. The amount of protein in the treated biological sample is compared with the amount in an untreated biological sample. A difference in the amount of protein between the two samples is indicative of a toxic response to the test compound in the treated sample.

Microarrays may be prepared, used, and analyzed using methods known in the art (Brennan, T. M. et al. (1995) U.S. Pat. No. 5,474,796; Schena, M. et al. (1996) Proc. Natl. Acad. Sci. USA 93:10614-10619; Baldeschweiler et al. (1995) PCT application WO95/25116; Shalon, D. et al. (1995) PCT application WO95/35505; Heller, R. A. et al. (1997) Proc. Natl. Acad. Sci. USA 94:2150-2155; Heller, M. J. et al. (1997) U.S. Pat. No. 5,605,662). Various types of microarrays are well known and thoroughly described in Schena, M., ed. (1999; *DNA Microarrays: A Practical Approach*, Oxford University Press, London).

In another embodiment of the invention, nucleic acid sequences encoding KPP may be used to generate hybridization probes useful in mapping the naturally occurring genomic sequence. Either coding or noncoding sequences may be used, and in some instances, noncoding sequences may be preferable over coding sequences. For example, conservation of a coding sequence among members of a multigene family may potentially cause undesired cross hybridization during chromosomal mapping. The sequences may be mapped to a particular chromosome, to a specific region of a chromosome, or to artificial chromosome constructions, e.g., human artificial chromosomes (HACs), yeast artificial chromosomes (YACs), bacterial artificial chromosomes (BACs), bacterial P1 constructions, or single chromosome cDNA libraries (Harrington, J. J. et al. (1997) Nat. Genet. 15:345-355; Price, C. M. (1993) Blood Rev. 7:127-134; Trask, B. J. (1991) Trends Genet. 7:149-154). Once mapped, the nucleic acid sequences may be used to develop genetic linkage maps, for example, which correlate the inheritance of a disease state with the inheritance of a particular chromosome region or restriction fragment length polymorphism (RFLP) (Lander, E. S. and D. Botstein (1986) Proc. Natl. Acad. Sci. USA 83:7353-7357).

Fluorescent in situ hybridization (FISH) may be correlated with other physical and genetic map data (Heinz-Ulrich, et al. (1995) in Meyers, supra, pp. 965-968). Examples of genetic map data can be found in various scientific journals or at the Online Mendelian Inheritance in Man (OMIM) World Wide Web site. Correlation between the location of the gene encoding KPP on a physical map and a specific disorder, or a predisposition to a specific disorder, may help define the region of DNA associated with that disorder and thus may further positional cloning efforts.

In situ hybridization of chromosomal preparations and physical mapping techniques, such as linkage analysis using established chromosomal markers, may be used for extending genetic maps. Often the placement of a gene on the chromosome of another mammalian species, such as mouse, may reveal associated markers even if the exact chromosomal locus is not known. This information is valuable to investigators searching for disease genes using positional cloning or other gene discovery techniques. Once the gene or genes responsible for a disease or syndrome have been crudely localized by genetic linkage to a particular genomic region, e.g., ataxia-telangiectasia to 11q22-23, any sequences mapping to that area may represent associated or regulatory genes for further investigation (Gatti, R. A. et al. (1988) Nature 336:577-580). The nucleotide sequence of the instant invention may also be used to detect differences in the chromosomal location due to translocation, inversion, etc., among normal, carrier, or affected individuals.

In another embodiment of the invention, KPP, its catalytic or immunogenic fragments, or oligopeptides thereof can be used for screening libraries of compounds in any of a variety of drug screening techniques. The fragment employed in such screening may be free in solution, affixed to a solid support, borne on a cell surface, or located intracellularly. The formation of binding complexes between KPP and the agent being tested may be measured.

Another technique for drug screening provides for high throughput screening of compounds having suitable binding affinity to the protein of interest (Geysen, et al. (1984) PCT application WO84/03564). In this method, large numbers of different small test compounds are synthesized on a solid substrate. The test compounds are reacted with KPP, or fragments thereof, and washed. Bound KPP is then detected by methods well known in the art. Purified KPP can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding KPP specifically compete with a test compound for binding KPP. In this manner, antibodies can be used to detect the presence of any peptide which shares one or more antigenic determinants with KPP.

In additional embodiments, the nucleotide sequences which encode KPP may be used in any molecular biology techniques that have yet to be developed, provided the new techniques rely on properties of nucleotide sequences that are currently known, including, but not limited to, such properties as the triplet genetic code and specific base pair interactions.

Without further elaboration, it is believed that one skilled in the aft can, using the preceding description, utilize the present invention to its fullest extent. The following embodiments are, therefore, to be construed as merely illustrative, and not limitative of the remainder of the disclosure in any way whatsoever.

The disclosures of all patents, applications, and publications mentioned above and below, is including U.S. Ser. No.

60/467,491, U.S. Ser. No. 60/469,441, U.S. Ser. No. 60/476,408, U.S. Ser. No. 60/494,656, U.S. Ser. No. 60/524,415, and U.S. Ser. No. 60/528,750, are hereby expressly incorporated by reference.

EXAMPLES

I. Construction of cDNA Libraries

Incyte cDNAs are derived from cDNA libraries described in the LIFFSEQ database (Incyte, Palo Alto Calif.). Some tissues are homogenized and lysed in guanidinium isothiocyanate, while others are homogenized and lysed in phenol or in a suitable mixture of denaturants, such as TRIZOL (Invitrogen), a monophasic solution of phenol and guanidine isothiocyanate. The resulting lysates are centrifuged over CsCl cushions or extracted with chloroform. RNA is precipitated from the lysates with either isopropanol or sodium acetate and ethanol, or by other routine methods.

Phenol extraction and precipitation of RNA are repeated as necessary to increase RNA purity. In some cases, RNA is treated with DNase. For most libraries, poly(A)+ RNA is isolated using oligo d(T)-coupled paramagnetic particles (Promega), OLIGOTEX latex particles (QIAGEN, Chatsworth Calif.), or an OLIGOTEX mRNA purification kit (QIAGEN). Alternatively, RNA is isolated directly from tissue lysates using other RNA isolation kits, e.g., the POLY(A) PURE mRNA purification kit (Ambion, Austin Tex.).

In some cases, Stratagene is provided with RNA and constructs the corresponding cDNA libraries. Otherwise, cDNA is synthesized and cDNA libraries are constructed with the UNIZAP vector system (Stratagene) or SUPERSCRIPT plasmid system (Invitrogen), using the recommended procedures or similar methods known in the art (Ausubel et al., supra, ch. 5). Reverse transcription is initiated using oligo d(T) or random primers. Synthetic oligonucleotide adapters are ligated to double stranded cDNA, and the cDNA is digested with the appropriate restriction enzyme or enzymes. For most libraries, the cDNA is size-selected (300-1000 bp) using SEPHACRYL S1000, SEPHAROSE CL2B, or SEPHAROSE CL4B column chromatography (Amersham Biosciences) or preparative agarose gel electrophoresis. cDNAs are ligated into compatible restriction enzyme sites of the polylinker of a suitable plasmid, e.g., PBLUESCRIPT plasmid (Stratagene), PSPORT1 plasmid (Invitrogen, Carlsbad Calif.), PcDNA2.1 plasmid (Invitrogen), PBK-CMV plasmid (Stratagene), PCR2-TOPOTA plasmid (Invitrogen), PCMV-ICIS plasmid (Stratagene), pIGEN (Incyte, Palo Alto Calif.), pRARE (Incyte), or pINCY (Incyte), or derivatives thereof. Recombinant plasmids are transformed into competent *E. coli* cells including XL1-Blue, XL1-BlueMRF, or SOLR from Stratagene or DH5α, DH10B, or ElectroMAX DH10B from Invitrogen.

II. Isolation of cDNA Clones

Plasmids obtained as described in Example I are recovered from host cells by in vivo excision using the UNIZAP vector system (Stratagene) or by cell lysis. Plasmids are purified using at least one of the following: a Magic or WIZARD Minipreps DNA purification system (Promega); an AGTC Miniprep purification kit (Edge Biosystems, Gaithersburg Md.); and QIAWELL 8 Plasmid, QIAWELL 8 Plus Plasmid, QIAWELL 8 Ultra Plasmid purification systems or the R.E.A.L. PREP 96 plasmid purification kit from QIAGEN. Following precipitation, plasmids are resuspended in 0.1 ml of distilled water and stored, with or without lyophilization, at 4° C.

Alternatively, plasmid DNA is amplified from host cell lysates using direct link PCR in a high-throughput format (Rao, V. B. (1994) Anal. Biochem. 216:1-14). Host cell lysis and thermal cycling steps are carried out in a single reaction mixture. Samples are processed and stored in 384-well plates, and the concentration of amplified plasmid DNA is quantified fluorometrically using PICOGREEN dye (Molecular Probes, Eugene Oreg.) and a FLUOROSKAN II fluorescence scanner (Labsystems Oy, Helsinki, Finland).

III. Sequencing and Analysis

Incyte cDNA recovered in plasmids as described in Example II are sequenced as follows. Sequencing reactions are processed using standard methods or high-throughput instrumentation such as the ABI CATALYST 800 (Applied Biosystems) thermal cycler or the PTC-200 thermal cycler (MJ Research) in conjunction with the HYDRA microdispenser (Robbins Scientific) or the MICROLAB 2200 (Hamilton) liquid transfer system. cDNA sequencing reactions are prepared using reagents provided by Amersham Biosciences or supplied in ABI sequencing kits such as the ABI PRISM BIGDYE Terminator cycle sequencing ready reaction kit (Applied Biosystems). Electrophoretic separation of cDNA sequencing reactions and detection of labeled polynucleotides are carried out using the MEGABACE 1000 DNA sequencing system (Amersham Biosciences); the ABI PRISM 373 or 377 sequencing system (Applied Biosystems) in conjunction with standard ABI protocols and base calling software; or other sequence analysis systems known in the art. Reading frames within the cDNA sequences are identified using standard methods (Ausubel et al., supra, ch. 7). Some of the cDNA sequences are selected for extension using the techniques disclosed in Example VIII.

Polynucleotide sequences derived from Incyte cDNAs are validated by removing vector, linker, and poly(A) sequences and by masking ambiguous bases, using algorithms and programs based on BLAST, dynamic programming, and dinucleotide nearest neighbor analysis. The Incyte cDNA sequences or translations thereof are then queried against a selection of public databases such as the GenBank primate, rodent, mammalian, vertebrate, and eukaryote databases, and BLOCKS, PRINTS, DOMO, PRODOM; PROTEOME databases with sequences from *Homo sapiens, Rattus norvegicus, Mus musculus, Caenorhabditis elegans, Saccharomyces cerevisiae, Schizosaccharomyces pombe*, and *Candida albicans* (Incyte, Palo Alto Calif.); hidden Markov model (HMM)-based protein family databases such as PFAM, INCY, and TIGRFAM (Haft, D. H. et al. (2001) Nucleic Acids Res. 29:41-43); and HMM-based protein domain databases such as SMART (Schultz, J. et al. (1998) Proc. Natl. Acad. Sci. USA 95:5857-5864; Letunic, I. et al. (2002) Nucleic Acids Res. 30:242-244). (HMM is a probabilistic approach which analyzes consensus primary structures of gene families; see, for example, Eddy, S. R. (1996) Curr. Opin. Struct. Biol. 6:361-365.) The queries are performed using programs based on BLAST, FASTA, BLIMPS, and HMMER. The Incyte cDNA sequences are assembled to produce full length polynucleotide sequences. Alternatively, GenBank cDNAs, GenBank ESTs, stitched sequences, stretched sequences, or Genscan-predicted coding sequences (see Examples IV and V) are used to extend Incyte cDNA assemblages to full length. Assembly is performed using programs based on Phred, Phrap, and Consed, and cDNA assemblages are screened for open reading frames using programs based on GeneMark, BLAST, and PASTA. The full length polynucleotide sequences are translated to derive the corresponding full length polypeptide sequences. Alternatively, a polypeptide may begin at any of the methionine residues of the full length translated polypeptide. Full length polypeptide sequences are subsequently analyzed by querying against databases such as the GenBank protein databases (genpept), SwissProt, the PROTEOME databases, BLOCKS, PRINTS, DOMO, PRODOM, Prosite, bidden Markov model (HMM)-based protein family databases such as PFAM, INCY, and TIGRFAM; and HMM-based protein domain databases such as SMART. Full length polynucleotide sequences are also analyzed using MAcDNASIS PRO software (MiraiBio, Alameda Calif.) and LASERGENE software (DNASTAR). Polynucleotide and polypeptide sequence alignments are generated using default parameters specified by the CLUSTAL algorithm as incorporated into the MEGALIGN multisequence alignment program (DNASTAR), which also calculates the percent identity between aligned sequences.

Table 7 summarizes tools, programs, and algorithms used for the analysis and assembly of Incyte cDNA and full length sequences and provides applicable descriptions, references, and threshold parameters. The first column of Table 7 shows the tools, programs, and algorithms used, the second column provides brief descriptions thereof, the third column presents appropriate references, all of which are incorporated by reference herein in their entirety, and the fourth column presents, where applicable, the scores, probability values, and other parameters used to evaluate the strength of a match between two sequences (the higher the score or the lower the probability value, the greater the identity between two sequences).

The programs described above for the assembly and analysis of full length polynucleotide and polypeptide sequences are also used to identify polynucleotide sequence fragments from SEQ ID NO:44-86. Fragments from about 20 to about 4000 nucleotides which are useful in hybridization and amplification technologies are described in Table 4, column 2.

IV. Identification and Editing of Coding Sequences from Genomic DNA

Putative kinases and phosphatases are initially identified by running the Genscan gene identification program against public genomic sequence databases (e.g., gbpri and gbhtg). Genscan is a general-purpose gene identification program which analyzes genomic DNA sequences from a variety of organisms (Burge, C. and S. Karlin (1997) J. Mol. Biol. 268:78-94; Burge, C. and S. Karlin (1998) Curr. Opin. Struct. Biol. 8:346-354). The program concatenates predicted exons to form an assembled cDNA sequence extending from a methionine to a stop codon. The output of Genscan is a FASTA database of polynucleotide and polypeptide sequences. The maximum range of sequence for Genscan to analyze at once is set to 30 kb. To determine which of these Genscan predicted cDNA sequences encode kinases and phosphatases, the encoded polypeptides are analyzed by querying against PFAM models for kinases and phosphatases. Potential kinases and phosphatases are also identified by homology to Incyte cDNA sequences that have been annotated as kinases and phosphatases. These selected Genscan-predicted sequences are then compared by BLAST analysis to the genpept and gbpri public databases. Where necessary, the Genscan-predicted sequences are then edited by comparison to the top BLAST bit from genpept to correct errors in the sequence predicted by Genscan, such as extra or omitted exons. BLAST analysis is also used to find any Incyte cDNA or public cDNA coverage of the Genscan-predicted sequences, thus providing evidence for transcription. When Incyte cDNA coverage is available, this information is used to correct or confirm the Genscan predicted sequence. Full length polynucleotide sequences are obtained by assembling Genscan-predicted coding sequences with Incyte cDNA sequences and/or public cDNA sequences using the assembly process described in Example III. Alternatively, full length polynucleotide sequences are derived entirely from edited or unedited Genscan-predicted coding sequences.

V. Assembly of Genomic Sequence Data with cDNA Sequence Data

"Stitched" Sequences

Partial cDNA sequences are extended with exons predicted by the Genscan gene identification program described in Example IV. Partial cDNAs assembled as described in Example III are mapped to genomic DNA and parsed into clusters containing related cDNAs and Genscan exon predictions from one or more genomic sequences. Each cluster is analyzed using an algorithm based on graph theory and dynamic programming to integrate cDNA and genomic information, generating possible splice variants that are subsequently confirmed, edited, or extended to create a full length sequence. Sequence intervals in which the entire length of the interval is present on more than one sequence in the cluster are identified, and intervals thus identified are considered to be equivalent by transitivity. For example, if an interval is present on a cDNA and two genomic sequences, then all three intervals are considered to be equivalent. This process allows unrelated but consecutive genomic sequences to be brought together, bridged by cDNA sequence. Intervals thus identified are then "stitched" together by the stitching algorithm in the order that they appear along their parent sequences to generate the longest possible sequence, as well as sequence variants. Linkages between intervals which proceed along one type of parent sequence (cDNA to cDNA or genomic sequence to genomic sequence) are given preference over linkages which change parent type (cDNA to genomic sequence). The resultant stitched sequences are translated and compared by BLAST analysis to the genpept and gbpri public databases. Incorrect exons predicted by Genscan are corrected by comparison to the top BLAST hit from genpept. Sequences are further extended with additional cDNA sequences, or by inspection of genomic DNA, when necessary.

"Stretched" Sequences

Partial DNA sequences are extended to full length with an algorithm based on BLAST analysis. First, partial cDNAs assembled as described in Example III are queried against public databases such as the GenBank primate, rodent, mammalian, vertebrate, and eukaryote databases using the BLAST program. The nearest GenBank protein homolog is then compared by BLAST analysis to either Incyte cDNA sequences or GenScan exon predicted sequences described in Example IV. A chimeric protein is generated by using the resultant high-scoring segment pairs (HSPs) to map the translated sequences onto the GenBank protein homolog. Insertions or deletions may occur in the chimeric protein with respect to the original GenBank protein homolog. The GenBank protein homolog, the chimeric protein, or both are used as probes to search for homologous genomic sequences from the public human genome databases. Partial DNA sequences are therefore "stretched" or extended by the addition of homologous genomic sequences. The resultant stretched sequences are examined to determine whether they contain a complete gene.

VI. Chromosomal Mapping of KPP Encoding Polynucleotides

The sequences used to assemble SEQ ID NO:44-86 are compared with sequences from the Incyte LIFESEQ database and public domain databases using BLAST and other implementations of the Smith-Waterman algorithm. Sequences from these databases that matched SEQ ID NO:44-86 are assembled into clusters of contiguous and overlapping sequences using assembly algorithms such as Phrap (Table 7). Radiation hybrid and genetic mapping data available from public resources such as the Stanford Human Genome Center (SHGC), Whitehead Institute for Genome Research (WIGR), and Genethon are used to determine if any of the clustered sequences have been previously mapped. Inclusion of a mapped sequence in a cluster results in the assignment of all sequences of that cluster, including its particular SEQ ID NO:, to that map location.

Map locations are represented by ranges, or intervals, of human chromosomes. The map position of an interval, in centiMorgans, is measured relative to the terminus of the chromosome's p-arm. (The centiMorgan (cM) is a unit of measurement based on recombination frequencies between chromosomal markers. On average, 1 cM is roughly equivalent to 1 megabase (Mb) of DNA in humans, although this can vary widely due to hot and cold spots of recombination.) The cM distances are based on genetic markers mapped by Généthon which provide boundaries for radiation hybrid markers whose sequences were included in each of the clusters. Human genome maps and other resources available to the public, such as the NCBI "GeneMap'99" World Wide Web site (ncbi.nlm.nih.gov/genemap/), can be employed to determine if previously identified disease genes map within or in proximity to the intervals indicated above.

VII. Analysis of Polynucleotide Expression

Northern analysis is a laboratory technique used to detect the presence of a transcript of a gene and involves the hybridization of a labeled nucleotide sequence to a membrane on which RNAs from a particular cell type or tissue have been bound (Sambrook and Russell, supra, ch. 7; Ausubel et al., supra, ch. 4).

Analogous computer techniques applying BLAST are used to search for identical or related molecules in databases such as GenBank or LIFESEQ (Incyte). This analysis is much faster than multiple membrane-based hybridizations. In addition, the sensitivity of the computer search can be modified to determine whether any particular match is categorized as exact or similar. The basis of the search is the product score, which is defined as:

$$\text{BLAST Score} \times \text{Percent Identity}/5 \times \text{minimum}\{\text{length}(\text{Seq. 1}), \text{length}(\text{Seq. 2})\}$$

The product score takes into account both the degree of similarity between two sequences and the length of the sequence match. The product score is a normalized value between 0 and 100, and is calculated as follows: the BLAST score is multiplied by the percent nucleotide identity and the product is divided by (5 times the length of the shorter of the two sequences). The BLAST score is calculated by assigning a score of +5 for every base that matches in a high-scoring segment pair (HSP), and −4 for every mismatch. Two sequences may share more than one HSP (separated by gaps). If there is more than one HSP, then the pair with the highest BLAST score is used to calculate the product score. The product score represents a balance between fractional overlap and quality in a BLAST alignment. For example, a product score of 100 is produced only for 100% identity over the entire length of the shorter of the two sequences being compared. A product score of 70 is produced either by 100% identity and 70% overlap at one end, or by 88% identity and 100% overlap at the other. A product score of 50 is produced either by 100% identity and 50% overlap at one end, or 79% identity and 100% overlap.

Alternatively, polynucleotides encoding KPP are analyzed with respect to the tissue sources from which they are derived. For example, some full length sequences are assembled, at least in part, with overlapping Incyte cDNA sequences (see Example III). Each cDNA sequence is derived from a cDNA library constructed from a human tissue. Each human tissue is classified into one of the following organ/tissue categories: cardiovascular system; connective tissue; digestive system; embryonic structures; endocrine system; exocrine glands; genitalia, female; genitalia, male; germ cells; hemic and immune system; liver; musculoskeletal system; nervous system; pancreas; respiratory system; sense organs; skin; stomatognathic system; unclassified/mixed; or urinary tract. The number of libraries in each category is counted and divided by the total number of libraries across all categories. Similarly, each human tissue is classified into one of the following disease/condition categories: cancer, cell line, developmental, inflammation, neurological, trauma, cardiovascular, pooled, and other, and the number of libraries in each category is counted and divided by the total number of libraries across all categories. The resulting percentages reflect the tissue- and disease-specific expression of cDNA encoding KPP. cDNA sequences and cDNA library/tissue information are found in the LIFESEQ database (Incyte, Palo Alto Calif.).

VIII. Extension of KPP Encoding Polynucleotides

Full length polynucleotides are produced by extension of an appropriate fragment of the full length molecule using oligonucleotide primers designed from this fragment. One primer is synthesized to initiate 5' extension of the known fragment, and the other primer is synthesized to initiate 3' extension of the known fragment. The initial primers are designed using OLIGO 4.06 software (National Biosciences), or another appropriate program, to be about 22 to 30 nucleotides in length, to have a GC content of about 50% or more, and to anneal to the target sequence at temperatures of about 68° C. to about 72° C. Any stretch of nucleotides which would result in hairpin structures and primer-primer dimerizations is avoided.

Selected human cDNA libraries are used to extend the sequence. If more than one extension is necessary or desired, additional or nested sets of primers are designed.

High fidelity amplification is obtained by PCR using methods well known in the art. PCR is performed in 96-well plates using the PTC-200 thermal cycler (MJ Research, Inc.). The reaction mix contains DNA template, 200 nmol of each primer, reaction buffer containing $Mg^{2+}$, $(NH_4)_2SO_4$, and 2-mercaptoethanol, Taq DNA polymerase (Amersham Biosciences), ELONGASE enzyme (Invitrogen), and Pfu DNA polymerase (Stratagene), with the following parameters for primer pair PCI A and PCI B: Step 1: 94° C., 3 min; Step 2: 94° C., 15 sec; Step 3: 60° C.; 1 min; Step 4: 68° C., 2 min; Step 5: Steps 2, 3, and 4 repeated 20 times; Step 6: 68° C., 5 min; Step 7: storage at 4° C. In the alternative, the parameters for primer pair T7 and SK+ are as follows: Step 1: 94° C., 3 min; Step 2: 94° C., 15 sec; Step 3: 57° C., 1 min; Step 4: 68° C., 2 min; Step 5: Steps 2, 3, and 4 repeated 20 times; Step 6: 68° C., 5 min; Step 7: storage at 4° C.

The concentration of DNA in each well is determined by dispensing 100 PICOGREEN quantitation reagent (0.25% (v/v) PICOGREEN; Molecular Probes, Eugene Oreg.) dissolved in 1×TE and 0.5 μl of undiluted PCR product into each well of an opaque fluorimeter plate (Corning Costar, Acton Mass.), allowing the DNA to bind to the reagent. The plate is scanned in a Fluoroskan II (Labsystems Oy, Helsinki, Finland) to measure the fluorescence of the sample and to quantify the concentration of DNA. A 5 μl to 10 μl aliquot of the reaction mixture is analyzed by electrophoresis on a 1% agarose gel to determine which reactions are successful in extending the sequence.

The extended nucleotides are desalted and concentrated, transferred to 384-well plates, digested with CviJI cholera virus endonuclease (Molecular Biology Research, Madison Wis.), and sonicated or sheared prior to religation into pUC 18 vector (Amersham Biosciences). For shotgun sequencing, the digested nucleotides are separated on low concentration (0.6 to 0.8%) agarose gels, fragments are excised, and agar digested with Agar ACE (Promega). Extended clones were religated using T4 ligase (New England Biolabs, Beverly Mass.) into pUC18 vector (Amersham Biosciences), treated with Pfu DNA polymerase (Stratagene) to fill-in restriction site overhangs, and transfected into competent *E. coli* cells. Transformed cells are selected on antibiotic-containing media, and individual colonies are picked and cultured overnight at 37° C. in 384-well plates in LB/2× carb liquid media.

The cells are lysed, and DNA is amplified by PCR using Taq DNA polymerase (Amersham Biosciences) and Pfu DNA polymerase (Stratagene) with the following parameters: Step 1: 94° C., 3 min; Step 2: 94° C., 15 sec; Step 3: 60° C., 1 min; Step 4: 72° C., 2 min; Step 5: steps 2, 3, and 4 repeated 29 times; Step 6: 72° C., 5 min; Step 7: storage at 4° C. DNA is quantified by PICOGREEN reagent (Molecular Probes) as described above. Samples with low DNA recoveries are reamplified using the same conditions as described above. Samples are diluted with 20% dimethysulfoxide (1:2, v/v), and sequenced using DYENAMIC energy transfer sequencing Primers and the DYENAMIC DIRECT kit (Amersham Biosciences) or the ABI PRISM BIGDYE Terminator cycle sequencing ready reaction kit (Applied Biosystems).

In like manner, full length polynucleotides are verified using the above procedure or are used to obtain 5' regulatory sequences using the above procedure along with oligonucleotides designed for such extension, and an appropriate genomic library.

IX. Identification of Single Nucleotide Polymorphisms in KPP Encoding Polynucleotides Common DNA sequence variants known as single nucleotide polymorphisms (SNPs) are identified in SEQ ID NO:44-86 using the LIFESEQ database (Incyte). Sequences from the same gene are clustered together and assembled as described in Example III, allowing the identification of all sequence variants in the gene. An algorithm consisting of a series of filters is used to distinguish SNPs from other sequence variants. Preliminary filters remove the majority of basecall errors by requiring a minimum Phred quality score of 15, and remove sequence alignment errors and errors resulting from improper trimming of vector sequences, chimeras, and splice variants. An automated procedure of advanced chromosome analysis is applied to the original chromatogram files in the vicinity of the putative SNP. Clone error filters use statistically generated algorithms to identify errors introduced during laboratory processing, such as those caused by reverse transcriptase, polymerase, or somatic mutation. Clustering error filters use statistically generated algorithms to identify errors resulting from clustering of close homologs or pseudogenes, or due to contamination by non-human sequences. A final set of filters removes duplicates and SNPs found in immunoglobulins or T-cell receptors.

Certain SNPs are selected for further characterization by mass spectrometry using the high throughput MASSARRAY system (Sequenom, Inc.) to analyze allele frequencies at the SNP sites in four different human populations. The Caucasian population comprises 92 individuals (46 male, 46 female), including 83 from Utah, four French, three Venezualan, and two Amish individuals. The African population comprises 194 individuals (97 male, 97 female), all African Americans. The Hispanic population comprises 324 individuals (162 male, 162 female), all Mexican Hispanic. The Asian population comprises 126 individuals (64 male, 62 female) with a reported parental breakdown of 43% Chinese, 31% Japanese, 13% Korean, 5% Vietnamese, and 8% other Asian. Allele frequencies are first analyzed in the Caucasian population; in some cases those SNPs which show no allelic variance in this population are not further tested in the other three populations.

X. Labeling and Use of Individual Hybridization Probes

Hybridization probes derived from SEQ ID NO:44-86 are employed to screen cDNAs, genomic DNAs, or mRNAs. Although the labeling of oligonucleotides, consisting of about 20 base pairs, is specifically described, essentially the same procedure is used with larger nucleotide fragments. Oligonucleotides are designed using state-of-the-art software such as OLIGO 4.06 software (National Biosciences) and labeled by combining 50 μmol of each oligomer, 250 μCi of [$\gamma$-$^{32}$P] adenosine triphosphate (Amersham Biosciences), and T4 polynucleotide kinase (DuPont NEN, Boston Mass.). The labeled oligonucleotides are substantially purified using a SEPHADEX G-25 superfine size exclusion dextran bead column (Amersham Biosciences). An aliquot containing $10^7$ counts per minute of the labeled probe is used in a typical membrane-based hybridization analysis of human genomic DNA digested with one of the following endonucleases: Ase I, Bgl II, Eco RI, Pst I, Xba I, or Pvu II (DuPont NEN).

The DNA from each digest is fractionated on a 0.7% agarose gel and transferred to NYTRAN PLUS nylon membranes (Schleicher & Schuell, Durham N.H.). Hybridization is carried out for 16 hours at 40° C. To remove nonspecific signals, blots are sequentially washed at room temperature under conditions of up to, for example, 0.1× saline sodium citrate and 0.5% sodium dodecyl sulfate. Hybridization patterns are visualized using autoradiography or an alternative imaging means and compared.

XI. Microarrays

The linkage or synthesis of array elements upon a microarray can be achieved utilizing photolithography, piezoelectric printing (ink jet printing; see, e.g., Baldeschweiler et al., supra), mechanical microspotting technologies, and derivatives thereof. The substrate in each of the aforementioned technologies should be uniform and solid with a non-porous surface (Schena, M., ed. (1999) *DNA Microarrays: A Practical Approach*, Oxford University Press, London). Suggested substrates include silicon, silica, glass slides, glass chips, and silicon wafers. Alternatively, a procedure analogous to a dot or slot blot may also be used to arrange and link elements to the surface of a substrate using thermal, UV, chemical, or mechanical bonding procedures. A typical array may be produced using available methods and machines well known to those of ordinary skill in the art and may contain any appropriate number of elements (Schena, M. et al. (1995) Science 270:467-470; Shalon, D. et al. (1996) Genome Res. 6:639-645; Marshall, A. and J. Hodgson (1998) Nat. Biotechnol. 16:27-31).

Full length cDNAs, Expressed Sequence Tags (SSTs), or fragments or oligomers thereof may comprise the elements of the microarray. Fragments or oligomers suitable for hybridization can be selected using software well known in the art such as LASERGENE software (DNASTAR). The array elements are hybridized with polynucleotides in a biological sample. The polynucleotides in the biological sample are conjugated to a fluorescent label or other molecular tag for ease of detection. After hybridization, nonhybridized nucleotides from the biological sample are removed, and a fluorescence scanner is used to detect hybridization at each array element. Alternatively, laser desorption and mass spectrometry may be used for detection of hybridization. The degree of complementarity and the relative abundance of each polynucleotide which hybridizes to an element on the microarray may be assessed. In one embodiment, microarray preparation and usage is described in detail below.

Tissue or Cell Sample Preparation

Total RNA is isolated from tissue samples using the guanidinium thiocyanate method and poly(A)$^+$ RNA is purified using the oligo-(dT) cellulose method. Each poly(A)$^+$ RNA sample is reverse transcribed using MMLV reverse-transcriptase, 0.05 pg/μl oligo-(dT) primer (21mer), 1× first strand buffer, 0.03 units/μl RNase inhibitor, 500 μM dATP, 500 μM dGTP, 500 AM dTTP, 40 μM dCTP, 40 μM dCTP-Cy3 (BDS) or dCTP-Cy5 (Amersham Biosciences). The reverse transcription reaction is performed in a 25 ml volume containing 200 ng poly(A)$^+$ RNA with GEMBRIGHT kits (Incyte). Specific control poly(A)$^+$ RNAs are synthesized by in vitro transcription from non-coding yeast genomic DNA. After incubation at 37° C. for 2 hr, each reaction sample (one with Cy3 and another with Cy5 labeling) is treated with 2.5 ml of 0.5 M sodium hydroxide and incubated for 20 minutes at 85° C. to the stop the reaction and degrade the RNA. Samples are purified using two successive CHROMA SPIN 30 gel filtration spin columns (BD Clontech, Palo Alto Calif.) and after combining, both reaction samples are ethanol precipitated using 1 ml of glycogen (1 mg/ml), 60 ml sodium acetate, and 300 ml of 100% ethanol. The sample is then dried to completion using a SpeedVAC (Savant Instruments Inc., Holbrook N.Y.) and resuspended in 14 μl 5×SSC/0.2% SDS.

Microarray Preparation

Sequences of the present invention are used to generate array elements. Each array element is amplified from bacterial cells containing vectors with cloned cDNA inserts. PCR amplification uses primers complementary to the vector sequences flanking the cDNA insert. Array elements are amplified in thirty cycles of PCR from an initial quantity of 1-2 ng to a final quantity greater than 5 μg. Amplified array elements are then purified using SEPHACRYL-400 (Amersham Biosciences).

Purified array elements are immobilized on polymer-coated glass slides. Glass microscope slides (Corning) are cleaned by ultrasound in 0.1% SDS and acetone, with extensive distilled water washes between and after treatments. Glass slides are etched in 4% hydrofluoric acid (VWR Scientific Products Corporation (VWR), West Chester Pa.), washed extensively in distilled water, and coated with 0.05% aminopropyl silane (Sigma-Aldrich, St. Louis Mo.) in 95% ethanol. Coated slides are cured in a 110° C. oven.

Array elements are applied to the coated glass substrate using a procedure described in U.S. Pat. No. 5,807,522, incorporated herein by reference. 1 μl of the array element DNA, at an average concentration of 100 ng/μl, is loaded into the open capillary printing element by a high-speed robotic apparatus. The apparatus then deposits about 5 nl of array element sample per slide.

Microarrays are UV-crosslinked using a STRATALINKER UV-crosslinker (Stratagene). Microarrays are washed at room temperature once in 0.2% SDS and three times in distilled water. Non-specific binding sites are blocked by incubation of microarrays in 0.2% casein in phosphate buffered saline (PBS) (Tropix, Inc., Bedford Mass.) for 30 minutes at 60° C. followed by washes in 0.2% SDS and distilled water as before.

Hybridization

Hybridization reactions contain 9 μl of sample mixture consisting of 0.2 μg each of Cy3 and Cy5 labeled cDNA synthesis products in 5×SSC, 0.2% SDS hybridization buffer. The sample mixture is heated to 65° C. for 5 minutes and is aliquoted onto the microarray surface and covered with an 1.8 $cm^2$ coverslip. The arrays are transferred to a waterproof chamber having a cavity just slightly larger than a microscope slide. The chamber is kept at 100% humidity internally by the addition of 140 μl of 5×SSC in a corner of the chamber. The chamber containing the arrays is incubated for about 6.5 hours at 60° C. The arrays are washed for 10 min at 45° C. in a first wash buffer (1×SSC, 0.1% SDS), three times for 10 minutes each at 45° C. in a second wash buffer (0.1×SSC), and dried.

Detection

Reporter-labeled hybridization complexes are detected with a microscope equipped with an Innova 70 mixed gas 10 W laser (Coherent, Inc., Santa Clara Calif.) capable of generating spectral lines at 488 nm for excitation of Cy3 and at 632 nm for excitation of Cy5. The excitation laser light is focused on the array using a 20.times. microscope Objective (Nikon, Inc., Melville N.Y.). The slide containing the array is placed on a computer-controlled X-Y stage on the microscope and raster-scanned past the objective. The 1.8 cm.times.1.8 cm array used in the present example is scanned with a resolution of 20 micrometers.

In two separate scans, a mixed gas multiline laser excites the two fluorophores sequentially. Emitted light is split, based on wavelength, into two photomultiplier tube detectors (PMT R1477, Hamamatsu Photonics Systems, Bridgewater N.J.) corresponding to the two fluorophores. Appropriate filters positioned between the array and the photomultiplier tubes are used to filter the signals. The emission maxima of the fluorophores used are 565 nm for Cy3 and 650 nm for Cy5. Each array is typically scanned twice, one scan per fluorophore using the appropriate filters at the laser source, although the apparatus is capable of recording the spectra from both fluorophores simultaneously.

The sensitivity of the scans is typically calibrated using the signal intensity generated by a cDNA control species added to the sample mixture at a known concentration. A specific location on the array contains a complementary DNA sequence, allowing the intensity of the signal at that location to be correlated with a weight ratio of hybridizing species of 1:100,000. When two samples from different sources (e.g., representing test and control cells), each labeled with a different fluorophore, are hybridized to a single array for the purpose of identifying genes that are differentially expressed, the calibration is done by labeling samples of the calibrating cDNA with the two fluorophores and adding identical amounts of each to the hybridization mixture.

The output of the photomultiplier tube is digitized using a 12-bit RTI-835H analog-to-digital (A/D) conversion board (Analog Devices, Inc., Norwood Mass.) installed in an IBM-compatible PC computer. The digitized data are displayed as an image where the signal intensity is mapped using a linear 20-color transformation to a pseudocolor scale ranging from blue (low signal) to red (high signal). The data is also analyzed quantitatively. Where two different fluorophores are excited and measured simultaneously, the data are first corrected for optical crosstalk (due to overlapping emission spectra) between the fluorophores using each fluorophore's emission spectrum.

A grid is superimposed over the fluorescence signal image such that the signal from each spot is centered in each element of the grid. The fluorescence signal within each element is then integrated to obtain a numerical value corresponding to the average intensity of the signal. The software used for signal analysis is the GEMTOOLS gene expression analysis program (Incyte). Array elements that exhibit at least about a two-fold change in expression, a signal-to-background ratio of at least about 2.5, and an element spot size of at least about 40%, are considered to be differentially expressed.

Expression

For example, SEQ ID NO:51, SEQ ID NO:53-54, and SEQ ID NO:57 were differentially expressed in breast carcinoma cell lines versus a cell line derived from normal breast epithelial tissue as determined by microarray analysis. Gene expression profiles of nonmalignant mammary epithelial cells were compared to gene expression profiles of various breast carcinoma lines at different stages of tumor progression. The cells were grown in defined serum-free H14 medium to 70-80% confluence prior to RNA harvest. Cell lines compared included: a) HMEC, a primary breast epithelial cell line isolated from a normal donor, b) MCF-10A, a breast mammary gland cell line isolated from a 36-year-old woman with fibrocystic breast disease, c) MCF7, a nonmalignant breast adenocarcinoma cell line isolated from the pleural effusion of a 69-year-old female, d) T-47D, a breast carcinoma cell line isolated from a pleural effusion obtained from a 54-year-old female with an infiltrating ductal carcinoma of the breast, e) Sk-BR-3, a breast adenocarcinoma cell line isolated from a malignant pleural effusion of a 43-year-old female, f) BT-20, a breast carcinoma cell line derived in vitro from cells emigrating out of thin slices of the tumor mass isolated from a 74-year-old female, g) MDA-nib-231, a breast tumor cell line isolated from the pleural effusion of a 51-year-old female, and h) MDA-mb-435S, a spindle-shaped strain that evolved from the parent line (435) isolated by R. Cailleau from pleural effusion of a 31-year-old female with metastatic, ductal adenocarcinoma of the breast. Expression of SEQ ID NO:53 was increased at least two-fold in MCF7 cells versus HMECs. In a similar experiment, expression of SEQ ID NO:51 was decreased at least two-fold in Sk-BR-3 cells versus HMECs. In a similar experiment, expression of SEQ ID NO:54 was decreased at least two-fold in Sk-BR-3, T-47D, and MCF7 cells versus HMECs. In a similar experiment, expression of SEQ ID NO:57 was decreased at least two-fold in MDA-mb-231 and MCF-10A cells versus HMECs. Therefore, in various embodiments, SEQ ID NO:51, SEQ ID NO:53-54, and SEQ ID NO:57 can be used for one or more of the following: i) monitoring treatment of breast cancer, diagnostic assays for breast cancer, and iii) developing therapeutics and/or other treatments for breast cancer.

In another example, SEQ ID NO:45, SEQ ID NO:51, SEQ ID NO:53-54, and SEQ ID NO:57 were differentially expressed in breast carcinoma cell lines versus a cell line derived from a donor with non-malignant, fibrocystic breast disease as determined by microarray analysis. Gene expression profiles of nonmalignant mammary epithelial cells were compared to gene expression profiles of various breast carcinoma lines at different stages of tumor progression. The cells were grown in defined serum-free TCH medium, defined serum-free H14 medium, or the supplier's recommended medium to 70-80% confluence prior to RNA harvest and compared to MCF-10A cells grown in the same medium. Cell lines compared included: a) MCF-10A, a breast mammary gland (luminal ductal characteristics) cell line isolated from a 36-year-old woman with fibrocystic breast disease; b) MCF7, a nonmalignant breast adenocarcinoma cell line isolated from the pleural effusion of a 69-year-old female, c) T-47D, a breast carcinoma cell line isolated from a pleural effusion obtained from a 54-year-old female with an infiltrating ductal carcinoma of the breast, d) Sk-BR-3, a breast adenocarcinoma cell line isolated from a malignant pleural effusion of a 43-year-old female, e) BT-20, a breast carcinoma cell line derived in vitro from the cells emigrating out of thin slices of the tumor mass isolated from a 74-year-old female, f) MDA-mb-231, a breast tumor cell line isolated from the pleural effusion of a 51-year old female, and g) MDA-nib-435S, a spindle shaped strain that evolved from the parent line (435) isolated from the pleural effusion of a 31-year-old female with metastatic, ductal adenocarcinoma of the breast. Expression of SEQ ID NO:45 was increased at least two-fold in MCF7 cells when grown in either the defined serum-free H14 medium or the supplier's recommended medium as compared with MCF-10A cells grown under the same conditions. In a similar experiment, expression of SEQ ID NO:51 was decreased at least two-fold in Sk-BR-3 cells when grown in any of the growth conditions as compared with MCF-10A cells grown under the same conditions. In a similar experiment, expression of SEQ ID NO:53 was increased at least two-fold in MCF7 cells when grown in any of the growth conditions as compared with MCF-10A cells grown under the same conditions. In a similar experiment, expression of SEQ ID NO:54 was decreased at least two-fold in Sk-BR-3 cells and T-47D cells when grown in any of the growth conditions as compared with MCF-10A cells grown under the same conditions. In a similar experiment, expression of SEQ ID NO:57 was increased at least two-fold in MDA-mb-231 cells when grown in either the defined serum-free H14 medium or the supplier's recommended medium as compared with MCF-10A cells grown under the same conditions. Therefore, in various embodiments, SEQ ID NO:45, SEQ ID NO:51, SEQ ID NO:53-54, and SEQ ID NO:57 can be used for one or more of the following: i) monitoring treatment of breast cancer, diagnostic assays for breast cancer, and developing therapeutics and/or other treatments for breast cancer.

In another example, expression of SEQ ID NO:47 was down-regulated in a breast cancer cell line (MCF7) treated with TNFα versus untreated MCF7 cells as determined by microarray analysis. MCF7 cells were treated with 10 ng/mL TNFα for 1, 4, 8, 12, 24, 48, and 72 hours. Treated cells were compared to untreated cells kept in culture for the same amount of time. Expression of SEQ ID NO:47 was decreased at least two-fold in MCF7 cells treated with 10 ng/mL TNFα for 4, 8, 24, or 48 hours as compared with untreated MCF7 cells. Therefore, in various embodiments, SEQ ID NO:47 can be used for one or more of the following: i) monitoring treatment of breast cancer, diagnostic assays for breast cancer, and developing therapeutics and/or other treatments for breast cancer.

In another example, expression of SEQ ID NO:51 was down-regulated in ovary tumor tissue versus normal ovary tissue as determined by microarray analysis. Expression of SEQ ID NO:51 was decreased at least two-fold in ovary tumor tissue as compared with matched normal ovary tissue from the same donor in 1 of 2 donors tested. Therefore, in various embodiments, SEQ ID NO:51 can be used for one or more of the following: i) monitoring treatment of ovarian cancer, diagnostic assays for ovarian cancer, and developing therapeutics and/or other treatments for ovarian cancer.

In another example, expression of SEQ ID NO:54 was down-regulated in brain tissue from donors with Alzheimer's disease (AD) versus brain tissue from a normal donor as determined by microarray analysis. Specific dissected brain regions from the cerebellum, dentate nucleus, and vermis of a normal donor were compared to: a) the corresponding regions dissected from the brain of a female with mild AD; and b) the corresponding regions dissected from the brain of a female with severe AD. The diagnosis of normal or mild AD was established by a certified neuropathologist based on microscopic examination of multiple sections throughout the brain. Expression of SEQ ID NO:54 was decreased at least two-fold in the striatum and globus pallidus region of the brain of a donor with severe AD and a donor with mild AD as compared with the corresponding region of the brain from a normal donor. Therefore, in various embodiments, SEQ ID NO:54 can be used for one or more of the following: i) monitoring treatment of AD, ii) diagnostic assays for AD, and iii) developing therapeutics and/or other treatments for AD.

In another example, expression of SEQ ID NO:57 was up-regulated in lung tumor tissue versus normal lung tissue as determined by microarray analysis. Expression of SEQ ID NO:57 was increased at least two-fold in lung tumor tissue as compared with matched normal lung tissue from the same donor in 3 of 4 donors tested. Therefore, in various embodiments, SEQ ID NO:57 can be used for one or more of the following: i) monitoring treatment of lung cancer, ii) diagnostic assays for lung cancer, and iii) developing therapeutics and/or other treatments for lung cancer.

In another example, expression of SEQ ID NO:57 was down-regulated to a lesser extent in preadipocytes taken from an obese donor versus preadipocytes taken from a non-obese donor as determined by microarray analysis. Primary subcutaneous preadipocytes were isolated from the adipose tissue of a non-obese donor, a 28-year-old healthy female with body mass index (BMI) of 23.59, and an obese donor, a 40-year-old healthy female with a body mass index (BMI) of 32.47. The preadipocytes from each donor were cultured and induced to differentiate into adipocytes by growing them in differentiation medium containing PPAR-γ agonist and human insulin (Zen-Bio). Some thiazolidinediones or PPAR-γ agonists, which bind and activate an orphan nuclear receptor, PPAR-γ, have been shown to induce human adipocyte differentiation. The preadipocytes were treated with human insulin and PPAR-γ agonist for 3 days and subsequently were switched to medium containing insulin for a range of time periods ranging from one to 20 days before the cells were collected for analysis. Differentiated adipocytes from each donor were compared to untreated preadipocytes, maintained in culture in the absence of differentiation-inducing agents, from the same donor. Between 80% and 90% of the preadipocytes finally differentiated to adipocytes as observed under phase contrast microscopy. Expression of SEQ ID NO:57 was decreased at least two-fold in differentiated preadipocytes from a normal donor versus non-differentiated preadipocytes from the same donor. In contrast, no differential expression was seen in differentiated preadipocytes from an obese donor versus non-differentiated preadipocytes from the same donor. These data suggest that SEQ ID NO:57 is differentially expressed in adipocytes from normal subjects but not in adipocytes from obese subjects. Therefore, in various embodiments, SEQ ID NO:57 can be used for one or more of the following: i) monitoring treatment of diabetes mellitus and other disorders, such as obesity and hypertension ii) diagnostic assays for diabetes mellitus and other disorders, such as obesity and hypertension iii) developing therapeutics and/or other treatments for diabetes mellitus and other disorders, such as obesity and hypertension.

In another example, SEQ ID NO:47, SEQ ID NO:54, and SEQ ID NO:56 showed tissue-specific expression as determined by microarray analysis. RNA samples isolated from a variety of normal human tissues were compared to a common reference sample. Tissues contributing to the reference sample were selected for their ability to provide a complete distribution of RNA in the human body and include brain (4%), heart (7%), kidney (3%), lung (8%), placenta (46%), small intestine (9%), spleen (3%), stomach (6%), testis (9%), and uterus (5%). The normal tissues assayed were obtained from at least three different donors. RNA from each donor was separately isolated and individually hybridized to the microarray. Since these hybridization experiments were conducted using a common reference sample, differential expression values are directly comparable from one tissue to another. The expression of SEQ ID NO:47 was increased by at least two-fold in small intestine and liver as compared to the reference sample. Therefore, SEQ ID NO:47 can be used as a tissue marker for small intestine and liver. The expression of SEQ ID NO:54 was increased by at least two-fold in brain (temporal cortex) and leukocytes as compared to the reference sample. Therefore, SEQ ID NO:54 can be used as a tissue marker for brain (temporal cortex) and leukocytes. The expression of SEQ ID NO:56 was increased by at least two-fold in brain as compared to the reference sample. Therefore, SEQ ID NO:56 can be used as a tissue marker for brain.

In another example, SEQ ID NO:44 showed tissue-specific expression as determined by microarray analysis. RNA samples isolated from a variety of normal human tissues were compared to a common reference sample. Tissues contributing to the reference sample were selected for their ability to provide a complete distribution of RNA in the human body and include brain (4%), heart (7%), kidney (3%), lung (8%), placenta (46%), small intestine (9%), spleen (3%), stomach (6%), testis (9%), and uterus (5%). The normal tissues assayed were obtained from at least three different donors. RNA from each donor was separately isolated and individually hybridized to the microarray. Since these hybridization experiments were conducted using a common reference sample, differential expression values are directly comparable from one tissue to another. The expression of SEQ ID NO:44 was increased by at least two-fold in leukocytes, thymus gland, and tonsil as compared to the reference sample. Therefore, SEQ ID NO:44 can be used as a tissue marker for leukocytes, thymus gland, and tonsil.

In another example, SEQ ID NO:48-50 showed tissue-specific expression as determined by microarray analysis. RNA samples isolated from a variety of normal human tissues were compared to a common reference sample. Tissues contributing to the reference sample were selected for their ability to provide a complete distribution of RNA in the human body and include brain (4%), heart (7%), kidney (3%), lung (8%), placenta (46%), small intestine (9%), spleen (3%), stomach (6%), testis (9%), and uterus (5%). The normal tissues assayed were obtained from at least three different donors. RNA from each donor was separately isolated and individually hybridized to the microarray. Since these hybridization experiments were conducted using a common reference sample, differential expression values are directly comparable from one tissue to another. The expression of SEQ ID NO:48-50 was increased by at least two-fold in muscle, adipose tissue, and liver as compared to the reference sample. Therefore, SEQ ID NO:48-50 can be used as a tissue marker for muscle, adipose tissue, and liver.

In another example, expression of SEQ ID NO:62 was up-regulated in breast cancer cell lines versus a breast epithelial cell line derived from normal breast tissue as determined by microarray analysis. Gene expression profiles of nonmalignant mammary epithelial cells were compared to gene expression profiles of various breast carcinoma lines at different stages of tumor progression. The cells were grown in defined serum-free H14 medium to 70-80% confluence prior to RNA harvest. Cell lines compared included: a) HMEC, a primary breast epithelial cell line isolated from a normal donor, b) MCF-10A, a breast mammary gland cell line isolated from a 36-year-old woman with fibrocystic breast disease, c) MCF7, a nonmalignant breast adenocarcinoma cell line isolated from the pleural effusion of a 69-year-old female, d) T-47D, a breast carcinoma cell line isolated from a pleural effusion obtained from a 54-year-old female with an infiltrating ductal carcinoma of the breast, e) Sk-BR-3, a breast adenocarcinoma cell line isolated from a malignant pleural effusion of a 43-year-old female, f) BT-20, a breast carcinoma cell line derived in vitro from cells emigrating out of thin slices of the tumor mass isolated from a 74-year-old female, g) MDA-mb-231, a breast tumor cell line isolated from the pleural effusion of a 51-year-old female, and h) MDA-mb-435S, a spindle-shaped strain that evolved from the parent line (435) isolated by R. Cailleau from pleural effusion of a 31-year-old female with metastatic, ductal adenocarcinoma of the breast. Expression of SEQ ID NO:62 was increased at least two-fold in two (MDA-mb-231 and MCF-10A) of seven breast cancer cell lines tested compared to HMECs. Therefore, in various embodiments, SEQ ID NO:62 can be used for one or more of the following: i) monitoring treatment of breast cancer, ii) diagnostic assays for breast cancer, and iii) developing therapeutics and/or other treatments for breast cancer.

In another example, expression of SEQ ID NO:62 was up-regulated in lung cancer tissue versus normal lung tissue as determined by microarray analysis. Expression of SEQ ID NO:62 was increased at least two-fold in lung tumor tissue versus matched normal lung tissue from the same donor in three of three donors with squamous cell cancer tested. Therefore, in various embodiments, SEQ ID NO:62 can be used for one or more of the following: i) monitoring treatment of lung cancer, ii) diagnostic assays for lung cancer, and iii) developing therapeutics and/or other treatments for lung cancer.

In another example, expression of SEQ ID NO:62 was down-regulated to a lesser extent in preadipocytes taken from an obese donor versus preadipocytes taken from a non-obese donor as determined by microarray analysis. Primary subcutaneous preadipocytes were isolated from the adipose tissue of a non-obese donor, a 28-year-old healthy female with body mass index (BMI) of 23.59, and an obese donor, a 40-year-old healthy female with a body mass index (BMI) of 32.47. The preadipocytes from each donor were cultured and induced to differentiate into adipocytes by growing them in differentiation medium containing PPAR-γ agonist and human insulin (Zen-Bio). Some thiazolidinediones or PPAR-γ agonists, which bind and activate an orphan nuclear receptor, PPAR-γ, have been shown to induce human adipocyte differentiation. The preadipocytes were treated with human insulin and PPAR-γ agonist for 3 days and subsequently were switched to medium containing insulin for a range of time periods ranging from one to 20 days before the cells were collected for analysis. Differentiated adipocytes from each donor were compared to untreated preadipocytes, maintained in culture in the absence of differentiation-inducing agents, from the same donor. Between 80% and 90% of the preadipocytes finally differentiated to adipocytes as observed under phase contrast microscopy. Expression of SEQ ID NO:62 was decreased at least two-fold in differentiated preadipocytes from a normal donor versus non-differentiated preadipocytes from the same donor. In contrast, no differential expression was seen in differentiated preadipocytes from an obese donor versus non-differentiated preadipocytes from the same donor. These data suggest that SEQ ID NO:62 is differentially expressed in adipocytes from normal subjects but not in adipocytes from obese subjects. Therefore, in various embodiments, SEQ ID NO:62 can be used for one or more of the following: i) monitoring treatment of diabetes mellitus and other disorders, such as obesity and hypertension ii) diagnostic assays for diabetes mellitus and other disorders, such as obesity and hypertension iii) developing therapeutics and/or other treatments for diabetes mellitus and other disorders, such as obesity and hypertension.

In another example, expression of SEQ ID NO:69 was down-regulated in diseased lung tissue versus normal lung tissue as determined by microarray analysis. Expression of SEQ ID NO:69 was decreased at least two-fold in the lung tumor tissue with squamous cell carcinoma as compared to grossly uninvolved lung tissue from the same donor using a pair comparison experimental design. Therefore, in various embodiments, SEQ ID NO:69 can be used for one or more of the following: i) monitoring treatment of lung cancer, diagnostic assays for lung cancer, and developing therapeutics and/or other treatments for lung cancer.

In another example, expression of SEQ ID NO:74 was downregulated in brain tissue affected by Alzheimer's Disease versus normal brain tissue as determined by microarray analysis. Specific dissected brain regions from the brain patients with AD were compared to dissected regions from normal brain. The diagnosis of normal or AD was established by a certified neuropathologist based on microscopic examination of multiple sections throughout the brain. Expression of SEQ ID NO:74 was decreased at least two-fold in 7 of 10 AD-affected tissue samples. Therefore, in various embodiments, SEQ ID NO:74 can be used for one or more of the following: i) monitoring treatment of Alzheimer's Disease, ii) diagnostic assays for Alzheimer's Disease, and iii) developing therapeutics and/or other treatments for Alzheimer's Disease as determined by microarray analysis.

As another example, SEQ ID NO:72 and SEQ ID NO:74 were downregulated in breast cancer cells versus nonmalignant mammary epithelial cells, as determined by microarray analysis. Cell lines compared included: a) MCF-10A, a breast mammary gland (luminal ductal characteristics) cell line isolated from a 36-year-old woman with fibrocystic breast disease, b) MCF7, a nonmalignant breast adenocarcinoma cell line isolated from the pleural effusion of a 69-year-old female, c) BT-20, a breast carcinoma cell line derived in vitro from the cells emigrating out of thin slices of tumor mass isolated from a 74-year-old female, d) T-47D, a breast carcinoma cell line isolated from a pleural effusion obtained from a 54-year-old female with an infiltrating ductal carcinoma of the breast, e) Sk-BR-3, a breast adenocarcinoma cell line isolated from a malignant pleural effusion of a 43-year-old female, f) MDA-mb-231, a breast tumor cell line isolated from the pleural effusion of a 51-year-old female, g) MDA-mb-435S, a spindle-shaped strain that evolved from the parent line (435) isolated by R. Cailleau from pleural effusion of a 31-year-old female with metastatic, ductal adenocarcinoma of the breast, and h) HMEC, a primary breast epithelial cell line isolated from a normal donor. Expression of SEQ ID NO:72 was decreased at least two-fold in the Sk-BR-3, BT-20, MDA-mb-435S, T-47D, and MCF7 cell lines as compared to the normal breast epithelial cells. Expression of SEQ ID NO:74 was decreased at least two-fold in the MCF-10A, T-47D, Sk-BR-3, and MCF7 cell lines as compared to the normal breast epithelial cells. Therefore, in various embodiments, SEQ ID NO:72 and SEQ ID NO:74 can be used for one or more of the following: i) monitoring treatment of breast cancer, diagnostic assays for breast cancer, and developing therapeutics and/or other treatments for breast cancer as determined by microarray analysis.

As another example, SEQ ID NO:74 and SEQ ID NO:77 showed tissue-specific expression as determined by microarray analysis. RNA samples isolated from a variety of normal human tissues were compared to a common reference sample. Tissues contributing to the reference sample were selected for their ability to provide a complete distribution of RNA in the human body and include brain (4%), heart (7%), kidney (3%), lung (8%), placenta (46%), small intestine (9%), spleen (3%), stomach (6%), testis (9%), and uterus (5%). The normal tissues assayed were obtained from at least three different donors. RNA from each donor was separately isolated and individually hybridized to the microarray. Since these hybridization experiments were conducted using a common reference sample, differential expression values are directly comparable from one tissue to another. The expression of SEQ ID NO:74 was increased by at least two-fold in brain cortex tissue as compared to the reference sample. Therefore, SEQ ID NO:74 can be used as a tissue marker for brain cortex tissue. The expression of SEQ ID NO:77 was increased by at least two-fold in heart tissue as compared to the reference sample. Therefore, SEQ ID NO:77 can be used as a tissue marker for heart tissue.

XII. Complementary Polynucleotides

Sequences complementary to the KPP-encoding sequences, or any parts thereof, are used to detect, decrease, or inhibit expression of naturally occurring KPP. Although use of oligonucleotides comprising from about 15 to 30 base pairs is described, essentially the same procedure is used with smaller or with larger sequence fragments. Appropriate oligonucleotides are designed using OLIGO 4.06 software (National Biosciences) and the coding sequence of KPP. To inhibit transcription, a complementary oligonucleotide is designed from the most unique 5' sequence and used to prevent promoter binding to the coding sequence. To inhibit translation, a complementary oligonucleotide is designed to prevent ribosomal binding to the KPP-encoding transcript.

XIII. Expression of KPP

Expression and purification of KPP is achieved using bacterial or virus-based expression systems. For expression of KPP in bacteria, cDNA is subcloned into an appropriate vector containing an antibiotic resistance gene and an inducible promoter that directs high levels of cDNA transcription. Examples of such promoters include, but are not limited to, the trp-lac (tac) hybrid promoter and the T5 or T7 bacteriophage promoter in conjunction with the lac operator regulatory element. Recombinant vectors are transformed into suitable bacterial hosts, e.g., BL21(DE3). Antibiotic resistant bacteria express KPP upon induction with isopropyl beta-D-thiogalactopyranoside (IPTG). Expression of KPP in eukaryotic cells is achieved by infecting insect or mammalian cell lines with recombinant *Autographica californica* nuclear polyhedrosis virus (AcMNPV), commonly known, as baculovirus. The nonessential polyhedrin gene of baculovirus is replaced with cDNA encoding KPP by either homologous recombination or bacterial-mediated transposition involving transfer plasmid intermediates. Viral infectivity is maintained and the strong polyhedrin promoter drives high levels of cDNA transcription. Recombinant baculovirus is used to infect *Spodoptera frugiperda* (Sf9) insect cells in most cases, or human hepatocytes, in some cases. Infection of the latter requires additional genetic modifications to baculovirus (Engelhard, E. K. et al. (1994) Proc. Natl. Acad. Sci. USA 91:3224-3227; Sandig, V. et al. (1996) Hum. Gene Ther. 7:1937-1945).

In most expression systems, KPP is synthesized as a fusion protein with, e.g., glutathione S-transferase (GST) or a peptide epitope tag, such as FLAG or 6-His (SEQ ID NO: 87), permitting rapid, single-step, affinity-based purification of recombinant fusion protein from crude cell lysates. GST, a 26-kilodalton enzyme from *Schistosoma japonicum*, enables the purification of fusion proteins on immobilized glutathione under conditions that maintain protein activity and antigenicity (Amersham Biosciences). Following purification, the GST moiety can be proteolytically cleaved from KPP at specifically engineered sites. FLAG, an 8-amino acid peptide, enables immunoaffinity purification using commercially available monoclonal and polyclonal anti-FLAG antibodies (Eastman Kodak). 6-His (SEQ ID NO: 87), a stretch of six consecutive histidine residues, enables purification on metal-chelate resins (QIAGEN). Methods for protein expression and purification are discussed in Ausubel et al. (supra, ch. 10 and 16). Purified KPP obtained by these methods can be used directly in the assays shown in Examples XVII, XVIII, XIX, XX, and XXI, where applicable.

XIV. Functional Assays

KPP function is assessed by expressing the sequences encoding KPP at physiologically elevated levels in mammalian cell culture systems. cDNA is subcloned into a mammalian expression vector containing a strong promoter that drives high levels of cDNA expression. Vectors of choice include PCMV SPORT plasmid (Invitrogen, Carlsbad Calif.) and PCR3.1 plasmid (Invitrogen), both of which contain the cytomegalovirus promoter. 5-10 μg of recombinant vector are transiently transfected into a human cell line, for example, an endothelial or hematopoietic cell line, using either liposome formulations or electroporation. 1-2 μg of an additional plasmid containing sequences encoding a marker protein are co-transfected. Expression of a marker protein provides a means to distinguish transfected cells from nontransfected cells and is a reliable predictor of cDNA expression from the recombinant vector. Marker proteins of choice include, e.g., Green Fluorescent Protein (GFP; BD Clontech), CD64, or a CD64-GFP fusion protein. Flow cytometry (FCM), an automated, laser optics-based technique, is used to identify transfected cells expressing GFP or CD64-GFP and to evaluate the apoptotic state of the cells and other cellular properties. FCM detects and quantifies the uptake of fluorescent molecules that diagnose events preceding or coincident with cell death. These events include changes in nuclear DNA content as measured by staining of DNA with propidium iodide; changes in cell size and granularity as measured by forward light scatter and 90 degree side light scatter; down-regulation of DNA synthesis as measured by decrease in bromodeoxyuridine uptake; alterations in expression of cell surface and intracellular proteins as measured by reactivity with specific antibodies; and alterations in plasma membrane composition as measured by the binding of fluorescein-conjugated Annexin V protein to the cell surface. Methods in flow cytometry are discussed in Ormerod, M. G. (1994; *Flow Cytometry*, Oxford, New York N.Y.).

The influence of KPP on gene expression can be assessed using highly purified populations of cells transfected with sequences encoding KPP and either CD64 or CD64-GFP. CD64 and CD64-GFP are expressed on the surface of transfected cells and bind to conserved regions of human immunoglobulin G (IgG). Transfected cells are efficiently separated from nontransfected cells using magnetic beads coated with either human IgG or antibody against CD64 (DYNAL, Lake Success N.Y.). mRNA can be purified from the cells using methods well known by those of skill in the art. Expression of mRNA encoding KPP and other genes of interest can be analyzed by northern analysis or microarray techniques.

XV. Production of KPP Specific Antibodies

KPP substantially purified using polyacrylamide gel electrophoresis (PAGE; see, e.g., Harrington, M. G. (1990) Methods Enzymol. 182:488-495), or other purification techniques, is used to immunize animals (e.g., rabbits, mice, etc.) and to produce antibodies using standard protocols.

Alternatively, the KPP amino acid sequence is analyzed using LASERGENE software (DNASTAR) to determine regions of high immunogenicity, and a corresponding oligopeptide is synthesized and used to raise antibodies by means known to those of skill in the art. Methods for selection of appropriate epitopes, such as those near the C-terminus or in hydrophilic regions are well described in the art (Ausubel et al., supra, ch. 11).

Typically, oligopeptides of about 15 residues in length are synthesized using an ABI 431A peptide synthesizer (Applied Biosystems) using FMOC chemistry and coupled to KLH (Sigma-Aldrich, St. Louis Mo.) by reaction with N-maleimidobenzoyl-N-hydroxysuccinimide ester (MBS) to increase immunogenicity (Ausubel et al., supra). Rabbits are immunized with the oligopeptide-KLH complex in complete Freund's adjuvant. Resulting antisera are tested for antipeptide and anti-KPP activity by, for example, binding the peptide or KPP to a substrate, blocking with 1% BSA, reacting with rabbit antisera, washing, and reacting with radio-iodinated goat anti-rabbit IgG.

XVI. Purification of Naturally Occurring KPP Using Specific Antibodies

Naturally occurring or recombinant KPP is substantially purified by immunoaffinity chromatography using antibodies specific for KPP. An immunoaffinity column is constructed by covalently coupling anti-KPP antibody to an activated chromatographic resin, such as CNBr-activated SEPHAROSE (Amersham Biosciences). After the coupling, the resin is blocked and washed according to the manufacturer's instructions.

Media containing KPP are passed over the immunoaffinity column, and the column is washed under conditions that allow the preferential absorbance of KPP (e.g., high ionic strength buffers in the presence of detergent). The column is eluted under conditions that disrupt antibody/KPP binding (e.g., a buffer of pH 2 to pH 3, or a high concentration of a chaotrope, such as urea or thiocyanate ion), and KPP is collected.

XVII. Identification of Molecules which Interact with KPP

KPP, or biologically active fragments thereof, are labeled with $^{125}$I Bolton-Hunter reagent (Bolton, A. E. and W. M. Hunter (1973) Biochem. J. 133:529-539). Candidate molecules previously arrayed in the wells of a multi-well plate are incubated with the labeled KPP, washed, and any wells with labeled KPP complex are assayed. Data obtained using different concentrations of KPP are used to calculate values for the number; affinity, and association of KPP with the candidate molecules.

Alternatively, molecules interacting with KPP are analyzed using the yeast two-hybrid system as described in Fields, S, and O, Song (1989; Nature 340:245-246), or using commercially available kits based on the two-hybrid system, such as the MATCHMAKER system (BD Clontech).

KPP may also be used in the PATHCALLING process (CuraGen Corp., New Haven Conn.) which employs the yeast two-hybrid system in a high-throughput manner to determine all interactions between the proteins encoded by two large libraries of genes (Nandabalan, K. et al. (2000) U.S. Pat. No. 6,057,101).

XVIII. Demonstration of KPP Activity

Generally, protein kinase activity is measured by quantifying the phosphorylation of a protein substrate by KPP in the presence of [γ-$^{32}$P]ATP. KPP is incubated with the protein substrate, $^{32}$P-ATP, and an appropriate kinase buffer. The $^{32}$P incorporated into the substrate is separated from free $^{32}$P-ATP by electrophoresis and the incorporated $^{32}$P is counted using a radioisotope counter. The amount of incorporated $^{32}$P is proportional to the activity of KPP. A determination of the specific amino acid residue phosphorylated is made by phosphoamino acid analysis of the hydrolyzed protein.

In one alternative, protein kinase activity is measured by quantifying the transfer of gamma phosphate from adenosine triphosphate (ATP) to a serine, threonine or tyrosine residue in a protein substrate. The reaction occurs between a protein kinase sample with a biotinylated peptide substrate and gamma $^{32}$P-ATP. Following the reaction, free avidin in solution is added for binding to the biotinylated $^{32}$P-peptide product. The binding sample then undergoes a centrifugal ultrafiltration process with a membrane which will retain the product-avidin complex and allow passage of free gamma $^{32}$P-ATP. The reservoir of the centrifuged unit containing the $^{32}$P-peptide product as retentate is then counted in a scintillation counter. This procedure allows the assay of any type of protein kinase sample, depending on the peptide substrate and kinase reaction buffer selected. This assay is provided in kit form (ASUA, Affinity Ultrafiltration Separation Assay, Transbio Corporation, Baltimore Md., U.S. Pat. No. 5,869,275). Suggested substrates and their respective enzymes include but are not limited to: Histone H1 (Sigma) and p34$^{cdc2}$ kinase, Annexin I, Angiotensin (Sigma) and EGF receptor kinase, Annexin II and src kinase, ERK1 & ERK2 substrates and MEK, and myelin basic protein and ERK (Pearson, J. D. et al. (1991) Methods Enzymol. 200:62-81).

In another alternative, protein kinase activity of KPP is demonstrated in an assay containing KPP, 50 μl of kinase buffer, 1 μg substrate, such as myelin basic protein (MBP) or synthetic peptide substrates, 1 mM DTT, 10 μg ATP, and 0.5 μCi [γ-$^{32}$P]ATP. The reaction is incubated at 30° C. for 30 minutes and stopped by pipetting onto P81 paper. The unincorporated [γ-$^{32}$P]ATP is removed by washing and the incorporated radioactivity is measured using a scintillation counter. Alternatively, the reaction is stopped by heating to 100° C. in the presence of SDS loading buffer and resolved on a 12% SDS polyacrylamide gel followed by autoradiography. The amount of incorporated $^{32}$P is proportional to the activity of KPP.

In yet another alternative, adenylate kinase or guanylate kinase activity of KPP may be measured by the incorporation of $^{32}$P from [γ-$^{32}$P]ATP into ADP or GDP using a gamma radioisotope counter. KPP, in a kinase buffer, is incubated together with the appropriate nucleotide mono-phosphate substrate (AMP or GMP) and $^{32}$P-labeled ATP as the phosphate donor. The reaction is incubated at 37° C. and terminated by addition of trichloroacetic acid. The acid extract is neutralized and subjected to gel electrophoresis to separate the mono-, di-, and triphosphonucleotide fractions. The diphosphonucleotide fraction is excised and counted. The radioactivity recovered is proportional to the activity of KPP.

In yet another alternative, other assays for KPP include scintillation proximity assays (SPA), scintillation plate technology and filter binding assays. Useful substrates include recombinant proteins tagged with glutathione transferase, or synthetic peptide substrates tagged with biotin.

Inhibitors of KPP activity, such as small organic molecules, proteins or peptides, may be identified by such assays.

In another alternative, phosphatase activity of KPP is measured by the hydrolysis of para-nitrophenyl phosphate (PNPP). KPP is incubated together with PNPP in HEPES buffer pH 7.5, in the presence of 0.1% .beta.-mercaptoethanol at 37° C. for 60 mM. The reaction is stopped by the addition of 6 ml of 10 N NaOH (Diamond, R. H. et al. (1994) Mol. Cell. Biol. 14:3752-62). Alternatively, acid phosphatase activity of KPP is demonstrated by incubating KPP-containing extract with 100 μl of 10 mM PNPP in 0.1 M sodium citrate, pH 4.5, and 50 μl of 40 mM NaCl at 37° C. for 20 min. The reaction is stopped by the addition of 0.5 ml of 0.4 M glycine/NaOH, pH 10.4 (Saftig, P. et al. (1997) J. Biol. Chem. 272:18628-18635). The increase in light absorbance at 410 nm resulting from the hydrolysis of PNPP is measured using a spectrophotometer. The increase in light absorbance is proportional to the activity of KPP in the assay.

In the alternative, KPP activity is determined by measuring the amount of phosphate removed from a phosphorylated protein substrate. Reactions are performed with 2 or 4 nM KPP in a final volume of 30 μl containing 60 mM Tris, pH 7.6, 1 mM EDTA, 1 mM EGTA, 0.1% β-mercaptoethanol and 10 μM substrate, $^{32}$P-labeled on serine/threonine or tyrosine, as appropriate. Reactions are initiated with substrate and incubated at 30° C. for 10-15 min. Reactions are quenched with 450 μl of 4% (w/v) activated charcoal in 0.6 M HCl, 90 mM $Na_4P_2O_7$, and 2 mM $NaH_2PO_4$, then centrifuged at 12,000×g for 5 min. Acid-soluble $^{32}$2Pi is quantified by liquid scintillation counting (Sinclair, C. et al. (1999) J. Biol. Chem. 274: 23666-23672).

XIX. Kinase Binding Assay

Binding of KPP to a FLAG-CD44 cyt fusion protein can be determined by incubating KPP with anti-KPP-conjugated immunoaffinity beads followed by incubating portions of the beads (having 10-20 ng of protein) with 0.5 ml of a binding buffer (20 mM Tris-HCL (pH 7.4), 150 mM NaCl, 0.1% bovine serum albumin, and 0.05% Triton X-100) in the presence of $^{125}$I-labeled FLAG-CD44cyt fusion protein (5,000 cpm/ng protein) at 4° C. for 5 hours. Following binding, beads were washed thoroughly in the binding buffer and the bead bound radioactivity measured in a scintillation counter (Bourguignon, L. Y. W. et al. (2001) J. Biol. Chem. 276:7327-7336). The amount of incorporated $^{32}$P is proportional to the amount of bound KPP.

XX. Identification of KPP Inhibitors

Compounds to be tested are arrayed in the wells of a 384-well plate in varying concentrations along with an appropriate buffer and substrate, as described in the assays in Example XVII. KPP activity is measured for each well and the ability of each compound to inhibit KPP activity can be determined, as well as the dose-response kinetics. This assay could also be used to identify molecules which enhance KPP activity.

XXI. Identification of KPP Substrates

A KPP "substrate-trapping" assay takes advantage of the increased substrate affinity that may be conferred by certain mutations in the PTP signature sequence of protein tyrosine phosphatases. KPP bearing these mutations form a stable complex with their substrate; this complex may be isolated biochemically. Site-directed mutagenesis of invariant residues in the PTP signature sequence in a clone encoding the catalytic domain of KPP is performed using a method standard in the art or a commercial kit, such as the MUM-GENE kit from BIO-RAD. For expression of KPP mutants in *Escherichia coli*, DNA fragments containing the mutation are exchanged with the corresponding wild-type sequence in an expression vector bearing the sequence encoding KPP or a glutathione S-transferase (GST)-KPP fusion protein. KPP mutants are expressed in *E. coli* and purified by chromatography.

The expression vector is transfected into COS1 or 293 cells via calcium phosphate-mediated transfection with 20 μg of CsCl-purified DNA per 10-cm dish of cells or 8 μg per 6-cm dish. Forty-eight hours after transfection, cells are stimulated with 100 ng/ml epidermal growth factor to increase tyrosine phosphorylation in cells, as the tyrosine kinase EGFR is abundant in COS cells. Cells are lysed in 50 mM Tris.HCl, pH 7.5/5 mM EDTA/150 mM NaCl/1% Triton X-100/5 mM iodoacetic acid/10 mM sodium phosphate/10 mM NaF/5 leupeptin/5 μg/ml aprotinin/1 mM benzamidine (1 ml per 10-cm dish, 0.5 ml per 6-cm dish). KPP is immunoprecipitated from lysates with an appropriate antibody. GST-KPP fusion proteins are precipitated with glutathione-Sepharose, 4 μg of mAb or 10 μl of beads respectively per mg of cell lysate. Complexes can be visualized by PAGE or further purified to identify substrate molecules (Flint, A. J. et al. (1997) Proc. Natl. Acad. Sci. USA 94:1680-1685).

Various modifications and variations of the described compositions, methods, and systems of the invention will be apparent to those skilled in the art without departing from the scope and spirit of the invention. It will be appreciated that the invention provides novel and useful proteins, and their encoding polynucleotides, which can be used in the drug discovery process, as well as methods for using these compositions for the detection, diagnosis, and treatment of diseases and conditions. Although the invention has been described in connection with certain embodiments, it should be understood that the invention as claimed should not be unduly limited to such specific embodiments. Nor should the description of such embodiments be considered exhaustive or limit the invention to the precise forms disclosed. Furthermore, elements from one embodiment can be readily recombined with elements from one or more other embodiments. Such combinations can form a number of embodiments within the scope of the invention. It is intended that the scope of the invention be defined by the following claims and their equivalents.

TABLE 1

| Incyte Project ID | Polypeptide SEQ ID NO: | Incyte Polypeptide ID | Polynucleotide SEQ ID NO: | Incyte Polynucleotide ID | Incyte Full Length Clones |
|---|---|---|---|---|---|
| 7517831 | 1 | 7517831CD1 | 44 | 7517831CB1 | 90040615CA2 |
| 7520272 | 2 | 7520272CD1 | 45 | 7520272CB1 | 95114642CA2, 95114758CA2, 95162524CA2, 95162564CA2 |
| 7521279 | 3 | 7521279CD1 | 46 | 7521279CB1 | 95121315CA2, 95121539CA2 |
| 7523965 | 4 | 7523965CD1 | 47 | 7523965CB1 | 95141143CA2 |
| 7524016 | 5 | 7524016CD1 | 48 | 7524016CB1 | 95183446CA2 |
| 7524680 | 6 | 7524680CD1 | 49 | 7524680CB1 | |
| 7524757 | 7 | 7524757CD1 | 50 | 7524757CB1 | |
| 7516229 | 8 | 7516229CD1 | 51 | 7516229CB1 | |
| 7516525 | 9 | 7516525CD1 | 52 | 7516525CB1 | |
| 7516533 | 10 | 7516533CD1 | 53 | 7516533CB1 | 90041659CA2 |
| 7516613 | 11 | 7516613CD1 | 54 | 7516613CB1 | 90136641CA2 |
| 7517068 | 12 | 7517068CD1 | 55 | 7517068CB1 | |
| 7517148 | 13 | 7517148CD1 | 56 | 7517148CB1 | |
| 7517238 | 14 | 7517238CD1 | 57 | 7517238CB1 | 90094269CA2 |
| 7518685 | 15 | 7518685CD1 | 58 | 7518685CB1 | |
| 7520192 | 16 | 7520192CD1 | 59 | 7520192CB1 | 90111670CA2 |
| 7520428 | 17 | 7520428CD1 | 60 | 7520428CB1 | 90198192CA2 |
| 7522586 | 18 | 7522586CD1 | 61 | 7522586CB1 | |
| 7524017 | 19 | 7524017CD1 | 62 | 7524017CB1 | |
| 7525773 | 20 | 7525773CD1 | 63 | 7525773CB1 | |
| 7525861 | 21 | 7525861CD1 | 64 | 7525861CB1 | 95132479CA2, 95206437CA2, 95206561CA2 |
| 2509577 | 22 | 2509577CD1 | 65 | 2509577CB1 | |
| 7505222 | 23 | 7505222CD1 | 66 | 7505222CB1 | |
| 7524408 | 24 | 7524408CD1 | 67 | 7524408CB1 | |
| 7526163 | 25 | 7526163CD1 | 68 | 7526163CB1 | |
| 7526158 | 26 | 7526158CD1 | 69 | 7526158CB1 | |
| 7519807 | 27 | 7519807CD1 | 70 | 7519807CB1 | 90124401CA2 |
| 7526180 | 28 | 7526180CD1 | 71 | 7526180CB1 | |
| 7526185 | 29 | 7526185CD1 | 72 | 7526185CB1 | |
| 7526192 | 30 | 7526192CD1 | 73 | 7526192CB1 | |
| 7526193 | 31 | 7526193CD1 | 74 | 7526193CB1 | |
| 7526196 | 32 | 7526196CD1 | 75 | 7526196CB1 | |
| 7526198 | 33 | 7526198CD1 | 76 | 7526198CB1 | |
| 7526208 | 34 | 7526208CD1 | 77 | 7526208CB1 | |
| 7526212 | 35 | 7526212CD1 | 78 | 7526212CB1 | |
| 7526213 | 36 | 7526213CD1 | 79 | 7526213CB1 | |
| 7526214 | 37 | 7526214CD1 | 80 | 7526214CB1 | |
| 7526228 | 38 | 7526228CD1 | 81 | 7526228CB1 | |
| 7526246 | 39 | 7526246CD1 | 82 | 7526246CB1 | |
| 7526258 | 40 | 7526258CD1 | 83 | 7526258CB1 | |
| 7526311 | 41 | 7526311CD1 | 84 | 7526311CB1 | |
| 7526315 | 42 | 7526315CD1 | 85 | 7526315CB1 | |
| 7526442 | 43 | 7526442CD1 | 86 | 7526442CB1 | |

TABLE 2

| Polypeptide SEQ ID NO: | Incyte Polypeptide ID | GenBank ID NO: or PROTEOME ID NO: | Probability Score | Annotation |
|---|---|---|---|---|
| 1 | 7517831CD1 | g775208 | 4.3E−21 | [*Homo sapiens*] p56lck<br>Vogel, L. B. et al., p70 phosphorylation and binding to p56lck is an early event in interleukin-2-induced onset of cell cycle progression in T-lymphocytes, J. Biol. Chem. 270, 2506-2511 (1995) |
| | | 342146\|LCK | 7.2E−20 | [*Homo sapiens*][Protein kinase; Transferase] Lymphocyte-specific protein tyrosine kinase, tyrosine kinase that is involved in T cell receptor signaling through Ras and MAPK pathways, activator of CASP8 in radiation-induced apoptosis; gene defect correlates with immunodeficiency plus CD4 lymphopenia<br>Su, S. B. et al., Inhibition of tyrosine kinase activation blocks the down-regulation of CXC chemokine receptor 4 by HIV-1 gp120 in CD4+ T cells, J Immunol 162, 7128-32 (1999). |
| | | 780711\|Lck | 8.0E−17 | [*Mus musculus*][Protein kinase; Transferase] Lymphocyte-specific protein tyrosine kinase, tyrosine kinase that is involved in T cell receptor signaling through Ras and MAPK pathways, regulates T cell development and apoptosis; human gene defect correlates with immunodeficiency plus CD4 lymphopenia<br>Legname, G. et al., Inducible expression of a p56Lck transgene reveals a central role for Lck in the differentiation of CD4 SP thymocytes, Immunity 12, 537-46 (2000). |

TABLE 2-continued

| Polypeptide SEQ ID NO: | Incyte Polypeptide ID | GenBank ID NO: or PROTEOME ID NO: | Probability Score | Annotation |
|---|---|---|---|---|
| 2 | 7520272CD1 | g439226 | 4.0E−152 | [*Homo sapiens*] fructose-1,6-bisphosphatase<br>Kikawa, Y. et al., cDNA sequences encoding human fructose 1,6-bisphosphatase from monocytes, liver and kidney: Application of monocytes to molecular analysis of human fructose 1,6-bisphosphatase deficiency, Cell. Mol. Biol. Res. 199, 687-693 (1994) |
| | | 753731\|FBP1 | 3.0E−153 | [*Homo sapiens*][Other phosphatase; Hydrolase] Fructose-1,6-bisphosphatase 1 (liver), hydrolyzes fructose-1,6-bisphosphate to fructose-6-phosphate and inorganic phosphate, regulatory step in gluconeogenesis; deficiency is associated with metabolic acidosis and fasting hypoglycemia<br>el-Maghrabi, M. R. et al., Isolation of a human liver fructose-1,6-bisphosphatase cDNA and expression of the protein in *Escherichia coli*. Role of ASP-118 and ASP-121 in catalysis, J Biol Chem 268, 9466-72 (1993). |
| 3 | 7521279CD1 | g1905761 | 4.1E−233 | [*Homo sapiens*] 6-phosphofructo-2-kinase/fructose-2,6-bisphosphatase<br>Sakai, A. et al., Cloning of cDNA encoding for a novel isozyme of fructose 6-phosphate, 2-kinase/fructose 2,6-bisphosphatase from human placenta, J. Biochem. 119, 506-511 (1996) |
| | | 341042\|PFKFB4 | 3.0E−234 | [*Homo sapiens*][Transferase; Other kinase; Other phosphatase; Hydrolase] 6-phosphofructo-2-kinase, fructose-2,6-biphosphatase, testis form, synthesizes and degrades fructose-2,6-bisphosphate and may be involved in the regulation of glycolysis<br>Manzano, A. et al., Cloning, expression and chromosomal localization of a human testis 6-phosphofructo-2-kinase/fructose-2,6-bisphosphatase gene, Gene 229, 83-9 (1999). |
| | | 609815\|Pfkfb4 | 1.1E−227 | [*Rattus norvegicus*][Transferase; Other kinase; Other phosphatase; Hydrolase] 6-phosphofructo-2-kinase, fructose-2,6-biphosphatase, testis form, synthesizes and degrades fructose-2,6-bisphosphate and may be involved in the regulation of glycolysis<br>Li, L. et al., Expression of chicken liver 6-phosphofructo-2-kinase/fructose-2,6-bisphosphatase in *Escherichia coli*, Biochem Biophys Res Commun 209, 883-93 (1995). |
| 4 | 7523965CD1 | g2661752 | 1.1E−120 | [*Homo sapiens*] phosphoenolpyruvate carboxykinase (GTP)<br>Modaressi, S. et al., Human mitochondrial phosphoenolpyruvate carboxykinase 2 gene. Structure, chromosomal localization and tissue-specific expression, Biochem. J. 333 (Pt 2), 359-366 (1998) |
| | | 341026\|PCK2 | 5.7E−121 | [*Homo sapiens*][Lyase; Other kinase][Cytoplasmic; Mitochondrial] Phosphoenolpyruvate carboxykinase 2, catalyzes the formation of phosphoenolpyruvate by decarboxylation of oxaloacetate, rate-limiting step of gluconeogenesis<br>Modaressi, S. et al., Molecular cloning, sequencing and expression of the cDNA of the mitochondrial form of phosphoenolpyruvate carboxykinase from human liver, Biochem J 315, 807-14 (1996). |
| | | 586739\|Pck1 | 2.6E−68 | [*Mus musculus*][Lyase; Other kinase][Cytoplasmic] Cytosolic phosphoenolpyruvate carboxykinase, catalyzes the formation of phosphoenolpyruvate by decarboxylation of oxaloacetate<br>She, P. et al., Phosphoenolpyruvate carboxykinase is necessary for the integration of hepatic energy metabolism, Mol Cell Biol 20, 6508-17 (2000). |
| 5 | 7524016CD1 | g35503 | 1.7E−94 | [*Homo sapiens*] 6-phosphofructo-2-kinase/fructose-2,6-bisphosphatase (AA 1-471)<br>Lange, A. J. et al., Sequence of human liver 6-phosphofructo-2-kinase/fructose-2,6-bisphosphatase, Nucleic Acids Res. 18, 3652 (1990) |
| | | 336898\|PFKFB1 | 1.2E−95 | [*Homo sapiens*][Protein phosphatase; Transferase; Other phosphatase; Other kinase; Hydrolase] 6-phosphofructo-2-kinase, fructose-2,6-biphosphatase 1, liver and muscle form, enzyme involved in regulating glycolysis, catalyzes the synthesis and degradation of fructose-2,6-bisphosphate<br>Lange, A. J. et al., Expression of human liver 6-phosphofructo-2-kinase/fructose-2,6-bisphosphatase in *Escherichia coli*. Role of N-2 proline in degradation of the protein, J Biol Chem 268, 8078-84 (1993). |
| | | 430618\|Pfkfb1 | 9.3E−89 | [*Rattus norvegicus*][Protein phosphatase; Transferase; Other phosphatase; Other kinase; Hydrolase] 6-phosphofructo-2-kinase, fructose-2,6-biphosphatase 1, liver and muscle form, enzyme involved in regulating glycolysis, catalyzes the synthesis and degradation of fructose-2,6-bisphosphate<br>Kurland, I. J. et al., Rat liver 6-phosphofructo-2-kinase/fructose-2,6-bisphosphatase. Properties of phospho- and dephospho-forms and of two mutants in which Ser32 has been changed by site-directed mutagenesis, J Biol Chem 267, 4416-23 (1992). |
| 6 | 7524680CD1 | g35503 | 1.3E−215 | [*Homo sapiens*] 6-phosphofructo-2-kinase/fructose-2,6-bisphosphatase (AA 1-471)<br>Lange, A. J. et al., Sequence of human liver 6-phosphofructo-2-kinase/fructose-2,6-bisphosphatase, Nucleic Acids Res. 18, 3652 (1990) |
| | | 336898\|PFKFB1 | 9.1E−217 | [*Homo sapiens*][Protein phosphatase; Transferase; Other phosphatase; Other kinase; Hydrolase] 6-phosphofructo-2-kinase, fructose-2,6-biphosphatase 1, liver and muscle form, enzyme involved in regulating glycolysis, catalyzes the synthesis and degradation of fructose-2,6-bisphosphate<br>Lange, A. J. et al., Expression of human liver 6-phosphofructo-2-kinase/fructose-2,6-bisphosphatase in *Escherichia coli*. Role of N-2 proline in degradation of the protein, J Biol Chem 268, 8078-84 (1993). |
| | | 430618\|Pfkfb1 | 1.2E−207 | [*Rattus norvegicus*][Protein phosphatase; Transferase; Other phosphatase; Other kinase; Hydrolase] 6-phosphofructo-2-kinase, fructose-2,6-bipbosphatase 1, liver and muscle form, enzyme involved in regulating glycolysis, catalyzes the synthesis and degradation of fructose-2,6-bisphosphate<br>Kurland, I. J. et al., Rat liver 6-phosphofructo-2-kinase/fructose-2,6-bisphosphatase. Properties of phospho- and dephospho-forms and of two mutants in which Ser32 has been changed by site-directed mutagenesis, J Biol Chem 267, 4416-23 (1992). |

TABLE 2-continued

| Polypeptide SEQ ID NO: | Incyte Polypeptide ID | GenBank ID NO: or PROTEOME ID NO: | Probability Score | Annotation |
|---|---|---|---|---|
| 7 | 7524757CD1 | g35503 | 3.7E−223 | [*Homo sapiens*] 6-phosphofructo-2-kinase/fructose-2,6-bisphosphatase (AA 1-471) Lange, A. J. et al., Sequence of human liver 6-phosphofructo-2-kinase/fructose-2,6-bisphosphatase, Nucleic Acids Res. 18, 3652 (1990) |
| | | 336898\|PFKFB1 | 2.7E−224 | [*Homo sapiens*][Protein phosphatase; Transferase; Other phosphatase; Other kinase; Hydrolase] 6-phosphofructo-2-kinase, fructose-2,6-biphosphatase 1, liver and muscle form, enzyme involved in regulating glycolysis, catalyzes the synthesis and degradation of fructose-2,6-bisphosphate Lange, A. J. et al., Expression of human liver 6-phosphofructo-2-kinase/fructose-2,6-bisphosphatase in *Escherichia coli*. Role of N-2 proline in degradation of the protein, J Biol Chem 268, 8078-84 (1993). |
| | | 430618\|Pfkfb1 | 3.7E−216 | [*Rattus norvegicus*][Protein phosphatase; Transferase; Other phosphatase; Other kinase; Hydrolase] 6-phosphofructo-2-kinase, fructose-2,6-biphosphatase 1, liver and muscle form, enzyme involved in regulating glycolysis, catalyzes the synthesis and degradation of fructose-2,6-bisphosphate Kurland, I. J. et al., Rat liver 6-phosphofructo-2-kinase/fructose-2,6-bisphosphatase. Properties of phospho- and dephospho-forms and of two mutants in which Ser32 has been changed by site-directed mutagenesis, J Biol Chem 267, 4416-23 (1992). |
| 8 | 7516229CD1 | g6760472 | 3.0E−190 | [*Homo sapiens*] type II phosphatidylinositol-phosphate 5-kinase 53K isoform Boronenkov, I. V. at al., The sequence of phosphatidylinositol-4-phosphate 5-kinase defines a novel family of lipid kinases, J. Biol. Chem. 270, 2881-2884 (1995) |
| | | 568490\|PIP5K2A | 2.1E−191 | [*Homo sapiens*][Transferase; Other kinase] Phosphatidylinositol-4-phosphate 5-kinase type II, alpha, a member of a family of kinases responsible for the synthesis of PtdIns(4,5)P2 Boronenkov, I. V. et al., The sequence of phosphatidylinositol-4-phosphate 5-kinase defines a novel family of lipid kinases, J Biol Chem 270, 2881-4 (1995). |
| | | 757680\|Pip5k2a | 5.0E−188 | [*Rattus norvegicus*] Phosphatidylinositol-4-phosphate 5-kinase type II alpha Itoh, T. et al., Autophospharylation of type I phosphatidylinositol phosphate kinase regulates its lipid kinase activity, J Biol Chem 275, 19389-94 (2000). |
| 9 | 7516525CD1 | g23499314 | 6.7E−270 | [*Homo sapiens*] (AF425232) CaMKK alpha protein |
| | | 716531\| DKFZp761M0423 | 4.6E−271 | [*Homo sapiens*] Protein with strong similarity to calcium-calmodulin-dependent protein kinase kinase 1 alpha (rat Camkk1), which phosphorylates and activates Ca(2+)-calmodulin (CaM)-dependent kinase I and IV but not CaM kinase II, contains a protein kinase domain |
| | | 711580\|Camkk1 | 2.4E−254 | [*Rattus norvegicus*][Protein kinase; Transferase] Calcium-calmodulin-dependent protein kinase kinase 1 alpha, phosphorylates and activates Ca(2+)-calmodulin (CaM)-dependent kinase I and IV but not CaM kinase II, involved in Ca(2+)-calmodulin signaling Okuno, S. et al., Regulation of Ca(2+)/Calmodulin-Dependent Protein Kinase Kinase alpha by cAMP-Dependent Protein Kinase: I. Biochemical Analysis, J Biochem (Tokyo) 130, 503-13. (2001). |
| 10 | 7516533CD1 | g189508 | 3.6E−240 | [*Homo sapiens*] p70 ribosomal S6 kinase alpha-I Grove, J. R. et al., Cloning and expression of two human p70 S6 kinase polypeptides differing only at their amino termini, Mol. Cell. Biol. 11, 5541-5550 (1991) |
| | | 337822\|RPS6KB1 | 2.5E−241 | [*Homo sapiens*][Protein kinase; Transferase] Ribosomal protein S6 kinase, 70 kD, a member of the ribosomal protein S6 kinase (RSK) family of protein kinases, insulin and mitogen activated, and plays roles in cell cycle progression and control of cell proliferation Brenneisen, P. et al., Activation of p70 ribosomal protein S6 kinase is an essential step in the DNA damage-dependent signaling pathway responsible for the ultraviolet B-mediated increase in interstitial collagenase (MMP-1) and stromelysin-1 (MMP-3) protein levels in human dermal fibroblasts, J Biol Chem 275, 4336-44. (2000). |
| | | 711952\|Rps6kb1 | 5.3E−239 | [*Rattus norvegicus*][Protein kinase; Transferase] Ribosomal protein S6 kinase, 70 kD, a member of the ribosomal protein S6 kinase (RSK) family of protein kinases, insulin and mitogen activated, and plays roles in cell cycle progression and control of cell proliferation Grove, J. R. et al., Cloning and expression of two human p70 S6 kinase polypeptides differing only at their amino termini, Mol Cell Biol 11, 5541-50 (1991). |
| 11 | 7516613CD1 | g1872546 | 0.0 | [*Mus musculus*] NIK Su, Y. C. et al., NIK is a new Ste20-related kinase that binds NCK and MEKK1 and activates the SAPK/JNK cascade via a conserved regulatory domain, EMBO J. 16, 1279- |
| | | 582239\|Map4k4 | 0.0 | [*Mus musculus*][Protein kinase; Transferase; Receptor (signalling)] Mitogen-activated protein kinase kinase kinase kinase 4, a serine-threonine kinase, interacts with Nck, interacts with MEKK1 (Map3k1) and activates the c-Jun N-terminal kinase (Mapk8) signaling pathway; mutants fail to develop somites or a hindgut Becker, E. et al., Nck-interacting Ste20 kinase couples Eph receptors to c-Jun N-terminal kinase and integrin activation, Mol Cell Biol 20, 1537-45. (2000). |
| | | 340694\|MAP4K4 | 0.0 | [*Homo sapiens*][Protein kinase; Transferase] Mitogen-activated protein kinase kinase kinase kinase 4, a serine-threonine kinase, activates the c-Jun N-terminal kinase (MAPK8) signaling pathway, does not activate the ERK or p38 (CSBP1) kinase pathways, may be involved in TNF-alpha (TNF) signaling Yao, Z. et al., A novel human STE20-related protein kinase, HGK, that specifically activates the c-Jun N-terminal kinase signaling pathway, J Biol Chem 274, 2118-25 (1999). |

TABLE 2-continued

| Polypeptide SEQ ID NO: | Incyte Polypeptide ID | GenBank ID NO: or PROTEOME ID NO: | Probability Score | Annotation |
|---|---|---|---|---|
| 12 | 7517068CD1 | g6110362 | 0.0 | [*Homo sapiens*] Traf2 and NCK interacting kinase, splice variant 7<br>Fu, C. A. et al., TNIK, a novel member of the germinal center kinase family that activates the c-Jun N-terminal kinase pathway and regulates the cytoskeleton, J. Biol. Chem. 274, 30729-30737 (1999) |
| | | 340694\|MAP4K4 | 0.0 | [*Homo sapiens*][Protein kinase; Transferase] Mitogen-activated protein kinase kinase kinase kinase 4, a serine-threonine kinase, activates the c-Jun N-terminal kinase (MAPK8) signaling pathway, does not activate the ERK or p38 (CSBP1) kinase pathways, may be involved in TNF-alpha (TNF) signaling<br>Yao, Z et al., A novel human STE20-related protein kinase, HGK, that specifically activates the c-Jun N-terminal kinase signaling pathway, J Biol Chem 274, 2118-25 (1999). |
| | | 582239\|Map4k4 | 0.0 | [*Mus musculus*][Protein kinase; Transferase; Receptor (signalling)] Mitogen-activated protein kinase kinase kinase kinase 4, a serine-threonine kinase, interacts with Nck, interacts with MEKK1 (Map3k1) and activates the c-Jun N-terminal kinase (Mapk8) signaling pathway; mutants fail to develop somites or a hindgut<br>Su, Y. C. et al., NIK is a new Ste20-related kinase that binds NCK and MEKK1 and activates the SAPK/JNK cascade via a conserved regulatory domain, Embo Journal 16, 1279-90 (1997). |
| 13 | 7517148CD1 | g312395 | 0.0 | [*Homo sapiens*] beta-adrenergic kinase 2<br>Parruti, G. et al., Molecular cloning, functional expression and mRNA analysis of human beta-adrenergic receptor kinase 2, Biochem. Biophys. Res. Commun. 190, 475-481 (1993) |
| | | 341946\|ADRBK2 | 0.0 | [*Homo sapiens*][Protein kinase; Transferase][Cytoplasmic; Plasma membrane] G-protein coupled receptor kinase 3, member of a family of protein kinases that specifically phosphorylate activated G protein coupled receptors, resulting in receptor desensitization, may represent a genetic marker for mood disorders<br>Parruti, G. et al., Molecular cloning, functional expression and mRNA analysis of human beta-adrenergic receptor kinase 2, Biochem Biophys Res Commun 190, 475-81 (1993). |
| | | 589791\|Adrbk2 | 0.0 | [*Rattus norvegicus*][Protein kinase; Transferase][Axon; Dense bodies] G-protein coupled receptor kinase 3, member of a family of protein kinases that specifically phosphorylate activated G protein coupled receptors, resulting in receptor desensitization, may regulate nociception, sperm chemotaxis and olfaction<br>Kovoor, A. et al., Agonist induced homologous desensitization of mu-opioid receptors mediated by G protein-coupled receptor kinases is dependent on agonist efficacy, Mol Pharmacol 54, 704-11 (1998). |
| 14 | 7517238CD1 | g15559349 | 0.0 | [*Homo sapiens*] Similar to likely ortholog of maternal embryonic leucine zipper kinase |
| | | 570006\|MELK | 0.0 | [*Homo sapiens*][Protein kinase; Transferase] Protein containing two C-terminal kinase associated domain 1 and two protein kinase domains, has low similarity to microtubule-MAP-affinity regulating kinase (rat LOC60328), which is a serine-threonine kinase that influences microtubule stability<br>Seong, H. A. et al., Phosphorylation of a novel zinc-finger-like protein, ZPR9, by murine protein serine/threonine kinase 38 (MPK38), Biochem J 361, 597-604. (2002). |
| | | 585291\|Melk | 6.8E−270 | [*Mus musculus*][Protein kinase; Transferase] Protein containing a protein kinase domain and a C-terminal kinase associated domain 1, has low similarity to rat LOC60328, which is a serine-threonine kinase that participates in microtubule stability and the control of cell polarity<br>Seong, H. A. et al., Phosphorylation of a novel zinc-finger-like protein, ZPR9, by murine protein serine/threonine kinase 38 (MPK38), Biochem J 361, 597-604. (2002). |
| 15 | 7518685CD1 | g4100632 | 0.0 | [*Homo sapiens*] lymphoid phosphatase LyP1<br>Cohen, S. et al., Cloning and characterization of a lymphoid-specific, inducible human protein tyrosine phosphatase, Lyp, Blood 93, 2013-2024 (1999) |
| | | 570850\|PTPN22 | 0.0 | [*Homo sapiens*][Protein phosphatase; Hydrolase] Protein tyrosine phosphatase non-receptor type 22, a protein tyrosine phosphatase that may be involved in T-cell development<br>Cohen, S. et al., Cloning and characterization of a lymphoid-specific, inducible human protein tyrosine phosphatase, Lyp, Blood 93, 2013-24 (1999). |
| | | 582663\|Ptpn8 | 4.2E−270 | [*Mus musculus*][Protein phosphatase; Hydrolase] Protein tyrosine phosphatase non-receptor type 8, a protein tyrosine phosphatase that inhibits T-cell receptor mediated T-cell activation and is required for B-cell antigen receptor-mediated growth arrest and apoptosis<br>Matthews, R. J. et al., Characterization of hematopoietic intracellular protein tyrosine phosphatases: description of a phosphatase containing an SH2 domain and another enriched in proline-, glutamic acid-, serine-, and threonine-rich sequences, Mol Cell Biol 12, 2396-405 (1992). |
| 16 | 7520192CD1 | g190748 | 4.7E−105 | [*Homo sapiens*] protein-tyrosine phophatase<br>Gu, M. X. et al., Identification, cloning, and expression of a cytosolic megakaryocyte protein-tyrosine-phosphatase with sequence homology to cytoskeletal protein 4.1, Proc. Natl. Acad. Sci. U.S.A. 88, 5867-5871 (1991) |
| | | 337402\|PTPN4 | 3.3E−106 | [*Homo sapiens*][Protein phosphatase; Hydrolase][Cytoplasmic] Protein tyrosine phosphatase non-receptor type 4, a non-membrane spanning protein tyrosine phosphatase that can inhibit cell proliferation, may play a role in signal transduction<br>Gu, M. et al., The properties of the protein tyrosine phosphatase PTPMEG, J Biol Chem 271, 27751-9. (1996). |
| | | 628499\|Ptpn4 | 1.2E−102 | [*Mus musculus*][Protein phosphatase; Hydrolase] Protein tyrosine phosphatase non-receptor type 4, a protein tyrosine phosphatase that may play a role in spermatogenesis<br>Hironaka, K. et al., The protein-tyrosine phosphatase PTPMEG interacts with glutamate receptor delta 2 and epsilon subunits, J Biol Chem 275, 16167-73 (2000). |

TABLE 2-continued

| Polypeptide SEQ ID NO: | Incyte Polypeptide ID | GenBank ID NO: or PROTEOME ID NO: | Probability Score | Annotation |
|---|---|---|---|---|
| 17 | 7520428CD1 | g13537204 | 0.0 | [*Homo sapiens*] MAST205 |
| | | 742582\|MAST205 | 0.0 | [*Homo sapiens*][Protein kinase; Transferase][Cytoskeletal] Protein with strong similarity to microtubule associated testis specific serine/threonine protein kinase (mouse Mtssk), which may act in spermatid maturation and microtubule organization, contains a protein kinase domain and a PDZ, DHR, or GLGF domain<br>Walden, P. D. et al., Increased activity associated with the MAST205 protein kinase complex during mammalian spermiogenesis, Biol Reprod 55, 1039-44 (1996). |
| | | 582149\|Mtssk | 0.0 | [*Mus musculus*][Protein kinase; Transferase][Cytoplasmic; Cytoskeletal] Microtubule associated testis specific serine/threonine protein kinase, may be involved in the organisation of manchette microtubules in spermatids, may have a role in spermatid maturation<br>Walden, P. D. et al., Increased activity associated with the MAST205 protein kinase complex during mammalian spermiogenesis, Biol Reprod 55, 1039-44 (1996). |
| 18 | 7522586CD1 | g507162 | 6.7E−54 | [*Homo sapiens*] PITSLRE alpha 2-3<br>Xiang, J. et al., Molecular cloning and expression of alternatively spliced PITSLRE protein kinase isoforms, J. Biol. Chem. 269, 15786-15794 (1994) |
| | | 618480\|CDC2L1 | 1.3E−53 | [*Homo sapiens*][Protein kinase; Transferase][Nuclear; Cytoplasmic] Cell division cycle 2 like 1, member of the p34 (CDC2) superfamily that contains a PSTAIRE box, a protein kinase involved in apoptosis and cell cycle control; mutation of the corresponding gene is associated with non-Hodgkin lymphoma and melanoma<br>Lahti, J. M. et al., PITSLRE protein kinase activity is associated with apoptosis, Mol Cell Biol 15, 1-11 (1995). |
| | | 581017\|Cdc2l2 | 2.9E−53 | [*Mus musculus*][Protein kinase; Transferase] Cell division cycle 2 like 2, a protein kinase that binds Src-homology 2 (SH2) domains, appears to be involved in cell proliferation during embryonic development, member of the p34(cdc2) superfamily<br>Malek, S. N. et al., A cyclin-dependent kinase homologue, p130PITSLRE is a phosphotyrosine-independent SH2 ligand, J Biol Chem 269, 33009-20 (1994). |
| 19 | 7524017CD1 | g1405935 | 4.4E−275 | [*Mus musculus*] serine/threonine kinase<br>Heyer, B. S. et al., New member of the Snf1/AMPK kinase family, Melk, is expressed in the mouse egg and preimplantation embryo, Mol. Reprod. Dev. 47, 148-156 (1997) |
| | | 570006\|MELK | 0.0 | [*Homo sapiens*][Protein kinase; Transferase] Protein containing two C-terminal kinase associated domain 1 and two protein kinase domains, has low similarity to microtubule-MAP-affinity regulating kinase (rat LOC60328), which is a serine-threonine kinase that influences microtuble stability<br>Seong, H. A. et al., Phosphorylation of a novel zinc-finger-like protein, ZPR9, by murine protein serine/threonine kinase 38 (MPK38), Biochem J 361, 597-604. (2002). |
| | | 585291\|Melk | 3.0E−276 | [*Mus musculus*][Protein kinase; Transferase] Protein containing a protein kinase domain and a C-terminal kinase associated domain 1, has low similarity to rat LOC60328, which is a serine-threonine kinase that participates in microtubule stability and the control of cell polarity<br>Gil, M. et al., Cloning and expression of a cDNA encoding a novel protein serine/threonine kinase predominantly expressed in hematopoietic cells, Gene 195, 295-301 (1997). |
| 20 | 7525773CD1 | g187561 | 1.1E−151 | [*Homo sapiens*] mevalonate kinase<br>Schafer, B. L. et al., Molecular cloning of human mevalonate kinase and identification of a missense mutation in the genetic disease mevalonic aciduria, J. Biol. Chem. 267, 13229-13238 (1992) |
| | | 339520\|MVK | 7.9E−153 | [*Homo sapiens*][Protein kinase; Transferase; Other kinase] Mevalonate kinase (mevalonic aciduria), a peroxisomal enzyme involved in isoprenoid and cholesterol biosynthesis; mutations in the corresponding gene cause mevalonic aciduria, hyperimmunoglobulinemia D and periodic fever syndrome<br>Cho, Y. K. et al., Investigation of invariant serine/threonine residues in mevalonate kinase. Tests of the functional significance of a proposed substrate binding motif and a site implicated in human inherited disease, J Biol Chem 276, 12573-8. (2001). |
| | | 704952\|Mvk | 1.8E−129 | [*Rattus norvegicus*][Transferase; Other kinase] Mevalonate kinase, a peroxisomal enzyme involved in isoprenoid and cholesterol biosynthesis; deficiency of human MVK causes mevalonic aciduria, hyperimmunoglobulinemia D and periodic fever syndrome<br>Potter, D. et al., Identification and functional characterization of an active-site lysine in mevalonate kinase, J Biol Chem 272, 5741-6. (1997). |
| 21 | 7525861CD1 | g22328117 | 8.6E−77 | [*Homo sapiens*] similar to protein-tyrosine-phosphatase homolog DKFZp566K0524.1 - human (fragment) |
| | | 425672\|DKFZP566K0524 | 1.1E−83 | [*Homo sapiens*][Protein phosphatase; Hydrolase][Cytoplasmic] Protein with high similarity to protein tyrosine phosphatase non-receptor type 20 (mouse Ptpn20), which is a testis-specific protein tyrosine phosphatase that may play a role in spermatogenesis or meiosis, member of the protein-tyrosine phosphatase family |
| | | 582661\|Ptpn20 | 2.5E−47 | [*Mus musculus*][Protein phosphatase; Hydrolase][Cytoplasmic] Protein tyrosine phosphatase non-receptor type 20, a testis-specific protein tyrosine phosphatase that may play a role in spermatogenesis or meiosis<br>Ohsugi, M. et al., Molecular cloning and characterization of a novel cytoplasmic protein-tyrosine phosphatase that is specifically expressed in spermatocytes, J Biol Chem 272, 33092-9 (1997). |

TABLE 2-continued

| Polypeptide SEQ ID NO: | Incyte Polypeptide ID | GenBank ID NO: or PROTEOME ID NO: | Probability Score | Annotation |
|---|---|---|---|---|
| 22 | 2509577CD1 | g10312094 | 6.4E−40 | NIMA-related serine/threonine kinase [*Mus musculus*] Kandli, M. et al. Isolation and characterization of two evolutionarily conserved murine kinases (Nek6 and nek7) related to the fungal mitotic regulator, NIMA. Genomics 68, 187-196 (2000) |
| | 2509577CD1 | 714317\|D1044.3 | 2.2E−130 | [*Caenorhabditis elegans*] Protein containing 16 EB module domains and a protein kinase domain, has a region of low similarity to NIMA (never in mitosis gene a) - related expressed kinase 6 (human NEK6), which activates the S6 ribosomal protein kinase p70S6K (RPS6KB1) Chervitz, S. A. et al. Comparison of the complete protein sets of worm and yeast: Orthology and divergence. Science 282, 2022-2028 (1998) |
| | 2509577CD1 | 789751\|NEK6 | 1.3E−40 | [*Homo sapiens*][Protein kinase; Transferase] NIMA (never in mitosis gene a) - related expressed kinase 6, a protein kinase that phosphorylates and activates the S6 ribosomal protein kinase p70S6K (RPS6KB1) Belham, C. et al. Identification of the NIMA family kinases NEK6/7 as regulators of the p70 ribosomal S6 kinase. Curr. Biol. 11, 1155-1167 (2001) |
| 23 | 7505222CD1 | g256855 | 5.4E−112 | serine/threonine- and tyrosine-specific protein kinase; Nek1 [Mus sp.] Letwin, K. et al. A mammalian dual specificity protein kinase, Nek1, is related to the NIMA cell cycle regulator and highly expressed in meiotic germ cells. EMBO J. 11, 3521-3531 (1992) |
| | 7505222CD1 | 750718\|NEK1 | 2.3E−110 | [*Homo sapiens*] Protein containing a protein kinase domain, has weak similarity to serine threonine kinase 2 (mouse Stk2), which undergoes cleavage by caspase 3 (mouse Casp3) and the released N-terminal kinase domain and C-terminal domain promote apoptosis Nagase, T. et al. Prediction of the coding sequences of unidentified human genes. XXI. The complete sequences of 60 new cDNA clones from brain which code for large proteins. DNA Res. 8, 179-187 (2001) |
| | 7505222CD1 | 430066\|Nek3 | 2.0E−92 | [*Mus musculus*][Protein kinase; Transferase][Cytoplasmic] NIMA-related kinase 3, a protein kinase that is involved in cell cycle control Chen, A. et al. NIMA-related kinases: isolation and characterization of murine nek3 and nek4 cDNAs, and chromosomal localization of nek1, nek2 and nek3. Gene 234, 127-137 (1999) |
| 24 | 7524408CD1 | g4583675 | 3.7E−264 | [*Homo sapiens*] apyrase Biederbick, A. et al. A human intracellular apyrase-like protein, LALP70, localizes to lysosomal/autophagic vacuoles. J. Cell. Sci. 112 (Pt 15), 2473-2484 (1999) |
| | 7524408CD1 | 340820\|LYSAL1 | 2.7E−265 | [*Homo sapiens*][Other phosphatase; Hydrolase][Lysosome/vacuole; Cytoplasmic] Lysosomal apyrase-like protein (Golgi apyrase), a member of the apyrase or GDA1/CD39 family that is a lysosomal membrane protein with four apyrase domains, alternative splice form is identical to uridine diphosphatase Biederbick, A. et al. First apyrase splice variants have different enzymatic properties. J. Biol. Chem. 275, 19018-19024 (2000) |
| | 7524408CD1 | 753913\|Lysal2 | 2.8E−160 | [*Mus musculus*] Protein with high similarity to lysosomal apyrase-like protein (Golgi apyrase, human LYSAL1), which is a lysosomal membrane protein with four apyrase domains, member of the GDA1 or CD39 family of nucleoside phosphatases Shi, J. D. et al. Molecular cloning and characterization of a novel mammalian endo-apyrase (LALP1). J. Biol. Chem. 276, 17474-17478 (2001) |
| 25 | 7526163CD1 | g13537204 | 0.0 | MAST205 [*Homo sapiens*] |
| | 7526163CD1 | 423529\|KIAA0561 | 0.0 | [*Homo sapiens*][Protein kinase; Transferase] Protein with high similarity to murine Mtssk, which is a protein kinase that interacts with microtubules and facilitates their organization in spermatids, contains a eukaryotic protein kinase domain and a PDZ domain Nagase, T. Prediction of the coding sequences of unidentified human genes. IX. The complete sequences of 100 new cDNA clones from brain which can code for large proteins in vitro. DNA Res. 5, 31-39 (1998) |
| | 7526163CD1 | 742582\|MAST205 | 0.0 | [*Homo sapiens*][Protein kinase; Transferase][Cytoskeletal] Protein with strong similarity to microtubule associated testis specific serine/threonine protein kinase (mouse Mtssk), which may act in spermatid maturation and microtubule organization, contains a protein kinase domain and a PDZ, DHR, or GLGF domain Walden, P. D. et al. Increased activity associated with the MAST205 protein kinase complex during mammalian spermiogenesis. Biol. Reprod. 55, 1039-1044 (1996) |
| 26 | 7526158CD1 | g406058 | 0.0 | protein kinase [*Mus musculus*] Walden, P. D. et al. A novel 205-kilodalton testis-specific serine/threonine protein kinase associated with microtubules of the spermatid manchette. Mol. Cell. Biol. 13, 7625-7635 (1993) |
| | 7526158CD1 | 423529\|KIAA0561 | 0.0 | [*Homo sapiens*][Protein kinase; Transferase] Protein with high similarity to murine Mtssk, which is a protein kinase that interacts with microtubules and facilitates their organization in spermatids, contains a eukaryotic protein kinase domain and a PDZ domain Nagase, T. DNA Res. 5, 31-39 (1998) supra |
| | 7526158CD1 | 582149\|Mtssk | 0.0E+00 | [*Mus musculus*][Protein kinase; Transferase][Cytoplasmic; Cytoskeletal] Microtubule associated testis specific serine/threonine protein kinase, may be involved in the organization of manchette microtubules in spermatids, may have a role in spermatid maturation Lumeng, C. et al. Interactions between beta 2-syntrophin and a family of microtubule-associated serine/threonine kinases. Nat. Neurosci. 2, 611-617 (1999) |

TABLE 2-continued

| Poly-pep-tide SEQ ID NO: | Incyte Poly-peptide ID | GenBank ID NO: or PROTEOME ID NO: | Proba-bility Score | Annotation |
|---|---|---|---|---|
| 27 | 7519807CD1 | g18148911 | 5.7E−35 | [*Homo sapiens*] SKRP1<br>Zama, T. et al., A novel dual specificity phosphatase SKRP1 interacts with the MAPK kinase MKK7 and inactivates the JNK MAPK pathway. Implication for the precise regulation of the particular MAPK pathway, J. Biol. Chem. 277, 23909-23918 (2002)<br>Zama, T. et al., Scaffold role of a mitogen-activated protein kinase phosphatase, SKRP1, for the JNK signaling pathway, J. Biol. Chem. 277, 23919-23926 (2002) |
| | | 773093\|SKRP1 | 3.4E−36 | [*Homo sapiens*] Protein containing two dual specificity phosphatase catalytic domains, has moderate similarity to dual specificity phosphatase 3 (vaccinia H1 related phosphatase, human DUSP3), which dephosphorylates phosphotyrosine and phosphoserine, and inactivates MAPK |
| 28 | 7526180CD1 | g8250239 | 1.4E−241 | protein phosphatase 4 regulatory subunit 2 [*Homo sapiens*]<br>Hastie, C. J. et al., A novel 50 kDa protein forms complexes with protein phosphatase 4 and is located at centrosomal microtubule organizing centres, Biochem. J. 347 Pt 3, 845-855 (2000) |
| | 7526180CD1 | 606258\|PPP4R2 | 7.8E−243 | [*Homo sapiens*][Regulatory subunit][Cytoplasmic; Centrosome/spindle pole body] Protein phosphatase 4 regulatory subunit 2, interacts with protein phosphatase 4 catalytic subunit (PPP4C), may target PPP4C to the centrosome and regulate its activity at centrosomal microtubule organizing centers<br>Hastie, C. J. et al. (supra) |
| 29 | 7526185CD1 | g2582413 | 8.0E−74 | STE20-like kinase 3 [*Homo sapiens*]<br>Schinkmann, K. A. et al., Cloning and characterization of a novel mammalian STE20-like kinase (mst-3), J. Biol. Chem. 272, 286995-286703 (1997) |
| | 7526185CD1 | 336486\|STK24 | 4.4E−75 | [*Homo sapiens*][Protein kinase; Transferase] Serine-threonine kinase 24 (Ste20 yeast homolog), member of the SPS1 subgroup of the STE20-like protein family, a serine-threonine kinase that prefers manganese as a cofactor and uses either GTP or ATP as a phosphate donor<br>Zhou, T. H. et al., Identification of a human brain-specific isoform of mammalian STE20-like kinase 3 that is regulated by cAMP-dependent protein kinase., J Biol Chem 275, 2513-9 (2000). |
| | 7526185CD1 | 743574\|MST4 | 4.0E−65 | [*Homo sapiens*][Protein kinase; Transferase] Mst3 and SOK1-related kinase, a protein kinase, induces apoptosis, involved in cell growth, appears to activate MAPK but not JNK nor p38 kinase pathways, alternative form MST4a may regulate MST4; gene maps to a region associated with mental retardation<br>Lin, J. L. et al., MST4, a new Ste20-related kinase that mediates cell growth and transformation via modulating ERK pathway. Oncogene 20, 6559-69. (2001). |
| 30 | 7526192CD1 | g2199529 | 1.5E−134 | casein kinase I gamma 2 [*Homo sapiens*]<br>Kitabayashi, A. N. et al., Cloning and chromosomal mapping of human casein kinase I gamma 2 (CSNK1G2), Genomics 46, 133-137 (1997) |
| | 7526192CD1 | 344104\|CSNK1G2 | 8.1E−136 | [*Homo sapiens*][Protein kinase; Transferase] Casein kinase 1 gamma 2, a putative serine/threonine protein kinase, may play a role in signal transduction<br>Kitabayashi, A. N. et al., Cloning and chromosomal mapping of human casein kinase I gamma 2 (CSNK1G2)., Genomics 46, 133-7 (1997). |
| | 7526192CD1 | 664931\|Csnk1g2 | 2.9E−129 | [*Rattus norvegicus*][Protein kinase; Transferase] Casein kinase 1 gamma 2, serine/threonine protein kinase, may play a role in receptor tyrosine kinase-mediated signal transduction<br>Voisin, L. et al., Angiotensin II stimulates serine phosphorylation of the adaptor protein Nck: physical association with the serine/threonine kinases Pak1 and casein kinase I., Biochem J 341, 217-23 (1999). |
| 31 | 7526193CD1 | g15215576 | 1.1E−166 | BMP-2 inducible kinase [*Mus musculus*]<br>Kearns, A. E. et al., Cloning and characterization of a novel protein kinase that impairs osteoblast differentiation in vitro, J. Biol. Chem. 276, 42213-42218 (2001) |
| | 7526193CD1 | 770160\|Bike | 6.1E−168 | [*Mus musculus*] Protein containing a protein kinase domain, has low similarity to *C. elegans* SEL-5, which is a serine-threonine protein kinase that likely regulates LIN-12 and GLP-1 signaling<br>Kearns, A. E. et al. (supra) |
| | 7526193CD1 | 244458\|sel-5 | 1.2E−60 | [*Caenorhabditis elegans*][Protein kinase][Cytoplasmic] Serine/threonine protein kinase which likely regulates LIN-12 and GLP-1 signaling; has similarity to S. cerevisiae Ark1p and Prk1p protein kinases which are involved in regulation of the cytoskeleton<br>Fares, H. et al., SEL-5, A Serine/Threonine Kinase That Facilitates lin-12 Activity in Caenorhabditis elegans., Genetics 153, 1641-1654 (1999). |
| 32 | 7526196CD1 | g2506080 | 4.5E−40 | HsGAK [*Homo sapiens*]<br>Kimura, S. H. et al., Structure, expression, and chromosomal localization of human GAK, Genomics 44, 179-187 (1997) |
| | 7526196CD1 | 342050\|GAK | 2.5E−41 | [*Homo sapiens*][Protein kinase; Transferase] Cyclin G-associated kinase, a putative serine/threonine protein kinase that shares homology with tensin and auxilin, may play a role in cell cycle regulation<br>Kimura, S. H. et al. (supra) |
| | 7526196CD1 | 704892\|Gak | 1.1E−40 | [*Rattus norvegicus*][Protein kinase; Transferase] Cyclin G-associated kinase, a serine/threonine protein kinase that shares homology with tensin and auxilin, interacts with cyclin G (Ccng1)-Cdk5 complex, involved in the dissociation of clathrin-coated vesicles in non-neuronal cells<br>Greener, T. et al., Role of cyclin G-associated kinase in uncoating clathrin-coated vesicles from non-neuronal cells., J Biol Chem 275, 1365-70. (2000). |

TABLE 2-continued

| Poly-pep-tide SEQ ID NO: | Incyte Poly-peptide ID | GenBank ID NO: or PROTEOME ID NO: | Proba-bility Score | Annotation |
|---|---|---|---|---|
| 33 | 7526198CD1 | g2506080 | 0.0 | HsGAK [*Homo sapiens*]<br>Kimura, S. H. et al. (supra) |
| | 7526198CD1 | 342050\|GAK | 0.0 | [*Homo sapiens*][Protein kinase; Transferase] Cyclin G-associated kinase, a putative serine/threonine protein kinase that shares homology with tensin and auxilin, may play a role in cell cycle regulation<br>Kimura, S. H. et al. (supra) |
| | 7526198CD1 | 704892\|Gak | 0.0 | [*Rattus norvegicus*][Protein kinase; Transferase] Cyclin G-associated kinase, a serine/threonine protein kinase that shares homology with tensin and auxilin, interacts with cyclin G (Ccng1)-Cdk5 complex, involved in the dissociation of clathrin-coated vesicles in non-neuronal cells<br>Greener, T. et al. (supra) |
| 34 | 7526208CD1 | g4426595 | 9.0E−255 | multifunctional calcium/calmodulin-dependent protein kinase II delta2 isoform [*Homo sapiens*]<br>Hoch, B. et al., Identification and expression of delta-isoforms of the multifunctional Ca2+/calmodulin-dependent protein kinase in failing and nonfailing human myocardium, Circ. Res. 84, 713-721 (1999) |
| | 7526208CD1 | 742886\|CAMK2D | 4.9E−256 | [*Homo sapiens*][Protein kinase; Transferase][Nuclear; Cytoplasmic] Calcium/calmodulin-dependent protein kinase II delta, member of the multifunctional CAMKII family involved in Ca2+ regulated processes; alternative form delta 3 is specifically upregulated in the myocardium of patients with heart failure<br>Hoch, B. et al.(supra) |
| | 7526208CD1 | 772372\|Camk2d | 3.1E−243 | [*Mus musculus*] Protein with strong similarity to calcium-calmodulin-dependent protein kinase II delta (rat Camk2d), which is involved in Ca2+ regulated processes, contains two protein kinase domains<br>Hoch, B. et al., delta-Ca(2+)/calmodulin-dependent protein kinase II expression pattern in adult mouse heart and cardiogenic differentiation of embryonic stem cells, J Cell Biochem 79, 293-300 (2000). |
| 35 | 7526212CD1 | g1661132 | 5.3E−169 | calcium/calmodulin-dependent protein kinase II delta 2-subunit [*Sus scrofa*]<br>Singer, H. A. et al., Novel Ca2+/calmodulin-dependent protein kinase II gamma-subunit variants expressed in vascular smooth muscle, brain, and cardiomyocytes, J. Biol. Chem. 272, 9393-9400 (1997) |
| | 7526212CD1 | 772372\|Camk2d | 2.9E−170 | [*Mus musculus*] Protein with strong similarity to calcium-calmodulin-dependent protein kinase II delta (rat Camk2d), which is involved in Ca2+ regulated processes, contains two protein kinase domains<br>Hoch, B. et al., J Cell Biochem 79, 293-300 (2000). (supra) |
| | 7526212CD1 | 742886\|CAMK2D | 1.6E−169 | [*Homo sapiens*][Protein kinase; Transferase][Nuclear; Cytoplasmic] Calcium/calmodulin-dependent protein kinase II delta, member of the multifunctional CAMKII family involved in Ca2+ regulated processes; alternative form delta 3 is specifically upregulated in the myocardium of patients with heart failure<br>Hoch, B. et al., Circ Res 84, 713-21. (1999). (supra) |
| 36 | 7526213CD1 | g15215576 | 2.1E−15 | BMP-2 inducible kinase [*Mus musculus*]<br>Kearns, A. E. et al. (supra) |
| | 7526213CD1 | 605792\|BIKE | 1.7E−27 | [*Homo sapiens*][Protein kinase; Transferase] Protein containing a eukaryotic protein kinase domain |
| | 7526213CD1 | 770160\|Bike | 1.1E−16 | [*Mus musculus*] Protein containing a protein kinase domain, has low similarity to *C. elegans* SEL-5, which is a serine-threonine protein kinase that likely regulates LIN-12 and GLP-1 signaling<br>Kearns, A. E. et al. (supra) |
| 37 | 7526214CD1 | g15215576 | 1.7E−16 | BMP-2 inducible kinase [*Mus musculus*]<br>Kearns, A. E. et al. (supra) |
| | 7526214CD1 | 605792\|BIKE | 3.8E−28 | [*Homo sapiens*][Protein kinase; Transferase] Protein containing a eukaryotic protein kinase domain |
| | 7526214CD1 | 770160\|Bike | 9.4E−18 | [*Mus musculus*] Protein containing a protein kinase domain, has low similarity to *C. elegans* SEL-5, which is a serine-threonine protein kinase that likely regulates LIN-12 and GLP-1 signaling<br>Kearns, A. E. et al. (supra) |
| 38 | 7526228CD1 | g2924624 | 4.6E−55 | TGF-beta activated kinase 1a [*Homo sapiens*]<br>Sakurai, H. et al., TGF-beta-activated kinase 1 stimulates NF-kappa B activation by an NF-kappa B-inducing kinase-independent mechanism, Biochem. Biophys. Res. Commun. 243, 545-549 (1998) |
| | 7526228CD1 | 338400\|MAP3K7 | 2.5E−56 | [*Homo sapiens*][Protein kinase; Transferase] Mitogen-activated protein kinase kinase kinase 7 (TGF beta activated kinase 1), mediates TGFbeta and IL1 signal transduction, induces NFkappaB activation, may act as a regulatory kinase of I kappa B kinases (IKKs)<br>Sakurai, H. et al., Functional interactions of transforming growth factor beta-activated kinase 1 with IkappaB kinases to stimulate NF-kappaB activation., J Biol Chem 274, 10641-8 (1999). |
| | 7526228CD1 | 338400\|MAP3K7 | 2.50E−56 | [*Homo sapiens*][Protein kinase; Transferase] Mitogen-activated protein kinase kinase kinase 7 (TGF beta activated kinase 1), mediates TGFbeta and IL1 signal transduction, induces NFkappaB activation, may act as a regulatory kinase of I kappa B kinases (IKKs)<br>Craig, R. et al., p38 MAPK and NF-kappa B collaborate to induce interleukin-6 gene expression and release. Evidence for a cytoprotective autocrine signaling pathway in a cardiac myocyte model system., J Biol Chem 275, 23814-24 (2000). |

TABLE 2-continued

| Polypeptide SEQ ID NO: | Incyte Polypeptide ID | GenBank ID NO: or PROTEOME ID NO: | Probability Score | Annotation |
|---|---|---|---|---|
| 39 | 7526246CD1 | g23272739 | 5.7E−96 | adrenergic, beta, receptor kinase 1 [*Homo sapiens*]<br>Strausberg, R. L. et al., Generation and initial analysis of more than 15,000 full-length human and mouse cDNA sequences, Proc. Natl. Acad. Sci. U.S.A. 99, 16899-16903 (2002) |
| | 7526246CD1 | 334086\|ADRBK1 | 3.1E−97 | [*Homo sapiens*][Protein kinase; Transferase][Cytoplasmic; Plasma membrane] Beta-adrenergic receptor kinase 1, kinase that mediates desensitization of G protein-coupled receptors, phosphorylated by PKC, may modulate cardiovascular function; mouse and rat Adrbk1 appear to be involved with cardiomyopathy and myocardial infarction<br>Shih, M. et al., Oligodeoxynucleotides antisense to mRNA encoding protein kinase A, protein kinase C, and beta-adrenergic receptor kinase reveal distinctive cell-type-specific roles in agonist-induced desensitization., Proc Natl Acad Sci USA 91, 12193-7 (1994). |
| | 7526246CD1 | 775647\|Adrbk1 | 1.1E−94 | [*Mus musculus*][Protein kinase; Transferase] Beta-adrenergic receptor kinase 1, a kinase that may mediate desensitization of G protein-coupled receptors, modulates myocardial function and involved in cardiomyopathy; human ADRBK1 may play roles in hypertension and cardiomyopathy<br>Proll, M. A. at al., Beta 2-adrenergic receptor mutants reveal structural requirements for the desensitization observed with long-term epinephrine treatment., Mol Pharmacol 44, 569-74 (1993). |
| 40 | 7526258CD1 | g33303889 | 9.6E−110 | FAST kinase [synthetic construct] |
| | 7526258CD1 | 743544\|FASTK | 5.2E−111 | [*Homo sapiens*][Protein kinase; Transferase] Fas-activated serine threonine kinase, a serine-threonine kinase that phosphorylases RNA binding protein TIA1 during Fas mediated apoptosis, upregulated in peripheral blood mononuclear cells of atopic asthmatics and atopic non asthmatic patients<br>Brutsche, M. H. et al., Apoptosis signals in atopy and asthma measured with cDNA arrays., Clin Exp Immunol 123, 181-7. (2001). |
| | 7526258CD1 | 685389\|MGC5297 | 1.6E−11 | [*Homo sapiens*] Protein of unknown function, has a region of low similarity to a region of fas-activated serine threonine kinase (human FASTK), which is a serine-threonine kinase that phosphorylates RNA binding protein human TIA1 during Fas mediated apoptosis |
| 41 | 7526311CD1 | g1088281 | 7.9E−67 | pyruvate dehydrogenase kinase [*Homo sapiens*]<br>Gudi, R. et al., Diversity of the pyruvate dehydrogenase kinase gene family in humans, J. Biol. Chem. 270, 28989-28994 (1995) |
| | 7526311CD1 | 336846\|PDK1 | 4.3E−68 | [*Homo sapiens*][Protein kinase; Transferase; Other kinase][Cytoplasmic; Mitochondrial] Pyruvate dehydrogenase kinase 1, phosphorylates and inactivates the pyruvate dehydrogenase complex and thus regulates pyruvate metabolism<br>Taylor, V. et al., 5' phospholipid phosphatase SHIP-2 causes protein kinase B inactivation and cell cycle arrest in glioblastoma cells., Mol Cell Biol 20, 6860-71 (2000). |
| | 7526311CD1 | 757382\|Pdk1 | 2.2E−55 | [*Rattus norvegicus*][Protein kinase; Transferase; Other kinase][Cytoplasmic; Mitochondrial] Pyruvate dehydrogenase kinase 1, phosphorylates and inactivates the pyruvate dehydrogenase complex and thus putatively regulates pyruvate metabolism<br>Sugden, M. C. et al., Expression and regulation of pyruvate dehydrogenase kinase isoforms in the developing rat heart and in adulthood: role of thyroid hormone status and lipid supply, Biochem J 352, 731-8. (2000). |
| 42 | 7526315CD1 | g12655099 | 7.2E−121 | Mixed lineage kinase-related kinase MRK-beta [*Homo sapiens*]<br>Strausberg, R. L. et al. (supra) |
| | 7526315CD1 | 476453\|ZAK | 3.9E−122 | [*Homo sapiens*] Mixed lineage kinase with a leucine zipper and a sterile alpha motif, a mixed lineage kinase-like protein that stimulates the JNK/SAPK pathway and activates NF-kappaB; overexpression induces apoptosis of a hepatoma cell line<br>Liu, T. C. et al., Cloning and expression of ZAK, a mixed lineage kinase-like protein containing a leucine-zipper and a sterile-alpha motif, Biochem Biophys Res Commun 274, 811-6 (2000). |
| | 7526315CD1 | 662697\|Zak | 2.7E−121 | [*Mus musculus*][Protein kinase; Transferase] Mixed lineage kinase with a leucine zipper and a sterile alpha motif, activated by osmotic shock; overexpression activates the p38 (Mapk14), JNK/SAPK, ERK (Mapk3), and ERK5 (Mapk7) pathways, alpha alternative form disrupts actin stress fibers<br>Gotoh, I. et al., Identification and characterization of a novel MAP kinase kinase kinase, MLTK., J Biol Chem 276, 4276-86 (2001). (supra) |
| 43 | 7526442CD1 | g12803641 | 3.5E−64 | CCRK protein [*Homo sapiens*]<br>Strausberg, R. L. et al. (supra) |
| | 7526442CD1 | 568698\|CCRK | 2.4E−65 | [*Homo sapiens*][Protein kinase; Transferase] Protein containing four protein kinase domains, has a region of moderate similarity to cyclin-dependent kinase 3 (human CDK3), which is a kinase that binds to cyclin A and is required for progression from G1 to S phase |
| | 7526442CD1 | 583769\|Cdk5 | 1.6E−22 | [*Mus musculus*][Protein kinase; Transferase][Cell body (soma); Growth cone] Cyclin-dependent protein kinase 5, serine-threonine kinase that associates with the regulatory subunit p35 (Cdk5r) and phosphorylates neuronal proteins, involved in neuronal differentiation, regulation of myogenesis, and adaptive responses to cocaine<br>Ohshima, T. et al., Targeted disruption of the cyclin-dependent kinase 5 gene results in abnormal corticogenesis, neuronal pathology and perinatal death., Proc Natl Acad Sci USA 93, 11173-8 (1996). |

TABLE 3

| SEQ ID NO: | Incyte Polypeptide ID | Amino Acid Residues | Signature Sequences, Domains and Motifs | Analytical Methods and Databases |
|---|---|---|---|---|
| 1 | 7517831CD1 | 83 | signal_cleavage: M1-T58 | SPSCAN |
| | | | KINASE TYROSINE-PROTEIN PROTO-ONCOGENE DOMAIN TRANSFERASE ATP-BINDING MYRISTATE PHOSPHORYLATION SH2 SH3 PD012180: G2-E43 | BLAST_PRODOM |
| | | | Potential Phosphorylation Sites: S7 | MOTIFS |
| | | | Potential Glycosylation Sites: N40, N67 | MOTIFS |
| 2 | 7520272CD1 | 292 | signal_cleavage: M1-A44 | SPSCAN |
| | | | Fructose-1-6-bisphosphatase: N12-H289 | HMMER_PFAM |
| | | | Inositol phosphatase/fructose-1,6-bisphosphatase IPB000146: G59-D100, G112-T135, Q155-P189, R198-P220, G228-G253 | BLIMPS_BLOCKS |
| | | | Fructose-1-6-bisphosphatase active site: H208-E255 | PROFILESCAN |
| | | | Fructose-1,6-bisphosphatase signature PR00115: D119-Y140, P156-L176, G181-G196, A197-P220, G228-G248, V257-V279 | BLIMPS_PRINTS |
| | | | Inositol phosphatase/fructose-1,6-bisphosphatase family signature PR00377: V115-N126, L211-A221, Y234-G248 | BLIMPS_PRINTS |
| | | | HYDROLASE CARBOHYDRATE METABOLISM FRUCTOSE-16-BISPHOSPHATASE FBPASE 1-PHOSPHOHYDROLASE D-FRUCTOSE-1,6-BISPHOSPHATE CYCLE CHLOROPLAST CALVIN PD001491: G68-P189 D188-V279 | BLAST_PRODOM |
| | | | FRUCTOSE1 6-BISPHOSPHATASE 1-PHOSPHOHYDROLASE FBPASE HYDROLASE CARBOHYDRATE METABOLISM D-FRUCTOSE-1,6-BISPHOSPHATE MULTI-GENE PD017713: T13-V66 | BLAST_PRODOM |
| | | | FRUCTOSE-1-6-BISPHOSPHATASE DM00535\|P09467\|10-331: V11-P189 P189-E287 | BLAST_DOMO |
| | | | FRUCTOSE-1-6-BISPHOSPHATASE DM00535\|A37295\|60-331: A61-P189 P189-E287 | BLAST_DOMO |
| | | | FRUCTOSE-1-6-BISPHOSPHATASE DM00535\|S46245\|11-332: T13-P189 D190-G274 | BLAST_DOMO |
| | | | FRUCTOSE-1-6-BISPHOSPHATASE DM00535\|P46267\|12-333: T13-P189 D190-Y286 | BLAST_DOMO |
| | | | Potential Phosphorylation Sites: S97, S125, S144, S149, S275, T145, T252 | MOTIFS |
| | | | Potential Glycosylation Sites: N65 | MOTIFS |
| | | | Fructose-1-6-bisphosphatase active site: G228-A240 | MOTIFS |
| 3 | 7521279CD1 | 434 | signal_cleavage: M1-G51 | SPSCAN |
| | | | 6-phosphofructo-2-kinase: Q30-P249 | HMMER_PFAM |
| | | | Phosphoglycerate mutase family: R250-I400 | HMMER_PFAM |
| | | | Phosphoglycerate mutase family IPB001345: I252-S284, V299-A311, G315-R347 | BLIMPS_BLOCKS |
| | | | Phosphoglycerate mutase family phosphohistidine signature: I234-K283 | PROFILESCAN |
| | | | 6-phosphofructo-2-kinase family signature PR00991: V125-A139, K151-I165, P177-F191, V230-S251, I252-L274 | BLIMPS_PRINTS |
| | | | MUTASE PROTEOME COMPLETE PHOSPHOGLYCERATE PGAM ISOMERASE GLYCOLYSIS BPG-DEPENDENT FRUCTOSE-2,6-BISPHOSPHATASE PHOSPHOGLYCEROMUTASE PD000730: Y253-D328 S330-L388 | BLAST_PRODOM |
| | | | KINASE FRUCTOSE-2,6-BISPHOSPHATASE INCLUDES: ISOZYME 6PF-2-K/FRU-6-PHOSPHOFRUCTO-2-KINASE/FRUCTOSE-2,6-BIPHOSPHATASE TRANSFERASE 2,6-P2ASE MULTI-FUNCTIONAL PD002665: T36-I252 | BLAST_PRODOM |
| | | | 6-BISPHOSPHATASE TRANSFERASE 6PF2K/FRU2 6-P2ASE INCLUDES: KINASE FRUCTOSE2 MULTI-FUNCTIONAL ENZYME ISOZYME PD009472: T389-H433 | BLAST_PRODOM |
| | | | 6-PF2K/FRU2,6-P2ASE TESTIS ISOZYME INCLUDES: 6-PHOSPHOFRUCTO 2-KINASE EC 2.7.1.105 FRUCTOSE-2,6-BISPHOSPHATASE 3.1.3.46 MULTI-FUNCTIONAL ENZYME TRANSFERASE KINASE HYDROLASE ATP-BINDING PD114268: M1-M35 | BLAST_PRODOM |
| | | | 6-PHOSPHOFRUCTO-2-KINASE/FRUCTOSE-2,6-BISPHOSPHATE 2-PHOSPHATASE DM01656\|JC1470\|184-441: E186-R337 Y331-V407 | BLAST_DOMO |
| | | | 6-PHOSPHOFRUCTO-2-KINASE/FRUCTOSE-2,6-BISPHOSPHATE 2-PHOSPHATASE DM01656\|JC2037\|185-444: N181-L352 S330-V407 | BLAST_DOMO |
| | | | 6-PHOSPHOFRUCTO-2-KINASE/FRUCTOSE-2,6-BISPHOSPHATE 2-PHOSPHATASE DM01656\|P07953\|184-442: G46-V82 D183-A329 S330-V407 | BLAST_DOMO |
| | | | 6-PHOSPHOFRUCTO-2-KINASE/FRUCTOSE-2,6-BISPHOSPHATE 2-PHOSPHATASE DM01656\|P25114\|183-441: D183-E349 S330-V407 | BLAST_DOMO |
| | | | Potential Phosphorylation Sites: S3, S56, S204, S275, S330, T60, T85, T133, T140, T248, T409, Y377 | MOTIFS |
| | | | Potential Glycosylation Sites: N132 | MOTIFS |
| | | | ATP/GTP-binding site motif A (P-loop): G46-T53 | MOTIFS |
| | | | Phosphoglycerate mutase family phosphohistidine signature: L254-N263 | MOTIFS |

TABLE 3-continued

| SEQ ID NO: | Incyte Polypeptide ID | Amino Acid Residues | Signature Sequences, Domains and Motifs | Analytical Methods and Databases |
|---|---|---|---|---|
| 4 | 7523965CD1 | 240 | Phosphoenolpyruvate carboxykinase (GTP) IPB000364: K88-P121, F148-L178, T179-L202, D204-P217 | BLIMPS_BLOCKS |
| | | | PHOSPHOENOLPYRUVATE CARBOXYKINASE LYASE GTP-BINDING CARBOXYLASE DECARBOXYLASE GLUCONEOGENESIS PD004738: D46-E232 | BLAST_PRODOM |
| | | | PHOSPHOENOLPYRUVATE CARBOXYKINASE, MITOCHONDRIAL PRECURSOR GTP EC 4.1.1.32 CARBOXYLASE PEPCKM GLUCONEOGENESIS LYASE DECARBOXYLASE GTP- BINDING MITOCHONDRION TRANSIT PEPTIDE MANGANES PD144568: M1-R45 | BLAST_PRODOM |
| | | | PHOSPHOENOLPYRUVATE CARBOXYKINASE (GTP) DM01781\|P05153\|15-621: V32-P240 DM01781\|P20007\|40-646: G35-E232 DM01781\|P21642\|33-639: L33-P240 DM01781\|Q05893\|30-640: V32-E232 | BLAST_DOMO |
| | | | Potential Phosphorylation Sites: S23, S51, S115, S136, S187, T29, T66, T75, T219 | MOTIFS |
| 5 | 7524016CD1 | 199 | signal_cleavage: M1-T33 | SPSCAN |
| | | | 6-phosphofructo-2-kinase: R7-W199 | HMMER_PFAM |
| | | | 6-phosphofructo-2-kinase family signature PR00991: V104-S118, K130-I144, P156-F170 | BLIMPS_PRINTS |
| | | | KINASE FRUCTOSE-2,6-BISPHOSPHATASE INCLUDES: ISOZYME 6PF-2-K/FRU-6-PHOSPHOFRUCTO-2-KINASE/FRUCTOSE-2,6-BIPHOSPHATASE TRANSFERASE 2,6-P2ASE MULTI-FUNCTIONAL PD002665: W45-W194, A10-A124 | BLAST_PRODOM |
| | | | 6-PHOSPHOFRUCTO-2-KINASE/FRUCTOSE-2,6-BISPHOSPHATE 2-PHOSPHATASE DM01457\|JC1470\|28-182: A10-C161 DM01457\|P07953\|29-182: A10-C161 DM01457\|P25114\|27-181: T16-D160 DM01457\|P26285\|26-180: T16-Y158 | BLAST_DOMO |
| | | | Potential Phosphorylation Sites: S36, S64, S98, T5, T112 | MOTIFS |
| | | | Potential Glycosylation Sites: N111 | MOTIFS |
| | | | ATP/GTP-binding site motif A (P-loop): G26-T33 | MOTIFS |
| 6 | 7524680CD1 | 406 | 6-phosphofructo-2-kinase: M1-P186 | HMMER_PFAM |
| | | | Phosphoglycerate mutase family: R187-I372 | HMMER_PFAM |
| | | | Phosphoglycerate mutase family IPB001345: I189-A221, V236-A248, G252-E284, E301-E346 | BLIMPS_BLOCKS |
| | | | Phosphoglycerate mutase family phosphohistidine signature: I171-Y220 | PROFILESCAN |
| | | | 6-phosphofructo-2-kinase family signature PR00991: V62-S76, K88-I102, P114-F128, V167-S188, I189-L211, A266-P282 | BLIMPS_PRINTS |
| | | | MUTASE PROTEOME COMPLETE PHOSPHOGLYCERATE PGAM ISOMERASE GLYCOLYSIS BPG-DEPENDENT FRUCTOSE-2,6-BISPHOSPHATASE PHOSPHOGLYCEROMUTASE PD000730: Y190-Y303 P298-L360 | BLAST_PRODOM |
| | | | KINASE FRUCTOSE-2,6-BISPHOSPHATASE INCLUDES: ISOZYME 6PF-2-K/FRU-6-PHOSPHOFRUCTO-2-KINASE/FRUCTOSE-2,6-BIPHOSPHATASE TRANSFERASE 2,6-P2ASE MULTI-FUNCTIONAL PD002665: K9-I189 | BLAST_PRODOM |
| | | | 6-BISPHOSPHATASE TRANSFERASE 6PF2K/FRU2 6-P2ASE INCLUDES: KINASE FRUCTOSE2 MULTI-FUNCTIONAL ENZYME ISOZYME PD009472: T361-Y406 | BLAST_PRODOM |
| | | | FRUCTOSE-2 SIMILAR PD114271: S232-V376 | BLAST_PRODOM |
| | | | 6-PHOSPHOFRUCTO-2-KINASE/FRUCTOSE-2,6-BISPHOSPHATE 2-PHOSPHATASE DM01656\|JC1470\|184-441: K123-V379 DM01656\|P07953\|184-442: D120-V379 DM01656\|P25114\|183-441: D120-V379 DM01656\|P26285\|182-441: D120-V379 | BLAST_DOMO |
| | | | Potential Phosphorylation Sites: S22, S56, S212, S233, S302, S343, T5, T70, T185, T273, T381, Y295, Y349 | MOTIFS |
| | | | Potential Glycosylation Sites: N69 | MOTIFS |
| | | | Phosphoglycerate mutase family phosphohistidine signature: L191-N200 | MOTIFS |
| 7 | 7524757CD1 | 426 | signal_cleavage: M1-T33 | SPSCAN |
| | | | 6-phosphofructo-2-kinase: R7-P206 | HMMER_PFAM |
| | | | Phosphoglycerate mutase family: R207-I392 | HMMER_PFAM |
| | | | Phosphoglycerate mutase family phosphohistidine signature: I191-Y240 | PROFILESCAN |
| | | | Phosphoglycerate mutase family IPB001345A: I209-A241, V256-A268, G272-E304, E321-E366 | BLIMPS_BLOCKS |
| | | | 6-phosphofructo-2-kinase family signature PR00991: V82-S96, K108-I122, P134-F148, V187-S208, I209-L231, A286-P302 | BLIMPS_PRINTS |
| | | | KINASE FRUCTOSE-2,6-BISPHOSPHATASE INCLUDES: ISOZYME 6PF-2-K/FRU-6-PHOSPHOFRUCTO-2-KINASE/FRUCTOSE-2,6-BIPHOSPHATASE TRANSFERASE 2,6-P2ASE MULTI-FUNCTIONAL PD002665: A10-A64 D52-I209 | BLAST_PRODOM |
| | | | MUTASE PROTEOME COMPLETE PHOSPHOGLYCERATE PGAM ISOMERASE GLYCOLYSIS BPG-DEPENDENT FRUCTOSE-2,6-BISPHOSPHATASE PHOSPHOGLYCEROMUTASE PD000730: Y210-Y323 P318-L380 | BLAST_PRODOM |
| | | | 6BISPHOSPHATASE TRANSFERASE 6PF2K/FRU2 6-P2ASE INCLUDES: KINASE FRUCTOSE2 MULTI-FUNCTIONAL ENZYME ISOZYME PD009472: T381-Y426 | BLAST_PRODOM |
| | | | FRUCTOSE-2 SIMILAR PD114271: S252-V396 | BLAST_PRODOM |
| | | | 6-PHOSPHOFRUCTO-2-KINASE/FRUCTOSE-2,6-BISPHOSPHATE 2-PHOSPHATASE DM01656\|JC1470\|184-441: K143-V399 DM01656\|JC2037\|185-444: D140-V399 DM01656\|P07953\|184-442: D140-V399 DM01656\|P25114\|183-441: D140-V399 | BLAST_DOMO |

TABLE 3-continued

| SEQ ID NO: | Incyte Polypeptide ID | Amino Acid Residues | Signature Sequences, Domains and Motifs | Analytical Methods and Databases |
|---|---|---|---|---|
| | | | Potential Phosphorylation Sites: S36, S76, S232, S253, S322, S363, T5, T90, T205, T293, T401, Y315, Y369 | MOTIFS |
| | | | Potential Glycosylation Sites: N89 | MOTIFS |
| | | | ATP/GTP-binding site motif A (P-loop): G26-T33 | MOTIFS |
| | | | Phosphoglycerate mutase family phosphohistidine signature: L211-N220 | MOTIFS |
| 8 | 7516229CD1 | 355 | signal_cleavage: M1-S48 | SPSCAN |
| | | | Phosphatidylinositol-4-phosphate 5-Kinase: M1-L354 | HMMER_PFAM |
| | | | Phosphatidylinositol phosphate kinases: M62-T355 | HMMER_SMART |
| | | | KINASE PHOSPHATIDYLINOSITOL-4-PHOSPHATE 5-KINASE-TYPE TRANSFERASE DIPHOSPHOINOSITIDE 1-PHOSPHATIDYLINOSITOL-4-PHOSPHATE PTDINS4P-5-KINASE ALPHA PD002308: M1-F112 F112-I353 | BLAST_PRODOM |
| | | | PHOSPHATIDYLINOSITOL; KINASE; DM07197\|P48426\|8-404: G8-Q113 Q113-T355 | BLAST_DOMO |
| | | | PHOSPHATIDYLINOSITOL; KINASE; DM07197\|P38994\|351-756: L41-F112 Q110-I350 | BLAST_DOMO |
| | | | Potential Phosphorylation Sites: S48, S150, S171, S296, S343, T18, T181, T261, T311, T325 | MOTIFS |
| | | | Potential Glycosylation Sites: N46 | MOTIFS |
| 9 | 7516525CD1 | 543 | Protein kinase domain: Y128-V447 | HMMER_PFAM |
| | | | Serine/Threonine protein kinases, catalytic domain: Y128-V447 | HMMER_SMART |
| | | | Receptor tyrosine kinase class V IPB001426: L294-K315, P316-D342 | BLIMPS_BLOCKS |
| | | | Protein kinases signatures and profile: Q289-D342 | PROFILESCAN |
| | | | Tyrosine kinase catalytic domain signature PR00109: Y303-L321, I416-V438, G350-I360, L372-D394 | BLIMPS_PRINTS |
| | | | KINASE TRANSFERASE ATP-BINDING SERINE/THREONINE-PROTEIN TYROSINE-PROTEIN RECEPTOR 2.7.1. - PHOSPHORYLATION PRECURSOR PD000001: Q127-A353 G340-E453 P414-W446 | BLAST_PRODOM |
| | | | KINASE ATP-BINDING TRANSFERASE SERINE/THREONINE-PROTEIN CA2/CALMODULIN-DEPENDENT BETA CG17698 CA/CALMODULIN-DEPENDENT ALPHA SERINE/THREONINE PD019141: V447-F501 | BLAST_PRODOM |
| | | | KINASE ATP-BINDING SERINE/THREONINE-PROTEIN CA2/CALMODULIN-DEPENDENT TRANSFERASE ALPHA SERINE/THREONINE GLYCOGEN CALCIUM/CALMODULIN PD027014: E502-S543 | BLAST_PRODOM |
| | | | KINASE ATP-BINDING SERINE/THREONINE-PROTEIN TRANSFERASE CA2/CALMODULIN-DEPENDENT BETA CA/CALMODULIN-DEPENDENT ALPHA SERINETHREONINE PD031900: M1-Q127 | BLAST_PRODOM |
| | | | PROTEIN KINASE DOMAIN DM00004\|A57156\|130-399: L130-L228 Q238-V438 | BLAST_DOMO |
| | | | PROTEIN KINASE DOMAIN DM00004\|P50526\|136-399: E133-Q231 P247-I436 | BLAST_DOMO |
| | | | PROTEIN KINASE DOMAIN DM00004\|P06782\|57-296: I134-K166 R195-Q231 D282-V438 | BLAST_DOMO |
| | | | PROTEIN KINASE DOMAIN DM00004\|JC1446\|20-261: K129-L164 E194-Q231 V267-V438 | BLAST_DOMO |
| | | | Potential Phosphorylation Sites: S69, S74, S82, S100, S117, S160, S266, S368, S457, S463, S475, S496, T26, T58, T108, T468 | MOTIFS |
| | | | Potential Glycosylation Sites: N147 | MOTIFS |
| | | | ATP/GTP-binding site motif A (P-loop): G523-S530 | MOTIFS |
| | | | Protein kinases ATP-binding region signature: I134-K157 | MOTIFS |
| | | | Serine/Threonine protein kinases active-site signature: I309-L321 | MOTIFS |
| 10 | 7516533CD1 | 445 | Protein kinase domain: I30-F272 | HMMER_PFAM |
| | | | Protein kinase C terminal domain: R273-I359 | HMMER_PFAM |
| | | | Extension to Ser/Thr-type protein kinases: R273-A335 | HMMER_SMART |
| | | | Serine/Threonine protein kinases, catalytic domain: E41-F272 | HMMER_SMART |
| | | | Receptor tyrosine kinase class II IPB002011: I66-F110, I134-L185, N217-G261 | BLIMPS_BLOCKS |
| | | | Tyrosine kinase catalytic domain signature PR00109: H128-L146, V194-E216, L92-E105, L236-A258 | BLIMPS_PRINTS |
| | | | KINASE S6 RIBOSOMAL SERINE/THREONINE-PROTEIN TRANSFERASE P70 BETA 2.7.1. - ATP-BINDING PHOSPHORYLATION PD032092: S337-L445 | BLAST_PRODOM |
| | | | PROTEIN KINASE DOMAIN DM00004\|A53300\|64-305: K55-G257 DM00004\|A57459\|61-302: V27-G257 DM00004\|P23443\|69-313: A48-G257 | BLAST_DOMO |
| | | | PROTEIN KINASE C ALPHA DM04692\|A37237\|1-676: I50-V334 | BLAST_DOMO |
| | | | Potential Phosphorylation Sites: S40, S96, S163, S295, S300, S314, S337, S341, S354, S361, S372, S399, S435, T60, T221, T310, T319, T390, Y11 | MOTIFS |
| | | | Serine/Threonine protein kinases active-site signature: I134-L146 | MOTIFS |

TABLE 3-continued

| SEQ ID NO: | Incyte Polypeptide ID | Amino Acid Residues | Signature Sequences, Domains and Motifs | Analytical Methods and Databases |
|---|---|---|---|---|
| 11 | 7516613CD1 | 1219 | CNH domain: Y901-R1199 | HMMER_PFAM |
| | | | Protein kinase domain: F25-I289 | HMMER_PFAM |
| | | | Domain found in NIK1-like kinases, mouse citron and yeast ROM1, ROM2: Y901-R1199 | HMMER_SMART |
| | | | Serine/Threonine protein kinases, catalytic domain: F25-I289 | HMMER_SMART |
| | | | Tyrosine kinase, catalytic domain: F25-I289 | HMMER_SMART |
| | | | Receptor tyrosine kinase class III IPB001824: T59-I113, W129-K168, G190-P232 | BLIMPS_BLOCKS |
| | | | Protein kinases signatures and profile: W129-V182 | PROFILESCAN |
| | | | KINASE SERINE/THREONINE-PROTEIN BINDING PHORBOL-ESTER ATP-BINDING TRANSFERASE GDP-GTP EXCHANGE RHO1 CDC42-BINDING PD014445: L919-S1043 F1074-S1197 | BLAST_PRODOM |
| | | | KINASE SERINE/THREONINE-PROTEIN ATP-BINDING TRANSFERASE MIG-15 TYROSINE-PROTEIN 2.7.1. - PD147188: I289-P500 S795-W915 | BLAST_PRODOM |
| | | | COIL COILED MYOSIN CHAIN ATP-BINDING HEAVY FILAMENT MUSCLE REPEAT INTERMEDIATE PD000002: K316-K517, Q292-Q471, Q301-Q490, L352-R569, I289-E466, Q292-R459, R358-E537 | BLAST_PRODOM |
| | | | ATP-BINDING TRANSFERASE NIK KINASE SERINE/THREONINE-PROTEIN PD147187: H501-K831, E514-W915 | BLAST_PRODOM |
| | | | PROTEIN KINASE DOMAIN<br>DM00004\|A53714\|17-262: L27-S279<br>DM00004\|P08458\|20-262: V31-S279<br>DM00004\|P10676\|18-272: L27-P278<br>DM00004\|P38692\|24-266: E29-S279 | BLAST_DOMO |
| | | | Potential Phosphorylation Sites: S9, S17, S77, S112, S255, S259, S264, S324, S326, S550, S554, S573, S625, S626, S633, S682, S683, S707, S721, S727, S756, S764, S880, S963, S1023, S1043, S1083, S1096, S1197, T59, T124, T187, T222, T309, T319, T351, T543, | MOTIFS |
| | | | S1023, S1043,T689, T690, T810, T816, T876, T996, T1057, Y321, Y323, Y467 | MOTIFS |
| | | | Potential Glycosylation Sites: N33, N570, N719, N818, N1151 | MOTIFS |
| | | | Leucine zipper pattern: L472-L493 | MOTIFS |
| | | | Protein kinases ATP-binding region signature: V31-K54 | MOTIFS |
| | | | Serine/Threonine protein kinases active-site signature: V149-L161 | MOTIFS |
| 12 | 7517068CD1 | 1168 | CNH domain: Y850-R1148 | HMMER_PFAM |
| | | | Protein kinase domain: F25-I289 | HMMER_PFAM |
| | | | Domain found in NIK1-like kinases, mouse citron and yeast ROM1, ROM2: Y850-R1148 | HMMER_SMART |
| | | | Serine/Threonine protein kinases, catalytic domain: F25-I289 | HMMER_SMART |
| | | | Tyrosine kinase, catalytic domain: F25-I289 | HMMER_SMART |
| | | | Eukaryotic protein kinase IPB000719: H145-L160, Y210-G220 | BLIMPS_BLOCKS |
| | | | Receptor tyrosine kinase class III IPB001824: T59-V113, W129-K168, G190-P232 | BLIMPS_BLOCKS |
| | | | Protein kinases signatures and profile: W129-T181 | PROFILESCAN |
| | | | Tyrosine kinase catalytic domain signature PR00109: M105-K118, H143-L161, S214-M236, G190-I200, W258-T280 | BLIMPS_PRINTS |
| | | | KINASE SERINE/THREONINE-PROTEIN BINDING PHORBOL-ESTER ATP-BINDING TRANSFERASE GDP-GTP EXCHANGE RHO1 CDC42-BINDING PD014445: L868-S992 F1023-S1146 | BLAST_PRODOM |
| | | | KINASE SERINE/THREONINE-PROTEIN ATP-BINDING TRANSFERASE MIG-15 TYROSINE-PROTEIN 2.7.1. - PD147188: I289-E648 V831-W864 | BLAST_PRODOM |
| | | | KINASE SERINE/THREONINE-PROTEIN ATP-BINDING TRANSFERASE NCK TRAF2 INTERACTING VARIANT SPLICE GCK PD043898: F993-P1039 | BLAST_PRODOM |
| | | | ATP-BINDING TRANSFERASE NIK KINASE SERINE/THREONINE-PROTEIN PD147187: R402-G756, S545-W864 | BLAST_PRODOM |
| | | | PROTEIN KINASE DOMAIN<br>DM00004\|A53714\|17-262: L27-P278<br>DM00004\|P10676\|18-272: L27-P278<br>DM00004\|P38692\|24-266: E29-R277<br>DM00004\|P50527\|388-627: V31-T280 | BLAST_DOMO |
| | | | Potential Phosphorylation Sites: S9, S77, S112, S255, S259, S264, S275, S324, S326, S426, S446, S504, S523, S571, S580, S639, S640, S646, S647, S696, S723, S767, S776, S793, S829, S912, S992, S1146, T59, T124, T187, T222, T309, T319, T349, T467, T627, T635, T716, T750, T795, T945, T1006, Y321, Y323 | MOTIFS |
| | | | Potential Gycosylation Sites: N33, N273, N333, N443, N507 | MOTIFS |
| | | | Protein kinases ATP-binding region signature: V31-K54 | MOTIFS |
| | | | Serine/Threonine protein kinases active-site signature: V149-L161 | MOTIFS |
| 13 | 7517148CD1 | 650 | Regulator of G protein signaling domain: T54-C175 | HMMER_PFAM |
| | | | Protein kinase domain: F191-F453 | HMMER_PFAM |
| | | | Regulator of G protein signalling domain: T54-C175 | HMMER_SMART |
| | | | Extension to Ser/Thr-type protein kinases: K454-T533 | HMMER_SMART |
| | | | Serine/Threonine protein kinases, catalytic domain: F191-F453 | HMMER_SMART |
| | | | Receptor tyrosine kinase class II IPB002011: L245-F289, V313-K364, D398-G442 | BLIMPS_BLOCKS |
| | | | Tyrosine kinase catalytic domain signature PR00109: L271-S284, H307-L325, F417-C439 | BLIMPS_PRINTS |
| | | | GPCR kinase signature PR00717: F171-N183, K230-T248, P468-I485, T493-Y506, K507-T524 | BLIMPS_PRINTS |
| | | | Regulator of G protein signalling domain proteins PF00615: M15-K21, F162-K178, I270-L283 | BLIMPS_PFAM |

TABLE 3-continued

| SEQ ID NO: | Incyte Polypeptide ID | Amino Acid Residues | Signature Sequences, Domains and Motifs | Analytical Methods and Databases |
|---|---|---|---|---|
| | | | PH (pleckstrin homology) domain proteins (P < 0.025) PF00169: S41-L47 | BLIMPS_PFAM |
| | | | KINASE RECEPTOR ATP-BINDING SERINE/THREONINE-PROTEIN TRANSFERASE COUPLED BETA-ADRENERGIC MULTI-GENE FAMILY G-PROTEIN PD007430: M1-I53 | BLAST_PRODOM |
| | | | BETA-ADRENERGIC RECEPTOR KINASE COUPLED TRANSFERASE SERINE/ THREONINE PROTEIN ATP-BINDING MULTI-GENE FAMILY BETA ARK1PD007640: T533-Q575 | BLAST_PRODOM |
| | | | BETA-ADRENERGIC RECEPTOR KINASE BETA ARK2 G-PROTEIN COUPLED TRANSFERASE SERINE/THREONINE PROTEIN ATP-BINDING MULTI-GENE PD151831: T612-L650 | BLAST_PRODOM |
| | | | PROTEIN KINASE DOMAIN DM00004\|P21146\|193-437: V193-G438 DM00004\|P32865\|193-438: V193-G438 DM00004\|Q09537\|205-450: V193-C439 DM00004\|Q09639\|193-439: V193-G438 | BLAST_DOMO |
| | | | Potential Phosphorylation Sites: S29, S38, S137, S156, S168, S247, S290, S343, S370, S423, S434, S487, S514, S596, S598, T187, T213, T366, T524, T533, T612, Y92 | MOTIFS |
| | | | Potential Glycosylation Sites: N610 | MOTIFS |
| | | | Protein kinases ATP-binding region signature: I197-K220 | MOTIFS |
| | | | Serine/Threonine protein kinases active-site signature: V313-L325 | MOTIFS |
| 14 | 7517238CD1 | 603 | Kinase associated domain 1: S554-V603 | HMMER_PFAM |
| | | | Protein kinase domain: Y11-I215 | HMMER_PFAM |
| | | | Serine/Threonine protein kinases, catalytic domain: Y11-I215 | HMMER_SMART |
| | | | KINASE SERINE/THREONINE-PROTEIN ATP-BINDING TRANSFERASE ZIPPER MATERNAL EMBRYONIC LEUCINE PK38 W03G1.6 PD017644: I215-V603 | BLAST_PRODOM |
| | | | PROTEIN KINASE DOMAIN DM00004\|S52244\|15-255: L13-E87 E88-M206 | BLAST_DOMO |
| | | | PROTEIN KINASE DOMAIN DM00004\|P06782\|57-296: E15-D93 E88-M206 | BLAST_DOMO |
| | | | PROTEIN KINASE DOMAIN DM00004\|P54645\|17-258: L13-E87 E88-M206 | BLAST_DOMO |
| | | | PROTEIN KINASE DOMAIN DM00004\|S51025\|18-258: L13-E87 E88-M206 | BLAST_DOMO |
| | | | Potential Phosphorylation Sites: S140, S205, S308, S315, S496, S501, S600, T56, T252, T313, T339, T380, T439, T441, T470, T517, T547, T552, Y10, Y379, Y590 | MOTIFS |
| | | | Potential Glycosylation Sites: N306, N437, N514 | MOTIFS |
| | | | Leucine zipper pattern: L117-L138 | MOTIFS |
| | | | Protein kinases ATP-binding region signature: I17-K40 | MOTIFS |
| 15 | 7518685CD1 | 750 | Protein-tyrosine phosphatase: N54-E231 | HMMER_PFAM |
| | | | Protein tyrosine phosphatase, catalytic domain: E23-K234 | HMMER_SMART |
| | | | Protein tyrosine phosphatase, catalytic domain motif: T127-E231 | HMMER_SMART |
| | | | Tyrosine specific protein phosphatase and dual specificity protein phosphatase family IPB000387: I168-G178 | BLIMPS_BLOCKS |
| | | | Tyrosine specific protein phosphatases signature and profiles: P147-V239 | PROFILESCAN |
| | | | Protein tyrosine phosphatase signature PR00700: S83-I90, Y99-E119, R126-S143, P165-I183, F199-S214, L215-V225 | BLIMPS_PRINTS |
| | | | *Salmonella*/*Yersinia* modular tyrosine phosphatase signature PR01371: E124-D138, I166-T177 | BLIMPS_PRINTS |
| | | | HYDROLASE PHOSPHATASE PROTEIN PROTEIN TYROSINE PRECURSOR SIGNAL TYROSINE TRANSMEMBRANE GLYCOPROTEIN RECEPTOR PD000167: N54-E119 F131-E231 | BLAST_PRODOM |
| | | | HYDROLASE PHOSPHATASE PROTEIN PROTEIN TYROSINE TYROSINE PRECURSOR SIGNAL TRANSMEMBRANE GLYCOPROTEIN RECEPTOR PD000155: E124-Q236 | BLAST_PRODOM |
| | | | HEMATOPOIETIC CELL PROTEIN TYROSINE PHOSPHATASE 70ZPEP HYDROLASE PD143889: E223-I750 | BLAST_PRODOM |
| | | | HEMATOPOIETIC CELL PROTEIN TYROSINE PHOSPHATASE 70ZPEP HYDROLASE PD166993: M1-K53 | BLAST_PRODOM |
| | | | PROTEIN-TYROSINE-PHOSPHATASE DM00089\|P29352\|22-291: E22-L123 E124-R235 | BLAST_DOMO |
| | | | PROTEIN-TYROSINE-PHOSPHATASE DM00089\|I48666\|14-296: K21-L123 E124-Q236 | BLAST_DOMO |
| | | | PROTEIN-TYROSINE-PHOSPHATASE DM00089\|Q05209\|14-295: K21-L123 E124-R235 | BLAST_DOMO |
| | | | PROTEIN-TYROSINE-PHOSPHATASE DM00089\|S48748\|14-295: K21-L123 E124-R235 | BLAST_DOMO |
| | | | Potential Phosphorylation Sites: S16, S35, S69, S78, S121, S143, S245, S295, S305, S413, S436, S489, S619, S624, S667, S677, S694, S736, T20, T47, T77, T109, T210, T275, T287, T319, T337, T393, T595, T681, Y44, Y66 | MOTIFS |
| | | | Potential Glycosylation Sites: N198, N259, N327, N411, N441, N454, N534, N674, N721, N722 | MOTIFS |
| | | | Tyrosine specific protein phosphatases active site: I168-I180 | MOTIFS |

TABLE 3-continued

| SEQ ID NO: | Incyte Polypeptide ID | Amino Acid Residues | Signature Sequences, Domains and Motifs | Analytical Methods and Databases |
|---|---|---|---|---|
| 16 | 7520192CD1 | 206 | signal_cleavage: M1-A42 | SPSCAN |
| | | | FERM domain (Band 4.1 family): C31-H149 | HMMER_PFAM |
| | | | Band 4.1 homologues: Q25-H149 | HMMER_SMART |
| | | | Band 4.1 family IPB000299: E129-K172 | BLIMPS_BLOCKS |
| | | | Band 4.1 family domain signatures and profile: K89-E131 | PROFILESCAN |
| | | | Band 4.1 family domain signatures and profile: G124-K172 | PROFILESCAN |
| | | | Band 4.1 protein family signature PR00935: L62-L74, E129-G145 | BLIMPS_PRINTS |
| | | | PROTEIN CYTOSKELETON STRUCTURAL PHOSPHATASE HYDROLASE PROTEIN TYROSINE PHOSPHORYLATION MOESIN TYROSINE BAND PD000961: V30-R123 R123-F148 | BLAST_PRODOM |
| | | | PROTEIN CYTOSKELETON STRUCTURAL PROTEIN TYROSINE PHOSPHATASE HYDROLASE BAND ALTERNATIVE SPLICING PHOSPHORYLATION PD014063: H149-E202 | BLAST_PRODOM |
| | | | PROTEIN TYROSINE PHOSPHATASE MEG1 EC 3.1.3.48 PTPASE MEG1 MEG STRUCTURAL PROTEIN CYTOSKELETON HYDROLASE PD129232: M1-V30 | BLAST_PRODOM |
| | | | BAND 4 DM00609\|P29074\|19-463: E19-R123 F110-L203 | BLAST_DOMO |
| | | | BAND 4 DM00609\|P11171\|200-623: R24-R123 K116-R200 | BLAST_DOMO |
| | | | BAND 4 DM00609\|P11434\|183-612: R24-R123 K116-R200 | BLAST_DOMO |
| | | | BAND 4 DM00609\|P28191\|18-438: E28-R123 G124-E202 | BLAST_DOMO |
| | | | Potential Phosphorylation Sites: S99, S126, S155, S189, T2, T65, T137 | MOTIFS |
| | | | Band 4.1 family domain signature 1: W84-D113 | MOTIFS |
| 17 | 7520428CD1 | 733 | Signal Peptide: M31-A54 | HMMER |
| | | | signal_cleavage: M1-S68 | SPSCAN |
| | | | Protein kinase domain: F427-F700 | HMMER_PFAM |
| | | | Serine/Threonine protein kinases, catalytic domain: F427-F700 | HMMER_SMART |
| | | | Eukaryotic protein kinase IPB000719: H542-L557, Y617-G627 | BLIMPS_BLOCKS |
| | | | Protein kinases signatures and profile: F494-M574 | PROFILESCAN |
| | | | Tyrosine kinase catalytic domain signature PR00109: M504-K517, Y540-I558, V621-D643 | BLIMPS_PRINTS |
| | | | PROTEIN KINASE SERINE/THREONINE KIN4 MICROTUBULE ASSOCIATED TESTIS SPECIFIC TESTIS-SPECIFIC MAST205 PD041650: K236-D426 | BLAST_PRODOM |
| | | | MICROTUBULE ASSOCIATED TESTIS SPECIFIC SERINE/THREONINE PROTEIN KINASE 205 KD TESTIS-SPECIFIC SERINE/THREONINE PROTEIN KINASE MAST205 KINASE PD135564: C83-Y235 | BLAST_PRODOM |
| | | | PROTEIN KINASE DOMAIN DM08046\|P05986\|1-397: D183-P206 S423-K573 V600-E733 | BLAST_DOMO |
| | | | PROTEIN KINASE DOMAIN DM00004\|S42867\|75-498: I430-T581 H587-F728 | BLAST_DOMO |
| | | | PROTEIN KINASE DOMAIN DM00004\|S42864\|41-325: E428-K573 H587-T688 | BLAST_DOMO |
| | | | PROTEIN KINASE DOMAIN DM00004\|A54602\|455-712: T429-G687 | BLAST_DOMO |
| | | | Potential Phosphorylation Sites: S75, S82, S86, S115, S119, S145, S168, S196, S395, S418, S423, S448, S690, S721, S726, T181, T421, T429, T480, T496, T644, T674, T701, T730 | MOTIFS |
| | | | Leucine zipper pattern: L515-L536 | MOTIFS |
| | | | Serine/Threonine protein kinases active-site signature: I546-I558 | MOTIFS |
| 18 | 7522586CD1 | 114 | PITSLRE ALPHA ISOFORM PROTEIN KINASE PBETA22 CELL DIVISION CYCLE 2LIKE PD009467: M1-K108 | BLAST_PRODOM |
| | | | Potential Phosphorylation Sites: S7, S43, S47, S72, S92, T12, T61 | MOTIFS |
| 19 | 7524017CD1 | 612 | Kinase associated domain 1: S563-V612 | HMMER_PFAM |
| | | | Protein kinase domain: Y11-I224 | HMMER_PFAM |
| | | | Serine/Threonine protein kinases, catalytic domain: Y11-I224 | HMMER_SMART |
| | | | Receptor tyrosine kinase class V IPB001426: F74-K95, P96-K122, C129-Y161 | BLIMPS_BLOCKS |
| | | | Phorbol esters/diacylglycerol binding domain IPB002219: T16-K26, V84-D93, C130-E139 | BLIMPS_BLOCKS |
| | | | Tyrosine kinase catalytic domain signature PR00109: L47-I60, Y83-F101, A151-D173, L193-M215 | BLIMPS_PRINTS |
| | | | KINASE PROTEIN KIAA0175 PK38 MATERNAL EMBRYONIC LEUCINE ZIPPER SERINE/THREONINE P69EG3 PD017644: I224-V612 | BLAST_PRODOM |
| | | | PROTEIN KINASE DOMAIN DM00004\|S52244\|15-255: L13-G48 L47-M215 | BLAST_DOMO |
| | | | PROTEIN KINASE DOMAIN DM00004\|P06782\|57-296: E15-L47 G52-M215 | BLAST_DOMO |
| | | | PROTEIN KINASE DOMAIN DM00004\|P54645\|17-258: L13-L47 Y49-M215 | BLAST_DOMO |
| | | | PROTEIN KINASE DOMAIN DM00004\|S24578\|18-262: L13-L47 Y49-M215 | BLAST_DOMO |
| | | | Potential Phosphorylation Sites: S66, S149, S214, S317, S324, S505, S510, S609, T261, T322, T348, T389, T448, T450, T479, T526, T556, T561, Y10, Y388, Y599 | MOTIFS |

TABLE 3-continued

| SEQ ID NO: | Incyte Polypeptide ID | Amino Acid Residues | Signature Sequences, Domains and Motifs | Analytical Methods and Databases |
|---|---|---|---|---|
| | | | Potential Glycosylation Sites: N315, N446, N523 | MOTIFS |
| | | | Leucine zipper pattern: L126-L147 | MOTIFS |
| | | | Prenyl group binding site (CAAX box): | MOTIFS |
| | | | Protein kinases ATP-binding region signature: I17-K40 | MOTIFS |
| | | | Serine/Threonine protein kinases active-site signature: Y89-F101 | MOTIFS |
| 20 | 7525773CD1 | 311 | GHMP kinases putative ATP-binding protein: V5-P311 | HMMER_PFAM |
| | | | mevalonate kinase: L7-S309 | HMMER_TIGRFAM |
| | | | GHMP kinases putative ATP-binding domain IPB001745: P11-H20, H276-C287 | BLIMPS_BLOCKS |
| | | | Mevalonate kinase signature PR00959: A10-N34, E141-G160, H276-K293 | BLIMPS_PRINTS |
| | | | KINASE ATP-BINDING TRANSFERASE GALACTOKINASE GALACTOSE METABOLISM MEVALONATE MK BIOSYNTHESIS PROTEIN PD002375: I144-L292 | BLAST_PRODOM |
| | | | MEVALONATE KINASE TRANSFERASE ATP-BINDING MK BIOSYNTHESIS STEROL PROTEIN CHOLESTEROL MVK PD007691: L6-I58 | BLAST_PRODOM |
| | | | MEVALONATE KINASE MK TRANSFERASE CHOLESTEROL BIOSYNTHESIS ATP-BINDING DISEASE MUTATION PD013931: K59-R124 | BLAST_PRODOM |
| | | | GHMP KINASES PUTATIVE ATP-BINDING DOMAIN DM02935\|Q03426\|1-379: M1-R124 R124-I296 | BLAST_DOMO |
| | | | GHMP KINASES PUTATIVE ATP-BINDING DOMAIN DM02935\|S42226\|162-540: M1-R124 R124-I296 | BLAST_DOMO |
| | | | GHMP KINASES PUTATIVE ATP-BINDING DOMAIN DM02935\|P46086\|1-376: A10-I119 A95-G295 | BLAST_DOMO |
| | | | GHMP KINASES PUTATIVE ATP-BINDING DOMAIN DM02935\|Q09780\|1-373: L2-I119 L130-P294 | BLAST_DOMO |
| | | | Potential Phosphorylation Sites: S73, S149, S171, S302, T104, T126, T214 | MOTIFS |
| 21 | 7525861CD1 | 206 | Protein tyrosine phosphatase signature PR00700: F165-G180, M181-C191 | BLIMPS_PRINTS |
| | | | PROTEIN TYROSINE PHOSPHATASE, NON-RECEPTOR TYPE 20 EC 3.1.3.48 PHOSPHO-TYROSINE PHOSPHATASE PTPASE HYDROLASE PD097276: M1-M164 | BLAST_PRODOM |
| | | | Potential Phosphorylation Sites: S3, S20, S34, S51, S57, S76, S95, S96, S120, T39, T84, T115 | MOTIFS |
| | | | Potential Glycosylation Sites: N18 | MOTIFS |
| 22 | 2509577CD1 | 1125 | Armadillo/beta-catenin-like repeat: V198-E238, S239-A279, E280-E320, N401-S448 | HMMER_PFAM |
| | | | Protein kinase domain: Y519-I783 | HMMER_PFAM |
| | | | Armadillo/beta-catenin-like repeats: A197-E238, C278-E320, N401-S448 | HMMER_SMART |
| | | | Serine/Threonine protein kinases, catalyti: Y519-L791 | HMMER_SMART |
| | | | Tyrosine kinase, catalytic domain: Y519-I783 | HMMER_SMART |
| | | | Receptor tyrosine kinase class II IPB002011: I578-K622, I651-K702, L735-V779 | BLIMPS_BLOCKS |
| | | | Protein kinases signatures and profile: R630-S684 | PROFILESCAN |
| | | | Tyrosine kinase catalytic domain signature PR00109: L645-L663, A710-T732, Y754-I776 | BLIMPS_PRINTS |
| | | | SERINE/THREONINE PROTEIN KINASE D1044.3 IN CHROMOSOME III EC 2.7.1. D775-Q813 C319-G517 | BLAST_PRODOM |
| | | | PROTEIN TRANSFERASE ATP-BINDING EGF-LIKE DOMAIN PD140750: E108-I334 | |
| | | | PROTEIN KINASE DOMAIN DM00004 \|P11837\|13-285: I521-H646 I651-D775 \|P41951\|433-687: I521-I776 \|P51954\|6-248: L522-I776 \|P51955\|10-261: I521-I776 | BLAST_DOMO |
| | | | Potential Phosphorylation Sites: S40, S235, S266, S376, S479, S540, S567, S618, S696, S755, S852 S900, S935, S974, S1039, S1068, S1108, T11, T15, T22, T58, T270, T324, T593, T670, T812, T898, T1077, T1092, T1123, Y746 | MOTIFS |
| | | | Potential Glycosylation Sites: N86, N96, N187, N401, N793, N911, N1105 | MOTIFS |
| | | | Protein kinases ATP-binding region signature: L525-K548 | MOTIFS |
| | | | Tyrosine protein kinases specific active-site signature: I651-L663 | MOTIFS |
| 23 | 7505222CD1 | 888 | Protein kinase domain: Y61-L316 | HMMER_PFAM |
| | | | Serine/Threonine protein kinases, catalyti: Y61-L316 | HMMER_SMART |
| | | | Tyrosine kinase, catalytic domain: Y61-L316 | HMMER_SMART |
| | | | Receptor tyrosine kinase class III IPB001824: M97-R151, Q161-A200, A218-P260 | BLIMPS_BLOCKS |
| | | | Protein kinases signatures and profile: Q161-S214 | PROFILESCAN |
| | | | Tyrosine kinase catalytic domain signature PR00109: M137-N150, H175-L193, T242-N264, F285-I307 | BLIMPS_PRINTS |
| | | | PROTEIN KINASE DOMAIN DM00004 \|P51954\|6-248: I64-I307 \|P51955\|10-261: V63-I307 \|P51957\|8-251: I64-I307 \|Q08942\|22-269: I67-I307 | BLAST_DOMO |
| | | | Potential Phosphorylation Sites: S53, S105, S126, S300, S399, S487, S501, S556, S574, S754, S781, S794, S804, S838, T32, T256, T442, T640, T660, T711, T763, T799, T821, T834, T865, T873, Y474, Y605 | MOTIFS |
| | | | Potential Glycosylation Sites: N212, N240, N636, N861 | MOTIFS |
| | | | Protein kinases ATP-binding region signature: I67-K90 | MOTIFS |
| | | | Serine/Threonine protein kinases active-site signature: I181-L193 | MOTIFS |

TABLE 3-continued

| SEQ ID NO: | Incyte Polypeptide ID | Amino Acid Residues | Signature Sequences, Domains and Motifs | Analytical Methods and Databases |
|---|---|---|---|---|
| 24 | 7524408CD1 | 487 | GDA1/CD39 (nucleoside phosphatase) family: T80-K487 | HMMER_PFAM |
| | | | Cytosolic domain: M1-I34<br>Transmembrane domain: M35-I54<br>Non-cytosolic domain: R55-K487 | TMHMMER |
| | | | GDA1/CD39 family of nucleoside phosphatase IPB000407: I91-Y105, P173-R183, I217-E238, G268-Y281 | BLIMPS_BLOCKS |
| | | | HYDROLASE TRANSMEMBRANE PROTEIN NUCLEOSIDE CD39 NUCLEOSIDE-TRIPHOSPHATASE TRIPHOSPHATE NTP-ASE PRECURSOR ATP-DIPHOSPHOHYDROLASE PD003822: N86-K487 I91-Y105 | BLAST_PRODOM |
| | | | GUANOSINE DIPHOSPHATASE-LIKE PROTEIN KIAA0392 PD070805: M1-P85 | BLAST_PRODOM |
| | | | ACTIVATION; NUCLEOSIDE; ANTIGEN; LYMPHOID; DM02628<br>\|I56242\|40-471: N86-S291 K264-F472<br>\|P49961\|40-471: N86-S291 K264-F472<br>\|P32621\|84-517: Y89-G235 T266-Y435<br>\|P40009\|1-462: N84-S479 | BLAST_DOMO |
| | | | Potential Phosphorylation Sites: S212, S218, S292, S479, T75, T144, T266, Y175, Y477 | MOTIFS |
| | | | Potential Glycosylation Sites: N404, N407 | MOTIFS |
| 25 | 7526163CD1 | 1309 | PDZ domain (Also known as DHR or GLGF): P950-L1037 | HMMER_PFAM |
| | | | Protein kinase domain: F367-F640 | HMMER_PFAM |
| | | | Domain present in PSD-95, Dlg, and ZO-1/2: K958-E1038 | HMMER_SMART |
| | | | Extension to Ser/Thr-type protein kinases: L641-F704 | HMMER_SMART |
| | | | Serine/Threonine protein kinases, catalyt: F367-F640 | HMMER_SMART |
| | | | Eukaryotic protein kinase IPB000719: H482-L497, Y557-G567 | BLIMPS_BLOCKS |
| | | | Tyrosine kinase catalytic domain signature PR00109: M444-K457, Y480-I498, V561-D583 | BLIMPS_PRINTS |
| | | | PROTEIN KINASE SERINE/THREONINE KIN4 MICROTUBULE ASSOCIATED TESTIS SPECIFIC TESTIS SPECIFIC MAST205 PD041650: R177-D366 | BLAST_PRODOM |
| | | | MICROTUBULE ASSOCIATED TESTIS SPECIFIC SERINE/THREONINE PROTEIN KINASE 205 KD TESTIS SPECIFIC SERINE/THREONINE PROTEIN KINASE MAST205 KINASE PD069998: T1034-D1128 | BLAST_PRODOM |
| | | | MICROTUBULE ASSOCIATED TESTIS SPECIFIC SERINE/THREONINE PROTEIN KINASE 205 KD TESTIS SPECIFIC SERINE/THREONINE PROTEIN KINASE MAST205 KINASE PD135564: G11-Y176 | BLAST_PRODOM |
| | | | MICROTUBULE ASSOCIATED TESTIS SPECIFIC SERINE/THREONINE PROTEIN KINASE 205 KD TESTIS SPECIFIC SERINE/THREONINE PROTEIN KINASE MAST205 KINASE PD182663: T719-W984 | BLAST_PRODOM |
| | | | PROTEIN KINASE DOMAIN<br>DM00004<br>\|S42867\|75-498: I370-K513 H527-F668 A1135-A1148<br>\|A54602\|455-712: T369-G627 | BLAST_DOMO |
| | | | PROTEIN KINASE DOMAIN<br>DM08046<br>\|P05986\|1-397: S365-K513 V540-E684<br>\|P06244\|1-396: D366-K513 V540-E684 | BLAST_DOMO |
| | | | Potential Phosphorylation Sites: S57, S61, S85, S108, S146, S257, S336, S358, S365, S621, S666, S672, S680, S690, S701, S709, S726, S738, S747, S767, S792, S793, S921, S930, S946, S956, S963, S985, S1031, S1041, S1060, S1063, S1074, S1080, S1101, S1180, S1273, S1215, S1257, S1262, T1068, T1181, T121, T420, T584, T670, T685, T721, T907, T1035, T1036, T235, T369, T436, T854, T1088, T1175, T1036 | MOTIFS |
| | | | Potential Glycosylation Sites: N64, N1039 | MOTIFS |
| | | | Serine/Threonine protein kinases active-site signature: I486-I498 | MOTIFS |
| 26 | 7526158CD1 | 1331 | PDZ domain (Also known as DHR or GLGF): P972-L1059 | HMMER_PFAM |
| | | | Protein kinase domain: F389-F662 | HMMER_PFAM |
| | | | Domain present in PSD-95, Dlg, and ZO-1/2: K980-E1060 | HMMER_SMART |
| | | | Serine/Threonine protein kinases, catalyt: F389-F662 | HMMER_SMART |
| | | | Eukaryotic protein kinase IPB000719: H504-L519, Y579-G589 | BLIMPS_BLOCKS |
| | | | Tyrosine kinase catalytic domain signature PR00109: M466-K479, Y502-I520, V583-D605 | BLIMPS_PRINTS |
| | | | PROTEIN KINASE SERINE/THREONINE KIN4 MICROTUBULE ASSOCIATED TESTIS SPECIFIC TESTIS SPECIFIC MAST205 PD041650: R199-D388 | BLAST_PRODOM |
| | | | MICROTUBULE ASSOCIATED TESTIS SPECIFIC SERINE/THREONINE PROTEIN KINASE 205 KD TESTIS SPECIFIC SERINE/THREONINE PROTEIN KINASE MAST205 KINASE PD069998: T1056-D1150 | BLAST_PRODOM |
| | | | MICROTUBULE ASSOCIATED TESTIS SPECIFIC SERINE/THREONINE PROTEIN KINASE 205 KD TESTIS SPECIFIC SERINE/THREONINE PROTEIN KINASE MAST205 KINASE PD135564: C47-Y198 | BLAST_PRODOM |
| | | | MICROTUBULE ASSOCIATED TESTIS SPECIFIC SERINE/THREONINE PROTEIN KINASE 205 KD TESTIS SPECIFIC SERINE/THREONINE PROTEIN KINASE MAST205 KINASE PD182663: T741-W1006 | BLAST_PRODOM |
| | | | PROTEIN KINASE DOMAIN<br>DM00004<br>\|S42867\|75-498: I392-K535 H549-F690 A1157-A1170<br>\|A54602\|455-712: T391-G649 | BLAST_DOMO |
| | | | PROTEIN KINASE DOMAIN DM08046<br>\|P05986\|1-397: S387-K535 V562-E706<br>\|P06244\|1-396: D388-K535 V562-E706 | BLAST_DOMO |

TABLE 3-continued

| SEQ ID NO: | Incyte Polypeptide ID | Amino Acid Residues | Signature Sequences, Domains and Motifs | Analytical Methods and Databases |
|---|---|---|---|---|
| | | | Potential Phosphorylation Sites: S3, S46, S79, S83, S107, S130, S168, S279, S358, S380, S387, S643, S688, S694, S702, S712, S723, S731, S748, S760, S769, S789, S814, S815, S943, S952, S968, S978, S985, S1007, S1053, S1063, S1082, S1085, S1096, S1102, S1123, S1202, S1284, S1295, S1237, S1279, S1284, T1090, T1203, T143, T442, T606, T692, T707, T743, T929, T1057, T1328, T257, T391, T458, T876, T1110, T1197, T1328 | MOTIFS |
| | | | Serine/Threonine protein kinases active-site signature: I508-I520 | MOTIFS |
| 27 | 7519807CD1 | 80 | MAM domain IPB000998: C54-V66 | BLIMPS_BLOCKS |
| | | | MAM domain signature PR00020: G52-K70 | BLIMPS_PRINTS |
| | | | Potential Phosphorylation Sites: T27, T34 | MOTIFS |
| 28 | 7526180CD1 | 495 | ACIDIC SERINE CLUSTER REPEAT DM03496\|P32583\|57-405: S261-D495 | BLAST_DOMO |
| | | | Potential Phosphorylation Sites: S141, S217, S239, S294, S296, S359, S430, S442, S451, S466, S476, T194, T196, T241, T251, T342, T375, T392, T412, T417 | MOTIFS |
| | | | Potential Glycosylation Sites: N192, N220, N289, N465 | MOTIFS |
| 29 | 7526185CD1 | 157 | Serine/Threonine protein kinases, catalytic domain: F24-Y157 | HMMER_SMART |
| | | | KINASE PROTEIN DOMAIN TRANSFERASE PD00584: L27-G36 | BLIMPS_PRODOM |
| | | | PROTEIN KINASE DOMAIN<br>DM00004\|A53714\|17-262: L27-V151<br>DM00004\|I49376\|270-509: K26-G153<br>DM00004\|P08458\|20-262: I30-V151<br>DM00004\|P38692\|24-266: K26-V151 | BLAST_DOMO |
| | | | Potential Phosphorylation Sites: S34, S75, S106, S137, T25, T46 | MOTIFS |
| | | | Potential Glycosylation Sites: N44 | MOTIFS |
| | | | Protein kinases ATP-binding region signature: I30-K53 | MOTIFS |
| 30 | 7526192CD1 | 305 | Protein kinase domain: F46-G305 | HMMER_PFAM |
| | | | Serine/Threonine protein kinases, catalytic domain: F46-G305 | HMMER_SMART |
| | | | Eukaryotic protein kinase IPB000719: H189-L204 | BLIMPS_BLOCKS |
| | | | Protein kinases signatures and profile: T173-P230 | PROFILESCAN |
| | | | CASEIN KINASE I GAMMA ISOFORM CKIGAMMA TRANSFERASE SERINE/THREONINEPROTEIN ATPBINDING MULTIGENE PD026544: M1-N45 | BLAST_PRODOM |
| | | | PROTEIN KINASE DOMAIN<br>DM00004\|B56711\|48-303: V48-L76 E109-R302<br>DM00004\|A56711\|46-303: V48-L76 E109-R302<br>DM00004\|C56711\|45-301: V48-L76 E109-R302<br>DM00004\|D56406\|31-276: V48-L76 E109-R302 | BLAST_DOMO |
| | | | Potential Phosphorylation Sites: S19, S99, S129, S262, T84, T183, T210, T232, T247 | MOTIFS |
| | | | Protein kinases ATP-binding region signature: I52-K75 | MOTIFS |
| | | | Serine/Threonine protein kinases active-site signature: L193-V205 | MOTIFS |
| 31 | 7526193CD1 | 930 | Signal_cleavage: M1-G68 | SPSCAN |
| | | | Protein kinase domain: V46-F310 | HMMER_PFAM |
| | | | Serine/Threonine protein kinases, catalytic domain: V46-K313 | HMMER_SMART |
| | | | Eukaryotic protein kinase IPB000719: C168-L183, I239-G249 | BLIMPS_BLOCKS |
| | | | PROTEIN REPEAT SIGNAL PRECURSOR PRION GLYCOPROTEIN NUCLEAR GPIANCHOR BRAIN MAJOR PD001091: G373-P626, G404-P626, P358-Q601, P349-Q574, P320-S519, P296-Q541 | BLAST_PRODOM |
| | | | PROTEIN KINASE DOMAIN<br>DM00004\|P38080\|36-309: L52-I304<br>DM00004\|P40494\|23-287: L52-I304<br>DM00004\|P51954\|6-248: L52-I304<br>DM00004\|P53974\|23-288: L52-I304 | BLAST_DOMO |
| | | | Potential Phosphorylation Sites: S7, S115, S224, S235, S311, S625, S679, S785, S815, S822, S833, S871, S879, T47, T147, T199, T221, T240, T241, T275, T389, T395, T628, T708, T743, T757, T829 | MOTIFS |
| | | | Potential Glycosylation Sites: N113, N273, N667, N703, N823, N905 | MOTIFS |
| | | | Serine/Threonine protein kinases active-site signature: I172-L184 | MOTIFS |
| 32 | 7526196CD1 | 118 | Signal Peptide: M1-G22 | HMMER |
| | | | Signal_cleavage: M1-G22 | SPSCAN |
| | | | Serine/threonine dehydratase pyridoxal-phosphate attachment site IPB000634: E95-S104 | BLIMPS_BLOCKS |
| | | | CYCLIN G-ASSOCIATED KINASE TRANSFERASE SERINE/THREONINEPROTEIN ATPBINDING HSGAK PD026473: M1-L40 | BLAST_PRODOM |
| | | | Potential Phosphorylation Sites: S6, S21, S62, S73, S92, S113 | MOTIFS |
| 33 | 7526198CD1 | 1355 | Protein kinase domain: L40-E315 | HMMER_PFAM |
| | | | DnaJ molecular chaperone homology domain: E1290-S1351 | HMMER_SMART |
| | | | Serine/Threonine protein kinases, catalytic domain: L40-A317 | HMMER_SMART |
| | | | Eukaryotic protein kinase IPB000719: Q165-L180, I240-G250 | BLIMPS_BLOCKS |
| | | | Protein kinases signatures and profile: V148-H200 | PROFILESCAN |
| | | | CYCLIN G-ASSOCIATED KINASE TRANSFERASE SERINE/THREONINEPROTEIN ATPBINDING HSGAK PD039449: A317-N402 | BLAST_PRODOM |
| | | | PROTEIN AUXILIN COAT REPEAT PHOSPHORYLATION KIAA0473 CYCLIN G-ASSOCIATED KINASE TRANSFERASE<br>PD010124: Q1215-Q1349<br>PD025411: S456-V640<br>PD151518: L641-L1093, P868-S1235, R320-E366 | BLAST_PRODOM |

TABLE 3-continued

| SEQ ID NO: | Incyte Polypeptide ID | Amino Acid Residues | Signature Sequences, Domains and Motifs | Analytical Methods and Databases |
|---|---|---|---|---|
| | | | PROTEIN KINASE DOMAIN<br>DM00004\|P38080\|36-309: L46-I306<br>DM00004\|P40494\|23-287: R41-I306<br>DM00004\|P53974\|23-288: R44-I306<br>DM00004\|Q09170\|169-423: R44-S305 | BLAST_DOMO |
| | | | Potential Phosphorylation Sites: S6, S21, S62, S73, S93, S305, S393, S456, S530, S540, S551, S661, S726, S737, S738, S784, S811, S906, S976, S1029, S1103, S1113, S1220, S1234, S1235, S1237, S1344, T155, T186, T382, T414, T459, T611, T680, T776, T805, T949, T1118, T1156, T1165, T1244, Y412 | MOTIFS |
| | | | Potential Glycosylation Sites: N677, N724, N809, N970, N1196 | MOTIFS |
| | | | Serine/Threonine protein kinases active-site signature: I169-L181 | MOTIFS |
| 34 | 7526208CD1 | 490 | Protein kinase domain: Y14-I252 | HMMER_PFAM |
| | | | Serine/Threonine protein kinases, catalytic domain: Y14-I252 | HMMER_SMART |
| | | | Eukaryotic protein kinase IPB000719: H108-L123, Y171-G181 | BLIMPS_BLOCKS |
| | | | Protein kinases signatures and profile: F65-D147 | PROFILESCAN |
| | | | Tyrosine kinase catalytic domain signature PR00109: H106-L124, V175-E197, V221-A243 | BLIMPS_PRINTS |
| | | | KINASE PROTEIN II CALCIUM/CALMODULIN-DEPENDENT TYPE SUBUNIT CALMODULINBINDING CHAIN TRANSFERASE SERINE/THREONINEPROTEIN PD001779: I252-K303 S312-V380 | BLAST_PRODOM |
| | | | KINASE PROTEIN II CALCIUM/CALMODULIN-DEPENDENT TYPE SUBUNIT CHAIN TRANSFERASE SERINE/THREONINEPROTEIN CALMODULINBINDING PD004250: E381-K469 | BLAST_PRODOM |
| | | | PROTEIN KINASE DOMAIN<br>DM00004\|JU0270\|16-262: E18-R53 V54-A243<br>DM00004\|A44412\|16-262: E18-R53 V54-A243<br>DM00004\|P11798\|15-261: E39-A243, L16-E63 | BLAST_DOMO |
| | | | KINASE; DEPENDENT; II; CALMODULIN;<br>DM05068\|P11798\|263-426: S244-A418 | BLAST_DOMO |
| | | | Potential Phosphorylation Sites: S51, S59, S89, S312, S313, S397, T36, T47, T74, T242, T327, T328, T369 | MOTIFS |
| | | | Potential Glycosylation Sites: N293, N326, N479 | MOTIFS |
| | | | Protein kinases ATP-binding region signature: L20-K43 | MOTIFS |
| | | | Serine/Threonine protein kinases active-site signature: V112-L124 | MOTIFS |
| 35 | 7526212CD1 | 344 | Protein kinase domain: Y14-I252 | HMMER_PFAM |
| | | | Serine/Threonine protein kinases, catalytic domain: Y14-I252 | HMMER_SMART |
| | | | Eukaryotic protein kinase IPB000719: H108-L123, Y171-G181 | BLIMPS_BLOCKS |
| | | | Protein kinases signatures and profile: F65-D147 | PROFILESCAN |
| | | | Tyrosine kinase catalytic domain signature PR00109: H106-L124, V175-E197, V221-A243 | BLIMPS_PRINTS |
| | | | KINASE PROTEIN II CALCIUM/CALMODULIN-DEPENDENT TYPE SUBUNIT CALMODULINBINDING CHAIN TRANSFERASE SERINE/THREONINEPROTEIN PD001779: I252-K324 | BLAST_PRODOM |
| | | | PROTEIN KINASE DOMAIN<br>DM00004\|JU0270\|16-262: E18-R53 V54-A243<br>DM00004\|A44412\|16-262: E18-R53 V54-A243<br>DM00004\|P08414\|44-285: E19-T242<br>DM00004\|P11798\|15-261: E39-A243, L16-E63 | BLAST_DOMO |
| | | | Potential Phosphorylation Sites: S51, S59, S89, T36, T47, T74, T242, T316, T317 | MOTIFS |
| | | | Potential Glycosylation Sites: N293, N315 | MOTIFS |
| | | | Protein kinases ATP-binding region signature: L20-K43 | MOTIFS |
| | | | Serine/Threonine protein kinases active-site signature: V112-L124 | MOTIFS |
| 36 | 7526213CD1 | 89 | Potential Phosphorylation Sites: S5, S56, S80, T52 | MOTIFS |
| | | | Hexokinase family IPB001312: S10-G24 | BLIMPS_BLOCKS |
| 37 | 7526214CD1 | 88 | Potential Phosphorylation Sites: S5, S56, S67, T52 | MOTIFS |
| | | | Hexokinase family IPB001312: S10-G24 | BLIMPS_BLOCKS |
| 38 | 7526228CD1 | 137 | Signal_cleavage: M1-A15 | SPSCAN |
| | | | PROTEIN KINASE DOMAIN<br>DM00004\|I38044\|100-349: V38-A117<br>DM00004\|P08630\|329-573: E35-N114<br>DM00004\|Q08881\|361-604: E35-L112 | BLAST_DOMO |
| | | | Potential Phosphorylation Sites: S14, S67, S69 | MOTIFS |
| | | | Leucine zipper pattern: L112-L133 | MOTIFS |
| | | | Protein kinases ATP-binding region signature: V42-K63 | MOTIFS |
| 39 | 7526246CD1 | 243 | Regulator of G protein signaling domain: T54-C175 | HMMER_PFAM |
| | | | Regulator of G protein signalling domain: T54-C175 | HMMER_SMART |
| | | | GPCR kinase signature PR00717: F171-N183 | BLIMPS_PRINTS |
| | | | Regulator of G protein signalling domain proteins PF00615: M15-K21, F162-K178 | BLIMPS_PFAM |
| | | | RECEPTOR KINASE TRANSFERASE SERINE/THREONINEPROTEIN ATPBINDING BETAADRENERGIC COUPLED PROTEIN MULTIGENE FAMILY PD007430: M1-V53 | BLAST_PRODOM |
| | | | KINASE; THREONINE; ATP; SERINE;<br>DM01747\|P21146\|152-191: E152-S187 | BLAST_DOMO |
| | | | N-TERMINAL DOMAIN<br>DM05135\|P21146\|33-150: L33-E151<br>DM05135\|P32865\|33-150: L34-E151<br>DM05135\|Q09639\|34-149: L34-I150 | BLAST_DOMO |
| | | | Potential Phosphorylation Sites: S29, S38, S60, S127, S168, T97 | MOTIFS |
| | | | Cell attachment sequence: R158-D160 | MOTIFS |

TABLE 3-continued

| SEQ ID NO: | Incyte Polypeptide ID | Amino Acid Residues | Signature Sequences, Domains and Motifs | Analytical Methods and Databases |
|---|---|---|---|---|
| 40 | 7526258CD1 | 463 | CELL CYCLE PROGRESSION PROTEIN FAST KINASE PD041692: L200-P417 | BLAST_PRODOM |
| | | | FAST KINASE PD135789: M1-R201 | BLAST_PRODOM |
| | | | Potential Phosphorylation Sites: S94, S246, S332, S373, S441, T138, T336, T365 | MOTIFS |
| 41 | 7526311CD1 | 184 | Signal Peptide: M1-G18, M1-A21 | HMMER |
| | | | Signal_cleavage: M1-A21 | SPSCAN |
| | | | Cytosolic domain: K163-T184<br>Transmembrane domain: W143-W162<br>Non-cytosolic domain: M1-T142 | TMHMMER |
| | | | KINASE DEHYDROGENASE TRANSFERASE PD01976: P54-G66, N69-S117 | BLIMPS_PRODOM |
| | | | KINASE PYRUVATE DEHYDROGENASE TRANSFERASE DEHYDROGENASE-LIPOAMIDE MITOCHONDRIAL PRECURSOR TRANSIT PEPTIDE MITOCHONDRION PD004994: V42-I135 | BLAST_PRODOM |
| | | | PYRUVATE DEHYDROGENASE-LIPOAMIDE KINASE ISOZYME 1, MITOCHONDRIAL PRECURSOR EC 2.7.1.99 DEHYDROGENASE ISOFORM 1 TRANSFERASE TRANSIT PEPTIDE MITOCHONDRION MULTIGENE FAMILY PD174825: M1-E39 | BLAST_PRODOM |
| | | | KINASE; DEHYDROGENASE; PYRUVATE; ACID;<br>DM01978\|A55305\|2-103: A37-E130<br>DM01978\|I55465\|28-129: F28-E130<br>DM01978\|I70159\|2-103: A37-E130<br>DM01978\|I70160\|1-99: V42-E130 | BLAST_DOMO |
| | | | Potential Phosphorylation Sites: S38, S58, S117, S128, S170 | MOTIFS |
| 42 | 7526315CD1 | 386 | Protein kinase domain: L16-V266 | HMMER_PFAM |
| | | | Serine/Threonine protein kinases, catalytic domain: L16-L262 | HMMER_SMART |
| | | | Protein kinases signatures and profile: I107-T161 | PROFILESCAN |
| | | | PROTEIN KINASE DOMAIN<br>DM00004\|A53800\|119-368: E20-K221<br>DM00004\|A55318\|159-389: D15-W216<br>DM00004\|JC2363\|126-356: D15-W216<br>DM00004\|Q05609\|553-797: E20-S233 | BLAST_DOMO |
| | | | Potential Phosphorylation Sites: S61, S89, S96, S233, S273, S277, S295, S341, S346, S360, S365, T345, Y274 | MOTIFS |
| | | | Potential Glycosylation Sites: N97, N159, N340 | MOTIFS |
| | | | Leucine zipper pattern: L225-L246, L232-L253 | MOTIFS |
| | | | Serine/Threonine protein kinases active-site signature: V129-I141 | MOTIFS |
| 43 | 7526442CD1 | 152 | Eukaryotic protein kinase IPB000719: H119-Q134 | BLIMPS_BLOCKS |
| | | | PROTEIN KINASE DOMAIN<br>DM00004\|I49592\|6-276: L7-R131<br>DM00004\|P23437\|6-286: R9-R131<br>DM00004\|P29620\|21-289: I10-P130<br>DM00004\|Q02399\|6-276: L7-R131 | BLAST_DOMO |
| | | | Protein kinases ATP-binding region signature: I10-K33 | MOTIFS |

TABLE 4

| Polynucleotide SEQ ID NO:/ Incyte ID/Sequence Length | Sequence Fragments |
|---|---|
| 44/7517831CB1/ 1916 | 1-937, 1-1916, 479-1163, 762-1440, 765-1648, 1025-1916 |
| 45/7520272CB1/ 926 | 1-584, 1-755, 1-764, 2-925, 149-926, 218-926 |
| 46/7521279CB1/ 1382 | 1-828, 530-1382, 591-1382, 635-1382, 989-1382 |
| 47/7523965CB1/ 1678 | 1-665, 1-876, 2-1677, 158-1087, 167-1047, 293-1057, 736-1536, 744-1267, 744-1526, 744-1593, 978-1678 |
| 48/7524016CB1/ 895 | 1-855, 2-812, 539-895 |
| 49/7524680CB1/ 1294 | 1-819, 2-764, 510-1294 |
| 50/7524757CB1/ 1354 | 1-647, 1-710, 2-677, 573-1354 |
| 51/7516229CB1/ 1204 | 1-726, 1-1179, 300-1179, 349-1204, 396-1180, 474-1201, 475-1201, 497-1201, 568-1201, 582-1201 |
| 52/7516525CB1/ 1859 | 1-425, 1-672, 1-701, 1-717, 1-935, 1-1859, 205-1118, 728-1623, 859-1858, 888-1859, 974-1859, 1050-1858, 1053-1859, 1092-1851, 1114-1859, 1130-1859, 1149-1859, 1167-1859, 1267-1858, 1289-1859 |
| 53/7516533CB1/ 1695 | 1-767, 1-1692, 28-1025, 694-1645, 844-1695 |

TABLE 4-continued

| Polynucleotide SEQ ID NO:/ Incyte ID/Sequence Length | Sequence Fragments |
|---|---|
| 54/7516613CB1/ 3891 | 1-176, 1-805, 1-914, 1-3891, 231-3891, 613-1352, 642-1329, 643-1438, 644-1447, 668-1289, 847-1618, 860-1623, 1380-2098, 1388-2109, 1541-1948, 1541-2000, 1558-1901, 1670-2559, 1872-2565, 1881-2589, 2304-3236, 2433-3222, 2438-3215, 2442-3223, 2470-3204, 2549-3214, 3007-3891, 3103-3891, 3270-3891, 3283-3891, 3337-3891 |
| 55/7517068CB1/ 3954 | 1-603, 1-778, 1-3954, 410-1315, 416-1127, 440-798, 1037-2445, 1132-2069, 1138-1925, 1623-2614, 1690-2567, 2379-3252, 2446-3954, 2613-3234, 3186-3954 |
| 56/7517148CB1/ 3357 | 1-655, 26-3357, 377-1295, 447-1269, 580-1302, 1190-1924, 1194-2055, 1230-1956, 1442-2298, 2241-2719, 2545-3357, 2678-3356 |
| 57/7517238CB1/ 2036 | 1-772, 1-2006, 418-1330, 573-1330, 732-1615, 746-1617, 1195-2029, 1199-2036, 1207-2029, 1268-2004, 1298-2036 |
| 58/7518685CB1/ 2541 | 1-645, 26-2541, 529-1345, 942-1833, 1752-2541, 1775-2541, 1950-2540 |
| 59/7520192CB1/ 2611 | 1-802, 1-803, 1-880, 1-2529, 208-1179, 464-1177, 707-1448, 732-1469, 1113-1952, 1143-1948, 1692-2582, 1781-2555, 1858-2611, 1916-2555, 2043-2555 |
| 60/7520428CB1/ 5216 | 1-781, 1-830, 2-5215, 44-5215, 190-723, 397-1135, 414-1120, 708-1383, 741-1569, 757-1546, 757-1606, 1186-2040, 1191-2029, 1556-2392, 1561-2342, 1967-2655, 2006-2059, 2120-2780, 2380-3164, 2407-3194, 2769-3419, 2771-3450, 3167-3823, 3193-3831, 3562-4286, 3565-4101, 3633-4506, 3770-4506, 3974-4724, 3975-4708, 4346-5082, 4352-4996, 4447-5215, 4448-5216, 4450-5216, 4457-5216, 4460-5216, 4478-5216, 4588-5216, 4771-5216, 4795-5216, 5125-5216, 5130-5216 |
| 61/7522586CB1/ 2554 | 1-817, 1-2554, 655-1515, 678-1376, 970-1849, 1110-1840, 1319-1729, 1462-2334, 1470-2177, 1470-2240, 1490-2270, 1765-2554 |
| 62/7524017CB1/ 2023 | 1-2022, 1035-1956, 1163-1951, 1175-2022, 1178-2023 |
| 63/7525773CB1/ 1129 | 1-847, 2-1128, 184-1129 |
| 64/7525861CB1/ 687 | 1-687, 2-686 |
| 65/2509577CB1/ 3912 | 1-3912, 692-1142, 692-1191, 692-1374, 692-1383, 692-1385, 991-1569, 1053-1112, 1118-1449, 1118-1619, 1118-1704, 1118-1717, 1118-1774, 1193-1462, 1193-1505, 1193-1625, 1193-1667, 1193-1687, 1193-1702, 1193-1716, 1193-1724, 1193-1735, 1202-1884, 1306-1624, 1308-1841, 1308-1866, 1308-1989, 1308-2001, 1308-2006, 1323-2016, 1333-1833, 1831-2300, 1831-2302, 1838-2524, 1911-2622, 1921-2796, 2158-2951, 2231-2430, 2266-2685, 2269-2951, 2359-2951, 2441-2632, 2441-2957, 2441-2965, 2466-3026, 2467-2943, 2475-3193, 2676-2925, 2969-3225 |
| 66/7505222CB1/ 3229 | 1-2813, 147-2813, 1800-2249, 1976-2224, 1976-2590, 2139-2331, 2290-2373, 2290-2484, 2290-2512, 2290-2573, 2290-2587, 2290-2592, 2290-2596, 2290-2601, 2290-2626, 2290-2636, 2290-2641, 2290-2669, 2290-2673, 2290-2702, 2290-2732, 2290-2755, 2290-2760, 2290-2770, 2290-2776, 2290-2783, 2290-2825, 2290-2861, 2290-2864, 2290-2871, 2290-2899, 2290-2981, 2295-2804, 2315-2833, 2427-3094, 2427-3215, 2465-3204, 2482-3211, 2495-2899, 2509-2900, 2536-3229, 2538-2900, 2575-2812, 2596-2819, 2649-3229 |
| 67/7524408CB1/ 2100 | 1-753, 1-877, 2-669, 2-676, 2-718, 2-2099, 529-1448, 548-1422, 631-1515, 640-1476, 1257-2100, 1319-2100, 1340-2099, 1345-2100, 1353-2099 |
| 68/7526163CB1/ 4213 | 1-718, 1-789, 11-4017, 14-590, 17-664, 17-674, 24-849, 79-221, 169-4213, 171-849, 241-929, 311-946, 380-828, 421-1058, 440-1069, 466-1171, 494-984, 494-1004, 494-1017, 494-1019, 494-1037, 494-1122, 494-1270, 494-1279, 509-1065, 541-1058, 559-1058, 654-1148, 674-1307, 676-1286, 722-874, 731-1267, 750-1460, 850-1386, 940-1516, 960-1765, 963-1639, 965-1553, 965-1590, 973-1633, 975-1571, 1023-1616, 1071-1647, 1079-1569, 1093-1716, 1101-1585, 1110-1658, 1110-1689, 1110-1725, 1117-1590, 1120-1788, 1127-1992, 1134-1635, 1135-1581, 1144-1648, 1145-1876, 1157-1598, 1161-1839, 1162-1772, 1196-1857, 1204-1762, 1207-1915, 1215-1877, 1262-1805, 1277-1775, 1280-1981, 1290-1915, 1298-1711, 1303-1964, 1349-1825, 1354-1973, 1367-2079, 1378-2014, 1384-2081, 1418-1946, 1422-1915, 1427-1948, 1431-1980, 1433-2054, 1440-2126, 1460-2112, 1488-1898, 1533-2187, 1544-2393, 1559-2390, 1570-2397, 1583-2386, 1608-2050, 1612-2210, 1639-2204, 1639-2221, 1639-2291, 1639-2342, 1641-2322, 1666-2393, 1676-2347, 1684-2366, 1692-2223, 1701-2393, 1704-2231, 1706-2320, 1706-2393, 1711-2531, 1724-2431, 1755-2310, 1760-2393, 1762-2192, 1763-2192, 1771-2398, 1793-2259, 1798-2393, 1809-2393, 1813-2393, 1816-2393, 1818-2333, 1820-2393, 1856-2393, 1858-2393, 1885-2393, 1897-2393, 1913-2393, 1915-2393, 1916-2393, 1936-2393, 1937-2393, 1980-2644, 1993-2393, 2005-2393, 2021-2484, 2029-2419, 2086-2393, 2148-2792, 2156-2180, 2276-3024, 2289-3020, 2314-3220, 2329-2786, 2329-2829, 2351-2940, 2363-3123, 2586-3050, 2602-3014, 2628-3274, 2696-3341, 2731-3244, 2840-3377, 2863-3679, 2945-3400, 3402-3605, 3428-3935, 3595-4034, 3627-4183, 3632-4061, 3638-4091, 3711-4185, 3720-4189, 3809-4191, 3809-4212, 3909-4160, 3909-4181, 4059-4213 |
| 69/7526158CB1/ 5991 | 1-882, 1-5991, 20-942, 36-335, 66-942, 99-314, 133-335, 175-942, 214-942, 241-334, 262-4306, 333-941, 333-942, 404-1039, 473-921, 473-932, 514-1151, 533-1162, 559-1264, 587-1077, 587-1097, 587-1110, 587-1112, 587-1130, 587-1215, 587-1363, 587-1372, 602-1158, 634-1151, 652-1151, 747-1241, 1068-1664, 1172-1662, 1186-1809, 1194-1678, 1213-1881, 1220-2085, 1238-1969, 1254-1932, 1297-1855, 1370-1868, 1373-2074, 1391-1804, 1442-1918, 1471-2107, 1477-2174, 1511-2039, 1515-2008, 1520-2041, 1524-2073, 1533-2219, 1553-2205, 1581-1991, 1626-2280, 1637-2486, 1652-2483, 1663-2490, 1676-2479, 1701-2143, 1705-2303, 1732-2297, 1732-2314, 1732-2384, 1732-2435, 1734-2415, 1759-2486, 1769-2440, 1777-2459, 1785-2316, 1794-2486, 1797-2324, 1799-2413, 1799-2486, 1804-2624, 1817-2524, 1848-2403, 1853-2486, 1864-2491, 1886-2352, 1891-2486, 1902-2486, 1906-2486, 1909-2486, 1913-2486, 1949-2486, 1951-2486, 1978-2486, 1990-2486, 2006-2486, 2008-2486, 2009-2486, 2029-2486, 2030-2486, 2073-2737, 2086-2486, 2098-2486, 2114-2577, 2122-2512, 2179-2486, 2241-2885, 2369-3117, 2382-3113, 2407-3313, 2422-2879, 2422-2922, 2444-3033, 2456-3216, 2679-3143, 2695-3107, 2721-3367, 2789-3434, 2824-3337, 2933-3470, 2956-3772, 3038-3493, 3495-3698, 3521-4028, 3720-4276, 3725-4154, 3731-4184, 3740-4127, 3804-4278, 3813-4282, 3902-4289, 3902-4305, 4002-4253, 4002-4274, 4152-4306, 4403-4463, 4537-4598 |
| 70/7519807CB1/ 669 | 1-669 |

TABLE 4-continued

| Polynucleotide SEQ ID NO:/ Incyte ID/Sequence Length | Sequence Fragments |
|---|---|
| 71/7526180CB1/ 2453 | 1-224, 1-361, 1-376, 1-409, 1-416, 1-432, 1-437, 1-443, 1-445, 1-455, 1-457, 1-483, 1-2049, 2-193, 2-424, 2-464, 2-504, 3-358, 3-419, 3-518, 4-190, 4-280, 7-860, 10-561, 10-579, 10-637, 14-445, 17-509, 34-331, 37-732, 37-762, 37-782, 37-784, 37-896, 39-695, 39-726, 39-758, 39-782, 39-814, 39-880, 40-808, 42-572, 53-804, 71-320, 71-699, 84-293, 85-614, 107-526, 120-572, 131-748, 141-420, 151-509, 154-525, 155-806, 182-475, 182-666, 186-525, 188-512, 188-525, 188-733, 203-504, 219-504, 219-525, 233-518, 233-630, 242-331, 248-699, 259-444, 260-614, 260-621, 260-653, 260-748, 260-749, 261-627, 273-840, 277-614, 353-568, 358-1005, 398-575, 401-1853, 426-650, 426-656, 426-800, 426-911, 426-1090, 432-1071, 434-690, 435-598, 439-1223, 444-693, 444-717, 444-767, 449-718, 451-637, 452-1071, 454-643, 454-1281, 454-1458, 459-1283, 463-981, 467-1018, 468-1168, 486-715, 493-699, 499-1095, 508-764, 508-1050, 511-1137, 527-778, 527-1031, 527-1032, 533-1049, 533-1171, 534-1033, 534-1049, 549-1095, 550-929, 575-1095, 580-1027, 593-1072, 595-767, 605-1031, 618-890, 618-1131, 620-798, 638-1335, 639-1032, 650-1105, 650-1133, 667-1200, 667-1207, 667-1227, 667-1251, 672-1176, 673-727, 678-1135, 679-975, 684-968, 711-1111, 718-1530, 724-1396, 724-1532, 724-1547, 726-1437, 738-1115, 739-1108, 739-1110, 747-1054, 749-1051, 749-1161, 752-1553, 774-1015, 774-1054, 790-1207, 792-1048, 792-1054, 792-1109, 792-1131, 792-1161, 792-1228, 792-1298, 793-1132, 801-1468, 817-1554, 838-1477, 842-1207, 843-1144, 849-1118, 854-1530, 865-1095, 885-1414, 889-1393, 903-1041, 903-1406, 905-1548, 907-1081, 920-1136, 932-1613, 939-1111, 939-1263, 945-1391, 950-1273, 973-1328, 1050-1429, 1060-1635, 1071-1147, 1076-1376, 1099-1558, 1120-1512, 1127-1259, 1147-1573, 1179-1878, 1194-1716, 1215-1622, 1222-1622, 1223-1478, 1241-1558, 1250-1739, 1259-2177, 1266-1671, 1271-1524, 1276-1544, 1284-1622, 1295-1554, 1299-1561, 1299-1573, 1325-1946, 1381-1619, 1381-1642, 1398-1601, 1398-1622, 1438-2095, 1443-1743, 1444-1558, 1453-1656, 1473-1704, 1484-1753, 1523-1573, 1531-1917, 1578-1763, 1578-1904, 1578-2059, 1578-2062, 1578-2063, 1578-2064, 1581-1999, 1581-2112, 1589-2045, 1594-1931, 1606-2042, 1616-2049, 1631-1867, 1672-2453, 1685-2408, 1697-2048, 1719-1980, 1742-2000, 1744-2112, 1784-2095, 1788-2408, 1796-2054, 1805-2095, 1817-2372, 1855-2408, 1869-2167, 1880-2071, 1880-2087, 1880-2091, 1880-2092, 1880-2097, 1880-2315, 1883-2353, 1905-2117, 1926-2141, 1941-2110, 1946-2054, 1951-2169, 1971-2408, 1971-2421, 1979-2408, 1980-2408, 1994-2408 |
| 72/7526185CB1/ 4430 | 1-4430, 313-1222, 358-592, 649-4430, 938-1574, 1084-1754, 1095-1765, 1185-1978, 1198-1884, 1204-1880, 1208-1859, 1214-2029, 1223-2017, 1255-1917, 1255-2004, 1259-1957, 1282-2255, 1298-1950, 1321-2017, 1335-2004, 1352-2002, 1354-2004, 1383-2002, 1396-2064, 1469-2171, 1503-2297, 1506-2183, 1515-2243, 1528-2457, 1546-2439, 1560-2428, 1560-2458, 1582-2282, 1582-2429, 1587-2305, 1599-2338, 1605-2350, 1625-2433, 1638-2413, 1640-2392, 1666-2445, 1693-2395, 1716-2469, 1718-2467, 1720-2469, 1724-2451, 1724-2463, 1724-2467, 1772-2468, 1775-2468, 1782-2468, 1782-2469, 1783-2431, 1786-2468, 1801-2467, 1809-2468, 1816-2469, 1829-2469, 1833-2469, 1852-2469, 1858-2469, 2196-2847, 2386-3249, 3402-4093, 3471-4274, 3698-4426 |
| 73/7526192CB1/ 3276 | 1-3276, 734-1407, 1223-1711, 1860-2512, 1860-2524, 1925-2468, 2447-3057, 2552-3009 |
| 74/7526193CB1/ 3910 | 1-344, 20-367, 20-3910, 99-612, 340-775, 464-775, 486-797, 500-746, 520-779, 537-799, 552-768, 560-779, 567-790, 582-1094, 587-1213, 610-895, 616-1173, 634-1307, 698-1094, 706-1162, 776-1097, 778-1097, 797-1101, 799-1093, 805-1348, 824-1456, 824-1504, 825-1466, 830-1503, 834-1412, 840-1124, 840-1426, 849-1097, 868-1096, 885-1348, 1048-1744, 1115-1714, 1124-1734, 1127-1742, 1146-1711, 1217-1481, 1222-1524, 1246-1525, 1249-1757, 1251-1509, 1295-1751, 1321-1832, 1334-1889, 1376-1647, 1376-1670, 1376-1768, 1387-1768, 1466-1742, 1470-1829, 1491-2092, 1497-1880, 1502-1820, 1520-2235, 1599-2231, 1961-1989, 1992-2298, 2014-2654, 2076-2336, 2092-2727, 2135-2425, 2135-2448, 2147-2580, 2153-2443, 2226-2705, 2476-2624, 2508-2889, 2511-2969, 2530-2930, 2807-3117, 2862-3393, 2870-3085, 3117-3543, 3343-3863, 3458-3789, 3569-3807 |
| 75/7526196CB1/ 4380 | 1-4380, 41-683, 763-1641, 818-1676, 884-1835, 887-1743, 887-1834, 887-1835, 897-1740, 900-1709, 954-1835, 1032-1590, 1035-1895, 1036-1729, 1036-1835, 1039-1835, 1065-1676, 1141-1738, 1169-1738, 1176-1738, 1188-1738, 1189-1737, 1198-1920, 1198-2052, 1202-1738, 1304-1944, 1353-2006, 1354-1879, 1354-1985, 1354-2016, 1354-2051, 1354-2086, 1356-2011, 1411-2084, 1411-2094, 1498-2168, 2279-2898, 2279-2901, 2279-2918, 2279-2945, 2279-2987, 2279-3041, 2279-3091, 2279-3111, 2279-3151, 2285-3136, 2361-2898, 2365-3037, 2368-3037, 2392-2942, 2398-3036, 2406-2999, 2422-3076, 2429-3046, 2430-3037, 2447-3014, 2500-3037, 2538-3118, 3013-3077, 3108-4157 |
| 76/7526198CB1/ 4293 | 1-622, 1-624, 1-4163, 3-677, 49-748, 76-607, 83-981, 86-731, 86-826, 101-650, 102-660, 102-693, 138-660, 138-847, 139-730, 139-807, 139-833, 139-847, 139-848, 139-914, 139-926, 139-1002, 194-827, 299-882, 318-882, 2082-2933, 2092-2695, 2092-2698, 2092-2715, 2092-2742, 2092-2784, 2092-2838, 2092-2888, 2092-2908, 2092-2948, 2158-2695, 2162-2834, 2165-2834, 2189-2739, 2195-2833, 2203-2796, 2219-2873, 2226-2843, 2227-2834, 2244-2811, 2297-2834, 2335-2915, 2810-2874, 2905-3964, 3908-4293 |
| 77/7526208CB1/ 6538 | 1-581, 21-6538, 438-1053, 581-1057, 589-1057, 906-1436, 1332-1978, 1483-2045, 1486-2135, 1645-2142, 2127-2864, 2129-2864, 2304-2751, 2382-2971, 2543-3089, 2564-3118, 2568-3068, 3104-3725, 3255-3883, 3376-3897, 3450-4136, 3459-4057, 3476-3968, 3478-4027, 3479-4046, 3481-4172, 3489-4296, 3502-4173, 3522-4172, 3533-4165, 3555-4177, 3564-4310, 3578-4049, 3643-4157, 3643-4275, 3652-4172, 3663-4244, 3676-4334, 3699-4147, 3806-4475, 3959-4517, 3972-4672, 4006-4691, 4007-4745, 4028-4745, 4040-4746, 4043-4695, 4067-4745, 4076-4745, 4078-4745, 4104-4659, 4116-4745, 4155-4745, 4165-4745, 4184-4745, 4194-4686, 4195-4685, 4215-4689, 4216-4688, 4242-4745, 4251-4702, 4284-4745, 4873-5519, 4878-5586, 5089-5766, 5144-5808, 5483-6067, 5491-6053, 5502-6329, 5571-6067, 5580-6040, 5586-6065, 5587-6067, 5587-6069, 5603-6069, 5614-6067 |
| 78/7526212CB1/ 2349 | 1-581, 1-2290, 438-1053, 581-1057, 589-1057, 906-1436, 1332-1978, 1483-2045, 1608-2349 |
| 79/7526213CB1/ 8015 | 1-8009, 203-877, 203-936, 571-1314, 571-1436, 571-1450, 577-1378, 586-1449, 594-1332, 652-1450, 731-1652, 747-1525, 756-1532, 799-1670, 806-1686, 833-1552, 833-1695, 833-1721, 833-1768, 843-1675, 849-1612, 850-1644, 850-1675, 855-1615, 856-1771, 857-1624, 857-1678, 915-1764, 928-1675, 928-1768, 928-1899, 933-1753, 933-1779, 934-1774, 943-1759, 947-1898, 950-1844, 1827-2719, 1829-2642, 1829-2704, 1829-2737, 1830-2720, 2108-3060, 2154-3036, 2155-3043, 2160-3084, 2161-3052, 2172-3054, 2174-3015, 2180-2972, 2212-3066, 2212-3163, 2215-2958, 2215-3030, 2277-3051, 2281-3068, 2422-3338, 2430-3130, 2430-3212, 2430-3244, 2430-3322, 2434-3184, 5975-6837, 6557-7314, 7215-7903, 7241-8015 |

TABLE 4-continued

| Polynucleotide SEQ ID NO:/ Incyte ID/Sequence Length | Sequence Fragments |
| --- | --- |
| 80/7526214CB1/ 7945 | 1-7945, 203-668, 203-955, 492-1352, 507-1304, 507-1371, 507-1385, 513-1313, 514-1304, 522-1384, 588-1385, 692-1396, 707-787, 735-1548, 742-1621, 769-1487, 769-1656, 769-1703, 785-1551, 786-1610, 787-1550, 787-1559, 788-1706, 790-1712, 791-1488, 792-1613, 796-1676, 863-1610, 863-1703, 863-1834, 868-1688, 868-1714, 869-1709, 878-1694, 882-1833, 885-1779, 1762-2657, 1764-2579, 1764-2642, 1764-2675, 1765-2658, 2418-3318, 2583-3356, 2664-3334, 2664-3380, 2664-3382, 2664-3389, 2664-3405, 2664-3422, 2664-3431, 2664-3445, 2664-3454, 2664-3458, 2664-3459, 2664-3464, 2664-3469, 2664-3470, 2664-3471, 2664-3480, 2664-3510, 2664-3511, 2664-3532, 2664-3562, 2668-3458, 2668-3609, 2668-3617, 2706-3617, 2711-3617, 2776-3617, 2779-3617, 2781-3654, 2782-3617, 2784-3654, 2804-3617, 2810-3654, 2823-3653, 2848-3654, 2849-3628, 2849-3651, 2849-3654, 2854-3654, 2876-3653, 2876-3654, 2899-3650, 2906-3654, 2915-3654, 2949-3654, 2952-3654, 2971-3654, 3008-3682, 3181-3922, 3471-4320, 3797-4551, 4066-4870, 4320-5134, 4541-5355, 4764-5490, 5247-5934, 5910-6772, 6492-7250, 6854-7555, 7150-7839, 7176-7945 |
| 81/7526228CB1/ 3149 | 1-528, 1-719, 30-3149, 217-706, 229-740, 239-1013, 243-910, 263-996, 402-1249, 1515-2354, 1538-2050, 1569-2354, 1889-2602, 2023-2773, 2112-2648, 2124-2819, 2147-2671, 2211-2688, 2566-3119 |
| 82/7526246CB1/ 3617 | 1-563, 118-3617, 407-1087, 412-1145, 506-1090, 521-563, 703-1270, 869-1158, 869-1501, 1194-1870, 1194-1985, 1194-1992, 1358-2314, 1371-2039, 1373-2314, 1376-2303, 1385-2314, 1421-2000, 1423-2016, 1423-2314, 1429-2101, 1439-2254, 1455-2314, 1457-2209, 1466-2314, 1471-2313, 1471-2314, 1478-2314, 1480-2314, 1492-2313, 1494-2313, 1494-2314, 1495-2351, 1497-2314, 1497-2351, 1509-2150, 1509-2351, 1515-2314, 1519-2303, 1520-2314, 1521-2249, 1529-2314, 1539-2152, 1542-2130, 1542-2336, 1542-2367, 1542-2412, 1544-2314, 1545-2247, 1557-2187, 1568-2313, 1568-2314, 1592-2177, 1594-2303, 1598-2314, 1599-2282, 1599-2351, 1601-2189, 1613-2314, 1616-2267, 1616-2314, 1625-2252, 1631-2190, 1638-2313, 1648-2404, 1653-2261, 1656-2242, 1661-2344, 1677-2397, 1679-2352, 1688-2368, 1714-2320, 1715-2528, 1728-2280, 1737-2340, 1740-2392, 1744-2314, 1773-2465, 1782-2351, 1797-2414, 1824-2428, 2599-3242 |
| 83/7526258CB1/ 1955 | 1-1955, 81-946, 715-1172, 812-1528, 987-1540 |
| 84/7526311CB1/ 2937 | 1-2937, 122-658, 122-690, 122-739, 123-1393, 539-1393, 621-1393, 807-1393, 1099-1644, 1237-1848, 1251-1561, 1390-2042, 1392-2069, 1396-2052, 1430-1987, 1495-1949, 1502-1940, 1531-2266, 1542-2039, 1549-2106, 1579-1965, 1658-2132, 1731-2380, 1737-2490, 1759-2540, 1837-2534, 1853-2606, 1871-2301, 1880-2223, 1925-2496, 1960-2513, 1971-2483, 1984-2421, 1984-2491, 1984-2567, 1984-2611, 1992-2496, 2000-2404, 2015-2565, 2021-2502, 2033-2567, 2038-2544, 2060-2394, 2062-2561, 2066-2606, 2083-2510, 2107-2572, 2109-2500, 2129-2573, 2136-2565, 2139-2582, 2147-2567, 2154-2547, 2156-2606, 2160-2609, 2169-2741, 2182-2609, 2223-2552, 2240-2586, 2246-2606, 2247-2568, 2247-2602, 2328-2878, 2355-2860, 2374-2890, 2472-2913, 2478-2937 |
| 85/7526315CB1/ 6122 | 1-6121, 193-871, 310-931, 573-982, 867-1481, 867-1492, 867-1496, 867-1573, 867-1595, 890-1609, 919-1643, 922-1655, 1103-1948, 2143-2950, 2339-3054, 2423-3023, 2471-3073, 2669-3237, 2738-3490, 2738-3554, 2800-3574, 3049-3795, 3247-3955, 4679-5357, 4789-5413, 5055-5683, 5121-5809, 5167-5854, 5317-6012, 5343-6045, 5356-6064, 5370-6043, 5370-6116, 5405-6106, 5410-6122, 5424-6117, 5458-6108, 5461-6122, 5479-6079, 5493-6117, 5495-6063, 5524-6117 |
| 86/7526442CB1/ 1914 | 1-437, 1-647, 1-1893, 1-1914, 260-862, 260-863, 684-1206, 684-1379, 720-1262, 741-1452, 744-1453, 748-1386, 750-1276, 760-1283, 762-1262, 784-1394, 789-1234, 789-1378, 791-1267, 794-1261, 796-1623, 807-1405, 814-1325, 818-1406, 821-1623, 845-1278, 845-1332, 856-1377, 863-1451, 876-1423, 880-1464, 953-1403, 960-1772, 961-1395, 969-1452, 1474-1914 |

TABLE 5

| Polynucleotide SEQ ID NO: | Incyte Project ID: | Representative Library |
| --- | --- | --- |
| 65 | 2509577CB1 | TESTNOC01 |
| 66 | 7505222CB1 | LUNGDIN02 |
| 68 | 7526163CB1 | BRAITDR02 |
| 69 | 7526158CB1 | THP1TXT04 |
| 71 | 7526180CB1 | BRSTNOT01 |
| 72 | 7526185CB1 | UTREDMF02 |
| 73 | 7526192CB1 | NERDTDN03 |
| 74 | 7526193CB1 | BRABDIR01 |
| 75 | 7526196CB1 | BRACNOK02 |
| 76 | 7526198CB1 | BRACNOK02 |

TABLE 5-continued

| Polynucleotide SEQ ID NO: | Incyte Project ID: | Representative Library |
| --- | --- | --- |
| 77 | 7526208CB1 | BLADDIT01 |
| 78 | 7526212CB1 | BRAINOR03 |
| 80 | 7526214CB1 | MYEPUNN01 |
| 81 | 7526228CB1 | MYEPUNF01 |
| 82 | 7526246CB1 | THYMNOE01 |
| 83 | 7526258CB1 | BLYRTXT03 |
| 84 | 7526311CB1 | SININOT04 |
| 85 | 7526315CB1 | OVARDIN02 |
| 86 | 7526442CB1 | PITUNON01 |

TABLE 6

| Library | Vector | Library Description |
| --- | --- | --- |
| BLADDIT01 | pINCY | Library was constructed using RNA isolated from diseased bladder tissue removed from a 73-year-old male during a total cystectomy. Pathology indicated the bladder mucosa showed mild chronic cystitis. Pathology for the associated tumor tissue indicated invasive grade 3 adenocarcinoma, which formed a friable mass situated within the proximal urethra, 14 cm from the distal urethral resection margin. The tumor invaded superficially into, but not through, muscularis propria. |
| BLYRTXT03 | pINCY | Library was constructed using RNA isolated from a treated Raji cell line derived from the B-lymphocyte cells of an 11-year- old Black male (ATCC CCL-86). The cells were treated for 18 hours with 10 ng/ml of interleukin 18 (IL-18). Pathology indicated Burkitt's lymphoma. |
| BRABDIR01 | pINCY | Library was constructed using RNA isolated from diseased cerebellum tissue removed from the brain of a 57-year-old Caucasian male, who died from a cerebrovascular accident. Patient history included Huntington's disease, emphysema, and tobacco abuse. |
| BRACNOK02 | PSPORT1 | This amplified and normalized library was constructed using RNA isolated from posterior cingulate tissue removed from an 85-year-old Caucasian female who died from myocardial infarction and retroperitoneal hemorrhage. Pathology indicated atherosclerosis, moderate to severe, involving the circle of Willis, middle cerebral, basilar and |

TABLE 6-continued

| Library | Vector | Library Description |
|---|---|---|
| | | vertebral arteries; infarction, remote, left dentate nucleus; and amyloid plaque deposition consistent with age. There was mild to moderate leptomeningeal fibrosis, especially over the convexity of the frontal lobe. There was mild generalized atrophy involving all lobes. The white matter was mildly thinned. Cortical thickness in the temporal lobes, both maximal and minimal, was slightly reduced. The substantia nigra pars compacta appeared mildly depigmented. Patient history included COPD, hypertension, and recurrent deep venous thrombosis. 6.4 million independent clones from this amplified library were normalized in one round using conditions adapted from Soares et al., PNAS (1994) 91: 9228-9232 and Bonaldo et al., Genome Research 6 (1996): 791. |
| BRAINOR03 | PBK-CMV | This random primed library was constructed using pooled cDNA from two donors. cDNA was generated using mRNA isolated from brain tissue removed from a Caucasian male fetus (donor A) who was stillborn with a hypoplastic left heart at 23 weeks' gestation and from brain tissue removed from a Caucasian male fetus (donor B), who died at 23 weeks' gestation from premature birth. Serologies were negative for both donors and family history for donor B included diabetes in the mother. |
| BRAITDR02 | PCDNA2.1 | This random primed library was constructed using RNA isolated from allocortex, neocortex, anterior and frontal cingulate tissue removed from a 55-year-old Caucasian female who died from cholangiocarcinoma. Pathology indicated mild meningeal fibrosis predominately over the convexities, scattered axonal spheroids in the white matter of the cingulate cortex and the thalamus, and a few scattered neurofibrillary tangles in the entorhinal cortex and the periaqueductal gray region. Pathology for the associated tumor tissue indicated well-differentiated cholangiocarcinoma of the liver with residual or relapsed tumor. Patient history included cholangiocarcinoma, post-operative Budd-Chiari syndrome, biliary ascites, hydrothorax, dehydration, malnutrition, oliguria and acute renal failure. Previous surgeries included cholecystectomy and resection of 85% of the liver. |
| BRSTNOT01 | PBLUESCRIPT | Library was constructed using RNA isolated from the breast tissue of a 56-year-old Caucasian female who died in a motor vehicle accident. |
| LUNGDIN02 | pINCY | This normalized lung tissue library was constructed from 7.6 million independent clones from a diseased lung tissue library. Starting RNA was made from RNA isolated from diseased lung tissue. Pathology indicated ideopathic pulmonary disease. The library was normalized in 2 rounds using conditions adapted from Soares et al., PNAS (1994) 91: 9228-9232 and Bonaldo et al., Genome Research 6 (1996): 791, except that a significantly longer (48 hours/round) reannealing hybridization was used. |
| MYEPUNF01 | pRARE | This 5' cap isolated full-length library was constructed using RNA isolated from an untreated K-562 cell line, derived from chronic myelogenous leukemia precursor cells removed from a 53-year-old female. |
| MYEPUNN01 | pRARE | This normalized untreated K-562 cell line tissue library was constructed from independent clones from a K-562 cell line library. Starting RNA was made from an untreated K-562 cell line, derived from chronic myelogenous leukemia precursor cells removed from a 53-year-old female. The library was normalized in one round using conditions adapted from Soares et al., PNAS (1994) 91: 9228-9232 and Bonaldo et al., Genome Research 6 (1996): 791, except that a significantly longer (48 hours/round) reannealing hybridization was used. |
| NERDTDN03 | pINCY | This normalized dorsal root ganglion tissue library was constructed from 1.05 million independent clones from a dorsal root ganglion tissue library. Starting RNA was made from dorsal root ganglion tissue removed from the cervical spine of a 32-year-old Caucasian male who died from acute pulmonary edema, acute bronchopneumonia, bilateral pleural effusions, pericardial effusion, and malignant lymphoma (natural killer cell type). The patient presented with pyrexia of unknown origin, malaise, fatigue, and gastrointestinal bleeding. Patient history included probable cytomegalovirus infection, liver congestion, and steatosis, splenomegaly, hemorrhagic cystitis, thyroid hemorrhage, respiratory failure, pneumonia of the left lung, natural killer cell lymphoma of the pharynx, Bell's palsy, and tobacco and alcohol abuse. Previous surgeries included colonoscopy, closed colon biopsy, adenotonsillectomy, and nasopharyngeal endoscopy and biopsy. Patient medications included Diflucan (fluconazole), Deltasone (prednisone), hydrocodone, Lortab, Alprazolam, Reazodone, ProMace-Cytabom, Etoposide, Cisplatin, Cytarabine, and dexamethasone. The patient received radiation therapy and multiple blood transfusions. The library was normalized in 2 rounds using conditions adapted from Soares et al., PNAS (1994) 91: 9228-9232 and Bonaldo et al., Genome Research 6 (1996): 791, except that a significantly longer (48 hours/round) reannealing hybridization was used. |
| OVARDIN02 | pINCY | This normalized ovarian tissue library was constructed from 5.76 million independent clones from an ovary library. Starting RNA was made from diseased ovarian tissue removed from a 39-year-old Caucasian female during total abdominal hysterectomy, bilateral salpingo-oophorectomy, dilation and curettage, partial colectomy, incidental appendectomy, and temporary colostomy. Pathology indicated the right and left adnexa, mesentery and muscularis propria of the sigmoid colon were extensively involved by endometriosis. Endometriosis also involved the anterior and posterior serosal surfaces of the uterus and the cul-de-sac. The endometrium was proliferative. Pathology for the associated tumor tissue indicated multiple (3 intramural, 1 subserosal) leiomyomata. The patient presented with abdominal pain and infertility. Patient history included scoliosis. Family history included hyperlipidemia, benign hypertension, atherosclerotic coronary artery disease, depressive disorder, brain cancer, and type II diabetes. The library was normalized in two rounds using conditions adapted from Soares et al., PNAS(1994) 91: 9228 and Bonaldo et al., Genome Research 6 (1996): 791, except that a significantly longer (48-hours/round) reannealing hybridization was used. |
| PITUNON01 | pINCY | This normalized pituitary gland tissue library was constructed from 6.92 million independent clones from a pituitary gland tissue library. Starting RNA was made from pituitary gland tissue removed from a 55-year-old male who died from chronic obstructive pulmonary disease. Neuropathology indicated there were no gross abnormalities, other than mild ventricular enlargement. There was no apparent microscopic abnormality in any of the neocortical areas examined, except for a number of silver positive neurons with apical dendrite staining, particularly in the frontal lobe. The significance of this was undetermined. The only other microscopic abnormality was that there was prominent silver staining with some swollen axons in the CA3 region of the anterior and posterior hippocampus. Microscopic sections of the cerebellum revealed mild Bergmann's gliosis in the Purkinje cell layer. Patient history included schizophrenia. The library was normalized in two rounds using conditions adapted from Soares et al., PNAS (1994) 91: 9228-9232 and Bonaldo et al., Genome Research (1996) 6: 791, except that a significantly longer (48 hours/round) reannealing hybridization was used. |
| SININOT04 | pINCY | Library was constructed using RNA isolated from diseased ileum tissue obtained from a 26-year-old Caucasian male during a partial colectomy, permanent colostomy, and an incidental appendectomy. Pathology indicated moderately to severely active Crohn's disease. Family history included enteritis of the small intestine. |
| TESTNOC01 | PBLUESCRIPT | This large size fractionated library was constructed using RNA isolated from testicular tissue removed from a pool of eleven, 10 to 61-year-old Caucasian males. |

TABLE 6-continued

| Library | Vector | Library Description |
|---|---|---|
| THP1TXT04 | pINCY | Library was constructed using RNA isolated from stimulated THP-1 cells. THP-1 is a human promonocyte line derived from the peripheral blood of a 1-year-old male (Abbott Sample) with acute monocytic leukemia (Int. J. Cancer 26 (1980): 171). |
| THYMNOE01 | PCDNA2.1 | This 5' biased random primed library was constructed using RNA isolated from thymus tissue removed from a 2-year-old Caucasian female during a thymectomy and patch closure of left atrioventricular fistula. Pathology indicated there was no gross abnormality of the thymus. The patient presented with congenital heart abnormalities. Patient history included double inlet left ventricle and a rudimentary right ventricle, pulmonary hypertension, cyanosis, subaortic stenosis, seizures, and a fracture of the skull base. Patient medications included Lasix and Captopril. Family history included reflux neuropathy in the mother. |
| UTREDMF02 | PCMV-ICIS | This full-length enriched library was constructed using 1.5 micrograms of polyA RNA isolated from endometrial tissue removed from a 32-year-old female. The endometrium was in secretory phase. |

TABLE 7

| Program | Description | Reference | Parameter Threshold |
|---|---|---|---|
| ABI FACTURA | A program that removes vector sequences and masks ambiguous bases in nucleic acid sequences. | Applied Biosystems, Foster City, CA. | |
| ABI/PARACEL FDF | A Fast Data Finder useful in comparing and annotating amino acid or nucleic acid sequences. | Applied Biosystems, Foster City, CA; Paracel Inc., Pasadena, CA. | Mismatch <50% |
| ABI AutoAssembler | A program that assembles nucleic acid sequences. | Applied Biosystems, Foster City, CA. | |
| BLAST | A Basic Local Alignment Search Tool useful in sequence similarity search for amino acid and nucleic acid sequences. BLAST includes five functions: blastp, blastn, blastx, tblastn, and tblastx. | Altschul, S. F. et al. (1990) J. Mol. Biol. 215: 403-410; Altschul, S. F. et al. (1997) Nucleic Acids Res. 25: 3389-3402. | ESTs: Probability value = 1.0E−8 or less; Full Length sequences: Probability value = 1.0E−10 or less |
| FASTA | A Pearson and Lipman algorithm that searches for similarity between a query sequence and a group of sequences of the same type. FASTA comprises as least five functions: fasta, tfasta, fastx, tfastx, and ssearch. | Pearson, W. R. and D. J. Lipman (1988) Proc. Natl. Acad Sci. USA 85: 2444-2448; Pearson, W. R. (1990) Methods Enzymol. 183: 63-98; and Smith, T. F. and M. S. Waterman (1981) Adv. Appl. Math. 2: 482-489. | ESTs: fasta E value = 1.06E−6; Assembled ESTs: fasta Identity = 95% or greater and Match length = 200 bases or greater; fastx E value = 1.0E−8 or less; Full Length sequences: fastx score = 100 or |
| BLIMPS | A BLocks IMProved Searcher that matches a sequence against those in BLOCKS, PRINTS, DOMO, PRODOM, and PFAM databases to search for gene families, sequence homology, and structural fingerprint regions. | Henikoff, S. and J. G. Henikoff (1991) Nucleic Acids Res. 19: 6565-6572; Henikoff, J. G. and S. Henikoff (1996) Methods Enzymol. 266: 88-105; and Attwood, T. K. et al. (1997) J. Chem. Inf. Comput. Sci. 37: 417-424. | Probability value = 1.0E−3 or less |
| HMMER | An algorithm for searching a query sequence against hidden Markov model (HMM)-based databases of protein family consensus sequences, such as PFAM, INCY, SMART and TIGRFAM. | Krogh, A. et al. (1994) J. Mol. Biol. 235: 1501-1531; Sonnhammer, E. L. L. et al. (1988) Nucleic Acids Res. 26: 320-322; Durbin, R. et al. (1998) Our World View, in a Nutshell, Cambridge Univ. Press, pp. 1-350. | PFAM, INCY, SMART or TIGRFAM hits: Probability value = 1.0E−3 or less; Signal peptide hits: Score = 0 or greater |
| ProfileScan | An algorithm that searches for structural and sequence motifs in protein sequences that match sequence patterns defined in Prosite. | Gribskov, M. et al. (1988) CABIOS 4: 61-66; Gribskov, M. et al. (1989) Methods Enzymol. 183: 146-159; Bairoch, A. et al. (1997) Nucleic Acids Res. 25: 217-221. | Normalized quality score ≧ GCG-specified "HIGH" value for that particular Prosite motif. Generally, score = 1.4-2.1. |
| Phred | A base-calling algorithm that examines automated sequencer traces with high sensitivity and probability. | Ewing, B. et al. (1998) Genome Res. 8: 175-185; Ewing, B. and P. Green (1998) Genome Res. 8: 186-194. | |

TABLE 7-continued

| Program | Description | Reference | Parameter Threshold |
|---|---|---|---|
| Phrap | A Phils Revised Assembly Program including SWAT and CrossMatch, programs based on efficient implementation of the Smith-Waterman algorithm, useful in searching sequence homology and assembling DNA sequences. | Smith, T. F. and M. S. Waterman (1981) Adv. Appl. Math. 2: 482-489; Smith, T. F. and M. S. Waterman (1981) J. Mol. Biol. 147: 195-197; and Green, P., University of Washington, Seattle, WA. | Score = 120 or greater; Match length = 56 or greater |
| Consed | A graphical tool for viewing and editing Phrap assemblies. | Gordon, D. et al. (1998) Genome Res. 8: 195-202. | |
| SPScan | A weight matrix analysis program that scans protein sequences for the presence of secretory signal peptides. | Nielson, H. et al. (1997) Protein Engineering 10: 1-6; Claverie, J. M. and S. Audic (1997) CABIOS 12: 431-439. | Score = 3.5 or greater |
| TMAP | A program that uses weight matrices to delineate transmembrane segments on protein sequences and determine orientation. | Persson, B. and P. Argos (1994) J. Mol. Biol. 237: 182-192; Persson, B. and P. Argos (1996) Protein Sci. 5: 363-371. | |
| TMHMMER | A program that uses a hidden Markov model (HMM) to delineate transmembrane segments on protein sequences and determine orientation. | Sonnhammer, E. L. et al. (1998) Proc. Sixth Intl. Conf. On Intelligent Systems for Mol. Biol., Glasgow et al., eds., The Am. Assoc. for Artificial Intelligence (AAAI) Press, Menlo Park, CA, and MIT Press, Cambridge, MA, pp. 175-182. | |
| Motifs | A program that searches amino acid sequences for patterns that matched those defined in Prosite. | Bairoch, A. et al. (1997) Nucleic Acids Res. 25: 217-221; Wisconsin Package Program Manual, version 9, page M51-59, Genetics Computer Group, Madison, WI. | |

TABLE 8

| SEQ ID NO: | PID | EST ID | SNP ID | EST SNP | CB1 SNP | EST Allele | Allele 1 | Allele 2 | Amino Acid | Caucasian Allele 1 frequency | African Allele 1 frequency | Asian Allele 1 frequency | Hispanic Allele 1 frequency |
|---|---|---|---|---|---|---|---|---|---|---|---|---|---|
| 44 | 7517831 | 142314T6 | SNP00003755 | 149 | 1721 | A | A | G | noncoding | n/a | n/a | n/a | n/a |
| 44 | 7517831 | 142314T6 | SNP00098537 | 3 | 1867 | C | C | T | noncoding | n/a | n/a | n/a | n/a |
| 44 | 7517831 | 142314T6 | SNP00149767 | 132 | 1738 | A | A | G | noncoding | n/a | n/a | n/a | n/a |
| 44 | 7517831 | 1531602H1 | SNP00023921 | 178 | 1271 | T | T | G | noncoding | n/d | n/a | n/a | n/a |
| 44 | 7517831 | 2655558T6 | SNP00003755 | 126 | 1744 | G | A | G | noncoding | n/a | n/a | n/a | n/a |
| 44 | 7517831 | 2655558T6 | SNP00149767 | 109 | 1761 | A | A | G | noncoding | n/a | n/a | n/a | n/a |
| 44 | 7517831 | 2829606H1 | SNP00027387 | 110 | 109 | G | G | A | D18 | n/a | n/a | n/a | n/a |
| 44 | 7517831 | 2836842T6 | SNP00003755 | 140 | 1730 | A | A | G | noncoding | n/a | n/a | n/a | n/a |
| 44 | 7517831 | 2836842T6 | SNP00149767 | 123 | 1747 | A | A | G | noncoding | n/a | n/a | n/a | n/a |
| 44 | 7517831 | 2876073T6 | SNP00003755 | 115 | 1755 | A | A | G | noncoding | n/a | n/a | n/a | n/a |
| 44 | 7517831 | 2876073T6 | SNP00149767 | 98 | 1772 | A | A | G | noncoding | n/a | n/a | n/a | n/a |
| 44 | 7517831 | 7758626H1 | SNP00126822 | 384 | 458 | C | C | A | noncoding | n/a | n/a | n/a | n/a |
| 45 | 7520272 | 1265056T6 | SNP00065601 | 250 | 838 | A | A | G | G274 | n/a | n/a | n/a | n/a |
| 45 | 7520272 | 1501560T6 | SNP00069832 | 52 | 916 | C | C | T | noncoding | n/a | n/a | n/a | n/a |
| 45 | 7520272 | 1501560T6 | SNP00075533 | 128 | 840 | C | C | T | S275 | n/d | n/a | n/a | n/a |
| 45 | 7520272 | 1968576T6 | SNP00075533 | 204 | 866 | C | C | T | Q284 | n/d | n/a | n/a | n/a |
| 47 | 7523965 | 1238421H1 | SNP00075756 | 56 | 794 | G | G | A | noncoding | n/a | n/a | n/a | n/a |
| 47 | 7523965 | 1324236T6 | SNP00033242 | 113 | 1642 | G | G | C | noncoding | n/d | n/a | n/a | n/a |
| 47 | 7523965 | 1394758F6 | SNP00100133 | 209 | 491 | A | A | G | M164 | n/d | n/d | n/d | n/d |
| 47 | 7523965 | 1394758T6 | SNP00033242 | 125 | 1605 | G | G | C | noncoding | n/d | n/a | n/a | n/a |
| 47 | 7523965 | 1631511T6 | SNP00033242 | 186 | 1543 | G | G | C | noncoding | n/d | n/a | n/a | n/a |
| 47 | 7523965 | 1964258H1 | SNP00033242 | 56 | 1542 | G | G | C | noncoding | n/d | n/a | n/a | n/a |
| 47 | 7523965 | 1964258H1 | SNP00136906 | 186 | 1672 | C | C | T | noncoding | n/a | n/a | n/a | n/a |
| 47 | 7523965 | 3149675H1 | SNP00057801 | 173 | 785 | G | G | A | noncoding | n/d | n/a | n/a | n/a |
| 47 | 7523965 | 3149675H1 | SNP00096467 | 177 | 789 | G | G | C | noncoding | n/a | n/a | n/a | n/a |
| 47 | 7523965 | 6595879J1 | SNP00075756 | 251 | 798 | G | G | A | noncoding | n/a | n/a | n/a | n/a |
| 47 | 7523965 | 759508T6 | SNP00033242 | 199 | 1553 | G | G | C | noncoding | n/d | n/a | n/a | n/a |
| 47 | 7523965 | 7636827H1 | SNP00033242 | 227 | 1534 | G | G | C | noncoding | n/d | n/a | n/a | n/a |
| 47 | 7523965 | 7636827H1 | SNP00136906 | 97 | 1664 | C | C | T | noncoding | n/a | n/a | n/a | n/a |
| 47 | 7523965 | 7637976J1 | SNP00075756 | 569 | 543 | G | G | A | stop181 | n/a | n/a | n/a | n/a |
| 51 | 7516229 | 1329019T6 | SNP00069933 | 170 | 1162 | G | T | G | noncoding | n/a | n/a | n/a | n/a |
| 51 | 7516229 | 6555450H1 | SNP00023019 | 310 | 656 | G | G | A | S200 | n/a | n/a | n/a | n/a |
| 52 | 7516525 | 2190612H1 | SNP00128124 | 49 | 1276 | A | G | A | E413 | n/a | n/a | n/a | n/a |
| 52 | 7516525 | 3780651H1 | SNP00074470 | 124 | 1682 | C | C | T | noncoding | 0.95 | 0.96 | 0.77 | 0.65 |
| 52 | 7516525 | 3825922H1 | SNP00074469 | 151 | 1667 | C | C | T | S543 | n/d | n/d | n/d | n/d |

TABLE 8-continued

| SEQ ID NO: | PID | EST ID | SNP ID | EST SNP | CB1 SNP | EST Allele | Allele 1 | Allele 2 | Amino Acid | Caucasian Allele 1 frequency | African Allele 1 frequency | Asian Allele 1 frequency | Hispanic Allele 1 frequency |
|---|---|---|---|---|---|---|---|---|---|---|---|---|---|
| 53 | 7516533 | 000364H1 | SNP00002194 | 28 | 1573 | G | A | G | noncoding | 0.78 | n/a | n/a | n/a |
| 53 | 7516533 | 2360696T6 | SNP00002194 | 447 | 1574 | G | A | G | noncoding | 0.78 | n/a | n/a | n/a |
| 53 | 7516533 | 2641486F6 | SNP00151695 | 95 | 1482 | A | A | G | noncoding | n/a | n/a | n/a | n/a |
| 53 | 7516533 | 3078274H1 | SNP00126890 | 34 | 1112 | A | A | G | P350 | n/a | n/a | n/a | n/a |
| 53 | 7516533 | 3505057H1 | SNP00126889 | 33 | 1081 | A | A | G | E340 | n/a | n/a | n/a | n/a |
| 53 | 7516533 | 3505057H1 | SNP00127060 | 80 | 1128 | C | C | A | R356 | n/a | n/a | n/a | n/a |
| 53 | 7516533 | 3505057H1 | SNP00127061 | 247 | 1295 | A | A | G | E411 | n/a | n/a | n/a | n/a |
| 53 | 7516533 | 3505057H1 | SNP00151694 | 133 | 1181 | T | T | G | P373 | n/a | n/a | n/a | n/a |
| 53 | 7516533 | 4376126H1 | SNP00127062 | 27 | 1369 | A | A | G | K436 | n/a | n/a | n/a | n/a |
| 54 | 7516613 | 1741505T6 | SNP00054334 | 116 | 2763 | G | G | A | R904 | n/d | n/d | n/d | n/d |
| 54 | 7516613 | 1741505T6 | SNP00124224 | 52 | 2827 | T | T | C | S925 | n/d | n/d | n/d | n/d |
| 54 | 7516613 | 1852144T6 | SNP00029583 | 89 | 3808 | C | C | T | noncoding | n/d | n/a | n/a | n/a |
| 54 | 7516613 | 2086173H1 | SNP00029583 | 150 | 3791 | C | C | T | noncoding | n/d | n/a | n/a | n/a |
| 54 | 7516613 | 2103173R6 | SNP00074035 | 137 | 331 | A | A | G | R93 | n/d | n/d | n/d | n/d |
| 54 | 7516613 | 2172576F6 | SNP00074035 | 62 | 327 | A | A | G | K92 | n/d | n/d | n/d | n/d |
| 54 | 7516613 | 2230058H1 | SNP00029582 | 57 | 2999 | C | C | T | H983 | n/d | n/a | n/a | n/a |
| 54 | 7516613 | 2502887T6 | SNP00029583 | 66 | 3831 | C | C | T | noncoding | n/d | n/a | n/a | n/a |
| 54 | 7516613 | 2606210F6 | SNP00029582 | 412 | 2998 | C | C | T | L982 | n/d | n/a | n/a | n/a |
| 54 | 7516613 | 2606210F6 | SNP00124225 | 348 | 2934 | A | A | G | K961 | n/a | n/a | n/a | n/a |
| 54 | 7516613 | 2606210H1 | SNP00054332 | 20 | 2607 | G | G | A | G852 | n/a | n/a | n/a | n/a |
| 54 | 7516613 | 2606210H1 | SNP00054333 | 135 | 2722 | G | G | A | R890 | n/d | n/a | n/a | n/a |
| 54 | 7516613 | 282T761H1 | SNP00124223 | 98 | 644 | G | G | A | E198 | n/d | n/d | n/d | n/d |
| 54 | 7516613 | 3136587H1 | SNP00124225 | 104 | 2935 | A | A | G | T961 | n/a | n/a | n/a | n/a |
| 54 | 7516613 | 5971646H1 | SNP00074036 | 28 | 1396 | A | G | A | E448 | n/d | n/d | n/d | n/d |
| 54 | 7516613 | 5971646H1 | SNP00074037 | 419 | 1786 | C | G | C | S578 | n/a | n/a | n/a | n/a |
| 54 | 7516613 | 6203324H1 | SNP00074038 | 314 | 1788 | T | T | C | L579 | n/a | n/a | n/a | n/a |
| 54 | 7516613 | 7367225H1 | SNP00098419 | 491 | 1864 | A | C | A | S604 | 0.86 | n/d | n/d | n/d |
| 55 | 7517068 | 201783T6 | SNP00127935 | 369 | 3700 | T | T | C | noncoding | n/a | n/a | n/a | n/a |
| 55 | 7517068 | 2836623F6 | SNP00067424 | 105 | 2443 | G | G | A | G807 | n/a | n/a | n/a | n/a |
| 55 | 7517068 | 2836623H1 | SNP00067424 | 105 | 2442 | G | G | A | A807 | n/a | n/a | n/a | n/a |
| 55 | 7517068 | 3003208F6 | SNP00115029 | 381 | 640 | A | A | G | Q206 | n/a | n/a | n/a | n/a |
| 55 | 7517068 | 6118733H1 | SNP00115032 | 336 | 2129 | C | C | T | S702 | n/d | n/a | n/a | n/a |
| 55 | 7517068 | 6448726H1 | SNP00115031 | 288 | 1428 | A | A | G | I469 | n/d | n/a | n/a | n/a |
| 55 | 7517068 | 6987676H1 | SNP00115029 | 331 | 641 | A | A | G | P206 | n/a | n/a | n/a | n/a |
| 55 | 7517068 | 7205376H1 | SNP00115030 | 297 | 767 | T | T | C | N248 | 0.65 | 0.49 | 0.87 | 0.64 |
| 55 | 7517068 | 7649056H2 | SNP00067424 | 283 | 2441 | G | G | A | A806 | n/a | n/a | n/a | n/a |
| 56 | 7517148 | 1301060F6 | SNP00028255 | 178 | 2035 | G | G | C | noncoding | 0.99 | n/d | n/d | n/d |
| 56 | 7517148 | 1436470H1 | SNP00028255 | 92 | 2091 | C | G | C | noncoding | 0.99 | n/d | n/d | n/d |
| 56 | 7517148 | 2008763H1 | SNP00122615 | 72 | 2814 | A | A | C | noncoding | n/a | n/a | n/a | n/a |
| 56 | 7517148 | 2487070T6 | SNP00122615 | 351 | 2839 | A | A | C | noncoding | n/a | n/a | n/a | n/a |
| 56 | 7517148 | 2504377T6 | SNP00122615 | 334 | 2857 | A | A | C | noncoding | n/a | n/a | n/a | n/a |
| 56 | 7517148 | 2747152T6 | SNP00067260 | 70 | 2411 | A | A | C | noncoding | n/a | n/a | n/a | n/a |
| 56 | 7517148 | 2836570F6 | SNP00067260 | 348 | 2366 | A | A | C | noncoding | n/a | n/a | n/a | n/a |
| 57 | 7517238 | 055029H1 | SNP00035691 | 30 | 998 | T | T | C | S288 | n/a | n/a | n/a | n/a |
| 60 | 7520428 | 1006039H1 | SNP00029126 | 28 | 4802 | A | A | G | noncoding | n/d | n/d | n/d | 0.99 |
| 60 | 7520428 | 1006039H1 | SNP00134113 | 62 | 4836 | G | G | C | noncoding | n/a | n/a | n/a | n/a |
| 60 | 7520428 | 1336820H1 | SNP00100525 | 156 | 3711 | C | C | T | noncoding | n/a | n/a | n/a | n/a |
| 60 | 7520428 | 1342990T6 | SNP00029126 | 341 | 4818 | A | A | G | noncoding | n/d | n/d | n/d | 0.99 |
| 60 | 7520428 | 1349339F6 | SNP00100526 | 22 | 3907 | C | C | T | noncoding | n/a | n/a | n/a | n/a |
| 60 | 7520428 | 1349339F6 | SNP00100527 | 61 | 3946 | C | C | A | noncoding | n/a | n/a | n/a | n/a |
| 60 | 7520428 | 1501365F6 | SNP00006017 | 178 | 2523 | A | A | G | noncoding | n/a | n/a | n/a | n/a |
| 60 | 7520428 | 1547712H1 | SNP00029124 | 105 | 3306 | G | G | A | noncoding | n/a | n/a | n/a | n/a |
| 60 | 7520428 | 1547712H1 | SNP00061149 | 173 | 3374 | A | A | G | noncoding | n/a | n/a | n/a | n/a |
| 60 | 7520428 | 1708824T6 | SNP00134113 | 303 | 4877 | G | G | C | noncoding | n/a | n/a | n/a | n/a |
| 60 | 7520428 | 1812674H1 | SNP00117686 | 180 | 4713 | C | C | T | noncoding | 0.99 | 0.96 | 0.95 | 0.96 |
| 60 | 7520428 | 1861030T6 | SNP00029126 | 368 | 4815 | A | A | G | noncoding | n/d | n/d | n/d | 0.99 |
| 60 | 7520428 | 1861030T6 | SNP00134113 | 334 | 4849 | G | G | C | noncoding | n/a | n/a | n/a | n/a |
| 60 | 7520428 | 1903968H1 | SNP00029125 | 37 | 4436 | A | A | G | noncoding | n/a | n/a | n/a | n/a |
| 60 | 7520428 | 2345238T6 | SNP00029126 | 377 | 4803 | A | A | G | noncoding | n/d | n/d | n/d | 0.99 |
| 60 | 7520428 | 2345238T6 | SNP00117686 | 466 | 4714 | C | C | T | noncoding | 0.99 | 0.96 | 0.95 | 0.96 |
| 60 | 7520428 | 2345238T6 | SNP00134113 | 343 | 4837 | G | G | C | noncoding | n/a | n/a | n/a | n/a |
| 60 | 7520428 | 2479846H1 | SNP00136971 | 133 | 2478 | T | T | G | noncoding | n/a | n/a | n/a | n/a |
| 60 | 7520428 | 264357T6 | SNP00029126 | 362 | 4831 | A | A | G | noncoding | n/d | n/d | n/d | 0.99 |
| 60 | 7520428 | 264357T6 | SNP00134113 | 328 | 4865 | G | G | C | noncoding | n/a | n/a | n/a | n/a |
| 60 | 7520428 | 2792180T6 | SNP00134113 | 339 | 4840 | G | G | C | noncoding | n/a | n/a | n/a | n/a |
| 60 | 7520428 | 3699304H1 | SNP00100524 | 54 | 3440 | G | G | A | noncoding | n/a | n/a | n/a | n/a |
| 60 | 7520428 | 3790573H1 | SNP00013785 | 201 | 4056 | T | C | T | noncoding | 0.23 | n/a | n/a | n/a |
| 60 | 7520428 | 4534017T1 | SNP00134113 | 324 | 4854 | G | G | C | noncoding | n/a | n/a | n/a | n/a |
| 60 | 7520428 | 6388557H1 | SNP00100523 | 201 | 1774 | C | C | T | L579 | n/a | n/a | n/a | n/a |
| 60 | 7520428 | 6831230J1 | SNP00029126 | 252 | 4827 | A | A | G | noncoding | n/d | n/d | n/d | 0.99 |
| 60 | 7520428 | 6831230J1 | SNP00117686 | 163 | 4738 | C | C | T | noncoding | 0.99 | 0.96 | 0.95 | 0.96 |
| 60 | 7520428 | 6831230J1 | SNP00134113 | 286 | 4861 | C | G | C | noncoding | n/a | n/a | n/a | n/a |
| 60 | 7520428 | 7688277H1 | SNP00100525 | 219 | 3712 | C | C | T | noncoding | n/a | n/a | n/a | n/a |
| 60 | 7520428 | 7689549J1 | SNP00006017 | 344 | 2522 | A | A | G | noncoding | n/a | n/a | n/a | n/a |
| 60 | 7520428 | 7689549J1 | SNP00136971 | 389 | 2477 | T | T | G | noncoding | n/a | n/a | n/a | n/a |

TABLE 8-continued

| SEQ ID NO: | PID | EST ID | SNP ID | EST SNP | CB1 SNP | EST Allele | Allele 1 | Allele 2 | Amino Acid | Caucasian Allele 1 frequency | African Allele 1 frequency | Asian Allele 1 frequency | Hispanic Allele 1 frequency |
|---|---|---|---|---|---|---|---|---|---|---|---|---|---|
| 60 | 7520428 | 7703916H1 | SNP00029124 | 221 | 3307 | G | G | A | noncoding | n/a | n/a | n/a | n/a |
| 60 | 7520428 | 7703916H1 | SNP00100524 | 82 | 3441 | G | G | A | noncoding | n/a | n/a | n/a | n/a |
| 60 | 7520428 | 7712761H1 | SNP00029125 | 196 | 4437 | A | A | G | noncoding | n/a | n/a | n/a | n/a |
| 60 | 7520428 | 7756221J1 | SNP00006017 | 74 | 2524 | A | A | G | noncoding | n/a | n/a | n/a | n/a |
| 60 | 7520428 | 7756221J1 | SNP00136971 | 119 | 2479 | T | T | G | noncoding | n/a | n/a | n/a | n/a |
| 60 | 7520428 | 990784R6 | SNP00013785 | 260 | 4057 | C | C | T | noncoding | 0.23 | n/a | n/a | n/a |
| 61 | 7522586 | 1242156H1 | SNP00114359 | 113 | 1870 | G | G | A | noncoding | n/a | n/a | n/a | n/a |
| 61 | 7522586 | 1285002H1 | SNP00049573 | 23 | 1642 | T | T | G | noncoding | 0.7 | 0.52 | 0.44 | 0.57 |
| 61 | 7522586 | 1342006H1 | SNP00008735 | 103 | 375 | C | T | C | R57 | n/a | n/a | n/a | n/a |
| 61 | 7522586 | 1377565F6 | SNP00039374 | 123 | 2054 | C | C | T | noncoding | n/d | n/d | n/d | n/d |
| 61 | 7522586 | 1377565F6 | SNP00047780 | 66 | 1997 | T | T | C | noncoding | n/a | n/a | n/a | n/a |
| 61 | 7522586 | 1377565F6 | SNP00047781 | 77 | 2008 | T | C | T | noncoding | n/a | n/a | n/a | n/a |
| 61 | 7522586 | 1377565H1 | SNP00039374 | 123 | 2053 | C | C | T | noncoding | n/d | n/d | n/d | n/d |
| 61 | 7522586 | 1377565H1 | SNP00047780 | 66 | 1996 | T | T | C | noncoding | n/a | n/a | n/a | n/a |
| 61 | 7522586 | 1377565H1 | SNP00047781 | 77 | 2007 | T | C | T | noncoding | n/a | n/a | n/a | n/a |
| 61 | 7522586 | 1377565T6 | SNP00047780 | 510 | 2003 | T | T | C | noncoding | n/a | n/a | n/a | n/a |
| 61 | 7522586 | 1377565T6 | SNP00047781 | 499 | 2014 | T | C | T | noncoding | n/a | n/a | n/a | n/a |
| 61 | 7522586 | 1705173H1 | SNP00018770 | 38 | 1406 | A | A | G | noncoding | n/d | n/d | n/d | n/d |
| 61 | 7522586 | 1857852H1 | SNP00092603 | 141 | 631 | G | A | G | noncoding | 0.14 | n/d | 0.19 | 0.17 |
| 61 | 7522586 | 2108516H1 | SNP00154337 | 44 | 169 | A | A | C | noncoding | n/a | n/a | n/a | n/a |
| 61 | 7522586 | 2655085H1 | SNP00065632 | 191 | 212 | T | T | G | G2 | n/a | n/a | n/a | n/a |
| 61 | 7522586 | 2889783H1 | SNP00152262 | 77 | 278 | G | G | A | K24 | n/a | n/a | n/a | n/a |
| 61 | 7522586 | 3861045H1 | SNP00059143 | 75 | 2014 | A | G | A | noncoding | 0.59 | n/a | n/a | n/a |
| 61 | 7522586 | 3948090T6 | SNP00036245 | 44 | 1239 | C | T | C | noncoding | n/a | n/a | n/a | n/a |
| 61 | 7522586 | 3948090T6 | SNP00126649 | 97 | 1186 | G | G | A | noncoding | n/a | n/a | n/a | n/a |
| 61 | 7522586 | 4550659T1 | SNP00152262 | 306 | 258 | G | G | A | E18 | n/a | n/a | n/a | n/a |
| 62 | 7524017 | 055029H1 | SNP00035691 | 30 | 981 | T | T | C | S297 | n/a | n/a | n/a | n/a |
| 63 | 7525773 | 1274616F6 | SNP00007308 | 253 | 167 | G | G | A | E50 | 0.87 | n/a | n/a | n/a |
| 63 | 7525773 | 2608313H1 | SNP00007308 | 169 | 172 | G | G | A | S52 | 0.87 | n/a | n/a | n/a |
| 63 | 7525773 | 4435787F7 | SNP00032647 | 519 | 847 | G | C | G | S277 | n/d | n/a | n/a | n/a |
| 65 | 2509577 | 5546336F7 | SNP00070606 | 44 | 2484 | T | T | C | V770 | n/a | n/a | n/a | n/a |
| 67 | 7524408 | 2749757H1 | SNP00121108 | 213 | 1411 | T | T | C | Y460 | n/a | n/a | n/a | n/a |
| 67 | 7524408 | 4739562R7 | SNP00033062 | 268 | 1957 | C | C | T | noncoding | n/a | n/a | n/a | n/a |
| 69 | 7526158 | 5206370H1 | SNP00130724 | 195 | 667 | G | G | C | G211 | n/a | n/a | n/a | n/a |
| 69 | 7526158 | 7960593H1 | SNP00071326 | 132 | 3236 | C | T | C | G1067 | 0.46 | 037 | 0.67 | 0.46 |
| 71 | 7526180 | 1458121H1 | SNP00146630 | 133 | 2374 | T | T | G | noncoding | n/a | n/a | n/a | n/a |
| 71 | 7526180 | 1458121H1 | SNP00146631 | 149 | 2390 | G | G | A | noncoding | n/a | n/a | n/a | n/a |
| 71 | 7526180 | 1663635F6 | SNP00040633 | 39 | 1961 | A | A | G | noncoding | 0.12 | n/a | n/a | n/a |
| 71 | 7526180 | 1663635F6 | SNP00040634 | 19 | 1981 | A | A | C | noncoding | n/a | n/a | n/a | n/a |
| 71 | 7526180 | 2013516T6 | SNP00007120 | 336 | 419 | C | C | T | T1 | 0.67 | n/a | n/a | n/a |
| 71 | 7526180 | 2013516T6 | SNP00049608 | 105 | 188 | C | G | C | noncoding | n/a | n/a | n/a | n/a |
| 71 | 7526180 | 2254891H1 | SNP00048399 | 135 | 961 | C | C | T | L182 | n/a | n/a | n/a | n/a |
| 71 | 7526180 | 2254891H1 | SNP00096777 | 60 | 1036 | G | G | T | V207 | 0.88 | n/a | n/a | n/a |
| 71 | 7526180 | 2254891R6 | SNP00127250 | 274 | 822 | G | A | G | M135 | n/a | n/a | n/a | n/a |
| 71 | 7526180 | 257026H1 | SNP00007121 | 25 | 2206 | A | G | A | noncoding | 0.15 | n/a | n/a | n/a |
| 71 | 7526180 | 257026H1 | SNP00096771 | 58 | 2239 | A | A | G | noncoding | n/a | n/a | n/a | n/a |
| 71 | 7526180 | 4712047F6 | SNP00096075 | 2 | 1290 | T | T | C | S291 | n/d | n/a | n/a | n/a |
| 71 | 7526180 | 6094776H1 | SNP00146629 | 5 | 1875 | A | A | G | E486 | n/a | n/a | n/a | n/a |
| 71 | 7526180 | 6355618F6 | SNP00102652 | 224 | 231 | C | C | T | noncoding | 0.42 | 0.44 | 0.45 | 0.46 |
| 71 | 7526180 | 6355618F6 | SNP00148688 | 356 | 99 | T | C | T | noncoding | n/a | n/a | n/a | n/a |
| 71 | 7526180 | 6731321H1 | SNP00096773 | 126 | 1600 | A | G | A | K395 | 0.74 | 0.91 | 0.31 | 0.76 |
| 72 | 7526185 | 125901F1 | SNP00047602 | 255 | 3028 | T | C | T | noncoding | 0.61 | 0.47 | 0.61 | 0.61 |
| 72 | 7526185 | 1553407H1 | SNP00155225 | 129 | 1488 | T | T | C | noncoding | n/a | n/a | n/a | n/a |
| 72 | 7526185 | 2197671T6 | SNP00155225 | 216 | 1533 | T | T | C | noncoding | n/a | n/a | n/a | n/a |
| 72 | 7526185 | 6723530H1 | SNP00051188 | 262 | 2713 | A | G | A | noncoding | n/a | n/a | n/a | n/a |
| 72 | 7526185 | 829638T6 | SNP00155225 | 181 | 1582 | C | T | C | noncoding | n/a | n/a | n/a | n/a |
| 73 | 7526192 | 1208904H1 | SNP00062572 | 151 | 2429 | G | G | A | noncoding | n/a | n/a | n/a | n/a |
| 73 | 7526192 | 1223444H1 | SNP00098139 | 99 | 2262 | C | C | T | noncoding | n/d | n/a | n/a | n/d |
| 73 | 7526192 | 1231274R6 | SNP00115694 | 8 | 1018 | C | C | T | S113 | n/a | n/a | n/a | n/a |
| 73 | 7526192 | 1341206H1 | SNP00068492 | 33 | 1909 | A | A | G | noncoding | n/d | n/a | n/a | n/a |
| 73 | 7526192 | 1405367T6 | SNP00062572 | 57 | 2446 | G | G | A | noncoding | n/a | n/a | n/a | n/a |
| 73 | 7526192 | 1405367T6 | SNP00098139 | 224 | 2279 | C | C | T | noncoding | n/d | n/a | n/a | n/d |
| 73 | 7526192 | 1417137T6 | SNP00062572 | 34 | 2482 | G | G | A | noncoding | n/a | n/a | n/a | n/a |
| 73 | 7526192 | 1553058T6 | SNP00062572 | 51 | 2453 | G | G | A | noncoding | n/a | n/a | n/a | n/a |
| 73 | 7526192 | 1678219T6 | SNP00098139 | 232 | 2271 | C | C | T | noncoding | n/d | n/a | n/a | n/d |
| 73 | 7526192 | 1722718F6 | SNP00068491 | 24 | 1686 | C | C | T | noncoding | n/a | n/a | n/a | n/a |
| 73 | 7526192 | 1722718F6 | SNP00068492 | 249 | 1911 | A | A | G | noncoding | n/d | n/a | n/a | n/a |
| 73 | 7526192 | 1722718H1 | SNP00068491 | 24 | 1683 | C | C | T | noncoding | n/a | n/a | n/a | n/a |
| 73 | 7526192 | 2997552T6 | SNP00062572 | 180 | 2342 | G | G | A | noncoding | n/a | n/a | n/a | n/a |
| 73 | 7526192 | 2997552T6 | SNP00098139 | 347 | 2177 | C | C | T | noncoding | n/d | n/a | n/a | n/d |
| 73 | 7526192 | 7674218H2 | SNP00068492 | 342 | 1908 | A | A | G | noncoding | n/d | n/a | n/a | n/a |
| 74 | 7526193 | 1328791H1 | SNP00057788 | 217 | 716 | G | G | T | noncoding | n/a | n/a | n/a | n/a |
| 74 | 7526193 | 4291033F6 | SNP00142508 | 164 | 1539 | A | A | G | N232 | n/a | n/a | n/a | n/a |
| 74 | 7526193 | 4291033F6 | SNP00142509 | 191 | 1566 | A | A | G | T241 | n/a | n/a | n/a | n/a |
| 74 | 7526193 | 7217965H1 | SNP00118120 | 200 | 145 | G | A | G | noncoding | n/d | n/a | n/a | n/a |

TABLE 8-continued

| SEQ ID NO: | PID | EST ID | SNP ID | EST SNP | CB1 SNP | EST Allele | Allele 1 | Allele 2 | Amino Acid | Caucasian Allele 1 frequen-cy | African Allele 1 frequen-cy | Asian Allele 1 frequen-cy | Hispanic Allele 1 frequen-cy |
|---|---|---|---|---|---|---|---|---|---|---|---|---|---|
| 74 | 7526193 | 7760201H1 | SNP00057788 | 118 | 715 | G | G | T | noncoding | n/a | n/a | n/a | n/a |
| 75 | 7526196 | 1216956H1 | SNP00006796 | 60 | 4315 | A | A | G | noncoding | 0.98 | n/a | n/a | n/a |
| 75 | 7526196 | 1224406H1 | SNP00124328 | 162 | 2487 | A | A | G | noncoding | n/d | n/a | n/a | n/a |
| 75 | 7526196 | 1436210H1 | SNP00006288 | 103 | 3533 | G | G | A | noncoding | 0.97 | n/a | n/a | n/a |
| 75 | 7526196 | 1438205H1 | SNP00124330 | 102 | 3121 | A | A | G | noncoding | n/d | n/a | n/a | n/a |
| 75 | 7526196 | 1555235H1 | SNP00006287 | 133 | 3401 | C | T | C | noncoding | 0.34 | n/a | n/a | n/a |
| 75 | 7526196 | 1597263F6 | SNP00124329 | 113 | 2824 | A | A | G | noncoding | n/d | n/d | n/d | n/d |
| 75 | 7526196 | 1669032H1 | SNP00124327 | 46 | 65 | C | T | C | noncoding | n/a | n/a | n/a | n/a |
| 75 | 7526196 | 2555446F6 | SNP00068980 | 190 | 1856 | A | A | G | noncoding | n/d | n/d | n/d | n/d |
| 75 | 7526196 | 2555446H1 | SNP00068980 | 190 | 1854 | A | A | G | noncoding | n/d | n/d | n/d | n/d |
| 75 | 7526196 | 3337906H1 | SNP00153438 | 134 | 2187 | G | G | A | noncoding | n/a | n/a | n/a | n/a |
| 75 | 7526196 | 3643184H1 | SNP00068979 | 155 | 1594 | C | C | T | noncoding | n/a | n/a | n/a | n/a |
| 75 | 7526196 | 6754284H1 | SNP00068978 | 420 | 1195 | A | A | G | noncoding | n/a | n/a | n/a | n/a |
| 75 | 7526196 | 7703764J1 | SNP00124330 | 162 | 3128 | A | A | G | noncoding | n/d | n/a | n/a | n/a |
| 75 | 7526196 | 7753868H1 | SNP00124329 | 510 | 2852 | A | A | G | noncoding | n/d | n/d | n/d | n/d |
| 75 | 7526196 | 7753868H1 | SNP00124330 | 213 | 3149 | A | A | G | noncoding | n/d | n/a | n/a | n/a |
| 75 | 7526196 | 8598525H1 | SNP00006287 | 238 | 3428 | T | T | C | noncoding | 0.34 | n/a | n/a | n/a |
| 75 | 7526196 | 8598525H1 | SNP00006288 | 370 | 3560 | G | G | A | noncoding | 0.97 | n/a | n/a | n/a |
| 76 | 7526198 | 1216956H1 | SNP00006796 | 60 | 4122 | A | A | G | K1309 | 0.98 | n/a | n/a | n/a |
| 76 | 7526198 | 1224406H1 | SNP00124328 | 162 | 2284 | A | A | G | K696 | n/d | n/a | n/a | n/a |
| 76 | 7526198 | 1436210H1 | SNP00006288 | 103 | 3331 | G | G | A | A1045 | 0.97 | n/a | n/a | n/a |
| 76 | 7526198 | 1438205H1 | SNP00124330 | 102 | 2918 | A | A | G | T908 | n/d | n/a | n/a | n/a |
| 76 | 7526198 | 1555235H1 | SNP00006287 | 133 | 3199 | C | T | C | S1001 | 0.34 | n/a | n/a | n/a |
| 76 | 7526198 | 1597263F6 | SNP00124329 | 113 | 2621 | A | A | G | N809 | n/d | n/d | n/d | n/d |
| 76 | 7526198 | 1669032H1 | SNP00124327 | 46 | 65 | C | T | C | noncoding | n/a | n/a | n/a | n/a |
| 76 | 7526198 | 1806969T6 | SNP00029581 | 329 | 4272 | C | C | T | noncoding | n/a | n/a | n/a | n/a |
| 76 | 7526198 | 1922794H1 | SNP00092542 | 84 | 4217 | G | G | A | D1341 | n/a | n/a | n/a | n/a |
| 76 | 7526198 | 2005750H1 | SNP00029581 | 61 | 4270 | C | C | T | noncoding | n/a | n/a | n/a | n/a |
| 76 | 7526198 | 2189973H1 | SNP00136926 | 25 | 4147 | C | C | T | A1317 | n/a | n/a | n/a | n/a |
| 76 | 7526198 | 2555446F6 | SNP00068980 | 190 | 1655 | A | A | G | N487 | n/d | n/d | n/d | n/d |
| 76 | 7526198 | 2555446H1 | SNP00068980 | 190 | 1653 | A | A | G | Y486 | n/d | n/d | n/d | n/d |
| 76 | 7526198 | 2936740H1 | SNP00006289 | 104 | 3928 | C | C | T | T1244 | 0.91 | n/a | n/a | n/a |
| 76 | 7526198 | 3337906H1 | SNP00153438 | 134 | 1984 | G | G | A | R596 | n/a | n/a | n/a | n/a |
| 76 | 7526198 | 3643184H1 | SNP00068979 | 155 | 1393 | C | C | T | S399 | n/a | n/a | n/a | n/a |
| 76 | 7526198 | 6754284H1 | SNP00068978 | 420 | 994 | A | A | G | G266 | n/a | n/a | n/a | n/a |
| 76 | 7526198 | 7703764J1 | SNP00124330 | 162 | 2925 | A | A | G | Q910 | n/d | n/a | n/a | n/a |
| 76 | 7526198 | 7753868H1 | SNP00124329 | 510 | 2649 | A | A | G | D818 | n/d | n/d | n/d | n/d |
| 76 | 7526198 | 7753868H1 | SNP00124330 | 213 | 2946 | A | A | G | H917 | n/d | n/a | n/a | n/a |
| 76 | 7526198 | 8598525H1 | SNP00006287 | 238 | 3226 | T | T | C | D1010 | 0.34 | n/a | n/a | n/a |
| 76 | 7526198 | 8598525H1 | SNP00006288 | 370 | 3358 | G | G | A | T1054 | 0.97 | n/a | n/a | n/a |
| 77 | 7526208 | 1236920F1 | SNP00033469 | 330 | 3805 | C | C | T | noncoding | n/a | n/a | n/a | n/a |
| 77 | 7526208 | 1284901H1 | SNP00013862 | 33 | 2502 | C | C | G | Q454 | 0.91 | n/a | n/a | n/a |
| 77 | 7526208 | 1915448H1 | SNP00003491 | 119 | 5753 | A | A | G | noncoding | n/a | n/a | n/a | n/a |
| 77 | 7526208 | 2528372H1 | SNP00053975 | 148 | 2683 | C | C | T | noncoding | n/a | n/a | n/a | n/a |
| 77 | 7526208 | 2681418H1 | SNP00053974 | 116 | 2185 | T | T | C | L348 | n/d | n/a | n/a | n/a |
| 77 | 7526208 | 2749684F6 | SNP00153340 | 187 | 1794 | T | T | C | W218 | n/a | n/a | n/a | n/a |
| 77 | 7526208 | 3331418H1 | SNP00132658 | 181 | 2866 | T | T | C | noncoding | n/a | n/a | n/a | n/a |
| 77 | 7526208 | 3693823H1 | SNP00053972 | 67 | 1115 | C | C | T | noncoding | n/d | n/a | n/a | n/a |
| 77 | 7S26208 | 3967421F6 | SNP00033469 | 163 | 3806 | C | C | T | noncoding | n/a | n/a | n/a | n/a |
| 77 | 7526208 | 5055874H1 | SNP00113323 | 139 | 5405 | T | T | G | noncoding | n/a | n/a | n/a | n/a |
| 77 | 7526208 | 6449431H1 | SNP00053973 | 480 | 1969 | T | C | T | V276 | n/a | n/a | n/a | n/a |
| 78 | 7526212 | 2749684F6 | SNP00153340 | 187 | 1794 | T | T | C | W218 | n/a | n/a | n/a | n/a |
| 78 | 7526212 | 3693823H1 | SNP00053972 | 67 | 1115 | C | C | T | noncoding | n/d | n/a | n/a | n/a |
| 78 | 7526212 | 6449431H1 | SNP00053973 | 480 | 1969 | T | C | T | V276 | n/a | n/a | n/a | n/a |
| 79 | 7526213 | 1430148F6 | SNP00014900 | 123 | 3197 | C | G | C | noncoding | 0.04 | n/a | n/a | n/a |
| 79 | 7526213 | 2113230H1 | SNP00044591 | 151 | 6811 | C | C | T | noncoding | n/a | n/a | n/a | n/a |
| 79 | 7526213 | 2113230R6 | SNP00044591 | 151 | 6814 | C | C | T | noncoding | n/a | n/a | n/a | n/a |
| 79 | 7526213 | 2556574H1 | SNP00139931 | 137 | 2468 | A | A | G | noncoding | n/a | n/a | n/a | n/a |
| 79 | 7526213 | 2987033F6 | SNP00153180 | 352 | 6398 | C | C | T | noncoding | n/a | n/a | n/a | n/a |
| 79 | 7526213 | 3844660H1 | SNP00014900 | 64 | 3198 | C | G | C | noncoding | 0.04 | n/a | n/a | n/a |
| 79 | 7526213 | 712904R6 | SNP00139930 | 72 | 2210 | A | G | A | noncoding | n/a | n/a | n/a | n/a |
| 80 | 7526214 | 1430148F6 | SNP00014900 | 123 | 3134 | C | G | C | noncoding | 0.04 | n/a | n/a | n/a |
| 80 | 7526214 | 2113230H1 | SNP00044591 | 151 | 6746 | C | C | T | noncoding | n/a | n/a | n/a | n/a |
| 80 | 7526214 | 2113230R6 | SNP00044591 | 151 | 6749 | C | C | T | noncoding | n/a | n/a | n/a | n/a |
| 80 | 7526214 | 2556574H1 | SNP00139931 | 137 | 2403 | A | A | G | noncoding | n/a | n/a | n/a | n/a |
| 80 | 7526214 | 2987033F6 | SNP00153180 | 352 | 6333 | C | C | T | noncoding | n/a | n/a | n/a | n/a |
| 80 | 7526214 | 3844660H1 | SNP00014900 | 64 | 3135 | C | G | C | noncoding | 0.04 | n/a | n/a | n/a |
| 81 | 7526228 | 1485690T6 | SNP00066816 | 319 | 2716 | G | G | A | noncoding | n/d | n/d | 0.96 | n/d |
| 81 | 7526228 | 1835249H1 | SNP00066816 | 8 | 2712 | G | G | A | noncoding | n/d | n/d | 0.96 | n/d |
| 81 | 7526228 | 2169542T6 | SNP00066816 | 241 | 2740 | G | G | A | noncoding | n/d | n/d | 0.96 | n/d |
| 81 | 7526228 | 2536771H1 | SNP00136441 | 18 | 234 | G | G | A | noncoding | n/a | n/a | n/a | n/a |
| 81 | 7526228 | 2805663T6 | SNP00066816 | 251 | 2787 | G | G | A | noncoding | n/d | n/d | 0.96 | n/d |
| 81 | 7526228 | 510019T6 | SNP00066816 | 194 | 2713 | G | G | A | noncoding | n/d | n/d | 0.96 | n/d |
| 82 | 7526246 | 1294154H1 | SNP00068998 | 123 | 2362 | A | A | G | noncoding | n/a | n/a | n/a | n/a |
| 82 | 7526246 | 1545488H1 | SNP00068997 | 78 | 2115 | C | C | G | noncoding | n/a | n/a | n/a | n/a |

TABLE 8-continued

| SEQ ID NO: | PID | EST ID | SNP ID | EST SNP | CB1 SNP | EST Allele | Allele 1 | Allele 2 | Amino Acid | Caucasian Allele 1 frequency | African Allele 1 frequency | Asian Allele 1 frequency | Hispanic Allele 1 frequency |
|---|---|---|---|---|---|---|---|---|---|---|---|---|---|
| 82 | 7526246 | 280325T6 | SNP00068997 | 58 | 2182 | C | C | G | noncoding | n/a | n/a | n/a | n/a |
| 82 | 7526246 | 4407121H1 | SNP00041996 | 224 | 2946 | A | A | G | noncoding | n/a | n/a | n/a | n/a |
| 82 | 7526246 | 7621966J1 | SNP00068997 | 165 | 2116 | C | C | G | noncoding | n/a | n/a | n/a | n/a |
| 82 | 7526246 | 7751044H1 | SNP00068998 | 486 | 2365 | A | A | G | noncoding | n/a | n/a | n/a | n/a |
| 83 | 7526258 | 1348638F6 | SNP00076027 | 241 | 328 | G | G | C | G74 | n/d | n/d | n/d | n/d |
| 83 | 7526258 | 1348638F6 | SNP00132757 | 63 | 150 | A | A | G | R14 | n/a | n/a | n/a | n/a |
| 83 | 7526258 | 1444773H1 | SNP00037439 | 67 | 402 | G | G | C | L98 | n/a | n/a | n/a | n/a |
| 83 | 7526258 | 1897166H1 | SNP00043983 | 191 | 1194 | T | T | C | P362 | n/a | n/a | n/a | n/a |
| 83 | 7526258 | 2770947H1 | SNP00154171 | 21 | 1113 | C | T | C | D335 | n/a | n/a | n/a | n/a |
| 83 | 7526258 | 3143852H1 | SNP00037440 | 73 | 1151 | T | C | T | L348 | n/d | n/d | n/d | n/d |
| 83 | 7526258 | 3143852H1 | SNP00111294 | 30 | 1108 | C | C | T | L334 | 1 | n/d | n/d | n/d |
| 84 | 7526311 | 1649261F6 | SNP00019740 | 300 | 2179 | T | T | C | noncoding | n/a | n/a | n/a | n/a |
| 84 | 7526311 | 1649261T6 | SNP00019740 | 252 | 2259 | T | T | C | noncoding | n/a | n/a | n/a | n/a |
| 84 | 7526311 | 268900T6 | SNP00019740 | 257 | 2257 | T | T | C | noncoding | n/a | n/a | n/a | n/a |
| 84 | 7526311 | 2745158H1 | SNP00058093 | 32 | 1282 | T | T | C | noncoding | 0.82 | 0.9 | 0.98 | 0.92 |
| 84 | 7526311 | 2745158H1 | SNP00114001 | 97 | 1347 | G | T | G | noncoding | n/a | n/a | n/a | n/a |
| 84 | 7526311 | 2921293T6 | SNP00019740 | 268 | 2235 | T | T | C | noncoding | n/a | n/a | n/a | n/a |
| 84 | 7526311 | 8011285H1 | SNP00125603 | 438 | 540 | C | C | T | A129 | n/a | n/a | n/a | n/a |
| 85 | 7526315 | 058064H1 | SNP00003740 | 186 | 1775 | A | A | G | noncoding | n/a | n/a | n/a | n/a |
| 85 | 7526315 | 1004004H1 | SNP00012539 | 79 | 5335 | T | C | T | noncoding | n/a | n/a | n/a | n/a |
| 85 | 7526315 | 1004004H1 | SNP00012540 | 191 | 5447 | G | A | G | noncoding | 0.71 | 0.63 | 0.86 | 0.64 |
| 85 | 7526315 | 1004004H1 | SNP00045700 | 205 | 5461 | C | C | T | noncoding | n/a | n/a | n/a | n/a |
| 85 | 7526315 | 1330039H1 | SNP00045701 | 48 | 5601 | G | G | C | noncoding | n/a | n/a | n/a | n/a |
| 85 | 7526315 | 1363254H1 | SNP00022215 | 65 | 2848 | A | A | C | noncoding | n/d | n/a | n/a | n/a |
| 85 | 7526315 | 1377277F1 | SNP00012538 | 87 | 4783 | C | C | T | noncoding | n/a | n/a | n/a | n/a |
| 85 | 7526315 | 1675313F6 | SNP00028237 | 82 | 3316 | T | T | C | noncoding | n/a | n/a | n/a | n/a |
| 85 | 7526315 | 1675313F6 | SNP00028238 | 133 | 3367 | A | G | A | noncoding | n/d | n/a | n/a | n/a |
| 85 | 7526315 | 1675313T6 | SNP00012538 | 16 | 4780 | C | C | T | noncoding | n/a | n/a | n/a | n/a |
| 85 | 7526315 | 1682961T7 | SNP00045701 | 458 | 5606 | G | G | C | noncoding | n/a | n/a | n/a | n/a |
| 85 | 7526315 | 3003741H1 | SNP00023889 | 140 | 215 | T | T | G | G5 | n/a | n/a | n/a | n/a |
| 85 | 7526315 | 403838T6 | SNP00028238 | 336 | 3387 | G | G | A | noncoding | n/d | n/a | n/a | n/a |
| 85 | 7526315 | 7622837J1 | SNP00028237 | 242 | 3317 | T | T | C | noncoding | n/a | n/a | n/a | n/a |
| 85 | 7526315 | 7622837J1 | SNP00028238 | 191 | 3368 | G | G | A | noncoding | n/d | n/a | n/a | n/a |
| 85 | 7526315 | 7625836H1 | SNP00028237 | 72 | 3299 | T | T | C | noncoding | n/a | n/a | n/a | n/a |
| 85 | 7526315 | 7625836H1 | SNP00028238 | 123 | 3348 | G | G | A | noncoding | n/d | n/a | n/a | n/a |
| 85 | 7526315 | 7752327H1 | SNP00045701 | 517 | 5600 | G | G | C | noncoding | n/a | n/a | n/a | n/a |
| 86 | 7526442 | 1265917F1 | SNP00149600 | 355 | 1648 | T | T | C | noncoding | n/a | n/a | n/a | n/a |
| 86 | 7526442 | 1382145F6 | SNP00149600 | 469 | 1646 | T | T | C | noncoding | n/a | n/a | n/a | n/a |
| 86 | 7526442 | 1824201F6 | SNP00066979 | 79 | 724 | C | C | T | S139 | n/d | n/d | n/a | n/d |
| 86 | 7526442 | 2046231H1 | SNP00114113 | 226 | 1004 | G | G | C | noncoding | n/d | n/a | n/a | n/a |
| 86 | 7526442 | 2744627F6 | SNP00022802 | 98 | 167 | C | C | G | noncoding | n/a | n/a | n/a | n/a |
| 86 | 7526442 | 691185T6 | SNP00149600 | 55 | 1722 | T | T | C | noncoding | n/a | n/a | n/a | n/a |
| 86 | 7526442 | 7622751H1 | SNP00031991 | 177 | 769 | C | C | T | noncoding | n/a | n/a | n/a | n/a |

What is claimed is:

1. An isolated polypeptide comprising the amino acid sequence of SEQ ID NO: 13.

2. The isolated polypeptide of claim 1 consisting of the amino acid sequence of SEQ ID NO: 13.

3. The isolated polypeptide of claim 1, wherein the polypeptide comprises a heterologous polypeptide.

4. A composition comprising the isolated polypeptide of claim 1.

5. The isolated polypeptide of claim 1, wherein the polypeptide is a fusion protein.

6. The isolated polypeptide of claim 5, wherein the fusion protein comprises a heterologous moeity for facilitating purification.

7. The isolated polypeptide of claim 6, wherein the fusion protein comprises a proteolytic cleavage site for cleaving the heterologous moeity.

8. A composition comprising the isolated polypeptide of claim 1 conjugated to a carrier protein or an aptamer.

* * * * *

SEQUENCE LISTING

```
<160> NUMBER OF SEQ ID NOS: 87

<210> SEQ ID NO 1
<211> LENGTH: 83
<212> TYPE: PRT
<213> ORGANISM: Homo sapiens

<400> SEQUENCE: 1

Met Gly Cys Gly Cys Ser Ser His Pro Glu Asp Asp Trp Met Glu Asn
1               5                   10                  15

Ile Asp Val Cys Glu Asn Cys His Tyr Pro Ile Val Pro Leu Asp Gly
            20                  25                  30

Lys Gly Thr Leu Leu Ile Arg Asn Gly Ser Glu Thr Thr Trp Leu Ser
        35                  40                  45

Leu Cys Thr Ala Met Ser Pro Leu Thr Thr Glu Ile Trp Ala Leu Arg
    50                  55                  60

Arg Gly Asn Ser Ser Ala Ser Trp Ser Arg Ala Ala Ser Gly Gly Arg
65                  70                  75                  80
```

Arg Ser Pro

<210> SEQ ID NO 2
<211> LENGTH: 292
<212> TYPE: PRT
<213> ORGANISM: Homo sapiens

<400> SEQUENCE: 2

```
Met Ala Asp Gln Ala Pro Phe Asp Thr Asp Val Asn Thr Leu Thr Arg
1               5                   10                  15

Phe Val Met Glu Glu Gly Arg Lys Ala Arg Gly Thr Gly Glu Leu Thr
            20                  25                  30

Gln Leu Leu Asn Ser Leu Cys Thr Ala Val Lys Ala Ile Ser Ser Ala
        35                  40                  45

Val Arg Lys Ala Gly Ile Ala His Leu Tyr Gly Ile Ala Gly Ser Thr
    50                  55                  60

Asn Val Thr Gly Asp Gln Val Lys Lys Leu Asp Val Leu Ser Asn Asp
65                  70                  75                  80

Leu Val Met Asn Met Leu Lys Ser Ser Phe Ala Thr Cys Val Leu Val
                85                  90                  95

Ser Glu Glu Asp Lys His Ala Ile Ile Val Glu Pro Glu Lys Arg Gly
            100                 105                 110

Lys Tyr Val Val Cys Phe Asp Pro Leu Asp Gly Ser Ser Asn Ile Asp
        115                 120                 125

Cys Leu Val Ser Val Gly Thr Ile Phe Gly Ile Tyr Arg Lys Lys Ser
    130                 135                 140

Thr Asp Glu Pro Ser Glu Lys Asp Ala Leu Gln Pro Gly Arg Asn Leu
145                 150                 155                 160

Val Ala Ala Gly Tyr Ala Leu Tyr Gly Ser Ala Thr Met Leu Val Leu
                165                 170                 175

Ala Met Asp Cys Gly Val Asn Cys Phe Met Leu Asp Pro Asp Asn Ser
            180                 185                 190

Ala Pro Tyr Gly Ala Arg Tyr Val Gly Ser Met Val Ala Asp Val His
        195                 200                 205

Arg Thr Leu Val Tyr Gly Gly Ile Phe Leu Tyr Pro Ala Asn Lys Lys
    210                 215                 220

Ser Pro Asn Gly Lys Leu Arg Leu Leu Tyr Glu Cys Asn Pro Met Ala
225                 230                 235                 240

Tyr Val Met Glu Lys Ala Gly Gly Met Ala Thr Thr Gly Lys Glu Ala
                245                 250                 255

Val Leu Asp Val Ile Pro Thr Asp Ile His Gln Arg Ala Pro Val Ile
            260                 265                 270

Leu Gly Ser Pro Asp Asp Val Leu Glu Phe Leu Lys Val Tyr Glu Lys
        275                 280                 285

His Ser Ala Gln
    290
```

<210> SEQ ID NO 3
<211> LENGTH: 434
<212> TYPE: PRT
<213> ORGANISM: Homo sapiens

<400> SEQUENCE: 3

```
Met Ala Ser Pro Arg Glu Leu Thr Gln Asn Pro Leu Lys Lys Ile Trp
1               5                   10                  15

Met Pro Tyr Ser Asn Gly Arg Pro Ala Leu His Ala Cys Gln Arg Gly
```

```
            20                  25                  30

Val Cys Met Thr Asn Cys Pro Thr Leu Ile Val Met Val Gly Leu Pro
        35                  40                  45

Ala Arg Gly Lys Thr Tyr Ile Ser Lys Lys Leu Thr Arg Tyr Leu Asn
    50                  55                  60

Trp Ile Gly Val Pro Thr Arg Glu Phe Asn Val Gly Gln Tyr Arg Arg
65                  70                  75                  80

Asp Val Val Lys Thr Tyr Lys Ser Phe Glu Phe Phe Leu Pro Asp Asn
                85                  90                  95

Glu Glu Gly Leu Lys Ile Arg Lys Gln Cys Ala Leu Ala Ala Leu Arg
            100                 105                 110

Asp Val Arg Arg Phe Leu Ser Glu Glu Gly Gly His Val Ala Val Phe
        115                 120                 125

Asp Ala Thr Asn Thr Thr Arg Glu Arg Arg Ala Thr Ile Phe Asn Phe
    130                 135                 140

Gly Glu Gln Asn Gly Tyr Lys Thr Phe Phe Val Glu Ser Ile Cys Val
145                 150                 155                 160

Asp Pro Glu Val Ile Ala Ala Asn Ile Val Gln Val Lys Leu Gly Ser
                165                 170                 175

Pro Asp Tyr Val Asn Arg Asp Ser Asp Glu Ala Thr Glu Asp Phe Met
            180                 185                 190

Arg Arg Ile Glu Cys Tyr Glu Asn Ser Tyr Glu Ser Leu Asp Glu Asp
        195                 200                 205

Leu Asp Arg Asp Leu Ser Tyr Ile Lys Ile Met Asp Val Gly Gln Ser
    210                 215                 220

Tyr Val Val Asn Arg Val Ala Asp His Ile Gln Ser Arg Ile Val Tyr
225                 230                 235                 240

Tyr Leu Met Asn Ile His Val Thr Pro Arg Ser Ile Tyr Leu Cys Arg
                245                 250                 255

His Gly Glu Ser Glu Leu Asn Leu Lys Gly Arg Ile Gly Gly Asp Pro
            260                 265                 270

Gly Leu Ser Pro Arg Gly Arg Glu Phe Ala Lys Ser Leu Ala Gln Phe
        275                 280                 285

Ile Ser Asp Gln Asn Ile Lys Asp Leu Lys Val Trp Thr Ser Gln Met
    290                 295                 300

Lys Arg Thr Ile Gln Thr Ala Glu Ala Leu Gly Val Pro Tyr Glu Gln
305                 310                 315                 320

Trp Lys Val Leu Asn Glu Ile Asp Ala Ser Tyr Glu Asp Leu Val Gln
                325                 330                 335

Arg Leu Glu Pro Val Ile Met Glu Leu Glu Arg Gln Glu Asn Val Leu
            340                 345                 350

Val Ile Cys His Gln Ala Val Met Arg Cys Leu Leu Ala Tyr Phe Leu
        355                 360                 365

Asp Lys Ala Ala Glu Gln Leu Pro Tyr Leu Lys Cys Pro Leu His Thr
    370                 375                 380

Val Leu Lys Leu Thr Pro Val Ala Tyr Gly Cys Lys Val Glu Ser Ile
385                 390                 395                 400

Phe Leu Asn Val Ala Ala Val Asn Thr His Arg Asp Arg Pro Gln Asn
                405                 410                 415

Val Asp Ile Ser Arg Pro Pro Glu Glu Ala Leu Val Thr Val Pro Ala
            420                 425                 430

His Gln
```

```
<210> SEQ ID NO 4
<211> LENGTH: 240
<212> TYPE: PRT
<213> ORGANISM: Homo sapiens

<400> SEQUENCE: 4

Met Ala Ala Leu Tyr Arg Pro Gly Leu Arg Leu Asn Trp His Gly Leu
1               5                   10                  15

Ser Pro Leu Gly Trp Pro Ser Cys Arg Ser Ile Gln Thr Leu Arg Val
            20                  25                  30

Leu Ser Gly Asp Leu Gly Gln Leu Pro Thr Gly Ile Arg Asp Phe Val
        35                  40                  45

Glu His Ser Ala Arg Leu Cys Gln Pro Glu Gly Ile His Ile Cys Asp
    50                  55                  60

Gly Thr Glu Ala Glu Asn Thr Ala Thr Leu Thr Leu Leu Glu Gln Gln
65                  70                  75                  80

Gly Leu Ile Arg Lys Leu Pro Lys Tyr Asn Asn Cys Trp Leu Ala Arg
                85                  90                  95

Thr Asp Pro Lys Asp Val Ala Arg Val Glu Ser Lys Thr Val Ile Val
            100                 105                 110

Thr Pro Ser Gln Arg Asp Thr Val Pro Leu Pro Pro Gly Gly Ala Arg
        115                 120                 125

Gly Gln Leu Gly Asn Trp Met Ser Pro Ala Asp Phe Gln Arg Ala Val
    130                 135                 140

Asp Glu Arg Phe Pro Gly Cys Met Gln Gly Arg Thr Met Tyr Val Leu
145                 150                 155                 160

Pro Phe Ser Met Gly Pro Val Gly Ser Pro Leu Ser Arg Ile Gly Val
                165                 170                 175

Gln Leu Thr Asp Ser Ala Tyr Val Val Ala Ser Met Arg Ile Met Thr
            180                 185                 190

Arg Leu Gly Thr Pro Val Leu Gln Ala Leu Gly Asp Gly Asp Phe Val
        195                 200                 205

Lys Cys Leu His Ser Val Gly Gln Pro Leu Thr Gly Gln Asp Pro Gly
    210                 215                 220

His His Gln Pro Cys Arg Glu Glu Ala Leu Cys Gly Ser Arg Leu Pro
225                 230                 235                 240


<210> SEQ ID NO 5
<211> LENGTH: 199
<212> TYPE: PRT
<213> ORGANISM: Homo sapiens

<400> SEQUENCE: 5

Met Glu Glu Lys Thr Ser Arg Ile Lys Ala Ser Ile Pro Gln Phe Thr
1               5                   10                  15

Asn Ser Pro Thr Met Val Ile Met Val Gly Leu Pro Ala Arg Gly Lys
            20                  25                  30

Thr Tyr Ile Ser Thr Lys Leu Thr Arg Tyr Leu Asn Trp Ile Gly Thr
        35                  40                  45

Pro Thr Lys Val Phe Asn Leu Gly Gln Tyr Arg Arg Glu Ala Val Ser
    50                  55                  60

Tyr Lys Asn Tyr Glu Phe Phe Leu Pro Asp Asn Met Glu Ala Leu Gln
65                  70                  75                  80

Ile Arg Lys Gln Cys Ala Leu Ala Ala Leu Lys Asp Val His Asn Tyr
                85                  90                  95

Leu Ser His Glu Glu Gly His Val Ala Val Phe Asp Ala Thr Asn Thr
            100                 105                 110
```

```
Thr Arg Glu Arg Arg Ser Leu Ile Leu Gln Phe Ala Lys Glu His Gly
        115                 120                 125

Tyr Lys Val Phe Phe Ile Glu Ser Ile Cys Asn Asp Pro Gly Ile Ile
    130                 135                 140

Ala Glu Asn Ile Arg Gln Val Lys Leu Gly Ser Pro Asp Tyr Ile Asp
145                 150                 155                 160

Cys Asp Arg Glu Lys Val Leu Glu Asp Phe Leu Lys Arg Ile Glu Cys
                165                 170                 175

Tyr Glu Val Asn Tyr Gln Pro Leu Asp Glu Glu Leu Asp Arg Ser Ser
            180                 185                 190

Thr Trp Ala His Ala Thr Trp
        195


<210> SEQ ID NO 6
<211> LENGTH: 406
<212> TYPE: PRT
<213> ORGANISM: Homo sapiens

<400> SEQUENCE: 6

Met Glu Glu Lys Thr Ser Arg Ile Lys Val Phe Asn Leu Gly Gln Tyr
1               5                   10                  15

Arg Arg Glu Ala Val Ser Tyr Lys Asn Tyr Glu Phe Phe Leu Pro Asp
            20                  25                  30

Asn Met Glu Ala Leu Gln Ile Arg Lys Gln Cys Ala Leu Ala Ala Leu
        35                  40                  45

Lys Asp Val His Asn Tyr Leu Ser His Glu Glu Gly His Val Ala Val
    50                  55                  60

Phe Asp Ala Thr Asn Thr Thr Arg Glu Arg Arg Ser Leu Ile Leu Gln
65                  70                  75                  80

Phe Ala Lys Glu His Gly Tyr Lys Val Phe Phe Ile Glu Ser Ile Cys
                85                  90                  95

Asn Asp Pro Gly Ile Ile Ala Glu Asn Ile Arg Gln Val Lys Leu Gly
            100                 105                 110

Ser Pro Asp Tyr Ile Asp Cys Asp Arg Glu Lys Val Leu Glu Asp Phe
        115                 120                 125

Leu Lys Arg Ile Glu Cys Tyr Glu Val Asn Tyr Gln Pro Leu Asp Glu
    130                 135                 140

Glu Leu Asp Ser His Leu Ser Tyr Ile Lys Ile Phe Asp Val Gly Thr
145                 150                 155                 160

Arg Tyr Met Val Asn Arg Val Gln Asp His Ile Gln Ser Arg Thr Val
                165                 170                 175

Tyr Tyr Leu Met Asn Ile His Val Thr Pro Arg Ser Ile Tyr Leu Cys
            180                 185                 190

Arg His Gly Glu Ser Glu Leu Asn Ile Arg Gly Arg Ile Gly Gly Asp
        195                 200                 205

Ser Gly Leu Ser Val Arg Gly Lys Gln Tyr Ala Tyr Ala Leu Ala Asn
    210                 215                 220

Phe Ile Gln Ser Gln Gly Ile Ser Ser Leu Lys Val Trp Thr Ser His
225                 230                 235                 240

Met Lys Arg Thr Ile Gln Thr Ala Glu Ala Leu Gly Val Pro Tyr Glu
                245                 250                 255

Gln Trp Lys Ala Leu Asn Glu Ile Asp Ala Gly Val Cys Glu Glu Met
            260                 265                 270

Thr Tyr Glu Glu Ile Gln Glu His Tyr Pro Glu Glu Phe Ala Leu Arg
        275                 280                 285
```

```
Asp Gln Asp Lys Tyr Arg Tyr Arg Tyr Pro Lys Gly Glu Ser Tyr Glu
    290                 295                 300

Asp Leu Val Gln Arg Leu Glu Pro Val Ile Met Glu Leu Glu Arg Gln
305                 310                 315                 320

Glu Asn Val Leu Val Ile Cys His Gln Ala Val Met Arg Cys Leu Leu
                325                 330                 335

Ala Tyr Phe Leu Asp Lys Ser Ser Asp Glu Leu Pro Tyr Leu Lys Cys
            340                 345                 350

Pro Leu His Thr Val Leu Lys Leu Thr Pro Val Ala Tyr Gly Cys Lys
        355                 360                 365

Val Glu Ser Ile Tyr Leu Asn Val Glu Thr Val Asn Thr His Arg Glu
    370                 375                 380

Lys Pro Glu Asn Val Asp Ile Thr Arg Glu Pro Glu Glu Ala Leu Asp
385                 390                 395                 400

Thr Val Pro Ala His Tyr
                405


<210> SEQ ID NO 7
<211> LENGTH: 426
<212> TYPE: PRT
<213> ORGANISM: Homo sapiens

<400> SEQUENCE: 7

Met Glu Glu Lys Thr Ser Arg Ile Lys Ala Ser Ile Pro Gln Phe Thr
1               5                   10                  15

Asn Ser Pro Thr Met Val Ile Met Val Gly Leu Pro Ala Arg Gly Lys
            20                  25                  30

Thr Tyr Ile Ser Thr Lys Leu Thr Arg Tyr Leu Asn Trp Ile Gly Thr
        35                  40                  45

Pro Thr Lys Asp Asn Met Glu Ala Leu Gln Ile Arg Lys Gln Cys Ala
    50                  55                  60

Leu Ala Ala Leu Lys Asp Val His Asn Tyr Leu Ser His Glu Glu Gly
65                  70                  75                  80

His Val Ala Val Phe Asp Ala Thr Asn Thr Thr Arg Glu Arg Arg Ser
                85                  90                  95

Leu Ile Leu Gln Phe Ala Lys Glu His Gly Tyr Lys Val Phe Phe Ile
            100                 105                 110

Glu Ser Ile Cys Asn Asp Pro Gly Ile Ile Ala Glu Asn Ile Arg Gln
        115                 120                 125

Val Lys Leu Gly Ser Pro Asp Tyr Ile Asp Cys Asp Arg Glu Lys Val
    130                 135                 140

Leu Glu Asp Phe Leu Lys Arg Ile Glu Cys Tyr Glu Val Asn Tyr Gln
145                 150                 155                 160

Pro Leu Asp Glu Glu Leu Asp Ser His Leu Ser Tyr Ile Lys Ile Phe
                165                 170                 175

Asp Val Gly Thr Arg Tyr Met Val Asn Arg Val Gln Asp His Ile Gln
            180                 185                 190

Ser Arg Thr Val Tyr Tyr Leu Met Asn Ile His Val Thr Pro Arg Ser
        195                 200                 205

Ile Tyr Leu Cys Arg His Gly Glu Ser Glu Leu Asn Ile Arg Gly Arg
    210                 215                 220

Ile Gly Gly Asp Ser Gly Leu Ser Val Arg Gly Lys Gln Tyr Ala Tyr
225                 230                 235                 240

Ala Leu Ala Asn Phe Ile Gln Ser Gln Gly Ile Ser Ser Leu Lys Val
                245                 250                 255
```

```
Trp Thr Ser His Met Lys Arg Thr Ile Gln Thr Ala Glu Ala Leu Gly
            260                 265                 270

Val Pro Tyr Glu Gln Trp Lys Ala Leu Asn Glu Ile Asp Ala Gly Val
        275                 280                 285

Cys Glu Glu Met Thr Tyr Glu Glu Ile Arg Glu His Tyr Pro Glu Glu
    290                 295                 300

Phe Ala Leu Arg Asp Gln Asp Lys Tyr Arg Tyr Arg Tyr Pro Lys Gly
305                 310                 315                 320

Glu Ser Tyr Glu Asp Leu Val Gln Arg Leu Glu Pro Val Ile Met Glu
                325                 330                 335

Leu Glu Arg Gln Glu Asn Val Leu Val Ile Cys His Gln Ala Val Met
            340                 345                 350

Arg Cys Leu Leu Ala Tyr Phe Leu Asp Lys Ser Ser Asp Glu Leu Pro
        355                 360                 365

Tyr Leu Lys Cys Pro Leu His Thr Val Leu Lys Leu Thr Pro Val Ala
    370                 375                 380

Tyr Gly Cys Lys Val Glu Ser Ile Tyr Leu Asn Val Glu Ala Val Asn
385                 390                 395                 400

Thr His Arg Glu Lys Pro Glu Asn Val Asp Ile Thr Arg Glu Pro Glu
                405                 410                 415

Glu Ala Leu Asp Thr Val Pro Ala His Tyr
            420                 425


<210> SEQ ID NO 8
<211> LENGTH: 355
<212> TYPE: PRT
<213> ORGANISM: Homo sapiens

<400> SEQUENCE: 8

Met Ala Thr Pro Gly Asn Leu Gly Ser Ser Val Leu Ala Ser Lys Thr
1               5                   10                  15

Lys Thr Lys Lys Lys His Phe Val Ala Gln Lys Val Lys Leu Phe Arg
            20                  25                  30

Ala Ser Asp Pro Leu Leu Ser Val Leu Met Trp Gly Val Asn His Ser
        35                  40                  45

Ile Asn Glu Leu Ser His Val Gln Ile Pro Val Met Leu Met Pro Asp
    50                  55                  60

Asp Phe Lys Ala Tyr Ser Lys Ile Lys Val Asp Asn His Leu Phe Asn
65                  70                  75                  80

Lys Glu Asn Met Pro Ser His Phe Lys Phe Lys Glu Tyr Cys Pro Met
                85                  90                  95

Val Phe Arg Asn Leu Arg Glu Arg Phe Gly Ile Asp Asp Gln Asp Phe
            100                 105                 110

Gln Tyr Ile Val Glu Cys His Gly Ile Thr Leu Leu Pro Gln Phe Leu
        115                 120                 125

Gly Met Tyr Arg Leu Asn Val Asp Gly Val Glu Ile Tyr Val Ile Val
    130                 135                 140

Thr Arg Asn Val Phe Ser His Arg Leu Ser Val Tyr Arg Lys Tyr Asp
145                 150                 155                 160

Leu Lys Gly Ser Thr Val Ala Arg Glu Ala Ser Asp Lys Glu Lys Ala
                165                 170                 175

Lys Glu Leu Pro Thr Leu Lys Asp Asn Asp Phe Ile Asn Glu Gly Gln
            180                 185                 190

Lys Ile Tyr Ile Asp Asp Asn Asn Lys Lys Val Phe Leu Glu Lys Leu
        195                 200                 205
```

```
Lys Lys Asp Val Glu Phe Leu Ala Gln Leu Lys Leu Met Asp Tyr Ser
    210                 215                 220

Leu Leu Val Gly Ile His Asp Val Glu Arg Ala Glu Gln Glu Glu Val
225                 230                 235                 240

Glu Cys Glu Glu Asn Asp Gly Glu Glu Glu Gly Glu Ser Asp Gly Thr
                245                 250                 255

His Pro Val Gly Thr Pro Pro Asp Ser Pro Gly Asn Thr Leu Asn Ser
            260                 265                 270

Ser Pro Pro Leu Ala Pro Gly Glu Phe Asp Pro Asn Ile Asp Val Tyr
        275                 280                 285

Gly Ile Lys Cys His Glu Asn Ser Pro Arg Lys Glu Val Tyr Phe Met
    290                 295                 300

Ala Ile Ile Asp Ile Leu Thr His Tyr Asp Ala Lys Lys Lys Ala Ala
305                 310                 315                 320

His Ala Ala Lys Thr Val Lys His Gly Ala Gly Ala Glu Ile Ser Thr
                325                 330                 335

Val Asn Pro Glu Gln Tyr Ser Lys Arg Phe Leu Asp Phe Ile Gly His
            340                 345                 350

Ile Leu Thr
        355


<210> SEQ ID NO 9
<211> LENGTH: 543
<212> TYPE: PRT
<213> ORGANISM: Homo sapiens

<400> SEQUENCE: 9

Met Glu Gly Gly Pro Ala Val Cys Cys Gln Asp Pro Arg Ala Glu Leu
1               5                   10                  15

Val Glu Arg Val Ala Ala Ile Asp Val Thr His Leu Glu Glu Ala Asp
            20                  25                  30

Gly Gly Pro Glu Pro Thr Arg Asn Gly Val Asp Pro Pro Pro Arg Ala
        35                  40                  45

Arg Ala Ala Ser Val Ile Pro Gly Ser Thr Ser Arg Leu Leu Pro Ala
    50                  55                  60

Arg Pro Ser Leu Ser Ala Arg Lys Leu Ser Leu Gln Glu Arg Pro Ala
65                  70                  75                  80

Gly Ser Tyr Leu Glu Ala Gln Ala Gly Pro Tyr Ala Thr Gly Pro Ala
                85                  90                  95

Ser His Ile Ser Pro Arg Ala Trp Arg Arg Pro Thr Ile Glu Ser His
            100                 105                 110

His Val Ala Ile Ser Asp Ala Glu Asp Cys Val Gln Leu Asn Gln Tyr
        115                 120                 125

Lys Leu Gln Ser Glu Ile Gly Lys Gly Ala Tyr Gly Val Val Arg Pro
    130                 135                 140

Ala Tyr Asn Glu Ser Glu Asp Arg His Tyr Ala Met Lys Val Leu Ser
145                 150                 155                 160

Lys Lys Lys Leu Leu Lys Gln Tyr Gly Phe Pro Arg Arg Pro Pro Pro
                165                 170                 175

Arg Gly Ser Gln Ala Ala Gln Gly Gly Pro Ala Lys Gln Leu Leu Pro
            180                 185                 190

Leu Glu Arg Val Tyr Gln Glu Ile Ala Ile Leu Lys Lys Leu Asp His
        195                 200                 205

Val Asn Val Val Lys Leu Ile Glu Val Leu Asp Asp Pro Ala Glu Asp
    210                 215                 220
```

```
Asn Leu Tyr Leu Ala Leu Gln Asn Gln Ala Gln Asn Ile Gln Leu Asp
225                 230                 235                 240

Ser Thr Asn Ile Ala Lys Pro His Ser Leu Leu Pro Ser Glu Gln Gln
                245                 250                 255

Asp Ser Gly Ser Thr Trp Ala Ala Arg Ser Val Phe Asp Leu Leu Arg
            260                 265                 270

Lys Gly Pro Val Met Glu Val Pro Cys Asp Lys Pro Phe Ser Glu Glu
        275                 280                 285

Gln Ala Arg Leu Tyr Leu Arg Asp Val Ile Leu Gly Leu Glu Tyr Leu
    290                 295                 300

His Cys Gln Lys Ile Val His Arg Asp Ile Lys Pro Ser Asn Leu Leu
305                 310                 315                 320

Leu Gly Asp Asp Gly His Val Lys Ile Ala Asp Phe Gly Val Ser Asn
                325                 330                 335

Gln Phe Glu Gly Asn Asp Ala Gln Leu Ser Ser Thr Ala Gly Thr Pro
            340                 345                 350

Ala Phe Met Ala Pro Glu Ala Ile Ser Asp Ser Gly Gln Ser Phe Ser
        355                 360                 365

Gly Lys Ala Leu Asp Val Trp Ala Thr Gly Val Thr Leu Tyr Cys Phe
    370                 375                 380

Val Tyr Gly Lys Cys Pro Phe Ile Asp Asp Phe Ile Leu Ala Leu His
385                 390                 395                 400

Arg Lys Ile Lys Asn Glu Pro Val Val Phe Pro Glu Gly Pro Glu Ile
                405                 410                 415

Ser Glu Glu Leu Lys Asp Leu Ile Leu Lys Met Leu Asp Lys Asn Pro
            420                 425                 430

Glu Thr Arg Ile Gly Val Pro Asp Ile Lys Leu His Pro Trp Val Thr
        435                 440                 445

Lys Asn Gly Glu Glu Pro Ile Pro Ser Glu Glu Glu His Cys Ser Val
    450                 455                 460

Val Glu Val Thr Glu Glu Glu Val Lys Asn Ser Val Arg Leu Ile Pro
465                 470                 475                 480

Ser Trp Thr Thr Val Ile Leu Val Lys Ser Met Leu Arg Lys Arg Ser
                485                 490                 495

Phe Gly Asn Pro Phe Glu Pro Gln Ala Arg Arg Glu Glu Arg Ser Met
            500                 505                 510

Ser Ala Pro Gly Asn Leu Leu Val Lys Glu Gly Phe Gly Glu Gly Gly
        515                 520                 525

Lys Ser Pro Glu Leu Pro Gly Val Gln Glu Asp Glu Ala Ala Ser
    530                 535                 540


<210> SEQ ID NO 10
<211> LENGTH: 445
<212> TYPE: PRT
<213> ORGANISM: Homo sapiens

<400> SEQUENCE: 10

Met Arg Arg Arg Arg Arg Arg Asp Gly Phe Tyr Pro Ala Pro Asp Phe
1               5                   10                  15

Arg Asp Arg Glu Ala Glu Asp Met Ala Gly Val Phe Asp Ile Asp Leu
            20                  25                  30

Asp Gln Pro Glu Asp Ala Gly Ser Glu Asp Glu Leu Glu Glu Gly Ala
        35                  40                  45

Met Ile Val Arg Asn Ala Lys Asp Thr Ala His Thr Lys Ala Glu Arg
    50                  55                  60
```

```
Asn Ile Leu Glu Glu Val Lys His Pro Phe Ile Val Asp Leu Ile Tyr
65                  70                  75                  80

Ala Phe Gln Thr Gly Gly Lys Leu Tyr Leu Ile Leu Glu Tyr Leu Ser
                85                  90                  95

Gly Gly Glu Leu Phe Met Gln Leu Glu Arg Glu Gly Ile Phe Met Glu
            100                 105                 110

Asp Thr Ala Cys Phe Tyr Leu Ala Glu Ile Ser Met Ala Leu Gly His
        115                 120                 125

Leu His Gln Lys Gly Ile Ile Tyr Arg Asp Leu Lys Pro Glu Asn Ile
    130                 135                 140

Met Leu Asn His Gln Gly His Val Lys Leu Thr Asp Phe Gly Leu Cys
145                 150                 155                 160

Lys Glu Ser Ile His Asp Gly Thr Val Thr His Thr Phe Cys Gly Thr
                165                 170                 175

Ile Glu Tyr Met Ala Pro Glu Ile Leu Met Arg Ser Gly His Asn Arg
            180                 185                 190

Ala Val Asp Trp Trp Ser Leu Gly Ala Leu Met Tyr Asp Met Leu Thr
        195                 200                 205

Gly Ala Pro Pro Phe Thr Gly Glu Asn Arg Lys Lys Thr Ile Asp Lys
    210                 215                 220

Ile Leu Lys Cys Lys Leu Asn Leu Pro Pro Tyr Leu Thr Gln Glu Ala
225                 230                 235                 240

Arg Asp Leu Leu Lys Lys Leu Leu Lys Arg Asn Ala Ala Ser Arg Leu
                245                 250                 255

Gly Ala Gly Pro Gly Asp Ala Gly Glu Val Gln Ala His Pro Phe Phe
            260                 265                 270

Arg His Ile Asn Trp Glu Glu Leu Leu Ala Arg Lys Val Glu Pro Pro
        275                 280                 285

Phe Lys Pro Leu Leu Gln Ser Glu Glu Asp Val Ser Gln Phe Asp Ser
    290                 295                 300

Lys Phe Thr Arg Gln Thr Pro Val Asp Ser Pro Asp Asp Ser Thr Leu
305                 310                 315                 320

Ser Glu Ser Ala Asn Gln Val Phe Leu Gly Phe Thr Tyr Val Ala Pro
                325                 330                 335

Ser Val Leu Glu Ser Val Lys Glu Lys Phe Ser Phe Glu Pro Lys Ile
            340                 345                 350

Arg Ser Pro Arg Arg Phe Ile Gly Ser Pro Arg Thr Pro Val Ser Pro
        355                 360                 365

Val Lys Phe Ser Pro Gly Asp Phe Trp Gly Arg Gly Ala Ser Ala Ser
    370                 375                 380

Ala Ala Asn Pro Gln Thr Pro Val Glu Tyr Pro Met Glu Thr Ser Gly
385                 390                 395                 400

Ile Glu Gln Met Asp Val Thr Met Ser Gly Glu Ala Ser Ala Pro Leu
                405                 410                 415

Pro Ile Arg Gln Pro Asn Ser Gly Pro Tyr Lys Lys Gln Ala Phe Pro
            420                 425                 430

Met Ile Ser Lys Arg Pro Glu His Leu Arg Met Asn Leu
        435                 440                 445
```

<210> SEQ ID NO 11
<211> LENGTH: 1219
<212> TYPE: PRT
<213> ORGANISM: Homo sapiens

<400> SEQUENCE: 11

```
Met Ala Asn Asp Ser Pro Ala Lys Ser Leu Val Asp Ile Asp Leu Ser
1               5                   10                  15

Ser Leu Arg Asp Pro Ala Gly Ile Phe Glu Leu Val Glu Val Val Gly
            20                  25                  30

Asn Gly Thr Tyr Gly Gln Val Tyr Lys Gly Arg His Val Lys Thr Gly
        35                  40                  45

Gln Leu Ala Ala Ile Lys Val Met Asp Val Thr Glu Asp Glu Glu Glu
    50                  55                  60

Glu Ile Lys Leu Glu Ile Asn Met Leu Lys Lys Tyr Ser His His Arg
65                  70                  75                  80

Asn Ile Ala Thr Tyr Tyr Gly Ala Phe Ile Lys Lys Ser Pro Pro Gly
                85                  90                  95

His Asp Asp Gln Leu Trp Leu Val Met Glu Phe Cys Gly Ala Gly Ser
            100                 105                 110

Ile Thr Asp Leu Val Lys Asn Thr Lys Gly Asn Thr Leu Lys Glu Asp
        115                 120                 125

Trp Ile Ala Tyr Ile Ser Arg Glu Ile Leu Arg Gly Leu Ala His Leu
    130                 135                 140

His Ile His His Val Ile His Arg Asp Ile Lys Gly Gln Asn Val Leu
145                 150                 155                 160

Leu Thr Glu Asn Ala Glu Val Lys Leu Val Asp Phe Gly Val Ser Ala
                165                 170                 175

Gln Leu Asp Gly Thr Val Gly Arg Arg Asn Thr Phe Ile Gly Thr Pro
            180                 185                 190

Tyr Trp Met Ala Pro Glu Val Ile Ala Cys Asp Glu Asn Pro Asp Ala
        195                 200                 205

Thr Tyr Asp Tyr Arg Ser Asp Leu Trp Ser Cys Gly Ile Thr Ala Ile
    210                 215                 220

Glu Met Gly Glu Gly Ala Pro Pro Leu Cys Asp Met His Pro Met Arg
225                 230                 235                 240

Ala Leu Phe Leu Ile Pro Arg Asn Pro Pro Pro Arg Leu Lys Ser Lys
                245                 250                 255

Lys Trp Ser Lys Lys Phe Phe Ser Phe Ile Glu Gly Cys Leu Val Lys
            260                 265                 270

Asn Tyr Met Gln Arg Pro Ser Thr Glu Gln Leu Leu Lys His Pro Phe
        275                 280                 285

Ile Arg Asp Gln Pro Asn Glu Arg Gln Val Arg Ile Gln Leu Lys Asp
    290                 295                 300

His Ile Asp Arg Thr Arg Lys Lys Arg Gly Glu Lys Asp Glu Thr Glu
305                 310                 315                 320

Tyr Glu Tyr Ser Gly Ser Glu Glu Glu Glu Glu Glu Val Pro Glu Gln
                325                 330                 335

Glu Gly Glu Pro Ser Ser Ile Val Asn Val Pro Gly Glu Ser Thr Leu
            340                 345                 350

Arg Arg Asp Phe Leu Arg Leu Gln Gln Glu Asn Lys Glu Arg Ser Glu
        355                 360                 365

Ala Leu Arg Arg Gln Gln Leu Leu Gln Glu Gln Gln Leu Arg Glu Gln
    370                 375                 380

Glu Glu Tyr Lys Arg Gln Leu Leu Ala Glu Arg Gln Lys Arg Ile Glu
385                 390                 395                 400

Gln Gln Lys Glu Gln Arg Arg Arg Leu Glu Glu Gln Gln Arg Arg Glu
                405                 410                 415

Arg Glu Ala Arg Arg Gln Gln Glu Arg Glu Gln Arg Arg Arg Glu Gln
```

```
            420                 425                 430

Glu Glu Lys Arg Arg Leu Glu Glu Leu Glu Arg Arg Arg Lys Glu Glu
        435                 440                 445

Glu Glu Arg Arg Gln Ala Glu Glu Glu Lys Arg Arg Val Glu Arg Glu
    450                 455                 460

Gln Glu Tyr Ile Arg Arg Gln Leu Glu Glu Glu Gln Arg His Leu Glu
465                 470                 475                 480

Val Leu Gln Gln Gln Leu Leu Gln Glu Gln Ala Met Leu Leu His Asp
                485                 490                 495

His Arg Arg Pro His Pro Gln His Ser Gln Gln Pro Pro Pro Pro Gln
            500                 505                 510

Gln Glu Arg Ser Lys Pro Ser Phe His Ala Pro Glu Pro Lys Ala His
        515                 520                 525

Tyr Glu Pro Ala Asp Arg Ala Arg Glu Val Pro Val Arg Thr Thr Ser
    530                 535                 540

Arg Ser Pro Val Leu Ser Arg Arg Asp Ser Pro Leu Gln Gly Ser Gly
545                 550                 555                 560

Gln Gln Asn Ser Gln Ala Gly Gln Arg Asn Ser Thr Ser Ser Ile Glu
                565                 570                 575

Pro Arg Leu Leu Trp Glu Arg Val Glu Lys Leu Met Pro Arg Pro Gly
            580                 585                 590

Ser Gly Ser Ser Ser Gly Ser Ser Asn Ser Gly Ser Gln Pro Gly Ser
        595                 600                 605

His Pro Gly Ser Gln Ser Gly Ser Gly Glu Arg Phe Arg Val Arg Ser
    610                 615                 620

Ser Ser Lys Ser Glu Gly Ser Pro Ser Gln Arg Leu Glu Asn Ala Val
625                 630                 635                 640

Lys Lys Pro Glu Asp Lys Lys Glu Val Phe Arg Pro Leu Lys Pro Ala
                645                 650                 655

Asp Leu Thr Ala Leu Ala Lys Glu Leu Arg Ala Val Glu Asp Val Arg
            660                 665                 670

Pro Pro His Lys Val Thr Asp Tyr Ser Ser Ser Ser Glu Glu Pro Gly
        675                 680                 685

Thr Thr Asp Glu Glu Asp Asp Asp Val Glu Gln Glu Gly Ala Asp Glu
    690                 695                 700

Ser Thr Ser Gly Pro Glu Asp Thr Arg Ala Ala Ser Ser Leu Asn Leu
705                 710                 715                 720

Ser Asn Gly Glu Thr Glu Ser Val Lys Thr Met Ile Val His Asp Asp
                725                 730                 735

Val Glu Ser Glu Pro Ala Met Thr Pro Ser Lys Glu Gly Thr Leu Ile
            740                 745                 750

Val Arg Gln Ser Thr Val Asp Gln Lys Arg Ala Ser His His Glu Ser
        755                 760                 765

Asn Gly Phe Ala Gly Arg Ile His Leu Leu Pro Asp Leu Leu Gln Gln
    770                 775                 780

Ser His Ser Ser Ser Thr Ser Ser Thr Ser Ser Ser Pro Ser Ser Ser
785                 790                 795                 800

Gln Pro Thr Pro Thr Met Ser Pro Gln Thr Pro Gln Asp Lys Leu Thr
                805                 810                 815

Ala Asn Glu Thr Gln Ser Ala Ser Ser Thr Leu Gln Lys His Lys Ser
            820                 825                 830

Ser Ser Ser Phe Thr Pro Phe Ile Asp Pro Arg Leu Leu Gln Ile Ser
        835                 840                 845
```

```
Pro Ser Ser Gly Thr Thr Val Thr Ser Val Val Gly Phe Ser Cys Asp
    850                 855                 860

Gly Met Arg Pro Glu Ala Ile Arg Gln Asp Pro Thr Arg Lys Gly Ser
865                 870                 875                 880

Val Val Asn Val Asn Pro Thr Asn Thr Arg Pro Gln Ser Asp Thr Pro
                885                 890                 895

Glu Ile Arg Lys Tyr Lys Lys Arg Phe Asn Ser Glu Ile Leu Cys Ala
            900                 905                 910

Ala Leu Trp Gly Val Asn Leu Leu Val Gly Thr Glu Ser Gly Leu Met
        915                 920                 925

Leu Leu Asp Arg Ser Gly Gln Gly Lys Val Tyr Pro Leu Ile Asn Arg
    930                 935                 940

Arg Arg Phe Gln Gln Met Asp Val Leu Glu Gly Leu Asn Val Leu Val
945                 950                 955                 960

Thr Ile Ser Gly Lys Lys Asp Lys Leu Arg Val Tyr Tyr Leu Ser Trp
                965                 970                 975

Leu Arg Asn Lys Ile Leu His Asn Asp Pro Glu Val Glu Lys Lys Gln
            980                 985                 990

Gly Trp Thr Thr Val Gly Asp Leu  Glu Gly Cys Val His  Tyr Lys Val
        995                 1000                1005

Val Lys  Tyr Glu Arg Ile Lys  Phe Leu Val Ile Ala  Leu Lys Ser
    1010                1015                1020

Ser Val  Glu Val Tyr Ala Trp  Ala Pro Lys Pro Tyr  His Lys Phe
    1025                1030                1035

Met Ala  Phe Lys Ser Phe Gly  Glu Leu Val His Lys  Pro Leu Leu
    1040                1045                1050

Val Asp  Leu Thr Val Glu Glu  Gly Gln Arg Leu Lys  Val Ile Tyr
    1055                1060                1065

Gly Ser  Cys Ala Gly Phe His  Ala Val Asp Val Asp  Ser Gly Ser
    1070                1075                1080

Val Tyr  Asp Ile Tyr Leu Pro  Thr His Ile Gln Cys  Ser Ile Lys
    1085                1090                1095

Pro His  Ala Ile Ile Ile Leu  Pro Asn Thr Asp Gly  Met Glu Leu
    1100                1105                1110

Leu Val  Cys Tyr Glu Asp Glu  Gly Val Tyr Val Asn  Thr Tyr Gly
    1115                1120                1125

Arg Ile  Thr Lys Asp Val Val  Leu Gln Trp Gly Glu  Met Pro Thr
    1130                1135                1140

Ser Val  Ala Tyr Ile Arg Ser  Asn Gln Thr Met Gly  Trp Gly Glu
    1145                1150                1155

Lys Ala  Ile Glu Ile Arg Ser  Val Glu Thr Gly His  Leu Asp Gly
    1160                1165                1170

Val Phe  Met His Lys Arg Ala  Gln Arg Leu Lys Phe  Leu Cys Glu
    1175                1180                1185

Arg Asn  Asp Lys Val Phe Phe  Ala Ser Val Arg Ser  Gly Gly Ser
    1190                1195                1200

Ser Gln  Val Tyr Phe Met Thr  Leu Gly Arg Thr Ser  Leu Leu Ser
    1205                1210                1215

Trp
```

<210> SEQ ID NO 12
<211> LENGTH: 1168
<212> TYPE: PRT
<213> ORGANISM: Homo sapiens

<400> SEQUENCE: 12

```
Met Ala Ser Asp Ser Pro Ala Arg Ser Leu Asp Glu Ile Asp Leu Ser
1               5                   10                  15

Ala Leu Arg Asp Pro Ala Gly Ile Phe Glu Leu Val Glu Leu Val Gly
            20                  25                  30

Asn Gly Thr Tyr Gly Gln Val Tyr Lys Gly Arg His Val Lys Thr Gly
        35                  40                  45

Gln Leu Ala Ala Ile Lys Val Met Asp Val Thr Gly Asp Glu Glu Glu
    50                  55                  60

Glu Ile Lys Gln Glu Ile Asn Met Leu Lys Lys Tyr Ser His His Arg
65                  70                  75                  80

Asn Ile Ala Thr Tyr Tyr Gly Ala Phe Ile Lys Lys Asn Pro Pro Gly
                85                  90                  95

Met Asp Asp Gln Leu Trp Leu Val Met Glu Phe Cys Gly Ala Gly Ser
            100                 105                 110

Val Thr Asp Leu Ile Lys Asn Thr Lys Gly Asn Thr Leu Lys Glu Glu
        115                 120                 125

Trp Ile Ala Tyr Ile Cys Arg Glu Ile Leu Arg Gly Leu Ser His Leu
    130                 135                 140

His Gln His Lys Val Ile His Arg Asp Ile Lys Gly Gln Asn Val Leu
145                 150                 155                 160

Leu Thr Glu Asn Ala Glu Val Lys Leu Val Asp Phe Gly Val Ser Ala
                165                 170                 175

Gln Leu Asp Arg Thr Val Gly Arg Arg Asn Thr Phe Ile Gly Thr Pro
            180                 185                 190

Tyr Trp Met Ala Pro Glu Val Ile Ala Cys Asp Glu Asn Pro Asp Ala
        195                 200                 205

Thr Tyr Asp Phe Lys Ser Asp Leu Trp Ser Leu Gly Ile Thr Ala Ile
    210                 215                 220

Glu Met Ala Glu Gly Ala Pro Pro Leu Cys Asp Met His Pro Met Arg
225                 230                 235                 240

Ala Leu Phe Leu Ile Pro Arg Asn Pro Ala Pro Arg Leu Lys Ser Lys
                245                 250                 255

Lys Trp Ser Lys Lys Phe Gln Ser Phe Ile Glu Ser Cys Leu Val Lys
            260                 265                 270

Asn His Ser Gln Arg Pro Ala Thr Glu Gln Leu Met Lys His Pro Phe
        275                 280                 285

Ile Arg Asp Gln Pro Asn Glu Arg Gln Val Arg Ile Gln Leu Lys Asp
    290                 295                 300

His Ile Asp Arg Thr Lys Lys Lys Arg Gly Glu Lys Asp Glu Thr Glu
305                 310                 315                 320

Tyr Glu Tyr Ser Gly Ser Glu Glu Glu Glu Glu Glu Asn Asp Ser Gly
                325                 330                 335

Glu Pro Ser Ser Ile Leu Asn Leu Pro Gly Glu Ser Thr Leu Arg Arg
            340                 345                 350

Asp Phe Leu Arg Leu Gln Leu Ala Asn Lys Glu Arg Ser Glu Ala Leu
        355                 360                 365

Arg Arg Gln Gln Leu Glu Gln Gln Arg Glu Asn Glu Glu His Lys
    370                 375                 380

Arg Gln Leu Leu Ala Glu Arg Gln Lys Arg Ile Glu Glu Gln Lys Glu
385                 390                 395                 400

Gln Arg Arg Arg Leu Glu Glu Ile Pro His Leu Val Ala Val Lys Ser
                405                 410                 415
```

```
Gln Gly Pro Ala Leu Thr Ala Ser Gln Ser Val His Glu Gln Pro Thr
            420                 425                 430

Lys Gly Leu Ser Gly Phe Gln Glu Ala Leu Asn Val Thr Ser His Arg
        435                 440                 445

Val Glu Met Pro Arg Gln Asn Ser Asp Pro Thr Ser Glu Asn Pro Pro
    450                 455                 460

Leu Pro Thr Arg Ile Glu Lys Phe Asp Arg Ser Ser Trp Leu Arg Gln
465                 470                 475                 480

Glu Glu Asp Ile Pro Pro Lys Val Pro Gln Arg Thr Thr Ser Ile Ser
                485                 490                 495

Pro Ala Leu Ala Arg Lys Asn Ser Pro Gly Asn Gly Ser Ala Leu Gly
            500                 505                 510

Pro Arg Leu Gly Ser Gln Pro Ile Arg Ala Ser Asn Pro Asp Leu Arg
        515                 520                 525

Arg Thr Glu Pro Ile Leu Glu Ser Pro Leu Gln Arg Thr Ser Ser Gly
    530                 535                 540

Ser Ser Ser Ser Ser Ser Thr Pro Ser Ser Gln Pro Ser Ser Gln Gly
545                 550                 555                 560

Gly Ser Gln Pro Gly Ser Gln Ala Gly Ser Ser Gly Arg Thr Arg Val
                565                 570                 575

Arg Ala Asn Ser Lys Ser Glu Gly Ser Pro Val Leu Pro His Glu Pro
            580                 585                 590

Ala Lys Val Lys Pro Glu Glu Ser Arg Asp Ile Thr Arg Pro Ser Arg
        595                 600                 605

Pro Ala Asp Leu Thr Ala Leu Ala Lys Glu Leu Arg Glu Leu Arg Ile
    610                 615                 620

Glu Glu Thr Asn Arg Pro Met Lys Lys Val Thr Asp Tyr Ser Ser Ser
625                 630                 635                 640

Ser Glu Glu Ser Glu Ser Ser Glu Glu Glu Glu Glu Asp Gly Glu Ser
                645                 650                 655

Glu Thr His Asp Gly Thr Val Ala Val Ser Asp Ile Pro Arg Leu Ile
            660                 665                 670

Pro Thr Gly Ala Pro Gly Ser Asn Glu Gln Tyr Asn Val Gly Met Val
        675                 680                 685

Gly Thr His Gly Leu Glu Thr Ser His Ala Asp Ser Phe Ser Gly Ser
    690                 695                 700

Ile Ser Arg Glu Gly Thr Leu Met Ile Arg Glu Thr Ser Gly Glu Lys
705                 710                 715                 720

Lys Arg Ser Gly His Ser Asp Ser Asn Gly Phe Ala Gly His Ile Asn
                725                 730                 735

Leu Pro Asp Leu Val Gln Gln Ser His Ser Pro Ala Gly Thr Pro Thr
            740                 745                 750

Glu Gly Leu Gly Arg Val Ser Thr His Ser Gln Glu Met Asp Ser Gly
        755                 760                 765

Thr Glu Tyr Gly Met Gly Ser Ser Thr Lys Ala Ser Phe Thr Pro Phe
    770                 775                 780

Val Asp Pro Arg Val Tyr Gln Thr Ser Pro Thr Asp Glu Asp Glu Glu
785                 790                 795                 800

Asp Glu Glu Ser Ser Ala Ala Ala Leu Phe Thr Ser Glu Leu Leu Arg
                805                 810                 815

Gln Glu Gln Ala Lys Leu Asn Glu Ala Arg Lys Ile Ser Val Val Asn
            820                 825                 830

Val Asn Pro Thr Asn Ile Arg Pro His Ser Asp Thr Pro Glu Ile Arg
        835                 840                 845
```

```
Gln Tyr Lys Lys Arg Phe Asn Ser Glu Ile Leu Cys Ala Ala Leu Trp
    850                 855                 860

Gly Val Asn Leu Leu Val Gly Thr Glu Asn Gly Leu Met Leu Leu Asp
865                 870                 875                 880

Arg Ser Gly Gln Gly Lys Val Tyr Asn Leu Ile Asn Arg Arg Arg Phe
                885                 890                 895

Gln Gln Met Asp Val Leu Glu Gly Leu Asn Val Leu Val Thr Ile Ser
            900                 905                 910

Gly Lys Lys Asn Lys Leu Arg Val Tyr Tyr Leu Ser Trp Leu Arg Asn
        915                 920                 925

Arg Ile Leu His Asn Asp Pro Glu Val Glu Lys Lys Gln Gly Trp Ile
    930                 935                 940

Thr Val Gly Asp Leu Glu Gly Cys Ile His Tyr Lys Val Val Lys Tyr
945                 950                 955                 960

Glu Arg Ile Lys Phe Leu Val Ile Ala Leu Lys Asn Ala Val Glu Ile
                965                 970                 975

Tyr Ala Trp Ala Pro Lys Pro Tyr His Lys Phe Met Ala Phe Lys Ser
            980                 985                 990

Phe Ala Asp Leu Gln His Lys Pro  Leu Leu Val Asp Leu  Thr Val Glu
        995                 1000                 1005

Glu Gly  Gln Arg Leu Lys Val  Ile Phe Gly Ser His  Thr Gly Phe
    1010                 1015                 1020

His Val  Ile Asp Val Asp Ser  Gly Asn Ser Tyr Asp  Ile Tyr Ile
    1025                 1030                 1035

Pro Ser  His Ile Gln Gly Asn  Ile Thr Pro His Ala  Ile Val Ile
    1040                 1045                 1050

Leu Pro  Lys Thr Asp Gly Met  Glu Met Leu Val Cys  Tyr Glu Asp
    1055                 1060                 1065

Glu Gly  Val Tyr Val Asp Thr  Tyr Gly Arg Ile Thr  Lys Asp Val
    1070                 1075                 1080

Val Leu  Gln Trp Gly Glu Met  Pro Thr Ser Val Ala  Tyr Ile His
    1085                 1090                 1095

Ser Asp  Gln Ile Met Gly Trp  Gly Glu Lys Ala Ile  Glu Ile Arg
    1100                 1105                 1110

Ser Val  Glu Thr Gly His Leu  Asp Gly Val Phe Met  His Lys Arg
    1115                 1120                 1125

Ala Gln  Arg Leu Lys Phe Leu  Cys Glu Arg Asn Asp  Lys Val Phe
    1130                 1135                 1140

Phe Ala  Ser Val Arg Ser Gly  Gly Ser Ser Gln Val  Phe Phe Met
    1145                 1150                 1155

Thr Leu  Asn Arg Asn Ser Met  Met Asn Trp
    1160                 1165


<210> SEQ ID NO 13
<211> LENGTH: 650
<212> TYPE: PRT
<213> ORGANISM: Homo sapiens

<400> SEQUENCE: 13

Met Ala Asp Leu Glu Ala Val Leu Ala Asp Val Ser Tyr Leu Met Ala
1               5                   10                  15

Met Glu Lys Ser Lys Ala Thr Pro Ala Ala Arg Ala Ser Lys Arg Ile
            20                  25                  30

Val Leu Pro Glu Pro Ser Ile Arg Ser Val Met Gln Lys Tyr Leu Ala
        35                  40                  45
```

```
Glu Arg Asn Glu Ile Thr Leu Asp Lys Ile Phe Asn Gln Lys Ile Gly
    50                  55                  60

Phe Leu Leu Phe Lys Asp Phe Cys Leu Asn Glu Ile Asn Glu Ala Val
65                  70                  75                  80

Pro Gln Val Lys Phe Tyr Glu Glu Ile Lys Glu Tyr Glu Lys Leu Asp
                85                  90                  95

Asn Glu Glu Asp Arg Leu Cys Arg Ser Arg Gln Ile Tyr Asp Ala Tyr
            100                 105                 110

Ile Met Lys Glu Leu Leu Ser Cys Ser His Pro Phe Ser Lys Gln Ala
        115                 120                 125

Val Glu His Val Gln Ser His Leu Ser Lys Lys Gln Val Thr Ser Thr
    130                 135                 140

Leu Phe Gln Pro Tyr Ile Glu Glu Ile Cys Glu Ser Leu Arg Gly Asp
145                 150                 155                 160

Ile Phe Gln Lys Phe Met Glu Ser Asp Lys Phe Thr Arg Phe Cys Gln
                165                 170                 175

Trp Lys Asn Val Glu Leu Asn Ile His Leu Thr Met Asn Glu Phe Ser
            180                 185                 190

Val His Arg Ile Ile Gly Arg Gly Gly Phe Gly Glu Val Tyr Gly Cys
        195                 200                 205

Arg Lys Ala Asp Thr Gly Lys Met Tyr Ala Met Lys Cys Leu Asp Lys
    210                 215                 220

Lys Arg Ile Lys Met Lys Gln Gly Glu Thr Leu Ala Leu Asn Glu Arg
225                 230                 235                 240

Ile Met Leu Ser Leu Val Ser Thr Gly Asp Cys Pro Phe Ile Val Cys
                245                 250                 255

Met Thr Tyr Ala Phe His Thr Pro Asp Lys Leu Cys Phe Ile Leu Asp
            260                 265                 270

Leu Met Asn Gly Gly Asp Leu His Tyr His Leu Ser Gln His Gly Val
        275                 280                 285

Phe Ser Glu Lys Glu Met Arg Phe Tyr Ala Thr Glu Ile Ile Leu Gly
    290                 295                 300

Leu Glu His Met His Asn Arg Phe Val Val Tyr Arg Asp Leu Lys Pro
305                 310                 315                 320

Ala Asn Ile Leu Leu Asp Glu His Gly His Ala Arg Ile Ser Asp Leu
                325                 330                 335

Gly Leu Ala Cys Asp Phe Ser Lys Lys Lys Pro His Ala Ser Val Gly
            340                 345                 350

Thr His Gly Tyr Met Ala Pro Glu Val Leu Gln Lys Gly Thr Ala Tyr
        355                 360                 365

Asp Ser Ser Ala Asp Trp Phe Ser Leu Gly Cys Met Leu Phe Lys Leu
    370                 375                 380

Leu Arg Gly His Ser Pro Phe Arg Gln His Lys Thr Lys Asp Lys His
385                 390                 395                 400

Glu Ile Asp Arg Met Thr Leu Thr Val Asn Val Glu Leu Pro Asp Thr
                405                 410                 415

Phe Ser Pro Glu Leu Lys Ser Leu Leu Glu Gly Leu Leu Gln Arg Asp
            420                 425                 430

Val Ser Lys Arg Leu Gly Cys His Gly Gly Gly Ser Gln Glu Val Lys
        435                 440                 445

Glu His Ser Phe Phe Lys Gly Val Asp Trp Gln His Val Tyr Leu Gln
    450                 455                 460

Lys Tyr Pro Pro Pro Leu Ile Pro Pro Arg Gly Glu Val Asn Ala Ala
```

465 470 475 480

Asp Ala Phe Asp Ile Gly Ser Phe Asp Glu Glu Asp Thr Lys Gly Ile
485 490 495

Lys Leu Leu Asp Cys Asp Gln Glu Leu Tyr Lys Asn Phe Pro Leu Val
500 505 510

Ile Ser Glu Arg Trp Gln Gln Glu Val Thr Glu Thr Val Tyr Glu Ala
515 520 525

Val Asn Ala Asp Thr Asp Lys Ile Glu Ala Arg Lys Arg Ala Lys Asn
530 535 540

Lys Gln Leu Gly His Glu Glu Asp Tyr Ala Leu Gly Lys Asp Cys Ile
545 550 555 560

Met His Gly Tyr Met Leu Lys Leu Gly Asn Pro Phe Leu Thr Gln Trp
565 570 575

Gln Arg Arg Tyr Phe Tyr Leu Phe Pro Asn Arg Leu Glu Trp Arg Gly
580 585 590

Glu Gly Glu Ser Arg Ser Asp Pro Glu Phe Val Gln Trp Lys Lys Glu
595 600 605

Leu Asn Glu Thr Phe Lys Glu Ala Arg Arg Leu Leu Arg Arg Ala Pro
610 615 620

Lys Phe Leu Asn Lys Pro Arg Ser Gly Thr Val Glu Leu Pro Lys Pro
625 630 635 640

Ser Leu Cys His Arg Asn Ser Asn Gly Leu
645 650

<210> SEQ ID NO 14
<211> LENGTH: 603
<212> TYPE: PRT
<213> ORGANISM: Homo sapiens

<400> SEQUENCE: 14

Met Lys Asp Tyr Asp Glu Leu Leu Lys Tyr Tyr Glu Leu His Glu Thr
1 5 10 15

Ile Gly Thr Gly Gly Phe Ala Lys Val Lys Leu Ala Cys His Ile Leu
20 25 30

Thr Gly Glu Met Val Ala Ile Lys Ile Met Asp Lys Asn Thr Leu Gly
35 40 45

Ser Asp Leu Pro Arg Ile Lys Thr Glu Ile Glu Ala Leu Lys Asn Leu
50 55 60

Arg His Gln His Ile Cys Gln Leu Tyr His Val Leu Glu Thr Ala Asn
65 70 75 80

Lys Ile Phe Met Val Leu Glu Glu Asn Leu Leu Phe Asp Glu Tyr His
85 90 95

Lys Leu Lys Leu Ile Asp Phe Gly Leu Cys Ala Lys Pro Lys Gly Asn
100 105 110

Lys Asp Tyr His Leu Gln Thr Cys Cys Gly Ser Leu Ala Tyr Ala Ala
115 120 125

Pro Glu Leu Ile Gln Gly Lys Ser Tyr Leu Gly Ser Glu Ala Asp Val
130 135 140

Trp Ser Met Gly Ile Leu Leu Tyr Val Leu Met Cys Gly Phe Leu Pro
145 150 155 160

Phe Asp Asp Asp Asn Val Met Ala Leu Tyr Lys Lys Ile Met Arg Gly
165 170 175

Lys Tyr Asp Val Pro Lys Trp Leu Ser Pro Ser Ser Ile Leu Leu Leu
180 185 190

Gln Gln Met Leu Gln Val Asp Pro Lys Lys Arg Ile Ser Met Lys Asn

```
        195                 200                 205

Leu Leu Asn His Pro Trp Ile Met Gln Asp Tyr Asn Tyr Pro Val Glu
    210                 215                 220

Trp Gln Ser Lys Asn Pro Phe Ile His Leu Asp Asp Asp Cys Val Thr
225                 230                 235                 240

Glu Leu Ser Val His His Arg Asn Asn Arg Gln Thr Met Glu Asp Leu
                245                 250                 255

Ile Ser Leu Trp Gln Tyr Asp His Leu Thr Ala Thr Tyr Leu Leu Leu
            260                 265                 270

Leu Ala Lys Lys Ala Arg Gly Lys Pro Val Arg Leu Arg Leu Ser Ser
        275                 280                 285

Phe Ser Cys Gly Gln Ala Ser Ala Thr Pro Phe Thr Asp Ile Lys Ser
    290                 295                 300

Asn Asn Trp Ser Leu Glu Asp Val Thr Ala Ser Asp Lys Asn Tyr Val
305                 310                 315                 320

Ala Gly Leu Ile Asp Tyr Asp Trp Cys Glu Asp Asp Leu Ser Thr Gly
                325                 330                 335

Ala Ala Thr Pro Arg Thr Ser Gln Phe Thr Lys Tyr Trp Thr Glu Ser
            340                 345                 350

Asn Gly Ala Glu Ser Lys Ser Leu Thr Pro Ala Leu Cys Arg Thr Pro
        355                 360                 365

Ala Asn Lys Leu Lys Asn Lys Glu Asn Val Tyr Thr Pro Lys Ser Ala
    370                 375                 380

Val Lys Asn Glu Glu Tyr Phe Met Phe Pro Glu Pro Lys Thr Pro Val
385                 390                 395                 400

Asn Lys Asn Gln His Lys Arg Glu Ile Leu Thr Thr Pro Asn Arg Tyr
                405                 410                 415

Thr Thr Pro Ser Lys Ala Arg Asn Gln Cys Leu Lys Glu Thr Pro Ile
            420                 425                 430

Lys Ile Pro Val Asn Ser Thr Gly Thr Asp Lys Leu Met Thr Gly Val
        435                 440                 445

Ile Ser Pro Glu Arg Arg Cys Arg Ser Val Glu Leu Asp Leu Asn Gln
    450                 455                 460

Ala His Met Glu Glu Thr Pro Lys Arg Lys Gly Ala Lys Val Phe Gly
465                 470                 475                 480

Ser Leu Glu Arg Gly Leu Asp Lys Val Ile Thr Val Leu Thr Arg Ser
                485                 490                 495

Lys Arg Lys Gly Ser Ala Arg Asp Gly Pro Arg Arg Leu Lys Leu His
            500                 505                 510

Tyr Asn Val Thr Thr Thr Arg Leu Val Asn Pro Asp Gln Leu Leu Asn
        515                 520                 525

Glu Ile Met Ser Ile Leu Pro Lys Lys His Val Asp Phe Val Gln Lys
    530                 535                 540

Gly Tyr Thr Leu Lys Cys Gln Thr Gln Ser Asp Phe Gly Lys Val Thr
545                 550                 555                 560

Met Gln Phe Glu Leu Glu Val Cys Gln Leu Gln Lys Pro Asp Val Val
                565                 570                 575

Gly Ile Arg Arg Gln Arg Leu Lys Gly Asp Ala Trp Val Tyr Lys Arg
            580                 585                 590

Leu Val Glu Asp Ile Leu Ser Ser Cys Lys Val
        595                 600
```

<210> SEQ ID NO 15
<211> LENGTH: 750

```
<212> TYPE: PRT
<213> ORGANISM: Homo sapiens

<400> SEQUENCE: 15

Met Asp Gln Arg Glu Ile Leu Gln Lys Phe Leu Asp Glu Ala Gln Ser
1               5                   10                  15

Lys Lys Ile Thr Lys Glu Glu Phe Ala Asn Glu Phe Leu Lys Leu Lys
            20                  25                  30

Arg Gln Ser Thr Lys Tyr Lys Ala Asp Lys Thr Tyr Pro Thr Thr Val
        35                  40                  45

Ala Glu Lys Pro Lys Asn Ile Lys Lys Asn Arg Tyr Lys Asp Ile Leu
    50                  55                  60

Pro Tyr Asp Tyr Ser Arg Val Glu Leu Ser Leu Ile Thr Ser Asp Glu
65                  70                  75                  80

Asp Ser Ser Tyr Ile Asn Ala Asn Phe Ile Lys Gly Val Tyr Gly Pro
                85                  90                  95

Lys Ala Tyr Ile Ala Thr Gln Gly Pro Leu Ser Thr Thr Leu Leu Asp
            100                 105                 110

Phe Trp Arg Met Ile Trp Glu Tyr Ser Val Leu Glu Thr Arg Thr Ile
        115                 120                 125

Tyr Gln Phe His Tyr Glu Asn Trp Pro Asp His Asp Val Pro Ser Ser
    130                 135                 140

Ile Asp Pro Ile Leu Glu Leu Ile Trp Asp Val Arg Cys Tyr Gln Glu
145                 150                 155                 160

Asp Asp Ser Val Pro Ile Cys Ile His Cys Ser Ala Gly Cys Gly Arg
                165                 170                 175

Thr Gly Val Ile Cys Ala Ile Asp Tyr Thr Trp Met Leu Leu Lys Asp
            180                 185                 190

Gly Ile Ile Pro Glu Asn Phe Ser Val Phe Ser Leu Ile Arg Glu Met
        195                 200                 205

Arg Thr Gln Arg Pro Ser Leu Val Gln Thr Gln Glu Gln Tyr Glu Leu
    210                 215                 220

Val Tyr Asn Ala Val Leu Glu Leu Phe Lys Arg Gln Met Asp Val Ile
225                 230                 235                 240

Arg Asp Lys His Ser Gly Thr Glu Ser Gln Ala Lys His Cys Ile Pro
                245                 250                 255

Glu Lys Asn His Thr Leu Gln Ala Asp Ser Tyr Ser Pro Asn Leu Pro
            260                 265                 270

Lys Ser Thr Thr Lys Ala Ala Lys Met Met Asn Gln Gln Arg Thr Lys
        275                 280                 285

Met Glu Ile Lys Glu Ser Ser Ser Phe Asp Phe Arg Thr Ser Glu Ile
    290                 295                 300

Ser Ala Lys Glu Glu Leu Val Leu His Pro Ala Lys Ser Ser Thr Ser
305                 310                 315                 320

Phe Asp Phe Leu Glu Leu Asn Tyr Ser Phe Asp Lys Asn Ala Asp Thr
                325                 330                 335

Thr Met Lys Trp Gln Thr Lys Ala Phe Pro Ile Val Gly Glu Pro Leu
            340                 345                 350

Gln Lys His Gln Ser Leu Asp Leu Gly Ser Leu Leu Phe Glu Gly Cys
        355                 360                 365

Ser Asn Ser Lys Pro Val Asn Ala Ala Gly Arg Tyr Phe Asn Ser Lys
    370                 375                 380

Val Pro Ile Thr Arg Thr Lys Ser Thr Pro Phe Glu Leu Ile Gln Gln
385                 390                 395                 400
```

```
Arg Glu Thr Lys Glu Val Asp Ser Lys Glu Asn Phe Ser Tyr Leu Glu
                405                 410                 415

Ser Gln Pro His Asp Ser Cys Phe Val Glu Met Gln Ala Gln Lys Val
            420                 425                 430

Met His Val Ser Ser Ala Glu Leu Asn Tyr Ser Leu Pro Tyr Asp Ser
        435                 440                 445

Lys His Gln Ile Arg Asn Ala Ser Asn Val Lys His His Asp Ser Ser
    450                 455                 460

Ala Leu Gly Val Tyr Ser Tyr Ile Pro Leu Val Glu Asn Pro Tyr Phe
465                 470                 475                 480

Ser Ser Trp Pro Pro Ser Gly Thr Ser Ser Lys Met Ser Leu Asp Leu
                485                 490                 495

Pro Glu Lys Arg Asp Gly Thr Val Phe Pro Ser Ser Leu Leu Pro Thr
            500                 505                 510

Ser Ser Thr Ser Leu Phe Ser Tyr Tyr Asn Ser His Asp Ser Leu Ser
        515                 520                 525

Leu Asn Ser Pro Thr Asn Ile Ser Ser Leu Leu Asn Gln Glu Ser Ala
    530                 535                 540

Val Leu Ala Thr Ala Pro Arg Ile Asp Asp Glu Ile Pro Pro Pro Leu
545                 550                 555                 560

Pro Val Arg Thr Pro Glu Ser Phe Ile Val Val Glu Glu Ala Gly Glu
                565                 570                 575

Phe Ser Pro Asn Val Pro Asn Pro Leu Ser Ser Ala Val Lys Val Lys
            580                 585                 590

Ile Gly Thr Ser Leu Glu Trp Gly Gly Thr Ser Glu Pro Lys Lys Phe
        595                 600                 605

Asp Asp Ser Val Ile Leu Arg Pro Ser Lys Ser Val Lys Leu Arg Ser
    610                 615                 620

Pro Lys Ser Glu Leu His Gln Asp Arg Ser Ser Pro Pro Pro Pro Leu
625                 630                 635                 640

Pro Glu Arg Thr Leu Glu Ser Phe Phe Leu Ala Asp Glu Asp Cys Met
                645                 650                 655

Gln Ala Gln Ser Ile Glu Thr Tyr Ser Thr Ser Tyr Pro Asp Thr Met
            660                 665                 670

Glu Asn Ser Thr Ser Ser Lys Gln Thr Leu Lys Thr Pro Gly Lys Ser
        675                 680                 685

Phe Thr Arg Ser Lys Ser Leu Lys Ile Leu Arg Asn Met Lys Lys Ser
    690                 695                 700

Ile Cys Asn Ser Cys Pro Pro Asn Lys Pro Ala Glu Ser Val Gln Ser
705                 710                 715                 720

Asn Asn Ser Ser Ser Phe Leu Asn Phe Gly Phe Ala Asn Arg Phe Ser
                725                 730                 735

Lys Pro Glu Gly Pro Arg Asn Pro Pro Pro Thr Trp Asn Ile
            740                 745                 750


<210> SEQ ID NO 16
<211> LENGTH: 206
<212> TYPE: PRT
<213> ORGANISM: Homo sapiens

<400> SEQUENCE: 16

Met Thr Ser Arg Phe Arg Leu Pro Ala Gly Arg Thr Tyr Asn Val Arg
1               5                   10                  15

Ala Ser Glu Leu Ala Arg Asp Arg Gln His Thr Glu Val Val Cys Asn
            20                  25                  30
```

```
Ile Leu Leu Leu Asp Asn Thr Val Gln Ala Phe Lys Val Asn Lys His
        35                  40                  45

Asp Gln Gly Gln Val Leu Leu Asp Val Val Phe Lys His Leu Asp Leu
    50                  55                  60

Thr Glu Gln Asp Tyr Phe Gly Leu Gln Leu Ala Asp Asp Ser Thr Asp
65                  70                  75                  80

Asn Pro Arg Trp Leu Asp Pro Asn Lys Pro Ile Arg Lys Gln Leu Lys
                85                  90                  95

Arg Gly Ser Pro Tyr Ser Leu Asn Phe Arg Val Lys Phe Phe Val Ser
            100                 105                 110

Asp Pro Asn Lys Leu Gln Glu Glu Tyr Thr Arg Gly Leu Ser Pro Ala
        115                 120                 125

Glu Ala Glu Phe Asn Tyr Leu Asn Thr Ala Arg Thr Leu Glu Leu Tyr
    130                 135                 140

Gly Val Glu Phe His Tyr Ala Arg Asp Gln Ser Asn Asn Glu Ile Met
145                 150                 155                 160

Ile Gly Val Met Ser Gly Gly Ile Leu Ile Tyr Lys Asn Arg Val Arg
                165                 170                 175

Met Asn Thr Phe Pro Trp Leu Lys Ile Val Lys Ile Ser Phe Lys Cys
            180                 185                 190

Lys Gln Phe Phe Ile Gln Leu Arg Lys Glu Leu Ile Pro Lys
        195                 200                 205


<210> SEQ ID NO 17
<211> LENGTH: 733
<212> TYPE: PRT
<213> ORGANISM: Homo sapiens

<400> SEQUENCE: 17

Met Met Lys Arg Arg Arg Glu Arg Leu Gly Ala Pro Cys Leu Arg Ile
1               5                   10                  15

Gln Ile Ser Thr Leu Cys Arg Gly Ala Glu Val Asn Gln His Met Phe
            20                  25                  30

Ser Pro Thr Ser Ala Pro Ala Leu Phe Leu Thr Lys Val Pro Phe Ser
        35                  40                  45

Ala Asp Cys Ala Leu Ala Thr Ser Pro Leu Ala Ile Phe Leu Asn Leu
    50                  55                  60

Arg Ala His Ser Ser Pro Gly Thr Pro Cys Ser Ser Arg Pro Leu Pro
65                  70                  75                  80

Trp Ser Cys Arg Thr Ser Asn Arg Lys Ser Leu Ile Val Thr Ser Ser
                85                  90                  95

Thr Ser Pro Thr Leu Pro Arg Pro His Ser Pro Leu His Gly His Thr
            100                 105                 110

Gly Asn Ser Pro Leu Asp Ser Pro Arg Asn Phe Ser Pro Asn Ala Pro
        115                 120                 125

Ala His Phe Ser Phe Val Pro Ala Arg Arg Thr Asp Gly Arg Arg Trp
    130                 135                 140

Ser Leu Ala Ser Leu Pro Ser Ser Gly Tyr Gly Thr Asn Thr Pro Ser
145                 150                 155                 160

Ser Thr Val Ser Ser Ser Cys Ser Ser Gln Glu Lys Leu His Gln Leu
                165                 170                 175

Pro Phe Gln Pro Thr Ala Asp Glu Leu His Phe Leu Thr Lys His Phe
            180                 185                 190

Ser Thr Glu Ser Val Pro Asp Glu Glu Gly Arg Gln Ser Pro Ala Met
        195                 200                 205
```

```
Arg Pro Arg Ser Arg Ser Leu Ser Pro Gly Arg Ser Pro Val Ser Phe
    210                 215                 220

Asp Ser Glu Ile Ile Met Met Asn His Val Tyr Lys Glu Arg Phe Pro
225                 230                 235                 240

Lys Ala Thr Ala Gln Met Glu Glu Arg Leu Ala Glu Phe Ile Ser Ser
                245                 250                 255

Asn Thr Pro Asp Ser Val Leu Pro Leu Ala Asp Gly Ala Leu Ser Phe
            260                 265                 270

Ile His His Gln Val Ile Glu Met Ala Arg Asp Cys Leu Asp Lys Ser
        275                 280                 285

Arg Ser Gly Leu Ile Thr Ser Gln Tyr Phe Tyr Glu Leu Gln Glu Asn
    290                 295                 300

Leu Glu Lys Leu Leu Gln Asp Ala His Glu Arg Ser Glu Ser Ser Glu
305                 310                 315                 320

Val Ala Phe Val Met Gln Leu Val Lys Lys Leu Met Ile Ile Ile Ala
                325                 330                 335

Arg Pro Ala Arg Leu Leu Glu Cys Leu Glu Phe Asp Pro Glu Glu Phe
            340                 345                 350

Tyr His Leu Leu Glu Ala Ala Glu Gly His Ala Lys Glu Gly Gln Gly
        355                 360                 365

Ile Lys Cys Asp Ile Pro Arg Tyr Ile Val Ser Gln Leu Gly Leu Thr
    370                 375                 380

Arg Asp Pro Leu Glu Glu Met Ala Gln Leu Ser Ser Cys Asp Ser Pro
385                 390                 395                 400

Asp Thr Pro Glu Thr Asp Asp Ser Ile Glu Gly His Gly Ala Ser Leu
                405                 410                 415

Pro Ser Lys Lys Thr Pro Ser Glu Glu Asp Phe Glu Thr Ile Lys Leu
            420                 425                 430

Ile Ser Asn Gly Ala Tyr Gly Ala Val Phe Leu Val Arg His Lys Ser
        435                 440                 445

Thr Arg Gln Arg Phe Ala Met Lys Lys Ile Asn Lys Gln Asn Leu Ile
    450                 455                 460

Leu Arg Asn Gln Ile Gln Gln Ala Phe Val Glu Arg Asp Ile Leu Thr
465                 470                 475                 480

Phe Ala Glu Asn Pro Phe Val Val Ser Met Phe Cys Ser Phe Asp Thr
                485                 490                 495

Lys Arg His Leu Cys Met Val Met Glu Tyr Val Glu Gly Gly Asp Cys
            500                 505                 510

Ala Thr Leu Leu Lys Asn Ile Gly Ala Leu Pro Val Asp Met Val Arg
        515                 520                 525

Leu Tyr Phe Ala Glu Thr Val Leu Ala Leu Glu Tyr Leu His Asn Tyr
    530                 535                 540

Gly Ile Val His Arg Asp Leu Lys Pro Asp Asn Leu Leu Ile Thr Ser
545                 550                 555                 560

Met Gly His Ile Lys Leu Thr Asp Phe Gly Leu Ser Lys Met Gly Leu
                565                 570                 575

Met Ser Leu Thr Thr Asn Leu Tyr Glu Gly His Ile Glu Lys Asp Ala
            580                 585                 590

Arg Glu Phe Leu Asp Lys Gln Val Cys Gly Thr Pro Glu Tyr Ile Ala
        595                 600                 605

Pro Glu Val Ile Leu Arg Gln Gly Tyr Gly Lys Pro Val Asp Trp Trp
    610                 615                 620

Ala Met Gly Ile Ile Leu Tyr Glu Phe Leu Val Gly Cys Val Pro Phe
625                 630                 635                 640
```

```
Phe Gly Asp Thr Pro Glu Glu Leu Phe Gly Gln Val Ile Ser Asp Glu
                645                 650                 655

Ile Val Trp Pro Glu Gly Asp Glu Ala Leu Pro Pro Asp Ala Gln Asp
            660                 665                 670

Leu Thr Ser Lys Leu Leu His Gln Asn Pro Leu Glu Arg Leu Gly Thr
        675                 680                 685

Gly Ser Ala Tyr Glu Val Lys Gln His Pro Phe Phe Thr Gly Leu Asp
    690                 695                 700

Trp Thr Gly Leu Leu Arg Gln Lys Ala Glu Phe Ile Pro Gln Leu Glu
705                 710                 715                 720

Ser Glu Asp Asp Thr Ser Tyr Phe Asp Thr Arg Ser Glu
                725                 730


<210> SEQ ID NO 18
<211> LENGTH: 114
<212> TYPE: PRT
<213> ORGANISM: Homo sapiens

<400> SEQUENCE: 18

Met Gly Asp Glu Lys Asp Ser Trp Lys Val Lys Thr Leu Asp Glu Ile
1               5                   10                  15

Leu Gln Glu Lys Lys Arg Arg Lys Glu Gln Glu Glu Lys Ala Glu Ile
            20                  25                  30

Lys Arg Leu Lys Asn Ser Asp Asp Arg Asp Ser Lys Arg Asp Ser Leu
        35                  40                  45

Glu Glu Gly Glu Leu Arg Asp His Cys Met Glu Ile Thr Ile Arg Asn
    50                  55                  60

Ser Pro Tyr Arg Arg Glu Asp Ser Met Glu Asp Arg Gly Glu Glu Asp
65                  70                  75                  80

Asp Ser Leu Ala Ile Lys Pro Pro Gln Gln Met Ser Arg Lys Glu Lys
                85                  90                  95

Val His His Arg Lys Asp Glu Lys Arg Lys Glu Lys Trp Thr Ala Trp
            100                 105                 110

Ser Ser


<210> SEQ ID NO 19
<211> LENGTH: 612
<212> TYPE: PRT
<213> ORGANISM: Homo sapiens

<400> SEQUENCE: 19

Met Lys Asp Tyr Asp Glu Leu Leu Lys Tyr Tyr Glu Leu His Glu Thr
1               5                   10                  15

Ile Gly Thr Gly Gly Phe Ala Lys Val Lys Leu Ala Cys His Ile Leu
            20                  25                  30

Thr Gly Glu Met Val Ala Ile Lys Ile Met Asp Lys Asn Thr Leu Gly
        35                  40                  45

Tyr Cys Pro Gly Gly Glu Leu Phe Asp Tyr Ile Ile Ser Gln Asp Arg
    50                  55                  60

Leu Ser Glu Glu Glu Thr Arg Val Val Phe Arg Gln Ile Val Ser Ala
65                  70                  75                  80

Val Ala Tyr Val His Ser Gln Gly Tyr Ala His Arg Asp Leu Lys Pro
                85                  90                  95

Glu Asn Leu Leu Phe Asp Glu Tyr His Lys Leu Lys Leu Ile Asp Phe
            100                 105                 110

Gly Leu Cys Ala Lys Pro Lys Gly Asn Lys Asp Tyr His Leu Gln Thr
```

```
        115                 120                 125

Cys Cys Gly Ser Leu Ala Tyr Ala Ala Pro Glu Leu Ile Gln Gly Lys
    130                 135                 140

Ser Tyr Leu Gly Ser Glu Ala Asp Val Trp Ser Met Gly Ile Leu Leu
145                 150                 155                 160

Tyr Val Leu Met Cys Gly Phe Leu Pro Phe Asp Asp Asp Asn Val Met
                165                 170                 175

Ala Leu Tyr Lys Lys Ile Met Arg Gly Lys Tyr Asp Val Pro Lys Trp
            180                 185                 190

Leu Ser Pro Ser Ser Ile Leu Leu Leu Gln Gln Met Leu Gln Val Asp
        195                 200                 205

Pro Lys Lys Arg Ile Ser Met Lys Asn Leu Leu Asn His Pro Trp Ile
    210                 215                 220

Met Gln Asp Tyr Asn Tyr Pro Val Glu Trp Gln Ser Lys Asn Pro Phe
225                 230                 235                 240

Ile His Leu Asp Asp Asp Cys Val Thr Glu Leu Ser Val His His Arg
                245                 250                 255

Asn Asn Arg Gln Thr Met Glu Asp Leu Ile Ser Leu Trp Gln Tyr Asp
            260                 265                 270

His Leu Thr Ala Thr Tyr Leu Leu Leu Leu Ala Lys Lys Ala Arg Gly
        275                 280                 285

Lys Pro Val Arg Leu Arg Leu Ser Ser Phe Ser Cys Gly Gln Ala Ser
    290                 295                 300

Ala Thr Pro Phe Thr Asp Ile Lys Ser Asn Asn Trp Ser Leu Glu Asp
305                 310                 315                 320

Val Thr Ala Ser Asp Lys Asn Tyr Val Ala Gly Leu Ile Asp Tyr Asp
                325                 330                 335

Trp Cys Glu Asp Asp Leu Ser Thr Gly Ala Ala Thr Pro Arg Thr Ser
            340                 345                 350

Gln Phe Thr Lys Tyr Trp Thr Glu Ser Asn Gly Val Glu Ser Lys Ser
        355                 360                 365

Leu Thr Pro Ala Leu Cys Arg Thr Pro Ala Asn Lys Leu Lys Asn Lys
    370                 375                 380

Glu Asn Val Tyr Thr Pro Lys Ser Ala Val Lys Asn Glu Glu Tyr Phe
385                 390                 395                 400

Met Phe Pro Glu Pro Lys Thr Pro Val Asn Lys Asn Gln His Lys Arg
                405                 410                 415

Glu Ile Leu Thr Thr Pro Asn Arg Tyr Thr Thr Pro Ser Lys Ala Arg
            420                 425                 430

Asn Gln Cys Leu Lys Glu Thr Pro Ile Lys Ile Pro Val Asn Ser Thr
        435                 440                 445

Gly Thr Asp Lys Leu Met Thr Gly Val Ile Ser Pro Glu Arg Arg Cys
    450                 455                 460

Arg Ser Val Glu Leu Asp Leu Asn Gln Ala His Met Glu Glu Thr Pro
465                 470                 475                 480

Lys Arg Lys Gly Ala Lys Val Phe Gly Ser Leu Glu Arg Gly Leu Asp
                485                 490                 495

Lys Val Ile Thr Val Leu Thr Arg Ser Lys Arg Lys Gly Ser Ala Arg
            500                 505                 510

Asp Gly Pro Arg Arg Leu Lys Leu His Tyr Asn Val Thr Thr Thr Arg
        515                 520                 525

Leu Val Asn Pro Asp Gln Leu Leu Asn Glu Ile Met Ser Ile Leu Pro
    530                 535                 540
```

```
Lys Lys His Val Asp Phe Val Gln Lys Gly Tyr Thr Leu Lys Cys Gln
545                 550                 555                 560

Thr Gln Ser Asp Phe Gly Lys Val Thr Met Gln Phe Glu Leu Glu Val
                565                 570                 575

Cys Gln Leu Gln Lys Pro Asp Val Val Gly Ile Arg Arg Gln Arg Leu
            580                 585                 590

Lys Gly Asp Ala Trp Val Tyr Lys Arg Leu Val Glu Asp Ile Leu Ser
        595                 600                 605

Ser Cys Lys Val
    610


<210> SEQ ID NO 20
<211> LENGTH: 311
<212> TYPE: PRT
<213> ORGANISM: Homo sapiens

<400> SEQUENCE: 20

Met Leu Ser Glu Val Leu Leu Val Ser Ala Pro Gly Lys Val Ile Leu
1               5                   10                  15

His Gly Glu His Ala Val Val His Gly Lys Val Ala Leu Ala Val Ser
            20                  25                  30

Leu Asn Leu Arg Thr Phe Leu Arg Leu Gln Pro His Ser Asn Gly Lys
        35                  40                  45

Val Asp Leu Ser Leu Pro Asn Ile Gly Ile Lys Arg Ala Trp Asp Val
    50                  55                  60

Ala Arg Leu Gln Ser Leu Asp Thr Ser Phe Leu Glu Gln Gly Asp Val
65                  70                  75                  80

Thr Thr Pro Thr Ser Glu Gln Val Glu Lys Leu Lys Glu Val Ala Gly
                85                  90                  95

Leu Pro Asp Asp Cys Ala Val Thr Glu Arg Leu Ala Val Leu Ala Phe
            100                 105                 110

Leu Tyr Leu Tyr Leu Ser Ile Cys Arg Lys Gln Arg Trp Thr Lys Glu
        115                 120                 125

Asp Leu Glu Leu Ile Asn Lys Trp Ala Phe Gln Gly Glu Arg Met Ile
    130                 135                 140

His Gly Asn Pro Ser Gly Val Asp Asn Ala Asp Ser Thr Trp Gly Gly
145                 150                 155                 160

Ala Leu Arg Tyr His Gln Gly Lys Ile Ser Ser Leu Lys Arg Ser Pro
                165                 170                 175

Ala Leu Gln Ile Leu Leu Thr Asn Ala Lys Val Pro Arg Asn Thr Arg
            180                 185                 190

Ala Leu Val Ala Gly Val Arg Asn Arg Leu Leu Lys Phe Pro Glu Ile
        195                 200                 205

Val Ala Pro Leu Leu Thr Ser Ile Asp Ala Ile Ser Leu Glu Cys Glu
    210                 215                 220

Arg Val Leu Gly Glu Met Gly Glu Ala Pro Ala Pro Glu Gln Tyr Leu
225                 230                 235                 240

Val Leu Glu Glu Leu Ile Asp Met Asn Gln His His Leu Asn Ala Leu
                245                 250                 255

Gly Val Gly His Ala Ser Leu Asp Gln Leu Cys Gln Val Thr Arg Ala
            260                 265                 270

Arg Gly Leu His Ser Lys Leu Thr Gly Ala Gly Gly Gly Gly Cys Gly
        275                 280                 285

Ile Thr Leu Leu Lys Pro Gly Ile Pro Gly Gly Trp Ser Ser Gln Lys
    290                 295                 300
```

```
Trp Arg Pro Arg Ser Arg Pro
305                 310


<210> SEQ ID NO 21
<211> LENGTH: 206
<212> TYPE: PRT
<213> ORGANISM: Homo sapiens

<400> SEQUENCE: 21

Met Ser Ser Pro Arg Gly Phe Arg Ala Glu Pro Val Asn Asp Tyr Glu
1               5                   10                  15

Gly Asn Asp Ser Glu Ala Glu Asp Leu Asn Phe Arg Glu Thr Leu Pro
            20                  25                  30

Ser Ser Ser Gln Glu Asn Thr Pro Arg Ser Lys Val Phe Glu Asn Lys
        35                  40                  45

Val Asn Ser Glu Lys Val Lys Leu Ser Leu Arg Asn Phe Pro His Asn
    50                  55                  60

Asp Tyr Glu Asp Val Phe Glu Glu Pro Ser Glu Ser Gly Ser Asp Pro
65                  70                  75                  80

Ser Met Trp Thr Ala Arg Gly Pro Phe Arg Arg Gly Arg Trp Ser Ser
                85                  90                  95

Glu Asp Glu Glu Ala Ala Gly Pro Ser Gln Ala Leu Ser Pro Leu Leu
            100                 105                 110

Ser Asp Thr Arg Lys Ile Val Ser Glu Gly Glu Leu Asp Gln Leu Ala
        115                 120                 125

Gln Ile Arg Pro Leu Ile Phe Asn Phe His Glu Gln Thr Ala Ile Lys
    130                 135                 140

Asp Cys Leu Lys Ile Leu Glu Glu Lys Thr Ala Ala Tyr Asp Ile Met
145                 150                 155                 160

Gln Glu Phe Met Phe Asn Ile Met Asp Ile Val Ala Gln Met Arg Glu
                165                 170                 175

Gln Arg Ser Gly Met Val Gln Thr Lys Glu Gln Tyr His Phe Cys Tyr
            180                 185                 190

Asp Ile Val Leu Glu Val Leu Arg Lys Leu Leu Thr Leu Asp
        195                 200                 205


<210> SEQ ID NO 22
<211> LENGTH: 1125
<212> TYPE: PRT
<213> ORGANISM: Homo sapiens

<400> SEQUENCE: 22

Met Pro Asp Gln Asp Lys Lys Val Lys Thr Thr Glu Lys Ser Thr Asp
1               5                   10                  15

Lys Gln Gln Glu Ile Thr Ile Arg Asp Tyr Ser Asp Leu Lys Arg Leu
            20                  25                  30

Arg Cys Leu Leu Asn Val Gln Ser Ser Lys Gln Gln Leu Pro Ala Ile
        35                  40                  45

Asn Phe Asp Ser Ala Gln Asn Ser Met Thr Lys Ser Glu Pro Ala Ile
    50                  55                  60

Arg Ala Gly Gly His Arg Ala Arg Gly Gln Trp His Glu Ser Thr Glu
65                  70                  75                  80

Ala Val Glu Leu Glu Asn Phe Ser Ile Asn Tyr Lys Asn Glu Arg Asn
                85                  90                  95

Phe Ser Lys His Pro Gln Arg Lys Leu Phe Gln Glu Ile Phe Thr Ala
            100                 105                 110

Leu Val Lys Asn Arg Leu Ile Ser Arg Glu Trp Val Asn Arg Ala Pro
```

```
        115                 120                 125

Ser Ile His Phe Leu Arg Val Leu Ile Cys Leu Arg Leu Leu Met Arg
    130                 135                 140

Asp Pro Cys Tyr Gln Glu Ile Leu His Ser Leu Gly Gly Ile Glu Asn
145                 150                 155                 160

Leu Ala Gln Tyr Met Glu Ile Val Ala Asn Glu Tyr Leu Gly Tyr Gly
                165                 170                 175

Glu Glu Gln His Thr Val Asp Lys Leu Val Asn Met Thr Tyr Ile Phe
            180                 185                 190

Gln Lys Leu Ala Ala Val Lys Asp Gln Arg Glu Trp Val Thr Thr Ser
        195                 200                 205

Gly Ala His Lys Thr Leu Val Asn Leu Leu Gly Ala Arg Asp Thr Asn
    210                 215                 220

Val Leu Leu Gly Ser Leu Leu Ala Leu Ala Ser Leu Ala Glu Ser Gln
225                 230                 235                 240

Glu Cys Arg Glu Lys Ile Ser Glu Leu Asn Ile Val Glu Asn Leu Leu
                245                 250                 255

Met Ile Leu His Glu Tyr Asp Leu Leu Ser Lys Arg Leu Thr Ala Glu
            260                 265                 270

Leu Leu Arg Leu Leu Cys Ala Glu Pro Gln Val Lys Glu Gln Val Lys
        275                 280                 285

Leu Tyr Glu Gly Ile Pro Val Leu Leu Ser Leu Leu His Ser Asp His
    290                 295                 300

Leu Lys Leu Leu Trp Ser Ile Val Trp Ile Leu Val Gln Val Cys Glu
305                 310                 315                 320

Asp Pro Glu Thr Ser Val Glu Ile Arg Ile Trp Gly Gly Ile Lys Gln
                325                 330                 335

Leu Leu His Ile Leu Gln Gly Asp Arg Asn Phe Val Ser Asp His Ser
            340                 345                 350

Ser Ile Gly Ser Leu Ser Ser Ala Asn Ala Ala Gly Arg Ile Gln Gln
        355                 360                 365

Leu His Leu Ser Glu Asp Leu Ser Pro Arg Glu Ile Gln Glu Asn Thr
    370                 375                 380

Phe Ser Leu Gln Ala Ala Cys Cys Ala Ala Leu Thr Glu Leu Val Leu
385                 390                 395                 400

Asn Asp Thr Asn Ala His Gln Val Val Gln Glu Asn Gly Val Tyr Thr
                405                 410                 415

Ile Ala Lys Leu Ile Leu Pro Asn Lys Gln Lys Asn Ala Ala Lys Ser
            420                 425                 430

Asn Leu Leu Gln Cys Tyr Ala Phe Arg Ala Leu Arg Phe Leu Phe Ser
        435                 440                 445

Met Glu Arg Asn Arg Pro Leu Phe Lys Arg Leu Phe Pro Thr Asp Leu
    450                 455                 460

Phe Glu Ile Phe Ile Asp Ile Gly His Tyr Val Arg Asp Ile Ser Ala
465                 470                 475                 480

Tyr Glu Glu Leu Val Ser Lys Leu Asn Leu Leu Val Glu Asp Glu Leu
                485                 490                 495

Lys Gln Ile Ala Glu Asn Ile Glu Ser Ile Asn Gln Asn Lys Ala Pro
            500                 505                 510

Leu Lys Tyr Ile Gly Asn Tyr Ala Ile Leu Asp His Leu Gly Ser Gly
        515                 520                 525

Ala Phe Gly Cys Val Tyr Lys Val Arg Lys His Ser Gly Gln Asn Leu
    530                 535                 540
```

```
Leu Ala Met Lys Glu Val Asn Leu His Asn Pro Ala Phe Gly Lys Asp
545                 550                 555                 560

Lys Lys Asp Arg Asp Ser Ser Val Arg Asn Ile Val Ser Glu Leu Thr
                565                 570                 575

Ile Ile Lys Glu Gln Leu Tyr His Pro Asn Ile Val Arg Tyr Tyr Lys
            580                 585                 590

Thr Phe Leu Glu Asn Asp Arg Leu Tyr Ile Val Met Glu Leu Ile Glu
        595                 600                 605

Gly Ala Pro Leu Gly Glu His Phe Ser Ser Leu Lys Glu Lys His His
    610                 615                 620

His Phe Thr Glu Glu Arg Leu Trp Lys Ile Phe Ile Gln Leu Cys Leu
625                 630                 635                 640

Ala Leu Arg Tyr Leu His Lys Glu Lys Arg Ile Val His Arg Asp Leu
                645                 650                 655

Thr Pro Asn Asn Ile Met Leu Gly Asp Lys Asp Lys Val Thr Val Thr
            660                 665                 670

Asp Phe Gly Leu Ala Lys Gln Lys Gln Glu Asn Ser Lys Leu Thr Ser
        675                 680                 685

Val Val Gly Thr Ile Leu Tyr Ser Cys Pro Glu Val Leu Lys Ser Glu
    690                 695                 700

Pro Tyr Gly Glu Lys Ala Asp Val Trp Ala Val Gly Cys Ile Leu Tyr
705                 710                 715                 720

Gln Met Ala Thr Leu Ser Pro Pro Phe Tyr Ser Thr Asn Met Leu Ser
                725                 730                 735

Leu Ala Thr Lys Ile Val Glu Ala Val Tyr Glu Pro Val Pro Glu Gly
            740                 745                 750

Ile Tyr Ser Glu Lys Val Thr Asp Thr Ile Ser Arg Cys Leu Thr Pro
        755                 760                 765

Asp Ala Glu Ala Arg Pro Asp Ile Val Glu Val Ser Ser Met Ile Ser
    770                 775                 780

Asp Val Met Met Lys Tyr Leu Asp Asn Leu Ser Thr Ser Gln Leu Ser
785                 790                 795                 800

Leu Glu Lys Lys Leu Glu Arg Glu Arg Arg Arg Thr Gln Arg Tyr Phe
                805                 810                 815

Met Glu Ala Asn Arg Asn Thr Val Thr Cys His His Glu Leu Ala Val
            820                 825                 830

Leu Ser His Glu Thr Phe Glu Lys Ala Ser Leu Ser Ser Ser Ser Ser
        835                 840                 845

Gly Ala Ala Ser Leu Lys Ser Glu Leu Ser Glu Ser Ala Asp Leu Pro
    850                 855                 860

Pro Glu Gly Phe Gln Ala Ser Tyr Gly Lys Asp Glu Asp Arg Ala Cys
865                 870                 875                 880

Asp Glu Ile Leu Ser Asp Asp Asn Phe Asn Leu Glu Asn Ala Glu Lys
                885                 890                 895

Asp Thr Tyr Ser Glu Val Asp Asp Glu Leu Asp Ile Ser Asp Asn Ser
            900                 905                 910

Ser Ser Ser Ser Ser Ser Pro Leu Lys Glu Ser Thr Phe Asn Ile Leu
        915                 920                 925

Lys Arg Ser Phe Ser Ala Ser Gly Gly Glu Arg Gln Ser Gln Thr Arg
    930                 935                 940

Asp Phe Thr Gly Gly Thr Gly Ser Arg Pro Arg Pro Gly Pro Gln Met
945                 950                 955                 960

Gly Thr Phe Leu Trp Gln Ala Ser Ala Gly Ile Ala Val Ser Gln Arg
                965                 970                 975
```

```
Lys Val Arg Gln Ile Ser Asp Pro Ile Gln Gln Ile Leu Ile Gln Leu
            980                 985                 990

His Lys Ile Ile Tyr Ile Thr Gln  Leu Pro Pro Ala Leu  His His Asn
        995                 1000                1005

Leu Lys  Arg Arg Val Ile Glu  Arg Phe Lys Lys Ser  Leu Phe Ser
    1010                1015                1020

Gln Gln  Ser Asn Pro Cys Asn  Leu Lys Ser Glu Ile  Lys Lys Leu
    1025                1030                1035

Ser Gln  Gly Ser Pro Glu Pro  Ile Glu Pro Asn Phe  Phe Thr Ala
    1040                1045                1050

Asp Tyr  His Leu Leu His Arg  Ser Ser Gly Gly Asn  Ser Leu Ser
    1055                1060                1065

Pro Asn  Asp Pro Thr Gly Leu  Pro Thr Ser Ile Glu  Leu Glu Glu
    1070                1075                1080

Gly Ile  Thr Tyr Glu Gln Met  Gln Thr Val Ile Glu  Glu Val Leu
    1085                1090                1095

Glu Glu  Ser Gly Tyr Tyr Asn  Phe Thr Ser Asn Arg  Tyr His Ser
    1100                1105                1110

Tyr Pro  Trp Gly Thr Lys Asn  His Pro Thr Lys Arg
    1115                1120                1125


<210> SEQ ID NO 23
<211> LENGTH: 888
<212> TYPE: PRT
<213> ORGANISM: Homo sapiens

<400> SEQUENCE: 23

Met Gln Ile Val Gly Ser Pro Gly Pro Gly Ala Ala Trp Pro Val Lys
1               5                   10                  15

Arg Val Val Phe Pro Asn Gly Glu Gln Phe Leu Leu Ser Val Ala Thr
            20                  25                  30

Lys Lys Val Ile Cys Leu Cys Leu Gly Lys Ala Gly Arg Lys Val Leu
        35                  40                  45

Ala Lys Lys Leu Ser Pro Leu Glu Thr Met Asp Lys Tyr Asp Val Ile
    50                  55                  60

Lys Ala Ile Gly Gln Gly Ala Phe Gly Lys Ala Tyr Leu Ala Lys Gly
65                  70                  75                  80

Lys Ser Asp Ser Lys His Cys Val Ile Lys Glu Ile Asn Phe Glu Lys
                85                  90                  95

Met Pro Ile Gln Glu Lys Glu Ala Ser Lys Lys Glu Val Ile Leu Leu
            100                 105                 110

Glu Lys Met Lys His Pro Asn Ile Val Ala Phe Phe Asn Ser Phe Gln
        115                 120                 125

Glu Asn Gly Arg Leu Phe Ile Val Met Glu Tyr Cys Asp Gly Gly Asp
    130                 135                 140

Leu Met Lys Arg Ile Asn Arg Gln Arg Gly Val Leu Phe Ser Glu Asp
145                 150                 155                 160

Gln Ile Leu Gly Trp Phe Val Gln Ile Ser Leu Gly Leu Lys His Ile
                165                 170                 175

His Asp Arg Lys Ile Leu His Arg Asp Ile Lys Ala Gln Asn Ile Phe
            180                 185                 190

Leu Ser Lys Asn Gly Met Val Ala Lys Leu Gly Asp Phe Gly Ile Ala
        195                 200                 205

Arg Val Leu Asn Asn Ser Met Glu Leu Ala Arg Thr Cys Ile Gly Thr
    210                 215                 220
```

```
Pro Tyr Tyr Leu Ser Pro Glu Ile Cys Gln Asn Lys Pro Tyr Asn Asn
225                 230                 235                 240

Lys Thr Asp Ile Trp Ser Leu Gly Cys Val Leu Tyr Glu Leu Cys Thr
                245                 250                 255

Leu Lys His Pro Phe Glu Gly Asn Asn Leu Gln Gln Leu Val Leu Lys
            260                 265                 270

Ile Cys Gln Ala His Phe Ala Pro Ile Ser Pro Gly Phe Ser Arg Glu
        275                 280                 285

Leu His Ser Leu Ile Ser Gln Leu Phe Gln Val Ser Pro Arg Asp Arg
    290                 295                 300

Pro Ser Ile Asn Ser Ile Leu Lys Arg Pro Phe Leu Glu Asn Leu Ile
305                 310                 315                 320

Pro Lys Tyr Leu Thr Pro Glu Val Ile Gln Glu Glu Phe Ser His Met
                325                 330                 335

Leu Ile Cys Arg Ala Gly Ala Pro Ala Ser Arg His Ala Gly Lys Val
            340                 345                 350

Val Gln Lys Cys Lys Ile Gln Lys Val Arg Phe Gln Gly Lys Cys Pro
        355                 360                 365

Pro Arg Ser Arg Ile Ser Val Pro Ile Lys Arg Asn Ala Ile Leu His
    370                 375                 380

Arg Asn Glu Trp Arg Pro Pro Ala Gly Ala Gln Lys Ala Arg Ser Ile
385                 390                 395                 400

Lys Met Ile Glu Arg Pro Lys Ile Ala Ala Val Cys Gly His Tyr Asp
                405                 410                 415

Tyr Tyr Tyr Ala Gln Leu Asp Met Leu Arg Arg Arg Ala His Lys Pro
            420                 425                 430

Ser Tyr His Pro Ile Pro Gln Glu Asn Thr Gly Val Glu Asp Tyr Gly
        435                 440                 445

Gln Glu Thr Arg His Gly Pro Ser Pro Ser Gln Trp Pro Ala Glu Tyr
    450                 455                 460

Leu Gln Arg Lys Phe Glu Ala Gln Gln Tyr Lys Leu Lys Val Glu Lys
465                 470                 475                 480

Gln Leu Gly Leu Arg Pro Ser Ser Ala Glu Pro Asn Tyr Asn Gln Arg
                485                 490                 495

Gln Glu Leu Arg Ser Asn Gly Glu Glu Pro Arg Phe Gln Glu Leu Pro
            500                 505                 510

Phe Arg Lys Asn Glu Met Lys Glu Gln Glu Tyr Trp Lys Gln Leu Glu
        515                 520                 525

Glu Ile Arg Gln Gln Tyr His Asn Asp Met Lys Glu Ile Arg Lys Lys
    530                 535                 540

Met Gly Arg Glu Pro Glu Glu Asn Ser Lys Ile Ser His Lys Thr Tyr
545                 550                 555                 560

Leu Val Lys Lys Ser Asn Leu Pro Val His Gln Asp Ala Ser Glu Gly
                565                 570                 575

Glu Ala Pro Val Gln Asp Ile Glu Lys Asp Leu Lys Gln Met Arg Leu
            580                 585                 590

Gln Asn Thr Lys Glu Ser Lys Asn Pro Glu Gln Lys Tyr Lys Ala Lys
        595                 600                 605

Gly Val Lys Phe Glu Ile Asn Leu Asp Lys Cys Ile Ser Asp Glu Asn
    610                 615                 620

Ile Leu Gln Glu Glu Glu Ala Met Asp Ile Pro Asn Glu Thr Leu Thr
625                 630                 635                 640

Phe Glu Asp Gly Met Lys Phe Lys Glu Tyr Glu Cys Val Lys Glu His
```

```
                645                 650                 655

Gly Asp Tyr Thr Asp Lys Ala Phe Glu Lys Leu His Cys Pro Glu Ala
            660                 665                 670

Gly Phe Ser Thr Gln Thr Val Ala Ala Val Gly Asn Arg Arg Gln Trp
        675                 680                 685

Asp Gly Gly Ala Pro Gln Thr Leu Leu Gln Met Met Ala Val Ala Asp
    690                 695                 700

Ile Thr Ser Thr Cys Pro Thr Gly Pro Asp Asn Gly Gln Val Ile Val
705                 710                 715                 720

Ile Glu Gly Ile Pro Gly Asn Arg Lys Gln Trp Arg His Glu Ala Pro
                725                 730                 735

Gly Thr Leu Met Ser Val Leu Ala Ala Ala His Leu Thr Ser Ser Ser
            740                 745                 750

Phe Ser Ala Asp Glu Glu Phe Ala Met Gly Thr Leu Lys Gln Trp Leu
        755                 760                 765

Pro Lys Glu Glu Asp Glu Gly Lys Val Glu Met Val Ser Gly Ile Glu
    770                 775                 780

Val Asp Glu Glu Gln Leu Glu Pro Arg Ser Asp Asp Asp Asp Thr Asn
785                 790                 795                 800

Phe Glu Glu Ser Glu Asp Glu Leu Arg Asp Glu Val Val Glu Tyr Leu
                805                 810                 815

Glu Lys Leu Ala Thr Phe Lys Gly Glu Glu Lys Thr Glu Glu Ala Ser
            820                 825                 830

Ser Thr Ser Lys Asp Ser Arg Lys Ser Arg Glu Arg Glu Gly Ile Ser
        835                 840                 845

Met Gln Lys Ser Glu Glu Leu Arg Glu Gly Leu Glu Asn Ile Ser Thr
    850                 855                 860

Thr Ser Asn Asp His Ile Cys Ile Thr Asp Glu Asp Gln Gly Thr Ser
865                 870                 875                 880

Thr Thr Ser Gln Asn Ile Gln Val
                885
```

<210> SEQ ID NO 24
<211> LENGTH: 487
<212> TYPE: PRT
<213> ORGANISM: Homo sapiens

<400> SEQUENCE: 24

```
Met Gly Arg Ile Gly Ile Ser Cys Leu Phe Pro Ala Ser Trp His Phe
1               5                   10                  15

Ser Ile Ser Pro Val Gly Cys Pro Arg Ile Leu Asn Thr Asn Leu Arg
            20                  25                  30

Gln Ile Met Val Ile Ser Val Leu Ala Ala Ala Val Ser Leu Leu Tyr
        35                  40                  45

Phe Ser Val Val Ile Ile Arg Asn Lys Tyr Gly Arg Leu Thr Arg Asp
    50                  55                  60

Lys Lys Phe Gln Arg Tyr Leu Ala Arg Val Thr Asp Ile Glu Ala Thr
65                  70                  75                  80

Asp Thr Asn Asn Pro Asn Val Asn Tyr Gly Ile Val Val Asp Cys Gly
                85                  90                  95

Ser Ser Gly Ser Arg Val Phe Val Tyr Cys Trp Pro Arg His Asn Gly
            100                 105                 110

Asn Pro His Asp Leu Leu Asp Ile Arg Gln Met Arg Asp Lys Asn Arg
        115                 120                 125

Lys Pro Val Val Met Lys Ile Lys Pro Gly Ile Ser Glu Phe Ala Thr
```

```
    130                 135                 140

Ser Pro Glu Lys Val Ser Asp Tyr Ile Ser Pro Leu Leu Asn Phe Ala
145                 150                 155                 160

Ala Glu His Val Pro Arg Ala Lys His Lys Glu Thr Pro Leu Tyr Ile
                165                 170                 175

Leu Cys Thr Ala Gly Met Arg Ile Leu Pro Glu Ser Gln Gln Lys Ala
            180                 185                 190

Ile Leu Glu Asp Leu Leu Thr Asp Ile Pro Val His Phe Asp Phe Leu
        195                 200                 205

Phe Ser Asp Ser His Ala Glu Val Ile Ser Gly Lys Gln Glu Gly Val
    210                 215                 220

Tyr Ala Trp Ile Gly Ile Asn Phe Val Leu Gly Arg Phe Glu His Ile
225                 230                 235                 240

Glu Asp Asp Asp Glu Ala Val Val Glu Val Asn Ile Pro Gly Ser Val
                245                 250                 255

Ser Ser Glu Ala Ile Val Arg Lys Arg Thr Ala Gly Ile Leu Asp Met
            260                 265                 270

Gly Gly Val Leu Thr Gln Ile Ala Tyr Glu Val Pro Lys Thr Ala Ser
        275                 280                 285

Phe Ala Ser Ser Gln Gln Glu Glu Val Ala Lys Asn Leu Leu Ala Glu
    290                 295                 300

Phe Asn Leu Gly Cys Asp Val His Gln Thr Glu His Val Tyr Arg Val
305                 310                 315                 320

Tyr Val Ala Thr Phe Phe Gly Phe Gly Gly Asn Ala Ala Arg Gln Arg
                325                 330                 335

Tyr Glu Asp Arg Ile Phe Ala Asn Thr Ile Gln Lys Asn Arg Leu Leu
            340                 345                 350

Gly Lys Gln Thr Gly Leu Thr Pro Asp Met Pro Tyr Leu Asp Pro Cys
        355                 360                 365

Leu Pro Leu Asp Ile Lys Asp Glu Ile Gln Gln Asn Gly Gln Thr Ile
    370                 375                 380

Tyr Leu Arg Gly Thr Gly Asp Phe Asp Leu Cys Arg Glu Thr Ile Gln
385                 390                 395                 400

Pro Phe Met Asn Lys Thr Asn Glu Thr Gln Thr Ser Leu Asn Gly Val
                405                 410                 415

Tyr Gln Pro Pro Ile His Phe Gln Asn Ser Glu Phe Tyr Gly Phe Ser
            420                 425                 430

Glu Phe Tyr Tyr Cys Thr Glu Asp Val Leu Arg Met Gly Gly Asp Tyr
        435                 440                 445

Asn Ala Ala Lys Phe Thr Lys Ala Ala Lys Asp Tyr Cys Ala Thr Lys
    450                 455                 460

Trp Ser Ile Leu Arg Glu Arg Phe Asp Arg Gly Leu Tyr Ala Ser His
465                 470                 475                 480

Ala Asp Leu His Arg Leu Lys
                485


<210> SEQ ID NO 25
<211> LENGTH: 1309
<212> TYPE: PRT
<213> ORGANISM: Homo sapiens

<400> SEQUENCE: 25

Met Asp Glu Ser Ser Leu Leu Arg Arg Arg Gly Leu Gln Lys Glu Leu
1               5                   10                  15

Ser Leu Pro Arg Arg Gly Arg Gly Cys Arg Ser Gly Asn Arg Lys Ser
```

```
            20                  25                  30

Leu Val Val Gly Thr Pro Ser Pro Thr Leu Ser Arg Pro Leu Ser Pro
        35                  40                  45

Leu Ser Val Pro Thr Ala Gly Ser Ser Pro Leu Asp Ser Pro Arg Asn
    50                  55                  60

Phe Ser Ala Ala Ser Ala Leu Asn Phe Pro Phe Ala Arg Arg Ala Asp
65                  70                  75                  80

Gly Arg Arg Trp Ser Leu Ala Ser Leu Pro Ser Ser Gly Tyr Gly Thr
                85                  90                  95

Asn Thr Pro Ser Ser Thr Leu Ser Ser Ser Ser Ser Ser Arg Glu Arg
            100                 105                 110

Leu His Gln Leu Pro Phe Gln Pro Thr Pro Asp Glu Leu His Phe Leu
        115                 120                 125

Ser Lys His Phe Arg Ser Ser Glu Asn Val Leu Asp Glu Glu Gly Gly
    130                 135                 140

Arg Ser Pro Arg Leu Arg Pro Arg Ser Arg Ser Leu Ser Pro Gly Arg
145                 150                 155                 160

Ala Thr Gly Thr Phe Asp Asn Glu Ile Val Met Met Asn His Val Tyr
                165                 170                 175

Arg Glu Arg Phe Pro Lys Ala Thr Ala Gln Met Glu Gly Arg Leu Gln
            180                 185                 190

Glu Phe Leu Thr Ala Tyr Ala Pro Gly Ala Arg Leu Ala Leu Ala Asp
        195                 200                 205

Gly Val Leu Gly Phe Ile His His Gln Ile Val Glu Leu Ala Arg Asp
    210                 215                 220

Cys Leu Ala Lys Ser Gly Glu Asn Leu Val Thr Ser Arg Tyr Phe Leu
225                 230                 235                 240

Glu Met Gln Glu Lys Leu Glu Arg Leu Leu Gln Asp Ala His Glu Arg
                245                 250                 255

Ser Asp Ser Glu Glu Val Ser Phe Ile Val Gln Leu Val Arg Lys Leu
            260                 265                 270

Leu Ile Ile Ile Ser Arg Pro Ala Arg Leu Leu Glu Cys Leu Glu Phe
        275                 280                 285

Asp Pro Glu Glu Phe Tyr His Leu Leu Glu Ala Ala Glu Gly His Ala
    290                 295                 300

Arg Glu Gly Gln Gly Ile Lys Thr Asp Leu Pro Gln Tyr Ile Ile Gly
305                 310                 315                 320

Gln Leu Gly Leu Ala Lys Asp Pro Leu Glu Glu Met Val Pro Leu Ser
                325                 330                 335

His Leu Glu Glu Glu Gln Pro Pro Ala Pro Glu Ser Pro Glu Ser Arg
            340                 345                 350

Ala Leu Val Gly Gln Ser Arg Arg Lys Pro Cys Glu Ser Asp Phe Glu
        355                 360                 365

Thr Ile Lys Leu Ile Ser Asn Gly Ala Tyr Gly Ala Val Tyr Leu Val
    370                 375                 380

Arg His Arg Asp Thr Arg Gln Arg Phe Ala Ile Lys Lys Ile Asn Lys
385                 390                 395                 400

Gln Asn Leu Ile Leu Arg Asn Gln Val Gln Gln Val Phe Val Glu Arg
                405                 410                 415

Asp Ile Leu Thr Phe Ala Glu Asn Pro Phe Val Val Ser Met Phe Cys
            420                 425                 430

Ser Phe Glu Thr Arg Arg His Leu Cys Met Val Met Glu Tyr Val Glu
        435                 440                 445
```

```
Gly Gly Asp Cys Ala Thr Leu Leu Lys Asn Met Gly Pro Leu Pro Val
    450                 455                 460

Asp Met Ala Arg Leu Tyr Phe Ala Glu Thr Val Leu Ala Leu Glu Tyr
465                 470                 475                 480

Leu His Asn Tyr Gly Ile Val His Arg Asp Leu Lys Pro Asp Asn Leu
                485                 490                 495

Leu Ile Thr Ser Leu Gly His Ile Lys Leu Thr Asp Phe Gly Leu Ser
            500                 505                 510

Lys Ile Gly Leu Met Ser Met Ala Thr Asn Leu Tyr Glu Gly His Ile
        515                 520                 525

Glu Lys Asp Ala Arg Glu Phe Ile Asp Lys Gln Val Cys Gly Thr Pro
    530                 535                 540

Glu Tyr Ile Ala Pro Glu Val Ile Phe Arg Gln Gly Tyr Gly Lys Pro
545                 550                 555                 560

Val Asp Trp Trp Ala Met Gly Val Val Leu Tyr Glu Phe Leu Val Gly
                565                 570                 575

Cys Val Pro Phe Phe Gly Asp Thr Pro Glu Glu Leu Phe Gly Gln Val
            580                 585                 590

Val Ser Asp Glu Ile Met Trp Pro Glu Gly Asp Glu Ala Leu Pro Ala
        595                 600                 605

Asp Ala Gln Asp Leu Ile Thr Arg Leu Leu Arg Gln Ser Pro Leu Asp
    610                 615                 620

Arg Leu Gly Thr Gly Gly Thr His Glu Val Lys Gln His Pro Phe Phe
625                 630                 635                 640

Leu Ala Leu Asp Trp Ala Gly Leu Leu Arg His Lys Ala Glu Phe Val
                645                 650                 655

Pro Gln Leu Glu Ala Glu Asp Asp Thr Ser Tyr Phe Asp Thr Arg Ser
            660                 665                 670

Glu Arg Tyr Arg His Leu Gly Ser Glu Asp Asp Glu Thr Asn Asp Glu
        675                 680                 685

Glu Ser Ser Thr Glu Ile Pro Gln Phe Ser Ser Cys Ser His Arg Phe
    690                 695                 700

Ser Lys Val Tyr Ser Ser Ser Glu Phe Leu Ala Val Gln Pro Thr Pro
705                 710                 715                 720

Thr Phe Ala Glu Arg Ser Phe Ser Glu Asp Arg Glu Glu Gly Trp Glu
                725                 730                 735

Arg Ser Glu Val Asp Tyr Gly Arg Arg Leu Ser Ala Asp Ile Arg Leu
            740                 745                 750

Arg Ser Trp Thr Ser Ser Gly Ser Ser Cys Gln Ser Ser Ser Ser Gln
        755                 760                 765

Pro Glu Arg Gly Pro Ser Pro Ser Leu Leu Asn Thr Ile Ser Leu Asp
    770                 775                 780

Thr Met Pro Lys Phe Ala Phe Ser Ser Glu Asp Glu Gly Val Gly Pro
785                 790                 795                 800

Gly Pro Ala Gly Pro Lys Arg Pro Val Phe Ile Leu Gly Glu Pro Asp
                805                 810                 815

Pro Pro Pro Ala Ala Thr Pro Val Met Pro Lys Pro Ser Ser Leu Ser
            820                 825                 830

Ala Asp Thr Ala Ala Leu Ser His Ala Arg Leu Arg Ser Asn Ser Ile
        835                 840                 845

Gly Ala Arg His Ser Thr Pro Arg Pro Leu Asp Ala Gly Arg Gly Arg
    850                 855                 860

Arg Leu Gly Gly Pro Arg Asp Pro Ala Pro Glu Lys Ser Arg Ala Ser
865                 870                 875                 880
```

```
Ser Ser Gly Gly Ser Gly Gly Gly Ser Gly Gly Arg Val Pro Lys Ser
                885                 890                 895

Ala Ser Val Ser Ala Leu Ser Leu Ile Ile Thr Ala Asp Asp Gly Ser
            900                 905                 910

Gly Gly Pro Leu Met Ser Pro Leu Ser Pro Arg Ser Leu Ser Ser Asn
        915                 920                 925

Pro Ser Ser Arg Asp Ser Ser Pro Ser Arg Asp Pro Ser Pro Val Cys
    930                 935                 940

Gly Ser Leu Arg Pro Pro Ile Val Ile His Ser Ser Gly Lys Lys Tyr
945                 950                 955                 960

Gly Phe Ser Leu Arg Ala Ile Arg Val Tyr Met Gly Asp Ser Asp Val
                965                 970                 975

Tyr Thr Val His His Val Val Trp Ser Val Glu Asp Gly Ser Pro Ala
            980                 985                 990

Gln Glu Ala Gly Leu Arg Ala Gly  Asp Leu Ile Thr His  Ile Asn Gly
        995                 1000                1005

Glu Ser  Val Leu Gly Leu Val  His Met Asp Val Val  Glu Leu Leu
    1010                1015                1020

Leu Lys  Ser Gly Asn Lys Ile  Ser Leu Arg Thr Thr  Ala Leu Glu
    1025                1030                1035

Asn Thr  Ser Ile Lys Val Gly  Pro Ala Arg Lys Asn  Val Ala Lys
    1040                1045                1050

Gly Arg  Met Ala Arg Arg Ser  Lys Arg Ser Arg Arg  Arg Glu Thr
    1055                1060                1065

Gln Asp  Arg Arg Lys Ser Leu  Phe Lys Lys Ile Ser  Lys Gln Thr
    1070                1075                1080

Ser Val  Leu His Thr Ser Arg  Ser Phe Ser Ser Gly  Leu His His
    1085                1090                1095

Ser Leu  Ser Ser Ser Glu Ser  Leu Pro Gly Ser Pro  Thr His Ser
    1100                1105                1110

Leu Ser  Pro Ser Pro Thr Thr  Pro Cys Arg Ser Pro  Ala Pro Asp
    1115                1120                1125

Val Pro  Ala Asp Thr Thr Ala  Ser Pro Pro Ser Ala  Ser Pro Ser
    1130                1135                1140

Ser Ser  Ser Pro Ala Ser Pro  Ala Ala Ala Gly His  Thr Arg Pro
    1145                1150                1155

Ser Ser  Leu His Gly Leu Ala  Ala Lys Leu Gly Pro  Pro Arg Pro
    1160                1165                1170

Lys Thr  Gly Arg Arg Lys Ser  Thr Ser Ser Ile Pro  Pro Ser Pro
    1175                1180                1185

Leu Ala  Cys Pro Pro Ile Ser  Ala Pro Pro Pro Arg  Ser Pro Ser
    1190                1195                1200

Pro Leu  Pro Gly His Pro Pro  Ala Pro Ala Arg Ser  Pro Arg Leu
    1205                1210                1215

Arg Arg  Gly Gln Ser Ala Asp  Lys Leu Gly Thr Gly  Glu Arg Leu
    1220                1225                1230

Asp Gly  Glu Ala Gly Arg Arg  Thr Arg Gly Pro Glu  Ala Glu Leu
    1235                1240                1245

Val Val  Met Arg Arg Leu His  Leu Ser Glu Arg Arg  Asp Ser Phe
    1250                1255                1260

Lys Lys  Gln Glu Ala Val Gln  Glu Val Ser Phe Asp  Glu Pro Gln
    1265                1270                1275

Glu Glu  Ala Thr Gly Leu Pro  Thr Ser Val Pro Gln  Ile Ala Val
```

```
    1280                1285                1290

Glu Gly  Glu Glu Ala Val Pro  Val Ala Leu Gly Pro  Thr Gly Arg
    1295                1300                1305

Asp


<210> SEQ ID NO 26
<211> LENGTH: 1331
<212> TYPE: PRT
<213> ORGANISM: Homo sapiens

<400> SEQUENCE: 26

Met Lys Ser Arg Arg Asp Lys Leu His Ile Pro Ala Leu Thr Leu Asp
1               5                   10                  15

Leu Ser Pro Ser Ser Gln Ser Pro Ser Leu Leu Gly Pro Ser Ser Pro
            20                  25                  30

Cys Ser Pro Cys Ser Pro Ser Leu Gly Leu His Pro Trp Ser Cys Arg
        35                  40                  45

Ser Gly Asn Arg Lys Ser Leu Val Val Gly Thr Pro Ser Pro Thr Leu
    50                  55                  60

Ser Arg Pro Leu Ser Pro Leu Ser Val Pro Thr Ala Gly Ser Ser Pro
65                  70                  75                  80

Leu Asp Ser Pro Arg Asn Phe Ser Ala Ala Ser Ala Leu Asn Phe Pro
                85                  90                  95

Phe Ala Arg Arg Ala Asp Gly Arg Arg Trp Ser Leu Ala Ser Leu Pro
            100                 105                 110

Ser Ser Gly Tyr Gly Thr Asn Thr Pro Ser Ser Thr Leu Ser Ser Ser
        115                 120                 125

Ser Ser Ser Arg Glu Arg Leu His Gln Leu Pro Phe Gln Pro Thr Pro
    130                 135                 140

Asp Glu Leu His Phe Leu Ser Lys His Phe Arg Ser Ser Glu Asn Val
145                 150                 155                 160

Leu Asp Glu Glu Gly Gly Arg Ser Pro Arg Leu Arg Pro Arg Ser Arg
                165                 170                 175

Ser Leu Ser Pro Gly Arg Ala Thr Gly Thr Phe Asp Asn Glu Ile Val
            180                 185                 190

Met Met Asn His Val Tyr Arg Glu Arg Phe Pro Lys Ala Thr Ala Gln
        195                 200                 205

Met Glu Gly Arg Leu Gln Glu Phe Leu Thr Ala Tyr Ala Pro Gly Ala
    210                 215                 220

Arg Leu Ala Leu Ala Asp Gly Val Leu Gly Phe Ile His His Gln Ile
225                 230                 235                 240

Val Glu Leu Ala Arg Asp Cys Leu Ala Lys Ser Gly Glu Asn Leu Val
                245                 250                 255

Thr Ser Arg Tyr Phe Leu Glu Met Gln Glu Lys Leu Glu Arg Leu Leu
            260                 265                 270

Gln Asp Ala His Glu Arg Ser Asp Ser Glu Glu Val Ser Phe Ile Val
        275                 280                 285

Gln Leu Val Arg Lys Leu Leu Ile Ile Ile Ser Arg Pro Ala Arg Leu
    290                 295                 300

Leu Glu Cys Leu Glu Phe Asp Pro Glu Glu Phe Tyr His Leu Leu Glu
305                 310                 315                 320

Ala Ala Glu Gly His Ala Arg Glu Gly Gln Gly Ile Lys Thr Asp Leu
                325                 330                 335

Pro Gln Tyr Ile Ile Gly Gln Leu Gly Leu Ala Lys Asp Pro Leu Glu
            340                 345                 350
```

```
Glu Met Val Pro Leu Ser His Leu Glu Glu Glu Gln Pro Pro Ala Pro
        355                 360                 365

Glu Ser Pro Glu Ser Arg Ala Leu Val Gly Gln Ser Arg Arg Lys Pro
    370                 375                 380

Cys Glu Ser Asp Phe Glu Thr Ile Lys Leu Ile Ser Asn Gly Ala Tyr
385                 390                 395                 400

Gly Ala Val Tyr Leu Val Arg His Arg Asp Thr Arg Gln Arg Phe Ala
                405                 410                 415

Ile Lys Lys Ile Asn Lys Gln Asn Leu Ile Leu Arg Asn Gln Ile Gln
            420                 425                 430

Gln Val Phe Val Glu Arg Asp Ile Leu Thr Phe Ala Glu Asn Pro Phe
        435                 440                 445

Val Val Ser Met Phe Cys Ser Phe Glu Thr Arg Arg His Leu Cys Met
    450                 455                 460

Val Met Glu Tyr Val Glu Gly Gly Asp Cys Ala Thr Leu Leu Lys Asn
465                 470                 475                 480

Met Gly Pro Leu Pro Val Asp Met Ala Arg Leu Tyr Phe Ala Glu Thr
                485                 490                 495

Val Leu Ala Leu Glu Tyr Leu His Asn Tyr Gly Ile Val His Arg Asp
            500                 505                 510

Leu Lys Pro Asp Asn Leu Leu Ile Thr Ser Leu Gly His Ile Lys Leu
        515                 520                 525

Thr Asp Phe Gly Leu Ser Lys Ile Gly Leu Met Ser Met Ala Thr Asn
    530                 535                 540

Leu Tyr Glu Gly His Ile Glu Lys Asp Ala Arg Glu Phe Ile Asp Lys
545                 550                 555                 560

Gln Val Cys Gly Thr Pro Glu Tyr Ile Ala Pro Glu Val Ile Phe Arg
                565                 570                 575

Gln Gly Tyr Gly Lys Pro Val Asp Trp Trp Ala Met Gly Val Val Leu
            580                 585                 590

Tyr Glu Phe Leu Val Gly Cys Val Pro Phe Phe Gly Asp Thr Pro Glu
        595                 600                 605

Glu Leu Phe Gly Gln Val Val Ser Asp Glu Ile Met Trp Pro Glu Gly
    610                 615                 620

Asp Glu Ala Leu Pro Ala Asp Ala Gln Asp Leu Ile Thr Arg Leu Leu
625                 630                 635                 640

Arg Gln Ser Pro Leu Asp Arg Leu Gly Thr Gly Gly Thr His Glu Val
                645                 650                 655

Lys Gln His Pro Phe Phe Leu Ala Leu Asp Trp Ala Gly Leu Leu Arg
            660                 665                 670

His Lys Ala Glu Phe Val Pro Gln Leu Glu Ala Glu Asp Asp Thr Ser
        675                 680                 685

Tyr Phe Asp Thr Arg Ser Glu Arg Tyr Arg His Leu Gly Ser Glu Asp
    690                 695                 700

Asp Glu Thr Asn Asp Glu Glu Ser Ser Thr Glu Ile Pro Gln Phe Ser
705                 710                 715                 720

Ser Cys Ser His Arg Phe Ser Lys Val Tyr Ser Ser Ser Glu Phe Leu
                725                 730                 735

Ala Val Gln Pro Thr Pro Thr Phe Ala Glu Arg Ser Phe Ser Glu Asp
            740                 745                 750

Arg Glu Glu Gly Trp Glu Arg Ser Glu Val Asp Tyr Gly Arg Arg Leu
        755                 760                 765

Ser Ala Asp Ile Arg Leu Arg Ser Trp Thr Ser Ser Gly Ser Ser Cys
```

```
    770                 775                 780

Gln Ser Ser Ser Ser Gln Pro Glu Arg Gly Pro Ser Pro Ser Leu Leu
785                 790                 795                 800

Asn Thr Ile Ser Leu Asp Thr Met Pro Lys Phe Ala Phe Ser Ser Glu
                805                 810                 815

Asp Glu Gly Val Gly Pro Gly Pro Ala Gly Pro Lys Arg Pro Val Phe
            820                 825                 830

Ile Leu Gly Glu Pro Asp Pro Pro Pro Ala Ala Thr Pro Val Met Pro
        835                 840                 845

Lys Pro Ser Ser Leu Ser Ala Asp Thr Ala Ala Leu Ser His Ala Arg
    850                 855                 860

Leu Arg Ser Asn Ser Ile Gly Ala Arg His Ser Thr Pro Arg Pro Leu
865                 870                 875                 880

Asp Ala Gly Arg Gly Arg Arg Leu Gly Gly Pro Arg Asp Pro Ala Pro
                885                 890                 895

Glu Lys Ser Arg Ala Ser Ser Ser Gly Gly Ser Gly Gly Gly Ser Gly
            900                 905                 910

Gly Arg Val Pro Lys Ser Ala Ser Val Ser Ala Leu Ser Leu Ile Ile
        915                 920                 925

Thr Ala Asp Asp Gly Ser Gly Gly Pro Leu Met Ser Pro Leu Ser Pro
    930                 935                 940

Arg Ser Leu Ser Ser Asn Pro Ser Ser Arg Asp Ser Ser Pro Ser Arg
945                 950                 955                 960

Asp Pro Ser Pro Val Cys Gly Ser Leu Arg Pro Pro Ile Val Ile His
                965                 970                 975

Ser Ser Gly Lys Lys Tyr Gly Phe Ser Leu Arg Ala Ile Arg Val Tyr
            980                 985                 990

Met Gly Asp Ser Asp Val Tyr Thr  Val His His Val Val  Trp Ser Val
        995                 1000                1005

Glu Asp  Gly Ser Pro Ala Gln  Glu Ala Gly Leu Arg  Ala Gly Asp
    1010                 1015                 1020

Leu Ile  Thr His Ile Asn Gly  Glu Ser Val Leu Gly  Leu Val His
    1025                 1030                 1035

Met Asp  Val Val Glu Leu Leu  Leu Lys Ser Gly Asn  Lys Ile Ser
    1040                 1045                 1050

Leu Arg  Thr Thr Ala Leu Glu  Asn Thr Ser Ile Lys  Val Gly Pro
    1055                 1060                 1065

Ala Arg  Lys Asn Val Ala Lys  Gly Arg Met Ala Arg  Arg Ser Lys
    1070                 1075                 1080

Arg Ser  Arg Arg Arg Glu Thr  Gln Asp Arg Arg Lys  Ser Leu Phe
    1085                 1090                 1095

Lys Lys  Ile Ser Lys Gln Thr  Ser Val Leu His Thr  Ser Arg Ser
    1100                 1105                 1110

Phe Ser  Ser Gly Leu His His  Ser Leu Ser Ser Ser  Glu Ser Leu
    1115                 1120                 1125

Pro Gly  Ser Pro Thr His Ser  Leu Ser Pro Ser Pro  Thr Thr Pro
    1130                 1135                 1140

Cys Arg  Ser Pro Ala Pro Asp  Val Pro Ala Asp Thr  Thr Ala Ser
    1145                 1150                 1155

Pro Pro  Ser Ala Ser Pro Ser  Ser Ser Ser Pro Ala  Ser Pro Ala
    1160                 1165                 1170

Ala Ala  Gly His Thr Arg Pro  Ser Ser Leu His Gly  Leu Ala Ala
    1175                 1180                 1185
```

```
Lys Leu  Gly Pro Pro Arg Pro  Lys Thr Gly Arg Arg  Lys Ser Thr
    1190                 1195                 1200

Ser Ser  Ile Pro Pro Ser Pro  Leu Ala Cys Pro Pro  Ile Ser Ala
    1205                 1210                 1215

Pro Pro  Pro Arg Ser Pro Ser  Pro Leu Pro Gly His  Pro Pro Ala
    1220                 1225                 1230

Pro Ala  Arg Ser Pro Arg Leu  Arg Arg Gly Gln Ser  Ala Asp Lys
    1235                 1240                 1245

Leu Gly  Thr Gly Glu Arg Leu  Asp Gly Glu Ala Gly  Arg Arg Thr
    1250                 1255                 1260

Arg Gly  Pro Glu Ala Glu Leu  Val Val Met Arg Arg  Leu His Leu
    1265                 1270                 1275

Ser Glu  Arg Arg Asp Ser Phe  Lys Lys Gln Glu Ala  Val Gln Glu
    1280                 1285                 1290

Val Ser  Phe Asp Glu Pro Gln  Glu Glu Ala Thr Gly  Leu Pro Thr
    1295                 1300                 1305

Ser Val  Pro Gln Ile Ala Val  Glu Gly Glu Glu Ala  Val Pro Val
    1310                 1315                 1320

Ala Leu  Gly Pro Thr Gly Arg  Asp
    1325                 1330
```

<210> SEQ ID NO 27
<211> LENGTH: 80
<212> TYPE: PRT
<213> ORGANISM: Homo sapiens

<400> SEQUENCE: 27

```
Met Tyr Ser Leu Asn Gln Glu Ile Lys Ala Phe Ser Arg Asn Asn Pro
1               5                   10                  15

Arg Lys Gln Cys Thr Arg Val Thr Thr Leu Thr Gly Lys Lys Ile Ile
            20                  25                  30

Glu Thr Trp Lys Asp Ala Arg Ile His Val Val Glu Glu Val Glu Pro
        35                  40                  45

Ser Ser Gly Gly Gly Cys Gly Tyr Val Gln Asp Leu Ser Ser Asp Gln
    50                  55                  60

Gln Val Gly Val Ile Lys Pro Trp Leu Leu Leu Gly Asp Ser Tyr Ser
65                  70                  75                  80
```

<210> SEQ ID NO 28
<211> LENGTH: 495
<212> TYPE: PRT
<213> ORGANISM: Homo sapiens

<400> SEQUENCE: 28

```
Met Cys Gln Ala Pro Cys Trp Arg Ala Gly Gly Ser Gly Leu Gly Arg
1               5                   10                  15

Cys Ser Leu Cys Arg Ser Cys Ser Leu Ala Arg Phe Pro Arg Leu Pro
            20                  25                  30

Ser Phe Pro Pro Pro Gly Arg Leu Arg Ala Gly Val Cys Ala Arg Glu
        35                  40                  45

Gly Glu Gly Val Gly Gly Val Gly Gly Gly Val Pro Val Pro Lys Arg
    50                  55                  60

Pro Ala Glu Gly Gly Gly Gly Cys Glu Gly Leu Arg Glu Ala Met Asp
65                  70                  75                  80

Val Glu Arg Leu Gln Glu Ala Leu Lys Asp Phe Glu Lys Arg Gly Lys
                85                  90                  95

Lys Glu Val Cys Pro Val Leu Asp Gln Phe Leu Cys His Val Ala Lys
```

```
            100                 105                 110

Thr Gly Glu Thr Met Ile Gln Trp Ser Gln Phe Lys Gly Tyr Phe Ile
        115                 120                 125

Phe Lys Leu Glu Lys Val Met Asp Asp Phe Arg Thr Ser Ala Pro Glu
    130                 135                 140

Pro Arg Gly Pro Pro Asn Pro Asn Val Glu Tyr Ile Pro Phe Asp Glu
145                 150                 155                 160

Met Lys Glu Arg Ile Leu Lys Ile Val Thr Gly Phe Asn Gly Ile Pro
                165                 170                 175

Phe Thr Ile Gln Arg Leu Cys Glu Leu Leu Thr Asp Pro Arg Arg Asn
            180                 185                 190

Tyr Thr Gly Thr Asp Lys Phe Leu Arg Gly Val Glu Lys Asn Val Met
        195                 200                 205

Val Val Ser Cys Val Tyr Pro Ser Ser Glu Lys Asn Asn Ser Asn Ser
    210                 215                 220

Leu Asn Arg Met Asn Gly Val Met Phe Pro Gly Asn Ser Pro Ser Tyr
225                 230                 235                 240

Thr Glu Arg Ser Asn Ile Asn Gly Pro Gly Thr Pro Arg Pro Leu Asn
                245                 250                 255

Arg Pro Lys Val Ser Leu Ser Ala Pro Met Thr Thr Asn Gly Leu Pro
            260                 265                 270

Glu Ser Thr Asp Ser Lys Glu Ala Asn Leu Gln Gln Asn Glu Glu Lys
        275                 280                 285

Asn His Ser Asp Ser Ser Thr Ser Glu Ser Glu Val Ser Ser Val Ser
    290                 295                 300

Pro Leu Lys Asn Lys His Pro Asp Glu Asp Ala Val Glu Ala Glu Gly
305                 310                 315                 320

His Glu Val Lys Arg Leu Arg Phe Asp Lys Glu Gly Glu Val Arg Glu
                325                 330                 335

Thr Ala Ser Gln Thr Thr Ser Ser Glu Ile Ser Ser Val Met Val Gly
            340                 345                 350

Glu Thr Glu Ala Ser Ser Ser Ser Gln Asp Lys Asp Lys Asp Ser Arg
        355                 360                 365

Cys Thr Arg Gln His Cys Thr Glu Glu Asp Glu Glu Glu Asp Glu Glu
    370                 375                 380

Glu Glu Glu Glu Ser Phe Met Thr Ser Arg Glu Met Ile Pro Glu Arg
385                 390                 395                 400

Lys Asn Gln Glu Lys Glu Ser Asp Asp Ala Leu Thr Val Asn Glu Glu
                405                 410                 415

Thr Ser Glu Glu Asn Asn Gln Met Glu Glu Ser Asp Val Ser Gln Ala
            420                 425                 430

Glu Lys Asp Leu Leu His Ser Glu Gly Ser Glu Asn Glu Gly Pro Val
        435                 440                 445

Ser Ser Ser Ser Ser Asp Cys Arg Glu Thr Glu Glu Leu Val Gly Ser
    450                 455                 460

Asn Ser Ser Lys Thr Gly Glu Ile Leu Ser Glu Ser Ser Met Glu Asn
465                 470                 475                 480

Asp Asp Glu Ala Thr Glu Val Thr Asp Glu Pro Met Glu Gln Asp
                485                 490                 495
```

<210> SEQ ID NO 29
<211> LENGTH: 157
<212> TYPE: PRT
<213> ORGANISM: Homo sapiens

<400> SEQUENCE: 29

```
Met Ala His Ser Pro Val Gln Ser Gly Leu Pro Gly Met Gln Asn Leu
1               5                   10                  15

Lys Ala Asp Pro Glu Glu Leu Phe Thr Lys Leu Glu Lys Ile Gly Lys
            20                  25                  30

Gly Ser Phe Gly Glu Val Phe Lys Gly Ile Asp Asn Arg Thr Gln Lys
        35                  40                  45

Val Val Ala Ile Lys Ile Ile Asp Leu Glu Glu Ala Glu Asp Glu Ile
    50                  55                  60

Glu Asp Ile Gln Gln Glu Ile Thr Val Leu Ser Gln Cys Asp Ser Pro
65                  70                  75                  80

Tyr Val Thr Lys Tyr Tyr Gly Ser Tyr Leu Lys Asp Thr Lys Leu Trp
                85                  90                  95

Ile Ile Met Glu Tyr Leu Gly Gly Gly Ser Ala Leu Asp Leu Leu Glu
            100                 105                 110

Pro Gly Pro Leu Asp Glu Thr Gln Ile Ala Thr Ile Leu Arg Glu Ile
        115                 120                 125

Leu Lys Gly Leu Asp Tyr Leu His Ser Glu Lys Lys Ile His Arg Asp
    130                 135                 140

Ile Lys Gly Arg His Leu Val Pro Gly His Asn Ser Tyr
145                 150                 155
```

<210> SEQ ID NO 30
<211> LENGTH: 305
<212> TYPE: PRT
<213> ORGANISM: Homo sapiens

<400> SEQUENCE: 30

```
Met Asp Phe Asp Lys Lys Gly Gly Lys Gly Glu Thr Glu Glu Gly Arg
1               5                   10                  15

Arg Met Ser Lys Ala Gly Gly Gly Arg Ser Ser His Gly Ile Arg Ser
            20                  25                  30

Ser Gly Thr Ser Ser Gly Val Leu Met Val Gly Pro Asn Phe Arg Val
        35                  40                  45

Gly Lys Lys Ile Gly Cys Gly Asn Phe Gly Glu Leu Arg Leu Gly Lys
    50                  55                  60

Asn Leu Tyr Thr Asn Glu Tyr Val Ala Ile Lys Leu Val Ser Arg Pro
65                  70                  75                  80

Leu His Pro Thr Pro Ala Asp Val Pro Pro Arg Asp Phe Arg Ala Ala
                85                  90                  95

Thr Arg Ser Pro Gly Asp Ser Leu Leu Cys Pro Gln Glu Pro Ile Lys
            100                 105                 110

Ser Arg Ala Pro Gln Leu His Leu Glu Tyr Arg Phe Tyr Lys Gln Leu
        115                 120                 125

Ser Ala Thr Glu Gly Val Pro Gln Val Tyr Tyr Phe Gly Pro Cys Gly
    130                 135                 140

Lys Tyr Asn Ala Met Val Leu Glu Leu Leu Gly Pro Ile Leu Glu Asp
145                 150                 155                 160

Leu Phe Asp Leu Cys Asp Arg Thr Phe Thr Leu Thr Thr Val Leu Met
                165                 170                 175

Ile Ala Ile Gln Leu Ile Thr Arg Met Glu Tyr Val His Thr Lys Ser
            180                 185                 190

Leu Ile Tyr Arg Asp Val Lys Pro Glu Asn Phe Leu Val Gly Arg Pro
        195                 200                 205

Gly Thr Lys Arg Gln His Ala Ile His Ile Ile Asp Phe Gly Leu Ala
```

```
    210                 215                 220

Lys Glu Tyr Ile Asp Pro Glu Thr Lys Lys His Ile Pro Tyr Arg Glu
225                 230                 235                 240

His Lys Ser Leu Thr Gly Thr Ala Arg Tyr Met Ser Ile Asn Thr His
                245                 250                 255

Leu Gly Lys Glu Gln Ser Arg Arg Asp Asp Leu Glu Ala Leu Gly His
            260                 265                 270

Met Phe Met Tyr Phe Leu Arg Gly Ser Leu Pro Trp Gln Gly Leu Lys
        275                 280                 285

Val Gly Glu Glu Ala Gly Gln Ala Gly Gly Asp Ala Gly Arg Glu Gln
    290                 295                 300

Gly
305


<210> SEQ ID NO 31
<211> LENGTH: 930
<212> TYPE: PRT
<213> ORGANISM: Homo sapiens

<400> SEQUENCE: 31

Met Lys Lys Phe Phe Asp Ser Arg Arg Glu Gln Gly Gly Ser Gly Leu
1               5                   10                  15

Gly Ser Gly Ser Ser Gly Gly Gly Gly Ser Thr Ser Gly Leu Gly Ser
            20                  25                  30

Gly Tyr Ile Gly Arg Val Phe Gly Ile Gly Arg Gln Gln Val Thr Val
        35                  40                  45

Asp Glu Val Leu Ala Glu Gly Gly Phe Ala Ile Val Phe Leu Val Arg
    50                  55                  60

Thr Ser Asn Gly Met Lys Cys Ala Leu Lys Arg Met Phe Val Asn Asn
65                  70                  75                  80

Glu His Asp Leu Gln Val Cys Lys Arg Glu Ile Gln Ile Met Arg Asp
                85                  90                  95

Leu Ser Gly His Lys Asn Ile Val Gly Tyr Ile Asp Ser Ser Ile Asn
            100                 105                 110

Asn Val Ser Ser Gly Asp Val Trp Glu Val Leu Ile Leu Met Asp Phe
        115                 120                 125

Cys Arg Gly Gly Gln Val Val Asn Leu Met Asn Gln Arg Leu Gln Thr
    130                 135                 140

Gly Phe Thr Glu Asn Glu Val Leu Gln Ile Phe Cys Asp Thr Cys Glu
145                 150                 155                 160

Ala Val Ala Arg Leu His Gln Cys Lys Thr Pro Ile Ile His Arg Asp
                165                 170                 175

Leu Lys Val Glu Asn Ile Leu Leu His Asp Arg Gly His Tyr Val Leu
            180                 185                 190

Cys Asp Phe Gly Ser Ala Thr Asn Lys Phe Gln Asn Pro Gln Thr Glu
        195                 200                 205

Gly Val Asn Ala Val Glu Asp Glu Ile Lys Lys Tyr Thr Thr Leu Ser
    210                 215                 220

Tyr Arg Ala Pro Glu Met Val Asn Leu Tyr Ser Gly Lys Ile Ile Thr
225                 230                 235                 240

Thr Lys Ala Asp Ile Trp Ala Leu Gly Cys Leu Leu Tyr Lys Leu Cys
                245                 250                 255

Tyr Phe Thr Leu Pro Phe Gly Glu Ser Gln Val Ala Ile Cys Asp Gly
            260                 265                 270

Asn Phe Thr Ile Pro Asp Asn Ser Arg Tyr Ser Gln Asp Met His Cys
```

```
        275                 280                 285

Leu Ile Arg Tyr Met Leu Glu Pro Asp Pro Asp Lys Arg Pro Asp Ile
    290                 295                 300

Tyr Gln Val Ser Tyr Phe Ser Phe Lys Leu Leu Lys Lys Glu Cys Pro
305                 310                 315                 320

Ile Pro Asn Val Gln Asn Ser Pro Ile Pro Ala Lys Leu Pro Glu Pro
                325                 330                 335

Val Lys Ala Ser Glu Ala Ala Ala Lys Lys Thr Gln Pro Lys Ala Arg
            340                 345                 350

Leu Thr Asp Pro Ile Pro Thr Thr Glu Thr Ser Ile Ala Pro Arg Gln
        355                 360                 365

Arg Pro Lys Ala Gly Gln Thr Gln Pro Asn Pro Gly Ile Leu Pro Ile
    370                 375                 380

Gln Pro Ala Leu Thr Pro Arg Lys Arg Ala Thr Val Gln Pro Pro Pro
385                 390                 395                 400

Gln Ala Ala Gly Ser Ser Asn Gln Pro Gly Leu Leu Ala Ser Val Pro
                405                 410                 415

Gln Pro Lys Pro Gln Ala Pro Pro Ser Gln Pro Leu Pro Gln Thr Gln
            420                 425                 430

Ala Lys Gln Pro Gln Ala Pro Pro Thr Pro Gln Gln Thr Pro Ser Thr
        435                 440                 445

Gln Ala Gln Gly Leu Pro Ala Gln Ala Gln Ala Thr Pro Gln His Gln
    450                 455                 460

Gln Gln Leu Phe Leu Lys Gln Gln Gln Gln Gln Gln Gln Pro Pro Pro
465                 470                 475                 480

Ala Gln Gln Gln Pro Ala Gly Thr Phe Tyr Gln Gln Gln Gln Ala Gln
                485                 490                 495

Thr Gln Gln Phe Gln Ala Val His Pro Ala Thr Gln Gln Pro Ala Ile
            500                 505                 510

Ala Gln Phe Pro Val Val Ser Gln Gly Gly Ser Gln Gln Gln Leu Met
        515                 520                 525

Gln Asn Phe Tyr Gln Gln Gln Gln Gln Gln Gln Gln Gln Gln Gln Gln
    530                 535                 540

Gln Gln Leu Ala Thr Ala Leu His Gln Gln Gln Leu Met Thr Gln Gln
545                 550                 555                 560

Ala Ala Leu Gln Gln Lys Pro Thr Met Ala Ala Gly Gln Gln Pro Gln
                565                 570                 575

Pro Gln Pro Ala Ala Ala Pro Gln Pro Ala Pro Ala Gln Glu Pro Ala
            580                 585                 590

Gln Ile Gln Ala Pro Val Arg Gln Gln Pro Lys Val Gln Thr Thr Pro
        595                 600                 605

Pro Pro Ala Val Gln Gly Gln Lys Val Gly Ser Leu Thr Pro Pro Ser
    610                 615                 620

Ser Pro Lys Thr Gln Arg Ala Gly His Arg Arg Ile Leu Ser Asp Val
625                 630                 635                 640

Thr His Ser Ala Val Phe Gly Val Pro Ala Ser Lys Ser Thr Gln Leu
                645                 650                 655

Leu Gln Ala Ala Ala Ala Glu Ala Ser Leu Asn Lys Ser Lys Ser Ala
            660                 665                 670

Thr Thr Thr Pro Ser Gly Ser Pro Arg Thr Ser Gln Gln Asn Val Tyr
        675                 680                 685

Asn Pro Ser Glu Gly Ser Thr Trp Asn Pro Phe Asp Asp Asp Asn Phe
    690                 695                 700
```

Ser Lys Leu Thr Ala Glu Glu Leu Leu Asn Lys Asp Phe Ala Lys Leu
705 710 715 720

Gly Glu Gly Lys His Pro Glu Lys Leu Gly Gly Ser Ala Glu Ser Leu
725 730 735

Ile Pro Gly Phe Gln Ser Thr Gln Gly Asp Ala Phe Ala Thr Thr Ser
740 745 750

Phe Ser Ala Gly Thr Glu Lys Leu Ile Glu Gly Leu Lys Ser Pro Asp
755 760 765

Thr Ser Leu Leu Leu Pro Asp Leu Leu Pro Met Thr Asp Pro Phe Gly
770 775 780

Ser Thr Ser Asp Ala Val Ile Glu Lys Ala Asp Val Ala Val Glu Ser
785 790 795 800

Leu Ile Pro Gly Leu Glu Pro Pro Val Pro Gln Arg Leu Pro Ser Gln
805 810 815

Thr Glu Ser Val Thr Ser Asn Arg Thr Asp Ser Leu Thr Gly Glu Asp
820 825 830

Ser Leu Leu Asp Cys Ser Leu Leu Ser Asn Pro Thr Thr Asp Leu Leu
835 840 845

Glu Glu Phe Ala Pro Thr Ala Ile Ser Ala Pro Val His Lys Ala Ala
850 855 860

Glu Asp Ser Asn Leu Ile Ser Gly Phe Asp Val Pro Glu Gly Ser Asp
865 870 875 880

Lys Val Ala Glu Asp Glu Phe Asp Pro Ile Pro Val Leu Ile Thr Lys
885 890 895

Asn Pro Gln Gly Gly His Ser Arg Asn Ser Ser Gly Ser Ser Glu Ser
900 905 910

Ser Leu Pro Asn Leu Ala Arg Ser Leu Leu Leu Val Asp Gln Leu Ile
915 920 925

Asp Leu
930

<210> SEQ ID NO 32
<211> LENGTH: 118
<212> TYPE: PRT
<213> ORGANISM: Homo sapiens

<400> SEQUENCE: 32

Met Ser Leu Leu Gln Ser Ala Leu Asp Phe Leu Ala Gly Pro Gly Ser
1 5 10 15

Leu Gly Gly Ala Ser Gly Arg Asp Gln Ser Asp Phe Val Gly Gln Thr
20 25 30

Val Glu Leu Gly Glu Leu Arg Leu Arg Val Arg Arg Val Leu Ala Glu
35 40 45

Gly Gly Phe Ala Phe Val Tyr Glu Ala Gln Asp Val Gly Ser Gly Arg
50 55 60

Glu Tyr Ala Leu Lys Arg Leu Leu Ser Asn Glu Glu Glu Lys Asn Arg
65 70 75 80

Ala Ile Ile Gln Glu Val Cys Phe Met Leu Cys Ser Leu Gly Glu Pro
85 90 95

Ala Gly Cys Leu Ser Val Gly Ser Gly Gly His Ser His Ala Ser Ala
100 105 110

Ser Leu Arg Thr Ala Pro
115

<210> SEQ ID NO 33
<211> LENGTH: 1355

<212> TYPE: PRT
<213> ORGANISM: Homo sapiens

<400> SEQUENCE: 33

```
Met Ser Leu Leu Gln Ser Ala Leu Asp Phe Leu Ala Gly Pro Gly Ser
1               5                   10                  15

Leu Gly Gly Ala Ser Gly Arg Asp Gln Ser Asp Phe Val Gly Gln Thr
            20                  25                  30

Val Glu Leu Gly Glu Leu Arg Leu Arg Val Arg Arg Val Leu Ala Glu
        35                  40                  45

Gly Gly Phe Ala Phe Val Tyr Glu Ala Gln Asp Val Gly Ser Gly Arg
    50                  55                  60

Glu Tyr Ala Leu Lys Arg Leu Leu Ser Asn Glu Glu Glu Lys Asn Arg
65                  70                  75                  80

Ala Ile Ile Gln Glu Val Cys Phe Met Lys Lys Leu Ser Gly His Pro
                85                  90                  95

Asn Ile Val Gln Phe Cys Ser Ala Ala Ser Ile Gly Lys Glu Glu Ser
            100                 105                 110

Asp Thr Gly Gln Ala Glu Phe Leu Leu Leu Thr Glu Leu Cys Lys Gly
        115                 120                 125

Gln Leu Val Glu Phe Leu Lys Lys Met Glu Ser Arg Gly Pro Leu Ser
    130                 135                 140

Cys Asp Thr Val Leu Lys Ile Phe Tyr Gln Thr Cys Arg Ala Val Gln
145                 150                 155                 160

His Met His Arg Gln Lys Pro Pro Ile Ile His Arg Asp Leu Lys Val
                165                 170                 175

Glu Asn Leu Leu Leu Ser Asn Gln Gly Thr Ile Lys Leu Cys Asp Phe
            180                 185                 190

Gly Ser Ala Thr Thr Ile Ser His Tyr Pro Asp Tyr Ser Trp Ser Ala
        195                 200                 205

Gln Arg Arg Ala Leu Val Glu Glu Glu Ile Thr Arg Asn Thr Thr Pro
    210                 215                 220

Met Tyr Arg Thr Pro Glu Ile Ile Asp Leu Tyr Ser Asn Phe Pro Ile
225                 230                 235                 240

Gly Glu Lys Gln Asp Ile Trp Ala Leu Gly Cys Ile Leu Tyr Leu Leu
                245                 250                 255

Cys Phe Arg Gln His Pro Phe Glu Asp Gly Ala Lys Leu Arg Ile Val
            260                 265                 270

Asn Gly Lys Tyr Ser Ile Pro Pro His Asp Thr Gln Tyr Thr Val Phe
        275                 280                 285

His Ser Leu Ile Arg Ala Met Leu Gln Val Asn Pro Glu Glu Arg Leu
    290                 295                 300

Ser Ile Ala Glu Val Val His Gln Leu Gln Glu Ile Ala Ala Ala Arg
305                 310                 315                 320

Asn Val Asn Pro Lys Ser Pro Ile Thr Glu Leu Leu Glu Gln Asn Gly
                325                 330                 335

Gly Tyr Gly Ser Ala Thr Leu Ser Arg Gly Pro Pro Pro Pro Val Gly
            340                 345                 350

Pro Ala Gly Ser Gly Tyr Ser Gly Gly Leu Ala Leu Ala Glu Tyr Asp
        355                 360                 365

Gln Pro Tyr Gly Gly Phe Leu Asp Ile Leu Arg Gly Gly Thr Glu Arg
    370                 375                 380

Leu Phe Thr Asn Leu Lys Asp Thr Ser Ser Lys Val Ile Gln Ser Val
385                 390                 395                 400
```

```
Ala Asn Tyr Ala Lys Gly Asp Leu Asp Ile Ser Tyr Ile Thr Ser Arg
                405                 410                 415

Ile Ala Val Met Ser Phe Pro Ala Glu Gly Val Glu Ser Ala Leu Lys
            420                 425                 430

Asn Asn Ile Glu Asp Val Arg Leu Phe Leu Asp Ser Lys His Pro Gly
        435                 440                 445

His Tyr Ala Val Tyr Asn Leu Ser Pro Arg Thr Tyr Arg Pro Ser Arg
    450                 455                 460

Phe His Asn Arg Val Ser Glu Cys Gly Trp Ala Ala Arg Arg Ala Pro
465                 470                 475                 480

His Leu His Thr Leu Tyr Asn Ile Cys Arg Asn Met His Ala Trp Leu
                485                 490                 495

Arg Gln Asp His Lys Asn Val Cys Val Val His Cys Met Asp Gly Arg
            500                 505                 510

Ala Ala Ser Ala Val Ala Val Cys Ser Phe Leu Cys Phe Cys Arg Leu
        515                 520                 525

Phe Ser Thr Ala Glu Ala Ala Val Tyr Met Phe Ser Met Lys Arg Cys
    530                 535                 540

Pro Pro Gly Ile Trp Pro Ser His Lys Arg Tyr Ile Glu Tyr Met Cys
545                 550                 555                 560

Asp Met Val Ala Glu Glu Pro Ile Thr Pro His Ser Lys Pro Ile Leu
                565                 570                 575

Val Arg Ala Val Val Met Thr Pro Val Pro Leu Phe Ser Lys Gln Arg
            580                 585                 590

Ser Gly Cys Arg Pro Phe Cys Glu Val Tyr Val Gly Asp Glu Arg Val
        595                 600                 605

Ala Ser Thr Ser Gln Glu Tyr Asp Lys Met Arg Asp Phe Lys Ile Glu
    610                 615                 620

Asp Gly Ile Ala Val Ile Pro Leu Gly Val Thr Val Gln Gly Asp Val
625                 630                 635                 640

Leu Ile Val Ile Tyr His Ala Arg Ser Thr Leu Gly Gly Arg Leu Gln
                645                 650                 655

Ala Lys Met Ala Ser Met Lys Met Phe Gln Ile Gln Phe His Thr Gly
            660                 665                 670

Phe Val Pro Arg Asn Ala Thr Thr Val Lys Phe Ala Lys Tyr Asp Leu
        675                 680                 685

Asp Ala Cys Asp Ile Gln Glu Lys Tyr Pro Asp Leu Phe Gln Val Asn
    690                 695                 700

Leu Glu Val Glu Val Glu Pro Arg Asp Arg Pro Ser Arg Glu Ala Pro
705                 710                 715                 720

Pro Trp Glu Asn Ser Ser Met Arg Gly Leu Asn Pro Lys Ile Leu Phe
                725                 730                 735

Ser Ser Arg Glu Glu Gln Gln Asp Ile Leu Ser Lys Phe Gly Lys Pro
            740                 745                 750

Glu Leu Pro Arg Gln Pro Gly Ser Thr Ala Gln Tyr Asp Ala Gly Ala
        755                 760                 765

Gly Ser Pro Glu Ala Glu Pro Thr Asp Ser Asp Ser Pro Pro Ser Ser
    770                 775                 780

Ser Ala Asp Ala Ser Arg Phe Leu His Thr Leu Asp Trp Gln Glu Glu
785                 790                 795                 800

Lys Glu Ala Glu Thr Gly Ala Glu Asn Ala Ser Ser Lys Glu Ser Glu
                805                 810                 815

Ser Ala Leu Met Glu Asp Arg Asp Glu Ser Glu Val Ser Asp Glu Gly
            820                 825                 830
```

```
Gly Ser Pro Ile Ser Ser Glu Gly Gln Glu Pro Arg Ala Asp Pro Glu
      835                 840                 845

Pro Pro Gly Leu Ala Ala Gly Leu Val Gln Gln Asp Leu Val Phe Glu
    850                 855                 860

Val Glu Thr Pro Ala Val Leu Pro Glu Pro Val Pro Gln Glu Asp Gly
865                 870                 875                 880

Val Asp Leu Leu Gly Leu His Ser Glu Val Gly Ala Gly Pro Ala Val
                885                 890                 895

Pro Pro Gln Ala Cys Lys Ala Pro Ser Ser Asn Thr Asp Leu Leu Ser
            900                 905                 910

Cys Leu Leu Gly Pro Pro Glu Ala Ala Ser Gln Gly Pro Pro Glu Asp
      915                 920                 925

Leu Leu Ser Glu Asp Pro Leu Leu Leu Ala Ser Pro Ala Pro Pro Leu
    930                 935                 940

Ser Val Gln Ser Thr Pro Arg Gly Gly Pro Pro Ala Ala Ala Asp Pro
945                 950                 955                 960

Phe Gly Pro Leu Leu Pro Ser Ser Gly Asn Asn Ser Gln Pro Cys Ser
                965                 970                 975

Asn Pro Asp Leu Phe Gly Glu Phe Leu Asn Ser Asp Ser Val Thr Val
            980                 985                 990

Pro Pro Ser Phe Pro Ser Ala His  Ser Ala Pro Pro Pro  Ser Cys Ser
      995                 1000                1005

Ala Asp  Phe Leu His Leu Gly  Asp Leu Pro Gly Glu  Pro Ser Lys
    1010                1015                1020

Met Thr  Ala Ser Ser Ser Asn  Pro Asp Leu Leu Gly  Gly Trp Ala
    1025                1030                1035

Ala Trp  Thr Glu Thr Ala Ala  Ser Ala Val Ala Pro  Thr Pro Ala
    1040                1045                1050

Thr Glu  Gly Pro Leu Phe Ser  Pro Gly Gly Gln Pro  Ala Pro Cys
    1055                1060                1065

Gly Ser  Gln Ala Ser Trp Thr  Lys Ser Gln Asn Pro  Asp Pro Phe
    1070                1075                1080

Ala Asp  Leu Gly Asp Leu Ser  Ser Gly Leu Gln Asp  Pro Gln Ala
    1085                1090                1095

Gln Ser  Thr Val Ser Pro Arg  Gly Gln Arg Val Cys  Thr Cys Ser
    1100                1105                1110

Arg Arg  Leu Pro Thr Gly Lys  Leu Lys Pro Gly Val  Ala Asp Thr
    1115                1120                1125

Gly Thr  Ala Ala Ser Pro His  Arg His Cys Gly Ser  Pro Ala Gly
    1130                1135                1140

Phe Pro  Pro Gly Gly Phe Ile  Pro Lys Thr Ala Thr  Thr Pro Lys
    1145                1150                1155

Gly Ser  Ser Ser Trp Gln Thr  Ser Arg Pro Pro Ala  Gln Gly Ala
    1160                1165                1170

Ser Trp  Pro Pro Gln Ala Lys  Pro Pro Pro Lys Ala  Cys Thr Gln
    1175                1180                1185

Pro Arg  Pro Asn Tyr Ala Ser  Asn Phe Ser Val Ile  Gly Ala Arg
    1190                1195                1200

Glu Glu  Arg Gly Val Arg Ala  Pro Ser Phe Ala Gln  Lys Pro Lys
    1205                1210                1215

Val Ser  Glu Asn Asp Phe Glu  Asp Leu Leu Ser Asn  Gln Gly Phe
    1220                1225                1230

Ser Ser  Arg Ser Asp Lys Lys  Gly Pro Lys Thr Ile  Ala Glu Met
```

```
    1235                1240                1245

Arg Lys  Gln Asp Leu Ala Lys  Asp Thr Asp Pro Leu  Lys Leu Lys
    1250                1255                1260

Leu Leu  Asp Trp Ile Glu Gly  Lys Glu Arg Asn Ile  Arg Ala Leu
    1265                1270                1275

Leu Ser  Thr Leu His Thr Val  Leu Trp Asp Gly Glu  Ser Arg Trp
    1280                1285                1290

Thr Pro  Val Gly Met Ala Asp  Leu Val Ala Pro Glu  Gln Val Lys
    1295                1300                1305

Lys His  Tyr Arg Arg Ala Val  Leu Ala Val His Pro  Asp Lys Ala
    1310                1315                1320

Ala Gly  Gln Pro Tyr Glu Gln  His Ala Lys Met Ile  Phe Met Glu
    1325                1330                1335

Leu Asn  Asp Ala Trp Ser Glu  Phe Glu Asn Gln Gly  Ser Arg Pro
    1340                1345                1350

Leu Phe
    1355


<210> SEQ ID NO 34
<211> LENGTH: 490
<212> TYPE: PRT
<213> ORGANISM: Homo sapiens

<400> SEQUENCE: 34

Met Ala Ser Thr Thr Thr Cys Thr Arg Phe Thr Asp Glu Tyr Gln Leu
1               5                   10                  15

Phe Glu Glu Leu Gly Lys Gly Ala Phe Ser Val Val Arg Arg Cys Met
            20                  25                  30

Lys Ile Pro Thr Gly Gln Glu Tyr Ala Ala Lys Ile Ile Asn Thr Lys
        35                  40                  45

Lys Leu Ser Ala Arg Val Arg Leu His Asp Ser Ile Ser Glu Glu Gly
    50                  55                  60

Phe His Tyr Leu Val Phe Asp Leu Val Thr Gly Gly Glu Leu Phe Glu
65                  70                  75                  80

Asp Ile Val Ala Arg Glu Tyr Tyr Ser Glu Ala Asp Ala Ser His Cys
                85                  90                  95

Ile Gln Gln Ile Leu Glu Ala Val Leu His Cys His Gln Met Gly Val
            100                 105                 110

Val His Arg Asp Leu Lys Pro Glu Asn Leu Leu Leu Ala Ser Lys Ser
        115                 120                 125

Lys Gly Ala Ala Val Lys Leu Ala Asp Phe Gly Leu Ala Ile Glu Val
    130                 135                 140

Gln Gly Asp Gln Gln Ala Trp Phe Gly Phe Ala Gly Thr Pro Gly Tyr
145                 150                 155                 160

Leu Ser Pro Glu Val Leu Arg Lys Asp Pro Tyr Gly Lys Pro Val Asp
                165                 170                 175

Met Trp Ala Cys Gly Val Ile Leu Tyr Ile Leu Leu Val Gly Tyr Pro
            180                 185                 190

Pro Phe Trp Asp Glu Asp Gln His Arg Leu Tyr Gln Gln Ile Lys Ala
        195                 200                 205

Gly Ala Tyr Asp Phe Pro Ser Pro Glu Trp Asp Thr Val Thr Pro Glu
    210                 215                 220

Ala Lys Asp Leu Ile Asn Lys Met Leu Thr Ile Asn Pro Ala Lys Arg
225                 230                 235                 240

Ile Thr Ala Ser Glu Ala Leu Lys His Pro Trp Ile Cys Gln Arg Ser
```

```
                245                 250                 255

Thr Val Ala Ser Met Met His Arg Gln Glu Thr Val Asp Cys Leu Lys
            260                 265                 270

Lys Phe Asn Ala Arg Arg Lys Leu Lys Gly Ala Ile Leu Thr Thr Met
        275                 280                 285

Leu Ala Thr Arg Asn Phe Ser Ala Ala Lys Ser Leu Leu Lys Lys Pro
    290                 295                 300

Asp Gly Val Lys Lys Arg Lys Ser Ser Ser Ser Val Gln Met Met Glu
305                 310                 315                 320

Ser Thr Glu Ser Ser Asn Thr Thr Ile Glu Asp Glu Asp Val Glu Ala
                325                 330                 335

Arg Lys Gln Glu Ile Ile Lys Val Thr Glu Gln Leu Ile Glu Ala Ile
            340                 345                 350

Asn Asn Gly Asp Phe Glu Ala Tyr Thr Lys Ile Cys Asp Pro Gly Leu
        355                 360                 365

Thr Ala Phe Glu Pro Glu Ala Leu Gly Asn Leu Val Glu Gly Met Asp
    370                 375                 380

Phe His Arg Phe Tyr Phe Glu Asn Ala Leu Ser Lys Ser Asn Lys Pro
385                 390                 395                 400

Ile His Thr Ile Ile Leu Asn Pro His Val His Leu Val Gly Asp Asp
                405                 410                 415

Ala Ala Cys Ile Ala Tyr Ile Arg Leu Thr Gln Tyr Met Asp Gly Ser
            420                 425                 430

Gly Met Pro Lys Thr Met Gln Ser Glu Glu Thr Arg Val Trp His Arg
        435                 440                 445

Arg Asp Gly Lys Trp Gln Asn Val His Phe His Arg Ser Gly Ser Pro
    450                 455                 460

Thr Val Pro Ile Lys Pro Pro Cys Ile Pro Asn Gly Lys Glu Asn Phe
465                 470                 475                 480

Ser Gly Gly Thr Ser Leu Trp Gln Asn Ile
                485                 490


<210> SEQ ID NO 35
<211> LENGTH: 344
<212> TYPE: PRT
<213> ORGANISM: Homo sapiens

<400> SEQUENCE: 35

Met Ala Ser Thr Thr Thr Cys Thr Arg Phe Thr Asp Glu Tyr Gln Leu
1               5                   10                  15

Phe Glu Glu Leu Gly Lys Gly Ala Phe Ser Val Val Arg Arg Cys Met
            20                  25                  30

Lys Ile Pro Thr Gly Gln Glu Tyr Ala Ala Lys Ile Ile Asn Thr Lys
        35                  40                  45

Lys Leu Ser Ala Arg Val Arg Leu His Asp Ser Ile Ser Glu Glu Gly
    50                  55                  60

Phe His Tyr Leu Val Val Asp Leu Val Thr Gly Gly Glu Leu Phe Glu
65                  70                  75                  80

Asp Ile Val Ala Arg Glu Tyr Tyr Ser Glu Ala Asp Ala Ser His Cys
                85                  90                  95

Ile Gln Gln Ile Leu Glu Ala Val Leu His Cys His Gln Met Gly Val
            100                 105                 110

Val His Arg Asp Leu Lys Pro Glu Asn Leu Leu Leu Ala Ser Lys Ser
        115                 120                 125

Lys Gly Ala Ala Val Lys Leu Ala Asp Phe Gly Leu Ala Ile Glu Val
```

```
    130                 135                 140

Gln Gly Asp Gln Gln Ala Trp Phe Gly Phe Ala Gly Thr Pro Gly Tyr
145                 150                 155                 160

Leu Ser Pro Glu Val Leu Arg Lys Asp Pro Tyr Gly Lys Pro Val Asp
                165                 170                 175

Met Trp Ala Cys Gly Val Ile Leu Tyr Ile Leu Leu Val Gly Tyr Pro
            180                 185                 190

Pro Phe Trp Asp Glu Asp Gln His Arg Leu Tyr Gln Gln Ile Lys Ala
        195                 200                 205

Gly Ala Tyr Asp Phe Pro Ser Pro Glu Trp Asp Thr Val Thr Pro Glu
    210                 215                 220

Ala Lys Asp Leu Ile Asn Lys Met Leu Thr Ile Asn Pro Ala Lys Arg
225                 230                 235                 240

Ile Thr Ala Ser Glu Ala Leu Lys His Pro Trp Ile Cys Gln Arg Ser
                245                 250                 255

Thr Val Ala Ser Met Met His Arg Gln Glu Thr Val Asp Cys Leu Lys
            260                 265                 270

Lys Phe Asn Ala Arg Arg Lys Leu Lys Gly Ala Ile Leu Thr Thr Met
        275                 280                 285

Leu Ala Thr Arg Asn Phe Ser Ala Ala Lys Ser Leu Leu Lys Lys Pro
    290                 295                 300

Asp Gly Val Lys Glu Ser Thr Glu Ser Ser Asn Thr Thr Ile Glu Asp
305                 310                 315                 320

Glu Asp Val Lys Gly Thr Val Ala His Ala Cys Asn Pro Ser Thr Leu
                325                 330                 335

Gly Gly Arg Gly Gly Gln Ile Thr
            340


<210> SEQ ID NO 36
<211> LENGTH: 89
<212> TYPE: PRT
<213> ORGANISM: Homo sapiens

<400> SEQUENCE: 36

Met Lys Lys Phe Ser Arg Met Pro Lys Ser Glu Gly Gly Ser Gly Gly
1               5                   10                  15

Gly Ala Ala Gly Gly Gly Ala Gly Gly Ala Gly Ala Gly Ala Gly Cys
            20                  25                  30

Gly Ser Gly Gly Ser Ser Val Gly Val Arg Val Phe Ala Val Gly Arg
        35                  40                  45

His Gln Val Thr Leu Glu Glu Ser Leu Ala Glu Val Ile Gln Met Leu
    50                  55                  60

Pro Val Gln Glu Pro Arg Leu Glu Tyr Arg Val Pro Leu Ile Ser Ser
65                  70                  75                  80

Gly Arg Arg Arg Leu Arg Arg Arg Cys
                85


<210> SEQ ID NO 37
<211> LENGTH: 88
<212> TYPE: PRT
<213> ORGANISM: Homo sapiens

<400> SEQUENCE: 37

Met Lys Lys Phe Ser Arg Met Pro Lys Ser Glu Gly Gly Ser Gly Gly
1               5                   10                  15

Gly Ala Ala Gly Gly Gly Ala Gly Gly Ala Gly Ala Gly Ala Gly Cys
            20                  25                  30
```

Gly Ser Gly Gly Ser Ser Val Gly Val Arg Val Phe Ala Val Gly Arg
35 40 45

His Gln Val Thr Leu Glu Glu Ser Leu Ala Glu Gly Thr Gly Ala Arg
50 55 60

Gly Gly Ser Asp Arg Gln Val Asp Ser Pro Gln Phe Ser Ser Cys Val
65 70 75 80

Leu Thr Val Glu Ser Asp Val His
85

<210> SEQ ID NO 38
<211> LENGTH: 137
<212> TYPE: PRT
<213> ORGANISM: Homo sapiens

<400> SEQUENCE: 38

Met Ser Thr Ala Ser Ala Ala Ser Ser Ser Ser Ser Ser Ser Ala Gly
1 5 10 15

Glu Met Ile Glu Ala Pro Ser Gln Val Leu Asn Phe Glu Glu Ile Asp
20 25 30

Tyr Lys Glu Ile Glu Val Glu Glu Val Val Gly Arg Gly Ala Phe Gly
35 40 45

Val Val Cys Lys Ala Lys Trp Arg Ala Lys Asp Val Ala Ile Lys Gln
50 55 60

Ile Glu Ser Glu Ser Glu Arg Lys Ala Phe Ile Val Glu Leu Arg Gln
65 70 75 80

Leu Ser Arg Val Asn His Pro Asn Ile Val Lys Leu Tyr Gly Ala Cys
85 90 95

Leu Asn Pro Val Cys Leu Val Met Glu Tyr Ala Glu Gly Gly Ser Leu
100 105 110

Tyr Asn Val Cys Ala Phe Leu Ser Gln Cys Cys Met Val Leu Asn His
115 120 125

Cys His Ile Ile Leu Leu Pro Thr Gln
130 135

<210> SEQ ID NO 39
<211> LENGTH: 243
<212> TYPE: PRT
<213> ORGANISM: Homo sapiens

<400> SEQUENCE: 39

Met Ala Asp Leu Glu Ala Val Leu Ala Asp Val Ser Tyr Leu Met Ala
1 5 10 15

Met Glu Lys Ser Lys Ala Thr Pro Ala Ala Arg Ala Ser Lys Lys Ile
20 25 30

Leu Leu Pro Glu Pro Ser Ile Arg Ser Val Met Gln Lys Tyr Leu Glu
35 40 45

Asp Arg Gly Glu Val Thr Phe Glu Lys Ile Phe Ser Gln Lys Leu Gly
50 55 60

Tyr Leu Leu Phe Arg Asp Phe Cys Leu Asn His Leu Glu Glu Ala Arg
65 70 75 80

Pro Leu Val Glu Phe Tyr Glu Glu Ile Lys Lys Tyr Glu Lys Leu Glu
85 90 95

Thr Glu Glu Glu Arg Val Ala Arg Ser Arg Glu Ile Phe Asp Ser Tyr
100 105 110

Ile Met Lys Glu Leu Leu Ala Cys Ser His Pro Phe Ser Lys Ser Ala
115 120 125

```
Thr Glu His Val Gln Gly His Leu Gly Lys Lys Gln Val Pro Pro Asp
    130                 135                 140

Leu Phe Gln Pro Tyr Ile Glu Glu Ile Cys Gln Asn Leu Arg Gly Asp
145                 150                 155                 160

Val Phe Gln Lys Phe Ile Glu Ser Asp Lys Phe Thr Arg Phe Cys Gln
                165                 170                 175

Trp Lys Asn Val Glu Leu Asn Ile His Val Ser Gly Leu Gly Trp Gly
            180                 185                 190

Met Glu Ser His Ala Pro Cys Cys Ser Ser Pro Gly Ser Trp Ala Cys
        195                 200                 205

Gly Leu Ala Gly Arg Gly Arg Ser Gly Asp Val Cys Pro Leu Ala Pro
    210                 215                 220

Arg Ala Val Ala Met Gly Val Arg Ala Gly Ile Pro Ala Trp Gly Gly
225                 230                 235                 240

Arg Ser Arg


<210> SEQ ID NO 40
<211> LENGTH: 463
<212> TYPE: PRT
<213> ORGANISM: Homo sapiens

<400> SEQUENCE: 40

Met Arg Arg Pro Arg Gly Glu Pro Gly Pro Arg Ala Pro Arg Pro Thr
1               5                   10                  15

Glu Gly Ala Thr Cys Ala Gly Pro Gly Glu Ser Trp Ser Pro Ser Pro
            20                  25                  30

Asn Ser Met Leu Arg Val Leu Leu Ser Ala Gln Thr Ser Pro Ala Arg
        35                  40                  45

Leu Ser Gly Leu Leu Leu Ile Pro Pro Val Gln Pro Cys Cys Leu Gly
    50                  55                  60

Pro Ser Lys Trp Gly Asp Arg Pro Val Gly Gly Gly Pro Ser Ala Gly
65                  70                  75                  80

Pro Val Gln Gly Leu Gln Arg Leu Leu Glu Gln Ala Lys Ser Pro Gly
                85                  90                  95

Glu Leu Leu Arg Trp Leu Gly Gln Asn Pro Ser Lys Val Arg Ala His
            100                 105                 110

His Tyr Ser Val Ala Leu Arg Arg Leu Gly Gln Leu Leu Gly Ser Arg
        115                 120                 125

Pro Arg Pro Pro Pro Val Glu Gln Val Thr Leu Gln Asp Leu Ser Gln
    130                 135                 140

Leu Ile Ile Arg Asn Cys Pro Ser Phe Asp Ile His Thr Ile His Val
145                 150                 155                 160

Cys Leu His Leu Ala Val Leu Leu Gly Phe Pro Ser Asp Gly Pro Leu
                165                 170                 175

Val Cys Ala Leu Glu Gln Glu Arg Arg Leu Arg Leu Pro Pro Lys Pro
            180                 185                 190

Pro Pro Pro Leu Gln Pro Leu Leu Arg Glu Ala Arg Pro Glu Glu Leu
        195                 200                 205

Thr Pro His Val Met Val Leu Leu Ala Gln His Leu Ala Arg His Arg
    210                 215                 220

Leu Arg Glu Pro Gln Leu Leu Glu Ala Ile Thr His Phe Leu Val Val
225                 230                 235                 240

Gln Glu Thr Gln Leu Ser Ser Lys Val Val Gln Lys Leu Val Leu Pro
                245                 250                 255

Phe Gly Arg Leu Asn Tyr Leu Pro Leu Glu Gln Gln Phe Met Pro Cys
```

```
            260                 265                 270

Leu Glu Arg Ile Leu Ala Arg Glu Ala Gly Val Ala Pro Leu Ala Thr
        275                 280                 285

Val Asn Ile Leu Met Ser Leu Cys Gln Leu Arg Cys Leu Pro Phe Arg
    290                 295                 300

Ala Leu His Phe Val Phe Ser Pro Gly Phe Ile Asn Tyr Ile Ser Gly
305                 310                 315                 320

Thr Pro His Ala Leu Ile Val Arg Arg Tyr Leu Ser Leu Leu Asp Thr
                325                 330                 335

Ala Val Glu Leu Glu Leu Pro Gly Tyr Arg Gly Pro Arg Leu Pro Arg
            340                 345                 350

Arg Gln Gln Val Pro Ile Phe Pro Gln Pro Leu Ile Thr Asp Arg Ala
        355                 360                 365

Arg Cys Lys Tyr Ser His Lys Asp Ile Val Ala Glu Gly Leu Arg Gln
    370                 375                 380

Leu Leu Gly Glu Glu Lys Tyr Arg Gln Asp Leu Thr Val Pro Pro Gly
385                 390                 395                 400

Tyr Cys Thr Gly Glu Gln Gly Ala Gly Gly Arg Pro Gly Glu Thr Glu
                405                 410                 415

Pro Trp Leu Arg Pro Pro Ala Leu Leu Pro Ser Arg Leu Pro Ala Val
            420                 425                 430

Arg Gln Gln Leu Trp Cys Cys Ala Ser Arg Glu Asp Pro Gly Pro Leu
        435                 440                 445

Pro Ala Ile Pro Thr Lys Val Leu Pro Thr Gly Pro Gly Cys Leu
    450                 455                 460


<210> SEQ ID NO 41
<211> LENGTH: 184
<212> TYPE: PRT
<213> ORGANISM: Homo sapiens

<400> SEQUENCE: 41

Met Arg Leu Ala Arg Leu Leu Arg Gly Ala Ala Leu Ala Gly Pro Gly
1               5                   10                  15

Pro Gly Leu Arg Ala Ala Gly Phe Ser Arg Ser Phe Ser Ser Asp Ser
            20                  25                  30

Gly Ser Ser Pro Ala Ser Glu Arg Gly Val Pro Gly Gln Val Asp Phe
        35                  40                  45

Tyr Ala Arg Phe Ser Pro Ser Pro Leu Ser Met Lys Gln Phe Leu Asp
    50                  55                  60

Phe Gly Ser Val Asn Ala Cys Glu Lys Thr Ser Phe Met Phe Leu Arg
65                  70                  75                  80

Gln Glu Leu Pro Val Arg Leu Ala Asn Ile Met Lys Glu Ile Ser Leu
                85                  90                  95

Leu Pro Asp Asn Leu Leu Arg Thr Pro Ser Val Gln Leu Val Gln Ser
            100                 105                 110

Trp Tyr Ile Gln Ser Leu Gln Glu Leu Leu Asp Phe Lys Asp Lys Ser
        115                 120                 125

Ala Glu Asp Ala Lys Ala Ile Tyr Glu Arg Pro Arg Arg Thr Trp Leu
    130                 135                 140

Gln Val Ser Ser Leu Cys Cys Met Ala Cys Lys Met Ile Phe Ile Val
145                 150                 155                 160

Trp Trp Lys Arg Gln Arg Lys Ser Ile Ser Ser Lys Thr His Trp Lys
                165                 170                 175

His Lys Ser Lys Leu Gln Cys Thr
```

180

<210> SEQ ID NO 42
<211> LENGTH: 386
<212> TYPE: PRT
<213> ORGANISM: Homo sapiens

<400> SEQUENCE: 42

```
Met Ser Ser Leu Gly Ala Ser Phe Val Gln Ile Lys Phe Asp Asp Leu
1               5                   10                  15

Gln Phe Phe Glu Asn Cys Gly Gly Gly Ser Phe Gly Ser Val Tyr Arg
            20                  25                  30

Ala Lys Trp Ile Ser Gln Asp Lys Glu Val Ala Val Lys Lys Leu Leu
        35                  40                  45

Lys Ile Glu Lys Glu Ala Glu Ile Leu Ser Val Leu Ser His Arg Asn
    50                  55                  60

Ile Ile Gln Phe Tyr Gly Val Ile Leu Glu Pro Pro Asn Tyr Gly Ile
65                  70                  75                  80

Val Thr Glu Tyr Ala Ser Leu Gly Ser Leu Tyr Asp Tyr Ile Asn Ser
                85                  90                  95

Asn Arg Ser Glu Glu Met Asp Met Asp His Ile Met Thr Trp Ala Thr
            100                 105                 110

Asp Val Ala Lys Gly Met His Tyr Leu His Met Glu Ala Pro Val Lys
        115                 120                 125

Val Ile His Arg Asp Leu Lys Ser Arg Asn Val Val Ile Ala Ala Asp
    130                 135                 140

Gly Val Leu Lys Ile Cys Asp Phe Gly Ala Ser Arg Leu His Asn His
145                 150                 155                 160

Thr Thr His Met Ser Leu Val Gly Thr Phe Pro Trp Met Ala Pro Glu
                165                 170                 175

Val Ile Gln Ser Leu Pro Val Ser Glu Thr Cys Asp Thr Tyr Ser Tyr
            180                 185                 190

Gly Val Val Leu Trp Glu Met Leu Thr Arg Glu Val Pro Phe Lys Gly
        195                 200                 205

Leu Glu Gly Leu Gln Val Ala Trp Leu Val Val Glu Lys Asn Glu Arg
    210                 215                 220

Leu Lys Lys Leu Glu Arg Asp Leu Ser Phe Lys Glu Gln Glu Leu Lys
225                 230                 235                 240

Glu Arg Glu Arg Arg Leu Lys Met Trp Glu Gln Lys Leu Thr Glu Gln
                245                 250                 255

Ser Asn Thr Pro Leu Leu Leu Pro Leu Val Ala Arg Met Ser Glu Glu
            260                 265                 270

Ser Tyr Phe Glu Ser Lys Thr Glu Glu Ser Asn Ser Ala Glu Met Ser
        275                 280                 285

Cys Gln Ile Thr Ala Thr Ser Asn Gly Glu Gly His Gly Met Asn Pro
    290                 295                 300

Ser Leu Gln Ala Met Met Leu Met Gly Phe Gly Asp Ile Phe Ser Met
305                 310                 315                 320

Asn Lys Ala Gly Ala Val Met His Ser Gly Met Gln Ile Asn Met Gln
                325                 330                 335

Ala Lys Gln Asn Ser Ser Lys Thr Thr Ser Lys Arg Arg Gly Lys Lys
            340                 345                 350

Val Asn Met Ala Leu Gly Phe Ser Asp Phe Asp Leu Ser Glu Gly Asp
        355                 360                 365

Asp Asp Asp Asp Asp Asp Gly Glu Glu Glu Asp Asn Asp Met Asp Asn
```

370 375 380

Ser Glu
385

<210> SEQ ID NO 43
<211> LENGTH: 152
<212> TYPE: PRT
<213> ORGANISM: Homo sapiens

<400> SEQUENCE: 43

Met Asp Gln Tyr Cys Ile Leu Gly Arg Ile Gly Glu Gly Ala His Gly
1 5 10 15

Ile Val Phe Lys Ala Lys His Val Glu Thr Gly Glu Ile Val Ala Leu
20 25 30

Lys Lys Val Ala Leu Arg Arg Leu Glu Asp Gly Phe Pro Asn Gln Ala
35 40 45

Leu Arg Glu Ile Lys Ala Leu Gln Glu Met Glu Asp Asn Gln Tyr Val
50 55 60

Val Gln Leu Lys Ala Val Phe Pro His Gly Gly Gly Phe Val Leu Ala
65 70 75 80

Phe Glu Phe Met Leu Ser Asp Leu Ala Glu Val Val Arg His Ala Gln
85 90 95

Arg Pro Leu Ala Gln Ala Gln Val Lys Ser Tyr Leu Gln Met Leu Leu
100 105 110

Lys Gly Val Ala Phe Cys His Ala Asn Asn Ile Val His Arg Asp Leu
115 120 125

Pro Pro Arg Pro Ile Gln Gly Pro Pro Thr Ser Met Thr Ser Thr Trp
130 135 140

Thr Gly Leu Leu Arg Ser Arg Cys
145 150

<210> SEQ ID NO 44
<211> LENGTH: 1916
<212> TYPE: DNA
<213> ORGANISM: Homo sapiens

<400> SEQUENCE: 44
gttaggccag gaggaccatg tgaatggggc cagagggctc ccgggctggg caggaccatg 60
ggctgtggct gcagctcaca cccggaagat gactggatgg aaaacatcga tgtgtgtgag 120
aactgccatt atcccatagt cccactggat ggcaagggca cgctgctcat ccgaaatggc 180
tctgagacaa cctggttatc gctctgcaca gctatgagcc ctctcacgac ggagatctgg 240
gctttgagaa gggggaacag ctccgcatcc tggagcagag cggcgagtgg tggaaggcgc 300
agtccctgac cacgggccag gaaggcttca tccccttcaa ttttgtggcc aaagcgaaca 360
gcctggagcc cgaaccctgg ttcttcaaga acctgagccg caaggacgcg gagcggcagc 420
tcctggcgcc cgggaacact cacggctcct tcctcatccg ggagagcgag agcaccgcgg 480
gatcgttttc actgtcggtc cgggacttcg accagaacca gggagaggtg gtgaaacatt 540
acaagatccg taatctggac aacggtggct tctacatctc ccctcgaatc acttttcccg 600
gcctgcatga actggtccgc cattacacca atgcttcaga tgggctgtgc acacggttga 660
gccgcccctg ccagacccag aagccccaga agccgtggtg ggaggacgag tgggaggttc 720
ccagggagac gctgaagctg gtggagcggc tgggggctgg acagttcggg gaggtgtgga 780
tggggtacta caacgggcac acgaaggtgg cggtgaagag cctgaagcag ggcagcatgt 840
ccccggacgc cttcctggcc gaggccaacc tcatgaagca gctgcaacac cagcggctgg 900

```
ttcggctcta cgctgtggtc acccaggagc ccatctacat catcactgaa tacatggaga    960

atgggagtct agtggatttt ctcaagaccc cttcaggcat caagttgacc atcaacaaac   1020

tcctggacat ggcagcccaa ttgcagaagg catggcattc attgaagagc ggaattatat   1080

tcatcgtgac cttcgggctg ccaacattct ggtgtctgac accctgagct gcaagattgc   1140

agacttgggt ctagcacgcc tcattgagga caacgagtac acagccaggg agggggccaa   1200

gtttcccatt aagtggacag cgccagaagc cattaactac gggacattca ccatcaagtc   1260

agatgtgtgg tcttttggga tcctgctgac ggaaattgtc acccacggcc gcatcccctta  1320

cccagggatg accaacccgg aggtgattca gaacctggag cgaggctacc gcatggtgcg   1380

ccctgacaac tgtccagagg agctgtacca actcatgagg ctgtgctgga aggagcgccc   1440

agaggaccgg cccacctttg actacctgcg cagtgtgctg gaggacttct tcacggccac   1500

agagggccag taccagcctc agccttgaga ggccttgaga ggccctgggg ttctcccccct  1560

ttctctccag cctgacttgg ggagatggag ttcttgtgcc atagtcacat ggcctatgca   1620

catatggact ctgcacatga atcccaccca catgtgacac atatgcacct tgtgtctgta   1680

cacgtgtcct gtagttgcgt ggactctgca catgtcttgt acatgtgtag cctgtgcatg   1740

tatgtcttgg acactgtaca aggtacccct ttctggctct cccatttcct gagaccacag   1800

agagagggga gaagcctggg attgacagaa gcttctgccc acctactttt ctttcctcag   1860

atcatccaga agttcctcaa gggccaggac tttatctaat acctctgtgt gctcct       1916
```

<210> SEQ ID NO 45
<211> LENGTH: 926
<212> TYPE: DNA
<213> ORGANISM: Homo sapiens

<400> SEQUENCE: 45

```
tctacccggt tcaagcatgg ctgaccaggc gcccttcgac acggacgtca acaccctgac     60

ccgcttcgtc atggaggagg gcaggaaggc ccgcggcacg ggcgagttga cccagctgct    120

caactcgctc tgcacagcag tcaaagccat ctcttcggcg gtgcgcaagg cgggcatcgc    180

gcacctctat ggcattgctg gttctaccaa cgtgacaggt gatcaagtta agaagctgga    240

cgtcctctcc aacgacctgg ttatgaacat gttaaagtca tcctttgcca cgtgtgttct    300

cgtgtcagaa gaagataaac acgccatcat agtggaaccg gagaaaaggg gtaaatatgt    360

ggtctgtttt gatccccttg atggatcttc caacatcgat tgccttgtgt ccgttggaac    420

catttttggc atctatagaa agaaatcaac tgatgagcct tctgagaagg atgctctgca    480

accaggccgg aacctggtgg cagccggcta cgcactgtat ggcagtgcca ccatgctggt    540

ccttgccatg gactgtgggg tcaactgctt catgctggac ccggataatt cagctcctta    600

tggggcccgg tatgtgggct ccatggtggc tgatgttcat cgcactctgg tctacggagg    660

gatatttctg taccccgcta acaagaagag ccccaatgga aagctgagac tgctgtacga    720

atgcaacccc atggcctacg tcatggagaa ggctggggga atggccacca ctgggaagga    780

ggccgtgtta gacgtcattc ccacagacat tcaccagagg gcgcccggtga tcttggggtc   840

cccgacgac gtgctcgagt tcctgaaggt gtatgagaag cactctgccc agtgagcacc     900

tgccctgcct gcatctggag aattga                                         926
```

<210> SEQ ID NO 46
<211> LENGTH: 1382
<212> TYPE: DNA
<213> ORGANISM: Homo sapiens

<400> SEQUENCE: 46

```
tgatggcgtc cccacgggaa ttgacacaga accccctgaa gaagatctgg atgccataca     60
gcaatgggcg gcccgctctg cacgcttgcc agcgcggtgt gtgcatgacc aactgcccaa    120
ctctcattgt catggtgggc ctgcccgcca ggggcaagac ctacatctcc aagaagctga    180
ctcgatacct gaactggatt ggtgtgccca ctcgggagtt caatgttggc cagtatcgcc    240
gggacgtggt caagacctac aaatcttttg aatttttct ccccgacaat gaagagggcc     300
tgaaaatcag gaagcagtgt gccctggcag ccctccgtga cgtccggcgg ttccttagtg    360
aggagggggg acatgtggcg gtttttgatg ccacaaacac cacccgagaa cggagagcga    420
ccatctttaa ttttggagaa cagaatggct acaagacctt ttttgtcgag tccatctgtg    480
tggatcctga ggtcatagct gccaacatcg tgcaagtgaa actgggcagc cctgactatg    540
tcaaccgcga cagtgatgag gctacggagg acttcatgag gcgcattgag tgctatgaga    600
actcctacga gtcgctagat gaggacctgg atagggacct gtcctatatc aagatcatgg    660
atgtgggcca gagctacgtg gtgaaccgtg tggctgacca catccagagc cgcatcgtat    720
attacctcat gaacatccac gtgacccccc gctccatcta cctctgccgg cacggggaga    780
gcgagctcaa cctcaagggc cggattggcg gggacccagg actgtcccct cggggcaggg    840
agtttgccaa gagtctagcc cagttcatca gtgaccaaaa tatcaaggat ctgaaggtct    900
ggacaagcca gatgaagagg acaatccaga cggctgaggc actgggtgtg ccctatgaac    960
agtggaaggt cctcaacgag atcgatgcgt cctacgagga cctggtccag agactggagc   1020
ctgtcatcat ggagctggag aggcaagaga atgtgctggt catctgccac caggctgtga   1080
tgcgctgcct gctggcctac ttcctcgaca aggcagcaga acagctgccc tacctcaagt   1140
gtccgctgca cacagtcctg aagctgactc ctgtggcata tggttgtaaa gtggagtcca   1200
tattcctgaa cgtggctgct gtgaacacgc accgggacag gcctcagaac gtggacatct   1260
caagacctcc agaggaagcc cttgtcacgg tgcctgctca ccagtgacca tgttcatcca   1320
ctgtgaccac taggcaggca ctgctctctg cagagggggt cattccaggc cctccagtgt   1380
ga                                                                  1382
```

<210> SEQ ID NO 47
<211> LENGTH: 1678
<212> TYPE: DNA
<213> ORGANISM: Homo sapiens

<400> SEQUENCE: 47

```
tatggccgca ttgtaccgcc ctggcctgcg gcttaactgg catgggctga gccccttggg     60
ctggccatca tgccgtagca tccagaccct gcgagtgctt agtggagatc tgggccagct    120
tcccactggc attcgagatt ttgtagagca cagtgcccgc ctgtgccaac cagagggcat    180
ccacatctgt gatggaactg aggctgagaa tactgccaca ctgaccctgc tggagcagca    240
gggcctcatc cgaaagctcc ccaagtacaa taactgctgg ctggcccgca cagaccccaa    300
ggatgtggca cgagtagaga gcaagacggt gattgtaact ccttctcagc gggacacggt    360
accactcccg cctggtgggg cccgtgggca gctgggcaac tggatgtccc cagctgattt    420
ccagcgagct gtggatgaga ggtttccagg ctgcatgcag ggccgcacca tgtatgtgct    480
tccattcagc atgggtcctg tgggctcccc gctgtcccgc atcggggtgc agctcactga    540
ctcagcctat gtggtggcaa gcatgcgtat tatgacccga ctggggacac ctgtgcttca    600
ggccctggga gatggtgact ttgtcaagtg tctgcactcc gtgggccagc ccctgacagg    660
```

```
acaagatcct gggcatcacc agccctgcag ggaagaagcg ctatgtggca gccgccttcc    720
ctagtgcctg tggcaagacc aacctggcta tgatgcggcc tgcactgcca ggctggaaag    780
tggagtgtgt gggggatgat attgcttgga tgaggtttga cagtgaaggt cgactccggg    840
ccatcaaccc tgagaacggc ttctttgggg ttgcccctgg tacctctgcc accaccaatc    900
ccaacgccat ggctacaatc cagagtaaca ctatttttac caatgtggct gagaccagtg    960
atggtggcgt gtactgggag ggcattgacc agcctcttcc acctggtgtt actgtgacct   1020
cctggctggg caaaccctgg aaacctggtg acaaggagcc ctgtgcacat cccaactctc   1080
gattttgtgc ccggctcgc  cagtgcccca tcatggaccc agcctgggag gccccagagg   1140
gtgtccccat tgacgccatc atctttggtg gccgcagacc caaagggaag atcatcatgc   1200
acgacccatt tgccatgcgg cccttttttg gctacaactt cgggcactac ctggaacact   1260
ggctgagcat ggaagggcgc aagggggccc agctgccccg tatcttccat gtcaactggt   1320
tccggcgtga cgaggcaggg cacttcctgt ggccaggctt tggggagaat gctcgggtgc   1380
tagactggat ctgccggcgg ttagaggggg aggacagtgc ccgagagaca cccattgggc   1440
tggtgccaaa ggaaggagcc ttggatctca gcggcctcag agctatagac accactcagc   1500
tgttctccct ccccaaggac ttctgggaac aggaggttcg tgacattcgg agctacctga   1560
cagagcaggt caaccaggat ctgcccaaag aggtgttggc tgagcttgag gccctggaga   1620
gacgtgtgca caaaatgtga cctgaggccc tagtctagca agaggacata gcaccct a    1678
```

<210> SEQ ID NO 48
<211> LENGTH: 895
<212> TYPE: DNA
<213> ORGANISM: Homo sapiens

<400> SEQUENCE: 48

```
tctgtaaatg caagagaacc gagtgtggat aattagcgat ggaagaaaaa acctctagaa     60
taaaagcatc catacccccag tttaccaatt cccccacaat ggtgatcatg gtgggtttac  120
cagctcgagg caagacctat atctccacaa agctcacacg atatctcaac tggataggaa    180
caccaactaa agtgtttaat ttaggccagt atcgacgaga ggcagtgagc tacaagaact    240
atgaattctt tcttccagac aacatggaag ccctgcaaat caggaagcag tgcgccctgg    300
cagccctgaa ggatgttcac aactatctca gccatgagga aggtcatgtt gcggtttttg    360
atgccaccaa cactaccaga gaacgacggt cactgatcct gcagtttgca aaagaacatg    420
gttacaaggt gtttttcatt gagtccattt gtaatgaccc tggcataatt gcagaaaaca    480
tcaggcaagt gaaacttggc agccctgatt atatagactg tgaccgggaa aaggttctgg    540
aagactttct aaagagaatt gagtgctatg aggtcaacta ccaacccttg gatgaggaac    600
tggacagatc ttcgacgtgg gcacacgcta catggtgaac cgagtgcagg atcacatcca    660
gagccgcaca gtctactacc tcatgaatat ccatgtcaca cctcgctcca tctacctttg    720
ccgacatggc gagagtgaac tcaacatcag aggccgcatc ggaggtgact ctggcctctc    780
agttcgcggc aagcagtatg cctatgccct ggccaacttc attcagtccc agggcatcag    840
ctccctgaag gtgtggacca gtcacatgaa gaggaccatc cagacagctg aggcc        895
```

<210> SEQ ID NO 49
<211> LENGTH: 1294
<212> TYPE: DNA
<213> ORGANISM: Homo sapiens

<400> SEQUENCE: 49

```
tctgtaaatg caagagaacc gagtgttgga taattagcga tggaagaaaa aacctctaga     60
ataaaagtgt ttaatttagg ccagtatcga cgagaggcag tgagctacaa gaactatgaa    120
ttctttcttc cagacaacat ggaagccctg caaatcagga agcagtgcgc cctggcagcc    180
ctgaaggatg ttcacaacta tctcagccat gaggaaggtc atgttgcggt ttttgatgcc    240
accaacacta ccagagaacg acggtcactg atcctgcagt ttgcaaaaga acatggttac    300
aaggtgtttt tcattgagtc catttgtaat gaccctggca taattgcaga aaacatcagg    360
caagtgaaac ttggcagccc tgattatata gactgtgacc gggaaaaggt tctggaagac    420
tttctaaaga gaattgagtg ctatgaggtc aactaccaac ccttggatga ggaactggac    480
agccacctgt cctacatcaa gatcttcgac gtgggcacac gctacatggt gaaccgagtg    540
caggatcaca tccagagccg cacagtctac tacctcatga atatccatgt cacacctcgc    600
tccatctacc tttgccgaca tggcgagagt gaactcaaca tcagaggccg catcggaggt    660
gactctggcc tctcagttcg cggcaagcag tatgcctatg ccctggccaa cttcattcag    720
tcccagggca tcagctccct gaaggtgtgg accagtcaca tgaagaggac catccagaca    780
gctgaggccc tgggtgtccc ctatgagcag tggaaggccc tgaatgagat tgatgcgggt    840
gtctgtgagg agatgaccta tgaagaaatc caggaacatt accctgaaga atttgcactg    900
cgagaccaag ataaatatcg ctaccgctat cccaagggag agtcctatga ggatctggtt    960
cagcgtctgg agccagtgat aatggagcta gaacgacagg agaatgtact ggtgatctgc   1020
caccaggctg tcatgcggtg cctcctggcc tatttcctgg ataaaagttc agatgagctt   1080
ccatatctca agtgccctct gcacacagtg ctcaaactca ctcctgtggc ttatggctgc   1140
aaagtggaat ccatctacct gaatgtggag accgtgaaca cacaccggga gaagcctgag   1200
aatgtggaca tcacccggga acctgaggaa gccctggata ctgtcccagc ccactactga   1260
gccctttcca agaagtcaaa ctgcctgtgt ccta                               1294
```

<210> SEQ ID NO 50
<211> LENGTH: 1354
<212> TYPE: DNA
<213> ORGANISM: Homo sapiens

<400> SEQUENCE: 50

```
tctgtaaatg caagagaacc gagtgttgga taattagcga tggaagaaaa aacctctaga     60
ataaaagcat ccatacccca gtttaccaat tcccccacaa tggtgatcat ggtgggttta    120
ccagctcgag gcaagaccta tatctccaca aagctcacac gatatctcaa ctggatagga    180
acaccaacta aagacaacat ggaagccctg caaatcagga agcagtgcgc cctggcagcc    240
ctgaaggatg ttcacaacta tctcagccat gaggaaggtc atgttgcggt ttttgatgcc    300
accaacacta ccagagaacg acggtcactg atcctgcagt ttgcaaaaga acatggttac    360
aaggtgtttt tcattgagtc catttgtaat gaccctggca taattgcaga aaacatcagg    420
caagtgaaac ttggcagccc tgattatata gactgtgacc gggaaaaggt tctggaagac    480
tttctaaaga gaattgagtg ctatgaggtc aactaccaac ccttggatga ggaactggac    540
agccacctgt cctacatcaa gatcttcgac gtgggcacac gctacatggt gaaccgagtg    600
caggatcaca tccagagccg cacagtctac tacctcatga atatccatgt cacacctcgc    660
tccatctacc tttgccgaca tggcgagagt gaactcaaca tcagaggccg catcggaggt    720
gactctggcc tctcagttcg cggcaagcag tatgcctatg ccctggccaa cttcattcag    780
tcccagggca tcagctccct gaaggtgtgg accagtcaca tgaagaggac catccagaca    840
```

```
gctgaggccc tgggtgtccc ctatgagcag tggaaggccc tgaatgagat tgatgcgggt    900

gtctgtgagg agatgaccta tgaagaaatc cgggaacatt accctgaaga atttgcactg    960

cgagaccaag ataaatatcg ctaccgctat cccaagggag agtcctatga ggatctggtt   1020

cagcgtctgg agccagtgat aatggagcta gaacgacagg agaatgtact ggtgatctgc   1080

caccaggctg tcatgcggtg cctcctggcc tatttcctgg ataaaagttc agatgagctt   1140

ccatatctca agtgccctct gcacacagtg ctcaaactca ctcctgtggc ttatggctgc   1200

aaagtggaat ccatctacct gaatgtggag gccgtgaaca cacaccggga gaagcctgag   1260

aatgtggaca tcacccggga acctgaggaa gccctggata ctgtcccagc ccactactga   1320

gccctttcca agaagtcaaa ctgcctgtgt ccta                               1354
```

<210> SEQ ID NO 51
<211> LENGTH: 1204
<212> TYPE: DNA
<213> ORGANISM: Homo sapiens

<400> SEQUENCE: 51

```
agagggcggg tccccggcct cgggagcacg gcggtggagg ggacatagga ggcggccatg     60

gcgacccccg gcaacctagg gtcctctgtc ctggcgagca agaccaagac caagaagaag    120

cacttcgtag cgcagaaagt gaagctgttt cgggccagcg acccgctgct cagcgtcctc    180

atgtgggggg taaaccactc gatcaatgaa ctgagccatg ttcaaatccc tgttatgttg    240

atgccagatg acttcaaagc ctattcaaaa ataaaggtgg acaatcacct ttttaacaaa    300

gaaaacatgc cgagccattt caagtttaag gaatactgcc cgatggtctt ccgtaacctg    360

cgggagaggt ttggaattga tgatcaagat ttccagtaca tagtggaatg tcatgggatc    420

acccttcttc cccagttctt gggcatgtac cggcttaatg ttgatggagt tgaaatatat    480

gtgatagtta caagaaatgt attcagccac cgtttgtctg tgtataggaa atacgactta    540

aagggctcta cagtggctag agaagctagt gacaaagaaa aggccaaaga actgccaact    600

ctgaaagata atgatttcat taatgagggc caaaagattt atattgatga caacaacaag    660

aaggtcttcc tggaaaaact aaaaaaggat gttgagtttc tggcccagct gaagctcatg    720

gactacagtc tgctggtggg aattcatgat gtggagagag ccgaacagga ggaagtggag    780

tgtgaggaga acgatgggga ggaggagggc gagagcgatg gcacccaccc ggtgggaacc    840

cccccagata gccccgggaa tacactgaac agctcaccac ccctggctcc cggggagttc    900

gatccgaaca tcgacgtcta tggaattaag tgccatgaaa actcgcctag gaaggaggtg    960

tacttcatgg caattattga catccttact cattatgatg caaaaaagaa agctgcccat   1020

gctgcaaaaa ctgttaaaca tggcgctggc gcggagatct ccaccgtgaa cccagaacag   1080

tattcaaagc gctttttgga ctttattggc cacatcttga cgtaacctcc tgcgcagcct   1140

cggacagaca tgaacattgg agggacagag gtggcttcga agaacgaatt gcagcacact   1200

gcgg                                                                1204
```

<210> SEQ ID NO 52
<211> LENGTH: 1859
<212> TYPE: DNA
<213> ORGANISM: Homo sapiens

<400> SEQUENCE: 52

```
caacaaggct acgcagaaga accccccttga ctgaagcaat ggagggggt ccagctgtct     60

gctgccagga tcctcgggca gagctggtag aacgggtggc agccatcgat gtgactcact    120
```

```
tggaggaggc agatggtggc ccagagccta ctagaaacgg tgtggacccc ccaccacggg    180

ccagagctgc ctctgtgatc cctggcagta cttcaagact gctcccagcc cggcctagcc    240

tctcagccag gaagctttcc ctacaggagc ggccagcagg aagctatctg gaggcgcagg    300

ctgggcctta tgccacgggg cctgccagcc acatctcccc ccgggcctgg cggaggccca    360

ccatcgagtc ccaccacgtg gccatctcag atgcagagga ctgcgtgcag ctgaaccagt    420

acaagctgca gagtgagatt ggcaagggtg cctacggtgt ggtgaggccg gcctacaacg    480

aaagtgaaga cagacactat gcaatgaaag tcctttccaa aaagaagtta ctgaagcagt    540

atggctttcc acgtcgccct cccccgagag ggtcccaggc tgcccaggga ggaccagcca    600

agcagctgct gcccctggag cgggtgtacc aggagattgc catcctgaag aagctggacc    660

acgtgaatgt ggtcaaactg atcgaggtcc tggatgaccc agctgaggac aacctctatt    720

tggccctgca gaaccaggcc cagaatatcc agttagattc aacaaatatc gccaagcccc    780

actccctgct tccctctgag cagcaagaca gtggatccac gtgggctgcg cgctcagtgt    840

ttgacctcct gagaaagggg cccgtcatgg aagtgccctg tgacaagccc ttctcggagg    900

agcaagctcg cctctacctg cgggacgtca tcctgggcct cgagtacttg cactgccaga    960

agatcgtcca cagggacatc aagccatcca acctgctcct gggggatgat gggcacgtga   1020

agatcgccga ctttggcgtc agcaaccagt ttgaggggaa cgacgctcag ctgtccagca   1080

cggcgggaac cccagcattc atggcccccg aggccatttc tgattccggc cagagcttca   1140

gtgggaaggc cttggatgta tgggccactg gcgtcacgtt gtactgcttt gtctatggga   1200

agtgcccgtt catcgacgat ttcatcctgg ccctccacag gaagatcaag aatgagcccg   1260

tggtgtttcc tgaggggcca gaaatcagcg aggagctcaa ggacctgatc ctgaagatgt   1320

tagacaagaa tcccgagacg agaattgggg tgccagacat caagttgcac ccttgggtga   1380

ccaagaacgg ggaggagccc attccttcgg aggaggagca ctgcagcgtg gtggaggtga   1440

cagaggagga ggttaagaac tcagtcaggc tcatccccag ctggaccacg gtgatcctgg   1500

tgaagtccat gctgaggaag cgttcctttg ggaacccgtt tgagccccaa gcacggaggg   1560

aagagcgatc catgtctgct ccaggaaacc tactggtgaa agaagggttt ggtgaagggg   1620

gcaagagccc agagctcccc ggcgtccagg aagacgaggc tgcatcctga gcccctgcat   1680

gcacccaggg ccacccggca gcacactcat cccgcgcctc cagaggccca cccctcatgc   1740

aacagccgcc cccgcaggca gggggctggg gactgcagcc ccactcccgc ccctccccca   1800

tcgtgctgca tgacctccac gcacgcacgt ccagggacag actggaatgt atgtcattt    1859
```

<210> SEQ ID NO 53
<211> LENGTH: 1695
<212> TYPE: DNA
<213> ORGANISM: Homo sapiens

<400> SEQUENCE: 53

```
actgagccta agcagccggt gatggcggca gcggctgtgg tggctgcggc gggtccgggc     60

ccatgaggcg acgaaggagg cgggacggct tttacccagc cccggacttc cgagacaggg    120

aagctgagga catggcagga gtgtttgaca tagacctgga ccagccagag gacgcgggct    180

ctgaggatga gctggaggag ggggcaatga tagtaagaaa tgctaaagat acagctcata    240

caaaagcaga acggaatatt ctggaggaag taaagcatcc cttcatcgtg gatttaattt    300

atgcctttca gactggtgga aaactctacc tcatccttga gtatctcagt ggaggagaac    360

tatttatgca gttagaaaga gagggaatat ttatggaaga cactgcctgc ttttacttgg    420
```

```
cagaaatctc catggctttg gggcatttac atcaaaaggg gatcatctac agagacctga    480
agccggagaa tatcatgctt aatcaccaag gtcatgtgaa actaacagac tttggactat    540
gcaaagaatc tattcatgat ggaacagtca cacacacatt ttgtggaaca atagaataca    600
tggcccctga aatcttgatg agaagtggcc acaatcgtgc tgtggattgg tggagtttgg    660
gagcattaat gtatgacatg ctgactggag cacccccatt cactggggag aatagaaaga    720
aaacaattga caaaatcctc aaatgtaaac tcaatttgcc tccctacctc acacaagaag    780
ccagagatct gcttaaaaag ctgctgaaaa gaaatgctgc ttctcgtctg ggagctggtc    840
ctggggacgc tggagaagtt caagctcatc cattctttag acacattaac tgggaagaac    900
ttctggctcg aaaggtggag ccccccttta aacctctgtt gcaatctgaa gaggatgtaa    960
gtcagtttga ttccaagttt acacgtcaga cacctgtcga cagcccagat gactcaactc   1020
tcagtgaaag tgccaatcag gtctttctgg gttttacata tgtggctcca tctgtacttg   1080
aaagtgtgaa agaaaagttt tcctttgaac caaaaatccg atcacctcga agatttattg   1140
gcagcccacg aacacctgtc agcccagtca aattttctcc tggggatttc tggggaagag   1200
gtgcttcggc cagcgcagca aatcctcaga cacctgtgga atacccaatg gaaacaagtg   1260
gcatagagca gatggatgtg acaatgagtg gggaagcatc ggcaccactt ccaatacgac   1320
agccgaactc tgggccatac aaaaaacaag cttttcccat gatctccaaa cggccagagc   1380
acctgcgtat gaatctatga cagagcatgc ttttaatgaa tttaaggcaa aaaggtggag   1440
agggagatgt gtgagcatcc tgcaaggtga aacgactcaa aatgacagtt tcagagagtc   1500
aatgtcatta catagaacac ttcagacaca ggaaaaataa acgtggattt taaaaaatca   1560
atcaatggtg caaaaaaaaa cttaaagcaa atagtattgc tgaactctta ggcacatcaa   1620
ttaattgatt cctcgcgaca tcttctcaac cttatcaagg attttcatgt tgatgactcg   1680
aaactgacag tatta                                                    1695
```

<210> SEQ ID NO 54
<211> LENGTH: 3891
<212> TYPE: DNA
<213> ORGANISM: Homo sapiens

<400> SEQUENCE: 54

```
agagcgacag agacatttat tgttatttgt tttttggtgg caaaaaggga aaatggcgaa     60
cgactcccct gcaaaaagtc tggtggacat cgacctctcc tccctgcggg atcctgctgg    120
gatttttgag ctggtggaag tggttggaaa tggcacctat ggacaagtct ataagggtcg    180
acatgttaaa acgggtcagt tggcagccat caaagttatg gatgtcactg aggatgaaga    240
ggaagaaatc aaactggaga taaatatgct aaagaaatac tctcatcaca gaaacattgc    300
aacatattat ggtgctttca tcaaaaagag ccctccagga catgatgacc aactctggct    360
tgttatggag ttctgtgggg ctgggtccat tacagacctt gtgaagaaca ccaaagggaa    420
cacactcaaa gaagactgga tcgcttacat ctccagagaa atcctgaggg gactggcaca    480
tcttcacatt catcatgtga ttcaccggga tatcaagggc cagaatgtgt tgctgactga    540
gaatgcagag gtgaaacttg ttgactttgg tgtgagtgct cagctggacg ggactgtggg    600
gcggagaaat acgttcatag gcactcccta ctggatggct cctgaggtca tcgcctgtga    660
tgagaaccca gatgccacct atgattacag aagtgatctt tggtcttgtg gcattacagc    720
cattgagatg gggaaggtg ctcccccctct ctgtgacatg catccaatga gagcactgtt    780
tctcattccc agaaaccctc ctccccggct gaagtcaaaa aaatggtcga agaagttttt    840
```

```
tagttttata gaagggtgcc tggtgaagaa ttacatgcag cggccctcta cagagcagct    900
tttgaaacat ccttttataa gggatcagcc aaatgaaagg caagttagaa tccagcttaa    960
ggatcatata gatcgtacca ggaagaagag aggcgagaaa gatgaaactg agtatgagta   1020
cagtgggagt gaggaagaag aggaggaagt gcctgaacag gaaggagagc caagttccat   1080
tgtgaacgtg cctggtgagt ctactcttcg ccgagatttc ctgagactgc agcaggagaa   1140
caaggaacgt tccgaggctc ttcggagaca acagttacta caggagcaac agctccggga   1200
gcaggaagaa tataaaaggc aactgctggc agagagacag aagcggattg agcagcagaa   1260
agaacagagg cgacggctag aagagcaaca aaggagagag cgggaagcta gaaggcagca   1320
ggaacgtgaa cagcgaagga gagaacaaga agaaaagagg cgtctagagg agttggagag   1380
aaggcgcaaa gaagaagagg agaggagaca ggcagaagaa gaaaagagga gagttgaaag   1440
agaacaggag tatatcaggc gacagctaga agaggagcag cggcacttgg aagtccttca   1500
gcagcagctg ctccaggagc aggccatgtt actgcatgac cataggaggc cgcacccgca   1560
gcactcgcag cagccgccac caccgcagca ggaaaggagc aagccaagct tccatgctcc   1620
cgagcccaaa gcccactacg agcctgctga ccgagcgcga gaggttcctg tgagaacaac   1680
atctcgctcc cctgttctgt cccgtcgaga ttccccactg cagggcagtg ggcagcagaa   1740
tagccaggca ggacagagaa actccaccag cagtattgag cccaggcttc tgtgggagag   1800
agtggagaag ctgatgccca gacctggcag tggcagctcc tcagggtcca gcaactcagg   1860
atcccagccc gggtctcacc ctgggtctca gagtggctcc ggggaacgct tcagagtgag   1920
atcatcatcc aagtctgaag gctctccatc tcagcgcctg gaaaatgcag tgaaaaaacc   1980
tgaagataaa aaggaagttt tcagacccct caagcctgct gatctgaccg cactggccaa   2040
agagcttcga gcagtggaag atgtacggcc acctcacaaa gtaacggact actcctcatc   2100
cagtgaggag ccggggacga cggatgagga ggacgacgat gtggagcagg aaggggctga   2160
cgagtccacc tcaggaccag aggacaccag agcagcgtca tctctgaatt tgagcaatgg   2220
tgaaacggaa tctgtgaaaa ccatgattgt ccatgatgat gtagaaagtg agccggccat   2280
gaccccatcc aaggagggca ctctaatcgt ccgccagagt acagttgacc aaaagcgtgc   2340
cagccatcat gagagcaatg gctttgccgg tcgcattcac ctcttgccag atctcttaca   2400
gcaaagccat tcctcctcca cttcctccac ctcctcctcc ccatcctcca gccagccgac   2460
acccaccatg tccccacaga caccccagga caagctcact gctaatgaga ctcagtccgc   2520
tagtagcaca ctccagaaac acaaatcttc ctcctccttt acacctttta tagaccccag   2580
attactacag atttctccat ctagcggaac aacagtgaca tctgtggtgg gattttcctg   2640
tgatgggatg agaccagaag ccataaggca agatcctacc cggaaaggct cagtggtcaa   2700
tgtgaatcct accaacacta ggccacagag tgacaccccg gagattcgta aatacaagaa   2760
gaggtttaac tctgagattc tgtgtgctgc cttatgggga gtgaatttgc tagtgggtac   2820
agagagtggc ctgatgctgc tggacagaag tggccaaggg aaggtctatc ctcttatcaa   2880
ccgaagacga tttcaacaaa tggacgtact tgagggcttg aatgtcttgg tgacaatatc   2940
tggcaaaaag gataagttac gtgtctacta tttgtcctgg ttaagaaata aaatacttca   3000
caatgatcca gaagttgaga agaagcaggg atggacaacc gtaggggatt tggaaggatg   3060
tgtacattat aaagttgtaa aatatgaaag aatcaaattt ctggtgattg ctttgaagag   3120
ttctgtggaa gtctatgcgt gggcaccaaa gccatatcac aaatttatgg cctttaagtc   3180
atttggagaa ttggtacata agccattact ggtggatctc actgttgagg aaggccagag   3240
```

gttgaaagtg atctatggat cctgtgctgg attccatgct gttgatgtgg attcaggatc 3300
agtctatgac atttatctac caacacatat ccagtgtagc atcaaacccc atgcaatcat 3360
catcctcccc aatacagatg gaatggagct tctggtgtgc tatgaagatg agggggttta 3420
tgtaaacaca tatggaagga tcaccaagga tgtagttcta cagtggggag agatgcctac 3480
atcagtagca tatattcgat ccaatcagac aatgggctgg ggagagaagg ccatagagat 3540
ccgatctgtg gaaactggtc acttggatgg tgtgttcatg cacaaaaggg ctcaaagact 3600
aaaattcttg tgtgaacgca atgacaaggt gttctttgcc tctgttcggt ctggtggcag 3660
cagtcaggtt tatttcatga ccttaggcag gacttctctt ctgagctggt agaagcagtg 3720
tgatccaggg attactggcc tccagagtct tcaagatcct gagaacttgg aattccttgt 3780
aactggagct cggagctgca ccgagggcaa ccaggacagc tgtgtgtgca gacctcatgt 3840
gttgggttct ctcccctcct tcctgttcct cttatatacc agtttatccc c 3891

<210> SEQ ID NO 55
<211> LENGTH: 3954
<212> TYPE: DNA
<213> ORGANISM: Homo sapiens

<400> SEQUENCE: 55
atttctccag cgaagaagta gacatggcga gcgactcccc ggctcgaagc ctggatgaaa 60
tagatctctc ggctctgagg gaccctgcag ggatctttga attggtggaa cttgttggaa 120
atggaacata cgggcaagtt tataagggtc gtcatgtcaa aacgggccag cttgcagcca 180
tcaaggttat ggatgtcaca ggggatgaag aggaagaaat caaacaagaa attaacatgt 240
tgaagaaata ttctcatcac cggaatattg ctacatacta tggtgctttt atcaaaaaga 300
acccaccagg catggatgac caactttggt tggtgatgga gttttgtggt gctggctctg 360
tcaccgacct gatcaagaac acaaaaggta acacgttgaa agaggagtgg attgcataca 420
tctgcaggga aatcttacgg gggctgagtc acctgcacca gcataaagtg attcatcgag 480
atattaaagg gcaaaatgtc ttgctgactg aaaatgcaga agttaaacta gtggactttg 540
gagtcagtgc tcagcttgat cgaacagtgg gcaggaggaa tactttcatt ggaactccct 600
actggatggc accagaagtt attgcctgtg atgaaaaccc agatgccaca tatgatttca 660
agagtgactt gtggtctttg ggtatcaccg ccattgaaat ggcagaaggt gctccccctc 720
tctgtgacat gcaccccatg agagctctct tcctcatccc ccggaatcca gcgcctcggc 780
tgaagtctaa gaagtggtca aaaaaattcc agtcatttat tgagagctgc ttggtaaaga 840
atcacagcca gcgaccagca acagaacaat tgatgaagca tccatttata cgagaccaac 900
ctaatgagcg acaggtccgc attcaactca aggaccatat tgatagaaca aagaagaagc 960
gaggagaaaa agatgagaca gagtatgagt acagtggaag tgaggaagaa gaggaggaga 1020
atgactcagg agagcccagc tccatcctga atctgccagg ggagtcgacg ctgcggaggg 1080
actttctgag gctgcagctg gccaacaagg agcgttctga ggccctacgg aggcagcagc 1140
tggagcagca gcagcgggag aatgaggagc acaagcggca gctgctggcc gagcgtcaga 1200
agcgcatcga ggagcagaaa gagcagaggc ggcggctgga ggagatccca catctggtag 1260
ctgtaaaatc ccagggacct gccttgaccg cctcccagtc agtgcacgag cagcccacaa 1320
agggcctctc tgggtttcag gaggctctga acgtgacctc ccaccgcgtg gagatgccac 1380
gccagaactc agatcccacc tcggaaaatc ctcctctccc cactcgcatt gaaaagtttg 1440
accgaagctc ttggttacga caggaagaag acattccacc aaaggtgcct caaagaacaa 1500

```
cttctatatc cccagcatta gccagaaaga attctcctgg gaatggtagt gctctgggac   1560
ccagactagg atctcaaccc atcagagcaa gcaaccctga tctccggaga actgagccca   1620
tcttggagag ccccttgcag aggaccagca gtggcagttc ctccagctcc agcacccta    1680
gctcccagcc cagctcccaa ggaggctccc agcctggatc acaagcagga tccagtggac   1740
gcaccagagt tcgagccaac agtaagtcag aaggatcacc tgtgcttccc catgagcctg   1800
ccaaggtgaa accagaagaa tccagggaca ttacccggcc cagtcgacca gctgatctga   1860
cggcattagc caaagaacta agagaactcc ggattgaaga aacaaaccgc ccaatgaaga   1920
aggtgactga ttactcctcc tccagtgagg agtcagaaag tagcgaggaa gaggaggaag   1980
atggagagag cgagacccat gatgggacag tggctgtcag cgacataccc agactgatac   2040
caacaggagc tccaggcagc aacgagcagt acaatgtggg aatggtgggg acgcatgggc   2100
tggagacctc tcatgcggac agtttcagcg gcagtatttc aagagaagga accttgatga   2160
ttagagagac gtctggagag aagaagcgat ctggccacag tgacagcaat ggctttgctg   2220
gccacatcaa cctccctgac ctggtgcagc agagccattc tccagctgga accccgactg   2280
agggactggg gcgcgtctca acccattccc aggagatgga ctctgggact gaatatggca   2340
tggggagcag caccaaagcc tccttcaccc cctttgtgga ccccagagta taccagacgt   2400
ctcccactga tgaagatgaa gaggatgagg aatcatcagc cgcagctctg tttactagcg   2460
aacttcttag gcaagaacag gccaaactca atgaagcaag aaagatttcg gtggtaaatg   2520
taaacccaac caacattcgg cctcatagcg acacaccaga aatcagacaa tacaagaaac   2580
gattcaactc agaaatactt tgtgcagctc tgtggggtgt aaaccttctg gtggggactg   2640
aaaatggcct gatgcttttg gaccgaagtg ggcaaggcaa agtctataat ctgatcaacc   2700
ggaggcgatt tcagcagatg gatgtgctag agggactgaa tgtccttgtg acaatttcag   2760
gaaagaagaa taagctacga gtttactatc tttcatggtt aagaaacaga atactacata   2820
atgacccaga agtagaaaag aaacaaggct ggatcactgt tggggacttg gaaggctgta   2880
tacattataa agttgttaaa tatgaaagga tcaaattttt ggtgattgcc ttaaagaatg   2940
ctgtggaaat atatgcttgg gctcctaaac cgtatcataa attcatggca tttaagtctt   3000
ttgcagatct ccagcacaag cctctgctag ttgatctcac ggtagaagaa ggtcaaagat   3060
taaaggttat ttttggttca cacactggtt tccatgtaat tgatgttgat tcaggaaact   3120
cttatgatat ctacatacca tctcatattc agggcaatat cactcctcat gctattgtca   3180
tcttgcctaa aacagatgga atggaaatgc ttgtttgcta tgaggatgag gggggtttatg  3240
tagacaccta tggccggata actaaggatg tggtgctcca atggggagaa atgcccacgt   3300
ctgtggccta cattcattcc gatcagataa tgggctgggg cgagaaagct attgagatcc   3360
ggtcagtgga aacaggacat ttggatggag tatttatgca taagcgagct caaaggttaa   3420
agtttctatg tgaaagaaat gataaggtat tttttgcatc cgtgcgatct ggaggaagta   3480
gccaagtgtt tttcatgacc ctcaacagaa attccatgat gaactggtaa cagaagagca   3540
cttggcactt atcttcatgg cgttatttct aatttaaaag aacataactc atgtggactt   3600
atgccagtct agaggcagaa tcagaaggct tggttgaaca tatcgctttc ccttttttcct  3660
ctccctccgc ccctcccagt acagtccatc tttcaatgtt gcagcctggt tgagaaggag   3720
agaaaaaggt ggcaggaatt tccaggagat ccccaagaat gctgccttgt ctgtggacaa   3780
agatggacca tgtgcccttc ggaattaggg atagaaacaa atattgtgtg ctcttaacga   3840
ttaagctgtg ttatggtggg ttttcaggtt tttacctttt ttctttaccc ctctactctg   3900
```

caagaatggg gaaagaatgc atactgcgca aatgagtctt ttaaattctg tctg 3954

<210> SEQ ID NO 56
<211> LENGTH: 3357
<212> TYPE: DNA
<213> ORGANISM: Homo sapiens

<400> SEQUENCE: 56
agtgtgctgg aattcgcgcc ttttacgcca aagctcgcca acatggcgga cctggaggct 60
gtgctggccg atgtcagtta cctgatggcc atggagaaga gcaaggcgac cccggccgcc 120
cgcgccagca agaggatcgt cctgccggag cccagtatcc ggagtgtgat gcagaagtac 180
cttgcagaga gaaatgaaat aacccttgac aagattttca atcagaaaat tggtttcttg 240
ctatttaaag atttttgttt gaatgaaatt aatgaagctg tacctcaggt gaagttttat 300
gaagagataa aggaatatga aaaacttgat aatgaggaag accgcctttg cagaagtcga 360
caaatttatg atgcctacat catgaaggaa cttctttcct gttcacatcc tttctcaaag 420
caagctgtag aacacgtaca aagtcattta tccaagaaac aagtgacatc aactcttttt 480
cagccataca tagaagaaat ttgtgaaagc cttcgaggtg acatttttca aaaatttatg 540
gaaagtgaca agttcactag attttgtcag tggaaaaacg ttgaattaaa tatccatttg 600
accatgaatg agttcagtgt gcataggatt attggacgag gaggattcgg ggaagtttat 660
ggttgcagga aagcagacac tggaaaaatg tatgcaatga aatgcttaga taagaagagg 720
atcaaaatga aacaaggaga aacattagcc ttaaatgaaa gaatcatgtt gtctcttgtc 780
agcacaggag actgtccttt cattgtatgt atgacctatg ccttccatac cccagataaa 840
ctctgcttca tcctggatct gatgaacggg ggcgatttgc actaccacct ttcacaacac 900
ggtgtgttct ctgagaagga gatgcggttt tatgccactg aaatcattct gggtctggaa 960
cacatgcaca atcggtttgt tgtctacaga gatttgaagc cagcaaatat tctcttggat 1020
gaacatggac acgcaagaat atcagatctt ggtcttgcct gcgatttttc caaaaagaag 1080
cctcatgcga gtgttggcac ccatgggtac atggctcccg aggtgctgca gaaggggacg 1140
gcctatgaca gcagtgccga ctggttctcc ctgggctgca tgcttttcaa acttctgaga 1200
ggtcacagcc ctttcagaca acataaaacc aaagacaagc atgaaattga ccgaatgaca 1260
ctcaccgtga atgtggaact tccagacacc ttctctcctg aactgaagtc ccttttggag 1320
ggcttgcttc agcgagacgt tagcaagcgg ctgggctgtc acggaggcgg ctcacaggaa 1380
gtaaaagagc acagcttttt caaaggtgtt gactggcagc atgtctactt acaaaagtac 1440
ccaccaccct tgattcctcc ccggggagaa gtcaatgctg ctgatgcctt tgatattggc 1500
tcatttgatg aagaggatac caaagggatt aagctacttg attgcgacca agaactctac 1560
aagaacttcc ctttggtcat ctctgaacgc tggcagcaag aagtaacgga aacagtttat 1620
gaagcagtaa atgcagacac agataaaatc gaggccagga agagagctaa aaataagcaa 1680
cttggccacg aagaagatta cgctctgggg aaggactgta ttatgcacgg gtacatgctg 1740
aaactgggaa acccatttct gactcagtgg cagcgtcgct atttttacct ctttccaaat 1800
agacttgaat ggagaggaga gggagagtcc cggagtgatc cagagtttgt gcagtggaag 1860
aaagagttga acgaaacctt caaggaggcc cggcggctat tgcgtcgtgc cccgaagttc 1920
ctcaacaaac ctcggtcagg tactgtggag ctcccaaagc catccctctg tcacagaaac 1980
agcaacggcc tctagcaccc agaaacaggg agggtcctcg aggaggacac accagggtct 2040
cagccttttg ggtgaacga ggatgaggca tctgatctat tcgctaccgg gactcctcca 2100

```
ggctcccgag aggagtcggg acccttcggc ttggggtcag ctcagctccc tgccttgtca   2160
catttgtctg cattagaaac tactgaagaa ataaaagttc tttttctttg ctacacactt   2220
tggtacctat gaacctagaa cttgaagtga ctcctactta tcacgtaaat ttttatgtct   2280
gatatcaaac acatcttaga ctccccagaa tggaatttaa agatgttcag tgttgggtaa   2340
cagattgccc taagcattgc cacatattct gtctagtcgc tgctgatttt ctatgtcttt   2400
gctccatact gcagggggat gggagagcca cagtgtgttt cttttgtgca cttcgcaact   2460
gacttcttgt cctggggtta aaagttgaag atattttctg atgatattaa aagttgaaga   2520
tatttctgca cttgggccct cctctgggag ccgcacccac atgactgccc tgcctctgac   2580
cagtctgttc cggggccccc tcagccaggt gggaatgacg gacacgtact atccaagtgt   2640
atgggattaa ctaatcattg aaggcattca tccgtccatc attggaaaga tttacagtga   2700
ttctgaagga caggccgtgg agttttaggt ttcaggggca agagcagttt tcaaaagtct   2760
ttgagtccag tgtgcacgag tcgacaagca gtacctggca tgcaggagca ctcatgggtg   2820
agtccgtctc aggtctcgac aattagcagt tgtgtgacag tcattctggt tccttctgcc   2880
tgaccctggg agacatatca gtaatggatg tacaaaagca ggtctgtttt atgtcttagt   2940
ataatttcag atgaattgta ttgaaaaaat gctgaggaat gaatgtgtca aaatgggtta   3000
actgtgtata ttgactttca tgtcgtcatg catctgtcat gaatgaatga tactttgcac   3060
tgggctgtac gacagtgagg accttagggc atgaagcctt tttcctggtc ccagcagcat   3120
ctgccctgtg aagtttgttt tctcccactg cctccaggcc ccactgatac cccaaatag    3180
atgctgggtt atgagaacca gcgaaatccc ccatgtcatc agtcttaaaa aaaaaatttt   3240
acaaatccac gtatttgtcc cattcttgga gtagttttag tgtatgtctt tacattaact   3300
actaacagta taaataactt gacatcgtaa ttgtctgcat cctgtccttg atatttt      3357
```

<210> SEQ ID NO 57
<211> LENGTH: 2036
<212> TYPE: DNA
<213> ORGANISM: Homo sapiens

<400> SEQUENCE: 57

```
aagattctta ggaacgccgt acctgccgcg tctctcagga cagcaggccc ctgtccttct     60
gtcgggcgcc gctcagccgt gccctccgcc cctcaggttc tttttctaat tccaaataaa    120
cttgcaagag gactatgaaa gattatgatg aacttctcaa atattatgaa ttacatgaaa    180
ctattgggac aggtggcttt gcaaaggtca aacttgcctg ccatatcctt actggagaga    240
tggtagctat aaaaatcatg gataaaaaca cactagggag tgatttgccc cggatcaaaa    300
cggagattga ggccttgaag aacctgagac atcagcatat atgtcaactc taccatgtgc    360
tagagacagc caacaaaata ttcatggttc ttgaggaaaa tttgctgttt gatgaatatc    420
ataaattaaa gctgattgac tttggtctct gtgcaaaacc caagggtaac aaggattacc    480
atctacagac atgctgtggg agtctggctt atgcagcacc tgagttaata caaggcaaat    540
catatcttgg atcagaggca gatgtttgga gcatgggcat actgttatat gttcttatgt    600
gtggatttct accatttgat gatgataatg taatggcttt atacaagaag attatgagag    660
gaaaatatga tgttcccaag tggctctctc ccagtagcat tctgcttctt caacaaatgc    720
tgcaggtgga cccaaagaaa cggatttcta tgaaaaatct attgaaccat ccctggatca    780
tgcaagatta caactatcct gttgagtggc aaagcaagaa tccttttatt cacctcgatg    840
atgattgcgt aacagaactt tctgtacatc acagaaacaa caggcaaaca atggaggatt    900
```

```
taatttcact gtggcagtat gatcacctca cggctaccta tcttctgctt ctagccaaga    960
aggctcgggg aaaaccagtt cgtttaaggc tttcttcttt ctcctgtgga caagccagtg   1020
ctaccccatt cacagacatc aagtcaaata attggagtct ggaagatgtg accgcaagtg   1080
ataaaaatta tgtggcggga ttaatagact atgattggtg tgaagatgat ttatcaacag   1140
gtgctgctac tccccgaaca tcacagttta ccaagtactg gacagaatca aatggggcgg   1200
aatctaaatc attaactcca gccttatgca gaacacctgc aaataaatta aagaacaaag   1260
aaaatgtata tactcctaag tctgctgtaa agaatgaaga gtactttatg tttcctgagc   1320
caaagactcc agttaataag aaccagcata agagagaaat actcactacg ccaaatcgtt   1380
acactacacc ctcaaaagct agaaaccagt gcctgaaaga aactccaatt aaaataccag   1440
taaattcaac aggaacagac aagttaatga caggtgtcat tagccctgag aggcggtgcc   1500
gctcagtgga attggatctc aaccaagcac atatggagga gactccaaaa agaaagggag   1560
ccaaagtgtt tgggagcctt gaaagggggt tggataaggt tatcactgtg ctcaccagga   1620
gcaaaaggaa gggttctgcc agagacgggc ccagaagact aaagcttcac tataatgtga   1680
ctacaactag attagtgaat ccagatcaac tgttgaatga aataatgtct attcttccaa   1740
agaagcatgt tgactttgta caaaagggtt atacactgaa gtgtcaaaca cagtcagatt   1800
ttgggaaagt gacaatgcaa tttgaattag aagtgtgcca gcttcaaaaa cccgatgtgg   1860
tgggtatcag gaggcagcgg cttaagggcg atgcctgggt ttacaaaaga ttagtggaag   1920
acatcctatc tagctgcaag gtataattga tggattcttc catcctgccg gatgagtgtg   1980
ggtgtgatac agcctacata aagactaaga gcgaattcgc agcacactga cgccgg       2036
```

<210> SEQ ID NO 58
<211> LENGTH: 2541
<212> TYPE: DNA
<213> ORGANISM: Homo sapiens

<400> SEQUENCE: 58

```
ccgcagtgtg ctggaattcg cttttcctca cctacttata gactattttt cttgctctgc     60
agcatggacc aaagagaaat tctgcagaag ttcctggatg aggcccaaag caagaaaatt    120
actaaagagg agtttgccaa tgaatttctg aagctgaaaa ggcaatctac caagtacaag    180
gcagacaaaa cctatcctac aactgtggct gagaagccca agaatatcaa gaaaaacaga    240
tataaggata ttttgcccta tgattatagc cgggtagaac tatccctgat aacctctgat    300
gaggattcca gctacatcaa tgccaacttc attaagggag tttatggacc caaggcttat    360
attgccaccc agggtccttt atctacaacc ctcctggact tctggaggat gatttgggaa    420
tatagtgtcc ttgaaactcg aactatctac cagtttcatt acgagaattg gccagaccat    480
gatgtacctt catctataga ccctattctt gagctcatct gggatgtacg ttgttaccaa    540
gaggatgaca gtgttcccat atgcattcac tgcagtgctg gctgtggaag gactggtgtt    600
atttgtgcta ttgattatac atggatgttg ctaaaagatg ggataattcc tgagaacttc    660
agtgttttca gtttgatccg ggaaatgcgg acacagaggc cttcattagt tcaaacgcag    720
gaacaatatg aactggtcta caatgctgta ttagaactat ttaagagaca gatggatgtt    780
atcagagata aacattctgg aacagagagt caagcaaagc attgtattcc tgagaaaaat    840
cacactctcc aagcagactc ttattctcct aatttaccaa aaagtaccac aaaagcagca    900
aaaatgatga accaacaaag gacaaaaatg gaaatcaaag aatcttcttc ctttgacttt    960
aggacttctg aaataagtgc aaaagaagag ctagttttgc accctgctaa atcaagcact   1020
```

```
tcttttgact ttctggagct aaattacagt tttgacaaaa atgctgacac aaccatgaaa   1080
tggcagacaa aggcatttcc aatagttggg gagcctcttc agaagcatca aagtttggat   1140
ttgggctctc ttttgtttga gggatgttct aattctaaac ctgtaaatgc agcaggaaga   1200
tattttaatt caaaggtgcc aataacacgg accaaatcaa ctccttttga attgatacag   1260
cagagagaaa ccaaggaggt ggacagcaag gaaaactttt cttatttgga atctcaacca   1320
catgattctt gttttgtaga gatgcaggct caaaaagtaa tgcatgtttc ttcagcagaa   1380
ctgaattatt cactgccata tgactctaaa caccaaatac gtaatgcctc taatgtaaag   1440
caccatgact ctagtgctct tggtgtatat tcttacatac ctttagtgga aaatccttat   1500
ttttcatcat ggcctccaag tggtaccagt tctaagatgt ctcttgattt acctgagaag   1560
cgagatggca ctgtttttcc ttcttctctg ttgccaacat cctctacatc cctcttctct   1620
tattacaatt cacatgattc tttatcactg aattctccaa ccaatatttc ctcactattg   1680
aaccaggagt cagctgtact agcaactgct ccccggatag atgatgaaat ccccccctcca  1740
cttcctgtac ggacacctga atcatttatt gtggttgagg aagctggaga attctcacca   1800
aatgttccca atcccttatc ctcagctgtg aaggtaaaaa ttggaacatc actggaatgg   1860
ggtggaacat ctgaaccaaa gaaatttgat gactctgtga tacttagacc aagcaagagt   1920
gtaaaactcc gaagtcctaa atcagaacta catcaagatc gttcttctcc cccacctcct   1980
ctcccagaaa gaactctaga gtccttcttt cttgccgatg aagattgtat gcaggcccaa   2040
tctatagaaa catattctac tagctatcct gacaccatgg aaaattcaac atcttcaaaa   2100
cagacactga agactcctgg aaaaagtttc acaaggagta agagtttgaa aattttgcga   2160
aacatgaaaa agagtatctg taattcttgc ccaccaaaca agcctgcaga atctgttcag   2220
tcaaataact ccagctcatt tctgaatttt ggttttgcaa accgtttttc aaaacccgaa   2280
ggaccaagga atccaccacc aacttggaat atttaataaa actccagatt tataataata   2340
tgggctgcaa gtacacctgc aaataaaact actagaatac tgctagttaa aataagtgct   2400
ctatatgcat aatatcaaat atgaagatat gctaatgtgt taatagcttt taaaagaaaa   2460
gcaaaatgcc aataagtgcc agttttgcat tttcatatca tttgcattga gttgaaaact   2520
gcaaataaaa gtttgtcact t                                             2541
```

<210> SEQ ID NO 59
<211> LENGTH: 2611
<212> TYPE: DNA
<213> ORGANISM: Homo sapiens

<400> SEQUENCE: 59

```
atatacgaag actttgtgtg gacagtaatg acctcacgtt tccgattgcc tgctggcaga     60
acctacaatg tacgagcatc agagttggcc cgagacagac agcatactga agtggtttgc    120
aacatccttc ttctggataa cactgtacaa gccttcaaag tcaataaaca tgatcagggg    180
caagtcttgt tggatgtcgt cttcaagcat ctagatttga ctgagcagga ctattttggt    240
ttacagttgg ctgatgattc cacagataac ccaaggtggc tggatccaaa caaaccaata    300
aggaagcagc taaagagagg atctccttac agtttgaact ttagagtcaa attttttgta    360
agtgacccca acaagttaca agaagaatat acaagaggct tatctcctgc agaagcagaa    420
tttaattacc taaacacagc acgtacctta gaactctatg gagttgaatt ccactatgca    480
agggatcaga gtaacaatga aattatgatt ggagtgatgt caggaggaat tctgatttat    540
aagaacaggg tacgaatgaa tacctttcca tggttgaaga ttgtaaaaat ttcttttaag    600
```

```
tgcaaacagt tttttattca acttagaaaa gaattgatcc ccaagtaagc ccttggcacg     660
gaaattaatg gattgggaag tagtaagcag aaattcaata tctgatgaca ggttagaaac     720
acaaagtctt ccatcacgat ctccaccggg aactcctaat catcgaaatt ctacattcac     780
gcaggaagga acccggttac gaccatcttc agttggtcat ttggtagacc atatggttca     840
tacttcccca agcgaggtgt ttgtaaatca gagatctccg tcatcaacac aagctaatag     900
cattgttctg gaatcatcac catcacaaga gacccctgga gatgggaagc ctccagcttt     960
accacccaaa cagtcaaaga aaaacagttg gaaccaaatt cattattcac attcgcaaca    1020
agatctagaa agtcatatta atgaaacatt tgatattcca tcttctcctg aaaaacccac    1080
tcctaatggt ggtattccac atgataatct tgtcctaatc agaatgaaac ctgatgaaaa    1140
tgggaggttt ggattcaatg taaagggagg atatgatcag aagatgcctg tgattgtgtc    1200
tcgagtagca ccaggaacac ctgctgacct ctgtgtccct agactgaatg aaggggacca    1260
agttgtactg atcaatggtc gggacattgc agaacacact catgatcagg ttgtgctgtt    1320
tattaaagct agttgtgaga gacattctgg ggaactcatg cttctagttc gacctaatgc    1380
tgtatatgat gtagtggaag aaaagctaga aaatgagcca gatttccagt atattcctga    1440
gaaagcccca ctagatagtg tgcatcagga tgaccattcc ctgcgggagt caatgatcca    1500
gctagctgag ggcttatca ctggaacagt cctgacacag tttgatcaac tgtatcggaa     1560
aaaacctgga atgacaatgt cctgtgccaa attacctcag aatatttcca aaaatagata    1620
cagagatatt tcgccttatg atgccacacg ggtcatttta aaaggtaatg aagactacat    1680
caatgcgaac tatataaata tggaaattcc ttcttccagc attataaatc agtacattgc    1740
ttgtcaaggg ccattaccac acacttgtac agatttttgg cagatgactt gggaacaagg    1800
ctcctctatg gttgtaatgt tgaccgcaca agttgaacgt ggcagagtta aatgtcacca    1860
atattggcca gaacccacag gcagttcatc ttatggatgc taccaagtta cctgccactc    1920
tgaagaagga aacactgcct atatcttcag gaagatgacc ctatttaacc aagagaaaaa    1980
tgaaagtcgt ccactcactc agatccagta catagcctgg cctgaccatg gagtccctga    2040
tgattcgagt gactttctag attttgtttg tcatgtacga aacaagaggg ctggcaagga    2100
agaacccgtt gttgtccatt gcagtgctgg aatcggaaga actggggttc ttattactat    2160
ggaaacagcc atgtgtctca ttgaatgcaa tcagccagtt tatccactag atattgtaag    2220
aacaatgaga gatcagcgag ccatgatgat ccaaacacct agtcaataca gatttgtgtg    2280
tgaagctatt ttgaaagttt atgaagaagg ctttgttaaa cccttaacaa catcaacaaa    2340
taaataagaa agcaaaaaga tctgggatat gtgttggaaa actgctttcc cttatgttca    2400
ctgtgccata atgctgctcg caggaaatgg cattttacaa aaaaaaatga agaactcaaa    2460
aaaactttga aaacttcagc actgttgcac tttatgtttt aaaaaatgtc actctttcaa    2520
aatctataac tcatgtattt gaagactgtt tcatgaagga cgattccagc acactgcgcc    2580
gtaataacgt gcaggctcgc acgtgatgtt c                                   2611
```

<210> SEQ ID NO 60
<211> LENGTH: 5216
<212> TYPE: DNA
<213> ORGANISM: Homo sapiens

<400> SEQUENCE: 60

```
tactccagtg tgagggcaaa aacttgagta gccaggagaa tgatgaaacg gaggcgagag      60
agactgggag caccatgtct gcggattcaa atctctaccc tttgccgagg agctgaagta     120
```

```
aaccagcaca tgttttcacc cacatctgct ccagccctct tcctcactaa agtcccattt    180
agtgctgatt gtgctttggc tacttctcct cttgccattt tcctgaacct acgagcccac    240
agcagtcctg gcactccttg ttccagccgc ccactgccgt ggagttgtcg gacaagtaac    300
cgcaagagct tgattgtgac ctctagcaca tcacctacac taccacggcc acactcacca    360
ctccatggcc acacaggtaa cagtcctttg gacagccccc ggaatttctc tccaaatgca    420
cctgctcact tttcttttgt tcctgcccgt aggactgatg ggcggcgctg gtctttggcc    480
tctttgccct cttcaggata tggaactaac actcctagct ccactgtctc atcatcatgc    540
tcctcacagg aaaagctgca tcagttgcct ttccagccta cagctgatga gctgcacttt    600
ttgacgaagc atttcagcac agagagcgta ccagatgagg aaggacggca gtccccagcc    660
atgcggcctc gctcccggag cctcagtccc ggacgatccc cagtatcctt tgacagtgaa    720
ataataatga tgaatcatgt ttacaaagaa agattcccaa aggccaccgc acaaatggaa    780
gagcgactag cagagtttat ttcctccaac actccagaca gcgtgctgcc cttggcagat    840
ggagccctga gctttattca tcatcaggtg attgagatgg cccgagactg cctggataaa    900
tctcggagtg gcctcattac atcacaatac ttctacgaac ttcaagagaa tttggagaaa    960
cttttacaag atgctcatga gcgctcagag agctcagaag tggcttttgt gatgcagctg   1020
gtgaaaaagc tgatgattat cattgcccgc ccagcacgtc tcctggaatg cctggagttt   1080
gaccctgaag agttctacca ccttttagaa gcagctgagg gccacgccaa agagggacaa   1140
gggattaaat gtgacattcc ccgctacatc gttagccagc tgggcctcac ccgggatccc   1200
ctagaagaaa tggcccagtt gagcagctgt gacagtcctg acactccaga gacagatgat   1260
tctattgagg gccatggggc atctctgcca tctaaaaaga caccctctga agaggacttc   1320
gagaccatta agctcatcag caatggcgcc tatggggctg tatttctggt gcggcacaag   1380
tccacccggc agcgctttgc catgaagaag atcaacaagc agaacctgat cctacggaac   1440
cagatccagc aggccttcgt ggagcgtgac atactgactt tcgctgagaa cccctttgtg   1500
gtcagcatgt tctgctcctt tgataccaag cgccacttgt gcatggtgat ggagtacgtt   1560
gaagggggag actgtgccac tctgctgaag aatattgggg ccctgcctgt ggacatggtg   1620
cgtctatact ttgcggaaac tgtgctggcc ctggagtact tacacaacta tggcatcgtg   1680
caccgtgacc tcaagcctga caacctccta attacatcca tggggcacat caagctcacg   1740
gactttggac tgtccaaaat gggcctcatg agtctgacaa cgaacttgta tgagggtcat   1800
attgaaaagg atgcccggga attcctggac aagcaggtat gcgggacccc agaatacatt   1860
gcgcctgagg tgatcctgcg ccagggctat gggaagccag tggactggtg ggccatgggc   1920
attatcctgt atgagttcct ggtgggctgc gtcccttttt ttggagatac tccggaggag   1980
ctctttgggc aggtgatcag tgatgagatt gtgtggcctg agggtgatga ggcactgccc   2040
ccagacgccc aggacctcac ctccaaactg ctccaccaga accctctgga gagacttggc   2100
acaggcagtg cctatgaggt gaagcagcac ccattcttta ctggtctgga ctggacagga   2160
cttctccgcc agaaggctga atttattcct cagttggagt cagaggatga tactagctat   2220
tttgacaccc gctcagagtg ataccaccac atggactcgg aggatgagga agaagtgagt   2280
gaggatggct gccttgagat ccgccagttc tcttcctgct ctccaaggtt caacaaggtg   2340
tacagcagca tggagcggct ctcactgctc gaggagcgcc ggacaccacc cccgaccaag   2400
cgcagcctga gtgaggagaa ggaggaccat tcagatggcc tggcagggct caaaggccga   2460
gaccggagct gggtgattgg ctcccctgag atattacgga agcggctgtc ggtgtctgag   2520
```

```
tcgtcccaca cagagggtga ctcaagccct ccaatgacag tgcgacgccg ctgctcaggc   2580
ctcctggatg cgcctcggtt cccggagggc cctgaggagg ccagcagcac cctcaggagg   2640
caaccacagg agggtatatg ggtcctgaca cccccatctg gagagggggt atctgggcct   2700
gtcactgaac actcagggga gcagcggcca aagctggatg aggaagctgt tggccggagc   2760
agtggttcca gtccagctat ggagacccga ggccgtggga cctcacagct ggctgaggga   2820
gccacagcca aggccatcag tgacctggct gtgcgtaggg cccgccaccg gctgctctct   2880
ggggactcaa cagagaagcg cactgctcgc cctgtcaaca aagtgatcaa gtccgcctca   2940
gccacagccc tctcactcct cattccttcg gaacaccaca cctgctcccc gttggccagc   3000
cccatgtccc cacattctca gtcgtccaac ccatcatccc gggactcttc tccaagcagg   3060
gacttcttgc cagcccttgg cagcatgagg cctcccatca tcatccaccg agctggcaag   3120
aagtatggct tcaccctgcg ggccattcgc gtctacatgg gtgactccga tgtctacacc   3180
gtgcaccata tggtgtggca cgtggaggat ggaggtccgg ccagtgaggc agggcttcgt   3240
caaggtgacc tcatcaccca tgtcaatggg gaacctgtgc atggcctggt gcacacggag   3300
gtggtggagc tgatcctgaa gagtggaaac aaggtggcca tttcaacaac tcccctggag   3360
aacacatcca ttaaagtggg gccagctcgg aagggcagct acaaggccaa gatggcccga   3420
aggagcaaga ggagccgcgg caaggatggg caagaaagca gaaaaaggag ctccctgttc   3480
cgcaagatca ccaagcaagc atccctgctc cacaccagcc gcagcctttc ttcccttaac   3540
cgctccttgt catcagggga gagtgggcca ggctctccca cacacagcca cagcctttcc   3600
ccccgatctc ccactcaagg ctaccgggtg acccccgatg ctgtgcattc agtgggaggg   3660
aattcatcac agagcagctc cccccagctcc agcgtgccca gttccccagc cggctctggg   3720
cacacacggc ccagctccct ccacggtctg gcacccaagc tccaacgcca gtaccgctct   3780
ccacggcgca agtcagcagg cagcatccca ctgtcaccac tggcccacac cccttctccc   3840
ccaccccccaa cagcttcacc tcagcggtcc ccatcgcccc tgtctggcca tgtagcccag   3900
gcccttccca caaagcttca cttgtcacct cccctgggca ggcaactctc acggcccaag   3960
agtgcggagc caccccgttc accactactc aagagggtgc agtcggctga gaaactggca   4020
gcagcacttg ccgcctctga gaagaagcta gccacttctc gcaagcacag ccttgacctg   4080
ccccactctg aactaaagaa ggaactgccg cccagggaag tgagccctct ggaggtagtt   4140
ggagccagga gtgtgctgtc tggcaagggg gccctgccag ggaagggggt gctgcagcct   4200
gctccctcac gggccctagg caccctccgg caggaccgag ccgaacgacg ggagtcgctg   4260
cagaagcaag aagccattcg tgaggtggac tcctcagagg acgacaccga gggagggcct   4320
gagaacagcc agggtgcaca ggagctgagc ttggcacctc acccagaagt gagccagagt   4380
gtggccccta aggagcagg agagagtggg gaagaggatc ctttcccgtc cagagaccct   4440
aggagcctgg gcccaatggt cccaagccta ttgacaggga tcacactggg gcctcccaga   4500
atggaaagtc ccagtggtcc ccacaggagg ctcgggagcc cacaagccat tgaggaggct   4560
gccagctcct cctcagcggg ccccaaccta ggtcagtctg gagccacaga ccccatccct   4620
cctgaaggtt gctggaaggc ccagcacctc cacacccagg cactaacagc actttctccc   4680
agcacttcgg gactcacccc caccagcagt tgctctcctc ccagctccac ctctgggaag   4740
ctgagcatgt ggtcctggaa atcccttatt gagggcccag acagggcatc cccaagcaga   4800
aaggcaacca tggcaggtgg gctagccaac ctccaggatt tggaaaacac aactccagcc   4860
cagcctaaga acctgtctcc cagggagcag gggaagacac agccacctag tgcccccaga   4920
```

```
ctggcccacc catcttatga ggatcccagc cagggctggc tatgggagtc tgagtgtgca   4980

caagcagtga aagaggatcc agccctgagc atcacccaag tgcctgatgc ctcaggtgac   5040

agaaggcagg acgttccatg ccgaggctgc cccctcaccc agaagtctga gcccagcctc   5100

aggaggggcc aagaaccagg gggccatcaa aagcatcggg atttggcatt ggttccagat   5160

gagcttttaa agcaaacata gcagttgttt gccatttctt gcactcagac ctgtga       5216
```

<210> SEQ ID NO 61
<211> LENGTH: 2554
<212> TYPE: DNA
<213> ORGANISM: Homo sapiens

<400> SEQUENCE: 61

```
ctgttttatg cgtcatcatc ccgcgcagac acaggaagtg ccgcacagag cgagcccctg     60

tcgccttgag ttctgggcca gaggtcggct attatatcat cattaggcgt caacacagga    120

agtgaggata cttctggcga gcgccggttg ctgtttcttc tcaggctcag ggaccggccg    180

cggccccgta gggtgtttta actcaaatgg gtgatgaaaa ggactcttgg aaagtgaaaa    240

ctttagatga aattcttcag gaaaagaaac gaaggaagga acaagaggag aaagcagaga    300

taaaacgctt aaaaaattct gatgaccggg attccaagcg ggattccctt gaggaggggg    360

agctgagaga tcactgcatg gagatcacaa taaggaactc cccgtataga agagaagact    420

caatggaaga cagaggagaa gaagatgatt ctttggccat caaaccaccc cagcaaatgt    480

ctcggaaaga aaaagttcat cacagaaaag atgaaaagag aaaagaaaaa tggaccgctt    540

ggagcagtta gaaaggaagc gggagcggga gcgcaagatg cgggagcagc agaaggagca    600

gcgggagcag aaggagcgcg agcggcgggc ggaggagcgg cgcaaggagc gggaggcccg    660

cagggaagtg tctgcacatc accgaacgat gagagaggac tacagcgaca aagtgaaagc    720

cagccactgg agtcgcagcc cgcctcggcc gccgcgggag cggttcgagt tgggagacgg    780

ccggaagcca gtaaaagaag agaaaatgga agaaagggac ctgctgtccg acttacagga    840

catcagcgac agcgagagga agaccagctc ggccgagtcc tcgtcagcgg aatcaggctc    900

aggttctgag gaagaagagg aggaggagga agaggaggag gaggaaggga gcaccagtga    960

agaatcagag gaggaggagg aggaagagga agaggaggag gaggagaccg gcagcaactc   1020

tgaggaggca tcagagcagt ctgccgaaga agtaagtgag gaagaaatga gtgaagatga   1080

agaacgagaa aatgaaaacc acctcttggt tgttccagag tcacggttcg accgagattc   1140

cggggagagt gaagaagcag aggaagaagt gggtgaggga acgccgcaga gcagcgccct   1200

gacagagggc gactatgtgc ccgactcccc tgccctgtcg cccatcgagc tcaagcagga   1260

gctgcccaag tacctgccgg ccctgcaggg ctgccggagc gtcgaggagt tccagtgcct   1320

gaacaggatc gaggagggca cctatggagt ggtctacaga gcaaaagaca agaaaacaga   1380

tgaaattgtg gctctaaagc ggctgaagat ggagaaggag aaggagggct tcccgatcac   1440

gtcgctgagg gagatcaaca ccatcctcaa ggcccagcat cccaacatcg tcaccgttag   1500

agagattgtg gtgggcagca acatggacaa gatctacatc gtgatgaact atgtggagca   1560

cgacctcaag agcctgatgg agaccatgaa acagcccttc ctgccagggg aggtgaagac   1620

cctgatgatc cagctgctgc gtggggtgaa acacctgcac gacaactgga tcctgcaccg   1680

tgacctcaag acgtccaacc tgctgctgag ccacgctggc atcctcaagg tgggtgactt   1740

cgggctggcg cgggagtacg gatcccctct gaaggcctac accccggtcg tggtgaccct   1800

gtggtaccgc gccccagagc tgctgcttgg tgccaaggaa tactccacgg ccgtggacat   1860
```

```
gtggtcagtg ggttgcatct tcggggagct gctgactcag aagcctctgt tccccgggaa   1920
gtcagaaatc gatcagatca acaaggtgtt caaggatctg ggaccccta gtgagaaaat    1980
ctggcccggc tacagcgagc tcccagcagt caagaagatg accttcagcg agcaccccta   2040
caacaacctc cgcaagcgct tcggggctct gctctcagac cagggcttcg acctcatgaa   2100
caagttcctg acctacttcc ccgggaggag gatcagcgct gaggacggcc tcaagcatga   2160
gtatttccgc gagaccccc tccccatcga cccctccatg ttccccacgt ggcccgccaa    2220
gagcgggcag cagcgtgtga agcggggcac cagccccgagg cccccctgagg gaggcctggg 2280
ctacagccag ctgggtgacg acgacctgaa ggagacgggc ttccacctta ccaccacgaa   2340
ccagggggcc tctgccgcgg gccccggctt cagcctcaag ttctgaaggt cagagtggac   2400
cccgtcatgg ggagaactca gccgggacca caggcgtggc tactgcggct ggagctgcga   2460
tgagactcgg aactcctcgt cttactttgt gctccatgtt ttgtttttgt attttggttt   2520
gtaaatttgt agaattaaat cattttcctt gttg                               2554
```

<210> SEQ ID NO 62
<211> LENGTH: 2023
<212> TYPE: DNA
<213> ORGANISM: Homo sapiens

<400> SEQUENCE: 62

```
aggcccctgt ccttctgtcg ggcgccgctc agccgtgccc tccgcccctc aggttctttt     60
tctaattcca aataaacttg caagaggact atgaaagatt atgatgaact tctcaaatat    120
tatgaattac atgaaactat tgggacaggt ggctttgcaa aggtcaaact tgcctgccat    180
atccttactg gagagatggt agctataaaa atcatggata aaaacacact agggtactgc    240
cctggaggag agctgtttga ctatataatt tcccaggatc gcctgtcaga agaggagacc    300
cgggttgtct tccgtcagat agtatctgct gttgcttatg tgcacagcca gggctatgct    360
cacagggacc tcaagccaga aaatttgctg tttgatgaat atcataaatt aaagctgatt    420
gactttggtc tctgtgcaaa acccaagggt aacaaggatt accatctaca gacatgctgt    480
gggagtctgg cttatgcagc acctgagtta atacaaggca aatcatatct tggatcagag    540
gcagatgttt ggagcatggg catactgtta tatgttctta tgtgtggatt tctaccattt    600
gatgatgata atgtaatggc tttatacaag aagattatga gaggaaaata tgatgttccc    660
aagtggctct ctcccagtag cattctgctt cttcaacaaa tgctgcaggt ggacccaaag    720
aaacggattt ctatgaaaaa tctattgaac catccctgga tcatgcaaga ttacaactat    780
cctgttgagt ggcaaagcaa gaatcctttt attcacctcg atgatgattg cgtaacagaa    840
ctttctgtac atcacagaaa caacaggcaa acaatggagg atttaatttc actgtggcag    900
tatgatcacc tcacggctac ctatcttctg cttctagcca agaaggctcg gggaaaacca    960
gttcgtttaa ggctttcttc tttctcctgt ggacaagcca gtgctacccc attcacagac   1020
atcaagtcaa ataattggag tctggaagat gtgaccgcaa gtgataaaaa ttatgtggcg   1080
ggattaatag actatgattg gtgtgaagat gatttatcaa caggtgctgc tactccccga   1140
acatcacagt ttaccaagta ctggacagaa tcaaatgggg tggaatctaa atcattaact   1200
ccagccttat gcagaacacc tgcaaataaa ttaaagaaca aagaaaatgt atatactcct   1260
aagtctgctg taaagaatga agagtacttt atgtttcctg agccaaagac tccagttaat   1320
aagaaccagc ataagagaga aatactcact acgccaaatc gttacactac accctcaaaa   1380
gctagaaacc agtgcctgaa agaaactcca attaaaatac cagtaaattc aacaggaaca   1440
```

```
gacaagttaa tgacaggtgt cattagccct gagaggcggt gccgctcagt ggaattggat   1500

ctcaaccaag cacatatgga ggagactcca aaaagaaagg gagccaaagt gtttgggagc   1560

cttgaaaggg ggttggataa ggttatcact gtgctcacca ggagcaaaag gaagggttct   1620

gccagagacg ggcccagaag actaaagctt cactataatg tgactacaac tagattagtg   1680

aatccagatc aactgttgaa tgaaataatg tctattcttc caaagaagca tgttgacttt   1740

gtacaaaagg gttatacact gaagtgtcaa acacagtcag attttgggaa agtgacaatg   1800

caatttgaat tagaagtgtg ccagcttcaa aaacccgatg tggtgggtat caggaggcag   1860

cggcttaagg gcgatgcctg ggtttacaaa agattagtgg aagacatcct atctagctgc   1920

aaggtataat tgatggattc ttccatcctg ccggatgagt gtgggtgtga tacagcctac   1980

ataaagactg ttatgatcgc tttgatttta aagttcattg gaa                     2023
```

<210> SEQ ID NO 63
<211> LENGTH: 1129
<212> TYPE: DNA
<213> ORGANISM: Homo sapiens

<400> SEQUENCE: 63

```
taggattccc aggagccatg ttgtcagaag tcctactggt gtctgctccg gggaaagtca     60

tccttcatgg agaacatgcc gtggtacatg gcaaggtagc actggctgta tccttgaact    120

tgagaacatt cctccggctt caaccccaca gcaatgggaa agtggacctc agcttaccca    180

acattggtat caagcgggcc tgggatgtgg ccaggcttca gtcactggac acaagctttc    240

tggagcaagg tgatgtcaca acacccacct cagagcaagt ggagaagcta aaggaggttg    300

caggcttgcc tgacgactgt gctgtcaccg agcgcctggc tgtgctggcc tttctttact    360

tatacctgtc catctgccgg aagcagaggt ggaccaagga ggatttggag ctaattaaca    420

agtgggcctt ccaaggggag agaatgattc acgggaaccc ctccggagtg gacaatgctg    480

acagcacctg gggaggagcc ctccgatacc atcaagggaa gatttcatcc ttaaagaggt    540

cgccagctct ccagatcctg ctgaccaacg ccaaagtccc tcgcaatacc agggcccttg    600

tggctggcgt cagaaacagg ctgctcaagt tcccagagat cgtggccccc ctcctgacct    660

caatagatgc catctccctg gagtgtgagc gcgtgctggg agagatgggg gaagccccag    720

ccccggagca gtacctcgtg ctggaagagc tcattgacat gaaccagcac catctgaatg    780

ccctcggcgt gggccacgcc tctctggacc agctctgcca ggtgaccagg gcccgcggac    840

ttcacagcaa gctgactggc gcaggcggtg gtggctgtgg catcacactc ctcaagccag    900

gtatcccggg gggctggagc agccagaagt ggaggccacg aagcaggccc tgaccagctg    960

tggctttgac tgcttggaaa ccagcatcgg tgcccccggc gtctccatcc actcagccac   1020

ctccctggac agccgagtcc agcaagccct ggatggcctc tgagaggagc ccacgacact   1080

gcagccccac ccagatgccc ctttctggat tattctgggg gctgcagta               1129
```

<210> SEQ ID NO 64
<211> LENGTH: 687
<212> TYPE: DNA
<213> ORGANISM: Homo sapiens

<400> SEQUENCE: 64

```
tatgggaaca acatgtcttc acctaggggc tttagagcag agcctgtaaa cgattatgag     60

ggaaatgact ctgaagcaga agacttgaat ttcagggaga ctttgccttc atcaagtcag    120

gaaaacacac ctagatcaaa ggtttttgaa aataaagtta attcagagaa ggtaaaactt    180
```

```
tctcttcgga atttcccaca taatgattat gaggatgttt ttgaagagcc ttcagaaagt    240

ggcagtgatc ccagcatgtg gacagccaga ggccccttca gaagaggcag gtggagcagt    300

gaggatgagg aggctgcagg gccatcacag gctctctccc ctctactttc tgatacgcgc    360

aaaattgttt ctgaaggaga actagatcag ttggctcaga ttcggccatt aatattcaat    420

tttcatgagc agacagccat caaggattgt ttgaaaatcc ttgaggaaaa aacagcagcg    480

tatgatatca tgcaggaatt tatgttcaac atcatggata tagtggccca aatgagagaa    540

caacgttctg gcatggttca aacgaaggag cagtatcact tttgttacga tattgtgctt    600

gaagttcttc ggaaacttct gactttggat taagaaagac ttctgttgcc tctcacttga    660

aattaccaag tgggtttgca cctccta                                        687
```

<210> SEQ ID NO 65
<211> LENGTH: 3912
<212> TYPE: DNA
<213> ORGANISM: Homo sapiens

<400> SEQUENCE: 65

```
gaagaattgt cggcattggc ctggccagcg ctggttggtg gcctggagga ggatttgatt     60

ggaaaaccaa cggtgcagct ggccgcggtg tccctgagaa aagtcagaaa tggccaatga    120

agcttttgct tataaaagga atgcgatgtt aattctgggg cattgatgtt ttacaatgcc    180

tgatcaagat aaaaaggtga agaccacaga aaaatcaact gataaacagc aagaaatcac    240

catcagggac tattcagatc ttaaaagact tcggtgcctt ttgaacgtcc aatcaagcaa    300

acaacagctt ccagccatta acttcgatag tgcccaaaat agcatgacga agtctgagcc    360

cgccatcagg gcgggtggac acagagctcg gggtcagtgg catgaatcca cagaagctgt    420

tgaacttgaa aattttagta taaactacaa gaatgagaga aatttcagca aacatcctca    480

gcgtaaacta tttcaggaga tctttaccgc cttggtgaaa aatagactca taagcagaga    540

gtgggttaat cgagccccat ctattcattt tctgagagtg ttaatctgtc tgaggctact    600

aatgagggat ccatgttatc aggaaatact ccatagcttg ggtgggattg aaaacctagc    660

tcagtatatg gagattgtag ccaatgagta cctcggctat ggagaagagc agcacactgt    720

ggacaagctg gtcaacatga catatatttt tcaaaaactt gctgcagtca aagatcaaag    780

agaatgggtc accacaagtg gagcccacaa gacattagta aatttacttg gtgcccgaga    840

tactaatgtt ctattgggtt cccttctggc tctggctagt ttagcagaaa gtcaagaatg    900

tagggagaag ataagtgaac tcaacattgt agaaaatctg ttgatgattt tacatgaata    960

tgacttgctt tctaaaagac taacagcgga gttgctgcgc ctactttgtg cagagcccca   1020

ggtgaaagag caggtgaagc tctatgaggg gataccggtc ctcctcagtc tgctccactc   1080

tgaccacttg aagctcctct ggagcattgt ctggattctg gtacaggttt gtgaggaccc   1140

tgagaccagc gtggaaattc gcatttgggg aggcatcaaa cagcttcttc atattttaca   1200

aggagacaga aattttgttt ctgatcactc ctccattgga agcctgtcca gtgcaaatgc   1260

tgcaggccga atccagcagc ttcatttatc agaagacttg agccctaggg aaatacaaga   1320

aaatactttc tcacttcaag cagcctgctg tgctgccctc actgagctgg tgctcaatga   1380

caccaatgcc caccaggtgg ttcaggaaaa tggtgtatat acaatagcaa aattaatttt   1440

accaaataag caaaagaatg cagcaaaaag taatctatta cagtgttatg ctttcagagc   1500

cttgagattt ctcttcagta tggaaagaaa cagaccactc tttaaaagac ttttccccac   1560

agacttgttt gagatcttca ttgacatagg gcattatgta cgtgatatca gtgcttatga   1620
```

```
agaattggta tccaagctga atttattagt ggaggatgaa ctgaagcaaa ttgctgaaaa   1680
tattgaaagc attaatcaga acaaagctcc tttgaaatat ataggcaact atgcaatttt   1740
ggatcatctt ggaagtggag cttttggctg tgtttacaag gttagaaagc atagtggtca   1800
aaatctttta gcaatgaaag aggtcaattt acataaccca gcatttggaa aggataagaa   1860
agatcgagac agcagcgtaa ggaatattgt ttctgaatta acaataatta aagagcagct   1920
ttatcatccc aacattgtac gttattacaa aacatttctg gaaaacgata ggttgtacat   1980
agttatggag ctgatagaag gagccccgct tggagagcat ttcagttctt tgaaggaaaa   2040
acatcaccat tttactgaag aaagactatg gaaaatattt atacagctgt gcttagctct   2100
tcgatactta cacaaggaga agaggattgt ccatagagat ctgacaccaa acaacattat   2160
gttgggggat aaggacaaag taacagttac tgactttggc ctggcaaagc aaaaacaaga   2220
aaacagtaaa ctcacgtctg tggttggaac aatcctgtat tcttgccccg aggtactgaa   2280
gagtgagccg tatggggaga aggctgatgt ctgggcagta ggctgcatcc tttatcagat   2340
ggcgactttg agtccccct tctacagcac taacatgctg tccttggcta caaaaatagt   2400
ggaggcggta tatgaaccag tgccagaagg tatctactct gaaaaagtaa cagacaccat   2460
cagcaggtgc ctcactcctg atgcggaagc tcgtccagat attgtagaag tcagttcgat   2520
gatatcagat gtcatgatga aatatttaga caacttatct acatcccagt tgtccttgga   2580
aaagaagcta gaacgggaac gaagacgcac acaaaggtat tttatggaag ccaaccggaa   2640
caccgtcaca tgtcaccatg agctggctgt tctatctcac gagacctttg agaaggcaag   2700
tttgagtagc agcagcagtg gagcagccag cctgaaaagt gaactttcag aaagcgcaga   2760
cctgcccccct gaaggcttcc aggcctccta tggtaaagac gaagacaggg cctgtgacga   2820
aatcctgtca gatgataact tcaacctgga aaatgctgag aaagatacat attcagaggt   2880
agatgatgaa ttggacattt cggataactc cagcagctcc agttcaagcc ctctgaaaga   2940
atctacattc aacattttaa agagaagttt tagtgcttca ggaggagaaa gacaatccca   3000
aacaagggac ttcactggag gaacaggatc aagaccaaga ccagggccac agatgggcac   3060
attcttgtgg caagcatcag caggaattgc tgtgtcccag aggaaagtgc gtcagatcag   3120
tgatcctatt cagcagatat taattcagct gcacaaaata atctatatca cacagcttcc   3180
tccagctttg caccacaatt tgaaaagaag ggttatagag agattcaaga aatccctctt   3240
cagccagcag agtaaccctt gtaatttgaa atctgaaatt aaaaagttat ctcagggatc   3300
tccagaaccg attgagccca actttttcac agcagattac catttattac atcgttcatc   3360
cggtggaaac agcctgtccc caaatgaccc tacaggttta ccaaccagca ttgaattgga   3420
ggaaggaata acatatgaac agatgcagac tgtgattgaa gaagtccttg aggaaagtgg   3480
ctattacaat tttacatcta acaggtatca ttcctatcca tgggggacca agaatcaccc   3540
aaccaaaaga tgaaaatgct gcattttgag tggacttgat ttctcagtg aagttcaagt   3600
tctggacttc agccgctatt gcaagatgcc caaggattgg gtgctgctag agggtgtgga   3660
aaagaccaag atgccatggg gcctgcagga cttctttctg gggtcctgt gctggagtat   3720
atgacagctg cggtacttga gggcttcatt gccagaacac attatataca ggatgtcaga   3780
gctaccagtg tgctgctggg agaaaatgct gcaaaattca tcttttggag ggtgggggga   3840
aaacccaaaa acaacaacaa aaaaactctc ttacagaatt ttccttaaca ttaaaaaaaa   3900
cttgtcatat tt                                                       3912
```

<210> SEQ ID NO 66
<211> LENGTH: 3229
<212> TYPE: DNA
<213> ORGANISM: Homo sapiens

<400> SEQUENCE: 66

```
gtagcataaa gaggaaatag aaggaaagca ataagtaaga aagtacatat ttcaatctga     60
aaatgcttgg cactactacc cttggaaaat gtagagaagt agccagtagc cgcgcctggg    120
gagtcgcctg aacgtgacgg cagcaaatgc agattgttgg gtctccggga ccaggagcag    180
cgtggccagt gaagcgcgtg gttttcccaa atggtgaaca attcttgtta tctgtggcca    240
caaagaaagt tatttgtctc tgtcttggca aggctgggag gaaagtttta gctaagaaac    300
tcagcccatt ggagaccatg gataagtacg atgtgattaa ggccatcggg caaggtgcct    360
tcgggaaagc atacttagct aaagggaaat cagatagcaa gcactgtgtc ataaaagaga    420
tcaattttga aaagatgccc atacaagaaa aagaagcttc aaagaaagaa gtgattcttc    480
tggaaaagat gaaacatccc aacattgtag ccttcttcaa ttcatttcaa gagaatggca    540
ggctgtttat tgtaatggaa tattgtgatg gaggggatct catgaaaagg atcaatagac    600
aacggggtgt gttatttagt gaagatcaga tcctcggttg gtttgtacag atttctctag    660
gactaaaaca tattcatgac aggaagatat tacacaggga cataaaagct cagaacattt    720
ttcttagcaa gaacggaatg gtggcaaagc ttggggactt tggtatagca agagtcctga    780
ataattccat ggaacttgct cgaacttgta ttggaacacc ttactacctg tccccagaga    840
tctgtcagaa taaaccctac aacaataaaa cggatatttg gtctcttggc tgtgtcttat    900
atgagctctg cacacttaaa catccttttg agggtaacaa cttacagcag ctggttctga    960
agatttgtca agcacatttt gccccaatat ctccggggtt ttctcgtgag ctccattcct   1020
tgatatctca gctctttcaa gtatctcctc gagaccgacc atccataaat tccattttga   1080
aaaggccctt tttagagaat cttattccca aatatttgac tcctgaggtc attcaggaag   1140
aattcagtca catgcttata tgcagagcag gagcgccagc ttctcgacat gctgggaagg   1200
tggtccagaa gtgtaaaata caaaaagtga gattccaggg aaagtgccca ccaagatcaa   1260
ggatatctgt gccaattaaa aggaatgcta tattgcatag aaatgaatgg agaccaccag   1320
ctggagccca gaaggccaga tctataaaaa tgatagaaag acccaaaatt gctgctgtct   1380
gtggacatta tgattattat tatgctcaac ttgatatgct gaggaggaga gcccacaaac   1440
caagttatca ccctattcct caagaaaata ctggagttga ggattacggt caggaaacga   1500
ggcatggtcc atccccaagt caatggcctg ctgagtacct tcagagaaaa tttgaagctc   1560
aacaatataa gttgaaagtg gagaagcaat tgggtcttcg tccatcttct gccgagccaa   1620
attacaacca gagacaagag ctaagaagta atggagaaga gcctagattc caggagctgc   1680
catttaggaa aaacgaaatg aaggaacagg aatattggaa gcagttagag gaaatacgcc   1740
aacagtacca caatgacatg aaagaaatta gaaagaagat ggggagagaa ccagaggaga   1800
actcaaaaat aagtcataaa acctatttgg tgaagaagag taacctgcct gtccatcaag   1860
atgcatctga gggagaagca cctgtgcagg acattgaaaa agacttgaaa caaatgaggc   1920
ttcagaacac aaaggaaagt aaaaatccag aacagaaata taaagctaag gggggtaaaat   1980
ttgaaattaa tttagacaaa tgtatttctg atgaaaacat cctccaagag gaagaggcaa   2040
tggatatacc aaatgaaact ttgacctttg aggatggcat gaagtttaag gaatatgaat   2100
gtgtaaagga gcatggagat tatacagaca aagcatttga aaaacttcac tgcccagaag   2160
cagggttttc cacgcagact gtagctgctg tgggaaacag gaggcagtgg gatggaggag   2220
```

```
cgcctcagac tctgctgcag atgatggcag tggccgacat cacctccacc tgccccacgg   2280

ggcctgacaa tggccaagtt attgtgattg aaggcattcc aggaaacagg aaacagtggc   2340

ggcatgaagc tccaggaact ttaatgagtg ttttggcagc agcacatcta acgagtagct   2400

cattttctgc cgatgaagaa tttgcaatgg gaacattaaa acaatggcta cccaaagaag   2460

aagatgaagg gaaggtagaa atggtctctg gcattgaagt agatgaggaa caactagaac   2520

caagatctga tgatgatgat acaaattttg aagaatctga agatgagttg agagatgaag   2580

tagtagaata cttagaaaaa ctcgctactt tcaaagggga agaaaaaaca gaagaggcct   2640

ccagtacctc taaggactct agaaagtcaa gagaaagaga ggggataagt atgcagaaat   2700

ctgaagaatt aagggagggc ttggagaata tttctactac atctaatgac cacatttgta   2760

ttactgatga agaccaagga acatcaacaa ccagtcaaaa tatacaagtg tgattattgt   2820

actttttctt aagtaataag ttagtgtcta ttacctatag tatttatttg ggtacaagtc   2880

ataaatgctc atttactgta agggttttct agtaatctca aggatttatt aatttttctt   2940

tcaatttagg aagtagaact tttgaatata gccattaata tttttacttt aaagtttcta   3000

ttaagaaatc ttaggccggg cagtctcatc actttgggag gccaaggcag gcagatcatg   3060

aggtcaggag ttgagaccag tccaaccaac atggtgaaac cccgtctcta ctaaaaatac   3120

aaaattagct gggcatggtg gtgcatgcct gtaatcccag ttacttggga ggctgaggca   3180

ggagaatcac ctgaacccag gagatggaag ttgcaagtga gccgagatg               3229


<210> SEQ ID NO 67
<211> LENGTH: 2100
<212> TYPE: DNA
<213> ORGANISM: Homo sapiens

<400> SEQUENCE: 67

tagagcattg ccttgttgct gacctttcag tatggggagg attggcatct cctgtctttt     60

tcctgcttct tggcatttta gcatatctcc agtagggtgt cctcgaattc tgaataccaa    120

tttacgccaa attatggtca ttagtgtcct ggctgctgct gtttcacttt tatatttttc    180

tgttgtcata atccgaaata agtatgggcg actaaccaga gacaagaaat ttcaaaggta    240

cctggcacga gttaccgaca ttgaagctac agacaccaat aaccccaatg tgaactatgg    300

gatcgtggtg gactgtggta gcagtgggtc tcgagtattt gtttactgct ggccaaggca    360

taatggcaat ccacatgatc tgttggatat caggcaaatg agggataaaa accgaaagcc    420

agtggtcatg aagataaaac cgggcatttc agaatttgct acctctccag agaaagtcag    480

tgattacatt tctccacttt tgaactttgc tgcagagcat gtgccacggg caaaacacaa    540

agagacacct ctctacattc tctgcacggc tggaatgaga atcctccccg aaagccagca    600

gaaagctatt ctggaagacc ttctgaccga tatccccgtg cactttgact ttctgttttc    660

tgactctcat gcagaagtaa tttctgggaa acaagaaggt gtgtatgctt ggattggcat    720

taattttgtc cttggacgat ttgagcatat tgaagatgat gatgaggccg ttgtggaagt    780

taacattcct ggaagtgtaa gcagcgaagc cattgtccgt aaaaggacag cgggcattct    840

cgacatgggc ggcgtgttga ctcagatagc gtacgaagtc cccaaaactg caagctttgc    900

gtcctcacag caggaagaag tagctaaaaa cttgttagct gaatttaact tgggatgtga    960

tgttcaccaa actgagcatg tgtatcgagt ctatgtggcc acgttttttg ggtttggtgg   1020

caatgctgct cgacagagat acgaagacag aatatttgcc aacaccattc aaaagaacag   1080

gctcctgggt aaacagactg gtctgactcc tgatatgccg tacttggacc cctgcctacc   1140
```

```
cctagacatt aaagatgaaa tccagcaaaa tggacaaacc atatacctac gagggactgg   1200
agactttgac ctgtgtcgag agactatcca gcctttcatg aataaaacaa acgagaccca   1260
gacttccctc aatggggtct accagccccc aattcacttc cagaacagtg aattctatgg   1320
cttctccgaa ttctactact gcaccgagga tgtgttacga atgggggggag actacaatgc   1380
tgctaaattt actaaagctg caaaggatta ttgtgcaaca aagtggtcca ttttgcggga   1440
acgctttgac cgaggactgt acgcctctca tgctgacctc cacaggctta agtgaactgc   1500
tccatgttgt gggaccaggg atgtgaagca agtacatcaa ccttgaaacg cgcgcagttg   1560
gtttgggaga gccggcctga ggaagcccct gccccaaggc tgcccacaga gggaaggatt   1620
gtgtgtgtgt gtgtgtgtgt gccatcttga cagagtgagt cagtctgact tgcctttgtg   1680
cttgccgttt gtaggtatca gtgcttcaaa tcggcctgga tgtttgaggt gtttcatagg   1740
ggcttttcgt ttcctgtcaa ctataaaagc ttaaagactg ccttgcaagt ttacgacaag   1800
gaggttcagt ggacccttgg agccatcctc tacaggaccc gctttctacc attaagagac   1860
atccagcagg aggccttccg agccagtcac acccactggc ggggcgtttc ctttgtctac   1920
aaccactacc tgttctctgg ctgcttcctg gtggtgctgc tggccatcct gctgtacctg   1980
ctgcggctgc ggcgcatcca caggcgcact ccccggagca gctcggccgc cgccctctgg   2040
atggaggagg gccttcccgc ccagaatgcc ccggggacct tgtgatccag ctcacagcta   2100
```

<210> SEQ ID NO 68
<211> LENGTH: 4213
<212> TYPE: DNA
<213> ORGANISM: Homo sapiens

<400> SEQUENCE: 68

```
cccgggccat ggacgagtcg agcctcctgc ggcgccgcgg gctccagaag gagctgagcc     60
tgccacgccg aggacgtggc tgccgcagcg ggaaccgcaa gagcttggtg gtaggaacgc    120
cctccccgac cctctcccgg cccctgtcgc cattgtcggt cccaacggca ggcagcagcc    180
ccttggatag tcctcggaat ttctcggctg cctctgccct aaatttcccc tttgcccgga    240
gggcagacgg cagaagatgg tccctcgcgt ctctcccatc ttccggctat ggaaccaaca    300
cacccagctc caccctctcg tcaagctcat cctcccggga acgtctccac cagcttccct    360
tccagccgac gccggacgag ctgcacttcc tgtccaagca cttccgcagc tcagagaatg    420
tgcttgatga ggaaggcggc cggtcacccc gcctccgacc ccgctctcgc agtctcagcc    480
cgggccgtgc aacggggacc ttcgacaatg agattgtcat gatgaatcac gtgtaccggg    540
agaggttccc caaggccaca gcacagatgg agggccgtct gcaggagttc ctgacggcct    600
acgcgcccgg cgcccggctg gcgctggctg atggcgtctt gggcttcatc caccaccaga    660
tcgtcgagct ggcccgagac tgcttggcca agtctggcga gaacctcgtc acctcccgct    720
acttcctaga gatgcaggag aagctggagc ggcttctgca ggatgcccat gagcgttcgg    780
acagtgagga ggtcagcttc atcgtccagc ttgtccggaa actgctgatc atcatctcac    840
ggccagctcg gctgctggag tgtctggagt ttgaccctga ggaattttac cacctgctgg    900
aggcggctga gggccatgcg cgggagggcc aaggcattaa gactgacctt ccacagtaca    960
tcattgggca gctgggcctg gccaaggacc ccctggagga gatggtgcca ctgagtcacc   1020
tcgaagaaga acagccccca gcacctgagt ccccagagag ccgcgccctg gtcggccagt   1080
cacggaggaa gccatgcgaa agcgactttg agaccatcaa actcattagc aacggagcct   1140
atggggccgt ctacctggtg cggcaccgtg acacacggca gcgctttgcc atcaagaaga   1200
```

```
tcaacaaaca gaacttgatc ctgcgtaacc aggtccagca ggtctttgtg gagcgtgaca   1260
ttctcacctt tgccgagaac ccctttgtgg tcagcatgtt ctgctccttt gagacccggc   1320
gccacctatg tatggtcatg gaatacgtgg aaggcggcga ctgcgccacg ctcctgaaga   1380
acatgggccc gctgcccgtg gacatggccc gcctgtactt cgccgagacg gtgttggcgc   1440
tggagtacct gcataactat ggcatcgtgc accgtgacct caaaccagac aatctgctca   1500
tcacctcgct tggccacatc aagctcacgg acttcggcct gtccaagatc ggcctcatga   1560
gcatggccac caacctctat gagggccaca tcgagaagga cgcccgagag ttcatcgaca   1620
agcaggtgtg tgggacgccg gagtacatag cccccgaggt gatcttccgc cagggctatg   1680
ggaagccagt ggactggtgg gccatgggcg tcgtcctcta tgagtttctg gtgggctgcg   1740
tgcctttctt tggagatacc cccgaggaac tcttcggtca ggtggtcagc gatgagatca   1800
tgtggccaga gggagatgag gcccttccag cagacgccca ggacctcatc accaggttgc   1860
tccggcagag cccgctggac cgtctgggca ctggtggcac ccacgaagtg aagcagcacc   1920
ccttttttcct ggccctggac tgggcagggc ttctccgaca caaagccgag ttcgtgcccc   1980
agctcgaagc cgaggatgat accagctact ttgacacacg ttcggaacgt taccgccatc   2040
tgggctccga ggacgacgag accaatgatg aagaatcgtc cacagagatc ccccagttct   2100
cctcctgctc ccaccggttc agcaaggtct acagcagctc tgagttcctg gccgtccagc   2160
ccactcctac cttcgctgaa aggagcttca gtgaagaccg ggaggagggg tgggagcgca   2220
gcgaagtgga ctatggccgc cggctgagtg ctgacatccg gctgaggtcc tggacatcct   2280
ctggatcctc ctgtcagtca tcttcgtccc agcccgagcg gggtcccagc ccatctctcc   2340
tgaataccat cagcctggac acaatgccca agtttgcctt ctcatcagag gatgaggggg   2400
taggcccagg ccctgcaggc cccaagaggc ccgtcttcat tctaggggag cctgaccccc   2460
caccagcggc caccccagtg atgcccaagc cctcgagcct ttctgccgac acagctgctc   2520
tcagccacgc ccgcctacgg agcaatagca tcggcgcccg acactccaca ccaaggcctc   2580
tggatgccgg ccggggccgc cgccttgggg gcccaagaga cccagcccct gagaagtcca   2640
gagcctcctc cagcggtggc agtggtggcg gcagtggggg ccgcgtgccc aagtcagcct   2700
ctgtctctgc cctgtccctc atcatcacgg cagatgatgg cagcggcggc cccctcatga   2760
gcccccctttc cccgcgctct ctgtcctcga acccgtcgtc ccgtgactct tcgccgagcc   2820
gagacccgtc cccgtgtgt ggcagcctgc ggccccccat cgttatccac agctctggca   2880
agaagtacgg cttcagcctg cgggcgatcc gcgtctacat gggtgatagc gacgtctaca   2940
ctgtgcacca cgtcgtctgg agtgtggagg acggaagccc cgcccaggag gcgggcctgc   3000
gggctgggga cctcatcacc cacatcaacg gggagtcagt gctggggctg gtgcacatgg   3060
acgtcgtgga gctgctgctg aagagcggca acaagatatc cctgcggacc acagccctgg   3120
agaacacctc catcaaggtg ggccccgccc ggaagaatgt ggccaagggc cgcatggcac   3180
gcaggagcaa gaggagccgt cggcgggaga cccaggatcg gcggaagtca cttttcaaga   3240
agatctccaa gcagacctcc gtgctgcaca ccagccgcag cttctcctcc ggactccacc   3300
actcactgtc atccagtgag agcctccccg gctcgcccac ccacagcctc tcccccagcc   3360
ccaccactcc ctgccgaagc ccagcccctg atgtcccagc agataccact gcatccccac   3420
ccagcgcatc cccgagctcc agcagccccg cctccccagc tgctgctggc cacacccgcc   3480
ccagctccct gcacggcctg gctgccaagc ttgggccacc ccgccccaag actggccgcc   3540
gcaagtccac cagcagcatc ccgccctccc cgctggcctg cccgcccatc tccgcgcccc   3600
```

caccccgctc gccctcgccc ctgcccgggc acccgcccgc acctgcccga tccccgcggc 3660
tgcgccgggg ccagtcagct gacaagctgg gcacagggga gcggctggat ggggaggcgg 3720
ggcggcgcac tcgtgggcca gaggccgagc tcgtggtcat gcggcggctg cacctgtccg 3780
agcgccgaga ctccttcaag aagcaggagg ccgtgcagga ggttagcttc gatgagccgc 3840
aggaggaggc cactgggctg cccacctcag tgccacagat cgccgtggag ggcgaggaag 3900
ccgtgccagt agctctcggg cccaccggaa gagactgatc ccctgccagg tctctccctg 3960
gcatcaaagt tacgcgtttt cttgtgcaat gtttttttccg taaagtcatg cctggatggg 4020
gactgagcca ccagcctgac acccagaagg cgagaagcca tctcggtcct tgctggaagg 4080
tggagacatc gcttgtgttc tggtgtcaat caggggggctg gatggggcaa gaatggggga 4140
caagggtggc tttgtaaata gcagcaaatc cctgcaacta atttattact ttttcttttt 4200 ttttttttt ttt 4213

<210> SEQ ID NO 69
<211> LENGTH: 5991
<212> TYPE: DNA
<213> ORGANISM: Homo sapiens

<400> SEQUENCE: 69
gtaccccgcc gcacagaggc ggcctctgcc tcggcatgaa gtcccgcagg gacaagctgc 60
acatcccggc gctgaccctc gatctgtctc cgagcagcca gagcccgtcc ctgctgggtc 120
ccagcagccc ctgcagcccc tgtagcccct ccttgggcct gcacccctgg agctgccgca 180
gcgggaaccg caagagcttg gtggtaggaa cgccctcccc gaccctctcc cggcccctgt 240
cgccattgtc ggtcccaacg gcaggcagca gccccttgga tagtcctcgg aatttctcgg 300
ctgcctctgc cctaaatttc ccctttgccc ggagggcaga cggcagaaga tggtccctcg 360
cgtctctccc atcttccggc tatggaacca acacacccag ctccaccctc tcgtcaagct 420
catcctctcg ggaacgtctc caccagcttc ccttccagcc gacgccggac gagctgcact 480
tcctgtccaa gcacttccgc agctcagaga atgtgcttga tgaggaaggc ggccggtcac 540
cccgcctccg accccgctct cgcagtctca gcccgggccg tgcaacgggg accttcgaca 600
atgagattgt catgatgaat catgtgtacc gggagaggtt ccccaaggcc acagcacaga 660
tggagggccg tctgcaggag ttcctgacgg cctacgcgcc cggcgcccgg ctggcgctgg 720
ctgatggcgt cttgggcttc atccaccacc agatcgtcga gctggcccga gactgcttgg 780
ccaagtctgg cgagaacctc gtcacctccc gctacttcct agagatgcag gagaagctgg 840
agcggcttct gcaggatgcc catgagcgtt cggacagtga ggaggtcagc ttcatcgtcc 900
agcttgtccg gaaactgctg atcatcatct cacggccagc tcggctgctg gagtgtctgg 960
agtttgaccc tgaggaattt taccacctgc tggaggcggc tgagggccat gcgcgggagg 1020
gccaaggcat taagactgac cttccacagt acatcattgg gcagctgggc ctggccaagg 1080 acccccctgga ggagatggtg ccactgagtc acctcgaaga agaacagccc ccagcacctg 1140
agtccccaga gagccgcgcc ctggtcggcc agtcacggag gaagccatgc gaaagcgact 1200
ttgagaccat caaactcatt agcaacggag cctatggggc cgtctacctg gtgcggcacc 1260
gtgacacacg gcagcgcttt gccatcaaga agatcaacaa acagaacttg atcctgcgta 1320
accagatcca gcaggtcttt gtggagcgtg acattctcac ctttgccgag aaccccctttg 1380 tggtcagcat gttctgctcc tttgagaccc ggcgccacct atgtatggtc atggaatacg 1440
tggaaggcgg cgactgcgcc acgctcctga agaacatggg cccgctgccc gtggacatgg 1500

```
cccgcctgta cttcgccgag acggtgttgg cgctggagta cctgcataac tatggcatcg   1560
tgcaccgtga cctcaaacca gacaatctgc tcatcacctc gcttggccac atcaagctca   1620
cggacttcgg cctgtccaag atcggcctca tgagcatggc caccaacctc tatgagggcc   1680
acatcgagaa ggacgcccga gagttcatcg acaagcaggt gtgtgggacg ccggagtaca   1740
tagcccccga ggtgatcttc cgccagggct atgggaagcc agtggactgg tgggccatgg   1800
gcgtcgtcct ctatgagttt ctggtgggct gcgtgccttt ctttggagat acccccgagg   1860
aactcttcgg tcaggtggtc agcgatgaga tcatgtggcc agagggagat gaggcccttc   1920
cagcagacgc ccaggacctc atcaccaggt tgctccggca gagcccgctg gaccgtctgg   1980
gcactggtgg cacccacgaa gtgaagcagc accccttttt cctggccctg gactgggcag   2040
ggcttctccg acacaaagcc gagttcgtgc cccagctcga agccgaggat gataccagct   2100
actttgacac acgttcggaa cgttaccgcc atctgggctc cgaggacgac gagaccaatg   2160
atgaagaatc gtccacagag atcccccagt tctcctcctg ctcccaccgg ttcagcaagg   2220
tctacagcag ctctgagttc ctggccgtcc agcccactcc taccttcgct gaaaggagct   2280
tcagtgaaga ccgggaggag ggtgggagc gcagcgaagt ggactatggc cgccggctga    2340
gtgctgacat ccggctgagg tcctggacat cctctggatc ctcctgtcag tcatcttcgt   2400
cccagcccga gcggggtccc agcccatctc tcctgaatac catcagcctg gacacaatgc   2460
ccaagtttgc cttctcatca gaggatgagg gggtaggccc aggccctgca ggccccaaga   2520
ggcccgtctt cattctaggg gagcctgacc ccccaccagc ggccaccccca gtgatgccca  2580
agccctcgag cctttctgcc gacacagctg ctctcagcca cgcccgccta cggagcaata   2640
gcatcggcgc ccgacactcc acaccaaggc ctctggatgc cggccggggc cgccgccttg   2700
ggggcccaag agacccagcc cctgagaagt ccagagcctc ctccagcggt ggcagtggtg   2760
gcggcagtgg gggccgcgtg cccaagtcag cctctgtctc tgccctgtcc ctcatcatca   2820
cggcagatga tggcagcggc ggcccccctca tgagcccccct ttccccgcgc tctctgtcct 2880
cgaacccgtc gtcccgtgac tcttcgccga gccgagaccc gtcccccgtg tgtggcagcc   2940
tgcggccccc catcgttatc cacagctctg gcaagaagta cggcttcagc ctgcgggcga   3000
tccgcgtcta catgggtgat agcgacgtct acactgtgca ccacgtcgtc tggagtgtgg   3060
aggacggaag ccccgcccag gaggcgggcc tgcgggctgg ggacctcatc acccacatca   3120
acggggagtc agtgctgggg ctggtgcaca tggacgtcgt ggagctgctg ctgaagagcg   3180
gcaacaagat atccctgcgg accacagccc tggagaacac ctccatcaag gtgggccccg   3240
cccggaagaa tgtggccaag ggccgcatgg cacgcaggag caagaggagc cgtcggcggg   3300
agacccagga tcggcggaag tcacttttca agaagatctc caagcagacc tccgtgctgc   3360
acaccagccg cagcttctcc tccggactcc accactcact gtcatccagt gagagcctcc   3420
ccggctcgcc cacccacagc ctctccccca gccccaccac tccctgccga agcccagccc   3480
ctgatgtccc agcagatacc actgcatccc cacccagcgc atccccgagc tccagcagcc   3540
ccgcctcccc agctgctgct ggccacaccc gccccagctc cctgcacggc ctggctgcca   3600
agcttgggcc accccgcccc aagactggcc gccgcaagtc caccagcagc atcccgccct   3660
ccccgctggc ctgcccgccc atctccgcgc ccccaccccg ctcgccctcg cccctgcccg   3720
ggcacccgcc cgcacctgcc cgatccccgc ggctgcgccg ggccagtca gctgacaagc    3780
tgggcacagg ggagcggctg gatggggagg cggggcggcg cactcgtggg ccagaggccg   3840
agctcgtggt catgcggcgg ctgcacctgt ccgagcgccg agactccttc aagaagcagg   3900
```

```
aggccgtgca ggaggttagc ttcgatgagc cgcaggagga ggccactggg ctgcccacct   3960

cagtgccaca gatcgccgtg gagggcgagg aagccgtgcc agtagctctc gggcccaccg   4020

gaagagactg atcccctgcc aggtctctcc ctggcatcaa agttacgcgt tttcttgtgc   4080

aatgtttttt ccgtaaagtc atgcctggat ggggactgag ccaccagcct gacacccaga   4140

aggcgagaag ccatctcggt ccttgctgga aggtggagac atcgcttgtg ttctggtgtc   4200

aatcaggggg ctggatgggg caagaatggg ggacaagggt ggctttgtaa atagcagcaa   4260

atccctgcaa ctaatttatt actttttttt tttttttttt tttttttttt tgagacagag   4320

tctcactctg ttgcccgggc tggagtgcag cggcgtgatc tcagctcact gcaacctccg   4380

cctcccaagt tcaagcgatt gtcctgcctc agcttcccaa gtggctggga ttacaggcgc   4440

ccaccactat gcccagctaa tttttgtat ttttagtaca gacggggttt caccatgttg   4500

gtcaggctgg tctcgaactc ctgacctcat gatttgcctg cctttgcctc ccaaagtgct   4560

gggattacag gcgtgagcca ctgggcccag cctaatttat tactttttat aagcgatagc   4620

cgtactgagc cgcccctga aggcggctgc caggtcttgc cccaggcacc tgggactctg   4680

tttgcaggcc ctgccctctg ggctgagaag gatgcacttt ggacaagtca tctgtgtttg   4740

tgttttccag tttttctgta ctttttaagt gttttgtgtt acctggtctc attcccctcc   4800

ccacacctac ccatttgagg ggatggagtt gaagtcacct ggtcacctgt accggcccag   4860

ttcggctaca acctggagtg tccgtaaaca attcctctca cccacaaaac aatgtaatcc   4920

cagcgatgga ctggattctg aaggccactt cccaccatca tagctgccat gcccaggcag   4980

tgcctgctct atatatagag tctgcctcca atcctgctgg cttcagcctg gagaagggat   5040

atgggagctg gagctttgat ggatgaatag gtgttcaccg gatctgggca gaggggtcat   5100

ccgctcccca ggtgggcact gataaaggaa ggtacaggcc tcacctggaa ctgccaaggc   5160

agcctccaga aatgctcggc tgtctcgggg cacgctccag tatgccagtc ctgcgggatt   5220

acgtccagct acttccagaa acactcagtg tcccctcccc tcaggctctg ccttggcctg   5280

gccttgtcca gtctaccctg gacaagatgc cgtgtgtttg aggcccagca gagtaagccc   5340

ttggccgtga tgtgtctgaa acacctgtta ggggttccct ccatatgtca gagcctctct   5400

gggatgaagt tcaagccaga aaacccagtc gaggctcaag tttgaatttc agcttcactg   5460

tgtggctctg ggaaaatggc tttcccactc tgtgcctcag tttccttgtg tttacaagac   5520

taatcccatt gactgtttat taagcaccta ctgtgtgcca agcgctttta cgtggcttct   5580

ccctcagcca gccttgagaa ggctggaggt ggtgtcatca cctccatttt acagacaaag   5640

cagctgagac cccagcgagg ggcggagacc tgtcccacga tcacccagca ggagtcgtgg   5700

cagaacggag catcagccag accctgttgt gggcgttgtc atcaagggag cttgaatgga   5760

gggtctggtg tcagatacag ccgactccag ccccagctca tcccccatga tgctgtgtga   5820

cccactgggc actctggtga gggagctttc cagacatcaa cagcccactc tgcttccctt   5880

tctgagtccc ctgtccagca ctgcctagtg ttggagggta gaccaaggct gtgcatgatt   5940

caccccctcc ttccatcctg gagctggcag tgaataaaag cccgtattta c             5991
```

```
<210> SEQ ID NO 70
<211> LENGTH: 669
<212> TYPE: DNA
<213> ORGANISM: Homo sapiens

<400> SEQUENCE: 70

gcctgctgga tttgtttgta tttgttccca gccactgctc atgtaatgta ctcccttaac     60
```

```
caggaaatta aagcattctc ccggaataat cccaggaagc aatgcaccag ggtgacaacg    120
ctaactggaa agaaaattat agaaacatgg aaagatgcca gaattcatgt tgtggaagaa    180
gtagagccga gcagtggggg tggttgtggt tatgtgcagg accttagctc ggaccagcaa    240
gttggcgtta ttaagccatg gttgctccta ggtgactcat attcttaatg ttgcatatgg    300
agttgaaaat gctttcctca gtgactttac atataagagc atttctatat tggatctgcc    360
tgaaaccaac atcctgtctt attttccaga atgttttgaa tttattgaag aagcaaaaag    420
aaaagatgga gtggttcttg ttcattgtaa tgcaggcgtt tccagggctg ctgcaattgt    480
aataggtttc ctgatgaatt ctgaacaaac ctcatttacc agtgcttttt ctttggtgaa    540
aaatgcaaga ccttccatat gtccaaattc tggcttcatg gagcagcttc gtacatatta    600
agagggcaaa gaaagcaata agtgtgacag aatacaggag aacagttcat gagttgcatt    660
gtagcagac                                                            669
```

<210> SEQ ID NO 71
<211> LENGTH: 2453
<212> TYPE: DNA
<213> ORGANISM: Homo sapiens

<400> SEQUENCE: 71

```
actgtacaaa tgctttattt ctattcaata tttagaagac agttataaac aagatgcatt     60
caatagcatg gtggcagatg aacatcagga aggaacatcc atgagcttcc atccacggaa    120
cctcaccatg gatacgcttg tgatcaaggg cctggtctcc cctcaagaca cggtcacaga    180
tcagaggcca caccatccta gcagtggagc agtaccagct gggacagggt ccttctgtga    240
cacctgctgc atcaccaggc tgggtgaacg gacacaattg ccagaactca cagaatagaa    300
gtatcagcac cgaaacctca caggaaaaat ggtaagttct aagtttctcc attaatagta    360
actctcagat taatctctgt catccatcgc ttctccaaga aatgactttt tagggtgatg    420
tgccaggcgc catgttggag ggctggtggt agcggcttgg ggaggtgctc gctctgtcgg    480
tcttgctctc tcgcacgctt cccccggctc ccttcgtttc ccccccccgg tcgcctgcgt    540
gccggagtgt gtgcgaggga gggggagggc gtcggggggg tggggggagg cgttccggtc    600
cccaagagac ccgcggaggg aggcggaggc tgtgagggac tccgggaagc catggacgtc    660
gagaggctcc aggaggcgct gaaagatttt gagaagaggg ggaaaaagga agtttgtcct    720
gtcctggatc agtttctttg tcatgtagcc aagactggag aaacaatgat tcagtggtcc    780
caatttaaag gctattttat tttcaaactg gagaaagtga tggatgattt cagaacttca    840
gctcctgagc caagaggtcc tcccaaccct aatgtcgaat atattccctt tgatgaaatg    900
aaggaaagaa tactgaaaat tgtcactgga tttaatggta tcccttttac tattcagcga    960
ctatgtgaat tgttaacaga tccaaggaga aactatacag gaacagacaa atttctcaga   1020
ggagtagaaa agaatgtgat ggttgttagc tgtgtttatc cttcttcaga gaaaaacaat   1080
tccaatagtt taaatcgaat gaatggtgtt atgtttcctg gaaattcacc aagctatact   1140
gagaggtcta atataaatgg gcctgggaca cccaggccac ttaatcgacc aaaggtttct   1200
ttgtcagccc ccatgacaac aaatgggttg cctgagagca cagacagcaa agaggcaaat   1260
ttgcagcaaa atgaggagaa aaatcacagt gactcttcga cctctgaatc agaagtttcc   1320
tcagtgagcc ctttgaaaaa taaacatcca gatgaagatg ctgtggaagc tgaggggcat   1380
gaggtaaaaa gactcaggtt tgacaaagaa ggtgaagtca gagaaacagc cagtcaaacg   1440
acttccagcg aaatttcttc agttatggta ggagaaacag aagcatcatc ttcatctcag   1500
```

```
gataaagaca aagatagccg ttgtacccgg cagcactgta cagaagagga tgaagaagag   1560
gatgaagagg aagaagaaga gtcttttatg acatcaagag aaatgatccc agaaagaaaa   1620
aatcaagaaa aagaatctga tgatgcctta actgtgaatg aagagacttc tgaggaaaat   1680
aatcaaatgg aggaatctga tgtgtctcaa gctgagaaag atttgctaca ttctgaaggt   1740
agtgaaaacg aaggccctgt aagtagtagt tcttctgact gccgtgaaac agaagaatta   1800
gtaggatcca attccagtaa aactggagag attctttcag aatcatccat ggaaaatgat   1860
gacgaagcca cagaagtcac cgatgaacca atggaacaag actaactatt tagaaacatt   1920
tagatgcagt attttacata cagttctggt tttaacactg tataaaactt ttgtgtaata   1980
aaatggacct ttagttttac aagagaagca ggttgtaaaa taaagtactt tatggataat   2040
tcctgaaaga gttgtacatg taagaactgt gaatatcagc tcctctgggt cctgcttacc   2100
ttaccgctga cttttctttc tttctttttt tggtctgggc aaatcagtgg tttgtgtata   2160
gatttttttt ttttttaatt taggattgaa gtttttaaac tggaaggtaa ttacaatttt   2220
gaaaagtttt ttgagattat cacatttagt ttatacatat gcaagaagct ttttgtcttg   2280
tctctttctg atagctctag cagttttcat attttggtca tagtttcaac attttaacat   2340
gtgaattata gggtttcatg ctggtttcca gattttattg tttggctacg tacaatggaa   2400
ctttaagtca tatatacata catattatat atatataagg gggggggggg ggt          2453
```

<210> SEQ ID NO 72
<211> LENGTH: 4430
<212> TYPE: DNA
<213> ORGANISM: Homo sapiens

<400> SEQUENCE: 72

```
ccggctccag cggccagcgc gcgcgggccc aggccgcccg gctccagccc agcagtagcg     60
gcagcagcgg cggcggcggc agtgcgcgcg aggccctgcg cccccagcag ctcctccctg    120
gcgccgtgca tggagacgcg gcccgccacc cgccgctgag cccccgccgc ccggccggga    180
cccgccaggg ctggggtggc ctcgggctcc ggccggcccc gccgcccgag ggctgcgcgc    240
ggcccgcggg cctcgccgcc ccgcgcggat cgtcgcggcc cggccgtccc gtcccaggaa    300
gtggccgtcc tgagcgccat ggctcactcc ccggtgcagt cgggcctgcc cggcatgcag    360
aacctaaagg cagacccaga agagcttttt acaaaactag agaaaattgg gaagggctcc    420
tttggagagg tgttcaaagg cattgacaat cggactcaga aagtggttgc cataaagatc    480
attgatctgg aagaagctga agatgagata gaggacattc aacaagaaat cacagtgctg    540
agtcagtgtg acagtccata tgtaaccaaa tattatggat cctatctgaa ggatacaaaa    600
ttatggataa taatggaata tcttggtgga ggctccgcac tagatctatt agaacctggc    660
ccattagatg aaacccagat cgctactata ttaagagaaa tactgaaagg actcgattat    720
ctccattcgg agaagaaaat ccacagagac attaaaggca gacatctggt ccctgggcat    780
aacagctatt gaacttgcaa gaggggaacc acctcattcc gagctgcacc ccatgaaagt    840
tttattcctc attccaaaga acaacccacc gacgttggaa ggaaactaca gtaaacccct    900
caaggagttt gtggaggcct gtttgaataa ggagccgagc tttagaccca ctgctaagga    960
gttattgaag cacaagttta tactacgcaa tgcaaagaaa acttcctact tgaccgagct   1020
catcgacagg tacaagagat ggaaggccga gcagagccat gacgactcga gctccgagga   1080
ttccgacgcg gaaacagatg gccaagcctc gggggggcagt gattctgggg actggatctt   1140
cacaatccga gaaaaagatc ccaagaatct cgagaatgga gctcttcagc catcggactt   1200
```

-continued

```
ggacagaaat aagatgaaag acatcccaaa gaggcctttc tctcagtgtt tatctacaat   1260
tatttctcct ctgtttgcag agttgaagga gaagagccag gcgtgcggag ggaacttggg   1320
gtccattgaa gagctgcgag gggccatcta cctagcggag gaggcgtgcc ctggcatctc   1380
cgacaccatg gtggcccagc tcgtgcagcg gctccagaga tactctctaa gtggtggagg   1440
aacttcatcc cactgaaatt cctttggcat ttggggtttt gtttttcctt ttttccttct   1500
tcatcctcct cctttttttaa aagtcaacga gagccttcgc tgactccacc gaagaggtgc   1560
gccactggga gccaccccag tgccaggcgc ccgtccaggg acacacacag tcttcactgt   1620
gctgcagcca gatgaagtct ctcagatggg tggggagggt cagctccttc cagcgatcat   1680
tttattttat tttattactt ttgtttttaa ttttaaccat agtgcacata ttccaggaaa   1740
gtgtctttaa aaacaaaaac aaaccctgaa atgtatattt gggattatga taaggcaact   1800
aaagacatga aacctcaggt atcctgcttt aagttgataa ctccctctgg gagctggaga   1860
atcgctctgg tggatgggtg tacagatttg tatataatgt catttttacg gaaacccttt   1920
cggcgtgcat aaggaatcac tgtgtacaaa ctggccaagt gcttctgtag ataacgtcag   1980
tggagtaaat attcgacagg ccataacttg agtctattgc cttgccttta ttacatgtac   2040
attttgaatt ctgtgaccag tgatttgggt tttattttgt atttgcaggg tttgtcatta   2100
ataattaatg cccctctctt acagaacact cctatttgta cctcaacaaa tgcaaatttt   2160
ccccgtttgc cctacgcccc ttttggtaca cctagaggtt gatttccttt ttcatcgatg   2220
gtactatttc ttagtgtttt aaattggaac atatcttgcc tcatgaagct ttaaattata   2280
attttcagtt tctccccatg aagcgctctc gtctgacatt tgtttggaat cgtgccactg   2340
ctggtctgcg ccagatgtac cgtcctttcc aatacgattt tctgttgcac cttgtagtgg   2400
attctgcata tcatctttcc cacctaaaaa tgtctgaatg cttacacaaa taaattttat   2460
aacacgctta ttttgcatac tccttgaaat gtgactcttc agaggacagg gcacctgctg   2520
tgtatgtgtg gccgtgcgtg tgtactcgtg gctgtgtgtg tgtgatgaga cactttggaa   2580
gactccaggg agaagtcccc aggcctggag ctgccgagtg cccaggtcag cgccctggac   2640
tgcttgcgca cttgctcacc gagatgatgc agttggaggt tgctgatctg tgcgattgct   2700
gtagcggttg ccggggacct taagagttat tttgcttctc tggaaggggc ctatgcttgc   2760
taggcaggca gccagtgtgt ctgtttttct tggtttgctg tgggaccttg cttggcgagg   2820
gggaaaatct ctgggtttct ggagtgggag ggttcgtgca gcagctgttg actggtacat   2880
gaagcattct tttatgtttg ttgaagctga tgattgacat ctcccgtggg tgtgccagtt   2940
cttgtggagt taagacagga tttttggaag caaggaagtt agtgggtgag cttggggatg   3000
tagctcagct atctgctggt ctagtggcct ctaagctata gggaggggac agagccctga   3060
gctacagatg cttgagtggg ttattgtgtc ggtttgctag tgcagtctgg tttttaagct   3120
ctaaaattga ggtattttat tagaagtgga tttgggttga actcttaatt tgtataaggg   3180
atatattttg gttggggaaa tagaactgag ttgctaattc ttattgtact cattactcca   3240
tacaagaatg ttatgttgaa taataaaatt ggagaagatt tcattttgtg tttccaggga   3300
gtattctgtg tggggaactg tttccttacg tgaggccggc ggcataagtc aaagatgagt   3360
tttgtccttg cgaatcacac agattgagtc tgtgttcccc agggtgtgcc gttacctgat   3420
ttttaagtga gccagggcgg acagcagctt ttctgattta cagagttctt cagatttaca   3480
aatggacaat gacatcacag tttttagcac tgaagccagt ctcatgctag taacagtggg   3540
tgagccgctc gagggactgg gttctaatga atactggtat gaacggggag tctctgcagt   3600
```

```
cgccagacaa atcatactca gccccttccc ccgtagagca acaagtggtt cttttagagt   3660
tgactggcag catttcctgt cgggggaggt ggggtttgat ggagttagaa agctcgcctc   3720
tgtgtacatt ctctcctggg ctgttacttt ctgtagacgc acaaaatcag ccccaatgtt   3780
tttaagggca tcttagccaa ggaagctggc ttttgtgtcg ccacttccag gcctgcatta   3840
agagagagcc caggcaccag ggctaccact ggaacctgcc tcagcgtcaa ctgctgctgg   3900
tctgtagcca ggcccagcct ttgagacggg tttactgtca ccagtagcct ctcagtgcca   3960
gccctgagct gctcctggct cagctgccca gagcctgcag cctggggagg tactcagcct   4020
ctgggagacg agggccgtgg actgggtggc tggtagctcc tgcgtttttg agctgtgtcc   4080
tggctggctg ctgccaatga ggtggacacc agtgtggttt ggggtgcact ggccacttct   4140
tgctgggttc tgattttctt ggaagtgcat ctgccttcct tatccaatag ttttatccct   4200
gcattgctct tgtgaagtgg ctggtttggt tctgtatgta gcattttgta cctttcctct   4260
ggcaaaacac tgtcagttta taaacatttt ttatatttcc ctcctttaaa aacagcttgt   4320
gtatttctgc tataaaatgt gtcagcaaag gcagagtgac ctaatagggc atgttcttaa   4380
gcacagggac tgtatcatgc aggggccaat aaagctcaag aaaacgagta              4430
```

<210> SEQ ID NO 73
<211> LENGTH: 3276
<212> TYPE: DNA
<213> ORGANISM: Homo sapiens

<400> SEQUENCE: 73

```
caaaacgccg tggccgtcgc gcggcgccat ccgttgtcgc aaagcggcgc gagaaacgcc     60
cagccgggtg ttggccccgc cccgcgctgt gacgtcggcg gcgcgcgccc ccggcgccgt    120
ggccgcggct gcgcagtggg gcgcgtatgg ctgccgcccc ccgctggcag acgctggcgg    180
cgtaaggcgc gcgggccccg gagcgggcgc ggcggagcgc ggcgagcccg gcgcctcccg    240
tcccgaacat gcggaggccg gcccaggcgg cgcgggagcc ggagcggggg cccaagcggc    300
accggagccg gagcgcgagg gggcgcgggg cccggagcgg gggtccgcgc tgcgctgctg    360
aggccgggcc ggccgcccag acgctgcccg cgggcccggc cacggcggag ccaagctgtg    420
agccgtgagc tttgaggcgg tgggatgtgt cagcagaatg tctcctgccc ccgagagcga    480
ccccgaggcc actgagaaga gcagcgcggc ctggccggcc cgaacgcctg cgtctcagta    540
gctgggagcc acgggcccac gcccgcccac cggccgcagt gatgttctag ccacagagga    600
gccaagacct caggtttcca gagacttggg atttgcacgg cagcagagtc accgtggaga    660
ggccagggta tcacaaactt atggattttg acaagaaagg agggaaaggg gagacggagg    720
agggccggag aatgtccaag gccggcgggg gccggagcag ccacggcatc cggagctcgg    780
ggaccagctc gggggtcctg atggtgggcc ccaacttccg cgtcggcaag aagatcggct    840
gcggcaactt cggggagctc cgcctaggaa agaatctcta tacaaatgaa tacgtggcta    900
tcaaattggt gagtcggccc ctccacccca cccccgctga cgtgcccccc agggatttca    960
gggcagcgac ccggtcccct ggtgactcgc tcttgtgccc ccaggagccg atcaagtccc   1020
gggccccgca gctgcacctg gagtaccggt tctacaagca gctcagcgcc acagagggcg   1080
tccctcaggt ctactacttc ggtccgtgcg ggaagtacaa cgccatggtg ctggagctgc   1140
tggggcccat cctggaggac ctgttcgacc tgtgcgaccg gaccttcacg ctcacgacgg   1200
tgctgatgat cgccatccag ctgatcacgc gcatggagta tgtgcacacc aagagcctaa   1260
tctaccggga cgtgaagccc gagaacttcc tggtgggccg cccggggacc aagcggcagc   1320
```

```
atgccatcca catcatcgac ttcgggctgg ccaaggagta catcgacccc gagaccaaga   1380
agcacatccc gtaccgcgag cacaagagcc tgacgggcac ggcgcgctac atgagcatca   1440
acacgcacct gggcaaggag cagagccgcc gcgacgacct ggaggcgctg ggccacatgt   1500
tcatgtactt cctgcgcggc agcctcccct ggcaggggct caaggtgggc gaggaggccg   1560
ggcaggcggg cggggacgca gggcgggagc aaggctgacc acagaccccc gcaggccgac   1620
acgctcaagg agcggtacca gaagatcggg gacaccaaac gcgccacgcc catcgaggtg   1680
ctctgcgaga acttcccaga ggagatggcc acgtacctgc gctatgtgcg gcgcctggac   1740
ttcttcgaga agcccgacta tgactacctg cggaagctct tcaccgacct cttcgaccgc   1800
agtggcttcg tgttcgacta tgagtacgac tgggccggga agcccctgcc gacccccatc   1860
ggcaccgtcc acaccgacct gccctcccag cctcagctcc gggacaaagc ccagccgcac   1920
agcaaaaacc aggcgttgaa ctccaccaac ggggagctga atgcggacga ccccacggcc   1980
ggccactcca acgccccgat cacagcgcct gcagaggtgg aggtggccga tgaaaccaaa   2040
atgctgcacc aaagctcggg cgccgcgggc acggctgctg cagtctcttc ccagcctggc   2100
cctggcaagg ggcgggtggg cgctgccagg cgggtgcttc tcgacgcact tgctcccgga   2160
ggctgcgccc cggcgcctgg aacccgaggt gggaggaccg gttggtgtca ccctgctcgg   2220
ccctcagccc tgccgcgtgg ggcgcgtggg cacggagctt cttgcctctc tgctccgaca   2280
cccggcaagc agccggagac aaaacgcctt aaagcccccg gcccagccct gcaggtatat   2340
tgcaggggcc tgggggcggc cctggactgg cgggcggttc cccagtgggg tgccctggag   2400
gctgccgggc agagtggagc agcttggggc cgtgcccagg gcggtggctg tgagtctagt   2460
ttttgcttta ccaagtgtac agaaatggca tttacgtttc tctgatgctc ccttgaagcc   2520
atagaattta ggggcttttt taaaaaaata aaagaaaaat gaaaccaaac ccaagtgtag   2580
agggatttgt ctgggctttc cacgaagctt gacctggaac gggcgttgct tccatcccca   2640
tcctgcctgt ccgggacgag tccggagcgg ctggcggcct ccggtaacag aaaccgactg   2700
atgaggcgga aggtaaggaa gatggaagca gagggcagag ctgggctctg tctggggaga   2760
gggcaggaga cgagtgttca cgtaccatgg aaaggggaag tcacacacat gcgacttggc   2820
cccgggggtc ccgttccccg acactacaca aacatacctg aaagcctcag cgacggggcc   2880
caggcaggat ggtcctggct gctctgacgg cggaaggcct ccttgactcc ctctgttcac   2940
gcagcagggc agaaaacatc tccacggggg ccacgacact gtgaagggaa tcagcagtag   3000
ctcccagaag aacagcggaa actgcaggca ggtgaagacc ttgcagcact agccccggct   3060
ccgccccgtg ccttctcccc agacaacacc ccatacccgg cagcaagggt ggaagaccag   3120
taccaccgta atatgttgtg acaaagcaga aataatgcac ctgtaagagt cagatggcaa   3180
gagggaaatg gaatgagctc atcgatggtt ttcccggcag tagcttgggg ataaggacta   3240
cttgtcatgt gctttatata tttacccaca tgttaa                            3276
```

<210> SEQ ID NO 74
<211> LENGTH: 3910
<212> TYPE: DNA
<213> ORGANISM: Homo sapiens

<400> SEQUENCE: 74

```
tgcggggggc tgggggggga acttagttgt tggcagtttc ttcacgggat gtgtttaaat     60
tgccgagtcc ccacatacgc gccaccccac aaatctcctt cgaggccgtg gaggccacac    120
ggctgccgcc tcgccctctc ctccaggagt atgctgggat ttgtagtcca gcagccggac    180
```

```
tgtgccgagc tacctttccc agcttgccct gcggctcggg tgatatcaac agtcttttcc    240
agaactctgt ctgcactgag accctcttcc cccagtcctc ttctcgcggt cgactccttc    300
ccatccgtgg cgacagaacg gcggttgcag gagaggcccc ggtccctcgc cgcgccgccc    360
cgaggggcac ttccggcggc ggttcacttc ctggttgggt ggatggagcc gggcgggagc    420
gcgcgcgggg gaggggcggc gggtcagtct ccgcccggcg ctcccgggat cagctggcgg    480
gcgggcggga gccgagcgcg gccccggctc tcgctgcagc gccgcctctt ctctgcgtcg    540
caggccggcc cggcggccgt gacaatgtcg cggggctggt agcagggcgc cggccgccga    600
gccgtctcaa gtttaaactt acacgaatcg ctttctggag gaggagggga cccgctgcgc    660
gattgacacg catattccta taggcatcct ccctcagccc ccacccccac ggccggattc    720
gggtggctcc tctccgaggt gaaatctgag aagaaatcct tggatctctt ttcttaaaaa    780
aaaaaaaaaa aaaaaaaaaa tctagaaacc atcggtattt tgctttgctg ctccctattc    840
gcaagatgaa gaagtttttc gactcccggc gagagcaggg cggctctggc ctgggctccg    900
gctccagcgg aggagggggc agcacctcgg gcctgggcag tggctacatc ggaagagtct    960
tcggcatcgg gcgacagcag gtcacagtgg acgaggtgtt ggcggaaggt ggatttgcta   1020
ttgtatttct ggtgaggaca agcaatggga tgaaatgtgc cttgaaacgc atgtttgtca   1080
acaatgagca tgatctccag gtgtgcaaga gagaaatcca gataatgagg gatctttcag   1140
ggcacaagaa tattgtgggt tacattgatt ctagtatcaa caacgtgagt agcggtgatg   1200
tatgggaagt gctcattctg atggactttt gtagaggtgg ccaggtggta aacctgatga   1260
accagcgcct gcaaacaggc tttacagaga atgaagtgct ccagatattt tgtgatacct   1320
gtgaagctgt tgcccgcctg catcagtgca aaactcctat tatccaccgg gacctgaagg   1380
ttgaaaacat cctcttgcat gaccgaggcc actatgtcct gtgtgacttt ggaagcgcca   1440
ccaacaaatt ccagaatcca caaactgagg gagtcaatgc agtagaagat gagattaaga   1500
aatacacaac gctgtcctat cgagcaccag aaatggtcaa cctgtacagt ggcaaaatca   1560
tcactacgaa ggcagacatt tgggctcttg gatgtttgtt gtataaatta tgctacttca   1620
ctttgccatt tggggaaagt caggtggcaa tttgtgatgg aaacttcaca attcctgata   1680
attctcgata ttctcaagac atgcactgcc taattaggta tatgttggaa ccagaccctg   1740
acaaaaggcc ggatatttac caggtgtcct acttctcatt taagctactc aagaaagagt   1800
gcccaattcc aaatgtacag aactctccca ttcctgcaaa gcttcctgaa ccagtgaaag   1860
ccagtgaggc agctgcaaaa aagacccagc caaaggccag actgacagat cccattccca   1920
ccacagagac ttcaattgca ccccgccaga ggcctaaagc tgggcagact cagccgaacc   1980
caggaatcct tcccatccag ccagcgctga caccccggaa gagggccact gttcagcccc   2040
cacctcaggc tgcaggatcc agcaatcagc ctggcctttt agccagtgtt ccccaaccaa   2100
aaccccaagc ccccacccagc cagcctctgc cgcaaactca ggccaagcag ccacaggctc   2160
ctcccactcc acagcagacg ccttctactc aggcccaggg tctgcccgct caggcccagg   2220
ccacacccca gcaccagcag caactcttcc tcaagcagca acagcagcag caacagccac   2280
cgccagcaca gcagcagccg gcaggcacgt tttaccagca gcagcaggcc cagactcagc   2340
agtttcaggc agtacatcca gcaacccagc aaccagcaat tgctcagttc cctgtggtgt   2400
cccaaggagg ctctcaacag cagctaatgc agaatttcta ccagcagcag cagcagcagc   2460
aacaacaaca gcaacagcaa cagctggcca cagccctgca tcaacaacag ctgatgactc   2520
agcaggctgc cttgcagcaa aagcccacta tggcagcagg acagcagccc cagccacagc   2580
```

```
cagctgcagc cccacagcca gcccctgccc aggagccagc gcagattcaa gccccagtaa   2640

gacaacagcc aaaggttcag acaaccccac ctcctgccgt ccaggggcag aaagttggat   2700

ctctcactcc accctcatcc cccaaaaccc aacgtgctgg gcacaggcgt attctcagtg   2760

acgtaaccca cagtgcagtc tttggggtcc ctgccagcaa atcaacccag ctgctccagg   2820

cagctgcagc tgaggccagt ctcaataagt ccaagtctgc aaccaccact ccatcaggct   2880

ctcctcggac ctctcaacaa aacgtttata atccttcaga agggtctacg tggaatccct   2940

ttgatgacga taatttctcc aaactcacag ctgaagaact gctaaacaag gactttgcca   3000

agcttgggga aggcaaacat cccgagaagc ttggaggctc agctgagagt ttgatcccag   3060

gctttcaatc aacccaaggt gatgcttttg ctacgacctc attttctgct ggaactgaaa   3120

aactaattga gggactcaaa tctcctgaca cttctcttct gctccctgac ctcttgccta   3180

tgacagatcc ttttggtagc acttctgatg ctgtaattga aaaagctgat gttgctgttg   3240

agagtctcat accaggactg gagcccccag ttccccagcg cctcccatct cagacggaat   3300

ctgtgacctc gaatcgcaca gattctctca ccggggaaga ttccctgctt gattgctctc   3360

tgctctctaa ccctactact gaccttctgg aagagtttgc ccccacagca atctctgctc   3420

cagtccataa agctgcagaa gatagtaatc tcatctcagg ttttgatgtc cctgagggct   3480

cggacaaggt ggctgaagat gagtttgacc ctattcctgt attgataacc aaaaacccac   3540

aaggtgggca ctctagaaac agcagtggga gctctgagtc cagtcttccc aacctagcca   3600

ggtctttact gctggtggat cagctcatag acctgtagcc gtgacccagt agcagatgca   3660

gttctgtaac cttcataccg taaaatacat tttcattacg gagttatgaa aaaaatgatt   3720

tttttaaaaa aatctgcaaa taaggggccc tccagccctt ttctcctacc ccttgccttc   3780

tcctgtagaa atgataagga aagaaaatca ctttgggcct ccagatattc cttgggcagt   3840

tcctccttgt tagtttgctg tgttttctca ttacccttct tcaatagcat tatcttaaat   3900

caagcactag                                                          3910
```

<210> SEQ ID NO 75
<211> LENGTH: 4380
<212> TYPE: DNA
<213> ORGANISM: Homo sapiens

<400> SEQUENCE: 75

```
gccgcggcgg aggggacggg gctaggccgg gtcgccgcct gacgcgacgc gtcctcacgg     60

gcgcctacgt cacggcgtcg aggcggaaga tggtgcacct ccgggccggc ggttgctgag    120

ctgacccgga cggcgaggga gcgggagccc gagcccgacc actccggctg ccgcggggtg    180

cggcgcagcc accgccatgt cgctgctgca gtcggcgctc gacttcttgg cgggtccagg    240

ctccctgggc ggtgcttccg gccgcgacca gagtgacttc gtggggcaga cggtggaact    300

gggcgagctg cggctgcggg tgcggcgggt cctggccgaa ggagggtttg catttgtgta    360

tgaagctcaa gatgtgggga gtggcagaga gtatgcatta aagaggctat tatccaatga    420

agaggaaaag aacagagcca tcattcaaga agtttgcttc atgctctgtt cactcggaga    480

gcccgccggc tgcctgagtg tgggttcggg tggacacagc cacgcctcag cctccctgcg    540

cacagccccc tgagggccct gcctcctcct gccacgcgcg ggatggactt tggtgtcgct    600

gtggtcagtg cacagaactg tggacatggt tatgtacgtt ctcctttaaa caagacaact    660

gcagaaaaag ctttccggcc acccgaacat tgtccagttt tgttctgcag cgtctatagg    720

aaaagaggag tcagacacgg ggcaggctga gttcctcttg ctcacagagc tctgtaaagg    780
```

```
gcagctggtg gaatttttga agaaaatgga atctcgaggc cccctttcgt gcgacacggt    840

tctgaagatc ttctaccaga cgtgccgcgc cgtgcagcac atgcaccggc agaagccgcc    900

catcatccac agggacctca aggttgagaa cttgttgctt agtaaccaag ggaccattaa    960

gctgtgtgac tttggcagtg ccacgaccat ctcgcactac cctgactaca gctggagcgc   1020

ccagaggcga gccctggtgg aggaagagat cacgaggaat acaacaccaa tgtatagaac   1080

accagaaatc atagacttgt attccaactt cccgatcggc gagaagcagg atatctgggc   1140

cctgggctgc atcttgtacc tgctgtgctt ccggcagcac ccttttgagg atggagcgaa   1200

acttcgaata gtcaatggga agtactcgat ccccccgcac gacacgcagt acacggtctt   1260

ccacagcctc atccgcgcca tgctgcaggt gaacccggag gagcggctgt ccatcgccga   1320

ggtggtgcac cagctgcagg agatcgcggc cgcccgcaac gtgaacccca agtctcccat   1380

cacagagctc ctggagcaga atggaggcta cgggagcgcc acactgtccc gagggccacc   1440

ccctcccgtg ggccccgctg gcagtggcta cagtggaggc ctggcgctgg cggagtacga   1500

ccagccgtat ggcggcttcc tggacattct gcggggtggg acagagcggc tcttcaccaa   1560

cctcaaggac acctcctcca aggtcatcca gtccgtcgct aattatgcaa agggtgacct   1620

ggacatatct tacatcacat ccagaattgc agtgatgtca ttcccagcag aaggtgtgga   1680

gtcagcgctc aaaaacaaca tcgaagatgt gcggttgttc ctggactcca agcacccagg   1740

gcactatgcc gtctacaacc tgtccccgag gacctaccgg ccctccaggt tccacaaccg   1800

ggtctccgag tgtggctggg cagcacggcg ggccccacac ctgcacaccc tgtacaacat   1860

ctgcaggaac atgcacgcct ggctgcggca ggaccacaag aacgtctgcg tcgtgcactg   1920

catggacggg agagccgcgt ctgctgtggc cgtctgctcc ttcctgtgct tctgccgtct   1980

cttcagcacc gcggaggccg ccgtgtacat gttcagcatg aagcgctgcc caccaggcat   2040

ctggccatcc cacaaaaggt acatcgagta catgtgtgac atggtggcgg aggagcccat   2100

cacaccccac agcaagccca tcctggtgag ggccgtggtc attgacaccc gtgccgcgtg   2160

ttcagcaagc agaggagcgg ctgcaggccc ttctgcgagg tctacgtggg ggacgagcgt   2220

gtggccagca cctcccagga gtacgacaag atgcgggact ttaagattga agatggcata   2280

ggggtgattc ccctgggcgt cacggtgcaa ggagacgtgc tcatcgtcat ctatcacgcc   2340

cggtccactc tgggcggccg gctgcaggcc aagatggcat ccatgaagat gttccagatt   2400

cagttccaca cggggtttgt gcctcggaac gccaccactg tgaaatttgc caagtatgac   2460

ctggacgcgt gtgacattca agaaaaatac ccggatttat ttcaagtgaa cctggaagtg   2520

gaggtggagc ccagggacag gccgagccgg gaagccccac catgggagaa ctcgagcatg   2580

agggggctga accccaaaat cctgttttcc agccgggagg agcagcaaga cattctgtct   2640

aagtttggga agccggagct tccccggcag cctggctcca cggctcagta tgatgctggg   2700

gcagggtccc cggaagccga acccacagac tctgactcac cgccaagcag cagcgcggac   2760

gccagtcgct tcctgcacac gctggactgg caggaagaga aggaggcaga gactggtgca   2820

gaaaatgcct cttccaagga gagcgagtct gccctgatgg aggacagaga cgagagtgag   2880

gtgtcagatg aaggggggatc cccgatctcc agcgagggcc aggaacccag ggccgaccca   2940

gagccccccg gcctggcagc agggctggtg cagcaggact tggtttttga ggtggagaca   3000

ccggctgtgc tgccagagcc tgtgccacag gaagacgggg tcgacctcct gggcctgcac   3060

tccgaggtgg gcgcagggcc agctgtaccc ccgcaggcct gcaaggcccc ctccagcaac   3120

accgacctgc tcagctgcct ccttgggccc cctgaggccg cctcccaggg gcccccggag   3180
```

```
gatctgctca gcgaggaccc gctgctcctg gcaagcccgg cccctcccct gagcgtgcag   3240

agcccccaag aggagggccc cctgccgctg ctgacccctt tggcccgctt ctgccgtctt   3300

caggcaacaa ctcccagccc tgctccaatc ctgatctctt cggcgaattt ctcaattcgg   3360

actctgtgac cgtcccacca tccttcccgt ctgcccacag cgctccgccc ccatcctgca   3420

gcgccgactt cctgcacctg ggggatctgc caggagagcc cagcaagatg acagcctcgt   3480

ccagcaaccc agacctgctg ggaggatggg ctgcctggac cgagactgca gcgtcggcag   3540

tggcccccac gccagccaca gaaggccccc tcttctctcc tggaggtcag ccggcccctt   3600

gtggctctca ggccagctgg accaagtctc agaacccgga cccatttgct gaccttggcg   3660

acctcagctc cggcctccaa gacccccaag cccagagcac agtgagccca aggggacagc   3720

gtgtctgcac ctgttccagg cgactgccaa ctggcaagct aaaaccggga gttgctgaca   3780

ctggcactgc tgccagcccc caccggcatt gtggctcacc agctggattc cctcctgggg   3840

gcttcattcc caaaacggcc accacgccca aaggcagcag ctcctggcag acaagtcggc   3900

cgccagccca gggcgcctca tggcccccctc aggccaagcc gccccccaaa gcctgcacac   3960

agccaaggcc taactatgcc tcgaacttca gtgtgatcgg ggcgcgggaa gagcgggggg   4020

tccgcgcacc agctttgctc aaaaccaaaa gtctctgaga acgactttga agattgttgt   4080

ccaataaggc ttctcctcca ggtctgaaag aaagggcaaa gacattgcag agatgaggag   4140

aggacctggc taaagacacg gacccactca agctgaagct cctggactgg attgagggca   4200

aggagcggaa catccgggcc ctgctgtcca cgctgcacac agtgctgtgg gacggggaga   4260

gccgctggac gcccgtgggc atggccgacc tggtggctcc ggagcaagtg aagaagcact   4320

atcgccgcgc ggtgctggct gtgcaccccg acaaggtgag cagagctgcc aggcggccgc   4380
```

<210> SEQ ID NO 76
<211> LENGTH: 4293
<212> TYPE: DNA
<213> ORGANISM: Homo sapiens

<400> SEQUENCE: 76

```
gccgcggcgg aggggacggg gctaggccgg gtcgccgcct gacgcgacgc gtcctcacgg     60

gcgcttacgt cacggcgtcg aggcggaaga tggtgcacct ccgggccggc ggttgctgag    120

ctgacccgga cggcgaggga gcgggagccc gagcccgacc actccggctg ccgcggggtg    180

cggcgcagcc accgccatgt cgctgctgca gtcggcgctc gacttcttgg cgggtccagg    240

ctccctgggc ggtgcttccg gccgcgacca gagtgacttc gtggggcaga cggtggaact    300

gggcgagctg cggctgcggg tgcggcgggt cctggccgaa ggagggtttg catttgtgta    360

tgaagctcaa gatgtgggga gtggcagaga gtatgcatta aagaggctat tatccaatga    420

agaggaaaag aacagagcca tcattcaaga agtttgcttc atgaaaaagc tttccggcca    480

cccgaacatt gtccagtttt gttctgcagc gtctatagga aaagaggagt cagacacggg    540

gcaggctgag ttcctcttgc tcacagagct ctgtaaaggg cagctggtgg aatttttgaa    600

gaaaatggaa tctcgaggcc cccttttcgtg cgacacggtt ctgaagatct tctaccagac    660

gtgccgcgcc gtgcagcaca tgcaccggca gaagccgccc atcatccaca gggacctcaa    720

ggttgagaac ttgttgctta gtaaccaagg gaccattaag ctgtgtgact ttggcagtgc    780

cacgaccatc tcgcactacc ctgactacag ctggagcgcc cagaggcgag ccctggtgga    840

ggaagagatc acgaggaata caacaccaat gtatagaaca ccagaaatca tagacttgta    900

ttccaacttc ccgatcggcg agaagcagga tatctgggcc ctgggctgca tcttgtacct    960
```

-continued

```
gctgtgcttc cggcagcacc cttttgagga tggagcgaaa cttcgaatag tcaatgggaa    1020
gtactcgatc cccccgcacg acacgcagta cacggtcttc cacagcctca tccgcgccat    1080
gctgcaggtg aacccggagg agcggctgtc catcgccgag gtggtgcacc agctgcagga    1140
gatcgcggcc gcccgcaacg tgaaccccaa gtctcccatc acagagctcc tggagcagaa    1200
tggaggctac gggagcgcca cactgtcccg agggccaccc cctcccgtgg gccccgctgg    1260
cagtggctac agtggaggcc tggcgctggc ggagtacgac cagccgtatg gcggcttcct    1320
ggacattctg cggggtggga cagagcggct cttcaccaac ctcaaggaca cctcctccaa    1380
ggtcatccag tccgtcgcta attatgcaaa gggtgacctg gacatatctt acatcacatc    1440
cagaattgca gtgatgtcat tcccagcaga aggtgtggag tcagcgctca aaaacaacat    1500
cgaagatgtg cggttgttcc tggactccaa gcacccaggg cactatgccg tctacaacct    1560
gtccccgagg acctaccggc cctccaggtt ccacaaccgg gtctccgagt gtggctgggc    1620
agcacggcgg gccccacacc tgcacaccct gtacaacatc tgcaggaaca tgcacgcctg    1680
gctgcggcag gaccacaaga acgtctgcgt cgtgcactgc atggacggga gagccgcgtc    1740
tgctgtggcc gtctgctcct tcctgtgctt ctgccgtctc ttcagcaccg cggaggccgc    1800
cgtgtacatg ttcagcatga agcgctgccc accaggcatc tggccatccc acaaaaggta    1860
catcgagtac atgtgtgaca tggtggcgga ggagcccatc acaccccaca gcaagcccat    1920
cctggtgagg gccgtggtca tgacacccgt gccgctgttc agcaagcaga ggagcggctg    1980
caggcccttc tgcgaggtct acgtgggggga cgagcgtgtg gccagcacct cccaggagta    2040
cgacaagatg cgggacttta agattgaaga tggcatagcg gtgattcccc tgggcgtcac    2100
ggtgcaagga gacgtgctca tcgtcatcta tcacgcccgg tccactctgg gcggccggct    2160
gcaggccaag atggcatcca tgaagatgtt ccagattcag ttccacacgg ggtttgtgcc    2220
tcggaacgcc accactgtga aatttgccaa gtatgacctg gacgcgtgtg acattcaaga    2280
aaaatacccg gatttatttc aagtgaacct ggaagtggag gtggagccca gggacaggcc    2340
gagccgggaa gccccaccat gggagaactc gagcatgagg gggctgaacc ccaaaatcct    2400
gttttccagc cgggaggagc agcaagacat tctgtctaag tttgggaagc cggagcttcc    2460
ccggcagcct ggctccacgg ctcagtatga tgctggggca gggtccccgg aagccgaacc    2520
cacagactct gactcaccgc caagcagcag cgcggacgcc agtcgcttcc tgcacacgct    2580
ggactggcag gaagagaagg aggcagagac tggtgcagaa aatgcctctt ccaaggagag    2640
cgagtctgcc ctgatggagg acagagacga gagtgaggtg tcagatgaag gggatcccc     2700
gatctccagc gagggccagg aacccagggc cgacccagag cccccggcc tggcagcagg    2760
gctggtgcag caggacttgg tttttgaggt ggagacaccg gctgtgctgc cagagcctgt    2820
gccacaggaa gacggggtcg acctcctggg cctgcactcc gaggtgggcg cagggccagc    2880
tgtacccccg caggcctgca aggccccctc cagcaacacc gacctgctca gctgcctcct    2940
tgggccccct gaggccgcct cccaggggcc cccggaggat ctgctcagcg aggacccgct    3000
gctcctggca agcccggccc ctcccctgag cgtgcagagc accccaagag gagggccccc    3060
tgccgctgct gacccctttg gcccgcttct gccgtcttca ggcaacaact cccagccctg    3120
ctccaatcct gatctcttcg gcgaatttct caattcggac tctgtgaccg tcccaccatc    3180
cttcccgtct gcccacagtg ctccgccccc atcctgcagc gccgacttcc tgcacctggg    3240
ggatctgcca ggagagccca gcaagatgac agcctcgtcc agcaacccag acctgctggg    3300
aggatgggct gcctggaccg agactgcagc atcggcagtg gcccccacgc cagccacaga    3360
```

```
aggccccctc ttctctcctg gaggtcagcc ggccccttgt ggctctcagg ccagctggac   3420

caagtctcag aacccggacc catttgctga ccttggcgac ctcagctccg gcctccaaga   3480

cccccaagcc cagagcacag tgagcccaag gggacagcgt gtctgcacct gttccaggcg   3540

actgccaact ggcaagctaa aaccgggagt tgctgacact ggcactgctg ccagccccca   3600

ccggcattgt ggctcaccag ctggattccc tcctgggggc ttcattccca aaacggccac   3660

cacgcccaaa ggcagcagct cctggcagac aagtcggccg ccagcccagg gcgcctcatg   3720

gccccctcag gccaagccgc cccccaaagc ctgcacacag ccaaggccta actatgcctc   3780

gaacttcagt gtgatcgggg cgcgggagga gcggggggtc cgcgcaccca gctttgctca   3840

aaagccaaaa gtctctgaga acgactttga agatctgttg tccaatcaag gcttctcctc   3900

caggtctgac aagaaagggc caaagaccat tgcagagatg aggaagcagg acctggctaa   3960

agacacggac ccactcaagc tgaagctcct ggactggatt gagggcaagg agcggaacat   4020

ccgggccctg ctgtccacgc tgcacacagt gctgtgggac ggggagagcc gctggacgcc   4080

cgtgggcatg gccgacctgg tggctccgga gcaagtgaag aagcactatc gccgcgcggt   4140

gctggccgtg caccccgaca aggctgcggg gcagccgtac gagcagcacg ccaagatgat   4200

cttcatggag ctgaatgacg cctggtcgga gtttgagaac cagggctccc ggcccctctt   4260

ctgaggccgc agtggtggtg gctgcgcaca cag                                4293
```

<210> SEQ ID NO 77
<211> LENGTH: 6538
<212> TYPE: DNA
<213> ORGANISM: Homo sapiens

<400> SEQUENCE: 77

```
ggagttactc agaagggaag ggaaggtgtg gttgtgcggc ggagtttttg ctttcattct     60

tttaacgttc acagccaaag caaaggcctt tggggattgc cagagtctca gccaccatcc    120

tggaaaacag cgggggaggt gggcctggag gtggcaagtg taatgtggct caggggccgt    180

cattgcccct tgcagaaggg gctgcggggg agggagaaaa cctgcgcccg gttctgggga    240

gctggcgacg cagtgaaccc tgctgaggct gggttttgcc ccgacagtcg ctggtggctg    300

tgggaagggt tgggaccctt ctctgagagc agtgaacagc ccacatccgg cccctgctgt    360

gtcaactctg agcggcgtgg agatgaagtg gttgctctcc cttgctcggc ccaccgggtg    420

tcgtggcccg ggaaccggcc tggagaagtc cctgctgccc ggcgcccaaa acaggggcgt    480

gggcttccgc gacccagggc ggctgccccg ggccatcctc gagttgccct gcatcttccc    540

gctcagtcag ccccagattg aggcagcctt ctctgtgcgg gtttaaatgg gtaactgtga    600

cttctcgcct cattcaccca aacctccagt cttctccccc gcacatcctc ctccacccac    660

ctggtttctc cctagactgg tgtgctcgtg tgtgcaacca aaggagggag tgcgagagat    720

ccacgaaggg acaggcttgg agtcgctaga gggaggtgtg ggaccagcga ggagggggct    780

tcgccaggga gggggtgctg gcaggcggag ggagcggcgg gaggaggcgc cggaggagga    840

gacggaggcc tggggacggc agaagaggct tcgcctgagc cgagcgctct ttctctcgcc    900

gcgccgtctt gaagccgcgc gggctcgtga gcagcgcgag gccgccaagg tgcctcgctt    960

cgccggagcc gctgccgccc gccggaggga agccggcctc gggcgcgcac gctcgtcgga   1020

gccccggcgc gccccgcgcc tgagcctgct gacagcgccg cggggccagt cccggggtta   1080

gccgcgcgtc tgctcgcttc tggtccgtcg cgctcccagc cagggcacag cccggaccga   1140

ggatggcttc gaccacaacc tgcaccaggt tcacggacga gtatcagctt ttcgaggagc   1200
```

```
ttggaaaggg ggcattctca gtggtgagaa gatgtatgaa aattcctact ggacaagaat   1260
atgctgccaa aattatcaac accaaaaagc tttctgctag ggtgcgactt catgatagca   1320
tatcagaaga gggctttcac tacttggtgt ttgatttagt tactggaggt gaactgtttg   1380
aagacatagt ggcaagagaa tactacagtg aagctgatgc cagtcattgc attcagcaga   1440
tcctggaggc tgtgctacac tgccatcaga tgggcgtggt ccatcgggac ctgaagcctg   1500
agaatttgct tttagctagc aaatccaagg gagcagctgt gaaattggca gactttggct   1560
tagccataga agttcaaggg gaccagcagg cgtggtttgg ttttgctggc acacctggat   1620
atctttctcc agaagtttta cgtaaagatc cttatggaaa gccagtggat atgtgggcat   1680
gtggtgtcat tctctatatt ctacttgtgg ggtatccacc cttctgggat gaagaccaac   1740
acagactcta tcagcagatc aaggctggag cttatgattt tccatcacca gaatgggaca   1800
cggtgactcc tgaagccaaa gacctcatca ataaaatgct tactatcaac cctgccaaac   1860
gcatcacagc ctcagaggca ctgaagcacc catggatctg tcaacgttct actgttgctt   1920
ccatgatgca cagacaggag actgtagact gcttgaagaa atttaatgct agaagaaaac   1980
taaagggtgc catcttgaca actatgctgg ctacaaggaa tttctcagca gccaagagtt   2040
tgttgaagaa accagatgga gtaaagaaaa ggaagtccag ttcgagtgtt cagatgatgg   2100
agtcaactga gagttcaaat acaacaattg aggatgaaga tgtggaagca cgaaagcaag   2160
agattatcaa agtcactgaa caactgatcg aagctatcaa caatggggac tttgaagcct   2220
acacaaaaat ctgtgaccca ggccttactg cttttgaacc tgaagctttg ggtaatttag   2280
tggaagggat ggattttcac cgattctact ttgaaaatgc tttgtccaaa agcaataaac   2340
caatccacac tattattcta aaccctcatg tacatctggt aggggatgat gccgcctgca   2400
tagcatatat taggctcaca cagtacatgg atggcagtgg aatgccaaag acaatgcagt   2460
cagaagagac tcgtgtgtgg caccgccggg atggaaagtg gcagaatgtt cattttcatc   2520
gctcggggtc accaacagta cccatcaagc caccctgtat tccaaatggg aaagaaaact   2580
tctcaggagg cacctctttg tggcaaaaca tctaaggcct gaaaaccatt cacatatggg   2640
tcttctaaat ttcaacagtg ccacttctgc attctctgtt ctcaaggcac ctggatggtg   2700
accctgggcc gtcctctcct cctcttcatg catgtttctg agtgcatgaa gttgtgaagg   2760
tcctacatgt aatgcatatg tgatgcatca tcttatcata tattccttcc tatacattgt   2820
ttacacttca actacgggga tgttccacac aaacttaaat tactgttggc aaaacaatag   2880
ggggagatta gacaaaaaaa aaaatccaca atattccaag tacaactctt catcaagttt   2940
ctctgttaat gccaagattt aacagactta agaactattg ttctctgaat gacagttgta   3000
agagaaatgt aaatttttta gaactctttg ctgttaatct gttttggttt gtttggtttt   3060
tttttttttt tttaaggtaa aaaaaaaata caccttcagt ttcctggtgt gatcctggtt   3120
aaaatggatg atttttcatt gaaagttttg ctgattaaca attaaagtgg gatgatatgt   3180
gggcaaaatc acttatgaaa gtagaagcaa gaatcagttg gtttgctacc acataaagcc   3240
atgctgtttt tggtcaaact gtgtaaactg gaaaaattca catcatttct gagtttaatc   3300
actttaggat atattcacat tgttttggtg aatttgctga attgaattgt ttttctttct   3360
caaatctgtg atctcttttc tttatcctgt ttctttgttc ctttcgtttg ctttcttatt   3420
tttcttttgg ttccattctt ttcttacttt tttccctttt cctttttgg ggaggctggc   3480
tagtagtgtg tgagaaaaga atagaagtga aatttgcata atgaatgtaa aagggaaata   3540
aaagtctttt gaaggtagct atactagcac ttttgatcat cttcagggcc cacaaaaatg   3600
```

```
ttgtcaagat tttaaaggtt tataattctg cttaagctct agtttggact taggtatcct   3660
aactatgttg gaggtatttg cattgtttaa agttaggata aaagcaagtt cctcctgtga   3720
ctgcaacgtc ttactgattg ggacagttgc caggaggata ccaacttgat agcagagggg   3780
gttttatgca aacgcactca cctccgcctt ggggaatgaa agggtcactt ctgcatcatc   3840
actagctagt tttctagtgt tagagaggct tacaaatgtt tgccattctc ataagtgttt   3900
tgaacttgat ctttgtgact tgtgcttttt ttagcttctc tcttgaatca gagtatcatt   3960
gtcttcctcc aaggagttag aatttcccag tttaaaacaa aaagggaaat gtcctaggtt   4020
ttctttgtgc ttctcatttt tcctttgttg attcaattcc tgtgattttt gttctcttcc   4080
ctgaagtgct ttacagtgca tggaatctcc atcattgtta ttttaacgat agtaattcac   4140
agtcctcaga agcctatttt taaagcagaa gcaaaaaaga aaaacaaaat aacaaaaaca   4200
acccttcctc ttttctctca tctcacctct ctgtgttgat tactaatcat cttagatatt   4260
attgctagtg gatgtatggt agatgggttg aagcttttct gataattatt acacaattta   4320
aaacaacata tatatttaaa ataaatatat acagtaaata tattgagcca tgttaacctg   4380
ccaatgagat ctgtgaaaaa ataatggcct catttttctc tttttaattt cttttaccct   4440
tttgtgaagc agctatacgt ggcatacatg tatttaaaga aaaaaaaata gatgtagagt   4500
gtttttttta cacttttaac ttagcatgtg gtgttgaagt attactgtag atcaagtttg   4560
tcttccgcac taagatgtga ggaaattgtg atttgttctc tccaccacaa atgaattaca   4620
catttattat cttctatcat tttgaaacac tgcagtttac catgggacac tgtatatatt   4680
tcttgccata atggtaaagg actgattgat atatttaaga gttaataaat ttgtgatttc   4740
tgctgacagt gcgtccatct ttatttcttc agaagaggta ctgtatgtat gcctgcatag   4800
tgctggccag tgtcaagggc agtgtgtcct actctggtct catttagtac ataacaattt   4860
gcacttggtg aggaggacaa tatagttaac aactaagact cctaaaagct tctctaaact   4920
gtaccctcca atccagcctt cacatggctg cttttttttt ttttttaat acgaacctgt    4980
ccttgtaaca ctttgatgtt atcatttctg ggatacaggc aagcacccca gctcctgcta   5040
ctccccagct tgaacttgag catacatgga tgctcagctt cttttgattt gctaaaaaca   5100
tcacacttgc tcacatgcct gtttatgctg ttcatgttgt ttatgtttct tacctagaat   5160
aaatagtctc ttcccctact tcttttcctg acttcttact ttttcctaag attcagtgta   5220
cagcatcatg ctccacagca aaccttccta ggccctattc tgggcttgcc ttccctctca   5280
aaacctacat aatagattgt atttacctct cctgtcaacc acattgtttt gaaaatatat   5340
ttctatttgt gtctcctcta ctgcagtata atgtctccat gggcaagaac tgtgtattca   5400
tcattgcatt cctaaaccca aaccaaggcc aggaatggag atatcattga taaatagttg   5460
ttgaattgag gccaagccct tttgataaca gaagcctcaa ggggtaccca gatagtcctt   5520
gttttaatga tgggttctct caccactgtc ttgatgctct gagcaagtta cctcttccct   5580
ctgaccctca gtttccatat ttgtaaaatg agaataaaca taccaactta ataaagatat   5640
tgtgaggatt aatgggtaca gagtgactag aatgatattt gatagaaatt aaatggtagc   5700
agtataacta ttctgatcac tgacattaat attcctattg ttattattct ttactcacga   5760
gggtatacaa ctcttgtttt gctgttgggc tgccctcttt atgtaggttt actgttaatg   5820
ctgaggatat actcggactc aaatgtctca gcagaaggct gagagacacc aaatgaagtg   5880
gtcatctagc tgaatgtagg aaaaatgaaa tgtagtagca aatcagtata ttctaaggaa   5940
attttcaagg aatattaatc ttcacccaaa ttttgaattt ttatgtaaaa aattataatt   6000
```

```
taagggtaaa catagatgac acagctttcg agtgatttca ttgaataaaa ttctactgac   6060

ttctatgaac ctttcatggc tctgtggtct ttttatcaga ttttttaaag gtgagaatgt   6120

acaaaaagat tacaatgaag atcaggtact agaccatgtg tccatgaacg tgaacaaaca   6180

gctgtcataa accaccctaa cctgagaaag cagcaggaag catttacagc attcctgctt   6240

ttctctcaga caaaaccaat tctcagaaga gagctagaat gttctcctgc agactggagt   6300

aggaaaagtt gataacagat taagcagtaa ttgtactcca gaaggatttg catttaggct   6360

tttgctgctt tacaacagaa aaaaaaaatt cttgtttgtc cgtaaaaagt gtttttatgt   6420

ttttttaaat gtcaccaaca tttaaaaatt ggatatgtca tgtaaaagtc aagatttctg   6480

gcttaattaa tttgaaaaag tgtaaggtct gccccactgg ttctgtgttc actacagc     6538
```

<210> SEQ ID NO 78
<211> LENGTH: 2349
<212> TYPE: DNA
<213> ORGANISM: Homo sapiens

<400> SEQUENCE: 78

```
ggagttactc agaagggaag ggaaggtgtg gttgtgcggc ggagtttttg ctttcattct     60

tttaacgttc acagccaaag caaaggcctt tggggattgc cagagtctca gccaccatcc    120

tggaaaacag cgggggaggt gggcctggag gtggcaagtg taatgtggct caggggccgt    180

cattgcccct tgcagaaggg gctgcggggg agggagaaaa cctgcgcccg gttctgggga    240

gctggcgacg cagtgaaccc tgctgaggct gggttttgcc ccgacagtcg ctggtggctg    300

tgggaagggt tgggaccctt ctctgagagc agtgaacagc ccacatccgg cccctgctgt    360

gtcaactctg agcggcgtgg agatgaagtg gttgctctcc cttgctcggc ccaccgggtg    420

tcgtggcccg ggaaccggcc tggagaagtc cctgctgccc ggcgcccaaa acaggggcgt    480

gggcttccgc gacccagggc ggctgccccg ggccatcctc gagttgccct gcatcttccc    540

gctcagtcag ccccagattg aggcagcctt ctctgtgcgg gtttaaatgg gtaactgtga    600

cttctcgcct cattcaccca aacctccagt cttctccccc gcacatcctc ctccacccac    660

ctggtttctc cctagactgg tgtgctcgtg tgtgcaacca aaggagggag tgcgagagat    720

ccacgaaggg acaggcttgg agtcgctaga gggaggtgtg ggaccagcga ggagggggct    780

tcgccaggga gggggtgctg gcaggcggag ggagcggcgg gaggaggcgc cggaggagga    840

gacggaggcc tggggacggc agaagaggct tcgcctgagc cgagcgctct ttctctcgcc    900

gcgccgtctt gaagccgcgc gggctcgtga gcagcgcgag gccgccaagg tgcctcgctt    960

cgccggagcc gctgccgccc gccggaggga agccggcctc gggcgcgcac gctcgtcgga   1020

gccccggcgc gccccgcgcc tgagcctgct gacagcgccg cggggccagt cccggggtta   1080

gccgcgcgtc tgctcgcttc tggtccgtcg cgctcccagc cagggcacag cccggaccga   1140

ggatggcttc gaccacaacc tgcaccaggt tcacggacga gtatcagctt ttcgaggagc   1200

ttggaaaggg ggcattctca gtggtgagaa gatgtatgaa aattcctact ggacaagaat   1260

atgctgccaa aattatcaac accaaaaagc tttctgctag ggtgcgactt catgatagca   1320

tatcagaaga gggctttcac tacttggtgg ttgatttagt tactggaggt gaactgtttg   1380

aagacatagt ggcaagagaa tactacagtg aagctgatgc cagtcattgc attcagcaga   1440

tcctggaggc tgtgctacac tgccatcaga tgggcgtggt ccatcgggac ctgaagcctg   1500

agaatttgct tttagctagc aaatccaagg gagcagctgt gaaattggca gactttggct   1560

tagccataga agttcaaggg gaccagcagg cgtggtttgg ttttgctggc acacctggat   1620
```

```
atctttctcc agaagtttta cgtaaagatc cttatggaaa gccagtggat atgtgggcat   1680

gtggtgtcat tctctatatt ctacttgtgg ggtatccacc cttctgggat gaagaccaac   1740

acagactcta tcagcagatc aaggctggag cttatgattt tccatcacca gaatgggaca   1800

cggtgactcc tgaagccaaa gacctcatca ataaaatgct tactatcaac cctgccaaac   1860

gcatcacagc ctcagaggca ctgaagcacc catggatctg tcaacgttct actgttgctt   1920

ccatgatgca cagacaggag actgtagact gcttgaagaa atttaatgct agaagaaaac   1980

taaagggtgc catcttgaca actatgctgg ctacaaggaa tttctcagca gccaagagtt   2040

tgttgaagaa accagatgga gtaaaggagt caactgagag ttcaaataca acaattgagg   2100

atgaagatgt gaaaggcacg gtggctcacg cctgtaatcc cagcactttg ggaggtcgag   2160

gcgggcagat cacctgaggt caggagttca agaccagcat ggccaacatg gtgaaaccct   2220

gtctctacta aaaatacaaa aattagctgg gtgtggtggc aggcacctgt aatcccagct   2280

actctggagg ctgagacagg agaatcgctt gaacccggga ggtggaggtt gcagtgagcc   2340

gagatcaca                                                           2349
```

<210> SEQ ID NO 79
<211> LENGTH: 8015
<212> TYPE: DNA
<213> ORGANISM: Homo sapiens

<400> SEQUENCE: 79

```
agccgggcag ctgcagcgga gccgcggagc gggcggcggg gcccaggctg tgcgcttggg     60

gagcgcggaa tgtgaggctt ggcgggccgc agcacgctcg gacgggccag gggcggcgac    120

ccctcgcgga cgcccggctg cgcgccgggc cggggacttg cccttgcacg ctccctgcgc    180

cctccagctc gccggcggga ccatgaagaa gttctctcgg atgcccaagt cggagggcgg    240

cagcggcggc ggagcggcgg gtggcggggc tggcggggcc ggggccgggg ccggctgcgg    300

ctccggcggc tcgtccgtgg gggtccgggt gttcgcggtc ggccgccacc aggtcaccct    360

ggaagagtcg ctggccgaag tgatacagat gctgccggtt caggaaccac gtcttgagta    420

ccgagtacca ctgatttcga gcgggcgaag aagactaaga agaaggtgct agagaggtgg    480

attctccaca gttttcctcg tgcgtactca cggtggaatc cgatgtgcat tgaagcgaat    540

gtatgtcaat aacatgccag acctcaatgt ttgtaaaagg gaaattacaa ttatgaaaga    600

gctatctggt cacaaaaata ttgtgggcta tttgggctgt gctgttaatt caattagtga    660

taatgtatgg gaagtcctta tcttaatgga atattgtcga gctggacagg tagtgaatca    720

aatgaataag aagctacaga cgggttttac agaaccagaa gtgttacaga tattctgtga    780

tacctgtgaa gctgttgcaa ggttgcatca gtgtaagact ccaataattc accgggatct    840

gaaggtagaa aatattttgt tgaatgatgg tgggaactat gtactttgtg actttggcag    900

tgccactaat aaatttctta atcctcaaaa agatggagtt aatgtagtag aagaagaaat    960

taaaaagtat acaactctgt catacagagc cctgaaatg atcaaccttt atggagggaa    1020

acccatcacc accaaggctg atatctgggc actgggatgt ctactctata aactttgttt   1080

cttcactctt ccttttggtg agagtcaggt tgctatctgt gatggcaact tcaccatccc   1140

agacaattct cgttactccc gtaacataca ttgcttaata aggttcatgc ttgaaccaga   1200

tccggaacat agacctgata tatttcaagt gtcatatttt gcatttaaat ttgccaaaaa   1260

ggattgtcca gtctccaaca tcaataattc ttctattcct tcagctcttc ctgaaccgat   1320

gactgctagt gaagcagctg ctaggaaaag ccaaataaaa gccagaataa cagataccat   1380
```

```
tggaccaaca gaaacctcaa ttgcaccaag acaaagacca aaggccaact ctgctactac   1440

tgccactccc agtgtgctga ccattcaaag ttcagcaaca cctgttaaag tccttgctcc   1500

tggtgaattc ggtaaccata gaccaaaagg ggcactaaga cctggaaatg gccctgaaat   1560

tttattgggt cagggacctc ctcagcagcc gccacagcag catagagtac tccagcaact   1620

acagcaggga gattggagat tacagcaact ccatttacag catcgtcatc ctcaccagca   1680

gcagcagcag cagcagcagc aacagcaaca gcagcagcag caacagcaac agcagcagca   1740

gcagcagcag cagcagcagc agcaccacca ccaccaccac cacactactt caagatgctt   1800

atatgcagca gtatcaacat ggcaacacag cagcaacaga tgcttcaaca acaattttta   1860

atgcattcgg tatatcaacc acaaccttct gcatcacagt atcctacaat gatgccgcag   1920

tatcagcagg ctttctttca acagcagatg ctagctcaac atcagccgtc tcaacaacag   1980

gcatcacctg aatatcttac ctcccctcaa gagttctcac cagccttagt ttcctacact   2040

tcatcacttc cagctcaggt tggaaccata atggactcct cctatagtgc caataggtca   2100

gttgctgata aagaggccat tgcaaatttc acaaatcaga agaacatcag caatccacct   2160

gatatgtcag ggtggaatcc ttttggagag gataatttct ctaagttaac agaagaggaa   2220

ctattggaca gagaatttga ccttctaaga tcaagttctc ctgaaaagaa agctgaacat   2280

tcatctataa atcaagaaaa tggcactgca aaccctatca agaacggtaa aacaagtcca   2340

gcatctaaag atcagcggac tggaaagaaa acctcagtac agggtcaagt gcaaaagggg   2400

aatgatgaat ctgaaagtga ttttgaatca gatcccccct ctcctaagag cagtgaagag   2460

gaagagcaag atgatgaaga agttcttcag gggggaacaag gagattttaa tgatgatgat   2520

actgaaccag aaaatctggg tcataggcct ctcctcatgg attctgaaga tgaggaagaa   2580

gaggagaaac atagctctga ttctgattat gagcaggcta aagcaaagta cagtgacatg   2640

agctctgtct acagagacag atctggcagt ggaccaaccc aagatcttaa tacaatactc   2700

ctcacctcag cccaattatc ctctgatgtt gcagtggaga ctcccaaaca ggagtttgat   2760

gtatttggcg ctgtcccctt ctttgcagtg cgtgctcaac agccccagca agaaaagaat   2820

gaaaagaacc tccctcaaca caggtttcct gctgcaggac tggagcagga ggaatttgat   2880

gtattcacaa aggcgccttt tagcaagaag gtgaatgtac aagaatgcca tgcagtgggg   2940

cctgaggcac atactatccc tggttatccc aaaagtgtag atgtatttgg ctccactcca   3000

tttcagccct tcctcacatc aacaagtaaa agtgaaagca atgaggacct tttgggctt    3060

gtgccctttg atgaaataac ggggagccag cagcaaaaaa gtcaaacagc gcagcttaca   3120

gaaactgtcc tctcgccaaa ggcgcacaaa gcaggatatg tccaaaagta atgggaagcg   3180

gcatcatggc acgccaacta gcacaaagaa gactttgaag cctacctatc gcactccaga   3240

gagggctcgc aggcacaaaa aagtgggccg cgagactctc aaagtagcaa tgaattttta   3300

accatctcag actccaagga gaacattagt gttgcactga ctgatgggaa agatagggg    3360

aatgtcttac aacctgagga gagcctgttg gaccccttcg gtgccaagcc cttccattct   3420

ccagacctgt catggcaccc tccacatcag ggcctgagcg acatccgtgc tgatcacaat   3480

actgtcctgc cagggcggcc aagacaaaat tcactacatg ggtcattcca tagtgcagat   3540

gtattgaaaa tggatgattt tggtgccgtg ccctttacag aacttgtggt gcaaagcatc   3600

actccacatc agtcccaaca gtcccaacca gtcgaattag acccatttgg tgctgctcca   3660

tttccttcta aacagtagat acttctgatg gattctcggc attaactcct gtttcaaaaa   3720

agtgtgaaca gttttatgaa tttgaaagaa aatttggtag ctctttatag cattcattct   3780
```

```
taaagatcag tcagaatagg tgatttctaa ataaaccaaa tagaagaatg aagtatctct   3840
acagggtagt aacttgattc ctcttcagga gaaaagggag ctaaattgca agctctaact   3900
aagggtttct gctactgaca tcacaacaca gaaatgcaag tgtggtactt ccagtgaaag   3960
cacatggcac ctttctaggt gtgtagccac tgagaaggga cagtgaaact gttatttttg   4020
atatcagaat gtcattttta tgtgcatatc cctaaaatta gggttatttc tacatacact   4080
agttacactt gtgaattttt tttaaggtct cttttaattt ccagacagtt aaaaacaatc   4140
tagttatctt aaagcattag aaagttatta tctggagagt gcagagattt cagtccatac   4200
acctttctcc acaaagcaga gccagaagta actgactatt gtgcctaaaa ctctgtttca   4260
tttttaaaaa caagtgccat taaaatggaa tatctaatga taagcatatg aaataatgtg   4320
taattagctc aatttaacta ttccacaact tacatattcc aaaacaatgt tatacatgat   4380
aaatatatat aatttttgtc agttaaaaca aattaaaaaa atggactatc gtcgcacaga   4440
agcctagaac aaaaatatga agagaaatat ctgacatttg taaagaaatt ataagaagaa   4500
aaaaagatac agaacagaaa acattcacta ctttagaaac actttatgca tggcttcttg   4560
ccccaaactt ttattgtgat ggccctaata aagcagatta ttggaaaaat tggaggacaa   4620
gggttgtata aaaattttat tttatgaaga aaatatgtag cggaaactga attttcaaga   4680
catttacaat gtgaaatcat gttgcattta acaatgtact ttattagcaa cttcaccaaa   4740
tattccccaa gtcataagca acaattattt ttattaggtt ttggggggtg gagtagtttt   4800
aataaagtgc acagaatggt gacacccaca aagccttata taaaggcagg attcatgcat   4860
cctgctgcaa gtacctctgc actaatatac cagatcctaa aatgcatata aggtggacta   4920
gcatcttaat tctgctagtt gattgtgtct ttactgaaaa gaacccagct accaatttgc   4980
ctttttttac accacaaatc ctaattagaa acttgaggtt ttatagaaat catttaatga   5040
tagagattac atatgtgaat taatgtgaat atagtatctg tgcttcctgt gtctatgact   5100
attttaagat ataattgtgc tgcgctatca gattaacatt tggaagtttc tagaacagtt   5160
aatgctattt acagaaagga gtagaaactc atcaactggc actctctttg atttttatat   5220
tttaaattaa ctctcttcga tctcaaagta tattttacga gtaattttat taggaatctc   5280
ttatagtgcc ccaatgggat aagctatttg cctattttca cagttctgaa cttggaaaga   5340
agcaaagtat atgtaactaa accacatatt tgtcttttta ttgctttttc ccttctttta   5400
tatgctaaat caaatataga tttgtggata gggaagcaat atgtgaatca caatgtagca   5460
gaggcagacc aagcattaca ttattattta gagctggact gcaccaatta cttgtcctcg   5520
tgccaaaggc aaatatgttt gcaccttttt tttttttctt gattctcagg ttgattaata   5580
ctgctaatgc aaatgctcaa gtagatgttt aaaaacttta caaaatagat tcaagtgata   5640
ctttctttta aaagtgaaga gttgatgatt acacatagta aattcatgaa ctacagtagg   5700
tttgtatcaa acaatttttt ttaatgaaaa tctgttgagg tgtacacaat atgcttcttg   5760
attgtattag tccttggtct ctgctagacc tcatgagttt catcatttag aaaaggggta   5820
gaggatgaac taatgtctcc ttcagatgta aacatgaaat acctagagtt ttacttgctt   5880
ttcaatacac tgaataattt taaatgattc tgacactgat gtagaccctt tgacttataa   5940
attctgagga aacaactgac agcataaaat atttacattc ttataacaca gcacagtgac   6000
tttcttcttt caagattgta gctcagagaa aagatacagg attcaattgg gggttcaata   6060
ggatagaaat ggagagattc ctttgtgttg tagtagaggc attttcctaa ggagtataga   6120
tttatacttt gcattttcat tcatcatccc ccagaatcat ggtcaaggtg taggtcactc   6180
```

```
cacacagctg atgctcaggt tattcccttg tgagaattat gagaataaag ctcccaagat   6240

atgtgaaagt gcttaacaca gtacctggca cacagcactc aataaaagtt tggctctatt   6300

atgggatggt tcaattctgg tttaaggaag gaagaaaggt tattatatat gtaccactaa   6360

gcaaatatat atatatatat atatttgggg ttttttttcc ctaatattat ttgggtgtcc   6420

cctgtgcttc tttaggatgt agttataact aaacctgtta tacttgaaca tcactaagag   6480

aagtaaatta ttatgaagct agcaaaaatc ttgaggccaa agttgtttct taacagcttt   6540

aataatgctt gttgattttg aataatcctt taaaaagtgg accatttgct tattttaata   6600

tcacgtcagt aaaatgttag tattaaaaag atcagctttt tatggcattg aagaatgtat   6660

ctgctaagac acaaaaattg catggtaagt ataataggtg gaggaggaaa ggttgtaggc   6720

cggatgaaaa tttaactgac tagaacattt attcaggagt gtaattattt tcccttaccc   6780

caatccctgt gtacgtgttg ggtatagtta cgacattatc cggatttgca aatagacaca   6840

actttcagtc ttaccctgtt tattgtttaa gagtgataga ctgttgtcct cttgctggtg   6900

gaaaatctaa ggtggagccc actcttctat gctgaagttc accaggcaga gcagttttct   6960

tacaagtcag ctactctgct tggtttattt taggttttgg tacttcacgt aagcactgtt   7020

agaaggtaca agtgtattaa tatcactagt tttgaggcgc ttgggtacat ttgtttttaa   7080

tatatttaga atgtgcagta aacttttttc tcattttttt ttctttttag caaacttgtt   7140

attttaggtc caattattga gttgacagtc tactgtgaga atgagatgac atatctactg   7200

tgagaatacc ataaatgatg aatagtttat ttgagaactt ttatactcag tggtgtttat   7260

atattaagat aaaaatatgt acacacatgc atgtcacatc tctctactgt ggagttaatg   7320

tgaattttta aaaaatggaa ttgcaaccac aatcatatct aagagaacat tcactcctag   7380

tgagggttta caaaagctac taagagaata aggtagatga taatgcaaag ggtcatgatt   7440

tggggttatt tttgttttat tttaaaattt atactgctac ttttgaaaga attgttttta   7500

tgactatgct ctttttgtga ttgaaaagtc atctaataga agctgtatag aagctacttt   7560

ttaattgctg gcaaacagct ttaagtgcac tttctttgat tacacttcca tttttgtta   7620

aacttgaatt ttctgaagcc ttttatgtac cactaagcaa ataactttaa cctttaaata   7680

aagcaaattt acatctttat tgtatttcta cttgttacaa aacatacttg ctaaagtaac   7740

ttcagtcctc aaatatagct gggaaacaat tatgagatag actcagtctc cccctcccac   7800

cccttttccc ctgccatatc taattaagca ctaactgatt ttattacttt attgccttta   7860

cactgcttat tctttttgac tgaattctgt ccctgattca ctgttttgtt tgaaatttaa   7920

agttattttc ttactgtatt tatcatacct gttttaatct gttttcttta aatgcaataa   7980

atcccaaatg gattgcatat tctttataat cagtg                              8015
```

<210> SEQ ID NO 80
<211> LENGTH: 7945
<212> TYPE: DNA
<213> ORGANISM: Homo sapiens

<400> SEQUENCE: 80

```
agccgggcag ctgcagcgga gccgcggagc gggcggcggg gcccaggctg tgcgcttggg     60

gagcgcggaa tgtgaggctt ggcgggccgc agcacgctcg gacgggccag gggcggcgac    120

ccctcgcgga cgcccggctg cgcgccgggc cggggacttg cccttgcacg ctccctgcgc    180

cctccagctc gccggcggga ccatgaagaa gttctctcgg atgcccaagt cggagggcgg    240

cagcggcggc ggagcggcgg gtggcggggc tggcggggcc ggggccgggg ccggctgcgg    300
```

```
ctccggcggc tcgtccgtgg gggtccgggt gttcgcggtc ggccgccacc aggtcaccct    360
ggaagagtcg ctggccgaag gtacgggcgc ccggggaggc tcggacaggc aggtggattc    420
tccacagttt tcctcgtgcg tactcacggt ggaatccgat gtgcattgaa gcgaatgtat    480
gtcaataaca tgccagacct caatgtttgt aaaagggaaa ttacaattat gaaagagcta    540
tctggtcaca aaaatattgt gggctatttg gactgtgctg ttaattcaat tagtgataat    600
gtatgggaag tccttatctt aatggaatat tgtcgagctg gacaggtagt gaatcaaatg    660
aataagaagc tacagacggg ttttacagaa ccagaagtgt tacagatatt ctgtgatacc    720
tgtgaagctg ttgcaaggtt gcatcagtgt aagactccaa taattcaccg ggatctgaag    780
gtagaaaata tttgctgaat gatggtggga actatgtact ttgtgacttt ggcagtgcca    840
ctaataaatt tcttaatcct caaaaagatg gagttaatgt agtagaagaa gaaattaaaa    900
agtatacaac tctgtcatac agagcccctg aaatgatcaa cctttatgga gggaaaccca    960
tcaccaccaa ggctgatatc tgggcactgg gatgtctact ctataaactt tgtttcttca   1020
ctcttccttt tggtgagagt caggttgcta tctgtgatgg caacttcacc atcccagaca   1080
attctcgtta ctcccgtaac atacattgct taataaggtt catgcttgaa ccagatccgg   1140
aacatagacc tgatatattt caagtgtcat attttgcatt taaatttgcc aaaaaggatt   1200
gtccagtctc caacatcaat aattcttcta ttccttcagc tcttcctgaa ccgatgactg   1260
ctagtgaagc agctgctagg aaaagccaaa taaaagccag aataacagat accattggac   1320
caacagaaac ctcaattgca ccaagacaaa gaccaaaggc caactctgct actactgcca   1380
ctcccagtgt gctgaccatt caaagttcag caacacctgt taaagtcctt gctcctggtg   1440
aattcggtaa ccatagacca aaagggggcac taagacctgg aaatggccct gaaattttat   1500
tgggtcaggg acctcctcag cagccgccac agcagcatag agtactccag caactacagc   1560
agggagattg gagattacag caactccatt tacagcatcg tcatcctcac cagcagcagc   1620
agcagcagca gcagcaacag caacagcagc agcagcaaca gcaacagcag cagcagcagc   1680
agcagcagca gcagcagcac caccaccacc accaccaccc tacttcaaga tgcttatatg   1740
cagcagtatc aacatggcaa cacagcagca acagatgctt caacaacaat ttttaatgca   1800
ttcggtatat caaccacaac cttctgcatc acagtatcct acaatgatgc cgcagtatca   1860
gcaggctttc tttcaacagc agatgctagc tcaacatcag ccgtctcaac aacaggcatc   1920
acctgaatat cttacctccc ctcaagagtt ctcaccagcc ttagtttcct acacttcatc   1980
acttccagct caggttggaa ccataatgga ctcctcctat agtgccaata ggtcagttgc   2040
tgataaagag gccattgcaa atttcacaaa tcagaagaac atcagcaatc cacctgatat   2100
gtcagggtgg aatccttttg gagaggataa tttctctaag ttaacagaag aggaactatt   2160
ggacagagaa tttgaccttc taagatcaag ttctcctgaa aagaaagctg aacattcatc   2220
tataaatcaa gaaaatggca ctgcaaaccc tatcaagaac ggtaaaacaa gtccagcatc   2280
taaagatcag cggactggaa agaaaacctc agtacagggt caagtgcaaa aggggaatga   2340
tgaatctgaa agtgattttg aatcagatcc cccttctcct aagagcagtg aagaggaaga   2400
gcaagatgat gaagaagttc ttcagggggga acaaggagat tttaagtgat gatgatactg   2460
aaccagaaaa tctgggtcat aggcctctcc tcatggattc tgaagatgag gaagaagagg   2520
agaaacatag ctctgattct gattatgagc aggctaaagg caaagtacag tgacatgagc   2580
tctgtctaca gagacggatc tggcagtggg accaacccaa gatcttaata caatactcct   2640
cacctcagcc caattatcct ctgatgttgc agtggagact cccaaacagg agtttgatgt   2700
```

-continued

```
atttggcgct gtccccttct ttgcagtgcg tgctcaacag ccccagcaag aaaagaatga   2760
aaagaacctc cctcaacaca ggtttcctgc tgcaggactg gagcaggagg aatttgatgt   2820
attcacaaag gcgcctttta gcaagaaggt gaatgtacaa gaatgccatg cagtggggcc   2880
tgaggcacat actatccctg gttatcccaa aagtgtagat gtatttggct ccactccatt   2940
tcagcccttc ctcacatcaa caagtaaaag tgaaagcaat gaggaccttt ttgggcttgt   3000
gccctttgat gaaataacgg ggagccagca gcaaaaagtc aaacagcgca gcttacagaa   3060
actgtcctct cgccaaaggc gcacaaagca ggatatgtcc aaaagtaatg ggaagcggca   3120
tcatggcacg ccaactagca caaagaagac tttgaagcct acctatcgca ctccagagag   3180
ggctcgcagg cacaaaaaag tgggccgccg agactctcaa agtagcaatg aatttttaac   3240
catctcagac tccaaggaga acattagtgt tgcactgact gatgggaaag ataggggggaa   3300
tgtcttacaa cctgaggaga gcctgttgga ccccttcggt gccaagccct tccattctcc   3360
agacctgtca tggcaccctc cacatcaggg cctgagcgac atccgtgctg atcacaatac   3420
tgtcctgcca gggcggccaa gacaaaattc actacatggg tcattccata gtgcagatgt   3480
attgaaaatg gatgattttg gtgccgtgcc ctttacagaa cttgtggtgc aaagcatcac   3540
tccacatcag tcccaacagt cccaaccagt cgaattagac ccatttggtg ctgctccatt   3600
tccttctaaa cagtagatac ttctgatgga ttctcggcat taactcctgt ttcaaaaaag   3660
tgtgaacagt tttatgaatt tgaaagaaaa tttggtagct ctttatagca ttcattctta   3720
aagatcagtc agaataggtg atttctaaat aaaccaaata gaagaatgaa gtatctctac   3780
agggtagtaa ctcgattcct cttcaggaga aaagggagct aaattgcaag ctctaactaa   3840
gggtttctgc tactgacatc acaacacaga aatgcaagtg tggtacttcc agtgaaagca   3900
catggcacct ttctaggtgt gtagccactg agaagggaca gtgaaactgt tatttttgat   3960
atcagaatgt catttttatg tgcatatccc taaaattagg gttatttcta catacactag   4020
ttacacttgt gaattttttt taaggtctct tttaatttcc agacagttaa aaacaatcta   4080
gttatcttaa agcattagaa agttattatc tggagagtgc agagatttca gtccatacac   4140
ctttctccac aaagcagagc cagaagtaac tgactattgt gcctaaaact ctgtttcatt   4200
tttaaaaaca agtgccatta aaatggaata tctaatgata agcatatgaa ataatgtgta   4260
attagctcaa tttaactatt ccacaactta catattccaa aacaatgtta tacatgataa   4320
atatatataa tttttgtcag ttaaaacaaa ttaaaaaaat ggactatcgt cgcacagaag   4380
cctagaacaa aaatatgaag agaaatatct gacatttgta aagaaattat aagaagaaaa   4440
aaagatacag aacagaaaac attcactact ttagaaacac tttatgcatg gcttcttgcc   4500
ccaaactttt attgtgatgg ccctaataaa gcagattatt ggaaaaattg gaggacaagg   4560
gttgtataaa aattttattt tatgaagaaa atatgtagcg gaaactgaat tttcaagaca   4620
tttacaatgt gaaatcatgt tgcatttaac aatgtacttt attagcaact tcaccaaata   4680
ttccccaagt cataagcaac aattattttt attaggtttt ggggggtgga gtagttttaa   4740
taaagtgcac agaatggtga cacccacaaa gccttatata aaggcaggat tcatgcatcc   4800
tgctgcaagt acctctgcac taatatacca gatcctaaaa tgcatataag gtggactagc   4860
atcttaattc tgctagttga ttgtgtcttt actgaaaaga acccagctac caatttgcct   4920
ttttttacac cacaaatcct aattagaaac ttgaggtttt atagaaatca tttaatgata   4980
gagattacat atgtgaatta atgtgaatat agtatctgtg cttcctgtgt ctatgactat   5040
tttaagatat aattgtgctg cgctatcaga ttaacatttg gaagtttcta gaacagttaa   5100
```

```
tgctatttac agaaaggagt agaaactcat caactggcac tctctttgat tttatattt   5160
taaattaact ctcttcgatc tcaaagtata ttttacgagt aattttatta ggaatctctt  5220
atagtgcccc aatgggataa gctattgcct attttcacag ttctgaactt ggaaagaagc  5280
aaagtatatg taactaaagc acatattgtc tttttattgc tttttccctt cttttatatg  5340
ctaaatcaat atagatttgt ggatagggaa gcaatatgtg aatcacaatg tagcagaggc  5400
agaccaagca ttacattatt atttagagct ggactgcacc aattacttgt cctcgtgcca  5460
aaggcaaata tgtttgcacc tttttttttt tttctgattc tcaggttgat taatactgct  5520
aatgcaaatg ctcaagtaga tgtttaaaaa ctttacaaaa tagattcaag tgatactttc  5580
ttttaaaagt gaagagttga tgattacaca tagtaaattc atgaactaca gtaggtttgt  5640
atcaaacaat tttttttaat gaaaatctgt tgaggtgtac acaatatgct tcttgattgt  5700
attagtcctt ggtctctgct agacctcatg agtttcatca tttagaaaag gggtagagga  5760
tgaactaatg tctccttcag atgtaaacat gaaataccta gagttttact tgcttttcaa  5820
tacactgaat aattttaaat gattctgaca ctgatgtaga ccctttgact tataaattct  5880
gaggaaacaa ctgacagcat aaaatattta cattcttata acacagcaca gtgactttct  5940
tctttcaaga ttgtagctca gagaaaagat acaggattca attgggggtt caataggata  6000
gaaatggaga gattcctttg tgttgtagta gaggcatttt cctaaggagt atagatttat  6060
actttgcatt ttcattcatc atcccccaga atcatggtca aggtgtaggt cactccacac  6120
agctgatgct caggttattc ccttgtgaga attatgagaa taaagctccc aagatatgtg  6180
aaagtgctta acacagtacc tggcacacag cactcaataa aagtttggct ctattatggg  6240
atggttcaat tctggtttaa ggaaggaaga aaggttatta tatatgtacc actaagcaaa  6300
tatatatata tatatatatt tggggttttt tttccctaat attatttggg tgtcccctgt  6360
gcttctttag gatgtagtta taactaaacc tgttatactt gaacatcact aagagaagta  6420
aattattatg aagctagcaa aaatcttgag gccaaagttg tttcttaaca gctttaataa  6480
tgcttgttga ttttgaataa tcctttaaaa agtggaccat ttgcttattt taatatcacg  6540
tcagtaaaat gttagtatta aaaagatcag ctttttatgg cattgaagaa tgtatctgct  6600
aagacacaaa aattgcatgg taagtataat aggtggagga ggaaaggttg taggccggat  6660
gaaaatttaa ctgactagaa catttattca ggagtgtaat tattttccct taccccaatc  6720
cctgtgtacg tgttgggtat agttacgaca ttatccggat ttgcaaatag acacaacttt  6780
cagtcttacc ctgtttattg tttaagagtg atagactgtt gtcctcttgc tggtggaaaa  6840
tctaaggtgg agcccactct tctatgctga agttcaccag gcagagcagt tttcttacaa  6900
gtcagctact ctgcttggtt tattttaggt tttggtactt cacgtaagca ctgttagaag  6960
gtacaagtgt attaatatca ctagttttga ggcgcttggg tacatttgtt tttaatatat  7020
ttagaatgtg cagtaaactt ttttctcatt tttttttctt tttagcaaac ttgttatttt  7080
aggtccaatt attgagttga cagtctactg tgagaatgag atgacatatc tactgtgaga  7140
ataccataaa tgatgaatag tttatttgag aacttttata ctcagtggtg ttttatatat  7200
taagataaaa atatgtacac acatgcatgt cacatctctc tactgtggag ttaatgtgaa  7260
tttttaaaaa atggaattgc aaccacaatc atatctaaga gaacattcac tcctagtgag  7320
ggtttacaaa agctactaag agaataaggt agatgataat gcaaagggtc atgatttggg  7380
gttatttttg ttttatttta aaatttatac tgctactttt gaaagaattg tttttatgac  7440
tatgctcttt ttgtgattga aaagtcatct aatagaagct gtatagaagc tactttttaa  7500
```

```
ttgctggcaa acagctttaa gtgcactttc tttgattaca cttccatttt ttgttaaact   7560

tgaattttct gaagcctttt atgtaccact aagcaaataa ctttaacctt taaataaagc   7620

aaatttacat ctttattgta tttctacttg ttacaaaaca tacttgctaa agtaacttca   7680

gtcctcaaat atagctggga aacaattatg agatagactc agtctccccc tcccacccct   7740

tttcccctgc catatctaat taagcactaa ctgattttat tactttattg cctttacact   7800

gcttattctt tttgactgaa ttctgtccct gattcactgt tttgtttgaa atttaaagtt   7860

attttcttac tgtatttatc atacctgttt taatctgttt tctttaaatg caataaatcc   7920

caaatggatt gcatattctt tataa                                         7945
```

<210> SEQ ID NO 81
<211> LENGTH: 3149
<212> TYPE: DNA
<213> ORGANISM: Homo sapiens

<400> SEQUENCE: 81

```
ctcgcggtat catccggtgc tgaggccctg taataaaggt ctcgcgaaat ttgttctaga     60

ggtccaagtt gcttcttagc ttactccacc ccaccccaa cctgtccctc cttttctttc     120

caagtcacaa aattctcccc tcccctaccc cggagtttac ggccctcctc ctgtttccga    180

tttcagcccg gaaccggaag tgaagtgggc ggggcccgtc ggcggaaaac gcagcggagc    240

cagagccgga cacggctgtg gccgctgcct ctaccccgc cacggatcgc cgggtagtag     300

gactgcgcgg ctccaggctg agggtcggtc cggaggcggg tgggcgcggg tctcacccgg    360

attgtccggg tggcaccgtt cccggcccca ccgggcgccg cgagggatca tgtctacagc    420

ctctgccgcc tcctcctcct cctcgtcttc ggccggtgag atgatcgaag ccccttccca    480

ggtcctcaac tttgaagaga tcgactacaa ggagatcgag gtggaagagg ttgttggaag    540

aggagccttt ggagttgttt gcaaagctaa gtggagagca aaagatgttg ctattaaaca    600

aatagaaagt gaatctgaga ggaaagcgtt tattgtagag cttcggcagt tatcccgtgt    660

gaaccatcct aatattgtaa agctttatgg agcctgcttg aatccagtgt gtcttgtgat    720

ggaatatgct gaagggggct ctttatataa tgtttgtgcc tttctttcgc agtgctgcat    780

ggtgctgaac cattgccata ttatactgct gcccacgcaa tgagttggtg tttacagtgt    840

tcccaaggag tggcttatct tcacagcatg caacccaaag cgctaattca cagggacctg    900

aaaccaccaa acttactgct ggttgcaggg gggacagttc taaaaatttg tgattttggt    960

acagcctgtg acattcagac acacatgacc aataacaagg ggagtgctgc ttggatggca   1020

cctgaagttt ttgaaggtag taattacagt gaaaaatgtg acgtcttcag ctggggtatt   1080

attctttggg aagtgataac gcgtcggaaa ccccttttgat gagattggtg gcccagcttt  1140

ccgaatcatg tgggctgttc ataatggtac tcgaccacca ctgataaaaa atttacctaa   1200

gcccattgag agcctgatga ctcgttgttg gtctaaagat ccttcccagc gcccttcaat   1260

ggaggaaatt gtgaaaataa tgactcactt gatgcggaga aatatttgct gttttcttca   1320

agactatcta gactccaatg taagctagat tcttagtact ttccaggagc agatgagcca   1380

ttacagtatc cttgtcagta ttcagatgaa ggacagagca actctgccac cagtacaggc   1440

tcattcatgg acattgcttc tacaaatacg agtaacaaaa gtgacactaa tatggagcaa   1500

gttcctgcca caaatgatac tattaagcgc ttagaatcaa aattgttgaa aaatcaggca   1560

aagcaacaga gtgaatctgg acgtttaagc ttggggagcc tcccgtggga gcagtgtgga   1620

gagcttgccc ccaacctctg agggcaagag gatgagtgct gacatgtctg aaatagaagc   1680
```

```
taggatcgcc gcaaccacag gcaacggaca gccaagacgt agatccatcc aagacttgac   1740

tgtaactgga acagaacctg gtcaggtgag cagtaggtca tccagtccca gtgtcagaat   1800

gattactacc tcaggaccaa cctcagaaaa gccaactcga agtcatccat ggacccctga   1860

tgattccaca gataccaatg gatcagataa ctccatccca atggcttatc ttacactgga   1920

tcaccaacta cagcctctag caccgtgccc aaactccaaa gaatctatgg cagtgtttga   1980

acagcattgt aaaatggcac aagaatatat gaaagttcaa acagaaattg cattgttatt   2040

acagagaaag caagaactag ttgcagaact ggaccaggat gaaaaggacc agcaaaatac   2100

atctcgcctg gtacaggaac ataaaaagct tttagatgaa aacaaaagcc tttctactta   2160

ctaccagcaa tgcaaaaaac aactagaggt catcagaagt cagcagcaga aacgacaagg   2220

cacttcatga ttctctggga ccgttacatt ttgaaatatg caaagaaaga ctttttttta   2280

aggaaaggaa aaccttataa tgacgattca tgagtgttag ctttttggcg tgttctgaat   2340

gccaactgcc tatatttgct gcattttttt cattgtttat tttccttttc tcatggtgga   2400

catacaattt tactgtttca ttgcataaca tggtagcatc tgtgacttga atgagcagca   2460

ctttgcaact tcaaaacaga tgcagtgaac tgtggctgta tatgcatgct cattgtgtga   2520

aggctagcct aacagaacag gaggtatcaa actagctgct atgtgcaaac agcgtccatt   2580

ttttcatatt agaggtggaa cctcaagaat gactttattc ttgtatctca tctcaaaata   2640

ttaataattt ttttcccaaa agatggtata taccaagtta aagacagggt attataaatt   2700

tagagtgatt ggtggtatat tacggaaata cggaaccttt agggatagtt ccgtgtaagg   2760

gctttgatgc cagcatcctt ggatcagtac tgaactcagt tccatccgta aaatatgtaa   2820

agataagcaa gatctaagaa gttatcaaaa ctattcttta aaatgctaaa gcagctcctg   2880

tagccagaga tcacaggtct tccctgtgaa actttggttt ctttctataa atgtgtgtgg   2940

ttttcagcgc tcaactcctg tcttcaaatg gtagtaagtt ctacttctac ttctgtcatt   3000

cagaacattt tatgtcaaat gatgtaatgc agaaattctt gtgcatattt gtaactgaag   3060

gaagcttttt agatttattt ttgtttttaa taaaattcag attcctattc taaactggta   3120

cataaaagtg gtgaatgact tgtatcagc                                     3149
```

<210> SEQ ID NO 82
<211> LENGTH: 3617
<212> TYPE: DNA
<213> ORGANISM: Homo sapiens

<400> SEQUENCE: 82

```
taagatggcg gacctggagg cggtgctggc cgacgtgagc tacctgatgg ccatggagaa     60

gagcaaggcc acgccggccg cgcgcgccag caagaagata ctgctgcccg agcccagcat    120

ccgcagtgtc atgcagaagt acctggagga ccggggcgag gtgacctttg agaagatctt    180

ttcccagaag ctggggtacc tgctcttccg agacttctgc ctgaaccacc tggaggaggc    240

caggcccttg gtggaattct atgaggagat caagaagtac gagaagctgg agacggagga    300

ggagcgtgtg gcccgcagcc gggagatctt cgactcatac atcatgaagg agctgctggc    360

ctgctcgcat cccttctcga agagtgccac tgagcatgtc caaggccacc tggggaagaa    420

gcaggtgcct ccggatctct tccagccata catcgaagag atttgtcaaa acctccgagg    480

ggacgtgttc cagaaattca ttgagagcga taagttcaca cggttttgcc agtggaagaa    540

tgtggagctc aacatccacg tgagtgggct tgggtggggc atggaaagcc acgcaccctg    600

ctgctcctct cccgggagct gggcctgtgg cttggctggg agggggaggt caggggatgt    660
```

```
ctgtccttta gcccccaggg ccgtggctat gggggtcagg gccgggatcc cagcatgggg    720
aggccggagc aggtaaatat gtggcaagga tggccaggac atgggtatgg ggaccctggc    780
atggggccag cccctgctgc ccaggtgcct ctgccccagg gctgggcaga ggcagcctgt    840
ggtgaccgca gctgtcgctg cccctcagct gaccatgaat gacttcagcg tgcatcgcat    900
cattgggcgc gggggctttg gcgaggtcta tgggtgccgg aaggctgaca caggcaagat    960
gtacgccatg aagtgcctgg acaaaaagcg catcaagatg aagcaggggg agaccctggc   1020
cctgaacgag cgcatcatgc tctcgctcgt cagcactggg gactgcccat tcattgtctg   1080
catgtcatac gcgttccaca cgccagacaa gctcagcttc atcctggacc tcatgaacgg   1140
tggggacctg cactaccacc tctcccagca cggggtcttc tcagaggctg acatgcgctt   1200
ctatgcggcc gagatcatcc tgggcctgga gcacatgcac aaccgcttcg tggtctaccg   1260
ggacctgaag ggcacccac gggtacatgg ctccggaggt cctgcagaag ggcgtggcct    1320
acgacagcag tgccgactgg ttctctctgg ggtgcatgct cttcaagttg ctgcgggggc   1380
acagcccctt ccggcagcac aagaccaaag acaagcatga gatcgaccgc atgacgctga   1440
cgatggccgt ggagctgccc gactccttct cccctgaact acgctccctg ctggaggggt   1500
tgctgcagag ggatgtcaac cggagattgg gctgcctggg ccgaggggct caggaggtga   1560
aagagagccc ctttttccgc tccctggact ggcagatggt cttcttgcag aagtaccctc   1620
ccccgctgat ccccccacga ggggaggtga acgcggccga cgccttcgac attggctcct   1680
tcgatgagga ggacacaaaa ggaatcaagt tactggacag tgatcaggag ctctaccgca   1740
acttccccct caccatctcg gagcggtggc agcaggaggt ggcagagact gtcttcgaca   1800
ccatcaacgc tgagacagac cggctggagg ctcgcaagaa agccaagaac aagcagctgg   1860
gccatgagga agactacgcc ctgggcaagg actgcatcat gcatggctac atgtccaaga   1920
tgggcaaccc cttcctgacc cagtggcagc ggcggtactt ctacctgttc cccaaccgcc   1980
tcgagtggcg gggcgagggc gaggccccgc agagcctgct gaccatggag gagatccagt   2040
cggtggagga gacgcagatc aaggagcgca agtgcctgct cctcaagatc cgcggtggga   2100
aacagttcat tttgcagtgc gatagcgacc ctgagctggt gcagtggaag aaggagctgc   2160
gcgacgccta ccgcgaggcc cagcagctgg tgcagcgggt gcccaagatg aagaacaagc   2220
cgcgctcgcc cgtggtggag ctgagcaagg tgccgctggt ccagcgcggc agtgccaacg   2280
gcctctgacc cgcccacccg ccttttataa acctctaatt tattttgtcg aatttttatt   2340
atttgttttc ccgccaagcg gaaaaggttt tattttgtaa ttattgtgat ttcccgtggc   2400
cccagcctgg cccagctccc ccgggagggg cccgcttgcc tcggctcctg ctgcaccaac   2460
ccagccgctg cccggcgccc tctgtcctga cttcaggggc tgcccgctcc cagtgtcttc   2520
ctgtggggga agagcacagc cctcccgccc cttccccgag ggatgatgcc acaccaagct   2580
gtgccaccct gggctctgtg ggctgcactc tgtgcccatg ggcactgctg ggtggcccat   2640
ccccccctcac cagggcaggc acagcacagg gatccgactt gaattttccc actgcacccc   2700
ctcctgctgc agaggggcag gccctgcact gtcctgctcc acagtgttgg cgagaggagg   2760
ggcccgttgt ctccctggcc ctcaaggcct cccacagtga ctcgggctcc tgtgccctta   2820
ttcaggaaaa gcctctgtgt cactggctgc ctccactccc acttccctga cactgcgggg   2880
cttggctgag agagtggcat tggcagcagg tgctgctacc ctccctgctg tcccctcttg   2940
ccccaacccc cagcacccgg gctcagggac cacagcaagg cacctgcagg ttgggccata   3000
ctggcctcgc ctggcctgag gtctcgctga tgctgggctg ggtgccgccg cctcgcccac   3060
```

```
cgcatgcccc ctcgtgccag tcgcgctgcc tgtgtggtgt cgcgccttct cccccccggg   3120
gctgggttgg cgcaccctcc cctcccgtct actcattccc cggggcgttt ctttgccgat   3180
ttttgaatgt gattttaaag agtgaaaaat gagactatgc gtttttataa aaaatggtgc   3240
ctgattcggc tgtctcagac tctttttgta cctggtgacc ccttttcagc ttctgctggg   3300
ctggggcctg atggggaggg tctcggtggt accaggtctc ctccaccgcc atggcttcca   3360
aggtggtctg ctcgggccca ggccatcttc caggtggggt gaggcagtgg gtcccacttc   3420
ccctcctacc cctcccagct gacagtcctc tccacctagt ggctgtccag tgcccattcc   3480
tcaccttttc ccggggagga gagagcagct tctgccactt cccaggtaag caggaggagg   3540
tgccaacagt gttaggcctg gcacagtgtc tgggctgact gggaccgtct caggcccaca   3600
gaacacccct gcacagc                                                   3617
```

<210> SEQ ID NO 83
<211> LENGTH: 1955
<212> TYPE: DNA
<213> ORGANISM: Homo sapiens

<400> SEQUENCE: 83

```
agtgcctgcc gggagccacg tctccgaaga ccgatagctg cttcgggatt ggcgtccggg     60
cggctatcta ggggctgctg ggaagatggc ggactcggtg gctagccgat gaggaggccg    120
cggggggaac ccggcccccg ggccccgaga ccgactgagg gagcgacctg cgcagggccc    180
ggggagtcat ggtctccatc acccaactcc atgcttcgag tcctgctctc tgctcagacc    240
tcccctgctc ggctgtctgg cctgctgctg atccctccag tacagccctg ctgtttgggg    300
cccagcaaat ggggggaccg gcctgttgga ggaggcccca gtgcaggtcc tgtgcaagga    360
ctgcagcggc ttctggaaca ggcgaagagc cctggggagc tgctgcgctg gctgggccag    420
aaccccagca aggtgcgcgc ccaccactac tcggtggcgc ttcgtcgtct gggccagctc    480
ttggggtctc ggccacggcc ccctcctgtg gagcaggtca cactgcagga cttgagtcag    540
ctcatcatcc gtaactgccc ctcctttgac attcacacca tccacgtgtg tctgcacctt    600
gcagtcttac ttggctttcc atctgatggt cccctggtgt gtgccctgga acaggagcga    660
aggctccgcc tccctccgaa gccacctccc cctttgcagc cccttctccg agaggcaagg    720
ccagaggaac tgactcccca cgtgatggtg ctcctggccc agcacctggc ccggcaccgg    780
ttgcgggagc cccagcttct ggaagccatt acccacttcc tggtggttca ggaaacgcaa    840
ctcagcagca aggtggtaca gaagttggtc ctgccctttg ggcgactgaa ctacctgccc    900
ctggaacagc agtttatgcc ctgccttgag aggatcctgg ctcgggaagc aggggtggca    960
cccctggcta cagtcaacat cttgatgtca ctgtgccaac tgcggtgcct gcccttcaga   1020
gccctgcact ttgtttttc ccctggcttc atcaactaca tcagtggcac ccctcatgct   1080
ctgattgtgc gtcgctacct ctccctgctg gacacggccg tggagctgga gctcccagga   1140
taccggggtc cccgccttcc ccgaaggcag caagtgccca tctttcccca gcctctcatc   1200
accgaccgtg cccgctgcaa gtacagtcac aaggacatag tagctgaggg gttgcgccag   1260
ctgctggggg aggagaaata ccgccaggac ctgactgtgc ctccaggcta ctgcacaggt   1320
gagcaagggg caggcggcag gcccggggag acggagccct ggctaaggcc gccggccctg   1380
ctcccctcca gacttcctgc tgtgcgccag cagctctggt gctgtgcttc ccgtgaggac   1440
ccaggacccc ttcctgccat acccaccaag gtcctgccca cagggccagg ctgcctctag   1500
cgccactact cgagaccctg cccagaggta aaggaggcag ggtgggggag ccctggccac   1560
```

```
cttgcccgcc atgccctgag ccacgtccct ccccctgcag ggtggtgctg gtgttgcggg   1620

aacgctggca tttctgccgg gacggccggg tgctgctggg ctcgagggcc ctgagggagc   1680

ggcacctagg cctgatgggc taccagctcc tgccgctacc cttcgaggaa ctggagtccc   1740

agagaggcct gccccagctc aagagctacc tgaggcagaa gctccaggcc ctgggcctgc   1800

gctgggggcc tgaagggggc tgaggggttg atgtggggtt caggatggcc cccccatggg   1860

gggtggatga tttgcacttt ggttccctgt gttttgattt ctcattaaag ttcctttcct   1920

tccccgttgt gaatctcagt tttgggacgg ggagc                               1955
```

<210> SEQ ID NO 84
<211> LENGTH: 2937
<212> TYPE: DNA
<213> ORGANISM: Homo sapiens

<400> SEQUENCE: 84

```
gcgcaggggg ccgggctccg gctaggaggg tgggggccgc gccggtgaca gccgatcccc     60

gcccctgctg cccgccacgt ccctcacgta ccactcggca gaggcgcggg gaaacctggc    120

gtactggctg tggcttctct agcgggactc ggcatgaggc tggcgcggct gcttcgcgga    180

gccgccttgg ccggcccggg cccggggctg cgcgccgccg gcttcagccg cagcttcagc    240

tcggactcgg gctccagccc ggcgtccgag cgcggcgttc cgggccaggt ggacttctac    300

gcgcgcttct cgccgtcccc gctctccatg aagcagttcc tggacttcgg atcagtgaat    360

gcttgtgaaa agacctcatt tatgtttctg cggcaagagt tgcctgtcag actggcaaat    420

ataatgaaag aaataagtct ccttccagat aatcttctca ggacaccatc cgttcaattg    480

gtacaaagct ggtatatcca gagtcttcag gagcttcttg attttaagga caaaagtgct    540

gaggatgcta aagctattta tgaaaggcct agaagaacat ggttgcaggt ctctagttta    600

tgctgtatgg cctgcaagat gatctttatt gtttggtgga aaaggcaaag gaagtccatc    660

tcatcgaaaa cacattggaa gcataaatcc aaactgcaat gtacttgaag ttattaaaga    720

tggctatgaa aatgctaggc gtctgtgtga tttgtattat attaactctc ccgaactaga    780

acttgaagaa ctaaatgcaa aatcaccagg acagccaata caagtggttt atgtaccatc    840

ccatctctat cacatggtgt ttgaactttt caagaatgca atgagagcca ctatggaaca    900

ccatgccaac agaggtgttt acccccctat tcaagttcat gtcacgctgg gtaatgagga    960

tttgactgtg aagatgagtg accgaggagg tggcgttcct ttgaggaaaa ttgacagact   1020

tttcaactac atgtattcaa ctgcaccaag acctcgtgtt gagacctccc gcgcagtgcc   1080

tctggctggt tttggttatg gattgcccat atcacgtctt tacgcacaat acttccaagg   1140

agacctgaag ctgtattccc tagagggtta cgggacagat gcagttatct acattaaggc   1200

tctgtcaaca gactcaatag aaagactccc agtgtataac aaagctgtct ggaagcatta   1260

caacaccaac cacgaggctg atgactggtg cgtccccagc agagaaccca aagacatgac   1320

gacgttccgc agtgcctaga cacacttggg acatcggaaa atccaaatgt ggcttttgta   1380

ttaaatttgg aagtgtggcc cagagttgct cagaattgga gcagagcctg agacgtatct   1440

gcagatcctg tcatcagctg gcaagtccag gagactgtgt catttagaga ctgtgttgtt   1500

agttatccct caacatcttc taaggtggca ggaaataata ttggaaataa cattttaaag   1560

taaaaatttt aaagtttaaa gaagagtttt gccacttaaa caggggagct ttgtctggaa   1620

aatacactga gttgaaacac ttcatccttg gaaggattat ataagatgaa cagttgtgat   1680

aaatgtgtag attagaggga tgtgaatggg cagttagtcc agtgccctca tttaagaggc   1740
```

caagatcctg attcagagga ggcatccttt gcccagagct gcttagctaa tctgaccaaa 1800
tgttgggaaa aatgtctcac ctaacccact attccttaat tatggatttt gtgaaaaaca 1860
atagaacatg ttaatgagta atttatatta gttcgatgta ttacaatttt ttagctttaa 1920
attacagttt tcttataatg ttgaaatgtt ttagaatcct ttgaatctaa gtatttgttt 1980
cctaaatgaa acatttgtac aacatttgat gtttttactt atgaaatatt ctcctccccc 2040
aagaaaattt aaactttttc tctctattta aaagctaaga aatgttttaa aggaaaaatg 2100
aaattatctt cctttagctt atttttaagg taaaacagct ttttactctg ttattgtggt 2160
aatggacaga atattacata caaaaatatt ctgggagagc tttttcctag ttggttttaa 2220
atcattgtgc cacctgaaag gtttttagat tttataggag ctaatttgtc caccagcatt 2280
aatgtaacac agtgtagtta tgaaaatata ttgaaggaca ggaagtggac acgaagtgat 2340
ttttgtaacc tgagcagtta atgaatgtgc caacattttc taggaaggga cagcaagaat 2400
attctgctct gtagttaaaa tactggctgg cttttgatgt cttcatgctt aattgtgatc 2460
actttcttgc actgtgatgt ttttacgtga atatgttgaa gtagaagtct accatattat 2520
tttataaaat gttttctgta tggcaataaa ctgaaaacat ggatcaaccc ttcttttgaa 2580
aataaactga gtcaatttag ccttttaaaa atatagtcat ctcttttaaa tagaatcctc 2640
ttccaccatc aaggctcaac attttgtaag catccaaaaa attggtaatt agggggcttg 2700
cactaaattt cactatcttc agtagagagg aactgtttgg aacttagatt tccaatgtgt 2760
atattctaat ggagaaagca agaggtagag tttgtatgtt tgacttacct tagattttta 2820
ttttccatac atactgcaaa tgattgactt gttgcataaa tgaagatctt ctgttgtgtg 2880
cttttcaaac actgtaaata aatttgaaat ttgaataact ttccacagta taactgt 2937

<210> SEQ ID NO 85
<211> LENGTH: 6122
<212> TYPE: DNA
<213> ORGANISM: Homo sapiens

<400> SEQUENCE: 85
ctgagaggag acctggtgac acagtagcct ttcggcagag ctccttggga tgagtaggaa 60
gtgctgctgc aggttttgtc tgggggatat ctgagccatt tctctgtggg cagctgtgtt 120
tcaaagtctg ggcaggttgt tgttgaattt tgcgtgggct gccaggattt tgtggaagta 180
taatactttg tcattatgag atgtcgtctc tcggtgcctc ctttgtgcaa attaaatttg 240
atgacttgca gttttttgaa aactgcggtg gaggaagttt tgggagtgtt tatcgagcca 300
aatggatatc acaggacaag gaggtggctg taaagaagct cctcaaaata gagaaagagg 360
cagaaatact cagtgtcctc agtcacagaa acatcatcca gttttatgga gtaattcttg 420
aacctcccaa ctatggcatt gtcacagaat atgcttctct gggatcactc tatgattaca 480
ttaacagtaa cagaagtgag gagatggata tggatcacat tatgacctgg gccactgatg 540
tagccaaagg aatgcattat ttacatatgg aggctcctgt caaggtgatt cacagagacc 600
tcaagtcaag aaacgttgtt atagctgctg atggagtatt gaagatctgt gactttggtg 660
cctctcggct ccataaccat acaacacaca tgtccttggt tggaactttc ccatggatgg 720
ctccagaagt tatccagagt ctccctgtgt cagaaacttg tgacacatat tcctatggtg 780
tggttctctg ggagatgcta acaagggagg tcccctttaa aggtttggaa ggattacaag 840
tagcttggct tgtagtggaa aaaaacgaga ggctaaagaa actagagcgt gatctcagct 900
ttaaggagca ggagcttaaa gaacgagaaa gacgtttaaa gatgtgggag caaaagctga 960

```
cagagcagtc caacaccccg cttctcttgc ctcttgttgc aagaatgtct gaggagtctt   1020
actttgaatc taaaacagag gagtcaaaca gtgcagagat gtcatgtcag atcacagcaa   1080
caagtaacgg ggagggccat ggcatgaacc caagtctgca ggccatgatg ctgatgggct   1140
ttggggatat cttctcaatg aacaaagcag gagctgtgat gcattctggg atgcagataa   1200
acatgcaagc caagcagaat tcttccaaaa ccacatctaa gagaaggggg aagaaagtca   1260
acatggctct ggggttcagt gattttgact tgtcagaagg tgacgatgat gatgatgatg   1320
acggtgagga ggaggataat gacatggata atagtgaatg aaagcagaaa gcaaagtaat   1380
aaaatcacaa atgtttggaa aacacaaaag taacttgttt atctcagtct gtacaaaaac   1440
agtaaggagg cagaaagcca agcactgcat tttaggccaa atcacattta catgaccgta   1500
atttcttatc aattctactt ttatttttgc ttacagaaaa acgggggag aattaagcca   1560
aagaagtaca tttatgaatc agcaaatgtg gtgcctgatt atagaaattt gtgatcctat   1620
atacaatata ggacttttaa agttgtgaca ttctggcttt ttcttttaat gaatactttt   1680
tagtttgtat ttgactttat ttcctttatt caaatcattt ttaaaaactt acattttgaa   1740
caaacactct taactcctaa ttgttctttg acacgtagta attctgtgac atacttttt   1800
tttcttatag caatacactg taatatcaga aatggttggc ctgagcaacc tagtaagacc   1860
tcgtctctac taataattaa aaaactagct ggcatggtag cacacacctg tagtcccaga   1920
tacttgggag gccaaggcag gaggattgct tgagacctag caatcagtca gggctgcagt   1980
gagccatgat ggcaccactg cactctagcc tgggcaagag aacaagatcc tgtctcaaaa   2040
aacaaaaaaa agaaagaatt gatagtacaa aatccaacaa caatactgag atgatctaag   2100
aaggttataa caaaatgctc ttcagaaata cctaagtgct gagaattttt agtactaaag   2160
agcacagctg ctcaaagtaa agcctgagca gtgttctcag taatgtattt gaaggaaaaa   2220
taccctgatt tgaaaccaac agcagatgtt gcaaactttc ataccactgc tggccatgga   2280
agcctcttaa caacacactg tcatttaagg ctgtgcttgt gctttataca aagagaaaga   2340
ggtggtctta aggggatgct tccagggggt gagttcatgc ctctcctgta ttttccagca   2400
agtggggtat gtgtggtggt tgtttttag aggggcataa taatccagga ttctaagcat   2460
atgctcagct attttaaaga ggaaattaaa tattataaaa gaaatagtaa agataagtta   2520
tcctcactta ggcaaaagca caggtccttt ccatatcaag tttagcctac cagggttgtt   2580
ttttgtttta accctgctta ataatgttgg tgttttagaa gtagatacag gcactgctct   2640
gaaaacctgg ctagccaagg atattctcag aatgttatca cctgtttgtc aaagcttgtt   2700
taaattataa aacactttta attatatata tgaggcaaaa gaactaagac ttttttcaaa   2760
ctaaattaga aaggagtgtc attatttgac tgttaaacca aaatattttt ggtgggtctt   2820
tttatggaag tttaaagaaa ggacatcatc atagatatga tctaacagta tttctaacta   2880
tatttgatca ttaaaagcct cttggaattt gaagcgtgac gtgtttctaa tgccccttga   2940
gaggtgaaaa ataccacata atgatcagta tgctgtgcca gcttcatttg gggagaaata   3000
actagtagaa agttctgggt gtgaggtgta cagcagtcta ggtggcatag tgatgaagaa   3060
agggatcaga gtctgactgt cactcagaat cctgggctca gttgcttgac aaccttggga   3120
aaattgtttt atctttgtgc gtctgtttgc tgatcttcag cgtgggaata ataacagtac   3180
ctacttgaaa ggatcattgt gcggattaaa agaaataata tatgtaaagc actttaacac   3240
agcaccaggc ccacggaaag tggctaatgt tagctactat gaatggtgcc agtgaagaca   3300
ctgaaaaata agtgatttca gtaaccttct ggaaagctat cagtttcaaa taatattttc   3360
```

```
tctgtagtat gagatgaaat taaaagtgga tagctttcag gaaagataaa gagaacatgc   3420
ttagaatgta agctaaacag attttttctg ttgctctttg aaaactatga gccctggcca   3480
gcttaacctg gtctgaggtg agactaaaca caaaaacagt agataaatct ctccctaaaa   3540
gatggattcc cccacatacc catgctacta gtttctctgt ctattcacac atatgtacaa   3600
atacatgaac acagcctgtc tgtgctcaga catagagaag tactacctga cttgagtcaa   3660
tgcacccaag aagaaaagct tggagtagag cagaagggag ggcttgggac tcctgtcttt   3720
ccagcatgcc ctggggtgca gtggtcagcc acctgaagag agagccaata gccatggggt   3780
ttacaaggca aagatagtca ttcattcaaa cacatattca tagaagctcc ttctctgtgc   3840
cagacaactg ttctggaaga tagctagatg aaaatctttg cactcacagg agcttaacat   3900
gccagtgagt gaagatcgat gataaataaa gcaaatgcat catatgttca catttgataa   3960
gtatatgcca aaaaatgaag ccgggaagga ggacaaggcc catgggtggg tgttgaggtt   4020
tttaaagtgt ggtcaggaaa ggccccactg ataaggtaac atttgagcaa gtctgaaaaa   4080
ggcaagggga tctttggggc taacttcggg atccctgcac tttatgtaag aatgtaaacc   4140
tggagtctca tttaagaatg atcagcaata cgtttagaac atatgaactg aatgaaatgg   4200
acatttttc ttaatttatg tataaatcca tatgattata cataaagttc tgatgcatta   4260
ataaaagcag ccaaataggg ccaaagagaa aaataacagg actctgtact ggacctaact   4320
ttatcattaa ttaggtaata ttttcctcat ttctttactg ctgccatttt cctcaccagt   4380
attccagaga tggtcatagc tcattactct accaccaaga acctaaaagg aattagaata   4440
cagcagaatt ggcctcagtg aagagcttaa aattgttctc ctcgtagaac tggactattg   4500
atcattacca cgtgacgttg gctctattac tttctgttcc caatgtcctt ctagtggttt   4560
gaaaatgtta aaacatccaa aaaaaaacaa cccggtagca ttgtcccttc cccactgaca   4620
aacttatcaa atccagaagc tttagagttt cgtctctaat tatttttctc ctgaacaaaa   4680
ttacccaagt caaaacaaaa tgtattttta gaattacggc agcatacgac ctgaattttg   4740
tgagtttcgt ggctttatct taaatcacca tttccctaaa aatggtttct ttctccttag   4800
aaatgctggt ggcaacttga tgaaacagcc aaatgcacca gggcaggtca ctttcccatt   4860
acactgattc cacaattaaa aaaataaaaa aaagaaaaaa aactcattga gatagctaca   4920
gttctatagg ttaatttaaa gcctcctttt tctactcatt tttgaaagca aaattacatt   4980
ttactatttt acataaccag tgaaaagacg ttgaaagcct acagctcact gttttgggtg   5040
ctctggaaat gttgagggtg ggtttttaac cagtgatttt taacgtgcag tgaatttgtt   5100
agacttttaa acaccagcta aggtagtcaa acttgatccc cattaaaaat caaggaatta   5160
ggggtcgggg gagggtttag gagtgatcca gaatgacctc ccagaattac tgtgcgtaca   5220
actttatttt tcagagtttt cattgggaat ggtaagagtg tttatgaaag acagttttaa   5280
aacttattct gagttaaata ttaatacttt aaaaaaattat tgtactagac ttatcgcagc   5340
cttttgaaag tagcagagtt tcatcatacc acatatataa cagagcataa attttctata   5400
atcaggcacc ttttgctgct tttgagtaag actgttttcc tgtttaagtg ttaagcatcg   5460
ccagacataa aaatctattc tctcctctcg attgtagcat agcctgacag ctctagatac   5520
agcatttcta tgatgaaaaa tgagtatcca tcaggaaatc tagaagacta gccgtgtttt   5580
ctcagactcc acctttgttt gcactctgtt gcctgtgagg agctttctgg catgtgatta   5640
tttacttcaa aactagagtt ccaagcacct acattaatta ttttatattg tgtgcagaat   5700
agtatatctt ttaatgtcag atatgataca ctgcacatat tgcttttgca ctcttaaaat   5760
```

```
ttttgtacta aataatagaa aatatttata ttctttgagt gtgagctttg aatagatggc   5820

attatcactt tattgttttt ttaacaaaaa ctttttctca attattctat tgcaatgtta   5880

ttctgagcaa gtcctatgcc aaatatcttg tataatgttt gtatggaaga ttaaatttta   5940

ctcttgtgtg gtaagactat ttcagttact gattttatag ttggaatttg atattccagc   6000

acaaagtcca cagtgtattc agaaatccaa gttggtgtca tacatttcat tttgatgtga   6060

acttttcttt gctttccttt gttctaagac tccattttgc aataaacgtt ttgacagcaa   6120

aa                                                                  6122
```

```
<210> SEQ ID NO 86
<211> LENGTH: 1914
<212> TYPE: DNA
<213> ORGANISM: Homo sapiens

<400> SEQUENCE: 86

gctgtcatcg ttccgtgggc cctgctgcgg gcacgctctc ggcgcatgcg tttttatgc     60

gggattaagc ttgctgctgc gtgacagcgg agggctagga aaaggcgcag tggggcccgg    120

agctgtcacc cctgactcga cgcagcttcc gttctcctgg tgacgtcgcc tacaggaacc    180

gccccagtgg tcagctgccg cgctgttgct aggcaacagc gtgcgagctc agatcagcgt    240

ggggtggagg agaagtggag tttggaagtt caggggcaca ggggcacagg cccacgactg    300

cagcgggatg gaccagtact gcatcctggg ccgcatcggg gagggcgccc acggcatcgt    360

cttcaaggcc aagcacgtgg agactggcga gatagttgcc ctcaagaagg tggccctaag    420

gcggttggaa gacggcttcc ctaaccaggc cctgcgggag attaaggctc tgcaggagat    480

ggaggacaat cagtatgtgg tacaactgaa ggctgtgttc ccacacggtg gaggctttgt    540

gctggccttt gagttcatgc tgtcggatct ggccgaggtg gtgcgccatg cccagaggcc    600

actagcccag gcacaggtca agagctacct gcagatgctg ctcaagggtg tcgccttctg    660

ccatgccaac aacattgtac atcgggacct gcccccaagg cccatccagg gcccccccac    720

atccatgact tccacgtgga ccggcctctt gaggagtcgc tgttgaaccc agagctgatt    780

cggcccttca tcctggaggg gtgagaagtt ggccctggtc ccgtctgcct gctcctcagg    840

accactcagt ccacctgttc ctctgccacc tgcctggctt caccctccaa ggcctcccca    900

tggccacagt gggcccacac cacaccctgc cccttagccc ttgcgagggt tggtctcgag    960

gcagaggtca tgttcccagc caagagtatg agaacatcca gtcgagcaga ggagattcat   1020

ggcctgtgct cggtgagcct taccttctgt gtgctactga cgtacccatc aggacagtga   1080

gctctgctgc cagtcaaggc ctgcatatgc agaatgacga tgcctgcctt ggtgctgctt   1140

ccccgagtgc tgcctcctgg tcaaggagaa gtgcagagag taaggtgtcc ttatgttgga   1200

aactcaagtg gaaggaagat ttggtttggt tttattctca gagccattaa acactagttc   1260

agtatgtgag atatagattc taaaaacctc aggtggctct gccttatgtc tgttcctcct   1320

tcatttctct caagggaaat ggctaaggtg gcattgtctc atggctctcg tttttggggt   1380

catggggagg gtagcaccag gcatagccac ttttgccctg agggactcct gtgtacttca   1440

catcactgag cactcattta gaagtgaggg agacagaagt ctaggcccag ggatggctcc   1500

agttggggat ccagcaggag accctctgca catgaggctg gtttaccaac atctactccc   1560

tcaggatgag cgtgagccag aagcagctgt gtatttaagg aaacaagcgt tcctggaatt   1620

aatttataaa tttaataaat cccaatataa tcccagctag tgctttttcc ttattataat   1680

ttgataaggt gattataaaa gatacatgga aggaagtgga accagatgca gaagaggaaa   1740
```

```
tgatggaagg acttatggta tcagatacca atatttaaaa gtttgtataa taataaagag   1800

tatgattgtg gttcaaggat aaaaacagac tagagaaact tattcttagc catcctttat   1860

ttttatttta tttatttttt gatggagtct tgcactccag cctggtgaca gact        1914


<210> SEQ ID NO 87
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 87

His His His His His His
1               5
```